(12) United States Patent
Turnbull et al.

(10) Patent No.: US 8,673,948 B2
(45) Date of Patent: *Mar. 18, 2014

(54) CHEMICAL COMPOUNDS

(75) Inventors: Philip Stewart Turnbull, Durham, NC (US); Rodolfo Cadilla, Durham, NC (US); Andrew Larkin, Durham, NC (US); Huiquiang Zhou, Durham, NC (US); Eugene L. Stewart, Durham, NC (US); Katherine Stetson, Durham, NC (US); Darryl Lynn McDougald, Durham, NC (US); Amarjit Sab Randhawa, Durham, NC (US); John A. Ray, Durham, NC (US)

(73) Assignee: GlaxoSmithKline, LLC, Wilmington, DE (US)

( * ) Notice: Subject to any disclaimer, the term of this patent is extended or adjusted under 35 U.S.C. 154(b) by 332 days.

This patent is subject to a terminal disclaimer.

(21) Appl. No.: 13/213,978

(22) Filed: Aug. 19, 2011

(65) Prior Publication Data

US 2011/0301203 A1    Dec. 8, 2011

Related U.S. Application Data

(63) Continuation of application No. 12/496,374, filed on Jul. 1, 2009, now Pat. No. 8,026,262, which is a continuation of application No. 11/862,531, filed on Sep. 27, 2007, now Pat. No. 7,572,820.

(60) Provisional application No. 60/971,038, filed on Sep. 10, 2007, provisional application No. 60/827,522, filed on Sep. 29, 2006.

(51) Int. Cl.
*A61K 31/427* (2006.01)
*C07D 271/06* (2006.01)
*C07D 413/06* (2006.01)

(52) U.S. Cl.
USPC ............ 514/364; 548/125; 548/131; 514/361

(58) Field of Classification Search
USPC .......................... 548/125, 131; 514/361, 364
See application file for complete search history.

(56) References Cited

U.S. PATENT DOCUMENTS

| | | | |
|---|---|---|---|
| 3,669,987 A | 6/1972 | Sato et al. | |
| 6,337,344 B1 | 1/2002 | Defossa et al. | |
| 6,441,004 B1 | 8/2002 | Faull et al. | |
| 6,613,942 B1 | 9/2003 | Ling et al. | |
| 6,673,815 B2 | 1/2004 | Devasthale et al. | |
| 6,787,651 B2 | 9/2004 | Stolle et al. | |
| 6,828,344 B1 | 12/2004 | Seehra et al. | |
| 7,129,220 B2 | 10/2006 | Beavers et al. | |
| 7,129,264 B2 | 10/2006 | Smallheer et al. | |
| 7,173,048 B2 | 2/2007 | Dehmlow et al. | |
| 7,572,820 B2 | 8/2009 | Turnbull et al. | |
| 8,026,262 B2 * | 9/2011 | Turnbull et al. | ............. 514/361 |
| 2004/0006123 A1 | 1/2004 | Alkan et al. | |
| 2006/0089353 A1 | 4/2006 | Iwahashi et al. | |
| 2008/0146646 A1 | 6/2008 | Dubois et al. | |

FOREIGN PATENT DOCUMENTS

| | | |
|---|---|---|
| WO | 9506032 A1 | 3/1995 |
| WO | 0147882 A2 | 7/2001 |
| WO | 0157020 A1 | 8/2001 |
| WO | 2004041782 A1 | 5/2004 |
| WO | 2005056012 A1 | 6/2005 |
| WO | 2005060958 A1 | 7/2005 |
| WO | 2005077373 A2 | 8/2005 |
| WO | 2005090282 A1 | 9/2005 |
| WO | 2007030559 A2 | 3/2007 |

OTHER PUBLICATIONS

Beavers et al.; "Preparation of Substituted indole-O-glucosides for the Treatment of Diabetes and Syndrome X", CAPLUS No. 2005:120879.
Hennequin; "Preparation of Quinazolines as Inhibitors of VEGF Receptor Tyrosine Kinases"; CAPLUS No. 2005:141059.
Bhide et al., "Discovery and Preclinical Studies of (R)-1-(4-(4-Fluoro-2-methyl-1H-indol-5-yloxy)-5-methylpyrrolo[2,1-f] [1,2,4]triazin-6-yloxy)propan-2-ol (BMS-540215), an in Vivo Active Potent VGFR-2 Inhibitor," Journal of Medicinal Chemistry, 2006, vol. 49, No. 7, pp. 2143-2146.
Bohme et al., "Synthesis and Pharmacology of Benzoxazines as Highly Selective Antagonists at M4 Muscarinic Receptors," Journal of Medicinal Chemistry, 2002, vol. 45, No. 14, pp. 3094-3102.
Cadilla et al., "Selective Androgen Receptor Modulators in Drug Discovery: Medicinal Chemistry and Therapeutic Potential," Current Topics in Medicinal Chemistry, 2006, vol. 6, No. 3, pp. 245-270.
Mckew et al., "Inhibition of Cytosolic Phospholipase A2α: Hit to Lead Optimization," Journal of Medicinal Chemistry, 2006, vol. 49, No. 1, pp. 135-158.
Smart et al., "Inhibition of the Complete Set of Mammalian Secreted Phospholipases A2 by Indole Analogues: a Structure-Guided Study," Bioorganic & Medicinal Chemistry, 2004, vol. 12, No. 7, pp. 1737-1749.

* cited by examiner

*Primary Examiner* — Golam M M Shameem
(74) *Attorney, Agent, or Firm* — Nora L. Stein; Theodore R. Furman

(57) ABSTRACT

This invention relates to non-steroidal compounds that are modulators of androgen receptor, and also to the methods for the making and use of such compounds.

15 Claims, No Drawings

CHEMICAL COMPOUNDS

CROSS-REFERENCE TO RELATED APPLICATIONS

This application is a Continuation of U.S. patent application Ser. No. 12/496,374, filed Jul. 1, 2009, now allowed; which is a Continuation of U.S. patent application Ser. No. 11/862,531, filed Sep. 27, 2007, issued U.S. Pat. No. 7,572,820; which claims the benefit of U.S. Provisional Application No. 60/971,038, filed Sep. 10, 2007 and U.S. Provisional Application No. 60/827,522, filed Sep. 29, 2006, all of which are herein incorporated in their entirety by reference.

FIELD OF THE INVENTION

This invention relates to non-steroidal compounds that are modulators of androgen receptor, and also to the methods for the making and use of such compounds.

BACKGROUND OF THE INVENTION

Nuclear receptors (NRs) are a class of structurally related proteins that modulate gene expression by acting as ligand-dependent transcription factors [Evans, R. M. *Science* 1988, 240, 889-95]. The steroid receptors, namely the androgen receptor (AR), the estrogen receptor (ER), the glucocorticoid receptor (GR), the mineralocorticoid receptor (MR), and the progesterone receptor (PR) represent a subclass of the nuclear receptor superfamily. NR ligands in this subclass exert their effects by binding to an intracellular steroid hormone receptor. In the presence of an agonist ligand the AR binds as a homodimer to the androgen response element (ARE), a consensus sequence for steroid receptors (GGTACAnnnTGT-TCT) [Beato M. *Cell* 1989, 56, 335-44. Cato, A. C. B. and Peterziel, H. *TEM* 1998, 9, 150-154. Wong, C. I.; Zhou, Z. X.; Sar, M.; Wilson, E. M. *J. Biol. Chem.* 1993, 268, 19004-12].

Certain NR ligands are known to exert their action in a tissue selective manner [Smith, C. L.; O'Malley, B. W. *Endoc. Rev.* 2004, 25, 45-71]. This selectivity stems from the particular ability of these ligands to function as agonists in some tissues, while having no effect or even an antagonist effect in other tissues. The term "selective receptor modulator" (SRM) has been given to these molecules. A synthetic compound that binds to an intracellular receptor and mimics the effects of the native hormone is referred to as an agonist. A compound that inhibits the effect of the native hormone is called an antagonist. The term "modulators" refers to compounds that have a spectrum of activities ranging from full agonism to partial agonism to full antagonism.

Steroidal NR ligands are known to play important roles in the health of both men and women. In regard to men's health, testosterone (T) and dihydrotestosterone (DHT) are endogenous steroidal ligands for the AR that likely play a role in every tissue type found in the mammalian body. During the development of the fetus, androgens play a role in sexual differentiation and development of male sexual organs. Further sexual development is mediated by androgens during puberty. Androgens play diverse roles in the adult including stimulation and maintenance of male sexual accessory organs and maintenance of the musculoskeletal system. Cognitive function, sexuality, aggression, and mood are some of the behavioral aspects mediated by androgens. Androgens affect the skin, bone, and skeletal muscle, as well as blood lipids and blood cells [Chang, C. 2002, 503 pp. Publisher: (Kluwer Academic Publishers, Norwell, Mass.)].

The study of androgen action and male reproductive dysfunction continues to expand significantly. In fact, only recently has the definition of a disease state been associated with hormonal changes that occur in aging men. This syndrome, previously referred to as "Andropause," has more recently been described as Androgen Deficiency in the Aging Male, or "ADAM" [Morales, A. and Tenover, J. L. *Urologic Clinics of North America* 2002, 29, 975]. The onset of ADAM is unpredictable and its manifestations are subtle and variable. Clinical manifestations of ADAM include fatigue, depression, decreased libido, erectile dysfunction as well as changes in cognition and mood.

Published information indicates that androgen replacement therapy (ART) in men may have benefits in terms of improving body composition parameters (e.g. bone mineral density, lean muscle mass, and strength) as well as improving libido and mood in some men. Andrologists and other specialists are increasingly using ART for the treatment of the symptoms of ADAM. This use is with due caution given potential side effects of androgens. Nonetheless, there is increasing scientific rationale and evidence for androgen deficiency and treatment in the aging male In general, current ARTs fail to correctly mimic physiological testosterone levels and have potential side effects including exacerbation of pre-existing sleep apnoea, polycythemia (increased hematocrit), and/or gynaecomastia. Furthermore, the longer-term side effects on target organs such as the prostate or the cardiovascular system are yet to be fully elucidated. Importantly, the potential cancer promoting effects of testosterone on the prostate prevent many physicians from prescribing it to older men (i.e. age>60 years) who, ironically, stand to benefit most from treatment. The need for a novel selective androgen receptor modulator (SARM) is obviated by the potential side effect profile manifested by conventional treatments. An ideal SARM has all the beneficial effects of endogenous androgens, while sparing sexual accessory organs, specifically the prostate.

SARMs are currently in the early stages of development. Much of the preclinical and clinical understanding of the therapeutic promise of SARMs stems from work using anabolic steroids. Because of their highly selective anabolic properties and demonstrated prostate sparing activity, SARMs could be used for prevention or treatment of many diseases, including, but not limited to sarcopenia (muscle wasting), osteoporosis, frailty, and other conditions associated with aging or androgen deficiency. SARMs also show promise in the areas of hormonal male contraception and benign prostatic hyperplasia (BPH). The therapeutic potential of SARMs for treatment of androgen deficient disorders in women is a far less studied field. This review primarily focuses on the use of SARMs for the treatment and prevention of disease in males, but many of these therapies could apply to both genders.

Male hypogonadism represents a state of impaired testosterone production. There are two general types of hypogonadism: primary hypogonadism is due to testicular failure, while secondary hypogonadism is due to malfunction at the hypothalamic/pituitary level. Gonadotropins can be elevated or decreased depending on the localization of the condition. Severe symptoms are associated with the hypogonadal state. Symptomatic profiles differ depending on the time of onset of the condition. Symptoms in patients who experience hypogonadism after normal virilization include decreased muscle mass, osteopenia/osteoporosis, decreased fertility, increased visceral fat, and sexual dysfunction [Zitzmann, M.; Nieschlag, E. *Mol. Cell. Endo.* 2000, 161, 73-88].

A SARM in hypogonadal men would provide the anabolic effects of testosterone with the convenience of oral administration. Prostate drive is usually not a concern for young hypogonadal males, but the sparing effects of a SARM may still prove beneficial. Clinical studies in hypogonadal males using testosterone have provided compelling efficacy data [Wang, C.; Cunningham, G.; Dobs, A.; Iranmanesh, A.; Matsumoto, A. M.; Synder, P. J.; Weber, T.; Berman, N.; Hull, L.; Swerdloff, R. S. *J. Clin. Endo. Met.* 2004, 89, 2085-2098].

Over 80% of all illness, morbidity, and medical costs are concentrated in the years after age 65. With increased survival to more advanced ages, the absolute numbers of senior citizens will increase markedly in coming years. According to the United Nations World Health Organization report on Aging, it is anticipated that by 2030 one in five American will be over the age of 65 [Anonymous, Centers for Disease Control and Prevention (CDC) *MMWR Trends in Aging—United States and Worldwide. Morbidity and Mortality Weekly Report* 2003, 52, 101-4, 106]. Though decline in organ function is inevitable in this population, it may be possible to extend organ function, thereby increasing quality of life (QOL) in older people. Therapeutic interventions that reduce organ decline and increase QOL will clearly be widely accepted, both for their ability to decrease overall health care costs and to improve the length of functional life.

Clinical studies show that ART in men improves body composition parameters such as muscle mass, strength, and bone mineral density [Asthana, S.; Bhasin, S.; Butler, R. N.; Fillit, H.; Finkelstein, J.; Harman, S. M.; Holstein, L.; Korenman, S. G.; Matsumoto, A. M.; Morley, J. E.; Tsitouras, P.; Urban, R. *J. Ger., Series A: Biol. Sci. Med. Sci.* 2004, 59, 461-465]. There is also evidence of improvement in less tangible parameters such as libido and mood. Andrologists and other specialists are increasingly using androgens for the treatment of the symptoms of androgen deficiency. ART, using T and its congeners, is available in transdermal, injectable and oral dosage forms. All current treatment options have contraindications (e.g., prostate cancer) and side-effects, such as increased hematocrit, liver toxicity, and sleep apnoea.

Sarcopenia or muscle wasting is the aging-associated decline in neuromuscular function and performance [Lynch, G. S. *Exp. Opin. Emerg. Drugs* 2004, 9, 345-361]. Skeletal muscle atrophy and weakness are considered major contributing factors to the loss of mobility, independence, and frailty that affect many older adults [Doherty, T. J. *J. App. Phys.* 2003, 95, 1717-1727]. Relative muscle loss in aging men and women is similar, but because men start with higher baseline values, their absolute loss of strength is greater. Epidemiological data support the relationship between the fall in testosterone and the decline in muscle mass [Janssen, I.; Shepard, D. S.; Katzmarzyk, P. T.; Roubenoff, R. JAGS 2003, 80-85. Baumgartner, R. N.; Waters, D. L.; Gallagher, D.; Morley. J. E.; Garry, P. J. *Mechanisms of Ageing and Development* 1999, 107, 123-36]. As mentioned above, many clinical studies with testosterone have demonstrated significant gains in muscle mass and function along with decreases in visceral fat [Bhasin, S. *J. Gerontol. A Biol. Sci. Med. Sci.* 2003, 58, 1002-1008. Ferrando, A. A.; Sheffield-Moore, M.; Yeckel, C. W.; Gilkison, C.; Jiang, J.; Achacosa, A.; Lieberman, S. A.; Tipton, K.; Wolfe, R. R.; Urban, R. *J. Am. J. Phys. Endo. Met.* 2002, 282, E601-E607].

The actual mechanisms of androgen-promoted muscle anabolism are still not fully understood. It is generally believed that androgen-induced increases in muscle mass can be attributed to increases in muscle protein synthesis [Brodsky, I.; Balagopal, P.; Nair, K. *J. Clin. Endocrinol. Metab.* 1996, 81, 3469-3475]. Muscle size increases associated with androgen therapy occur through the hypertrophy of both type I and type II muscle fibers. Studies have shown that androgens promote increases in satellite cell number as well as myonuclei [Singh, R.; Artaza, J, N.; Taylor, W. E.; Gonzalez-Cadavid, N. F.; Bhasin, S. *Endocrinology* 2003, 144, 5081-5088]. Other studies have shown androgens to promote the commitment of pluripotent, mesenchymal cells into the myogenic lineage and to inhibit differentiation into the adipogenic lineage.

Men undergo a gradual reduction in bone mass in early to mid adulthood. In fact, when in their late 60's, men lose bone mass at a rate similar to women. There is increasing evidence that T plays an important role in the maintenance of bone [Notelovitz, M. *Fertil. Steril.* 2002, 77, S34-S41. Vanderschueren, D.; Vandenput, L. *Andrologia* 2000, 32, 125-30]. There have been multiple studies examining the relationship between bone mineral density (BMD) and related bone markers and T levels in men. Osteoporosis is common in men undergoing treatment for prostate cancer. Bilateral orchidectomy and gonadotropin-releasing hormone agonist treatment decrease BMD and increase fracture risk [Smith, M. R. *Cancer and Meta. Rev.* 2002, 21, 159-166]. Testosterone therapy increases bone mineral density in men with low T [Leifke, E.; Korner, H. C.; Link, T. M.; Behre, H. M.; Peters, P. E.; Nieschlag, E. *Eur. J. Endocrinol.* 1998, 138, 51-58. Schubert, M.; Bullmann, C.; Minnemann, T.; Reiners, C.; Krone, W.; Jockenhoevel, F. *Hormone Research* 2003, 60, 21-28]. It is not entirely clear if both T and E2 are required for healthy bone maintenance. A combination therapy of estrogen and androgen increases BMD to a greater extent than does estrogen therapy alone [Vanderschueren, D.; Vandenput, L. *Andrologia* 2000, 32, 125-30].

Androgens are important for skeletal homeostasis, affecting bone mineral density (BMD) by regulating the bone breakdown and remodeling process. Androgen action on AR expressing osteoblasts inhibits osteoclastogenesis in the bone marrow cavity. Androgens increase cortical bone formation mainly by stimulating periosteal bone formation [Notelovitz, M. *Fertil. Steril.* 2002, 77, S34-S41].

Clinically employed antiresorptive therapies such as estrogen replacement, selective estrogen receptor modulators (SERMs), bisphosphonates, and cathepsin K inhibitors, do not restore bone mass in patients already showing significant bone loss. The clinical use of intermittent parathyroid hormone (PTH) treatment to promote bone formation is limited because of side effects and possible association with osteosarcoma. Like T therapy, SARMs offer promise not only as antiresorptive agents, but also as osteoanabolic agents. A few preclinical studies demonstrating the promise of SARMs in the treatment of osteoporosis have been published [Hanada, K.; Furuya, K.; Yamamoto, N.; Nejishima, H.; Ichikawa, K.; Nakamura, T.; Miyakawa, M.; Amano, S.; Sumita, Y.; Oguro, N. *Biol. Pharm. Bull.* 2003, 26, 1563-1569. Rosen, J. and Negro-Vilar J. *Musc. Neur. Interact.* 2002, 2, 222-224. Kearbey, J. D.; Gao, W.; Miller, D. D.; and Dalton, J. T. *Pharm. Sci.* 2003, 5, R61-R67]. SARMs were shown to significantly increased BMD and bone strength in ORX rats [Hanada, K.; Furuya, K.; Yamamoto, N.; Nejishima, H.; Ichikawa, K.; Nakamura, T.; Miyakawa, M.; Amano, S.; Sumita, Y.; Oguro, N. *Biol. Pharm. Bull.* 2003, 26, 1563-1569]. Administration of the SARM, S-40503, to ORX rats for 4 weeks increased bone mineral density (BMD) of femur and levator ani muscle weight as markedly as DHT. Prostate weight was not elevated over that for eugonadal rats at any doses tested. In order to further validate the bone anabolic effect, S-40503 was given to ovariectomized (OVX) rats over a 2 month period. The SARM significantly increased BMD and biomechanical strength of femoral cortical bone, whereas the antiresorptive estrogen did not. An increase in periosteal mineral apposition rate of the femur showed direct bone formation activity of S-40503. The increase in BMD was not attributed to muscle anabolism as hind limb suspended rats showed like increases in BMD.

Benign prostatic hyperplasia (BPH) affects the majority of men in the United States over the age of 50. Prostatic drive is determined by the local concentration of androgen. DHT, the androgen of the prostate, is produced in the prostate by the action 5-α-reductase on T. BPH can lead to many problems including acute urinary retention, recurrent bladder infection, bladder calcul, and a general decrease in a patient's quality of life [Kirby, R. S. *Urology* 2000, 56, 3-6. Andriole, G.; Bruchovsky, N.; Chung, L. W. K.; Matsumoto, A. M.; Rittmaster, R.; Roehrborn, C.; Russell, D.; Tindall, D. *J. of Urology* 2004, 172, 1399-1403. Djavan, B.; Barkin, J. *European Urology, Supplements* 2003, 2, 20-26].

SARMs that compete with prostatic binding of DHT, but that do not elicit an agonist response, may provide a therapeutic approach to the treatment of BPH. The true novelty of such a therapy is realized when prostate volume reduction is combined with the other desirable pharmacologic features of a SARM. Drug-related adverse events from 5-α-reductase inhibitors include erectile dysfunction, decrease libido, and decreased ejaculate volume [Andriole, G.; Bruchovsky, N.; Chung, L. W. K.; Matsumoto, A. M.; Rittmaster, R.; Roehrborn, C.; Russell, D.; Tindall, D. *J. of Urology* 2004, 172, 1399-1403]. A comparison study of the pharmacologic activity of a SARM to an antiandrogen, and a 5-α-reductase inhibitor in intact male rats was recently reported [Gao, W.; Kearbey, J. D.; Nair, V. A.; Chung, K.; Parlow, A. F.; Miller, D. D.; Dalton, J. T. *Endocrinology,* 2004, 145, 5420-5428].

Large studies investigating the use of high doses of testosterone as a means of male contraception have been and are currently being conducted [Gao, W.; Kearbey, J. D.; Nair, V. A.; Chung, K.; Parlow, A. F.; Miller, D. D.; Dalton, J. T. *Endocrinology,* 2004, 145, 5420-5428. World Health Organization Task Force on Methods for the Regulation of Male Fertility. *Lancet* 1990, 336, 955-959]. Testosterone is a necessary component in the generation of sperm, but high doses actually inhibit formation of mature sperm. Sperm maturation relies on the secretion of LH and FSH. LH regulates testicular testosterone production by the Leydig cells and FSH stimulates Sertoli cells to provide nutrients to maturing sperm. T production is regulated through a feedback loop that involves the hypothalamus and pituitary glands. Testosterone signals the hypothalamus and pituitary to decrease production of gonadotropin releasing hormone which in turn lowers the secretion of LH and FSH. Supraphysiological levels of testosterone serve to inhibit LH and FSH secretion through the feedback loop [Wang, C.; Swerdloff, R. S. *Am. J. Obstet. Gynecol.* 2004, 190, S60-S68. Wang, C.; Swerdloff, R. S. Endocrine Updates 1999, 5, 303-319]. Lowered intratesticular levels of T and FSH decrease sperm production [Sharpe, R. M.; Donachie, K.; Cooper, I. *J. Endo.* 1988, 117, 19-26.].

A SARMs efficacy in male contraception is dependent on its ability to interfere with the HPT axis and also on its potential action on androgen receptors in the testes. A SARM from the aryl-propionamide class, C-6, exhibited significant gonadotropin suppression in castrated male rats [Chen, J.; Hwang, D. J.; Bohl, C. E.; Miller, D. D.; Dalton, J. T. *J. Pharmacol. Exp. Ther.* 2005, 312, 546-553]. While this study focused on the central mediation of spermatogenesis, further investigation of the direct effects of SARMs on androgen receptors in the Sertoli, Leydig, peritubular myoid, and vascular smooth muscle cells of the testis would increase our understanding of spermatogenic inhibitory mechanisms [Collins, L. L.; Lee, H.-J.; Chen, Y.-T.; Chang, M.; Hsu, H.-Y.; Yeh, S.; Chang, C. *Cytogenet Genome Res.* 2003, 103, 299-301].

Inhibition of spermatogenesis may not be a desired effect for individuals seeking the benefits of hormone replacement. In such cases, a desirable SARM profile would show no effects on the endogenous hormone levels and/or spermatogenesis, while still demonstrating marked anabolic effects in muscle and bone.

Hypoactive sexual desire disorder (HSDD) is prevalent in both men and women, though it is thought to be less common in men [Laumann E. O.; Paik A.; Rosen R. C. *JAMA* 1999, 281, 537-44]. There are multiple factors contributing to HSDD in men. The two major components are decreased libido and erectile dysfunction. Libido decreases with aging in men. Adequate plasma T levels are required for maintenance of normal libido. Testosterone deficiency decreases libido, but the threshold level of testosterone under which libido problems may occur is relatively low (290 ng/dL) [Buena, F.; Swerdloff, R. S.; Steiner, B. S.; Lutchmansingh, P.; Peterson, M. A.; Pandian M. R.; Galmarini, M.; Bhasin, S. *Fertil. Steril.* 1993, 59, 1118-23]. Low libido in aging men is associated with deficiency of bioavailable testosterone, whereas total testosterone showed no or only weak associations [Ansong, K. S.; Punwaney, R. B. *J. Urol.* 1999, 162, 719-721. Davidson, J. M.; Chen, J. J.; Crapo, L.; Gray, G. D.; Greenleaf, W. J.; Catania, J. A. *J. Clin. Endo. Met.* 1983, 57, 71-7]. Clinical studies investigating the effects of testosterone on male sexual dysfunction have been conducted [Morley, J. E.; Perry, H. M. 3rd Andropause: an Old Concept in New Clothing. *Clinics in Geriatric Medicine* 2003, 19, 507-28. Hajjar, R. R.; Kaiser, F. E.; Morley, J. E. *J. Clin. Endo. Met.* 1997, 82, 3793-3796. Morales, A.; Johnston, B.; Heaton, J. P. W.; Lundie, M. *J. Urol.* 1997, 157, 849-854]. Establishment of efficacy in these studies relies on the collection of soft data such as daily diary recordings and questionnaires regarding perceived libido. Testosterone replacement appears to have positive effects on libido, but the establishment of common clinically validated tools would serve to allow meaningful study interpretation and comparisons.

Incidence of erectile dysfunction increases with aging [Johannes, C. B.; Araujo, A. B.; Feldman, H. A.; Derby, C. A.; Kleinman, K. P.; McKinlay, J. B *J. Urol.* 2000, 163, 460-3]. The etiology of erectile dysfunction is usually multifactorial, and late-onset hypogonadism is a contributing factor in a minor percentage (8-15%) of cases [Kaiser F. E. *Medical Clinics of North America* 1999, 83, 1267-78]. There is an association between serum testosterone level and frequency, duration and degree of spontaneous nocturnal erections [Carani, C.; Bancroft, J.; Granata, A.; Del Rio, G.; Marrama, P. *Psychoneuroendocrinology* 1992, 17, 647-54]. Although some studies found no relationship with testosterone levels in older men [Ahn, H. S.; Park, C. M.; Lee, S. W. *BJU International* 2002, 89, 526-530. Cunningham, G. R; Hirshkowitz, M; Korenman, S. G; Karacan, I. *J. Clin. Endo. Met.* 1990, 70, 792-7], other studies have reported reduced testosterone levels in patients with erectile dysfunction [Rhoden, E. L.; Teloken, C.; Sogari, P. R.; Souto, C. A. V. *J. Urol.* 2002, 167, 1745-1748].

Although no studies have been published to date, the use of SARMs for HSDD offers the potential to increase libido while not driving the stimulation of sexual accessory organs such as the prostate. T has been shown to aid in the treatment of erectile dysfunction. Because the threshold value for T required to enhance libido is so low, very low doses of a SARM may be employed in order to provide treatment.

The use of androgens to alleviate the physiological consequences of testosterone deficiency is well recognized in men. The concept of androgen deficiency in women, however, is not readily embraced. The clinical manifestations of T deficiency in women are decreased libido, lowered mood, a diminished sense of well-being, blunted motivation, and persistent fatigue. Clinically, the use of androgens in women has been shown to enhance sexual function, maintain BMD, and increase fat-free mass [Cameron, D. R.; Braunstein, G. D. *Fert. Steril.* 2004, 82, 273-289].

SARMs have the potential to offer the same benefits in women as androgen therapies without the unwanted side effects. Side effects from androgen therapy in women include: acne, hirsutism, and lowering of high-density lipoprotein (HDL) cholesterol levels. Limited preclinical studies exploring the use of SARMs for female indications have been published. [Hanada, K.; Furuya, K.; Yamamoto, N.; Nejishima, H.; Ichikawa, K.; Nakamura, T.; Miyakawa, M.; Amano, S.; Sumita, Y.; Oguro, N. *Biol. Pharm. Bull.* 2003, 26, 1563-1569. Gao, W.; Reiser, P. J.; Coss, C. C.; Phelps, M. A.; Kearbey, J. D.; Miller, D. D.; Dalton, J. T. *Endocrinology* 2005, 146(11), 4887-4897].

Thus, modulators of steroid hormone nuclear receptors that are highly specific for one receptor could offer greater benefit with less side effects in the treatment of both female and male related hormone responsive diseases.

BRIEF SUMMARY OF INVENTION

Briefly, in one aspect, the present invention provides compounds of formula (I)

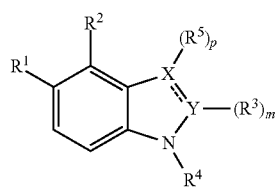

or a salt or solvate thereof, wherein
X and Y are each independently C or N;
X and Y are not both N;
$R^1$ is H, OH, CN, halogen, $C_{1-6}$alkoxy, or nitro;
$R^2$ is H, $C_{1-6}$alkyl, $C_{1-6}$alkoxy, $C_{1-6}$haloalkyl, halogen, or CN;
$R^3$ is H, halogen, $C_{1-6}$alkyl, $C_{2-6}$alkenyl, $C_{1-6}$haloalkyl, —C(O)$R^6$, —CH$_2$OH, or (CH$_2$)$_q$$R^x$;
$R^x$ is —$C_{3-6}$cycloalkyl, —C(O)OCH$_3$, —C(O)O$R^7$, or —CN;
q is 0, 1, 2, or 3;
$R^4$ is H, or ($R^8$)($R^9$);
$R^5$ is H, $C_{1-6}$alkyl, or halogen;
$R^6$ is H, $C_{1-6}$alkyl, or NH$_2$;
$R^7$ is $C_{1-6}$alkyl;
$R^8$ is $C_{1-6}$alkylene;
$R^9$ is $C_{1-6}$alkyl, $C_{1-6}$alkoxy, $C_{2-6}$alkenyl, $C_{3-6}$cycloalkyl, $C_{1-3}$haloalkyl, CN, —C(O)$R^{19}$, —C(CH$_2$)C(O)OCH$_3$, —C(NOH)NH$_2$, or —O$R^{11}$; or
$R^9$ is phenyl optionally substituted with one or more substituents independently selected from halogen, $C_{1-6}$alkyl, $C_{1-3}$haloalkyl, $C_{1-6}$alkoxy, CN, and $R^b$; or
$R^9$ is heterocyclyl, wherein said heterocyclyl is optionally substituted with one or more substituents independently selected from $R^a$ and $R^b$; wherein $R^a$ is CN, —C(O)$R^6$, —N$R^{12}R^{13}$, $C_{1-6}$alkyl, $C_{3-6}$cycloalkyl, $C_{1-3}$haloalkyl, halogen, or heterocyclyl, wherein said heterocyclyl is optionally substituted with one or more substituents independently selected from halogen, CN, $C_{1-6}$alkyl, $C_{1-3}$haloalkyl, —SCH$_3$, and —S(O)$_2$CH$_3$;
$R^b$ is phenyl optionally substituted with one or more substituents independently selected from —OH, halogen, $C_{1-6}$alkyl, $C_{1-3}$haloalkyl, $C_{1-3}$haloalkoxy, CN, nitro, $C_{1-3}$alkoxy, $C_{3-6}$cycloalkyl, heterocyclyl, —C(O)OCH$_3$, —SCH$_3$, —C(O)OH, —C(O)N$R^{12}R^{13}$, —S(O)$_2$CH$_3$, and —C(O)CH$_3$;
$R^{10}$ is —O$C_{1-6}$alkyl, —NH$_2$, —NHCH$_2$CH$_3$, or —N(CH$_3$)$_2$;
$R^{11}$ is $C_{1-6}$alkyl, $C_{1-6}$alkoxy$C_{1-6}$alkylene, or H; or
$R^{11}$ is heterocyclyl or phenyl, wherein said heterocyclyl or phenyl is optionally substituted with one or more substituents independently selected from $C_{1-3}$alkyl, $C_{1-3}$alkoxy, halogen, CN, —SO$_2$CH$_3$, —NHC(O)CH$_3$, and $C_{1-3}$haloalkyl;
$R^{12}$ and $R^{13}$ are each independently selected from H and $C_{1-6}$alkyl;
m is 0 or 1;
p is 0 or 1;
$R^1$ and $R^2$ are not both H;
when $R^4$ is H, $R^3$ is not H;
when Y is N, m is 0; and
when X is N, p is 0.

Another aspect of the present invention provides a compound substantially as hereinbefore defined with reference to any one of the Examples.

Another aspect of the present invention provides a pharmaceutical composition comprising a compound of the present invention.

Another aspect of the present invention provides a compound of the present invention for use as an active therapeutic substance.

Another aspect of the present invention provides a compound of the present invention for use in the treatment of hypogonadism, sarcopenia, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as an anabolic agent.

Another aspect of the present invention provides the use of a compound of the present invention in the manufacture of a medicament for use in the treatment of hypogonadism, sarcopenia, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as an anabolic agent.

Another aspect of the present invention provides a method for the treatment of hypogonadism, sarcopenia, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, endometriosis, acne, hirsutism, male contraception, impotence, and a method of male and female hormone replacement therapy, stimulation of hematopoiesis, and anabolism, comprising the administration of a compound of the present invention.

DETAILED DESCRIPTION OF THE INVENTION

Terms are used within their accepted meanings. The following definitions are meant to clarify, but not limit, the terms defined.

As used herein the term "alkyl" refers to a straight or branched chain hydrocarbon, preferably having from one to six carbon atoms. Examples of "alkyl" as used herein include, but are not limited to, methyl, ethyl, propyl, isopropyl, isobutyl, n-butyl, tert-butyl, isopentyl, and n-pentyl.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds. Examples include, but are not limited to, vinyl and the like.

As used herein, the term "alkylene" refers to a straight or branched chain divalent hydrocarbon radical, preferably having from one to six carbon atoms ($C_{1-6}$ alkylene). In some embodiments, the alkylene group has from one to four carbon atoms ($C_{1-4}$ alkyene). Examples of "alkylene" as used herein include, but are not limited to, methylene (—$CH_2$—), ethylene (—$CH_2$—$CH_2$—), propylene (—$CH_2$—$CH_2$—$CH_2$), and branched versions thereof such as (—$CH(CH_3)$—), —$CH_2$—$CH(CH_3)$—, —$CH(CH_3)$—$CH_2$—, —$CH_2$—$CH(CH_3)$—$CH_2$—, —$CH_2$—$C(CH_3)_2$— and the like.

As used herein, the term "cycloalkyl" refers to a non-aromatic cyclic hydrocarbon ring. Exemplary "cycloalkyl" groups include, but are not limited to, cyclopropyl, cyclobutyl, cyclopentyl, cyclohexyl, cycloheptyl, and the like.

As used herein, the term "heterocycle" or "heterocyclyl" refers to a mono- or poly-cyclic ring system containing one or more heteroatoms and optionally containing one or more degrees of unsaturation, including monocyclic five to seven membered aromatic or non-aromatic rings, or a fused bicyclic aromatic or non-aromatic ring system comprising two of such rings. Preferred heteroatoms include N, O, and S. Preferably the ring is three to ten-membered. Such rings may be optionally fused to one or more of another "heterocycle" ring(s), "aryl" ring(s), or "cycloalkyl" ring(s). Examples of "heterocycle" groups include, but are not limited to, oxadiazole, pyridine, thiadiazole, furan, thiazole, thiophene, oxazole, imidazole, isoxazole, pyrazolopyradine, and pyrazole, and the like. Preferred heterocyclyl groups include oxadiazolyl, pyridinyl, thiadiazolyl, furanyl, thiazolyl, thiophenyl, oxazolyl, imidazolyl, isoxazolyl, pyrazolopyradinyl, and pyrazolyl.

As used herein, the term "aryl" refers to a benzene ring or to a fused benzene ring system, for example anthracene, phenanthrene, or naphthalene ring systems. Examples of "aryl" groups include, but are not limited to, phenyl, 2-naphthyl, 1-naphthyl, biphenyl, and the like. One preferred aryl group is phenyl.

As used herein the term "halogen" refers to fluorine, chlorine, bromine, or iodine.

As used herein the term "haloalkyl" refers to an alkyl group, as defined herein that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents such as —$CF_3$, —$CHF_2$, —$CH_2F$, or —$CH_2$—$CF_3$, and the like.

As used herein the term "alkoxy" refers to a group —$OR_a$, where $R_a$ is alkyl as herein defined.

As used herein the term "haloalkoxy" refers to a group —$OR_a$, where $R_a$ is haloalkyl as defined herein.

As used herein the term "alkoxyalkylene" refers to a group —$R_aR_b$, where $R_a$ is alkylene as defined herein and $R_b$ is alkoxy as defined herein.

As used herein the term "nitro" refers to a group —$NO_2$.

The dashed line in formula (I) "-----" represents the existence or absence of a double bond. For example, when X and Y are carbon and a single bond exists between them, the parent structure would be an indoline. In a related scenario, when X and Y are carbon and a double bond exists between them, the parent structure would be an indole As used herein throughout the present specification, the phrase "optionally substituted" or variations thereof denote an optional substitution, including multiple degrees of substitution, with one or more substituent groups. The phrase should not be interpreted so as to be imprecise or duplicative of substitution patterns herein described or depicted specifically. Rather, those of ordinary skill in the art will appreciate that the phrase is included to provide for obvious modifications, which are encompassed within the scope of the appended claims. Preferably, "one or more substitutents" as used herein refers to one or two substituent groups.

The present invention provides compounds of formula (I) or a salt or solvate thereof as herein before defined.

In one embodiment, $R^1$ is halogen or CN. In another embodiment, $R^1$ is CN.

In one embodiment, $R^2$ is $C_{1-6}$haloalkyl, halogen, or CN. In another embodiment, $R^2$ is $CF_3$, Cl, or CN. In a further embodiment, $R^2$ is $CF_3$.

In one embodiment, X and Y are both C.

In another embodiment, p is 1 and $R^5$ is H.

In one embodiment, m is 1 and $R^3$ is H, $C_{1-6}$alkyl, $C_{1-6}$haloalkyl or $(CH_2)_qR^x$. In another embodiment, $R^x$ is —$C_{3-6}$ cycloalkyl and q is 0. In a further embodiment, $R^3$ is $C_{1-6}$alkyl.

In one embodiment, $R^4$ is $(R^8)(R^9)$. In another embodiment, $R^8$ is $C_{1-2}$alkylene. In a further embodiment, $R^8$ is methylene.

In one embodiment, $R^9$ is $C_{1-3}$haloalkyl, —$C(O)R^{10}$, or heterocyclyl substituted with one or more substituents independently selected from $R^a$ and $R^b$.

In another embodiment, $R^9$ is $CF_3$ or —$C(O)NH_2$.

In one embodiment, $R^9$ is heterocyclyl substituted with one or more substituents independently selected from $R^a$ and $R^b$. In a further embodiment, $R^9$ is oxadiazolyl substituted with one or more substituents independently selected from $R^a$ and $R^b$. In a further embodiment, $R^a$ is heterocyclyl substituted with one or more halogens. In another embodiment, $R^b$ is phenyl substituted with one or more substituents independently selected from $C_{1-3}$haloalkyl, CN, and halogen. In another embodiment, $R^b$ is phenyl substituted with one or more substituents independently selected from $CF_3$, CN, and halogen. In a further embodiment, $R^b$ is phenyl substituted with $CF_3$.

While the embodiments and preferred groups for each variable have generally been listed above separately for each variable, compounds of this invention include those in which several of each variable in formula (I) are selected from the aspects or embodiments, and preferred, more preferred, or most preferred groups for each variable. Therefore, this invention is intended to include all combinations of all aspect, embodiments, and preferred, more preferred, and most preferred groups.

The compounds of the present invention are believed to modulate the function of one or more nuclear hormone receptor(s). Particularly, the compounds of the present invention modulate the androgen receptor ("AR"). The present invention includes compounds that are selective agonists, partial agonists, antagonists, or partial antagonists of the AR. Compounds of the present invention are useful in the treatment of AR-associated diseases and conditions, for example, a disease or condition that is prevented, alleviated, or cured through the modulation of the function or activity of AR. Such modulation may be isolated within certain tissues or widespread throughout the body of the subject being treated.

As used herein, the term "treatment" refers to alleviating the specified condition, eliminating or reducing the symptoms of the condition, slowing or eliminating the progression of the condition and preventing or delaying the initial occurrence of the condition in a subject, or reoccurrence of the condition in a previously afflicted subject.

One embodiment of the present invention provides compounds of the present invention for use in medical therapy. Particularly, the present invention provides for the treatment of disorders mediated by androgenic activity. More particularly, the present invention provides treatment of disorders responsive to tissue-selective anabolic and or androgenic activity. A further embodiment of the invention provides a method of treatment of a mammal suffering from a disorder mediated by androgenic activity, which includes administering to said subject an effective amount of a compound of the present invention.

One embodiment of the present invention is the use of the compounds of the present invention for the treatment of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, aortic smooth muscle cell proliferation, male hormone replacement, or ADAM.

A further embodiment of the invention provides a method of treatment of a mammal requiring the treatment of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), dry eye, sarcopenia, chronic fatigue syndrome, chronic myaligia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, artherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, aortic smooth muscle cell proliferation, male hormone replacement, or ADAM. Preferably the compounds of the present invention are used as male and female hormone replacement therapy or for the treatment or prevention of hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents, which use includes administering to a subject an effective amount of a compound of the present invention. The mammal requiring treatment with a compound of the present invention is typically a human being.

The compounds of the present invention may crystallize in more than one form, a characteristic known as polymorphism, and such polymorphic forms ("polymorphs") are within the scope of formula (I). Polymorphism generally may occur as a response to changes in temperature, pressure, or both. Polymorphism may also result from variations in the crystallization process. Polymorphs may be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula (I)) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. The biological or medical response may be considered a prophylactic response or a treatment response. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I) may be administered as the raw chemical. Additionally, the active ingredient may be presented as a pharmaceutical composition.

Accordingly, the invention further provides pharmaceutical compositions that include effective amounts of compounds of the present invention and one or more pharmaceutically acceptable carriers, diluents, or excipients. The compounds of the present invention are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the present invention with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. An effective amount of a compound of the present invention for the treatment of humans suffering from disorders such as frailty, generally, should be in the range of 0.01 to 100 mg/kg body weight of recipient (mammal) per day. More usually the effective amount should be in the range of 0.01 to 10 mg/kg body weight per day. Thus, for a 70 kg adult mammal the actual amount per day would usually be from 0.7 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.1 mg to 1 g of a compound of the present invention, depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component may be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents may also be present.

Capsules can be made by preparing a powder, liquid, or suspension mixture and encapsulating with gelatin or some other appropriate shell material. Glidants and lubricants such as colloidal silica, talc, magnesium stearate, calcium stearate, or solid polyethylene glycol may be added to the mixture before the encapsulation. A disintegrating or solubilizing agent such as agar-agar, calcium carbonate or sodium carbonate may also be added to improve the availability of the medicament when the capsule is ingested. Moreover, when desired or necessary, suitable binders, lubricants, disintegrating agents, and coloring agents may also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets can be formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture may be wet-granulated with a binder such as syrup, starch paste, acadia mucilage or solutions of cellulosic or polymeric materials, and forcing through a screen. As an alternative to granulating, the powder mixture may be run through the tablet machine and the result is imperfectly formed slugs broken into granules. The granules may be lubricated to prevent sticking to the tablet forming dies by means of the addition of stearic acid, a stearate salt, talc or mineral oil. The lubricated mixture is then compressed into tablets. The compounds of the present invention may also be combined with a free flowing inert carrier and compressed into tablets directly without going through the granulating or slugging steps. A clear or opaque protective coating consisting of a sealing coat of shellac, a coating of sugar or polymeric material, and a polish coating of wax may be provided. Dyestuffs may be added to these coatings to distinguish different unit dosages.

Oral fluids such as solutions, syrups, and elixirs may be prepared in dosage unit form so that a given quantity contains a predetermined amount of the compound. Syrups may be prepared, for example, by dissolving the compound in a suitably flavored aqueous solution, while elixirs are prepared through the use of a non-toxic alcoholic vehicle. Suspensions may be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like may also be added.

Where appropriate, dosage unit formulations for oral administration may be microencapsulated. The formulation may also be prepared to prolong or sustain the release as for example by coating or embedding particulate material in polymers, wax or the like.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

The compounds of the present invention may also be delivered by the use of monoclonal antibodies as individual carriers to which the compound molecules are coupled.

The compounds of the present invention may also be coupled with soluble polymers as targetable drug carriers. Such polymers may include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents for the treatment of the above-mentioned conditions. For example, in frailty therapy, combination may be had with other anabolic or osteoporosis therapeutic agents. As one example, osteoporosis combination therapies according to the present invention would thus comprise the administration of at least one compound of the present invention and the use of at least one other osteoporosis therapy. As a further example, combination therapies according to the present invention include the administration of at least one compound of the present invention and at least one other osteoporosis treatment agent, for example, an anti-bone resorption agent. The compound(s) of the present invention and the other pharmaceutically active agent(s) may be administered together or separately and, when administered separately, administration may occur simultaneously or sequentially, in any order. The amounts of the compound(s) of the present invention and the other pharmaceutically active agent(s) and the relative timings of administration will be selected in order to achieve the desired combined therapeutic effect. The administration in combination of a compound of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Another potential osteoporosis treatment agent is a bone building (anabolic) agent. Bone building agents may lead to increases in parameters such as bone mineral density that are greater than those than may be achieved with anti-resorptive agents. In some cases, such anabolic agents may increase trabecular connectivity leading to greater structural integrity of the bone.

Other potential therapeutic combinations include the compounds of the present invention combined with other compounds of the present invention, growth promoting agents, growth hormone secretagogues, growth hormone releasing factor and its analogs, growth hormone and its analogs, somatomedins, alpha-adrenergic agonists, serotonin 5-$HT_D$ agonists, agents that inhibit somatostatin or its release, 5-α-reductase inhibitors, aromatase inhibitors, GnRH agonists or antagonists, parathyroid hormone, bisphosphonates, estrogen, testosterone, SERMs, progesterone receptor agonists or antagonists, and/or with other modulators of nuclear hormone receptors.

The compounds of the present invention may be used in the treatment of a variety of disorders and conditions and, as such, the compounds of the present invention may be used in combination with a variety of other suitable therapeutic agents useful in the treatment of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the compounds of the present invention may be combined with nutritional supplements such as amino acids, triglycerides, vitamins, minerals, creatine, piloic acid, carnitine, or coenzyme Q10.

In particular, the compounds of the present invention are believed useful, either alone or in combination with other agents, in the treatment of hypogonadism, sarcopenia, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as anabolic agents.

The compounds of this invention may be made by a variety of methods, including well-known standard synthetic methods. Illustrative general synthetic methods are set out below and then specific compounds of the invention are prepared in the working Examples.

In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis or by resolution of the final product or any convenient intermediate. Resolution of the final product, an intermediate, or a starting material may be effected by any suitable method known in the art. See, for example, *Stereochemistry of Organic Com-*

*pounds* by E. L. Eliel, S. H. Wilen, and L. N. Mander (Wiley-Interscience, 1994), incorporated by reference with regard to stereochemistry.

Representative AR modulator compounds, agonists, partial agonists, and antagonists according to the current invention include:

Ethyl 1-(cyclopropylmethyl)-5-nitro-1H-indole-2-carboxylate;
2-Methyl-5-nitro-1-({5-[4-(trifluoromethyl)phenyl]-1,2,4-oxadiazol-3-yl}methyl)-1H-indole;
2-Methyl-5-nitro-1-({5-[3-(trifluoromethyl)phenyl]-1,2,4-oxadiazol-3-yl}methyl)-1H-indole;
1-({5-[3-(Trifluoromethyl)phenyl]-1,2,4-oxadiazol-3-yl}methyl)-1H-indole-5-carbonitrile;
Ethyl 5-hydroxy-1-(2,2,2-trifluoroethyl)-1H-indole-2-carboxylate;
Ethyl 4-chloro-5-cyano-1-(2,2,2-trifluoroethyl)-1H-indole-2-carboxylate;
Ethyl 4,5-dicyano-1-(2,2,2-trifluoroethyl)-1H-indole-2-carboxylate;
Ethyl 5-hydroxy-4-iodo-1-(2,2,2-trifluoroethyl)-1H-indole-2-carboxylate;
4-Chloro-5-cyano-1-(2,2,2-trifluoroethyl)-1H-indole-2-carboxamide;
4-Chloro-2-(hydroxymethyl)-1-(2,2,2-trifluoroethyl)-1H-indole-5-carbonitrile;
2-(Hydroxymethyl)-1-(2,2,2-trifluoroethyl)-1H-indole-5-carbonitrile;
4-Chloro-2-formyl-1-(2,2,2-trifluoroethyl)-1H-indole-5-carbonitrile;
4-Chloro-2-[(1Z)-1-propen-1-yl]-1-(2,2,2-trifluoroethyl)-1H-indole-5-carbonitrile;
4-Chloro-2-[(1E)-1-propen-1-yl]-1-(2,2,2-trifluoroethyl)-1H-indole-5-carbonitrile;
4-Chloro-2-propyl-1-(2,2,2-trifluoroethyl)-1H-indole-5-carbonitrile;
4-Chloro-2-ethenyl-1-(2,2,2-trifluoroethyl)-1H-indole-5-carbonitrile;
4-Chloro-2-ethyl-1-(2,2,2-trifluoroethyl)-1H-indole-5-carbonitrile;
4-Chloro-1-(2,2,2-trifluoroethyl)-1H-indole-2,5-dicarbonitrile;
2-(Fluoromethyl)-1-(2,2,2-trifluoroethyl)-1H-indole-5-carbonitrile;
4-Chloro-2-(fluoromethyl)-1-(2,2,2-trifluoroethyl)-1H-indole-5-carbonitrile;
4-Chloro-2-(difluoromethyl)-1-(2,2,2-trifluoroethyl)-1H-indole-5-carbonitrile;
4-Chloro-2-(difluoromethyl)-1H-indole-5-carbonitrile;
4-Chloro-2-(difluoromethyl)-1-{[5-(3,5-difluorophenyl)-1,2,4-oxadiazol-3-yl]methyl}-1H-indole-5-carbonitrile;
4-Chloro-2-(difluoromethyl)-1-({5-[3-(trifluoromethyl)phenyl]-1,2,4-oxadiazol-3-yl}methyl)-1H-indole-5-carbonitrile;
1-{[5-(5-Bromo-3-pyridinyl)-1,3,4-oxadiazol-2-yl]methyl}-4-chloro-2-(difluoromethyl)-1H-indole-5-carbonitrile;
4-Chloro-1-{[5-(5-cyano-3-pyridinyl)-1,3,4-oxadiazol-2-yl]methyl}-2-(difluoromethyl)-1H-indole-5-carbonitrile;
4-Chloro-1-(cyanomethyl)-2-(difluoromethyl)-1H-indole-5-carbonitrile;
Methyl [4-chloro-5-cyano-2-(difluoromethyl)-1H-indol-1-yl]acetate;
2-[4-Chloro-5-cyano-2-(difluoromethyl)-1H-indol-1-yl]acetamide;
2-[4-Chloro-5-cyano-2-(difluoromethyl)-1H-indol-1-yl]propanamide;
2-[4-Chloro-5-cyano-2-(difluoromethyl)-1H-indol-1-yl]-N,N-dimethylpropanamide;
4-Chloro-2-(difluoromethyl)-1-{[5-(2-pyridinyl)-1,2,4-oxadiazol-3-yl]methyl}-1H-indole-5-carbonitrile;
1-{[5-(5-Bromo-3-pyridinyl)-1,2,4-oxadiazol-3-yl]methyl}-4-chloro-2-(difluoromethyl)-1H-indole-5-carbonitrile;
4-Chloro-2-(difluoromethyl)-1-{[5-(2,4-difluorophenyl)-1,2,4-oxadiazol-3-yl]methyl}-1H-indole-5-carbonitrile;
4-Chloro-2-(difluoromethyl)-1-{[5-(2,4-difluorophenyl)-1,3,4-oxadiazol-2-yl]methyl}-1H-indole-5-carbonitrile;
4-Chloro-2-(difluoromethyl)-1-{[5-(3,5-difluorophenyl)-1,3,4-oxadiazol-2-yl]methyl}-1H-indole-5-carbonitrile;
4-Chloro-2-(difluoromethyl)-1-{[3-(2-pyridinyl)-1,2,4-oxadiazol-5-yl]methyl}-1H-indole-5-carbonitrile;
4-Chloro-2-(difluoromethyl)-1-{[5-(6-fluoro-2-pyridinyl)-1,3,4-oxadiazol-2-yl]methyl}-1H-indole-5-carbonitrile;
4-Chloro-2-(difluoromethyl)-1-{[5-(3,5-dimethyl-4-isoxazolyl)-1,2,4-oxadiazol-3-yl]methyl}-1H-indole-5-carbonitrile;
4-Chloro-2-(difluoromethyl)-1-(1,3-thiazol-4-ylmethyl)-1H-indole-5-carbonitrile;
1-({5-[3,5-Bis(trifluoromethyl)phenyl]-1,2,4-oxadiazol-3-yl}methyl)-4-chloro-2-(difluoromethyl)-1H-indole-5-carbonitrile;
4-Chloro-2-(difluoromethyl)-1-{[5-(trifluoromethyl)-2-furanyl]methyl}-1H-indole-5-carbonitrile;
4-Chloro-2-(difluoromethyl)-1-(2-pyridinylmethyl)-1H-indole-5-carbonitrile;
4-Chloro-1-[(5-cyclopropyl-1,3,4-thiadiazol-2-yl)methyl]-2-(difluoromethyl)-1H-indole-5-carbonitrile;
4-Chloro-2-(difluoromethyl)-1-{2-[(6-fluoro-3-pyridinyl)oxy]ethyl}-1H-indole-5-carbonitrile;
4-Chloro-2-(difluoromethyl)-1-(2-{[4-(methylsulfonyl)phenyl]oxy}ethyl)-1H-indole-5-carbonitrile;
4-Chloro-2-(difluoromethyl)-1-{2-[(2,4-difluorophenyl)oxy]ethyl}-1H-indole-5-carbonitrile;
4-Chloro-1-{2-[(4-cyano-3-fluorophenyl)oxy]ethyl}-2-(difluoromethyl)-1H-indole-5-carbonitrile;
4-Chloro-1-{2-[(5-chloro-3-pyridinyl)oxy]ethyl}-2-(difluoromethyl)-1H-indole-5-carbonitrile;
4-Chloro-1-{2-[(6-chloro-3-pyridinyl)oxy]ethyl}-2-(difluoromethyl)-1H-indole-5-carbonitrile;
4-Chloro-2-(difluoromethyl)-1-{2-[(4-fluorophenyl)oxy]ethyl}-1H-indole-5-carbonitrile;
N-[4-({2-[4-Chloro-5-cyano-2-(difluoromethyl)-1H-indol-1-yl]ethyl}oxy)phenyl]acetamide;
2-(Difluoromethyl)-1-(2,2,2-trifluoroethyl)-1H-indole-4,5-dicarbonitrile;
2-(Difluoromethyl)-1-({5-[3-(trifluoromethyl)phenyl]-1,2,4-oxadiazol-3-yl}methyl)-1H-indole-4,5-dicarbonitrile;
1-{[5-(5-Bromo-3-pyridinyl)-1,3,4-oxadiazol-2-yl]methyl}-2-(difluoromethyl)-1H-indole-4,5-dicarbonitrile;
1-({5-[3,5-bis(Trifluoromethyl)phenyl]-1,2,4-oxadiazol-3-yl}methyl)-2-(difluoromethyl)-1H-indole-4,5-dicarbonitrile;
2-(Difluoromethyl)-1-{[5-(3,5-difluorophenyl)-1,2,4-oxadiazol-3-yl]methyl}-1H-indole-4,5-dicarbonitrile;
4-Chloro-2-(difluoromethyl)-1-(2,2,2-trifluoroethyl)-2,3-dihydro-1H-indole-5-carbonitrile;
4-Chloro-2-(difluoromethyl)-1-({5-[3-(trifluoromethyl)phenyl]-1,2,4-oxadiazol-3-yl}methyl)-2,3-dihydro-1H-indole-5-carbonitrile;
4-(Trifluoromethyl)-1-({5-[3-(trifluoromethyl)phenyl]-1,2,4-oxadiazol-3-yl}methyl)-1H-indole-5-carbonitrile;
5-Chloro-4-(trifluoromethyl)-1-({5-[3-(trifluoromethyl)phenyl]-1,2,4-oxadiazol-3-yl}methyl)-1H-indole;

1-(Cyanomethyl)-4-(trifluoromethyl)-1H-indole-5-carbonitrile;
1-({5-[3,5-Bis(trifluoromethyl)phenyl]-1,2,4-oxadiazol-3-yl}methyl)-4-(trifluoromethyl)-1H-indole-5-carbonitrile;
2-[5-Cyano-4-(trifluoromethyl)-1H-indol-1-yl]-N-hydroxy-ethanimidamide;
1-({5-[2-Fluoro-5-(trifluoromethyl)phenyl]-1,2,4-oxadiazol-3-yl}methyl)-4-(trifluoromethyl)-1H-indole-5-carbonitrile;
1-({5-[3-Nitro-5-(trifluoromethyl)phenyl]-1,2,4-oxadiazol-3-yl}methyl)-4-(trifluoromethyl)-1H-indole-5-carbonitrile;
1-({5-[4-Fluoro-3-(trifluoromethyl)phenyl]-1,2,4-oxadiazol-3-yl}methyl)-4-(trifluoromethyl)-1H-indole-5-carbonitrile;
1-({5-[3-Fluoro-5-(trifluoromethyl)phenyl]-1,2,4-oxadiazol-3-yl}methyl)-4-(trifluoromethyl)-1H-indole-5-carbonitrile;
1-({5-[3-Chloro-2-fluoro-5-(trifluoromethyl)phenyl]-1,2,4-oxadiazol-3-yl}methyl)-4-(trifluoromethyl)-1H-indole-5-carbonitrile;
1-({5-[2-Chloro-5-(trifluoromethyl)phenyl]-1,2,4-oxadiazol-3-yl}methyl)-4-(trifluoromethyl)-1H-indole-5-carbonitrile;
1-({5-[4-(Methyloxy)-3-(trifluoromethyl)phenyl]-1,2,4-oxadiazol-3-yl}methyl)-4-(trifluoromethyl)-1H-indole-5-carbonitrile;
1-({5-[4-Chloro-3-(trifluoromethyl)phenyl]-1,2,4-oxadiazol-3-yl}methyl)-4-(trifluoromethyl)-1H-indole-5-carbonitrile;
1-({5-[3-Methyl-5-(trifluoromethyl)-4-isoxazolyl]-1,2,4-oxadiazol-3-yl}methyl)-4-(trifluoromethyl)-1H-indole-5-carbonitrile;
1-{[5-(3-Cyanophenyl)-1,2,4-oxadiazol-3-yl]methyl}-4-(trifluoromethyl)-1H-indole-5-carbonitrile;
1-{[5-(3-Bromo-4-methylphenyl)-1,2,4-oxadiazol-3-yl]methyl}-4-(trifluoromethyl)-1H-indole-5-carbonitrile;
1-{[5-(4-Acetylphenyl)-1,2,4-oxadiazol-3-yl]methyl}-4-(trifluoromethyl)-1H-indole-5-carbonitrile;
1-({5-[2-Chloro-3-(trifluoromethyl)phenyl]-1,2,4-oxadiazol-3-yl}methyl)-4-(trifluoromethyl)-1H-indole-5-carbonitrile;
1-{[5-(3-Bromo-4-fluorophenyl)-1,2,4-oxadiazol-3-yl]methyl}-4-(trifluoromethyl)-1H-indole-5-carbonitrile;
1-({5-[2-Fluoro-3-(trifluoromethyl)phenyl]-1,2,4-oxadiazol-3-yl}methyl)-4-(trifluoromethyl)-1H-indole-5-carbonitrile;
1-{[5-(4-Cyanophenyl)-1,2,4-oxadiazol-3-yl]methyl}-4-(trifluoromethyl)-1H-indole-5-carbonitrile;
1-{[5-(3-Bromo-4-chlorophenyl)-1,2,4-oxadiazol-3-yl]methyl}-4-(trifluoromethyl)-1H-indole-5-carbonitrile;
1-{[5-(3,4-Dichlorophenyl)-1,2,4-oxadiazol-3-yl]methyl}-4-(trifluoromethyl)-1H-indole-5-carbonitrile;
4-(Trifluoromethyl)-1-[(5-{4-[(trifluoromethyl)oxy]phenyl}-1,2,4-oxadiazol-3-yl)methyl]-1H-indole-5-carbonitrile;
1-{[5-(3-Chlorophenyl)-1,2,4-oxadiazol-3-yl]methyl}-4-(trifluoromethyl)-1H-indole-5-carbonitrile;
4-(Trifluoromethyl)-1-[(5-{3-[(trifluoromethyl)oxy]phenyl}-1,2,4-oxadiazol-3-yl)methyl]-1H-indole-5-carbonitrile;
1-{[5-(3,4-Difluorophenyl)-1,2,4-oxadiazol-3-yl]methyl}-4-(trifluoromethyl)-1H-indole-5-carbonitrile;
1-{[5-(3-Hydroxy-4-methylphenyl)-1,2,4-oxadiazol-3-yl]methyl}-4-(trifluoromethyl)-1H-indole-5-carbonitrile;
1-{[5-(3-Bromophenyl)-1,2,4-oxadiazol-3-yl]methyl}-4-(trifluoromethyl)-1H-indole-5-carbonitrile;
1-{[5-(4-Chlorophenyl)-1,2,4-oxadiazol-3-yl]methyl}-4-(trifluoromethyl)-1H-indole-5-carbonitrile;
4-(Trifluoromethyl)-1-({5-[3-(trifluoromethyl)phenyl]-1,2,4-oxadiazol-3-yl}methyl)-1H-indole-5-carbonitrile;
1-(1,3-Thiazol-4-ylmethyl)-4-(trifluoromethyl)-1H-indole-5-carbonitrile;
1-{[5-(2-Thienyl)-1,2,4-oxadiazol-3-yl]methyl}-4-(trifluoromethyl)-1H-indole-5-carbonitrile;
1-({5-[4-(Methyloxy)phenyl]-1,2,4-oxadiazol-3-yl}methyl)-4-(trifluoromethyl)-1H-indole-5-carbonitrile;
1-(2,2,2-Trifluoroethyl)-4-(trifluoromethyl)-1H-indole-5-carbonitrile;
1-({5-[2-(Methylthio)-3-pyridinyl]-1,2,4-oxadiazol-3-yl}methyl)-4-(trifluoromethyl)-1H-indole-5-carbonitrile;
1-[(5-Phenyl-1,2,4-oxadiazol-3-yl)methyl]-4-(trifluoromethyl)-1H-indole-5-carbonitrile;
4-(Trifluoromethyl)-1-{[5-(trifluoromethyl)-2-furanyl]methyl}-1H-indole-5-carbonitrile;
1-{[5-(3,5-Dimethyl-4-isoxazolyl)-1,2,4-oxadiazol-3-yl]methyl}-4-(trifluoromethyl)-1H-indole-5-carbonitrile;
1-({5-[2-(Methyloxy)phenyl]-1,2,4-oxadiazol-3-yl}methyl)-4-(trifluoromethyl)-1H-indole-5-carbonitrile;
4-(Trifluoromethyl)-1-({5-[4-(trifluoromethyl)phenyl]-1,2,4-oxadiazol-3-yl}methyl)-1H-indole-5-carbonitrile;
1,1-Dimethylethyl [5-cyano-4-(trifluoromethyl)-1H-indol-1-yl]acetate;
1-{[3-(2-Pyridinyl)-1,2,4-oxadiazol-5-yl]methyl}-4-(trifluoromethyl)-1H-indole-5-carbonitrile;
1-({3-[3,5-bis(Trifluoromethyl)phenyl]-1,2,4-oxadiazol-5-yl}methyl)-4-(trifluoromethyl)-1H-indole-5-carbonitrile;
1-{[5-(2,4-Difluorophenyl)-1,3,4-oxadiazol-2-yl]methyl}-4-(trifluoromethyl)-1H-indole-5-carbonitrile;
1-{[5-(2-Pyridinyl)-1,3,4-oxadiazol-2-yl]methyl}-4-(trifluoromethyl)-1H-indole-5-carbonitrile;
1-{[5-(5-Bromo-3-pyridinyl)-1,3,4-oxadiazol-2-yl]methyl}-4-(trifluoromethyl)-1H-indole-5-carbonitrile;
1-{[5-(5-Bromo-2-furanyl)-1,3,4-oxadiazol-2-yl]methyl}-4-(trifluoromethyl)-1H-indole-5-carbonitrile;
1-{[5-(4-Methyl-1,2,3-thiadiazol-5-yl)-1,3,4-oxadiazol-2-yl]methyl}-4-(trifluoromethyl)-1H-indole-5-carbonitrile;
1-{[5-(2,5-Difluorophenyl)-1,3,4-oxadiazol-2-yl]methyl}-4-(trifluoromethyl)-1H-indole-5-carbonitrile;
1-{[5-(3,5-Difluorophenyl)-1,3,4-oxadiazol-2-yl]methyl}-4-(trifluoromethyl)-1H-indole-5-carbonitrile;
3-Bromo-4-(trifluoromethyl)-1-({5-[3-(trifluoromethyl)phenyl]-1,2,4-oxadiazol-3-yl}methyl)-1H-indole-5-carbonitrile;
3-Chloro-4-(trifluoromethyl)-1-({5-[3-(trifluoromethyl)phenyl]-1,2,4-oxadiazol-3-yl}methyl)-1H-indole-5-carbonitrile;
4-(Trifluoromethyl)-1-({5-[3-(trifluoromethyl)phenyl]-1,2,4-oxadiazol-3-yl}methyl)-2,3-dihydro-1H-indole-5-carbonitrile;
2-Methyl-4-(trifluoromethyl)-1H-indole;
1-(Cyclopropylmethyl)-2-methyl-4-(trifluoromethyl)-1H-indole;
2-Methyl-4-(trifluoromethyl)-1-({5-[3-(trifluoromethyl)phenyl]-1,2,4-oxadiazol-3-yl}methyl)-1H-indole;
5-Bromo-2-methyl-4-(trifluoromethyl)-1H-indole;
5-Bromo-1-(cyclopropylmethyl)-2-methyl-4-(trifluoromethyl)-1H-indole;
5-Bromo-2-methyl-4-(trifluoromethyl)-1-({5-[3-(trifluoromethyl)phenyl]-1,2,4-oxadiazol-3-yl}methyl)-1H-indole;
2-Methyl-4-(trifluoromethyl)-1H-indole-5-carbonitrile;
1-(Cyclopropylmethyl)-2-methyl-4-(trifluoromethyl)-1H-indole-5-carbonitrile;

2-[5-Cyano-2-methyl-4-(trifluoromethyl)-1H-indol-1-yl]acetamide;
1-(2,2-Dimethylpropyl)-2-methyl-4-(trifluoromethyl)-1H-indole-5-carbonitrile;
2-Methyl-4-(trifluoromethyl)-1-({5-[3-(trifluoromethyl)phenyl]-1,2,4-oxadiazol-3-yl}methyl)-1H-indole-5-carbonitrile;
2-Methyl-1-(1,3-thiazol-4-ylmethyl)-4-(trifluoromethyl)-1H-indole-5-carbonitrile;
1-[(3-Cyanophenyl)methyl]-2-methyl-4-(trifluoromethyl)-1H-indole-5-carbonitrile;
1-({5-[3,5-Bis(trifluoromethyl)phenyl]-1,2,4-oxadiazol-3-yl}methyl)-2-methyl-4-(trifluoromethyl)-1H-indole-5-carbonitrile;
1-{[5-(3,5-Dimethyl-4-isoxazolyl)-1,2,4-oxadiazol-3-yl]methyl}-2-methyl-4-(trifluoromethyl)-1H-indole-5-carbonitrile;
2-Methyl-4-(trifluoromethyl)-1-{[5-(trifluoromethyl)-2-furanyl]methyl}-1H-indole-5-carbonitrile;
2-Methyl-4-(trifluoromethyl)-1-({3-[3-(trifluoromethyl)phenyl]-1,2,4-oxadiazol-5-yl}methyl)-1H-indole-5-carbonitrile;
1-({3-[3,5-Bis(trifluoromethyl)phenyl]-1,2,4-oxadiazol-5-yl}methyl)-2-methyl-4-(trifluoromethyl)-1H-indole-5-carbonitrile;
2-Methyl-4-(trifluoromethyl)-1-({5-[6-(trifluoromethyl)-3-pyridinyl]-1,3,4-oxadiazol-2-yl}methyl)-1H-indole-5-carbonitrile;
1-{[5-(5-Bromo-3-pyridinyl)-1,3,4-oxadiazol-2-yl]methyl}-2-methyl-4-(trifluoromethyl)-1H-indole-5-carbonitrile;
2-[5-Cyano-2-methyl-4-(trifluoromethyl)-1H-indol-1-yl]-N-ethylacetamide;
2-Methyl-1-{[5-(3-pyridinyl)-1,3,4-oxadiazol-2-yl]methyl}-4-(trifluoromethyl)-1H-indole-5-carbonitrile;
N-[4-({2-[5-Cyano-2-methyl-4-(trifluoromethyl)-1H-indol-1-yl]ethyl}oxy)phenyl]acetamide;
1-{2-[(6-Fluoro-3-pyridinyl)oxy]ethyl}-2-methyl-4-(trifluoromethyl)-1H-indole-5-carbonitrile;
1-{[5-(4-Fluorophenyl)-1,3,4-oxadiazol-2-yl]methyl}-2-methyl-4-(trifluoromethyl)-1H-indole-5-carbonitrile;
2-Methyl-4-(trifluoromethyl)-1-(2-{[5-(trifluoromethyl)-2-pyridinyl]oxy}ethyl)-1H-indole-5-carbonitrile;
3-Fluoro-2-methyl-4-(trifluoromethyl)-1-({5-[3-(trifluoromethyl)phenyl]-1,2,4-oxadiazol-3-yl}methyl)-1H-indole-5-carbonitrile;
1-{[5-(3,5-Difluorophenyl)-1,2,4-oxadiazol-3-yl]methyl}-3-fluoro-2-methyl-4-(trifluoromethyl)-1H-indole-5-carbonitrile;
2-Methyl-4-(trifluoromethyl)-1-(1-{5-[3-(trifluoromethyl)phenyl]-1,2,4-oxadiazol-3-yl}ethyl)-1H-indole-5-carbonitrile;
1-{1-[3-(4-Fluorophenyl)-1,2,4-oxadiazol-5-yl]ethyl}-2-methyl-4-(trifluoromethyl)-1H-indole-5-carbonitrile;
1-{1-[3-(4-Fluorophenyl)-1,2,4-oxadiazol-5-yl]-1-methylethyl}-2-methyl-4-(trifluoromethyl)-1H-indole-5-carbonitrile;
2-[5-Cyano-2-ethyl-4-(trifluoromethyl)-1H-indol-1-yl]acetamide;
1-{[5-(5-Bromo-3-pyridinyl)-1,3,4-oxadiazol-2-yl]methyl}-2-ethyl-4-(trifluoromethyl)-1H-indole-5-carbonitrile;
2-Ethyl-4-(trifluoromethyl)-1-({5-[3-(trifluoromethyl)phenyl]-1,2,4-oxadiazol-3-yl}methyl)-1H-indole-5-carbonitrile;
2-Ethyl-1-(1-ethylpropyl)-4-(trifluoromethyl)-1H-indole-5-carbonitrile;
1-(Cyclopropylmethyl)-2-ethyl-4-(trifluoromethyl)-1H-indole-5-carbonitrile;
2-Ethyl-1-(2-propen-1-yl)-4-(trifluoromethyl)-1H-indole-5-carbonitrile;
1-({5-[3,5-Bis(trifluoromethyl)phenyl]-1,2,4-oxadiazol-3-yl}methyl)-2-ethyl-4-(trifluoromethyl)-1H-indole-5-carbonitrile;
1-{[5-(3,5-Difluorophenyl)-1,2,4-oxadiazol-3-yl]methyl}-2-ethyl-4-(trifluoromethyl)-1H-indole-5-carbonitrile;
1-(Cyclopropylmethyl)-2-propyl-4-(trifluoromethyl)-1H-indole-5-carbonitrile;
2-Propyl-4-(trifluoromethyl)-1-({5-[3-(trifluoromethyl)phenyl]-1,2,4-oxadiazole-3-yl}methyl)-1H-indole-5-carbonitrile;
1-({5-[3,5-Bis(trifluoromethyl)phenyl]-1,2,4-oxadiazol-3-yl}methyl)-2-propyl-4-(trifluoromethyl)-1H-indole-5-carbonitrile;
1-{[5-(3,5-Difluorophenyl)-1,2,4-oxadiazol-3-yl]methyl}-2-propyl-4-(trifluoromethyl)-1H-indole-5-carbonitrile;
1-{[5-(5-Bromo-3-pyridinyl)-1,3,4-oxadiazol-2-yl]methyl}-2-propyl-4-(trifluoromethyl)-1H-indole-5-carbonitrile;
2-[5-Cyano-2-propyl-4-(trifluoromethyl)-1H-indol-1-yl]acetamide;
2-Butyl-1-(cyclopropylmethyl)-4-(trifluoromethyl)-1H-indole-5-carbonitrile;
2-Butyl-4-(trifluoromethyl)-1-({5-[3-(trifluoromethyl)phenyl]-1,2,4-oxadiazol-3-yl}methyl)-1H-indole-5-carbonitrile;
1-({5-[3,5-Bis(trifluoromethyl)phenyl]-1,2,4-oxadiazol-3-yl}methyl)-2-butyl-4-(trifluoromethyl)-1H-indole-5-carbonitrile;
2-Butyl-1-{[5-(3,5-difluorophenyl)-1,2,4-oxadiazol-3-yl]methyl}-4-(trifluoromethyl)-1H-indole-5-carbonitrile;
1-{[5-(5-Bromo-3-pyridinyl)-1,3,4-oxadiazol-2-yl]methyl}-2-butyl-4-(trifluoromethyl)-1H-indole-5-carbonitrile;
2-[2-Butyl-5-cyano-4-(trifluoromethyl)-1H-indol-1-yl]acetamide;
2-Cyclopropyl-1-(cyclopropylmethyl)-4-(trifluoromethyl)-1H-indole-5-carbonitrile;
1-({5-[3,5-Bis(trifluoromethyl)phenyl]-1,2,4-oxadiazol-3-yl}methyl)-2-cyclopropyl-4-(trifluoromethyl)-1H-indole-5-carbonitrile;
2-Cyclopropyl-4-(trifluoromethyl)-1-({5-[3-(trifluoromethyl)phenyl]-1,2,4-oxadiazol-3-yl}methyl)-1H-indole-5-carbonitrile;
1-{[5-(5-Bromo-3-pyridinyl)-1,3,4-oxadiazol-2-yl]methyl}-2-cyclopropyl-4-(trifluoromethyl)-1H-indole-5-carbonitrile;
2-Cyclopropyl-1-{[5-(3,5-difluorophenyl)-1,2,4-oxadiazol-3-yl]methyl}-4-(trifluoromethyl)-1H-indole-5-carbonitrile;
2-[5-Cyano-2-cyclopropyl-4-(trifluoromethyl)-1H-indol-1-yl]acetamide;
1-(Cyclopropylmethyl)-2-(2-methylpropyl)-4-(trifluoromethyl)-1H-indole-5-carbonitrile;
1-({5-[3,5-Bis(trifluoromethyl)phenyl]-1,2,4-oxadiazol-3-yl}methyl)-2-(2-methylpropyl)-4-(trifluoromethyl)-1H-indole-5-carbonitrile;
2-(2-Methylpropyl)-4-(trifluoromethyl)-1-({5-[3-(trifluoromethyl)phenyl]-1,2,4-oxadiazol-3-yl}methyl)-1H-indole-5-carbonitrile;
1-{[5-(3,5-Difluorophenyl)-1,2,4-oxadiazol-3-yl]methyl}-2-(2-methylpropyl)-4-(trifluoromethyl)-1H-indole-5-carbonitrile;
1-{[5-(5-Bromo-3-pyridinyl)-1,3,4-oxadiazol-2-yl]methyl}-2-(2-methylpropyl)-4-(trifluoromethyl)-1H-indole-5-carbonitrile;
2-[5-Cyano-2-(2-methylpropyl)-4-(trifluoromethyl)-1H-indol-1-yl]acetamide;

5-Bromo-1-(cyclopropylmethyl)-2-methyl-4-(trifluoromethyl)-2,3-dihydro-1H-indole;
5-Bromo-2-methyl-4-(trifluoromethyl)-1-({5-[3-(trifluoromethyl)phenyl]-1,2,4-oxadiazol-3-yl}methyl)-2,3-dihydro-1H-indole;
1-(Cyclopropylmethyl)-2-methyl-4-(trifluoromethyl)-2,3-dihydro-1H-indole-5-carbonitrile;
2-[5-Cyano-2-methyl-4-(trifluoromethyl)-2,3-dihydro-1H-indol-1-yl]acetamide;
2-Methyl-1-(1,3-thiazol-4-ylmethyl)-4-(trifluoromethyl)-2,3-dihydro-1H-indole-5-carbonitrile;
1-[(3-Cyanophenyl)methyl]-2-methyl-4-(trifluoromethyl)-2,3-dihydro-1H-indole-5-carbonitrile;
1-({5-[3,5-Bis(trifluoromethyl)phenyl]-1,2,4-oxadiazol-3-yl}methyl)-2-methyl-4-(trifluoromethyl)-2,3-dihydro-1H-indole-5-carbonitrile;
2-Methyl-4-(trifluoromethyl)-1-({5-[3-(trifluoromethyl)phenyl]-1,2,4-oxadiazol-3-yl}methyl)-2,3-dihydro-1H-indole-5-carbonitrile;
1-{[5-(3,5-Dimethyl-4-isoxazolyl)-1,2,4-oxadiazol-3-yl]methyl}-2-methyl-4-(trifluoromethyl)-2,3-dihydro-1H-indole-5-carbonitrile;
2-Methyl-4-(trifluoromethyl)-1-{[5-(trifluoromethyl)-2-furanyl]methyl}-2,3-dihydro-1H-indole-5-carbonitrile;
2-Methyl-4-(trifluoromethyl)-1-({3-[3-(trifluoromethyl)phenyl]-1,2,4-oxadiazol-5-yl}methyl)-2,3-dihydro-1H-indole-5-carbonitrile;
1-({3-[3,5-Bis(trifluoromethyl)phenyl]-1,2,4-oxadiazol-5-yl}methyl)-2-methyl-4-(trifluoromethyl)-2,3-dihydro-1H-indole-5-carbonitrile;
N-[4-({2-[5-Cyano-2-methyl-4-(trifluoromethyl)-2,3-dihydro-1H-indol-1-yl]ethyl}oxy)phenyl]acetamide;
2-Methyl-4-(trifluoromethyl)-1-(2-{[5-(trifluoromethyl)-2-pyridinyl]oxy}ethyl)-2,3-dihydro-1H-indole-5-carbonitrile;
2-[5-Cyano-2,4-bis(trifluoromethyl)-1H-indol-1-yl]acetamide;
2,4-Bis(trifluoromethyl)-1-({5-[3-(trifluoromethyl)phenyl]-1,2,4-oxadiazol-3-yl}methyl)-1H-indole-5-carbonitrile;
1-{[5-(5-Bromo-3-pyridinyl)-1,3,4-oxadiazol-2-yl]methyl}-2,4-bis(trifluoromethyl)-1H-indole-5-carbonitrile;
1-{[5-(3,5-Difluorophenyl)-1,2,4-oxadiazol-3-yl]methyl}-2,4-bis(trifluoromethyl)-1H-indole-5-carbonitrile;
4-Chloro-2-ethyl-1-(2,2,2-trifluoroethyl)-1H-benzimidazole-5-carbonitrile;
5-Bromo-4-chloro-2-ethyl-1-({5-[3-(trifluoromethyl)phenyl]-1,2,4-oxadiazol-3-yl}methyl)-1H-benzimidazole;
4-Chloro-2-ethyl-1-({5-[3-(trifluoromethyl)phenyl]-1,2,4-oxadiazol-3-yl}methyl)-1H-benzimidazole-5-carbonitrile;
4-Chloro-1-{[5-(3,5-dimethyl-4-isoxazolyl)-1,2,4-oxadiazol-3-yl]methyl}-2-ethyl-1H-benzimidazole-5-carbonitrile;
1-({5-[3,5-Bis(trifluoromethyl)phenyl]-1,2,4-oxadiazol-3-yl}methyl)-4-chloro-2-ethyl-1H-benzimidazole-5-carbonitrile;
4-Chloro-2-ethyl-1-{[5-(2-pyridinyl)-1,3,4-oxadiazol-2-yl]methyl}-1H-benzimidazole-5-carbonitrile;
4-Chloro-2-ethyl-1-({5-[6-(trifluoromethyl)-3-pyridinyl]-1,3,4-oxadiazol-2-yl}methyl)-1H-benzimidazole-5-carbonitrile;
4-Chloro-2-ethyl-1-{[5-(trifluoromethyl)-2-furanyl]methyl}-1H-benzimidazole-5-carbonitrile;
4-Chloro-1-(1,3-thiazol-4-ylmethyl)-2-(trifluoromethyl)-1H-benzimidazole-5-carbonitrile;
4-Chloro-1-{[5-(2-pyridinyl)-1,3,4-oxadiazol-2-yl]methyl}-2-(trifluoromethyl)-1H-benzimidazole-5-carbonitrile;
4-Chloro-1-(2,2,2-trifluoroethyl)-2-(trifluoromethyl)-1H-benzimidazole-5-carbonitrile;
4-Chloro-2-ethyl-5-(methyloxy)-1-({5-[3-(trifluoromethyl)phenyl]-1,2,4-oxadiazol-3-yl}methyl)-1H-benzimidazole;
4-Chloro-2-ethyl-1-({5-[3-(trifluoromethyl)phenyl]-1,2,4-oxadiazol-3-yl}methyl)-1H-benzimidazol-5-ol;
1-(Cyclopropylmethyl)-5-nitro-1H-indazole;
5-Nitro-1-({5-[3-(trifluoromethyl)phenyl]-1,2,4-oxadiazol-3-yl}methyl)-1H-indazole;
4-(Trifluoromethyl)-1-({5-[3-(trifluoromethyl)phenyl]-1,2,4-oxadiazol-3-yl}methyl)-1H-indazole-5-carbonitrile;
1-({5-[3-(Trifluoromethyl)phenyl]-1,2,4-oxadiazol-3-yl}methyl)-1H-indazole-4,5-dicarbonitrile; and salts and solvates thereof.

Additional AR modulator compounds, agonists, partial agonists, and antagonists according to the current invention include:

4-Chloro-2-propyl-1-({5-[3-(trifluoromethyl)phenyl]-1,2,4-oxadiazol-3-yl}methyl)-1H-indole-5-carbonitrile;
4-Chloro-1-{[5-(3,5-difluorophenyl)-1,2,4-oxadiazol-3-yl]methyl}-2-propyl-1H-indole-5-carbonitrile;
1-{[5-(5-Bromo-3-pyridinyl)-1,3,4-oxadiazol-2-yl]methyl}-4-chloro-2-propyl-1H-indole-5-carbonitrile;
4-Chloro-2-methyl-1-({5-[3-(trifluoromethyl)phenyl]-1,2,4-oxadiazol-3-yl}methyl)-1H-indole-5-carbonitrile;
4-Chloro-1-{[5-(3,5-difluorophenyl)-1,2,4-oxadiazol-3-yl]methyl}-2-methyl-1H-indole-5-carbonitrile;
1-{[5-(5-Bromo-3-pyridinyl)-1,3,4-oxadiazol-2-yl]methyl}-4-chloro-2-methyl-1H-indole-5-carbonitrile;
1-({5-[3,5-bis(Trifluoromethyl)phenyl]-1,2,4-oxadiazol-3-yl}methyl)-4-chloro-2-propyl-1H-indole-5-carbonitrile;
N-(4-{[2-(4-Chloro-5-cyano-2-propyl-1H-indol-1-yl)ethyl]oxy}phenyl)acetamide;
4-Chloro-1-{[5-(3,5-dimethyl-4-isoxazolyl)-1,2,4-oxadiazol-3-yl]methyl}-2-propyl-1H-indole-5-carbonitrile;
4-Chloro-1-{2-[(4-fluorophenyl)oxy]ethyl}-2-propyl-1H-indole-5-carbonitrile;
4-Chloro-1-{2-[(2,4-difluorophenyl)oxy]ethyl}-2-propyl-1H-indole-5-carbonitrile;
1-({5-[3,5-bis(Trifluoromethyl)phenyl]-1,2,4-oxadiazol-3-yl}methyl)-4-chloro-2-methyl-1H-indole-5-carbonitrile;
4-Chloro-1-{[5-(3,5-dimethyl-4-isoxazolyl)-1,2,4-oxadiazol-3-yl]methyl}-2-methyl-1H-indole-5-carbonitrile;
4-Chloro-1-{2-[(2,4-difluorophenyl)oxy]ethyl}-2-methyl-1H-indole-5-carbonitrile;
4-Chloro-1-{2-[(4-fluorophenyl)oxy]ethyl}-2-methyl-1H-indole-5-carbonitrile;
N-(4-{[2-(4-Chloro-5-cyano-2-methyl-1H-indol-1-yl)ethyl]oxy}phenyl)acetamide;
1-({5-[3,5-bis(Trifluoromethyl)phenyl]-1,2,4-oxadiazol-3-yl}methyl)-4-chloro-2-(trifluoromethyl)-1H-indole-5-carbonitrile;
4-Chloro-1-{[5-(3,5-dimethyl-4-isoxazolyl)-1,2,4-oxadiazol-3-yl]methyl}-2-(trifluoromethyl)-1H-indole-5-carbonitrile;
1-({5-[3,5-bis(Trifluoromethyl)phenyl]-1,2,4-oxadiazol-3-yl}methyl)-2-propyl-1H-indole-4,5-dicarbonitrile;
1-{[5-(3,5-Difluorophenyl)-1,2,4-oxadiazol-3-yl]methyl}-2-propyl-1H-indole-4,5-dicarbonitrile;
2-Propyl-1-({5-[3-(trifluoromethyl)phenyl]-1,2,4-oxadiazol-3-yl}methyl)-1H-indole-4,5-dicarbonitrile;
1-{[5-(5-Bromo-3-pyridinyl)-1,3,4-oxadiazol-2-yl]methyl}-2-propyl-1H-indole-4,5-dicarbonitrile;
4-Chloro-1-({5-[3-(trifluoromethyl)phenyl]-1,2,4-oxadiazol-3-yl}methyl)-2-(3,3,3-trifluoropropyl)-1H-indole-5-carbonitrile;

4-Chloro-1-{[5-(2,6-dichloro-4-pyridinyl)-1,2,4-oxadiazol-3-yl]methyl}-2-propyl-1H-indole-5-carbonitrile;

4-Chloro-1-({5-[3-methyl-5-(trifluoromethyl)-4-isoxazolyl]-1,2,4-oxadiazol-3-yl}methyl)-2-propyl-1H-indole-5-carbonitrile;

4-Chloro-1-{[5-(1,3-dimethyl-1H-pyrazol-5-yl)-1,2,4-oxadiazol-3-yl]methyl}-2-propyl-1H-indole-5-carbonitrile;

4-Chloro-1-({5-[5-chloro-1-methyl-3-(trifluoromethyl)-1H-pyrazol-4-yl]-1,2,4-oxadiazol-3-yl}methyl)-2-propyl-1H-indole-5-carbonitrile;

4-Chloro-1-({5-[1-methyl-5-(trifluoromethyl)-1H-pyrazol-4-yl]-1,2,4-oxadiazol-3-yl}methyl)-2-propyl-1H-indole-5-carbonitrile;

4-Chloro-1-({5-[1-methyl-3-(trifluoromethyl)-1H-pyrazol-4-yl]-1,2,4-oxadiazol-3-yl}methyl)-2-propyl-1H-indole-5-carbonitrile;

1-({5-[4-Chloro-3-(trifluoromethyl)phenyl]-1,2,4-oxadiazol-3-yl}methyl)-4-(trifluoromethyl)-1H-indole-5-carbonitrile;

4-Trifluoromethyl)-1-{[5-(3,4,5-trifluorophenyl)-1,2,4-oxadiazol-3-yl]methyl}-1H-indole-5-carbonitrile;

4-(Trifluoromethyl)-1-{[5-(2,4,6-trifluorophenyl)-1,2,4-oxadiazol-3-yl]methyl}-1H-indole-5-carbonitrile;

1-{[5-(4-Chloro-3-fluorophenyl)-1,2,4-oxadiazol-3-yl]methyl}-4-(trifluoromethyl)-1H-indole-5-carbonitrile;

1-[(5-{3-Chloro-4-[(trifluoromethyl)oxy]phenyl}-1,2,4-oxadiazol-3-yl)methyl]-4-(trifluoromethyl)-1H-indole-5-carbonitrile;

1-{[5-(3-Chloro-2-fluorophenyl)-1,2,4-oxadiazol-3-yl]methyl}-4-(trifluoromethyl)-1H-indole-5-carbonitrile;

1-{[5-(3,5-Dichlorophenyl)-1,2,4-oxadiazol-3-yl]methyl}-4-(trifluoromethyl)-1H-indole-5-carbonitrile;

1-{[5-(2,3-Dichlorophenyl)-1,2,4-oxadiazol-3-yl]methyl}-4-(trifluoromethyl)-1H-indole-5-carbonitrile;

1-{[5-(3-Chloro-2,4-difluorophenyl)-1,2,4-oxadiazol-3-yl]methyl}-4-(trifluoromethyl)-1H-indole-5-carbonitrile;

1-{[5-(2,5-Dichlorophenyl)-1,2,4-oxadiazol-3-yl]methyl}-4-(trifluoromethyl)-1H-indole-5-carbonitrile;

1-{[5-(5-Chloro-2-fluorophenyl)-1,2,4-oxadiazol-3-yl]methyl}-4-(trifluoromethyl)-1H-indole-5-carbonitrile;

1-{[5-(3-Chloro-4,5-difluorophenyl)-1,2,4-oxadiazol-3-yl]methyl}-4-(trifluoromethyl)-1H-indole-5-carbonitrile;

1-{[5-(3-Chloro-2,6-difluorophenyl)-1,2,4-oxadiazol-3-yl]methyl}-4-(trifluoromethyl)-1H-indole-5-carbonitrile;

1-({5-[3-Chloro-2,5-difluoro-4-(1H-imidazol-1-yl)phenyl]-1,2,4-oxadiazol-3-yl}methyl)-4-(trifluoromethyl)-1H-indole-5-carbonitrile;

1-({5-[2-(1H-Imidazol-1-yl)-5-(trifluoromethyl)phenyl]-1,2,4-oxadiazol-3-yl}methyl)-4-(trifluoromethyl)-1H-indole-5-carbonitrile;

1-{1-[3-(4-Fluorophenyl)-1,2,4-oxadiazol-5-yl]ethyl}-4-(trifluoromethyl)-1H-indole-5-carbonitrile;

1-{[5-(4-Fluorophenyl)-3-isoxazolyl]methyl}-2-propyl-4-(trifluoromethyl)-1H-indole-5-carbonitrile;

1-[(3-Phenyl-5-isoxazolyl)methyl]-2-propyl-4-(trifluoromethyl)-1H-indole-5-carbonitrile;

1-[(3-Phenyl-5-isoxazolyl)methyl]-4-(trifluoromethyl)-1H-indole-5-carbonitrile;

1-{[5-(4-Fluorophenyl)-3-isoxazolyl]methyl}-2-methyl-4-(trifluoromethyl)-1H-indole-5-carbonitrile;

2-Methyl-1-[(3-phenyl-5-isoxazolyl)methyl]-4-(trifluoromethyl)-1H-indole-5-carbonitrile;

2-Methyl-4-(trifluoromethyl)-1-({5-[6-(trifluoromethyl)-2-pyridinyl]-1,2,4-oxadiazol-3-yl}methyl)-1H-indole-5-carbonitrile;

2-Methyl-4-(trifluoromethyl)-1-({5-[5-(trifluoromethyl)-3-pyridinyl]-1,2,4-oxadiazol-3-yl}methyl)-1H-indole-5-carbonitrile;

2-Methyl-4-(trifluoromethyl)-1-({5-[4-(trifluoromethyl)-2-pyridinyl]-1,2,4-oxadiazol-3-yl}methyl)-1H-indole-5-carbonitrile;

2-Methyl-4-(trifluoromethyl)-1-({5-[2-(trifluoromethyl)-4-pyridinyl]-1,2,4-oxadiazol-3-yl}methyl)-1H-indole-5-carbonitrile;

1-[(5-Cyclopropyl-1,3,4-thiadiazol-2-yl)methyl]-2-propyl-4-(trifluoromethyl)-1H-indole-5-carbonitrile;

2-Propyl-4-(trifluoromethyl)-1-{[5-(trifluoromethyl)-2-furanyl]methyl}-1H-indole-5-carbonitrile;

1-({5-[4-(1,1-Dimethylethyl)phenyl]-1,2,4-oxadiazol-3-yl}methyl)-2-propyl-4-(trifluoromethyl)-1H-indole-5-carbonitrile;

1-({5-[2-(Methylthio)-3-pyridinyl]-1,2,4-oxadiazol-3-yl}methyl)-2-propyl-4-(trifluoromethyl)-1H-indole-5-carbonitrile;

2-Propyl-1-(1,3-thiazol-4-ylmethyl)-4-(trifluoromethyl)-1H-indole-5-carbonitrile;

5-{[5-Cyano-2-propyl-4-(trifluoromethyl)-1H-indol-1-yl]methyl}-2-furancarboxamide;

1-[(5-Cyano-2-furanyl)methyl]-2-propyl-4-(trifluoromethyl)-1H-indole-5-carbonitrile;

1-(Cyanomethyl)-2-propyl-4-(trifluoromethyl)-1H-indole-5-carbonitrile;

2-Propyl-1-{[5-(2-thienyl)-1,2,4-oxadiazol-3-yl]methyl}-4-(trifluoromethyl)-1H-indole-5-carbonitrile;

1-{[5-(2,5-Difluorophenyl)-1,2,4-oxadiazol-3-yl]methyl}-2-propyl-4-(trifluoromethyl)-1H-indole-5-carbonitrile;

1-{[5-(3,4-Difluorophenyl)-1,2,4-oxadiazol-3-yl]methyl}-2-propyl-4-(trifluoromethyl)-1H-indole-5-carbonitrile;

2-Propyl-4-(trifluoromethyl)-1-({5-[4-(trifluoromethyl)phenyl]-1,2,4-oxadiazol-3-yl}methyl)-1H-indole-5-carbonitrile;

1-{[5-(3-Cyanophenyl)-1,2,4-oxadiazol-3-yl]methyl}-2-propyl-4-(trifluoromethyl)-1H-indole-5-carbonitrile;

1-({5-[3-Chloro-2-fluoro-5-(trifluoromethyl)phenyl]-1,2,4-oxadiazol-3-yl}methyl)-2-propyl-4-(trifluoromethyl)-1H-indole-5-carbonitrile;

2-Propyl-4-(trifluoromethyl)-1-{[5-(3,4,5-trifluorophenyl)-1,2,4-oxadiazol-3-yl]methyl}-1H-indole-5-carbonitrile;

1-({5-[2-Fluoro-5-(trifluoromethyl)phenyl]-1,2,4-oxadiazol-3-yl}methyl)-2-propyl-4-(trifluoromethyl)-1H-indole-5-carbonitrile;

2-Propyl-4-(trifluoromethyl)-1-({5-[3-(trifluoromethyl)phenyl]-1,2,4-oxadiazol-3-yl}methyl)-1H-indole-5-carbonitrile;

1-({5-[2-Chloro-5-(trifluoromethyl)phenyl]-1,2,4-oxadiazol-3-yl}methyl)-2-propyl-4-(trifluoromethyl)-1H-indole-5-carbonitrile;

1-{[5-(2,5-Dichloro-3-thienyl)-1,2,4-oxadiazol-3-yl]methyl}-2-propyl-4-(trifluoromethyl)-1H-indole-5-carbonitrile;

1-{[5-(2,5-Dichlorophenyl)-1,2,4-oxadiazol-3-yl]methyl}-2-propyl-4-(trifluoromethyl)-1H-indole-5-carbonitrile;

1-{[5-(2-Bromo-5-chlorophenyl)-1,2,4-oxadiazol-3-yl]methyl}-2-propyl-4-(trifluoromethyl)-1H-indole-5-carbonitrile;

1-{[5-(5-Bromo-2-chlorophenyl)-1,2,4-oxadiazol-3-yl]methyl}-2-propyl-4-(trifluoromethyl)-1H-indole-5-carbonitrile;

1-{[5-(2-Chloro-3-pyridinyl)-1,2,4-oxadiazol-3-yl]methyl}-2-propyl-4-(trifluoromethyl)-1H-indole-5-carbonitrile;

1-{[5-(2,5-Dichloro-3-pyridinyl)-1,2,4-oxadiazol-3-yl]methyl}-2-propyl-4-(trifluoromethyl)-1H-indole-5-carbonitrile;

1-{[5-(4-Chloro-3-pyridinyl)-1,2,4-oxadiazol-3-yl]methyl}-2-propyl-4-(trifluoromethyl)-1H-indole-5-carbonitrile;

1-{[5-(2-Chloro-5-iodophenyl)-1,2,4-oxadiazol-3-yl]methyl}-2-propyl-4-(trifluoromethyl)-1H-indole-5-carbonitrile;

1-{[5-(5-Chloro-1,3-dimethyl-1H-pyrazolo[3,4-b]pyridin-6-yl)-1,2,4-oxadiazol-3-yl]methyl}-2-propyl-4-(trifluoromethyl)-1H-indole-5-carbonitrile;

Methyl 4-chloro-3-(3-{[5-cyano-2-propyl-4-(trifluoromethyl)-1H-indol-1-yl]methyl}-1,2,4-oxadiazol-5-yl)benzoate;

1-{[5-(2-Chloro-5-nitrophenyl)-1,2,4-oxadiazol-3-yl]methyl}-2-propyl-4-(trifluoromethyl)-1H-indole-5-carbonitrile;

4-Chloro-3-(3-{[5-cyano-2-propyl-4-(trifluoromethyl)-1H-indol-1-yl]methyl}-1,2,4-oxadiazol-5-yl)benzamide;

4-Chloro-3-(3-{[5-cyano-2-propyl-4-(trifluoromethyl)-1H-indol-1-yl]methyl}-1,2,4-oxadiazol-5-yl)-N-methylbenzamide;

4-Chloro-3-(3-{[5-cyano-2-propyl-4-(trifluoromethyl)-1H-indol-1-yl]methyl}-1,2,4-oxadiazol-5-yl)-N,N-dimethylbenzamide;

1-({5-[2-(Methylthio)phenyl]-1,2,4-oxadiazol-3-yl}methyl)-2-propyl-4-(trifluoromethyl)-1H-indole-5-carbonitrile;

1-{[5-(Dimethylamino)-1,2,4-oxadiazol-3-yl]methyl}-2-propyl-4-(trifluoromethyl)-1H-indole-5-carbonitrile;

1-({5-[2-Chloro-5-(methylthio)phenyl]-1,2,4-oxadiazol-3-yl}methyl)-2-propyl-4-(trifluoromethyl)-1H-indole-5-carbonitrile;

1-({5-[2-Chloro-5-(methylsulfonyl)phenyl]-1,2,4-oxadiazol-3-yl}methyl)-2-propyl-4-(trifluoromethyl)-1H-indole-5-carbonitrile;

2-[5-Cyano-4-(trifluoromethyl)-2-(3,3,3-trifluoropropyl)-1H-indol-1-yl]acetamide;

1-{[5-(3,5-Difluorophenyl)-1,2,4-oxadiazol-3-yl]methyl}-4-(trifluoromethyl)-2-(3,3,3-trifluoropropyl)-1H-indole-5-carbonitrile;

4-(Trifluoromethyl)-1-({5-[3-(trifluoromethyl)phenyl]-1,2,4-oxadiazol-3-yl}methyl)-2-(3,3,3-trifluoropropyl)-1H-indole-5-carbonitrile;

1-{[5-(5-Bromo-3-pyridinyl)-1,2,4-oxadiazol-3-yl]methyl}-4-(trifluoromethyl)-2-(3,3,3-trifluoropropyl)-1H-indole-5-carbonitrile;

1-{[2-(2-Chlorophenyl)-1,3-thiazol-4-yl]methyl}-2-methyl-4-(trifluoromethyl)-1H-indole-5-carbonitrile;

1-{[2-(4-Chlorophenyl)-1,3-thiazol-4-yl]methyl}-2-methyl-4-(trifluoromethyl)-1H-indole-5-carbonitrile;

2-Methyl-4-(trifluoromethyl)-1-({2-[4-(trifluoromethyl)phenyl]-1,3-thiazol-4-yl}methyl)-1H-indole-5-carbonitrile;

1-({5-[2-Fluoro-5-(trifluoromethyl)phenyl]-1,2,4-oxadiazol-3-yl}methyl)-2-methyl-4-(trifluoromethyl)-1H-indole-5-carbonitrile;

2-Cyclopropyl-4-(trifluoromethyl)-1-({5-[3-(trifluoromethyl)phenyl]-2-furanyl}methyl)-1H-indole-5-carbonitrile;

2-Methyl-4-(trifluoromethyl)-1-({2-[3-(trifluoromethyl)phenyl]-1,3-thiazol-4-yl}methyl)-1H-indole-5-carbonitrile;

1-{[2-(3,5-Difluorophenyl)-1,3-thiazol-4-yl]methyl}-2-methyl-4-(trifluoromethyl)-1H-indole-5-carbonitrile;

1-({2-[3,5-bis(Trifluoromethyl)phenyl]-1,3-thiazol-4-yl}methyl)-2-methyl-4-(trifluoromethyl)-1H-indole-5-carbonitrile;

2-Methyl-4-(trifluoromethyl)-1-({5-[3-(trifluoromethyl)phenyl]-2-thienyl}methyl)-1H-indole-5-carbonitrile;

1-{[5-(3,5-Difluorophenyl)-2-thienyl]methyl}-2-methyl-4-(trifluoromethyl)-1H-indole-5-carbonitrile;

1-({5-[3,5-bis(Trifluoromethyl)phenyl]-2-thienyl}methyl)-2-methyl-4-(trifluoromethyl)-1H-indole-5-carbonitrile;

2-Methyl-1-({4-methyl-2-[4-(trifluoromethyl)phenyl]-1,3-thiazol-5-yl}methyl)-4-(trifluoromethyl)-1H-indole-5-carbonitrile;

2-Methyl-4-(trifluoromethyl)-1-{[3'-(trifluoromethyl)-3-biphenylyl]methyl}-1H-indole-5-carbonitrile;

2-Methyl-4-(trifluoromethyl)-1-{[4'-(trifluoromethyl)-3-biphenylyl]methyl}-1H-indole-5-carbonitrile;

1-{[3',5'-bis(Trifluoromethyl)-3-biphenylyl]methyl}-2-methyl-4-(trifluoromethyl)-1H-indole-5-carbonitrile;

1-({2-[3,5-bis(Trifluoromethyl)phenyl]-1,3-thiazol-5-yl}methyl)-2-methyl-4-(trifluoromethyl)-1H-indole-5-carbonitrile;

2-Methyl-4-(trifluoromethyl)-1-({2-[3-(trifluoromethyl)phenyl]-1,3-thiazol-5-yl}methyl)-1H-indole-5-carbonitrile;

1-({5-[3,5-bis(Trifluoromethyl)phenyl]-3-isoxazolyl}methyl)-2-methyl-4-(trifluoromethyl)-1H-indole-5-carbonitrile;

2-Methyl-4-(trifluoromethyl)-1-({5-[3-(trifluoromethyl)phenyl]-3-isoxazolyl}methyl)-1H-indole-5-carbonitrile;

1-[(3-Bromo-5-isoxazolyl)methyl]-2-methyl-4-(trifluoromethyl)-1H-indole-5-carbonitrile;

1-[(5-Chloro-1,2,4-thiadiazol-3-yl)methyl]-2-methyl-4-(trifluoromethyl)-1H-indole-5-carbonitrile;

1-({5-[3,5-bis(Trifluoromethyl)phenyl]-1,2,4-thiadiazol-3-yl}methyl)-2-methyl-4-(trifluoromethyl)-1H-indole-5-carbonitrile;

2-Methyl-4-(trifluoromethyl)-1-({5-[3-(trifluoromethyl)phenyl]-1,2,4-thiadiazol-3-yl}methyl)-1H-indole-5-carbonitrile;

1-[(1R)-2-Hydroxy-1-methylethyl]-2-methyl-4-(trifluoromethyl)-1H-indole-5-carbonitrile;

N-[4-({(2R)-2-[5-Cyano-2-methyl-4-(trifluoromethyl)-1H-indol-1-yl]propyl}oxy)phenyl]acetamide;

1-{(1R)-2-[(6-Fluoro-3-pyridinyl)oxy]-1-methylethyl}-2-methyl-4-(trifluoromethyl)-1H-indole-5-carbonitrile;

2-Methyl-1-[(1R)-1-methyl-2-(3-pyridinyloxy)ethyl]-4-(trifluoromethyl)-1H-indole-5-carbonitrile;

1-{2-[(4-Fluorophenyl)oxy]ethyl}-2-methyl-4-(trifluoromethyl)-1H-indole-5-carbonitrile;

2-Methyl-1-[(1R)-1-methyl-2-(2-pyridinyloxy)ethyl]-4-(trifluoromethyl)-1H-indole-5-carbonitrile;

1-(2-Hydroxypropyl)-2-methyl-4-(trifluoromethyl)-1H-indole-5-carbonitrile;

1-{2-[(6-Fluoro-3-pyridinyl)oxy]propyl}-2-methyl-4-(trifluoromethyl)-1H-indole-5-carbonitrile;

2-Methyl-1-[2-(3-pyridinyloxy)propyl]-4-(trifluoromethyl)-1H-indole-5-carbonitrile;

N-[4-({2-[5-Cyano-2-methyl-4-(trifluoromethyl)-1H-indol-1-yl]-1-methylethyl}oxy)phenyl]acetamide;

2-Methyl-1-[2-(2-pyridinyloxy)propyl]-4-(trifluoromethyl)-1H-indole-5-carbonitrile;

1-{2-[(4-Cyano-3-fluorophenyl)oxy]ethyl}-2-methyl-4-(trifluoromethyl)-1H-indole-5-carbonitrile;

1-{2-[(6-Chloro-3-pyridinyl)oxy]ethyl}-2-methyl-4-(trifluoromethyl)-1H-indole-5-carbonitrile;

2-Methyl-1-[2-(methyloxy)ethyl]-4-(trifluoromethyl)-1H-indole-5-carbonitrile;

2-Methyl-1-(2-{[2-(methyloxy)ethyl]oxy}ethyl)-4-(trifluoromethyl)-1H-indole-5-carbonitrile;
2-Methyl-1-[(1R)-1-methyl-2-(methyloxy)ethyl]-4-(trifluoromethyl)-1H-indole-5-carbonitrile;
1-(2-Hydroxy-2-methylpropyl)-2-methyl-4-(trifluoromethyl)-1H-indole-5-carbonitrile;
2-Methyl-1-[2-(methyloxy)propyl]-4-(trifluoromethyl)-1H-indole-5-carbonitrile;
2-Methyl-1-[2-methyl-2-(methyloxy)propyl]-4-(trifluoromethyl)-1H-indole-5-carbonitrile;
1-(3-Hydroxypropyl)-2-methyl-4-(trifluoromethyl)-1H-indole-5-carbonitrile;
2-Methyl-1-[3-(methyloxy)propyl]-4-(trifluoromethyl)-1H-indole-5-carbonitrile;
Methyl 2-{[5-cyano-2-methyl-4-(trifluoromethyl)-1H-indol-1-yl]methyl}-2-propenoate;
1-(3-Hydroxy-2-methylpropyl)-2-methyl-4-(trifluoromethyl)-1H-indole-5-carbonitrile;
2-Methyl-1-[2-methyl-3-(methyloxy)propyl]-4-(trifluoromethyl)-1H-indole-5-carbonitrile;
2-methyl-4-(Trifluoromethyl)-1-({2-[3-(trifluoromethyl)phenyl]-1,3-oxazol-4-yl}methyl)-1H-indole-5-carbonitrile;
1-({2-[3,5-bis(Trifluoromethyl)phenyl]-1,3-oxazol-4-yl}methyl)-2-methyl-4-(trifluoromethyl)-1H-indole-5-carbonitrile;
Methyl 3-[5-cyano-4-(trifluoromethyl)-1-({5-[2-(trifluoromethyl)phenyl]-1,2,4-oxadiazol-3-yl}methyl)-1H-indol-2-yl]propanoate;
1-({5-[3,5-bis(Trifluoromethyl)phenyl]-2-furanyl}methyl)-2-cyclopropyl-4-(trifluoromethyl)-1H-indole-5-carbonitrile;
2-Cyclopropyl-1-{[5-(3,5-difluorophenyl)-2-furanyl]methyl}-4-(trifluoromethyl)-1H-indole-5-carbonitrile;
2-Cyclopropyl-1-({5-[2-fluoro-5-(trifluoromethyl)phenyl]-2-furanyl}methyl)-4-(trifluoromethyl)-1H-indole-5-carbonitrile;
1-{[2-(2-Chlorophenyl)-1,3-thiazol-4-yl]methyl}-2-cyclopropyl-4-(trifluoromethyl)-1H-indole-5-carbonitrile;
1-{[2-(4-Chlorophenyl)-1,3-thiazol-4-yl]methyl}-2-cyclopropyl-4-(trifluoromethyl)-1H-indole-5-carbonitrile;
2-Cyclopropyl-4-(trifluoromethyl)-1-({2-[4-(trifluoromethyl)phenyl]-1,3-thiazol-4-yl}methyl)-1H-indole-5-carbonitrile;
2-Cyclopropyl-4-(trifluoromethyl)-1-({5-[3-(trifluoromethyl)phenyl]-1,3,4-oxadiazol-2-yl}methyl)-1H-indole-5-carbonitrile;
2-[5-Cyano-2-cyclopropyl-4-(trifluoromethyl)-1H-indol-1-yl]-N-ethylacetamide;
2-Cyclopropyl-4-(trifluoromethyl)-1-({5-[4-(trifluoromethyl)-2-pyridinyl]-1,2,4-oxadiazol-3-yl}methyl)-1H-indole-5-carbonitrile;
2-Cyclopropyl-4-(trifluoromethyl)-1-({5-[6-(trifluoromethyl)-2-pyridinyl]-1,2,4-oxadiazol-3-yl}methyl)-1H-indole-5-carbonitrile;
2-Cyclopropyl-1-({5-[2-fluoro-5-(trifluoromethyl)phenyl]-1,2,4-oxadiazol-3-yl}methyl)-4-(trifluoromethyl)-1H-indole-5-carbonitrile;
2-Cyclopropyl-4-(trifluoromethyl)-1-({5-[2-(trifluoromethyl)-4-pyridinyl]-1,2,4-oxadiazol-3-yl}methyl)-1H-indole-5-carbonitrile;
2-Cyclopropyl-4-(trifluoromethyl)-1-({3-[3-(trifluoromethyl)phenyl]-1H-1,2,4-triazol-5-yl}methyl)-1H-indole-5-carbonitrile;
2-Cyclopropyl-4-(trifluoromethyl)-1-({2-[3-(trifluoromethyl)phenyl]-1,3-oxazol-4-yl}methyl)-1H-indole-5-carbonitrile;
2-Methyl-4-(trifluoromethyl)-1-({2-[3-(trifluoromethyl)phenyl]-1,3-oxazol-5-yl}methyl)-1H-indole-5-carbonitrile;
2-Cyclopropyl-4-(trifluoromethyl)-1-({2-[3-(trifluoromethyl)phenyl]-1,3-oxazol-5-yl}methyl)-1H-indole-5-carbonitrile;
2-Cyclopropyl-4-(trifluoromethyl)-1-({5-[5-(trifluoromethyl)-3-pyridinyl]-1,2,4-oxadiazol-3-yl}methyl)-1H-indole-5-carbonitrile;
1-({5-[3,5-bis(Trifluoromethyl)phenyl]-1,2,4-oxadiazol-3-yl}methyl)-2,4-bis(trifluoromethyl)-1H-indole-5-carbonitrile;
1-({5-[3,5-bis(Trifluoromethyl)phenyl]-1,2,4-oxadiazol-3-yl}methyl)-2-(2,2,2-trifluoroethyl)-4-(trifluoromethyl)-1H-indole-5-carbonitrile;
2-[5-Cyano-2-(2,2,2-trifluoroethyl)-4-(trifluoromethyl)-1H-indol-1-yl]acetamide;
1-{[5-(3,5-Difluorophenyl)-1,2,4-oxadiazol-3-yl]methyl}-2-(2,2,2-trifluoroethyl)-4-(trifluoromethyl)-1H-indole-5-carbonitrile;
2-(2,2,2-Trifluoroethyl)-4-(trifluoromethyl)-1-({5-[3-(trifluoromethyl)phenyl]-1,2,4-oxadiazol-3-yl}methyl)-1H-indole-5-carbonitrile;
1-{[5-(5-Bromo-3-pyridinyl)-1,3,4-oxadiazol-2-yl]methyl}-2-(2,2,2-trifluoroethyl)-4-(trifluoromethyl)-1H-indole-5-carbonitrile;
2-(1,1-Difluoroethyl)-1-{[5-(3,5-difluorophenyl)-1,2,4-oxadiazol-3-yl]methyl}-4-(trifluoromethyl)-1H-indole-5-carbonitrile;
2-(1,1-Difluoroethyl)-4-(trifluoromethyl)-1-({5-[3-(trifluoromethyl)phenyl]-1,2,4-oxadiazol-3-yl}methyl)-1H-indole-5-carbonitrile;
1-{[5-(5-Bromo-3-pyridinyl)-1,3,4-oxadiazol-2-yl]methyl}-2-(1,1-difluoroethyl)-4-(trifluoromethyl)-1H-indole-5-carbonitrile;
1-({5-[3,5-Bis(trifluoromethyl)phenyl]-1,2,4-oxadiazol-3-yl}methyl)-2-(1,1-difluoroethyl)-4-(trifluoromethyl)-1H-indole-5-carbonitrile;
2-[5-Cyano-2-(1,1-difluoroethyl)-4-(trifluoromethyl)-1H-indol-1-yl]acetamide; or a salt or solvate thereof.

It is to be understood that the present invention covers all combinations of the compounds described hereinabove.

ABBREVIATIONS

As used herein the symbols and conventions used in these processes, schemes and examples are consistent with those used in the contemporary scientific literature, for example, the *Journal of the American Chemical Society or the Journal of Biological Chemistry*. Specifically, the following abbreviations may be used in the examples and throughout the specification:

g (grams);
L (liters);
μL (microliters);
M (molar);
Hz (Hertz);
mol (moles);
rt (room temperature);
h (hour);
TLC (thin layer chromatography);
TEA (triethylamine);
TFAA (trifluoroacetic anhydride);
CDCl$_3$ (deuterated chloroform);
SiO$_2$ (silica);
EtOAc (ethyl acetate);
HCl (hydrochloric acid);

DMF (N,N-dimethylformamide);
Cs$_2$CO$_3$ (cesium carbonate);
Et (ethyl);
MeOH (methanol);
Et$_2$O (diethyl ether);
MsCl (methanesulphonyl chloride);
sat'd (saturated);
K$_2$CO$_3$ (potassium carbonate);
DCE (1,2-dichloroethane);
EDCl (1-(3-dimethylaminopropyl)-3-ethylcarbodiimide hydrochloride);
P-BEMP (polymer-supported 2-tert-butylimino-2-diethylamino-1,3-dimethylperhydro-1,3,2-diaza-phosphorine);
mg (milligrams);
mL (milliliters);
psi (pounds per square inch);
mM (millimolar);
MHz (megahertz);
mmol (millimoles);
min (minute);
mp (melting point);
CH$_2$Cl$_2$ (methylene chloride);
TFA (trifluoroacetic acid);
THF (tetrahydrofuran);
CD$_3$OD (deuterated methanol);
DMSO (dimethylsulfoxide);
atm (atmosphere);
CHCl$_3$ (chloroform);
Ac (acetyl);
Me (methyl);
EtOH (ethanol);
t-Bu (tert-butyl);
N$_2$ (nitrogen);
DMAP (4-(dimethylamino)pyridine);
Ps (polymer supported);
TsCl (tosyl chloride);
Et$_3$SiH (triethylsilane);
CSA (camphor sulfonic acid);
TBDPSCl (tert-butyldiphenyl silylchloride);
HOAc (acetic acid);
DIBAL-H (diisobutyl aluminium hydride);
NIS (N-iodosuccinimide);
HATU (O-(7-Azabenzotriazole-1-yl)-N,N,N'N'-tetramethyluronium hexafluorophosphate);
DIEA (diisopropylethyl amine);
MeCN (acetonitrile);
NBS (N-bromosuccinimide);
TBAF (tetrabutylammonium fluoride);
AcCl (acetyl chloride);
NMP (N-methyl-2-pyrrolidone);
CDI (carbonyl diimidazole);
PTSA (paratoluene sulfonic acid);
MTBE (methyl tert-butyl ether);
DBAD (di-tert-butyl azodicarboxylate).

Unless otherwise indicated, all temperatures are expressed in ° C. (degrees Centigrade). All reactions conducted under an inert atmosphere at room temperature unless otherwise noted. Reagents employed without synthetic details are commercially available or made according to literature procedures.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or b (broad).

Scheme 1

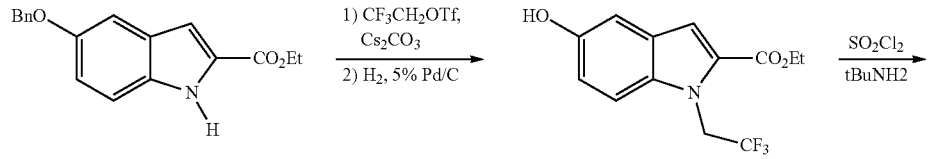

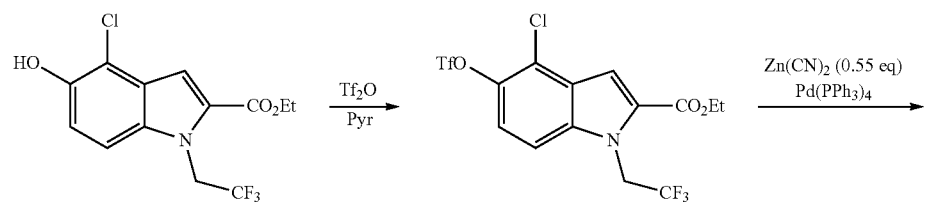

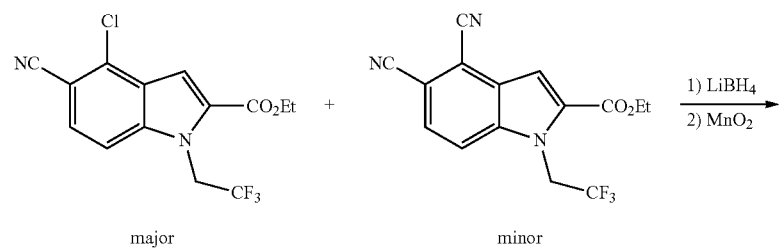

major    minor

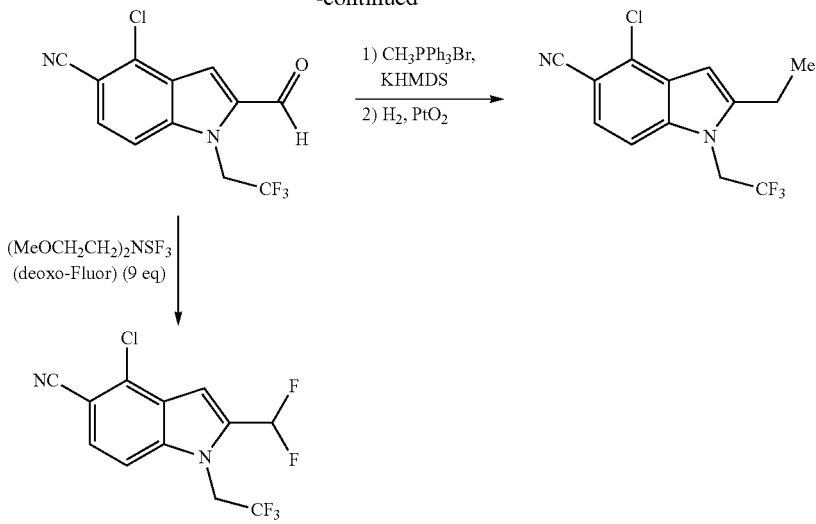

Tetrasubstituted indoles of formula (I) that bear a chloro or cyano at the indole 4-position can be constructed by directed chlorination of 5-hydroxy indoles with sulforyl chloride (Scheme 1). Palladium-mediated cyanation through the corresponding triflate then affords the desired 5-cyano-4-chloro indoles as well as the bis cyano indoles as side products. Further functionalization of the indole 2-position is afforded from the starting 2-position ester functionality.

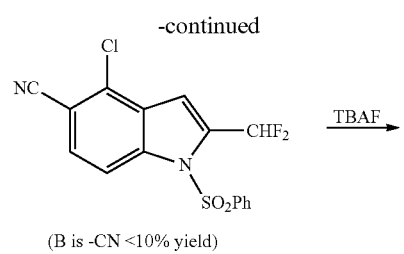

The same regioselective chlorination can be applied to protected 5-benzyloxy-2-formyl indoles (Scheme 2). Early commitment to 2-difluoromethyl substitution via Deoxofluor™ allows more flexibility to subsequently functionalize the indole 1-position.

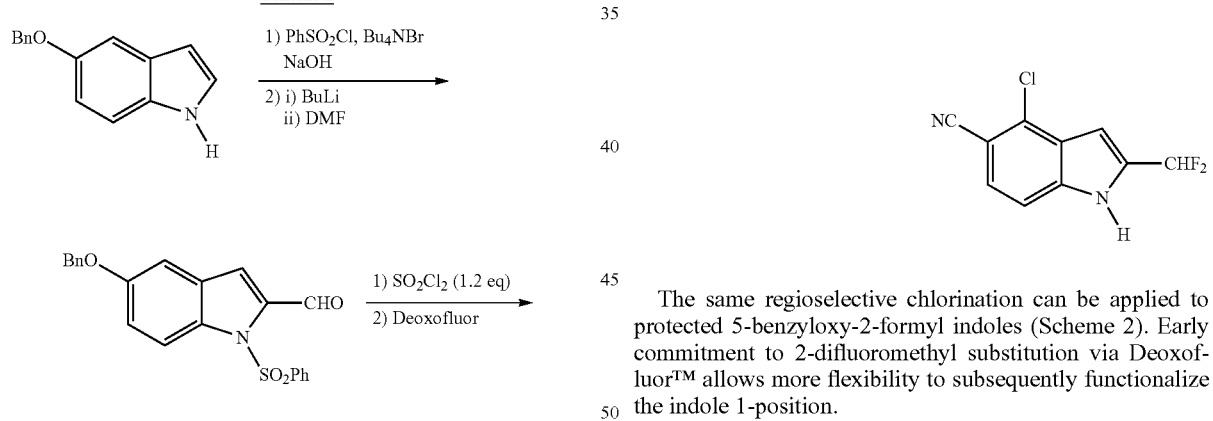

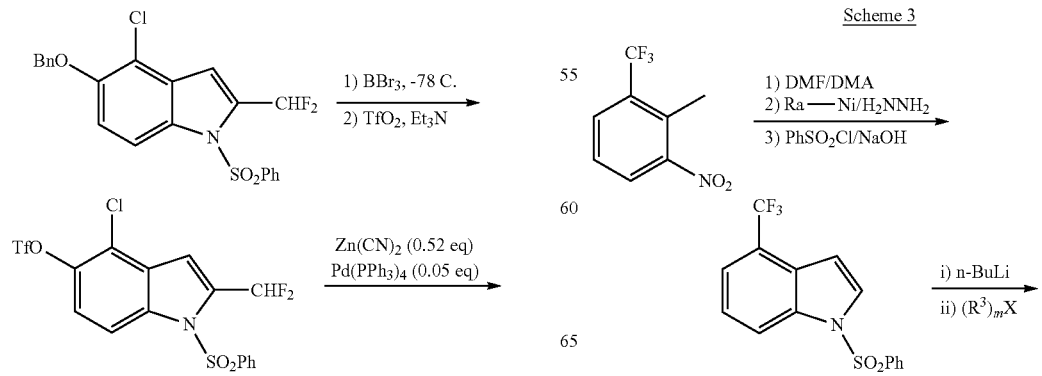

Scheme 4

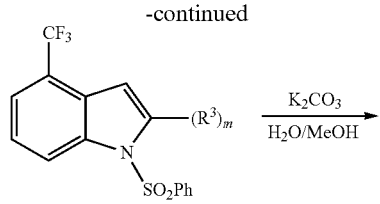
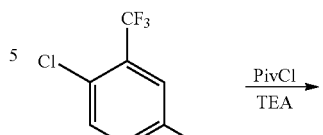
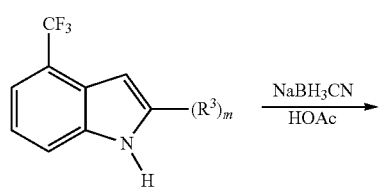
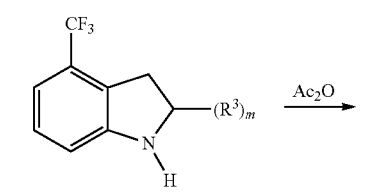
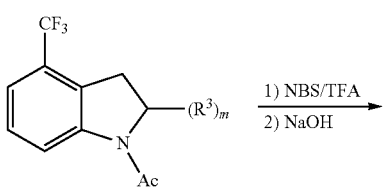
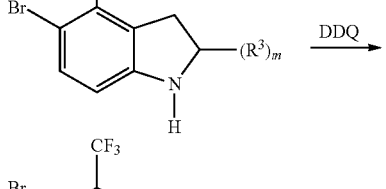
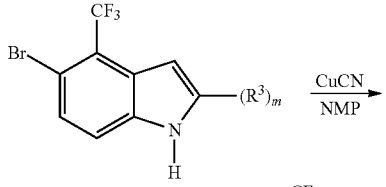
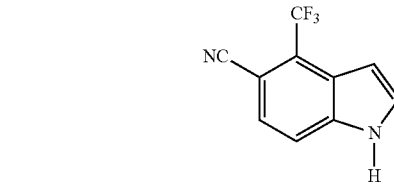

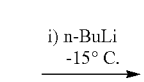
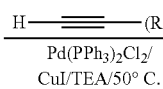
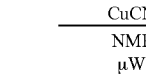
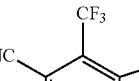
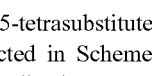

Highly substituted indoles used for the synthesis of compounds of formula (I) can be constructed starting with appropriately substituted nitroarenes (Scheme 3). For example, treatment of commercially available 2-methyl-1-nitro-3-(trifluoromethyl)benzene under classical indole synthesis conditions affords the corresponding 2, 4 disubstituted indole that can be further elaborated by directed deprotonation/alkylations and aromatic substitutions.

A more concise route to 1,2,4,5-tetrasubstituted indole precursors of formula (I) is depicted in Scheme 4. See, for example, International Patent Application No. WO03062241 published Jul. 31, 2003. Acylation of 4-chloro-3-trifluoromethyl aniline with pivaloyl chloride allows for directed ortho deprotonation. The intermediate aryllithium species is quenched with iodine to afford the desired 2-iodoarene in a 3.7 to 1 ratio of ortho regioisomers. Sonagoshira coupling of the iodoarene affords aryl alkynes. Next, a three step reaction cascade is employed to provide the desired indoles. The cascade provides indolization, depivoylation, and cyanation in one-pot through heating in a microwave at 250° C. or prolonged conventional heating at 200° C.

Scheme 5

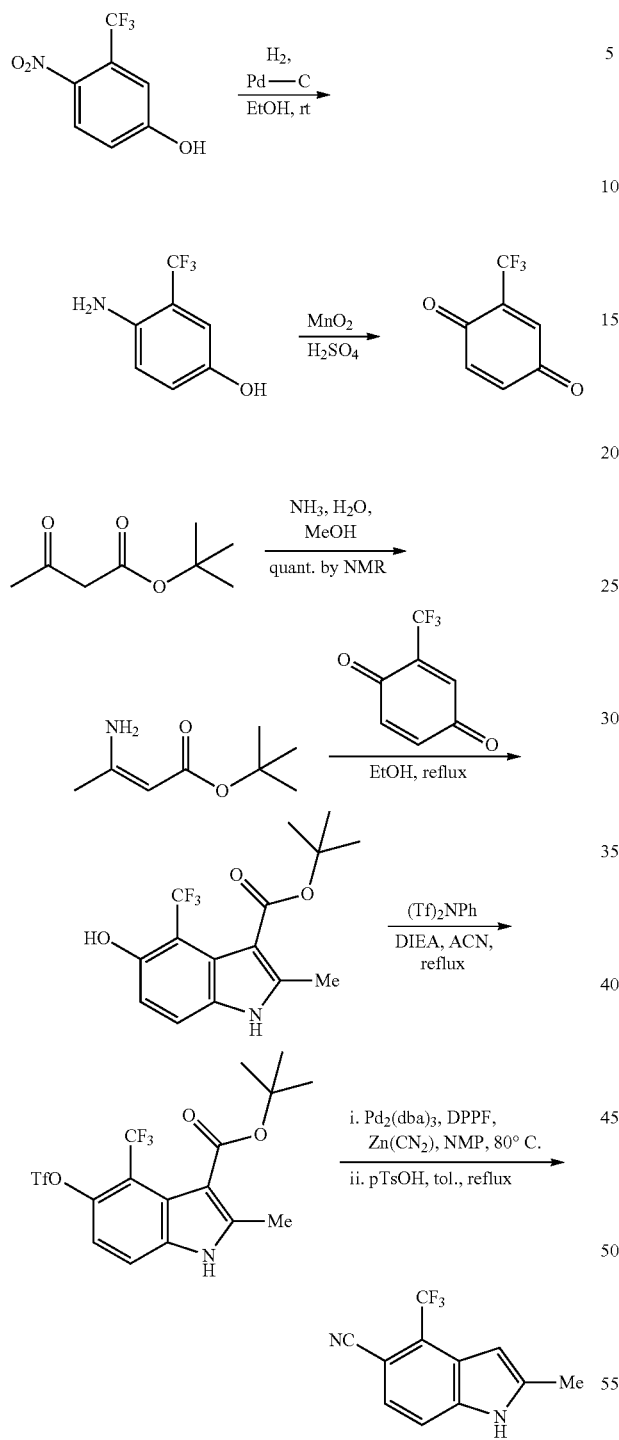

Scheme 6

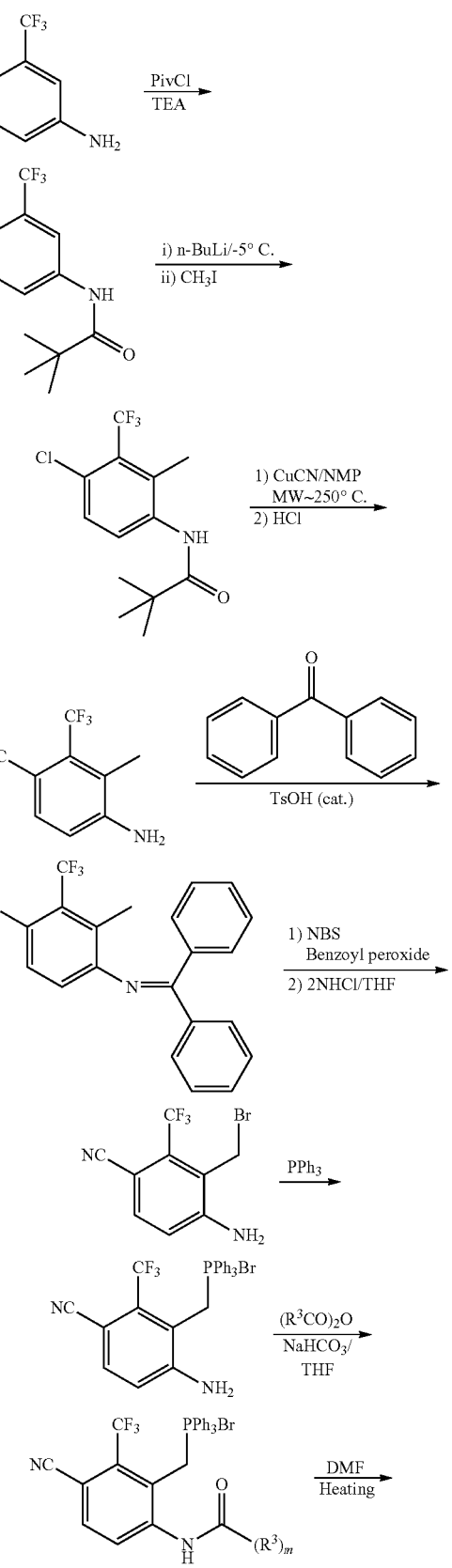

Yet a third means of synthesizing the desired precursors of compounds of formula (I) involves the condensation of 1,4 benzoquinones with enamines (Scheme 5), the Nenitzescu indole synthesis (Nenitzescu, C. D. *Bull. Soc. Chim. Romania*, 11, 37, 1929). The highly functionalized 5-hydroxy indoles afforded by this route are further elaborated through conversion to the corresponding triflate and subsequent palladium mediated cyanation.

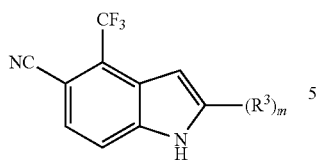

Another method for synthesizing indole precursors of formula (I) is depicted in Scheme 6. Ortho-directed deprotonation/alkylation akin to Scheme 4 affords tetrasubstituted arenes that can be selectively halogenated at the 2-position alkyl group. Conversion to the phosphonium salt and ring closure provides the desired indoles.

Scheme 7

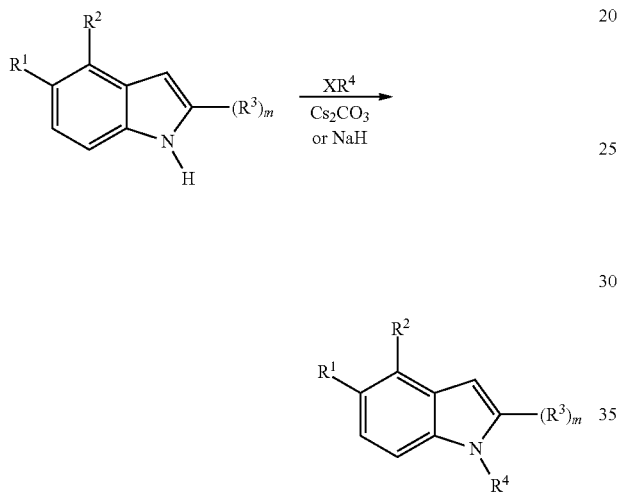

The highly substituted indole precursors of compounds of formula (I) may be further elaborated by alkylation of the indole 1-position with alkyl halides in the presence of a base. A typical non-limiting example of an alkylating agent would be (bromomethyl)cyclopropane, while a typical non-limiting example of a base would be cesium carbonate.

Scheme 8

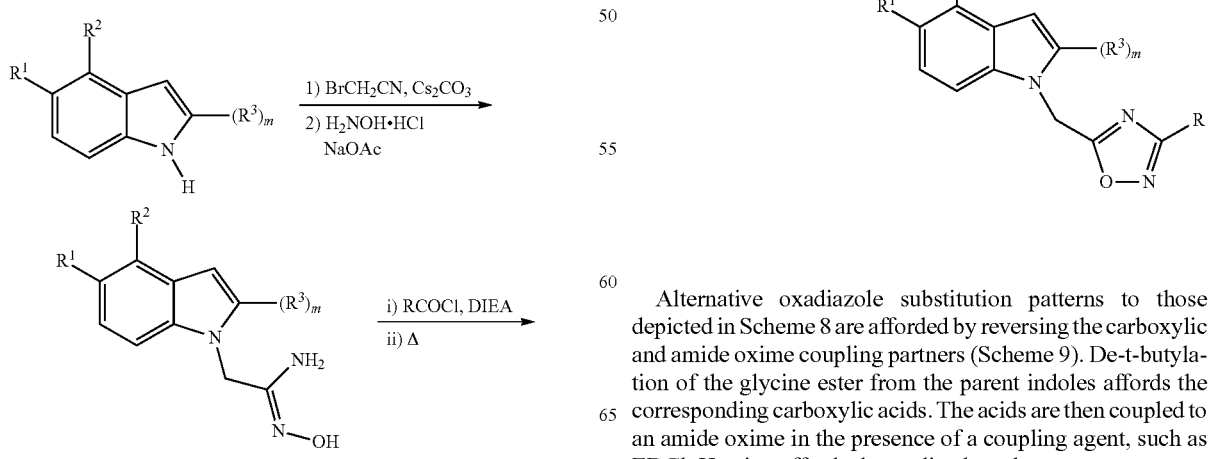

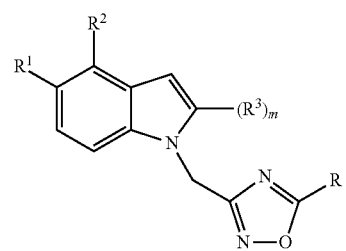

Heterocycle-bearing indoles that cannot be made from simple alkylation with, for example, commercially available 3-halomethyl-5-substituted 1,2,4-oxadiazoles (as in Scheme 7) may be synthesized by coupling of an amide oxime with an acid chloride followed by thermally-induced ring closure (Scheme 8). The requisite amide oximes of the parent indoles can be constructed by alkylation with bromoacetonitrile followed by treatment with hydroxylamine.

Scheme 9

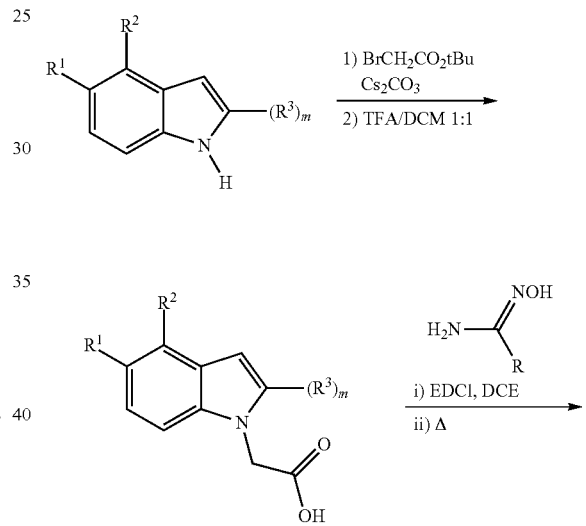

Alternative oxadiazole substitution patterns to those depicted in Scheme 8 are afforded by reversing the carboxylic and amide oxime coupling partners (Scheme 9). De-t-butylation of the glycine ester from the parent indoles affords the corresponding carboxylic acids. The acids are then coupled to an amide oxime in the presence of a coupling agent, such as EDCl. Heating affords the cyclized products.

Scheme 10

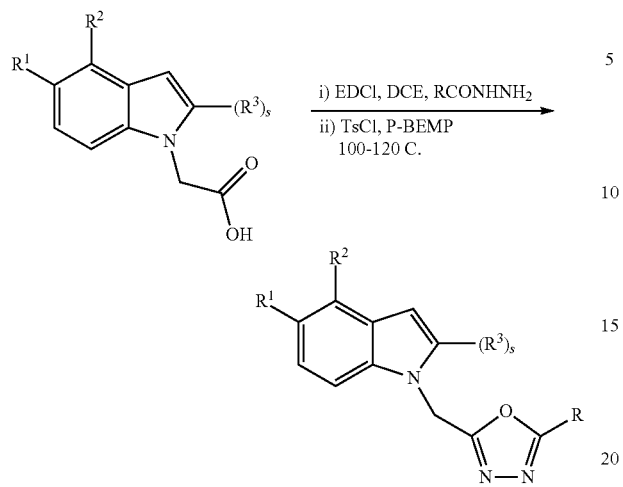

The same carboxylic acid reaction partner depicted in Scheme 9 may be used to afford 1,3,4-oxadiazole bearing compounds (Scheme 10). Reaction of a carboxylic acid with a carbohydrazide in the presence of a coupling agent, such as EDCl, is followed by treatment with tosyl chloride and P-BEMP as a base. The resulting mixture is then heated via microwave to give the desired heterocycles.

EXAMPLES

For the purposes of the following examples, when it is recited that a compound was "synthesized as described" in another example, it indicates that the compound was synthesized essentially as described in the other example with such modifications as are within the purview of the art.

Example 1

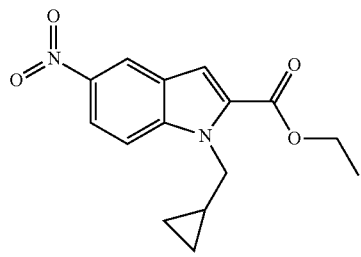 [SMILES: CCOC(=O)c1cc2cc([N+](=O)[O-])ccc2n1CC1CC1]

Ethyl 1-(cyclopropylmethyl)-5-nitro-1H-indole-2-carboxylate

To a suspension of commercially available ethyl 5-nitro-1H-indole-2-carboxylate (0.5 g, 2.13 mmol) in MeCN (7 mL) was added $Cs_2CO_3$ (1.39 g, 4.27 mmol) and (bromomethyl) cyclopropane (0.58 g, 4.27 mmol). The mixture was heated at 90° C., under $N_2$, for 5 h. Upon cooling, the mixture was concentrated in vacuo and partitioned between EtOAc and $H_2O$. The organic phase was washed with sat'd brine, dried ($Na_2SO_4$) and concentrated in vacuo. The residue was purified by flash chromatography (0-30% EtOAc-hexanes gradient). The product slowly crystallized from $CH_2Cl_2$-hexanes to afford the title compound as a light yellow solid (0.42 g, 68% yield): MS (ES) m/z 289 (M+1).

Example 2

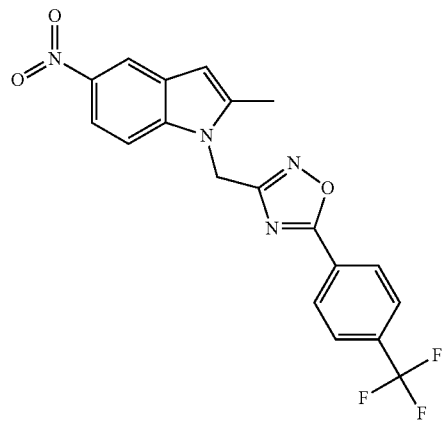 [SMILES: Cc1cc2cc([N+](=O)[O-])ccc2n1Cc1noc(-c2ccc(C(F)(F)F)cc2)n1]

2-Methyl-5-nitro-1-({5-[4-(trifluoromethyl)phenyl]-1,2,4-oxadiazol-3-yl}methyl)-1H-indole Synthesized as described in Example 1 using 1.3 eq each of $Cs_2CO_3$ and 3-(chloromethyl)-5-[4-(trifluoromethyl)phenyl]-1,2,4-oxadiazole, with heating at 70° C. for 15 h: MS (ES) m/z 403 (M+1).

Example 3

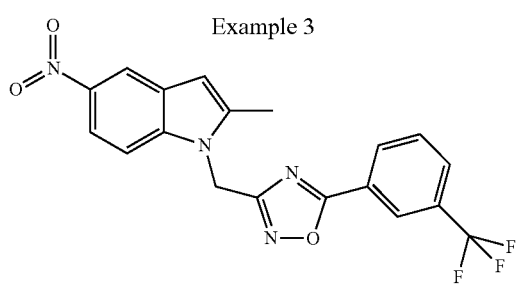

2-Methyl-5-nitro-1-({5-[3-(trifluoromethyl)phenyl]-1,2,4-oxadiazol-3-yl}methyl)-1H-indole Synthesized as described in Example 1 using 1.3 eq each of $Cs_2CO_3$ and 3-(chloromethyl)-5-[3-(trifluoromethyl)phenyl]-1,2,4-oxadiazole, with heating at 70° C. for 15 h: MS (ES) m/z 403 (M+1).

Example 4

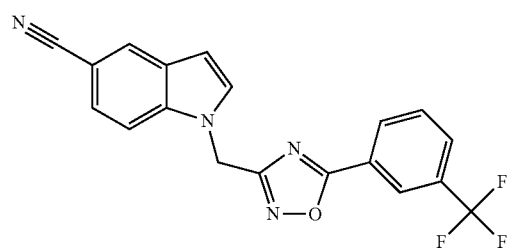 [SMILES: N#Cc1ccc2c(ccn2Cc2noc(-c3cccc(C(F)(F)F)c3)n2)c1]

1-({5-[3-(Trifluoromethyl)phenyl]-1,2,4-oxadiazol-3-yl}methyl)-1H-indole-5-carbonitrile To a solution of 1H-indole-5-carbonitrile (0.05 g, 0.35 mmol) in anhydrous DMF (2 mL) was added Cs$_2$CO$_3$ (0.18 g, 0.55 mmol) and 3-(chloromethyl)-5-[3-(trifluoromethyl)phenyl]-1,2,4-oxadiazole (0.14 g, 0.55 mmol). The mixture was heated at 90° C., under N$_2$, for 30 min. Upon cooling, the mixture was partitioned between Et$_2$O and H$_2$O. The aqueous phase was extracted with Et$_2$O (×2). The combined organic phases were washed with sat'd brine, dried (Na$_2$SO$_4$) and concentrated in vacuo. The residue was purified by flash chromatography (2-20% EtOAc-hexanes gradient) and the product crystallized from CH$_2$Cl$_2$-hexanes to afford the title compound as a white solid (0.1 g, 78% yield): MS (ES) m/z 369 (M+1).

Example 5

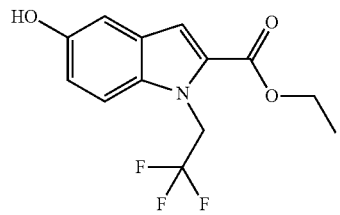 [SMILES: CCOC(=O)c1cc2cc(O)ccc2n1CC(F)(F)F]

Ethyl 5-hydroxy-1-(2,2,2-trifluoroethyl)-1H-indole-2-carboxylate

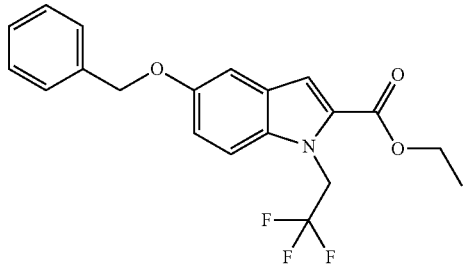 [SMILES: CCOC(=O)c1cc2cc(OCc3ccccc3)ccc2n1CC(F)(F)F]

A. Ethyl 5-[(phenylmethyl)oxy]-1-(2,2,2-trifluoroethyl)-1H-indole-2-carboxylate To a solution of ethyl 5-[(phenylmethyl)oxy]-1H-indole-2-carboxylate (0.3 g, 1 mmol) in 3:2 MeCN/DMF (5 mL) was added Cs$_2$CO$_3$ (0.36 g, 1.1 mmol) and 2,2,2-trifluoroethyl trifluoromethanesulfonate (0.26 g, 1.1 mmol). The mixture was stirred at rt, under N$_2$, for 4 h. Additional Cs$_2$CO$_3$ (0.033 g, 0.1 mmol) and 2,2,2-trifluoroethyl trifluoromethanesulfonate (0.023 g, 0.1 mmol) were added and stirring was continued at rt for 15 h. The mixture was partitioned between Et$_2$O and 0.05N HCl. The organic phase was washed with 0.05N HCl and sat'd brine, dried (Na$_2$SO$_4$) and concentrated in vacuo. The residue was purified by flash chromatography (0-20% EtOAc-hexanes gradient) to afford the title compound (0.23 g, 61% yield): $^1$H NMR (400 MHz, CDCl$_3$) δ 7.46 (d, J=7.1 Hz, 2H), 7.38 (t, J=7.1 Hz, 2H), 7.34-7.29 (m, 3H), 7.16-7.13 (m, 2H), 5.28 (q, J=8.5 Hz, 2H), 5.10 (s, 2H), 4.37 (q, J=7.1 Hz, 2H), 1.39 (t, J=7.1 Hz, 3H).

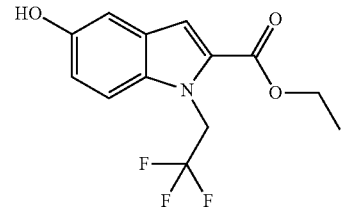 [SMILES: CCOC(=O)c1cc2cc(O)ccc2n1CC(F)(F)F]

B. Ethyl 5-hydroxy-1-(2,2,2-trifluoroethyl)-1H-indole-2-carboxylate

To a solution of ethyl 5-[(phenylmethyl)oxy]-1-(2,2,2-trifluoroethyl)-1H-indole-2-carboxylate (0.23 g, 0.6 mmol) in EtOAC (5 mL), under N$_2$, was added 5% Pd/C (0.12 g). The mixture was hydrogenated under balloon pressure for 3 h. The catalyst was filtered off and washed with EtOAc. The filtrate was concentrated to afford the title compound (0.15 g, 89% yield): MS (ES) m/z 288 (M+1).

Example 6 and 7

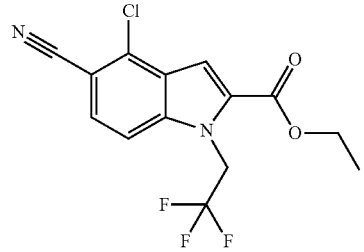

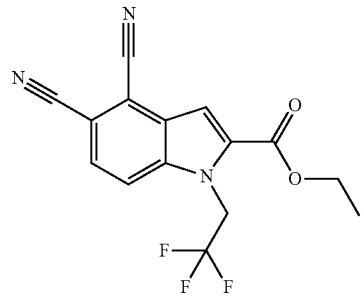

Ethyl 4-chloro-5-cyano-1-(2,2,2-trifluoroethyl)-1H-indole-2-carboxylate (Example 6) and ethyl 4,5-dicyano-1-(2,2,2-trifluoroethyl)-1H-indole-2-carboxylate (Example 7)

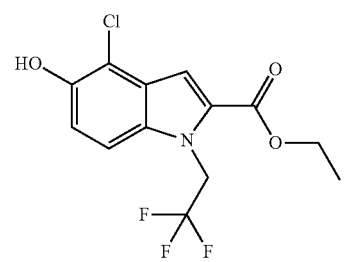 [SMILES: CCOC(=O)c1cc2c(Cl)c(O)ccc2n1CC(F)(F)F]

A. Ethyl 4-chloro-5-hydroxy-1-(2,2,2-trifluoroethyl)-1H-indole-2-carboxylate To a solution of ethyl 5-hydroxy-1-(2,2,2-trifluoroethyl)-1H-indole-2-carboxylate (0.7 g, 2.44 mmol) in toluene (30 mL) was added tert-butyl amine (0.014 g, 0.2 mmol) and the mixture was set in an oil bath preheated at 70° C. After 1 min, a solution of sulfuryl chloride (0.37 g, 2.49 mmol) in toluene (1 mL) was added. The reaction was followed by TLC (60% CH$_2$Cl$_2$-hexanes) and additional reagents were added accordingly. After 30 min, more tert-butylamine (0.014 g, 0.2 mmol) and sulfuryl chloride (0.06 g, 0.37 mmol) were added. After another 30 min additional tert-butylamine (0.014 g, 0.2 mmol) and sulfuryl chloride (0.019 g, 0.12 mmol) were added and heating was continued for 30 min. Upon cooling, the mixture was partitioned between EtOAc and 0.2N HCl. The organic phase was washed with 0.2N HCl and sat'd brine, dried (Na$_2$SO$_4$) and concentrated in vacuo. The residue was purified by flash chromatography (10-80% CH$_2$Cl$_2$-hexanes gradient) to afford the title compound (0.72 g, 92% yield, 95% purity): MS (ES) m/z 322 (M+1).

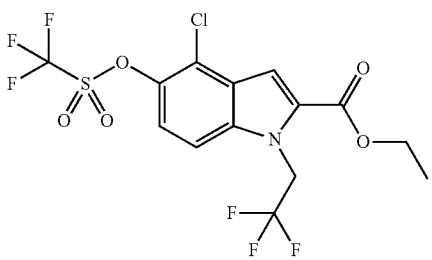 [SMILES: CCOC(=O)c1cc2c(Cl)c(OS(=O)(=O)C(F)(F)F)ccc2n1CC(F)(F)F]

B. Ethyl 4-chloro-1-(2,2,2-trifluoroethyl)-5-{[(trifluoromethyl)sulfonyl]oxy}-1H-indole-2-carboxylate To an ice-cold mixture of ethyl 4-chloro-5-hydroxy-1-(2,2,2-trifluoroethyl)-1H-indole-2-carboxylate (1.43 g, 4.43 mmol) and pyridine (0.53 g, 6.65 mmol) in CH$_2$Cl$_2$ (45 mL) was added triflic anhydride (1.38 g, 4.88 mmol) dropwise. The mixture was then stirred at rt. After 1 h, additional pyridine (0.1 g, 1.3 mmol) and triflic anhydride (0.5 g. 1.78 mmol) were added and stirring was continued at rt for 15 h. Additional pyridine (0.089 g, 1.1 mmol) and triflic anhydride (0.31 g, 1.1 mmol) were added and stirring was continued for another 1 h. The mixture was concentrated in vacuo and the residue was partitioned between EtOAc and 0.2N HCl. The organic phase was washed with 0.2N HCl and sat'd brine, dried (Na$_2$SO$_4$) and concentrated in vacuo. The residue was purified by flash chromatography (0-25% EtOAc-hexanes gradient) to afford the title compound (1.44 g, 72% yield): MS (ES) m/z 454 (M+1).

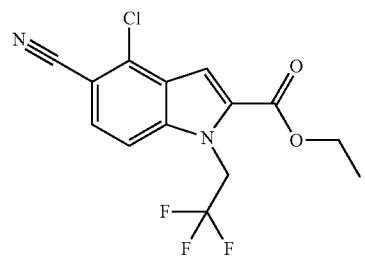

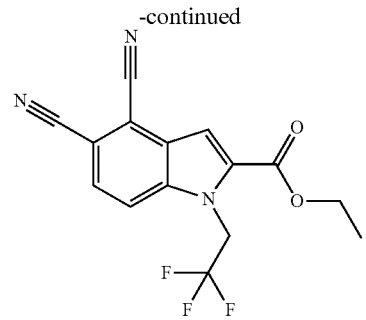

C. Ethyl 4-chloro-5-cyano-1-(2,2,2-trifluoroethyl)-1H-indole-2-carboxylate and ethyl 4,5-dicyano-1-(2,2,2-trifluoroethyl)-1H-indole-2-carboxylate To a solution of ethyl 4-chloro-1-(2,2,2-trifluoroethyl)-5-{[(trifluoromethyl)sulfonyl]oxy}-1H-indole-2-carboxylate (1.34 g, 2.96 mmol) in DMF (20 mL), under N$_2$, was added Zn(CN)$_2$ (0.19 g, 1.63 mmol) and Pd(PPh$_3$)$_4$ (0.14 g, 0.12 mmol). The mixture was heated at 120° C. under N$_2$ for 3 h. Upon cooling, the mixture was partitioned between Et$_2$O and water. The organic phase was washed with water. The combined aqueous phases were reextracted twice with Et$_2$O. The organic phases were combined and washed with sat'd brine, dried (Na$_2$SO$_4$) and concentrated in vacuo. The residue was purified by flash chromatography (0-30% EtOAc-hexanes gradient) to afford ethyl 4-chloro-5-cyano-1-(2,2,2-trifluoroethyl)-1H-indole-2-carboxylate (0.60 g, 61% yield) (MS (ES) m/z 331 (M+1)) and ethyl 4,5-dicyano-1-(2,2,2-trifluoroethyl)-1H-indole-2-carboxylate (0.091 g, 10% yield) (MS (ES) m/z 322 (M+1)).

Example 8

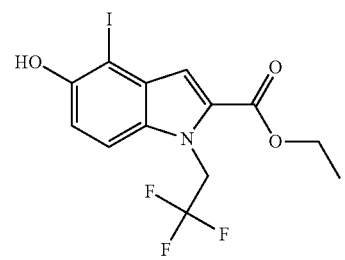 [SMILES: CCOC(=O)c1cc2c(I)c(O)ccc2n1CC(F)(F)F]

Ethyl 5-hydroxy-4-iodo-1-(2,2,2-trifluoroethyl)-1H-indole-2-carboxylate

Synthesized as described in Example 6A using NIS instead of sulfuryl chloride: MS (ES) m/z 414 (M+1).

Example 9

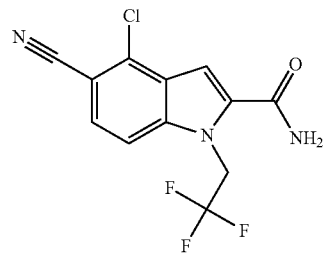 [SMILES: N#Cc1ccc2c(cc(C(N)=O)n2CC(F)(F)F)c1Cl]

4-Chloro-5-cyano-1-(2,2,2-trifluoroethyl)-1H-indole-2-carboxamide

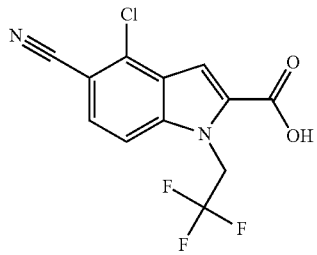 [SMILES: N#Cc1ccc2c(cc(C(=O)O)n2CC(F)(F)F)c1Cl]

A. 4-Chloro-5-cyano-1-(2,2,2-trifluoroethyl)-1H-indole-2-carboxylic acid

To a solution of ethyl 4-chloro-5-cyano-1-(2,2,2-trifluoroethyl)-1H-indole-2-carboxylate (0.02 g, 0.06 mmol) in 1:1 THF/MeOH (4 mL) was added 1N NaOH (1 mL) and the mixture was heated at 70° C. for 1.25 h. Upon cooling, the mixture was partially concentrated under vacuo. The residue was partitioned between EtOAc and 0.2N HCl. The organic phase was washed with sat'd brine. The combined aqueous phases were reextracted twice with EtOAc. The organic phases were combined and washed with sat'd brine, dried (Na$_2$SO$_4$) and concentrated in vacuo to afford the title compound (0.017 g, 94% yield): MS (ES) m/z 301 (M−1).

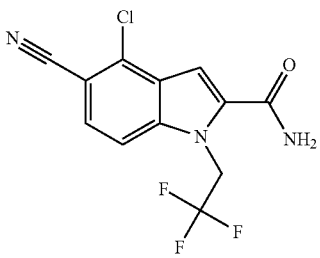 [SMILES: N#Cc1ccc2c(cc(C(N)=O)n2CC(F)(F)F)c1Cl]

B. 4-Chloro-5-cyano-1-(2,2,2-trifluoroethyl)-1H-indole-2-carboxamide

To a suspension of 4-chloro-5-cyano-1-(2,2,2-trifluoroethyl)-1H-indole-2-carboxylic acid (0.026 g, 0.086 mmol) in toluene (3 mL) was added thionyl chloride (0.01 g, 0.09 mmol) and a catalytic amount of DMF. The mixture was heated at 60° C. The reaction was followed by TLC at 30 min intervals, and additional thionyl chloride was added accordingly (an additional 0.082 g, 0.68 mmol was added). Upon cooling, a solution of NH$_3$ in MeOH (2M, 5 mL) was added and the mixture was stirred rapidly for 5 min. The mixture was concentrated in vacuo and the residue was partitioned between EtOAc and water. The organic phase was washed with sat'd brine, dried (Na$_2$SO$_4$) and concentrated in vacuo. The residue was purified by flash chromatography (10-80% EtOAc-hexanes gradient) and the product was crystallized from CH$_2$Cl$_2$-MeOH-hexanes to afford the title compound as a white solid (0.017 g, 65% yield): MS (ES) m/z 302 (M+1).

Example 10 and 11

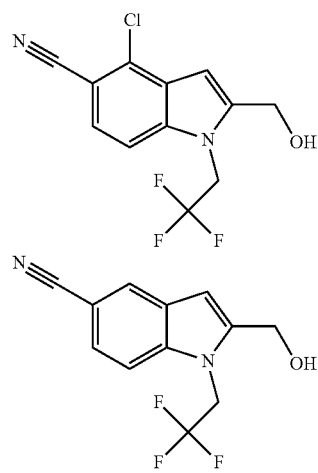

4-Chloro-2-(hydroxymethyl)-1-(2,2,2-trifluoroethyl)-1H-indole-5-carbonitrile (Example 10) and 2-(hydroxymethyl)-1-(2,2,2-trifluoroethyl)-1H-indole-5-carbonitrile (Example 11)

To an ice-cold solution of ethyl 4-chloro-5-cyano-1-(2,2,2-trifluoroethyl)-1H-indole-2-carboxylate (0.45 g, 1.36 mmol) in THF (12 mL), under N$_2$, was added LiBH$_4$ (2 M THF solution, 2.04 mL, 4.08 mmol). The mixture was stirred at rt for 8 h. Additional LiBH$_4$ (2M THF solution, 3 mL, 6 mmol) was added and stirred at rt for 60 h. The mixture was cooled in an ice bath and quenched by sequential dropwise addition of water and 1N HCl (exothermic). The mixture was partitioned between EtOAc and water. The organic phase was washed with sat'd brine, dried (Na$_2$SO$_4$) and concentrated in vacuo. The residue was purified by flash chromatography (10-80% EtOAc-hexanes gradient) to afford a mixture of the title compounds. A second flash chromatography (0-2% MeOH—CH$_2$Cl$_2$ gradient) afforded 4-chloro-2-(hydroxymethyl)-1-(2,2,2-trifluoroethyl)-1H-indole-5-carbonitrile (Example 10) as a white solid (0.25 g, 63% yield) (MS (ES) m/z 289 (M+1)) and 2-(hydroxymethyl)-1-(2,2,2-trifluoroethyl)-1H-indole-5-carbonitrile (Example 11) (0.021 g, 6% yield) (MS (ES) m/z 255 (M+1)).

Example 12

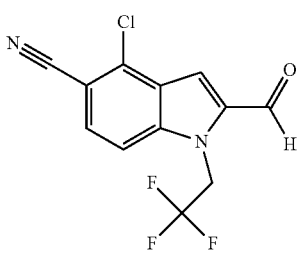 [SMILES: N#Cc1ccc2c(cc(C=O)n2CC(F)(F)F)c1Cl]

4-Chloro-2-formyl-1-(2,2,2-trifluoroethyl)-1H-indole-5-carbonitrile

To a solution of 4-chloro-2-(hydroxymethyl)-1-(2,2,2-trifluoroethyl)-1H-indole-5-carbonitrile (0.07 g, 0.24 mmol) in MeCN (3 mL) was added activated $MnO_2$ (0.21 g, 2.42 mmol). The mixture was stirred at rt for 2 h. Additional $MnO_2$ (0.11 g, 1.21 mmol) was added and stirred for 1 h. The solids were filtered off and washed with EtOAc, $CH_2Cl_2$ and MeOH. The filtrate was concentrated in vacuo and the residue was purified by radial chromatography (2-30% EtOAc-hexanes gradient) to afford the title compound (0.046 g, 67% yield): MS (ES) m/z 285 (M−1).

Example 13 and 14

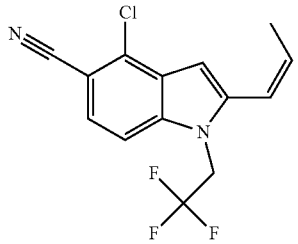

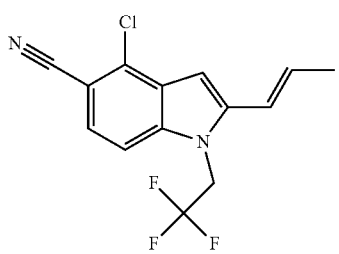

4-Chloro-2-[(1Z)-1-propen-1-yl]-1-(2,2,2-trifluoroethyl)-1H-indole-5-carbonitrile (Example 13) and 4-Chloro-2-[(1E)-1-propen-1-yl]-1-(2,2,2-trifluoroethyl)-1H-indole-5-carbonitrile (Example 14)

To a suspension of (ethyl)triphenylphosphonium bromide (0.069 g, 0.19 mmol) in THF (1 mL), under $N_2$, was added NaHMDS (1M THF solution, 0.19 mL, 0.19 mmol). After stirring at rt for 10 min, a solution of 4-chloro-2-formyl-1-(2,2,2-trifluoroethyl)-1H-indole-5-carbonitrile (0.041 g, 0.14 mmol) in THF (2 mL) was added. The reaction was followed by TLC and additional ylide reagent was added accordingly (the ylide reagent was prepared in a separate flask as initially indicated and then transferred via syringe to the reaction mixture). An additional total of 0.14 mmol of ylide was added in this fashion. After a total of 2 h, the mixture was partitioned between EtOAc and water. The organic phase was washed with sat'd brine, dried ($Na_2SO_4$) and concentrated in vacuo. The residue was purified by radial chromatography (10-70% $CH_2Cl_2$-hexanes gradient) to afford the title compounds as a ~2:1 mixture of the cis and trans isomers (0.032 g, 74% yield): MS (ES) m/z 299 (M+1).

Example 15

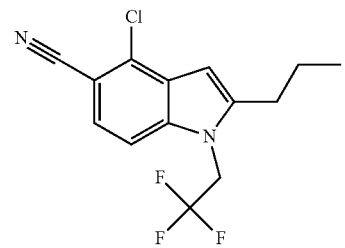 [SMILES: CCCc1cc2c(Cl)c(C#N)ccc2n1CC(F)(F)F]

4-Chloro-2-propyl-1-(2,2,2-trifluoroethyl)-1H-indole-5-carbonitrile

To a solution of 4-chloro-2-[(1Z)-1-propen-1-yl]-1-(2,2,2-trifluoroethyl)-1H-indole-5-carbonitrile (Example 13) and 4-chloro-2-[(1E)-1-propen-1-yl]-1-(2,2,2-trifluoroethyl)-1H-indole-5-carbonitrile (Example 14) (~2:1 mixture, 0.014 g, 0.046 mmol) in EtOAc (2 mL) under $N_2$, was added $PtO_2$ (4 mg) and the mixture was hydrogenated under balloon pressure for 15 min. The catalyst was filtered off and washed with EtOAc and MeOH. The filtrate was concentrated and the residue was purified by radial chromatography (2-30% EtOAc-hexanes gradient) to afford the title compound (0.013 g, 92% yield): MS (ES) m/z 301 (M+1).

Example 16

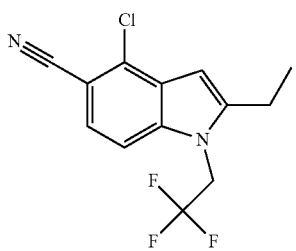 [SMILES: CCc1cc2c(Cl)c(C#N)ccc2n1CC(F)(F)F]

4-Chloro-2-ethenyl-1-(2,2,2-trifluoroethyl)-1H-indole-5-carbonitrile

Synthesized as described in Example 13-14 using (methyl)triphenylphosphonium bromide: MS (ES) m/z 285 (M+1).

Example 17

4-Chloro-2-ethyl-1-(2,2,2-trifluoroethyl)-1H-indole-5-carbonitrile

Synthesized as described in Example 15 from 4-chloro-2-ethenyl-1-(2,2,2-trifluoroethyl)-1H-indole-5-carbonitrile: MS (ES) m/z 287 (M+1).

Example 18

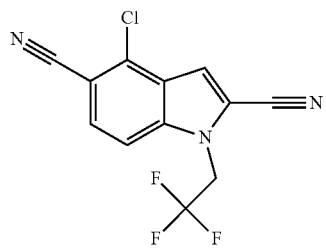 [SMILES: N#Cc1ccc2c(cc(C#N)n2CC(F)(F)F)c1Cl]

4-Chloro-1-(2,2,2-trifluoroethyl)-1H-indole-2,5-dicarbonitrile

To a suspension of 4-chloro-5-cyano-1-(2,2,2-trifluoroethyl)-1H-indole-2-carboxamide (0.05 g, 0.17 mmol) in CH$_2$Cl$_2$ (6 mL) was added pyridine (0.104 g, 1.32 mmol), followed by dropwise addition of TFAA (0.14 g, 0.66 mmol). The mixture was stirred at rt for 4 h and then concentrated in vacuo. The residue was partitioned between EtOAc and 0.5N HCl. The organic phase was washed with 0.5N HCl and sat'd brine, dried (Na$_2$SO$_4$) and concentrated in vacuo. The residue was purified by flash chromatography (0-50% EtOAc-hexanes gradient) and the product was crystallized from CH$_2$Cl$_2$-hexanes to afford the title compound as a white solid (0.033 g, 72% yield): MS (ES) m/z 284 (M+1).

Example 19

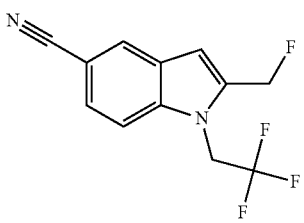 [SMILES: N#Cc1ccc2c(c1)cc(CF)n2CC(F)(F)F]

2-(Fluoromethyl)-1-(2,2,2-trifluoroethyl)-1H-indole-5-carbonitrile

To a solution of 2-(hydroxymethyl)-1-(2,2,2-trifluoroethyl)-1H-indole-5-carbonitrile (Example 11) (0.015 g, 0.059 mmol) in CH$_2$Cl$_2$ (3 mL) was added Deoxofluor (0.02 g, 0.089 mmol) and the resulting mixture was stirred at rt for 1 h. The mixture was partitioned between EtOAc and water. The organic phase was washed with sat'd brine, dried (Na$_2$SO$_4$) and concentrated in vacuo. The residue was purified by radial chromatography (5-40% EtOAc-hexanes gradient) and the product was crystallized from CH$_2$Cl$_2$-hexanes to afford the title compound as a white solid (0.005 g, 33% yield): MS (ES) m/z 257 (M+1).

Example 20

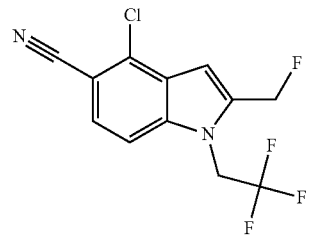 [SMILES: N#Cc1ccc2c(cc(CF)n2CC(F)(F)F)c1Cl]

4-Chloro-2-(fluoromethyl)-1-(2,2,2-trifluoroethyl)-1H-indole-5-carbonitrile Synthesized as described in Example 19 from 4-chloro-2-(hydroxymethyl)-1-(2,2,2-trifluoroethyl)-1H-indole-5-carbonitrile (Example 10): MS (ES) m/z 291 (M+1).

Example 21

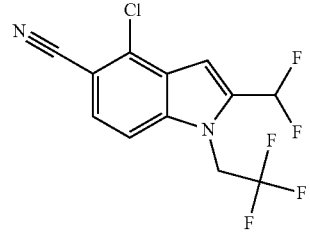 [SMILES: N#Cc1ccc2c(cc(C(F)F)n2CC(F)(F)F)c1Cl]

4-Chloro-2-(difluoromethyl)-1-(2,2,2-trifluoroethyl)-1H-indole-5-carbonitrile To a solution of 4-chloro-2-formyl-1-(2,2,2-trifluoroethyl)-1H-indole-5-carbonitrile (0.03 g, 0.11 mmol) in CH$_2$Cl$_2$ (2 mL) under N$_2$, at −78° C., was added Deoxofluor (0.072 g, 0.32 mmol). After 30 min, the cold bath was removed and the mixture was stirred at rt. After 5 h, additional Deoxofluor (0.07 g, 0.32 mmol) was added and the reaction was stirred at rt for 15 h. The mixture was partitioned between EtOAc and sat'd NaHCO$_3$. The organic phase was washed with sat'd brine, dried (Na$_2$SO$_4$) and concentrated in vacuo. $^1$HNMR of the residue showed 85% product and 15% starting aldehyde. The residue was redissolved in CH$_2$Cl$_2$ (3 mL) and treated with Deoxofluor (0.07 g, 0.32 mmol). After 15 h, the mixture was worked up as previously described. The residue was purified by radial chromatography (50-70% CH$_2$Cl$_2$-hexanes gradient) to afford the title compound (0.027 g, 84% yield): MS (ES) m/z 309 (M+1).

Example 22

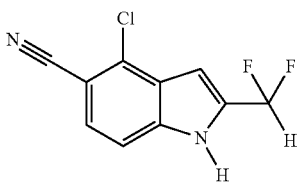 [SMILES: N#Cc1ccc2[nH]c(C(F)F)cc2c1Cl]

4-Chloro-2-(difluoromethyl)-1H-indole-5-carbonitrile

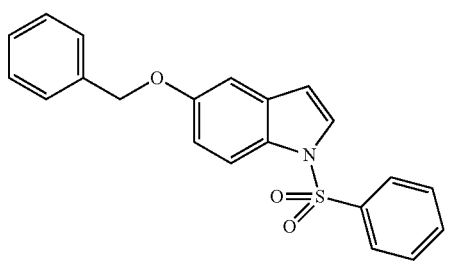 [SMILES: O=S(=O)(c1ccccc1)n1ccc2cc(OCc3ccccc3)ccc21]

A. 5-[(Phenylmethyl)oxy]-1-(phenylsulfonyl)-1H-indole

To a suspension of 5-[(phenylmethyl)oxy]-1H-indole (10 g, 44.78 mmol) in toluene (100 mL) was added benzenesulfonyl chloride (9.1 g, 51.5 mmol), tetrabutylammonium bromide (1.44 g, 4.48 mmol) and a solution of NaOH (23 g, 582 mmol) in 100 mL of water. The mixture was rapidly stirred at rt. After 30 min, additional benzenesulfonyl chloride (0.97 g, 5.5 mmol) was added and stirred for another 30 min. The mixture was partitioned between Et$_2$O and water. The aqueous phase was extracted with Et$_2$O. The combined organic phases were washed with water and sat'd brine, dried (Na$_2$SO$_4$) and concentrated in vacuo. The residue was purified by flash chromatography (0-30% EtOAc-hexanes gradient) to afford the title compound (14.2 g, 87% yield): $^1$H NMR (400 MHz, CDCl$_3$) δ 7.89 (d, J=9.0 Hz, 1H), 7.85 (d, J=7.6 Hz, 2H), 7.53-7.50 (m, 2H), 7.44-7.29 (m, 7H), 7.03 (d, J=2.4 Hz, 1H), 7.0 (dd, J=9.0, 2.4 Hz, 1H), 6.57 (d, J=3.7 Hz, 1H), 5.05 (s, 2H); MS (ES) m/z 364 (M+1).

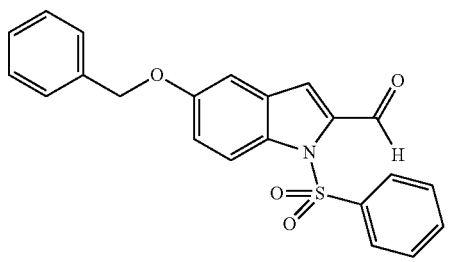 [SMILES: O=Cc1cc2cc(OCc3ccccc3)ccc2n1S(=O)(=O)c1ccccc1]

B. 5-[(Phenylmethyl)oxy]-1-(phenylsulfonyl)-1H-indole-2-carbaldehyde

To a solution of 5-[(phenylmethyl)oxy]-1-(phenylsulfonyl)-1H-indole (1.5 g, 4.12 mmol) in THF (20 mL), under N$_2$, at −78° C., was added n-BuLi (2.5M solution in hexane, 2.15 mL, 5.37 mmol) dropwise. After stirring at −78° C. for 30 min, anhydrous DMF (0.54 g, 7.42 mmol) was added. After 5 min, the −78° C. bath was replaced with an ice bath. After 45 min, sat'd NH$_4$Cl solution (20 mL) was added and the mixture was partitioned between Et$_2$O and water. The organic phase was washed with water and sat'd brine, dried (Na$_2$SO$_4$) and concentrated in vacuo. The residue was purified by flash chromatography (20-70% CH$_2$Cl$_2$-hexanes gradient) to afford the title compound (1.24 g, 77% yield): $^1$H NMR (400 MHz, CDCl$_3$) δ 10.5 (s, 1H), 8.14 (d, J=9.3 Hz, 1H), 7.74 (d, J=7.6 Hz, 2H), 7.53 (t, J=7.6 Hz, 1H), 7.43-7.31 (m, 8H), 7.22 (dd, J=9.3, 2.4 Hz, 1H), 7.06 (d, J=2.4 Hz, 1H), 5.06 (s, 2H); MS (ES) m/z 392 (M+1).

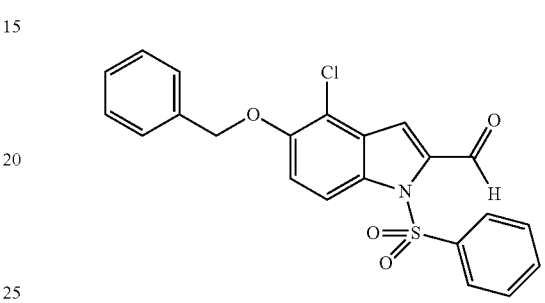

C. 4-Chloro-5-[(phenylmethyl)oxy]-1-(phenylsulfonyl)-1H-indole-2-carbaldehyde To a solution of 5-[(phenylmethyl)oxy]-1-(phenylsulfonyl)-1H-indole-2-carbaldehyde (3.22 g, 8.22 mmol) in 1:1 AcOH—CH$_2$Cl$_2$ (140 mL) was added sulfuryl chloride (1.24 g, 9.19 mmol) dropwise and the resulting mixture was stirred at rt for 15 h. Additional sulfuryl chloride (0.084 g, 0.62 mmol) was added and stirring was continued for 1 h. The mixture was partially concentrated to ~½ volume under a stream of N$_2$ and the resulting light yellow crystals were collected by filtration and washed sequentially with cold AcOH and hexanes, to afford the title compound (2.58 g, 74% yield): $^1$H NMR (400 MHz, CDCl$_3$) δ 10.49 (s, 1H), 8.05 (d, J=9.3 Hz, 1H), 7.74 (d, J=7.6 Hz, 2H), 7.58-7.54 (m, 2H), 7.46-7.30 (m, 7H), 7.22 (d, J=9 Hz, 1H), 5.19 (s, 2H).

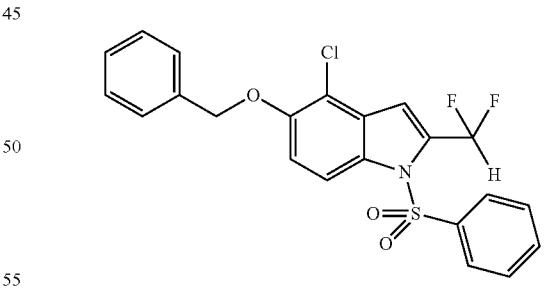

D. 4-Chloro-2-(difluoromethyl)-5-[(phenylmethyl)oxy]-1-(phenylsulfonyl)-1H-indole To a suspension of 4-chloro-5-[(phenylmethyl)oxy]-1-(phenylsulfonyl)-1H-indole-2-carbaldehyde (7.15 g, 16.82 mol) in anhydrous CH$_2$Cl$_2$ (40 mL) was slowly added Deoxofluor (18.62 g, 84.12 mmol). After 15 h, the mixture was partially concentrated in vacuo to ~⅓ volume. Hexane (~70 mL) was added slowly to the mixture while stirring and the solids were collected by filtration and washed with hexanes.

The solids were subsequently triturated with cold MeOH, collected by filtration and washed sequentially with cold MeOH and hexanes to afford the title compound as an off-white solid (6.64 g, 88% yield): $^1$H NMR (400 MHz, CDCl$_3$) δ 7.92 (d, J=9.0 Hz, 1H), 7.87 (d, J=7.8 Hz, 2H), 7.57 (t, J=7.5 Hz, 1H), 7.47-7.42 (m, 4H), 7.37 (t, J=7.3 Hz, 2H), 7.33-7.17 (m, 3H), 7.09 (d, J=9.0 Hz, 1H), 5.17 (s, 2H); MS (ES) m/z 446 (M−1).

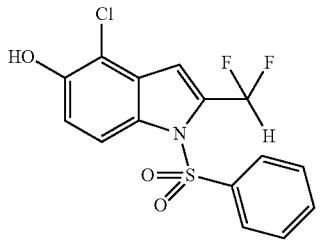 [SMILES: O=S(=O)(c1ccccc1)n1c(C(F)F)cc2c(Cl)c(O)ccc21]

E. 4-Chloro-2-(difluoromethyl)-1-(phenylsulfonyl)-1H-indol-5-ol

To a solution of 4-chloro-2-(difluoromethyl)-5-[(phenylmethyl)oxy]-1-(phenylsulfonyl)-1H-indole (2.6 g, 5.82 mmol) in anhydrous CH$_2$Cl$_2$ (80 mL), under N$_2$, at −78° C., was slowly added a solution of BBr$_3$ in CH$_2$Cl$_2$ (1M, 6.1 mL). After stirring at −78° C. for 30 min, additional BBr$_3$ solution (1M, 0.3 mL) was added and stirring was continued at −78° C. for 30 min. While at −78° C., sat'd aqueous NaHCO$_3$ solution (~10 mL) was added slowly, the cold bath was then removed and the reaction mixture brought to rt. The mixture was partitioned between CH$_2$Cl$_2$ and sat'd NaHCO$_3$ solution. The aqueous phase was washed with CH$_2$Cl$_2$. The combined organic phases were washed with sat'd brine, dried (Na$_2$SO$_4$) and concentrated in vacuo. The residue was purified by flash chromatography (0-40% EtOAc-hexanes gradient) to afford the title compound (1.87 g, 89% yield): $^1$H NMR (400 MHz, CDCl$_3$) δ 7.93 (d, J=9.0 Hz, 1H), 7.89 (d, J=7.6 Hz, 2H), 7.58 (t, J=7.6 Hz, 1H), 7.46 (t, J=7.6 Hz, 2H), 7.32 (t, J=54.2 Hz, 1H), 7.12-7.08 (m, 2H), 5.42 (bs, 1H); MS (ES) m/z 356 (M−1).

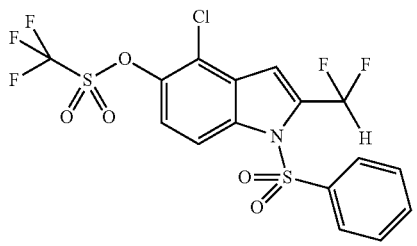 [SMILES: O=S(=O)(c1ccccc1)n1c(C(F)F)cc2c(Cl)c(OS(=O)(=O)C(F)(F)F)ccc21]

F. 4-Chloro-2-(difluoromethyl)-1-(phenylsulfonyl)-1H-indol-5-yl trifluoromethanesulfonate To a solution of 4-chloro-2-(difluoromethyl)-1-(phenylsulfonyl)-1H-indol-5-ol (1.85 g, 5.17 mmol) in CH$_2$Cl$_2$ (75 mL) was added Et$_3$N (0.58 g, 5.68 mmol) and triflic anhydride (1.6 g, 5.68 mmol). After stirring at rt for 1 h, additional Et$_3$N (0.052 g, 0.52 mmol) and triflic anhydride (0.147 g, 0.52 mmol) were added. After 1 h, the mixture was concentrated in vacuo and the residue was partitioned between EtOAc and 0.1N HCl. The organic phase was washed with water and brine, dried (Na$_2$SO$_4$) and concentrated in vacuo. The residue was purified by flash chromatography (0-20% EtOAc-hexanes gradient) to afford the title compound (2.25 g, 88% yield): $^1$H NMR (400 MHz, CDCl$_3$) δ 8.09 (d, J=9.0 Hz, 1H), 7.95 (d, J=7.8 Hz, 2H), 7.64 (t, J=7.5 Hz, 1H), 7.52 (t, J=7.8 Hz, 2H), 7.37 (d, J=9.3 Hz, 1H), 7.35 (t, J=54.2 Hz, 1H), 7.54 (s, 1H, partially overlapping CHCl$_3$ signal); MS (ES) m/z 488 (M−1).

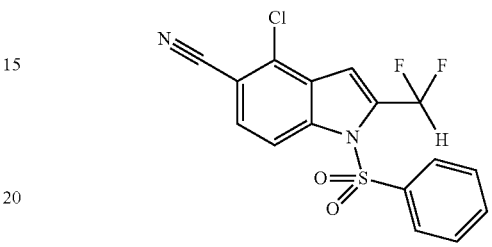

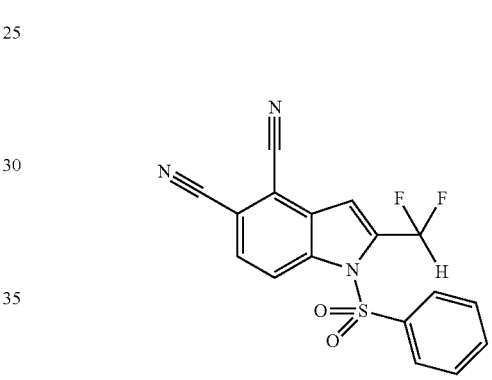

G. 4-Chloro-2-(difluoromethyl)-1-(phenylsulfonyl)-1H-indole-5-carbonitrile and 2-(Difluoromethyl)-1-(phenylsulfonyl)-1H-indole-4,5-dicarbonitrile To a solution of 4-chloro-2-(difluoromethyl)-1-(phenylsulfonyl)-1H-indol-5-yl trifluoromethanesulfonate (0.75 g, 1.53 mmol) in anhydrous DMF (10 mL) under N$_2$, was added Zn(CN)$_2$ (0.093 g, 0.80 mmol) and Pd(PPh$_3$)$_4$ (0.088 g, 0.077 mmol) and the resulting mixture was heated at 120° C. for 2 h. Upon cooling, the mixture was partitioned between Et$_2$O and water. The organic phase was washed with water. The combined aqueous phases were reextracted with Et$_2$O. The combined organic phases were washed with sat'd brine, dried (Na$_2$SO$_4$) and concentrated in vacuo. The residue was purified by flash chromatography (0-40% EtOAc-hexanes gradient) to afford 4-chloro-2-(difluoromethyl)-1-(phenylsulfonyl)-1H-indole-5-carbonitrile (0.35 g, 62% yield) $^1$H NMR (400 MHz, CDCl$_3$) δ 8.11 (d, J=8.8 Hz, 1H), 7.94 (d, J=7.8 Hz, 2H), 7.67-7.63 (m, 2H), 7.52 (t, J=7.8 Hz, 2H), 7.35 (t, J=54 Hz, 1H), 7.25 (s, 1H, overlapping CHCl$_3$ signal); MS (ES) m/z 365 (M−1)) and 2-(difluoromethyl)-1-(phenylsulfonyl)-1H-indole-4,5-dicarbonitrile (0.054 g, 10% yield) ($^1$H NMR (400 MHz, CDCl$_3$) δ 8.45 (d, J=8.8 Hz, 1H), 7.96 (d, J=7.8 Hz, 2H), 7.77 (d, J=8.8 Hz, 1H), 7.68 (t, J=7.6 Hz, 1H), 7.55 (t, J=7.8 Hz, 2H), 7.38 (t, J=54 Hz, 1H), 7.35 (s, 1H); MS (ES) m/z 356 (M−1)).

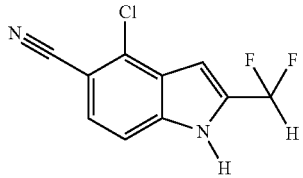 [SMILES: N#Cc1ccc2[nH]c(C(F)F)cc2c1Cl]

H. 4-Chloro-2-(difluoromethyl)-1H-indole-5-carbonitrile

To a solution of 4-chloro-2-(difluoromethyl)-1-(phenylsulfonyl)-1H-indole-5-carbonitrile (1.05 g, 2.85 mmol) in anhydrous THF (12 mL) under $N_2$, was added TBAF (1M in THF, 8.6 mL) and the mixture was heated at 75° C. for 2 h. Upon cooling, the mixture was partitioned between EtOAc and 0.2N HCl. The organic phase was washed with 0.2N HCl and sat'd brine. The combined aqueous phases were reextracted with EtOAc. The second EtOAc phase was washed with 0.2N HCl and sat'd brine. The combined organic phases were dried ($Na_2SO_4$) and concentrated in vacuo. The residue was purified by flash chromatography (0-50% EtOAc-hexanes gradient) to afford the title compound as a light yellow solid (0.595 g, 92% yield): $^1$H NMR (400 MHz, $CD_3OD$) δ 7.53 (d, J=8.6 Hz, 1H), 7.51 (d, J=8.8 Hz, 1H), 7.03 (t, J=54.2 Hz, 1H), 6.95 (bt, J=2 Hz, 1H); MS (ES) m/z 227 (M+1).

Example 23

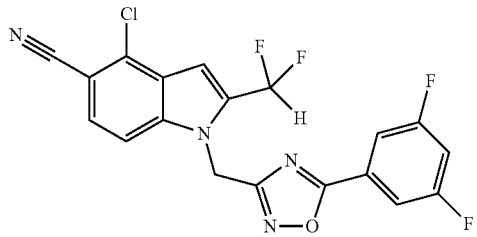 [SMILES: N#Cc1ccc2c(cc(C(F)F)n2Cc2noc(-c3cc(F)cc(F)c3)n2)c1Cl]

4-Chloro-2-(difluoromethyl)-1-{[5-(3,5-difluorophenyl)-1,2,4-oxadiazol-3-yl]methyl}-1H-indole-5-carbonitrile To a solution of 4-chloro-2-(difluoromethyl)-1H-indole-5-carbonitrile (0.23 g, 1.0 mmol) in anhydrous MeCN (5 mL) was added $Cs_2CO_3$ (0.38 g, 1.15 mmol) and 3-(chloromethyl)-5-(3,5-difluorophenyl)-1,2,4-oxadiazole (0.27 g, 1.15 mmol). The mixture was heated in a sealed tube at 95° C., under $N_2$, for 1 h. Upon cooling, the mixture was partitioned between EtOAc and water. The organic phase was washed with water and sat'd brine, dried ($Na_2SO_4$) and concentrated in vacuo. The residue was purified by flash chromatography (2-30% EtOAc-hexanes gradient) and the product was crystallized from $CH_2Cl_2$-hexanes to afford the title compound as a white solid (0.32 g, 77% yield): $^1$H NMR (400 MHz, acetone-$d_6$) δ 7.91 (d, J=8.8 Hz, 1H), 7.74 (d, J=8.8 Hz, 1H), 7.70 (m, 2H), 7.45 (t, J=53.4 Hz, 1H), 7.42 (tt, J=9.0, 2.4 Hz, 1H), 7.20 (s, 1H), 5.95 (s, 2H); MS (ES) m/z 421 (M+1).

Example 24

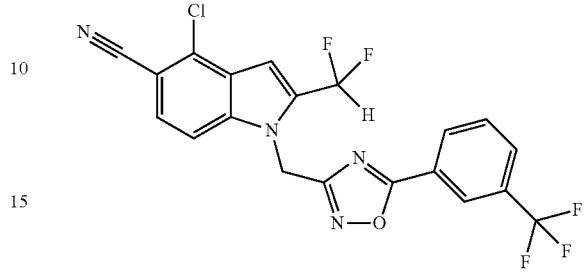

4-Chloro-2-(difluoromethyl)-1-({5-[3-(trifluoromethyl)phenyl]-1,2,4-oxadiazol-3-yl}methyl)-1H-indole-5-carbonitrile Synthesized as described in Example 23 using 3-(chloromethyl)-5-[3-(trifluoromethyl)phenyl]-1,2,4-oxadiazole: MS (ES) m/z 451 (M−1).

Example 25

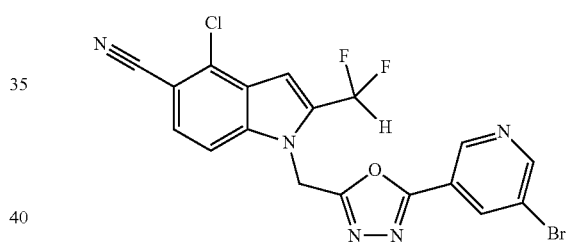

1-{[5-(5-Bromo-3-pyridinyl)-1,3,4-oxadiazol-2-yl]methyl}-4-chloro-2-(difluoromethyl)-1H-indole-5-carbonitrile

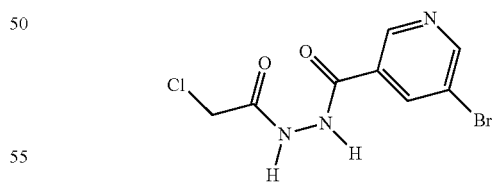

A. 5-Bromo-N'-(chloroacetyl)-3-pyridinecarbohydrazide

To an ice-cold suspension of 5-bromo-3-pyridinecarbohydrazide (3.0 g, 13.88 mmol) in anhydrous $CH_2Cl_2$ (60 mL) was added 4-methyl-morpholine (2.1 g, 20.82 mmol), followed by dropwise addition of chloroacetyl chloride (1.88 g, 16.67 mmol). The cold bath was then removed and the mixture stirred at rt for 15 h. Heavy precipitation occurred and the mixture was diluted with additional CH$_2$Cl$_2$ (50 mL) and stirring continued for 24 h. The solids were collected by filtration and washed with CH$_2$Cl$_2$ to afford the title compound (3.66 g, 90% yield): MS (ES) m/z 292 and 294 (M+1 Br isotopes).

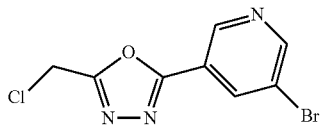 [SMILES: ClCc1nnc(-c2cncc(Br)c2)o1]

B. 3-Bromo-5-[5-(chloromethyl)-1,3,4-oxadiazol-2-yl]pyridine

A suspension of 5-bromo-N'-(chloroacetyl)-3-pyridinecarbohydrazide (3.65 g, 12.48 mmol) in POCl$_3$ (20 mL) was heated at 110° C. for 1.5 h. Upon cooling, the mixture was concentrated in vacuo. The residue was diluted with EtOAc and sat'd NaHCO$_3$ solution was added slowly while stirring. The pH of the aqueous phase was adjusted to ~8 by addition of sat'd K$_2$CO$_3$ solution. The phases were separated and the aqueous phase was extracted twice with EtOAc. The combined organic phases were washed with sat'd brine, dried (Na$_2$SO$_4$), and concentrated in vacuo. The residue was purified by flash chromatography (0-50% EtOAc-hexanes gradient) to afford the title compound as a light yellow solid (2.01 g, 59% yield): MS (ES) m/z 274 and 276 (M+1 Br isotopes).

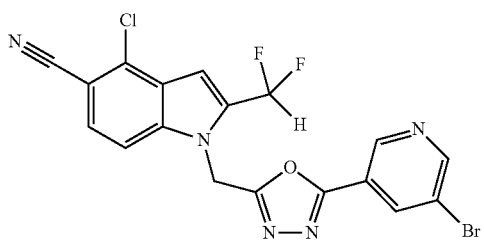 [SMILES: N#Cc1ccc2c(cc(C(F)F)n2Cc2nnc(-c3cncc(Br)c3)o2)c1Cl]

C. 1-{[5-(5-Bromo-3-pyridinyl)-1,3,4-oxadiazol-2-yl]methyl}-4-chloro-2-(difluoromethyl)-1H-indole-5-carbonitrile Synthesized as described in Example 23 using 3-bromo-5-[5-(chloromethyl)-1,3,4-oxadiazol-2-yl]pyridine: MS (ES) m/z 464 and 466 (M+1 Br isotopes).

Example 26

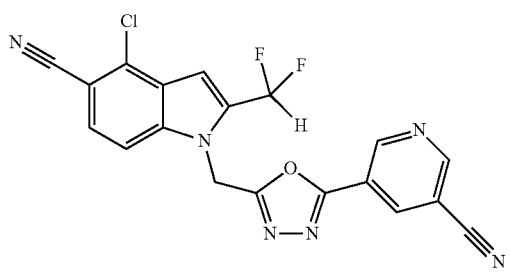 [SMILES: N#Cc1cncc(-c2nnc(Cn3c(C(F)F)cc4c(Cl)c(C#N)ccc43)o2)c1]

4-Chloro-1-{[5-(5-cyano-3-pyridinyl)-1,3,4-oxadiazol-2-yl]methyl}-2-(difluoromethyl)-1H-indole-5-carbonitrile To a solution of 1-{[5-(5-bromo-3-pyridinyl)-1,3,4-oxadiazol-2-yl]methyl}-4-chloro-2-(difluoromethyl)-1H-indole-5-carbonitrile (0.015 g, 0.032 mmol) in anhydrous DMF (1.5 mL) under N$_2$, was added Zn(CN)$_2$ (0.002 g, 0.016 mmol) and Pd(PPh$_3$)$_4$ (0.004 g, 0.0032 mmol). The mixture was heated at 120° C., under N$_2$ for 1 h. Additional Pd(PPh$_3$)$_4$ (0.004 g, 0.0032 mmol) was added and the mixture was heated at 120° C., under N$_2$ for another 40 min. Upon cooling, the mixture was partitioned between Et$_2$O and water. The organic phase was washed with water and sat'd brine. The combined aqueous phases were washed with EtOAc. The EtOAc phase was washed with water (2×) and brine. The Et$_2$O and EtOAc phases were combined, dried (Na$_2$SO$_4$) and concentrated in vacuo. The residue was purified by flash chromatography (5-70% EtOAc-hexanes gradient), followed by a second purification by radial chromatography (0-3% MeOH—CH$_2$Cl$_2$ gradient). The product was crystallized from CH$_2$Cl$_2$-hexanes to afford the title compound as a white solid (0.008 g, 61% yield): MS (ES) m/z 411 (M+1).

Example 27

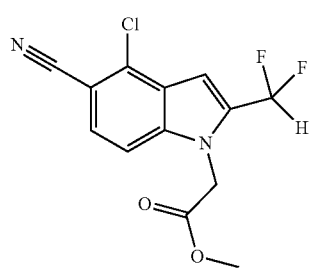 [SMILES: COC(=O)Cn1c(C(F)F)cc2c(Cl)c(C#N)ccc21]

4-Chloro-1-(cyanomethyl)-2-(difluoromethyl)-1H-indole-5-carbonitrile

Synthesized as described in Example 4 using 4-chloro-2-(difluoromethyl)-1H-indole-5-carbonitrile, bromoacetonitrile (2 eq) and Cs$_2$CO$_3$ (2 eq): MS (ES) m/z 264 (M−1).

Example 28

Methyl [4-chloro-5-cyano-2-(difluoromethyl)-1H-indol-1-yl]acetate

Synthesized as described in Example 4 using 4-chloro-2-(difluoromethyl)-1H-indole-5-carbonitrile, methyl bromoacetate (2 eq) and $Cs_2CO_3$ (2 eq): MS (ES) m/z 299 (M+1).

Example 29

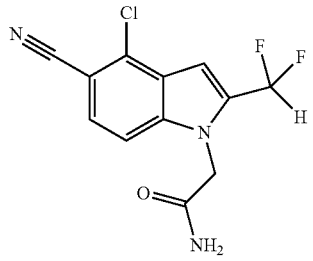 [SMILES: N#Cc1ccc2c(cc(C(F)F)n2CC(N)=O)c1Cl]

2-[4-Chloro-5-cyano-2-(difluoromethyl)-1H-indol-1-yl]acetamide

Synthesized as described in Example 4 using 4-chloro-2-(difluoromethyl)-1H-indole-5-carbonitrile, bromoacetamide (2 eq) and $Cs_2CO_3$ (2 eq): MS (ES) m/z 284 (M+1).

Example 30

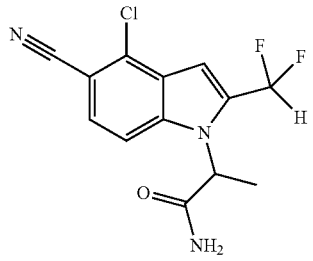 [SMILES: CC(C(N)=O)n1c(C(F)F)cc2c(Cl)c(C#N)ccc21]

2-[4-Chloro-5-cyano-2-(difluoromethyl)-1H-indol-1-yl]propanamide

Synthesized as described in Example 4 using 4-chloro-2-(difluoromethyl)-1H-indole-5-carbonitrile, 2-bromo-propionamide (2 eq) and $Cs_2CO_3$ (2 eq). After heating at 90° C. for 4 h, additional 2-bromo-propionamide (2 eq) and $Cs_2CO_3$ (2 eq) were added and the reaction mixture heated at 110° C. for 15 h: MS (ES) m/z 298 (M+1).

Example 31

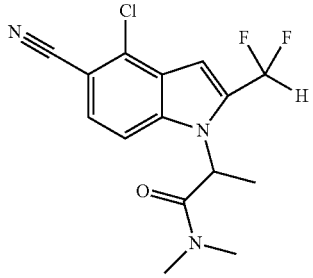 [SMILES: CC(C(=O)N(C)C)n1c(C(F)F)cc2c(Cl)c(C#N)ccc21]

2-[4-Chloro-5-cyano-2-(difluoromethyl)-1H-indol-1-yl]-N,N-dimethylpropanamide

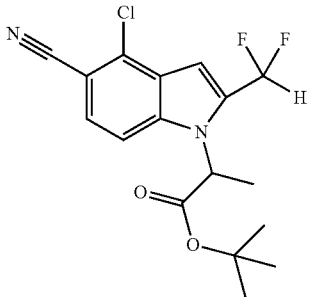 [SMILES: CC(C(=O)OC(C)(C)C)n1c(C(F)F)cc2c(Cl)c(C#N)ccc21]

A. 1,1-Dimethylethyl 2-[4-chloro-5-cyano-2-(difluoromethyl)-1H-indol-1-yl]propanoate Synthesized as described in Example 4 using 4-chloro-2-(difluoromethyl)-1H-indole-5-carbonitrile, 2-bromopropionic acid t-butyl ester (1.5 eq) and $Cs_2CO_3$ (1.5 eq): MS (ES) m/z 355 (M+1).

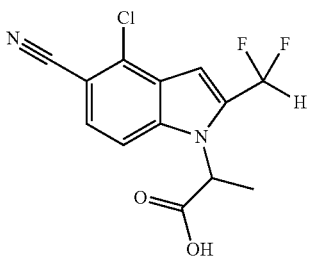 [SMILES: CC(C(=O)O)n1c(C(F)F)cc2c(Cl)c(C#N)ccc21]

B. 2-[4-Chloro-5-cyano-2-(difluoromethyl)-1H-indol-1-yl]propanoic acid

To a solution of 1,1-dimethylethyl 2-[4-chloro-5-cyano-2-(difluoromethyl)-1H-indol-1-yl]propanoate (0.072 g, 0.2 mmol) in $CH_2Cl_2$ (5 mL) was added TFA (5 mL) and stirred at rt for 4 h. The mixture was concentrated in vacuo. The residue was diluted with $Et_2O$ and hexane was added while stirring. The solids were collected by filtration and washed with hexane to afford the title compound as a white solid (0.058 g, 95% yield): MS (ES) m/z 299 (M+1).

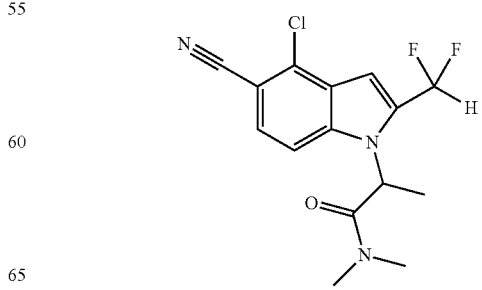

C. 2-[4-Chloro-5-cyano-2-(difluoromethyl)-1H-indol-1-yl]-N,N-dimethylpropanamide To a solution of 2-[4-chloro-5-cyano-2-(difluoromethyl)-1H-indol-1-yl]propanoic acid (0.010 g, 0.034 mmol) in anhydrous DMF (1.5 mL) was added HATU (0.014 g, 0.037 mmol) and DIEA (0.0048 g, 0.0037 mmol) and stirred at rt. After 10 min, dimethylamine (2M in THF, 0.17 mL, 0.34 mmol) was added and stirred at rt for 45 min. The mixture was partitioned between Et$_2$O and 0.2N HCl. The organic phase was washed with 0.2N HCl, 0.2N NaOH and sat'd brine, dried (Na$_2$SO$_4$) and concentrated in vacuo. The residue was purified by flash chromatography (0-1% MeOH—CH$_2$Cl$_2$ gradient) and the product was crystallized from CH$_2$Cl$_2$-hexanes to afford the title compound as a white solid (0.007 g, 64% yield): MS (ES) m/z 326 (M+1).

Example 32

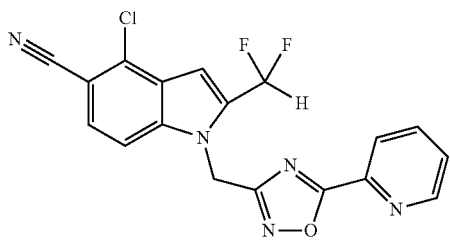 [SMILES: N#Cc1ccc2c(cc(C(F)F)n2Cc2noc(-c3ccccn3)n2)c1Cl]

4-Chloro-2-(difluoromethyl)-1-{[5-(2-pyridinyl)-1,2,4-oxadiazol-3-yl]methyl}-1H-indole-5-carbonitrile

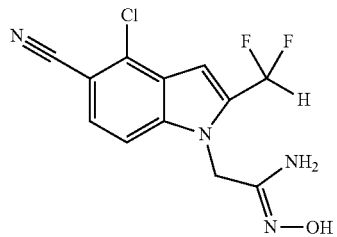 [SMILES: N#Cc1ccc2c(cc(C(F)F)n2C/C(N)=N/O)c1Cl]

A. (1Z)-2-[4-Chloro-5-cyano-2-(difluoromethyl)-1H-indol-1-yl]-N-hydroxyethanimidamide To a solution of 4-chloro-1-(cyanomethyl)-2-(difluoromethyl)-1H-indole-5-carbonitrile (Example 27) (0.147 g, 0.55 mmol) in anhydrous DMF (4 mL) was added H$_2$NOH.HCl (0.153 g, 2.2 mmol) and NaOAc (0.18 g, 2.2 mmol) and the mixture was stirred at rt for 15 h. The mixture was partitioned between Et$_2$O and sat'd NaHCO$_3$ solution. The organic phase was washed with water and sat'd brine, dried (Na$_2$SO$_4$) and concentrated in vacuo.

The residue was purified by flash chromatography (10-100% hexanes to EtOAc gradient) to afford the title compound as a white solid (0.147 g, 89% yield): MS (ES) m/z 299 (M+1).

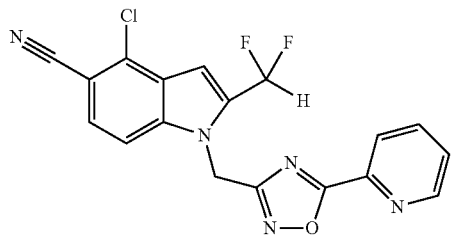 [SMILES: N#Cc1ccc2c(cc(C(F)F)n2Cc2noc(-c3ccccn3)n2)c1Cl]

B. 4-Chloro-2-(difluoromethyl)-1-{[5-(2-pyridinyl)-1,2,4-oxadiazol-3-yl]methyl}-1H-indole-5-carbonitrile To a solution of (1Z)-2-[4-chloro-5-cyano-2-(difluoromethyl)-1H-indol-1-yl]-N-hydroxyethanimidamide (0.011 g, 0.035 mmol) in anhydrous THF (1.5 mL), under N$_2$, was added picolinoyl chloride hydrochloride (0.0066 g, 0.037 mmol) and Et$_3$N (0.0078 g, 0.077 mmol). The mixture was stirred at rt for 30 min. The reaction was monitored by TLC and additional acid chloride (0.003 g, 0.018 mmol) and Et$_3$N (0.0035 g, 0.035 mmol) were added and stirring continued at rt for 1 h. The mixture was then heated in a microwave at 120° C. for 20 min, and subsequently at 150° C. for 2 h. Upon cooling, the mixture was partitioned between EtOAc and 0.1N HCl. The organic phase was washed with 0.1N HCl, sat'd NaHCO$_3$ solution and sat'd brine, dried (Na$_2$SO$_4$), and concentrated in vacuo. The residue was purified by flash chromatography (5-50% EtOAc-hexanes gradient), followed by a second purification by radial chromatography (5-70% EtOAc-hexanes gradient). The product was crystallized from CH$_2$Cl$_2$-hexanes to afford the title compound as a white solid (0.005 g, 38% yield): MS (ES) m/z 386 (M+1).

Example 33

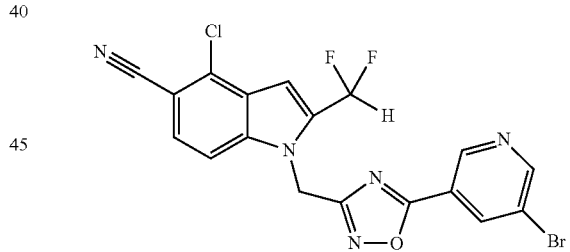

1-{[5-(5-Bromo-3-pyridinyl)-1,2,4-oxadiazol-3-yl]methyl}-4-chloro-2-(difluoromethyl)-1H-indole-5-carbonitrile To a solution of 5-bromonicotinic acid (0.017 g, 0.082 mmol) in anhydrous DMF (2 mL) was added HATU (0.031 g, 0.082 mmol) and DIEA (0.011 g, 0.082 mmol) and stirred at rt. After 10 min, a solution of (1Z)-2-[4-chloro-5-cyano-2-(difluoromethyl)-1H-indol-1-yl]-N-hydroxyethanimidamide (0.023 g, 0.077 mmol) in THF (1.5 mL) was added and stirring was continued at rt. After 30 min, the mixture was heated in a microwave at 150° C. for 20 min. Upon cooling, water (~5 mL) was added to the stirring reaction mixture and the precipitated solids were collected by filtration and washed sequentially with water and hexanes. The product was further purified by flash chromatography (0-20% EtOAc-hexanes gradient), followed by crystallization from CH₂Cl₂-hexanes to afford the title compound as a white solid (0.011 g, 31% yield): MS (ES) m/z 464 and 466 (M+1 Br isotopes).

Example 34

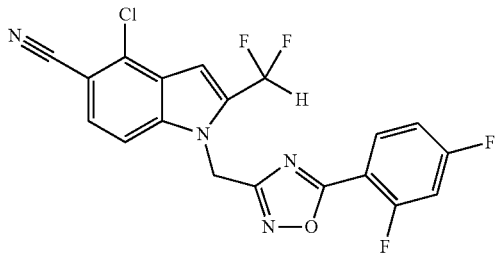 [SMILES: N#Cc1ccc2c(cc(C(F)F)n2Cc2noc(-c3ccc(F)cc3F)n2)c1Cl]

4-Chloro-2-(difluoromethyl)-1-{[5-(2,4-difluorophenyl)-1,2,4-oxadiazol-3-yl]methyl}-1H-indole-5-carbonitrile Synthesized as described in Example 32B using 2,4-difluorobenzoyl chloride (1.05 eq) and Et₃N (1.05 eq) with DCE-DMF (4:1) as the solvent and the heating step done in a microwave at 150 C for 40 min: MS (ES) m/z 419 (M−1).

Example 35

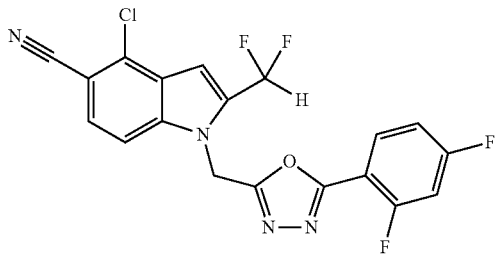 [SMILES: N#Cc1ccc2c(cc(C(F)F)n2Cc2nnc(-c3ccc(F)cc3F)o2)c1Cl]

4-Chloro-2-(difluoromethyl)-1-{[5-(2,4-difluorophenyl)-1,3,4-oxadiazol-2-yl]methyl}-1H-indole-5-carbonitrile

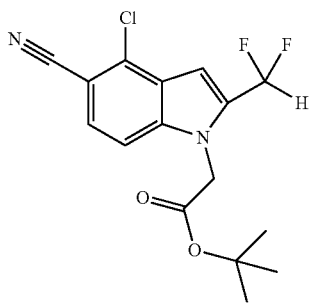 [SMILES: CC(C)(C)OC(=O)Cn1c(C(F)F)cc2c(Cl)c(C#N)ccc21]

A. 1,1-Dimethylethyl [4-chloro-5-cyano-2-(difluoromethyl)-1H-indol-1-yl]acetate

Synthesized as described in Example 4 using 4-chloro-2-(difluoromethyl)-1H-indole-5-carbonitrile, t-butyl bromoacetate (1.5 eq) and Cs₂CO₃ (1.5 eq) with MeCN as the solvent (in a sealed tube): MS (ES) m/z 341 (M+1).

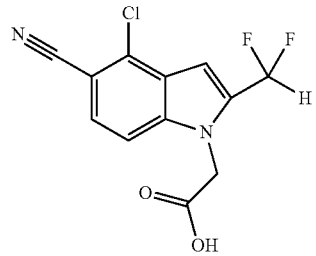 [SMILES: N#Cc1ccc2c(cc(C(F)F)n2CC(=O)O)c1Cl]

B. [4-Chloro-5-cyano-2-(difluoromethyl)-1H-indol-1-yl]acetic acid

Synthesized as described in Example 31B from 1,1-dimethylethyl [4-chloro-5-cyano-2-(difluoromethyl)-1H-indol-1-yl]acetate: MS (ES) m/z 285 (M+1).

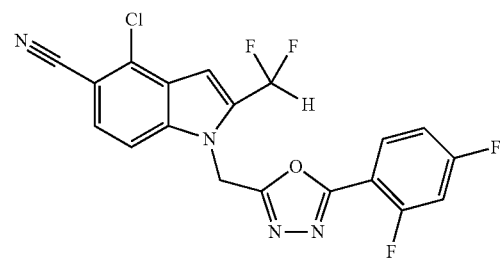 [SMILES: N#Cc1ccc2c(cc(C(F)F)n2Cc2nnc(-c3ccc(F)cc3F)o2)c1Cl]

C. 4-Chloro-2-(difluoromethyl)-1-{[5-(2,4-difluorophenyl)-1,3,4-oxadiazol-2-yl]methyl}-1H-indole-5-carbonitrile To a suspension of [4-chloro-5-cyano-2-(difluoromethyl)-1H-indol-1-yl]acetic acid (0.020 g, 0.070 mmol) in DCE (3 mL), under N₂, was added EDCl (0.016 g, 0.081 mmol) and stirred at rt. After 5 min, 2,4-difluorobenzohydrazide (0.014 g, 0.081 mmol) was added and stirring was continued at rt. After 30 min, TsCl (0.016 g, 0.084 mmol) and P-BEMP (loading 2.2 mmol/g, 0.127 g, 0.28 mmol) were added and the mixture was heated at 100° C. for 20 min. The reaction was monitored by LC/MS. Subsequently, the mixture was heated at 120° C. for 30 min. Additional TsCl (0.020 g, 0.105 mmol) and P-BEMP (0.127 g, 0.28 mmol) were added and the mixture was heated at 120° C. another 20 min. Upon cooling, the resin was filtered off and washed with EtOAc. The filtrate was concentrated in vacuo and the residue was purified by flash chromatography (10-70% EtOAc-hexanes gradient). The product was crystallized from CH₂Cl₂-hexanes to afford the title compound as a white solid (0.011 g, 38% yield): MS (ES) m/z 421 (M+1).

Example 36

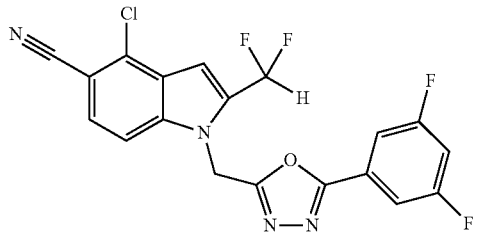 [SMILES: N#Cc1ccc2c(cc(C(F)F)n2Cc2nnc(-c3cc(F)cc(F)c3)o2)c1Cl]

4-Chloro-2-(difluoromethyl)-1-{[5-(3,5-difluorophenyl)-1,3,4-oxadiazol-2-yl]methyl}-1H-indole-5-carbonitrile Synthesized as described in Example 35C using 3,5-difluorobenzohydrazide: MS (ES) m/z 421 (M+1).

Example 37

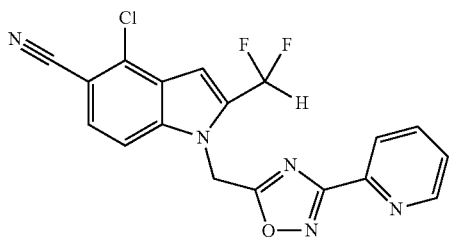 [SMILES: N#Cc1ccc2c(cc(C(F)F)n2Cc2nc(-c3ccccn3)no2)c1Cl]

4-Chloro-2-(difluoromethyl)-1-{[3-(2-pyridinyl)-1,2,4-oxadiazol-5-yl]methyl}-1H-indole-5-carbonitrile To a suspension of [4-chloro-5-cyano-2-(difluoromethyl)-1H-indol-1-yl]acetic acid (0.020 g, 0.070 mmol) in DCE (2 mL), under $N_2$ was added EDCl (0.015 g, 0.077 mmol) and the resulting mixture was stirred at rt. After 5 min, N-hydroxy-2-pyridinecarboximidamide (0.011 g, 0.077 mmol) was added. After stirring at rt for 30 min, the mixture was heated in a microwave at 150° C. for 20 min. Upon cooling, the mixture was partitioned between EtOAc and 0.1N HCl. The organic phase was washed with sat'd $NaHCO_3$ solution and brine, dried ($Na_2SO_4$) and concentrated in vacuo. The residue was purified by flash chromatography (0-100% EtOAc-hexanes gradient) and the product was crystallized from $CH_2Cl_2$-MeOH-hexanes to give the title compound as a white solid (0.016 g, 59% yield): MS (ES) m/z 386 (M+1).

Example 38

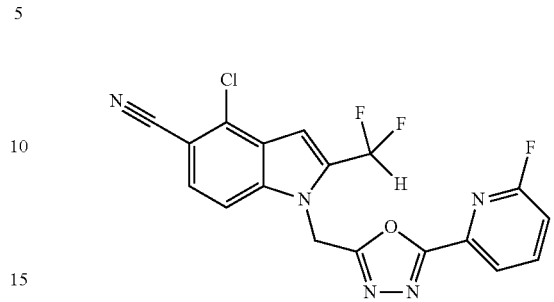

4-Chloro-2-(difluoromethyl)-1-{[5-(6-fluoro-2-pyridinyl)-1,3,4-oxadiazol-2-yl]methyl}-1H-indole-5-carbonitrile

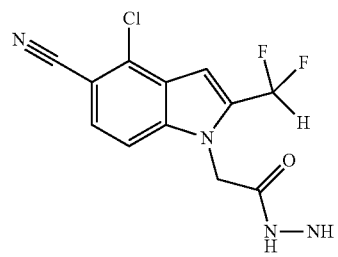 [SMILES: N#Cc1ccc2c(cc(C(F)F)n2CC(=O)NN)c1Cl]

A. 2-[4-Chloro-5-cyano-2-(difluoromethyl)-1H-indol-1-yl]acetohydrazide

To a solution of [4-chloro-5-cyano-2-(difluoromethyl)-1H-indol-1-yl]acetic acid (0.050 g, 0.175 mmol) in anhydrous THF (2 mL), under $N_2$, was added CDI (0.030 g, 0.184 mmol). The mixture was stirred at rt for 4 h and additional CDI (0.030 g, 0.184 mmol) was added. After 45 min, additional CDI (0.079 g, 0.49 mmol) was added. After 5 min, hydrazine (0.112 g, 3.5 mmol) was added and the mixture was stirred at rt for 30 min. The mixture was partitioned between EtOAc and 0.2N NaOH. The organic phase was washed with 0.2N NaOH and sat'd brine. The combined aqueous phases were extracted with EtOAc (×2). The second EtOAc phases were washed with sat'd $NaHCO_3$ solution and brine. The organic phases were combined, dried ($Na_2SO_4$) and concentrated in vacuo. The residue was purified by flash chromatography (0-10% MeOH—$CH_2Cl_2$ gradient) to afford the title compound (0.027 g, 52% yield): MS (ES) m/z 299 (M+1).

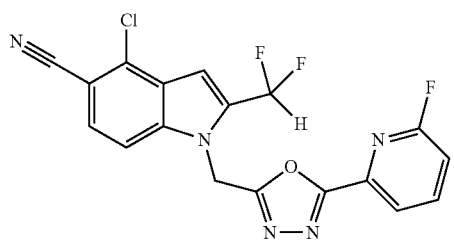 [SMILES: N#Cc1ccc2c(cc(C(F)F)n2Cc2nnc(-c3cccc(F)n3)o2)c1Cl]

B. 4-Chloro-2-(difluoromethyl)-1-{[5-(6-fluoro-2-pyridinyl)-1,3,4-oxadiazol-2-yl]methyl}-1H-indole-5-carbonitrile To a solution of 6-fluoro-2-pyridinecarboxylic acid (0.006 g, 0.043 mmol) in MeCN (2 mL), under $N_2$, was added EDCl (0.0085 g, 0.044 mmol). After 5 min, 2-[4-chloro-5-cyano-2-(difluoromethyl)-1H-indol-1-yl]acetohydrazide (0.012 g, 0.040 mmol) was added. After 1 h, additional 6-fluoro-2-pyridinecarboxylic acid (0.003 g, 0.02 mmol) and EDCl (0.0077 g, 0.040 mmol) were added. After another 15 min, additional 6-fluoro-2-pyridinecarboxylic acid (0.0014 g, 0.01 mmol) and EDCl (0.0046 g, 0.02 mmol) were added. After another 10 min, TsCl (0.009 g, 0.048 mmol) and P-BEMP (loading 2.2 mmol/g, 0.073 g, 0.16 mmol) were added and the mixture was heated at 120° C. for 20 min. Upon cooling, additional TsCl (0.0046 g, 0.024 mmol) and P-BEMP (0.037 g, 0.08 mmol) were added and the mixture was heated at 120° C. for another 20 min. Upon cooling, the resin was filtered off, washed with EtOAc and the filtrate was concentrated in vacuo. The residue was purified by flash chromatography (0-50% EtOAc-hexanes gradient) and the product was crystallized from $CH_2Cl_2$-hexanes to give the title compound as a white solid (0.005 g, 31% yield): MS (ES) m/z 404 (M+1).

Example 39

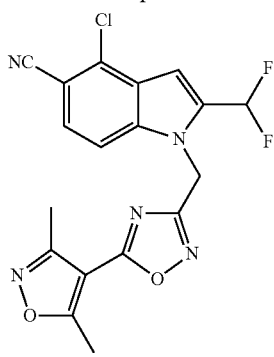

4-Chloro-2-(difluoromethyl)-1-{[5-(3,5-dimethyl-4-isoxazolyl)-1,2,4-oxadiazol-3-yl]methyl}-1H-indole-5-carbonitrile 4-Chloro-2-(difluoromethyl)-1H-indole-5-carbonitrile (0.004 g, 0.018 mmol), $Cs_2CO_3$ (0.007 g, 0.021 mmol), and 3-(chloromethyl)-5-(3,5-dimethyl-4-isoxazolyl)-1,2,4-oxadiazole (0.005 g, 0.021 mmol) were combined in DMF (2 mL). The reaction mixture was heated at 75° C. under $N_2$ for 1 h. Extraction with $Et_2O$, washing with water, and brine was followed by drying ($Na_2SO_4$), filtration, and concentrated in vacuo. Purification ($SiO_2$, EtOAc/hexanes) afforded the title compound (0.0038) g: MS (ESI) m/z 402 (M−1).

Example 40

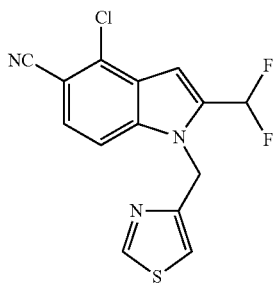 [SMILES: N#Cc1ccc2c(cc(C(F)F)n2Cc2cscn2)c1Cl]

4-Chloro-2-(difluoromethyl)-1-(1,3-thiazol-4-ylmethyl)-1H-indole-5-carbonitrile

Synthesized as described in Example 39 from 4-chloro-2-(difluoromethyl)-1H-indole-5-carbonitrile and 4-(chloromethyl)-1,3-thiazole: MS (ESI) m/z 324 (M+1)

Example 41

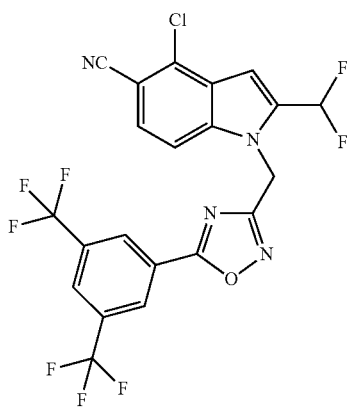 [SMILES: N#Cc1ccc2c(cc(C(F)F)n2Cc2noc(-c3cc(C(F)(F)F)cc(C(F)(F)F)c3)n2)c1Cl]

1-({5-[3,5-Bis(trifluoromethyl)phenyl]-1,2,4-oxadiazol-3-yl}methyl)-4-chloro-2-(difluoromethyl)-1H-indole-5-carbonitrile Synthesized as described in Example 39 from 4-chloro-2-(difluoromethyl)-1H-indole-5-carbonitrile and 5-[3,5-bis(trifluoromethyl)phenyl]-3-(chloromethyl)-1,2,4-oxadiazole: MS (ESI) m/z 519 (M−1).

Example 42

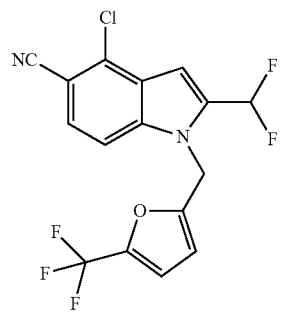 [SMILES: N#Cc1ccc2c(cc(C(F)F)n2Cc2ccc(C(F)(F)F)o2)c1Cl]

4-Chloro-2-(difluoromethyl)-1-{[5-(trifluoromethyl)-2-furanyl]methyl}-1H-indole-5-carbonitrile Synthesized as described in Example 39 from 4-chloro-2-(difluoromethyl)-1H-indole-5-carbonitrile and 2-(bromomethyl)-5-(trifluoromethyl)furan: MS (ESI) m/z 375 (M+1).

Example 43

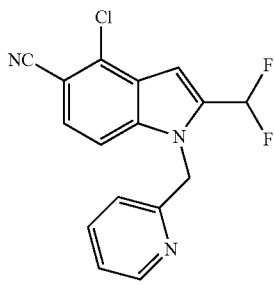 [SMILES: N#Cc1ccc2c(cc(C(F)F)n2Cc2ccccn2)c1Cl]

4-Chloro-2-(difluoromethyl)-1-(2-pyridinylmethyl)-1H-indole-5-carbonitrile

Synthesized as described in Example 39 from 4-chloro-2-(difluoromethyl)-1H-indole-5-carbonitrile and 2-(chloromethyl)pyridine hydrochloride. MS (ESI) m/z 318.07 (M+1).

Example 44

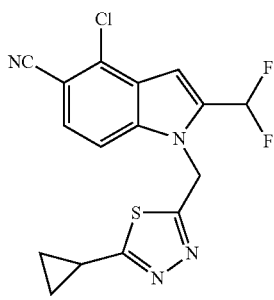 [SMILES: N#Cc1ccc2c(cc(C(F)F)n2Cc2nnc(C3CC3)s2)c1Cl]

4-Chloro-1-[(5-cyclopropyl-1,3,4-thiadiazol-2-yl)methyl]-2-(difluoromethyl)-1H-indole-5-carbonitrile Synthesized as described in Example 39 from 4-chloro-2-(difluoromethyl)-1H-indole-5-carbonitrile and 2-(chloromethyl)-5-cyclopropyl-1,3,4-thiadiazole: MS (ESI) m/z 365 (M+1).

Example 45

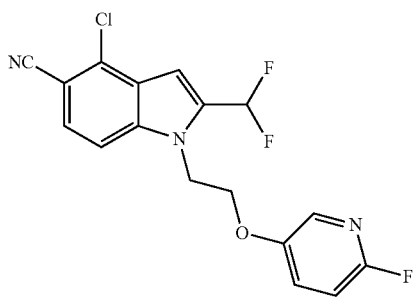 [SMILES: N#Cc1ccc2c(cc(C(F)F)n2CCOc2ccc(F)nc2)c1Cl]

4-Chloro-2-(difluoromethyl)-1-{2-[(6-fluoro-3-pyridinyl)oxy]ethyl}-1H-indole-5-carbonitrile Synthesized as described in Example 39 from 4-chloro-2-(difluoromethyl)-1H-indole-5-carbonitrile and 5-[(2-bromoethyl)oxy]-2-fluoropyridine: MS (ESI) m/z 366 (M+1).

Example 46

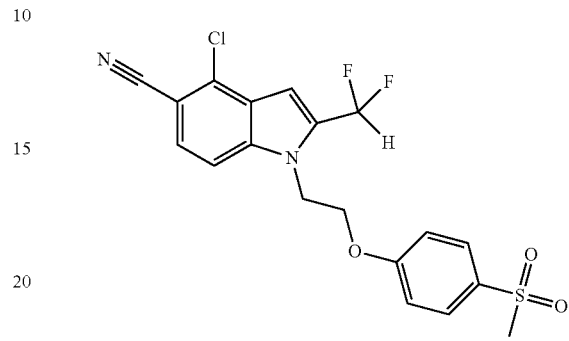

4-Chloro-2-(difluoromethyl)-1-(2-{[4-(methylsulfonyl)phenyl]oxy}ethyl)-1H-indole-5-carbonitrile

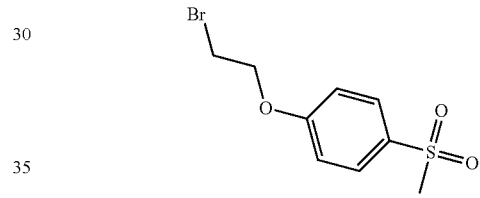

A. 4-[(2-Bromoethyl)oxy]phenyl methyl sulfone

To a solution of 4-(methylsulfonyl)phenol (0.30 g, 1.74 mmol) in MeCN (5 mL) was added Cs$_2$CO$_3$ (0.71 g, 2.18 mmol) and 1,2-dibromoethane (1.64 g, 8.71 mmol). The resulting mixture was heated in a sealed tube at 100° C. After 1.5 h, additional Cs$_2$CO$_3$ (0.4 g, 1.21 mmol) was added and heated at 100° C. for another 2 h. Upon cooling, the mixture was partitioned between EtOAc and 1N NaOH. The organic phase was washed with sat'd brine, dried (Na$_2$SO$_4$) and concentrated in vacuo. The residue was purified by flash chromatography (0-70% EtOAc-hexanes gradient) to afford the title compound as a white solid (0.255 g, 53% yield): MS (ES) m/z 279 and 281 (M+1 Br isotopes).

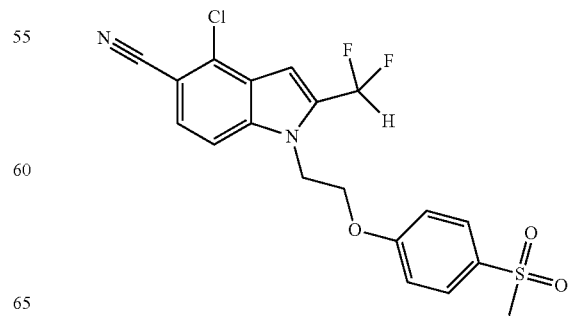

B. 4-Chloro-2-(difluoromethyl)-1-(2-{[4-(methylsulfonyl)phenyl]oxy}ethyl)-1H-indole-5-carbonitrile To a solution of 4-chloro-2-(difluoromethyl)-1H-indole-5-carbonitrile (0.019 g, 0.084 mmol) in MeCN (2 mL), under $N_2$, was added $Cs_2CO_3$ (0.055 g, 0.17 mmol) and 4-[(2-bromoethyl)oxy]phenyl methyl sulfone (0.047 g, 0.17 mmol). The mixture was heated in a sealed tube at 100° C. for 1 h. Upon cooling, the mixture was partitioned between EtOAc and water. The organic phase was washed with sat'd brine, dried ($Na_2SO_4$) and concentrated in vacuo. The residue was purified by flash chromatography (0-70% EtOAc-hexanes gradient) and the product was crystallized from $CH_2Cl_2$-hexanes to give the title compound as a white solid (0.022 g, 61% yield): MS (ES) m/z 425 (M+1).

Example 47

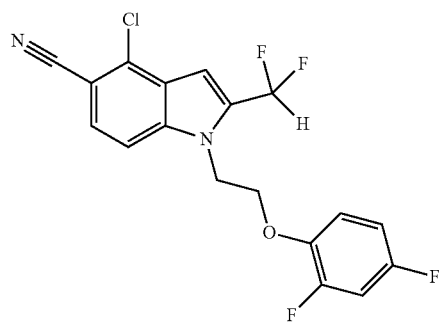 [SMILES: N#Cc1ccc2c(cc(C(F)F)n2CCOc2ccc(F)cc2F)c1Cl]

4-Chloro-2-(difluoromethyl)-1-{2-[(2,4-difluorophenyl)oxy]ethyl}-1H-indole-5-carbonitrile

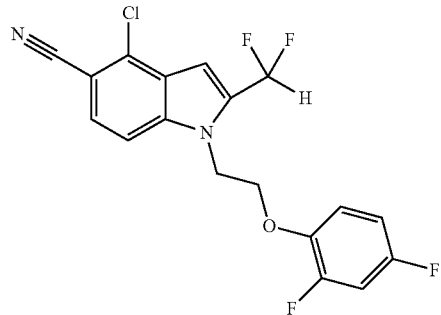 [SMILES: N#Cc1ccc2c(cc(C(F)F)n2CCOc2ccc(F)cc2F)c1Cl]

A. 2-Bromoethyl 2,4-difluorophenyl ether

Synthesized as described in Example 46A using 2,4-difluorophenol: $^1$H NMR (400 MHz, $CDCl_3$) δ 6.94 (td, J=9.0, 5.3 Hz, 1H), 6.86 (ddd, J=11.0, 8.5, 3.2 Hz, 1H), 6.81-6.75 (m, 1H), 4.30 (t, J=6.2 Hz, 2H), 3.62 (t, J=6.2 Hz, 2H).

B. 4-Chloro-2-(difluoromethyl)-1-{2-[(2,4-difluorophenyl)oxy]ethyl}-1H-indole-5-carbonitrile Synthesized as described in Example 46B using 2-bromoethyl 2,4-difluorophenyl ether: MS (ES) m/z 383 (M+1).

Example 48

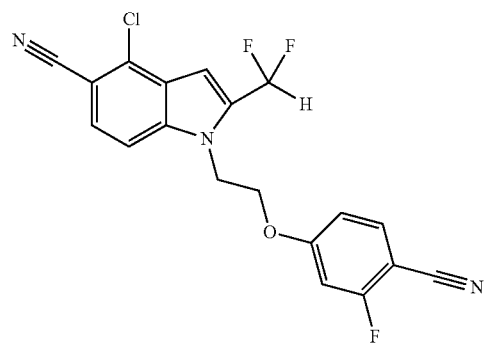 [SMILES: N#Cc1ccc(OCCn2c(C(F)F)cc3c(Cl)c(C#N)ccc32)cc1F]

4-Chloro-1-{2-[(4-cyano-3-fluorophenyl)oxy]ethyl}-2-(difluoromethyl)-1H-indole-5-carbonitrile

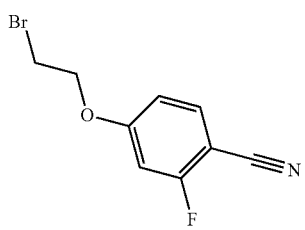 [SMILES: N#Cc1ccc(OCCBr)cc1F]

A. 4-[(2-Bromoethyl)oxy]-2-fluorobenzonitrile

Synthesized as described in Example 46A using 2-fluoro-4-hydroxybenzonitrile: MS (ES) m/z 244 and 246 (M+1 Br isotopes).

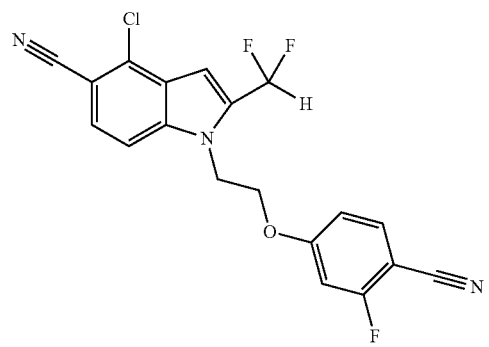 [SMILES: N#Cc1ccc(OCCn2c(C(F)F)cc3c(Cl)c(C#N)ccc32)cc1F]

B. 4-Chloro-1-{2-[(4-cyano-3-fluorophenyl)oxy]ethyl}-2-(difluoromethyl)-1H-indole-5-carbonitrile Synthesized as described in Example 46B using 4-[(2-bromoethyl)oxy]-2-fluorobenzonitrile: MS (ES) m/z 390 (M+1).

Example 49

4-Chloro-1-{2-[(5-chloro-3-pyridinyl)oxy]ethyl}-2-(difluoromethyl)-1H-indole-5-carbonitrile

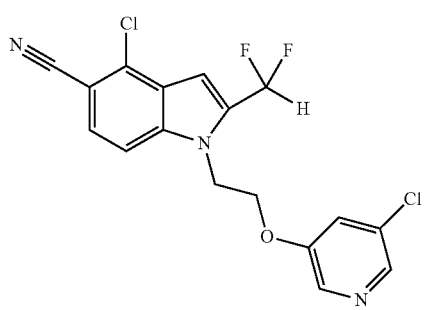 [SMILES: N#Cc1ccc2c(cc(C(F)F)n2CCOc2cncc(Cl)c2)c1Cl]

A. 3-[(2-Bromoethyl)oxy]-5-chloropyridine

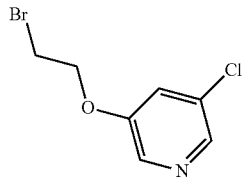 [SMILES: Clc1cncc(OCCBr)c1]

Synthesized as described in Example 46A using 5-chloro-3-pyridinol: MS (ES) m/z 236 and 238 (M+1 Br isotopes).

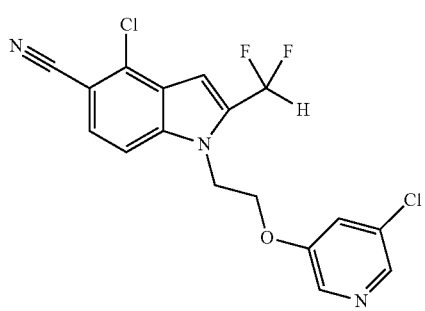 [SMILES: N#Cc1ccc2c(cc(C(F)F)n2CCOc2cncc(Cl)c2)c1Cl]

B. 4-Chloro-1-{2-[(5-chloro-3-pyridinyl)oxy]ethyl}-2-(difluoromethyl)-1H-indole-5-carbonitrile Synthesized as described in Example 46B using 3-[(2-bromoethyl)oxy]-5-chloropyridine: MS (ES) m/z 382 (M+1).

Example 50

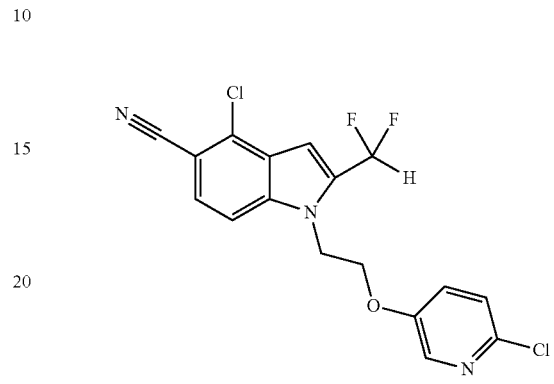

4-Chloro-1-{2-[(6-chloro-3-pyridinyl)oxy]ethyl}-2-(difluoromethyl)-1H-indole-5-carbonitrile

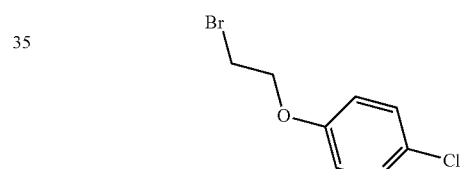

A. 5-[(2-Bromoethyl)oxy]-2-chloropyridine

Synthesized as described in Example 46A using 6-chloro-3-pyridinol: MS (APCI) m/z 236 and 238 (M+1 Br isotopes).

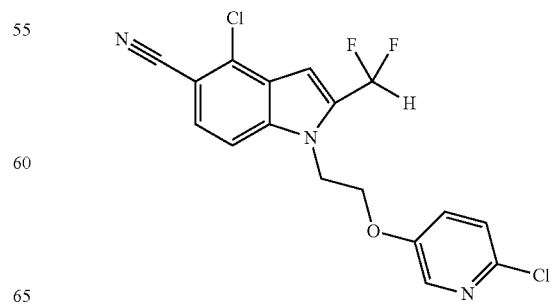

B. 4-Chloro-1-{2-[(6-chloro-3-pyridinyl)oxy]ethyl}-2-(difluoromethyl)-1H-indole-5-carbonitrile Synthesized as described in Example 46B using 5-[(2-bromoethyl)oxy]-2-chloropyridine: MS (ES) m/z 382 (M+1).

Example 51

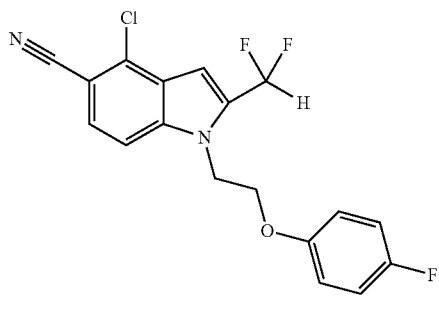 [SMILES: N#Cc1ccc2c(cc(C(F)F)n2CCOc2ccc(F)cc2)c1Cl]

4-Chloro-2-(difluoromethyl)-1-{2-[(4-fluorophenyl)oxy]ethyl}-1H-indole-5-carbonitrile Synthesized as described in Example 46B using commercially available 2-bromoethyl 4-fluorophenyl ether: MS (APCI) m/z 365 (M+1).

Example 52

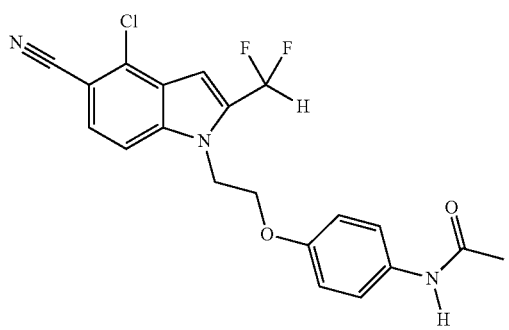 [SMILES: CC(=O)Nc1ccc(OCCn2c(C(F)F)cc3c(Cl)c(C#N)ccc32)cc1]

N-[4-({2-[4-Chloro-5-cyano-2-(difluoromethyl)-1H-indol-1-yl]ethyl}oxy)phenyl]acetamide Synthesized as described in Example 46B using N-{4-[(2-bromoethyl)oxy]phenyl}acetamide: MS (ES) m/z 404 (M+1).

Example 53

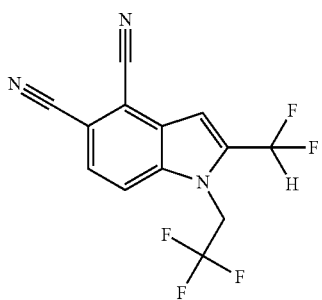 [SMILES: N#Cc1ccc2c(cc(C(F)F)n2CC(F)(F)F)c1C#N]

2-(Difluoromethyl)-1-(2,2,2-trifluoroethyl)-1H-indole-4,5-dicarbonitrile

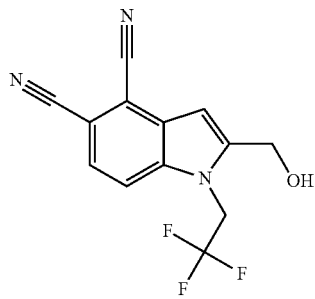 [SMILES: N#Cc1ccc2c(cc(CO)n2CC(F)(F)F)c1C#N]

A. 2-(Hydroxymethyl)-1-(2,2,2-trifluoroethyl)-1H-indole-4,5-dicarbonitrile

Synthesized as described in Example 10 from ethyl 4,5-dicyano-1-(2,2,2-trifluoroethyl)-1H-indole-2-carboxylate (Example 7): MS (ES) m/z 280 (M+1).

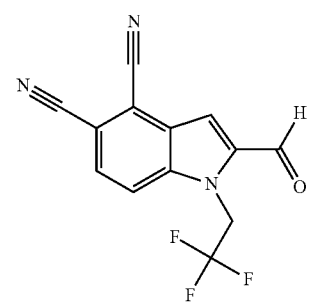 [SMILES: N#Cc1ccc2c(cc(C=O)n2CC(F)(F)F)c1C#N]

B. 2-Formyl-1-(2,2,2-trifluoroethyl)-1H-indole-4,5-dicarbonitrile

Synthesized as described in Example 12 from 2-(hydroxymethyl)-1-(2,2,2-trifluoroethyl)-1H-indole-4,5-dicarbonitrile: MS (ES) m/z 276 (M−1).

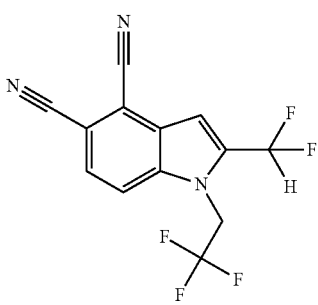 [SMILES: N#Cc1ccc2c(cc(C(F)F)n2CC(F)(F)F)c1C#N]

C. 2-(Difluoromethyl)-1-(2,2,2-trifluoroethyl)-1H-indole-4,5-dicarbonitrile

Synthesized as described in Example 21 from 2-formyl-1-(2,2,2-trifluoroethyl)-1H-indole-4,5-dicarbonitrile using 10 eq of Deoxofluor: MS (ES) m/z 300 (M+1).

Example 54

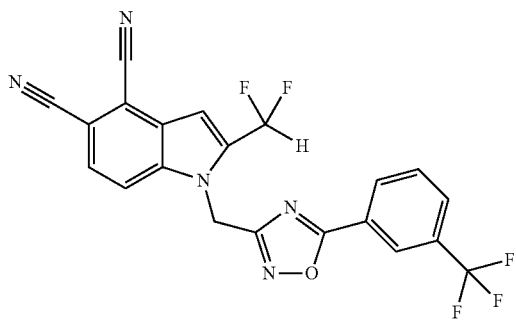 [SMILES: N#Cc1ccc2c(cc(C(F)F)n2Cc2noc(-c3cccc(C(F)(F)F)c3)n2)c1C#N]

2-(Difluoromethyl)-1-({5-[3-(trifluoromethyl)phenyl]-1,2,4-oxadiazol-3-yl}methyl)-1H-indole-4,5-dicarbonitrile

A. 2-(Difluoromethyl)-1H-indole-4,5-dicarbonitrile

Synthesized as described in Example 22H from 2-(difluoromethyl)-1-(phenylsulfonyl)-1H-indole-4,5-dicarbonitrile (intermediate 22G): MS (ES) m/z 218 (M+1).

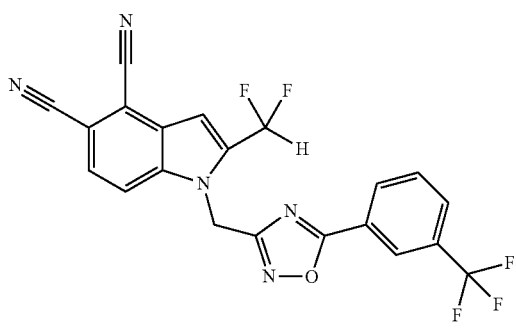 [SMILES: N#Cc1ccc2c(cc(C(F)F)n2Cc2noc(-c3cccc(C(F)(F)F)c3)n2)c1C#N]

B. 2-(Difluoromethyl)-1-({5-[3-(trifluoromethyl)phenyl]-1,2,4-oxadiazol-3-yl}methyl)-1H-indole-4,5-dicarbonitrile Synthesized as described in Example 23 from 2-(difluoromethyl)-1H-indole-4,5-dicarbonitrile and 3-(chloromethyl)-5-[3-(trifluoromethyl)phenyl]-1,2,4-oxadiazole: MS (ES) m/z 444 (M+1).

Example 55

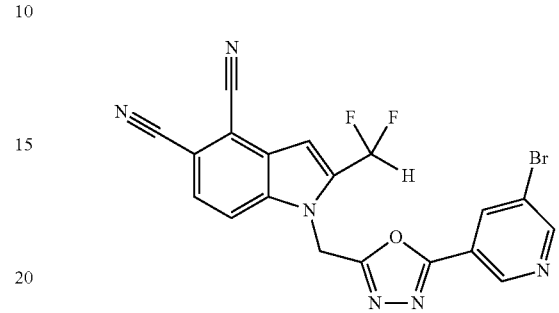

1-{[5-(5-Bromo-3-pyridinyl)-1,3,4-oxadiazol-2-yl]methyl}-2-(difluoromethyl)-1H-indole-4,5-dicarbonitrile Synthesized as described in Example 23 from 2-(difluoromethyl)-1H-indole-4,5-dicarbonitrile and 3-bromo-5-[5-(chloromethyl)-1,3,4-oxadiazol-2-yl]pyridine: MS (ES) m/z 455 and 457 (M+1 Br isotopes).

Example 56

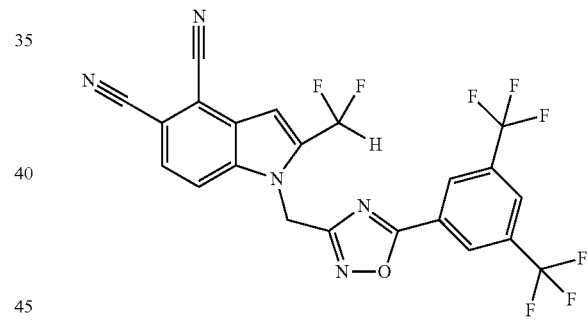

1-({5-[3,5-bis(Trifluoromethyl)phenyl]-1,2,4-oxadiazol-3-yl}methyl)-2-(difluoromethyl)-1H-indole-4,5-dicarbonitrile Synthesized as described in Example 23 from 2-(difluoromethyl)-1H-indole-4,5-dicarbonitrile and 5-[3,5-bis(trifluoromethyl)phenyl]-3-(chloromethyl)-1,2,4-oxadiazole: MS (ES) m/z 510 (M−1).

Example 57

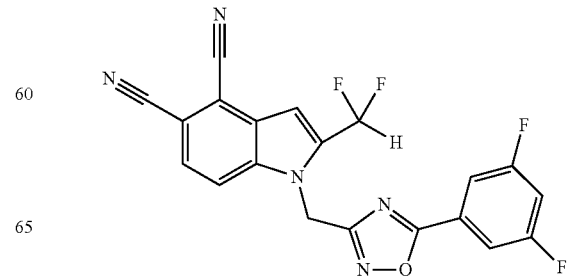

2-(Difluoromethyl)-1-{[5-(3,5-difluorophenyl)-1,2,4-oxadiazol-3-yl]methyl}-1H-indole-4,5-dicarbonitrile Synthesized as described in Example 23 from 2-(difluoromethyl)-1H-indole-4,5-dicarbonitrile and 3-(chloromethyl)-5-(3,5-difluorophenyl)-1,2,4-oxadiazole: MS (ES) m/z 412 (M+1).

Example 58

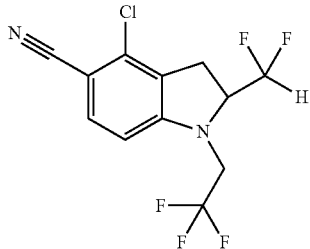 [SMILES: N#Cc1ccc2c(c1Cl)CC(C(F)F)N2CC(F)(F)F]

4-Chloro-2-(difluoromethyl)-1-(2,2,2-trifluoroethyl)-2,3-dihydro-1H-indole-5-carbonitrile To an ice-cold suspension of 4-chloro-2-(difluoromethyl)-1H-indole-5-carbonitrile (0.010 g, 0.044 mmol) in TFA (1 mL) was added NaCNBH₃ (0.028 g, 0.44 mmol) in portions. After 10 min, the cold bath was removed and the mixture stirred at rt. After 1.5 h, additional NaCNBH₃ (0.014 g, 0.22 mmol) was added and the mixture was stirred at rt another 20 min. The mixture was concentrated to dryness in in vacuo at 45° C. The residue was partitioned between EtOAc and 0.2N NaOH. The organic phase was washed with a sat'd NaHCO₃ solution and brine, dried (Na₂SO₄) and concentrated in vacuo. The residue was purified by radial chromatography (10-100% CH₂Cl₂-hexanes) to afford 4-chloro-2-(difluoromethyl)-1-(2,2,2-trifluoroethyl)-2,3-dihydro-1H-indole-5-carbonitrile (0.004 g, 29% yield) (MS (ES) m/z 311 (M+1)) and 4-chloro-2-(difluoromethyl)-2,3-dihydro-1H-indole-5-carbonitrile (0.004 g, 40% yield) (MS (ES) m/z 229 (M+1)).

Example 59

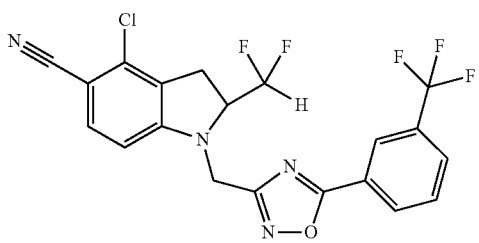 [SMILES: N#Cc1ccc2c(c1Cl)CC(C(F)F)N2Cc1noc(-c2cccc(C(F)(F)F)c2)n1]

4-Chloro-2-(difluoromethyl)-1-({5-[3-(trifluoromethyl)phenyl]-1,2,4-oxadiazol-3-yl}methyl)-2,3-dihydro-1H-indole-5-carbonitrile Synthesized as described in Example 23 from 2-(difluoromethyl)-2,3-dihydro-1H-indole-4,5-dicarbonitrile (a byproduct obtained in the synthesis of Example 79) and 3-(chloromethyl)-5-[3-(trifluoromethyl)phenyl]-1,2,4-oxadiazole: MS (ES) m/z 455 (M+1).

Example 60

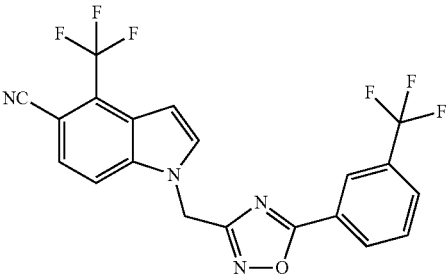 [SMILES: N#Cc1ccc2c(ccn2Cc2noc(-c3cccc(C(F)(F)F)c3)n2)c1C(F)(F)F]

4-(Trifluoromethyl)-1-({5-[3-(trifluoromethyl)phenyl]-1,2,4-oxadiazol-3-yl}methyl)-1H-indole-5-carbonitrile

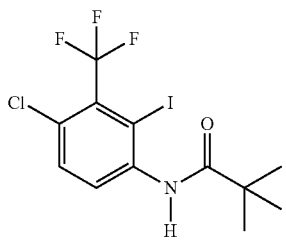 [SMILES: CC(C)(C)C(=O)Nc1ccc(Cl)c(C(F)(F)F)c1I]

A. N-[4-Chloro-2-iodo-3-(trifluoromethyl)phenyl]-2,2-dimethylpropanamide

A THF (20 mL) solution of known N-[4-chloro-3-(trifluoromethyl)phenyl]-2,2-dimethylpropanamide (1.49 g, 5.34 mmol) at ca. −5° C. was treated with n-BuLi (2.5 M, 5.33 mL). After 30 min, the reaction was treated with I₂ (2.03 g, 8.01 mmol) dissolved in THF (3 mL). The resulting mixture was then quenched with sat. aqueous NH₄Cl after 10 min. Excess I₂ was removed with 10% aqueous sodium metabisulfite. The mixture was diluted with EtOAc (20 mL) and H₂O (20 mL) and partitioned. The aqueous portion was extracted with EtOAc (20 mL). The combined organic portions were washed with H₂O followed by brine. Drying (Na₂SO₄) was followed by filtration and concentration. ¹H NMR of the crude mixture showed a 3.7:1 ratio of the desired (2-iodo) to the undesired regioisomer. Column chromatography (SiO₂; hexanes/EtOAc) provided the title compound as a white solid (1.34 g, 62%): ¹H NMR (CDCl₃) δ 8.33 (d, J=6.0 Hz, 1H), 8.16 (bs, 1H), 7.49 (d, J=6.0 Hz, 1H), 1.38 (s, 9H).

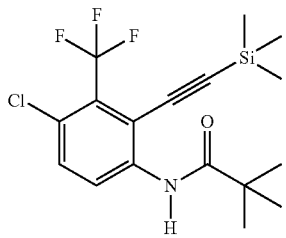 [SMILES: CC(C)(C)C(=O)Nc1ccc(Cl)c(C(F)(F)F)c1C#C[Si](C)(C)C]

B. N-{4-Chloro-3-(trifluoromethyl)-2-[(trimethylsilyl)ethynyl]phenyl}-2,2-dimethylpropanamide A triethylamine (2.2 mL) solution of N-[4-chloro-2-iodo-3-(trifluoromethyl)phenyl]-2,2-dimethylpropanamide (0.413 g, 1.02 mmol) was treated with TMS acetylene (0.158 mL, 1.12 mmol) followed by copper iodide (0.019 g, 0.102 mmol) and PdCl$_2$(PPh$_3$)$_2$ (0.021 g, 0.031 mmol). The reaction vessel was purged with N$_2$, sealed and heated to 50° C. for 14 h. TLC at this time showed excellent conversion to the desired product. The cooled mixture was filtered through a plug of celite and partitioned between EtOAc (10 mL) and H$_2$O (10 mL). The organic portion was dried (Na$_2$SO$_4$), filtered, and concentrated. Column chromatography (SiO$_2$, EtOAc/hexanes) afforded the title compound as a light brown solid: $^1$H NMR (CDCl$_3$) δ 8.72 (bs, 1H), 8.64 (d, J=6.0 Hz, 1H), 7.41 (d, J=6.0 Hz, 1H), 1.34 (s, 9H), 0.29 (s, 9H).

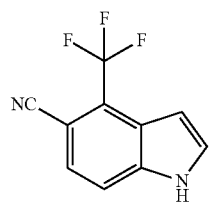 [SMILES: N#Cc1ccc2[nH]ccc2c1C(F)(F)F]

C. 4-(Trifluoromethyl)-1H-indole-5-carbonitrile

An NMP solution (15 mL) of N-{4-chloro-3-(trifluoromethyl)-2-[(trimethylsilyl)ethynyl]phenyl}-2,2-dimethylpropanamide (1.04 g, 2.77 mmol) was treated with CuCN (1.04 g, 11.01 mmol) and the resulting mixture was heated at 250° C. in a microwave for 5.5 h. The dark brown reaction mixture was poured into crushed ice (250 mL) containing conc. ammonium hydroxide (30 mL). The resulting slurry was filtered and rinsed with Et$_2$O. The filtrate was diluted with Et$_2$O (50 mL) and partitioned. The aqueous portion was extracted with Et$_2$O (2×25 mL). The combined organic portions were washed with H$_2$O (25 mL) and brine (25 mL). Drying (Na$_2$SO$_4$) and filtration were followed by concentration to a brown/yellow solid (0.723 g) that was used for the next reaction without further purification.

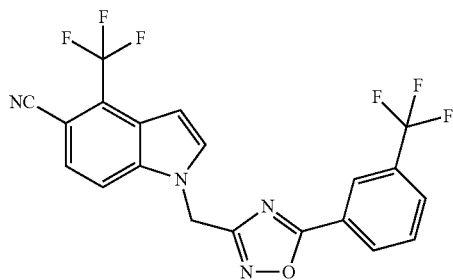 [SMILES: N#Cc1ccc2c(ccn2Cc2noc(-c3cccc(C(F)(F)F)c3)n2)c1C(F)(F)F]

D. 4-(Trifluoromethyl)-1-({5-[3-(trifluoromethyl)phenyl]-1,2,4-oxadiazol-3-yl}methyl)-1H-indole-5-carbonitrile A DMF solution (25 mL) of 4-(trifluoromethyl)-1H-indole-5-carbonitrile (2.66 mmol max) was treated with Cs$_2$CO$_3$ (1.73 g, 5.32 mmol) followed by 3-(chloromethyl)-5-[3-(trifluoromethyl)phenyl]-1,2,4-oxadiazole (0.699 g, 2.66 mmol). The resulting suspension was heated to 90° C. for 30 min. The cooled reaction mixture was diluted with H$_2$O (25 mL) and then extracted with EtOAc (3×25 mL). The pooled organic portions were washed with H$_2$O and brine. Drying (Na$_2$SO$_4$) and filtration were followed by concentration. Column chromatography (SiO$_2$, EtOAc/hexanes) afforded the title compound in excellent purity as a pale yellow solid (900 g, 75% over two stages): $^1$H NMR (DMSO-d$_6$) δ 8.32 (d, J=6.0 Hz, 1H), 8.25 (bs, 1H), 8.11-8.06 (m, 2H), 7.98 (d, J=3.0 Hz, 1H), 8.86-8.81 (m, 2H), 6.82-6.81 (m, 1H), 5.95 (s, 2H).

Example 61

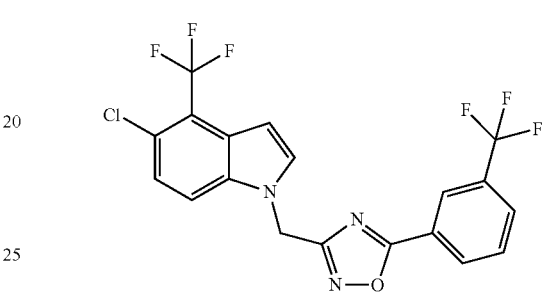

5-Chloro-4-(trifluoromethyl)-1-({5-[3-(trifluoromethyl)phenyl]-1,2,4-oxadiazol-3-yl}methyl)-1H-indole

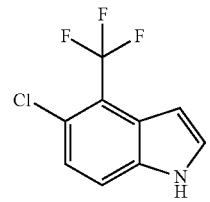 [SMILES: FC(F)(F)c1c(Cl)ccc2[nH]ccc12]

A. 5-Chloro-4-(trifluoromethyl)-1H-indole

A solution of N-{4-chloro-3-(trifluoromethyl)-2-[(trimethylsilyl)ethynyl]phenyl}-2,2-dimethylpropanamide (Example 60B) in THF (10 mL) was treated with TBAF (3.2 mL, 1 M in THF, 3 equiv) and the reaction mixture was left to stir at ambient temperature for 14 h. Concentration was followed by partitioning between EtOAc and water. The organic portion was dried (Na$_2$SO$_4$), filtered, and concentrated to a waxy yellow solid. This material was used for the next reaction without further purification: MS (ESI): m/z 218 (M−1).

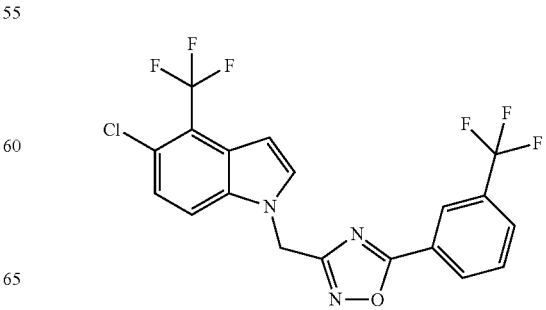

B. 5-Chloro-4-(trifluoromethyl)-1-({5-[3-(trifluoromethyl)phenyl]-1,2,4-oxadiazol-3-yl}methyl)-1H-indole Synthesized as described in Example 60D from 5-chloro-4-(trifluoromethyl)-1H-indole: MS (ESI): m/z 446 (M+1).

Example 62

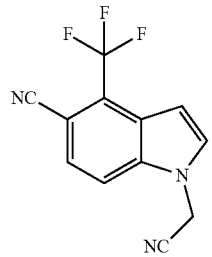 [SMILES: N#CCn1ccc2c(C(F)(F)F)c(C#N)ccc21]

1-(Cyanomethyl)-4-(trifluoromethyl)-1H-indole-5-carbonitrile

To 4-(trifluoromethyl)-1H-indole-5-carbonitrile (0.210 g, 1.00 mmol) in DMF (20 mL), was added $Cs_2CO_3$ (0.489 g, 1.50 mmol) and bromoacetonitrile (0.180 g, 1.50 mmol). The reaction mixture was heated at 75° C. under an $N_2$ atmosphere for 1 hr. Dilution with water was followed by extraction with $Et_2O$. The combined organic portions were washed with brine, dried ($Na_2SO_4$), filtered, and concentrated in vacuo. Purification ($SiO_2$, EtOAc/hexanes) afforded 0.211 g of the title compound: MS (ESI): m/z 250 (M+1).

Example 63

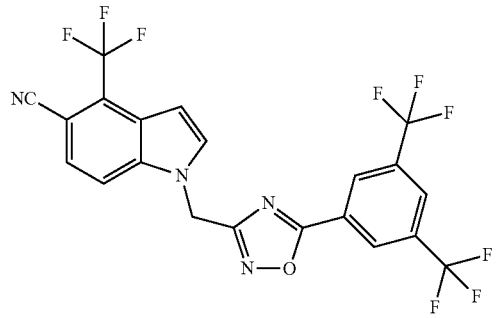 [SMILES: N#Cc1ccc2c(ccn2Cc2noc(-c3cc(C(F)(F)F)cc(C(F)(F)F)c3)n2)c1C(F)(F)F]

1-({5-[3,5-Bis(trifluoromethyl)phenyl]-1,2,4-oxadiazol-3-yl}methyl)-4-(trifluoromethyl)-1H-indole-5-carbonitrile Synthesized as described in Example 62 from 4-(trifluoromethyl)-1H-indole-5-carbonitrile and 5-[3,5-bis(trifluoromethyl)phenyl]-3-(chloromethyl)-1,2,4-oxadiazole: MS (ESI): m/z 503 (M−1).

Example 64

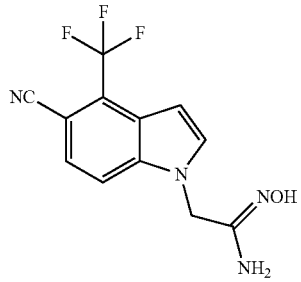

2-[5-Cyano-4-(trifluoromethyl)-1H-indol-1-yl]-N-hydroxyethanimidamide

To 4-(trifluoromethyl)-1H-indole-5-carbonitrile (0.210 g, 0.85 mmol) in DMF (15 mL), was added $NaOAc/3H_2O$ (0.346 g, 2.54 mmol) and $H_2NOH/HCl$ (0.176 g, 2.54 mmol). The resulting mixture was stirred at rt for 15 h. $H_2O$ (30 mL) and sat'd aqueous $NaHCO_3$ (45 mL) were added to the reaction mixture. Extraction with $Et_2O$ (3×50 mL) was followed by washing with brine, drying ($Na_2SO_4$), filtration, and concentration in vacuo. Trituration with hexanes/$CH_2Cl_2$ afforded 0.282 g of the title compound in good purity: $^1$NMR (400 MHz, $CDCl_3$) δ 7.71 (d, J=8.6 Hz, 1H), 7.51 (d, J=8.6 Hz, 1H), 7.42 (d, J=3.4 Hz, 1H), 6.75 (m, 1H), 4.80 (s, 2H); MS (ESI): m/z 283 (M+1).

Example 65

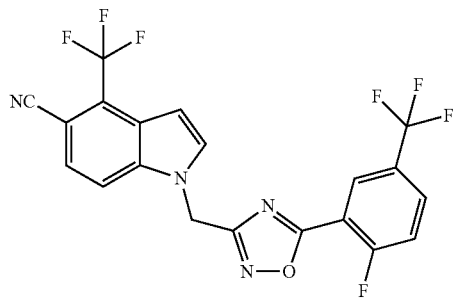 [SMILES: N#Cc1ccc2c(ccn2Cc2noc(-c3cc(C(F)(F)F)ccc3F)n2)c1C(F)(F)F]

1-({5-[2-Fluoro-5-(trifluoromethyl)phenyl]-1,2,4-oxadiazol-3-yl}methyl)-4-(trifluoromethyl)-1H-indole-5-carbonitrile 2-Fluoro-5-(trifluoromethyl)benzoic acid (0.016 g, 0.075 mmol) and EDCl (0.015 g, 0.078 mmol) were stirred in DCE (2 mL) for 5 min at rt and then 2-[5-cyano-4-(trifluoromethyl)-1H-indol-1-yl]-N-hydroxyethanimidamide (0.020 g, 0.071 mmol) was added. After 1 h at rt, the reaction was heated to 80° C. for 15 h. Direct purification ($SiO_2$, EtOAc/hexanes) provided the title compound (0.016 g): MS (ESI): m/z 455 (M+1).

Example 66

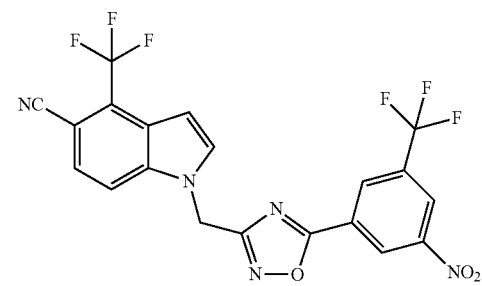 [SMILES: N#Cc1ccc2c(ccn2Cc2noc(-c3cc([N+](=O)[O-])cc(C(F)(F)F)c3)n2)c1C(F)(F)F]

1-({5-[3-Nitro-5-(trifluoromethyl)phenyl]-1,2,4-oxadiazol-3-yl}methyl)-4-(trifluoromethyl)-1H-indole-5-carbonitrile Synthesized as described in Example 65 from 2-[5-cyano-4-(trifluoromethyl)-1H-indol-1-yl]-N-hydroxyethanimidamide and 3-nitro-5-(trifluoromethyl)benzoic acid: MS (ESI): m/z 482 (M+1).

Example 67

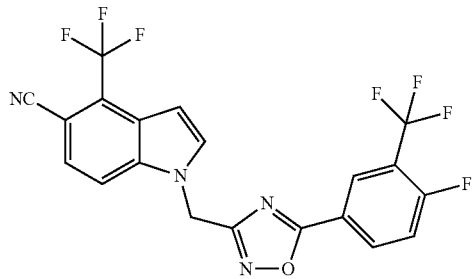 [SMILES: N#Cc1ccc2c(ccn2Cc2noc(-c3ccc(F)c(C(F)(F)F)c3)n2)c1C(F)(F)F]

1-({5-[4-Fluoro-3-(trifluoromethyl)phenyl]-1,2,4-oxadiazol-3-yl}methyl)-4-(trifluoromethyl)-1H-indole-5-carbonitrile Synthesized as described in Example 65 from 2-[5-cyano-4-(trifluoromethyl)-1H-indol-1-yl]-N-hydroxyethanimidamide and 4-fluoro-3-(trifluoromethyl)benzoic acid: MS (ESI): m/z 455 (M+1).

Example 68

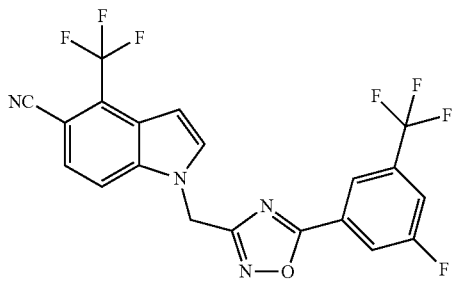 [SMILES: N#Cc1ccc2c(ccn2Cc2noc(-c3cc(F)cc(C(F)(F)F)c3)n2)c1C(F)(F)F]

1-({5-[3-Fluoro-5-(trifluoromethyl)phenyl]-1,2,4-oxadiazol-3-yl}methyl)-4-(trifluoromethyl)-1H-indole-5-carbonitrile Synthesized as described in Example 65 from 2-[5-cyano-4-(trifluoromethyl)-1H-indol-1-yl]-N-hydroxyethanimidamide and 3-fluoro-5-(trifluoromethyl)benzoic acid: MS (ESI): m/z 455 (M+1).

Example 69

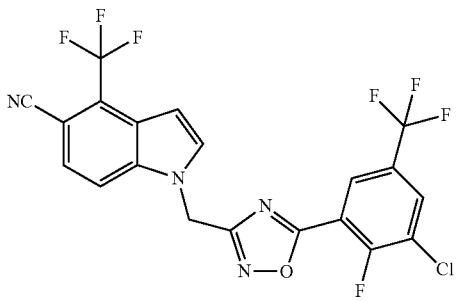 [SMILES: N#Cc1ccc2c(ccn2Cc2noc(-c3cc(C(F)(F)F)cc(Cl)c3F)n2)c1C(F)(F)F]

1-({5-[3-Chloro-2-fluoro-5-(trifluoromethyl)phenyl]-1,2,4-oxadiazol-3-yl}methyl)-4-(trifluoromethyl)-1H-indole-5-carbonitrile Synthesized as described in Example 65 from 2-[5-cyano-4-(trifluoromethyl)-1H-indol-1-yl]-N-hydroxyethanimidamide and 3-chloro-2-fluoro-5-(trifluoromethyl)benzoic acid: MS (ESI): m/z 487 (M−1).

Example 70

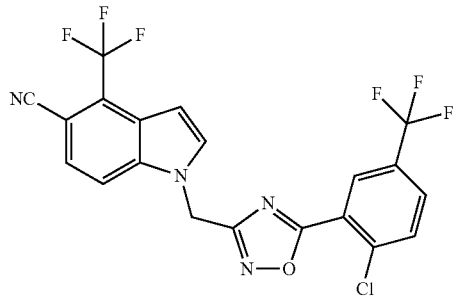 [SMILES: N#Cc1ccc2c(ccn2Cc2noc(-c3cc(C(F)(F)F)ccc3Cl)n2)c1C(F)(F)F]

1-({5-[2-Chloro-5-(trifluoromethyl)phenyl]-1,2,4-oxadiazol-3-yl}methyl)-4-(trifluoromethyl)-1H-indole-5-carbonitrile 2-Chloro-5-(trifluoromethyl)benzoyl chloride (0.017 g, 0.071 mmol), Et₃N (0.008 g. 0.078 mmol) and 2-[5-cyano-4-(trifluoromethyl)-1H-indol-1-yl]-N-hydroxyethanimidamide (0.020 g, 0.071 mmol) were combined in CH₃CN (1.5 mL). After stirring at rt for 1 h, the mixture was heated to 150° C. in a microwave for 10 min. Purification (SiO₂, EtOAc/hexanes) afforded the title compound (0.025 g): MS (ESI): m/z 469 (M−1).

Example 71

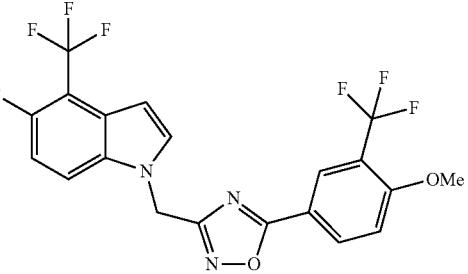

1-({5-[4-(Methyloxy)-3-(trifluoromethyl)phenyl]-1,2,4-oxadiazol-3-yl}methyl)-4-(trifluoromethyl)-1H-indole-5-carbonitrile Synthesized as described in Example 70 from 2-[5-cyano-4-(trifluoromethyl)-1H-indol-1-yl]-N-hydroxyethanimidamide and 4-(methyloxy)-3-(trifluoromethyl)benzoyl chloride. MS (ESI): m/z 467 (M+1).

Example 72

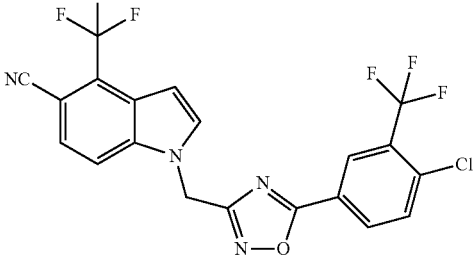

1-({5-[4-Chloro-3-(trifluoromethyl)phenyl]-1,2,4-oxadiazol-3-yl}methyl)-4-(trifluoromethyl)-1H-indole-5-carbonitrile 4-Chloro-3-(trifluoromethyl)benzoic acid (0.016 g, 0.071 mmol) and CDI (0.012 g, 0.071 mmol) were combined in CH₃CN (3 mL). 2-[5-Cyano-4-(trifluoromethyl)-1H-indol-1-yl]-N-hydroxyethanimidamide (0.020 g, 0.071 mmol) was added after 5 min. After stirring at rt for 1 h, the reaction was heated at 150° C. in a microwave for 10 min. Purification (SiO₂, EtOAc/hexanes) afforded the title compound (0.022 g): MS (ESI): m/z 471 (M+1).

Example 73

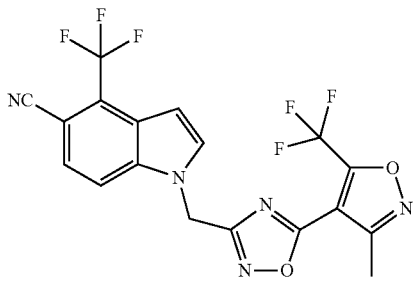 [SMILES: Cc1noc(C(F)(F)F)c1-c1nc(Cn2ccc3c(C(F)(F)F)c(C#N)ccc32)no1]

1-({5-[3-Methyl-5-(trifluoromethyl)-4-isoxazolyl]-1,2,4-oxadiazol-3-yl}methyl)-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-methyl-5-(trifluoromethyl)-4-isoxazolecarboxylic acid: MS (ESI): m/z 442 (M+1).

Example 74

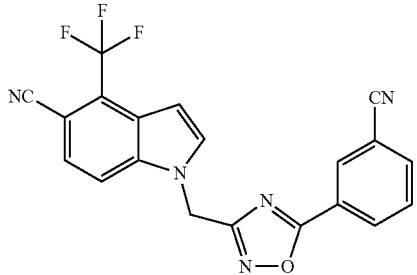 [SMILES: N#Cc1cccc(-c2nc(Cn3ccc4c(C(F)(F)F)c(C#N)ccc43)no2)c1]

1-{[5-(3-Cyanophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-cyanobenzoic acid: MS (ESI): m/z 392 (M−1).

Example 75

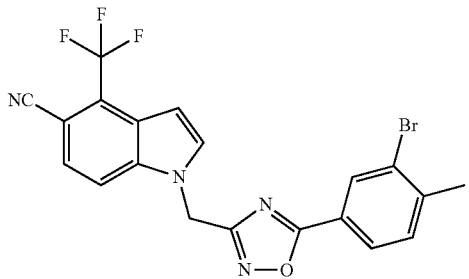 [SMILES: Cc1ccc(-c2nc(Cn3ccc4c(C(F)(F)F)c(C#N)ccc43)no2)cc1Br]

1-{[5-(3-Bromo-4-methylphenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-bromo-4-methylbenzoic acid: MS (ESI): m/z 461 (M⁺).

Example 76

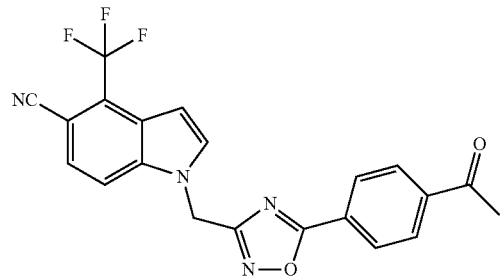 [SMILES: CC(=O)c1ccc(-c2nc(Cn3ccc4c(C(F)(F)F)c(C#N)ccc43)no2)cc1]

1-{[5-(4-Acetylphenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 4-acetylbenzoic acid: MS (ESI): m/z 411 (M+1).

Example 77

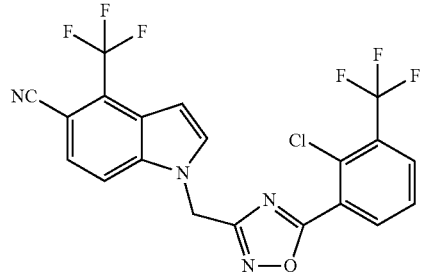 [SMILES: N#Cc1ccc2c(ccn2Cc2noc(-c3cccc(C(F)(F)F)c3Cl)n2)c1C(F)(F)F]

1-({5-[2-Chloro-3-(trifluoromethyl)phenyl]-1,2,4-oxadiazol-3-yl}methyl)-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 2-chloro-3-(trifluoromethyl)benzoic acid: MS (APCI): m/z 471 (M+1).

Example 78

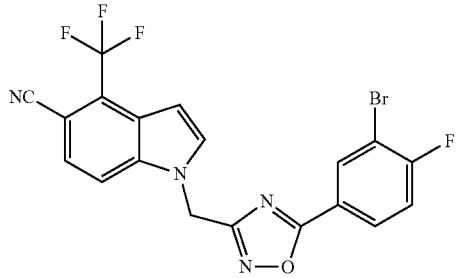 [SMILES: N#Cc1ccc2c(ccn2Cc2noc(-c3ccc(F)c(Br)c3)n2)c1C(F)(F)F]

1-{[5-(3-Bromo-4-fluorophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-bromo-4-fluorobenzoic acid: MS (ESI): m/z 465 (M+1).

Example 79

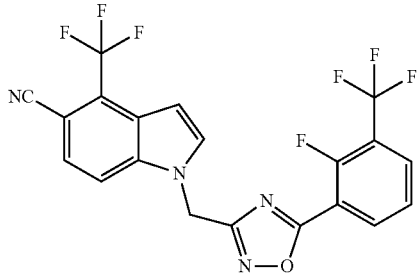 [SMILES: N#Cc1ccc2c(ccn2Cc2noc(-c3cccc(C(F)(F)F)c3F)n2)c1C(F)(F)F]

1-({5-[2-Fluoro-3-(trifluoromethyl)phenyl]-1,2,4-oxadiazol-3-yl}methyl)-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 2-fluoro-3-(trifluoromethyl)benzoic acid: MS (ESI): m/z 455 (M+1).

Example 80

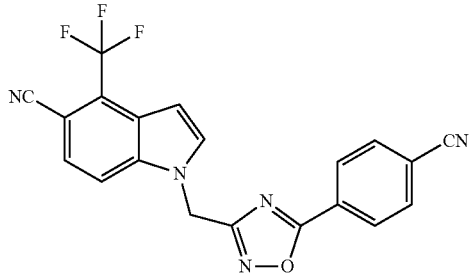 [SMILES: N#Cc1ccc(-c2nc(Cn3ccc4c(C(F)(F)F)c(C#N)ccc43)no2)cc1]

1-{[5-(4-Cyanophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 4-cyanobenzoic acid: MS (ESI): m/z 394 (M+1).

Example 81

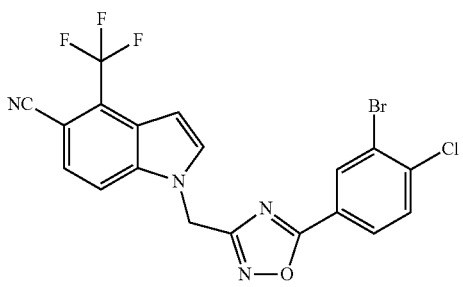 [SMILES: N#Cc1ccc2c(ccn2Cc2noc(-c3ccc(Cl)c(Br)c3)n2)c1C(F)(F)F]

1-{[5-(3-Bromo-4-chlorophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-bromo-4-chlorobenzoic acid: MS (ESI): m/z 481 (M+1).

Example 82

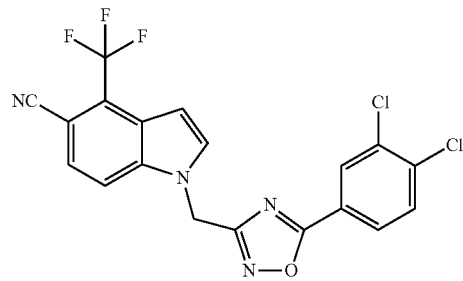 [SMILES: N#Cc1ccc2c(ccn2Cc2noc(-c3ccc(Cl)c(Cl)c3)n2)c1C(F)(F)F]

1-{[5-(3,4-Dichlorophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3,4-dichlorobenzoic acid: MS (ESI): m/z 437 (M+1).

Example 83

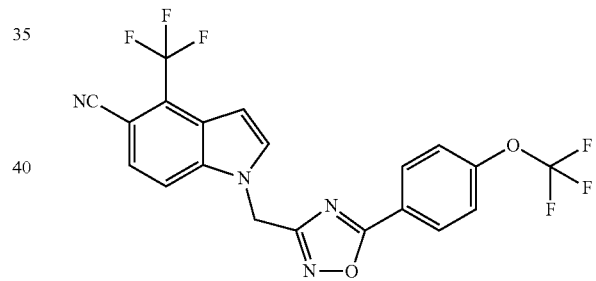

4-(Trifluoromethyl)-1-[(5-{4-[(trifluoromethyl)oxy]phenyl}-1,2,4-oxadiazol-3-yl)methyl]-1H-indole-5-carbonitrile Synthesized as described in Example 72 from 2-[5-cyano-4-(trifluoromethyl)-1H-indol-1-yl]-N-hydroxyethanimidamide and 4-[(trifluoromethyl)oxy]benzoic acid: MS (ESI): m/z 453 (M+1).

Example 84

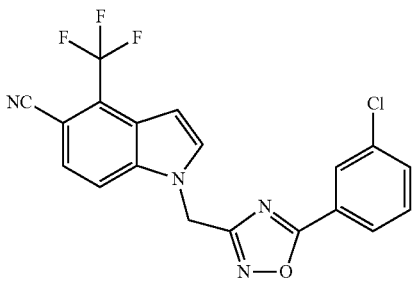 [SMILES: N#Cc1ccc2c(ccn2Cc2noc(-c3cccc(Cl)c3)n2)c1C(F)(F)F]

95

1-{[5-(3-Chlorophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-chlorobenzoic acid: MS (ESI): m/z 403 (M+1).

Example 85

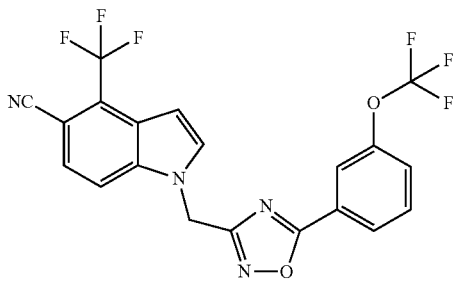 [SMILES: N#Cc1ccc2c(ccn2Cc2noc(-c3cccc(OC(F)(F)F)c3)n2)c1C(F)(F)F]

4-(Trifluoromethyl)-1-[(5-{3-[(trifluoromethyl)oxy]phenyl}-1,2,4-oxadiazol-3-yl)methyl]-1H-indole-5-carbonitrile Synthesized as described in Example 72 from 2-[5-cyano-4-(trifluoromethyl)-1H-indol-1-yl]-N-hydroxyethanimidamide and 3-[(trifluoromethyl)oxy]benzoic acid: MS (APCI): m/z 453 (M+1).

Example 86

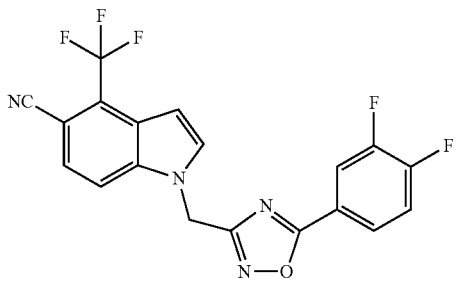 [SMILES: N#Cc1ccc2c(ccn2Cc2noc(-c3ccc(F)c(F)c3)n2)c1C(F)(F)F]

1-{[5-(3,4-Difluorophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3,4-difluorobenzoic acid: MS (APCI): m/z 405 (M+1).

Example 87

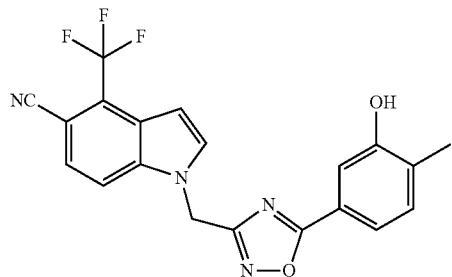 [SMILES: Cc1ccc(-c2nc(Cn3ccc4c(C(F)(F)F)c(C#N)ccc43)no2)cc1O]

96

1-{[5-(3-Hydroxy-4-methylphenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-hydroxy-4-methylbenzoic acid: MS (APCI): m/z 399 (M+1).

Example 88

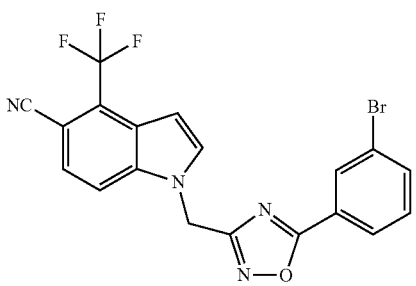

1-{[5-(3-Bromophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 3-bromobenzoic acid: MS (ESI): m/z 449 (M+1).

Example 89

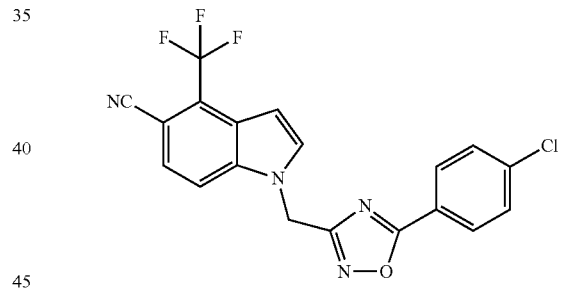

1-{[5-(4-Chlorophenyl)-1,2,4-oxadiazol-3-yl]methyl}-4-(trifluoromethyl)-1H-indole-5-carbonitrile Synthesized as described in Example 72 from 2-[5-cyano-4-(trifluoromethyl)-1H-indol-1-yl]-N-hydroxyethanimidamide and 4-chlorobenzoic acid: MS (ESI): m/z 403 (M+1).

Example 90

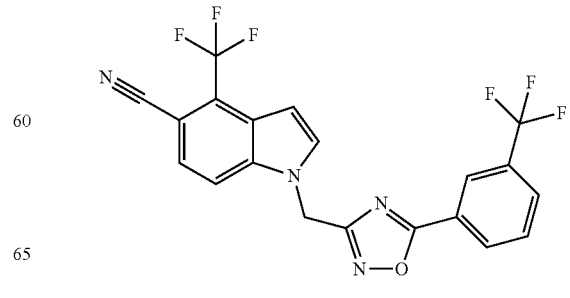

4-(Trifluoromethyl)-1-({5-[3-(trifluoromethyl)phenyl]-1,2,4-oxadiazol-3-yl}methyl)-1H-indole-5-carbonitrile Synthesized as described in Example 23 using 4-(trifluoromethyl)-1H-indole-5-carbonitrile and 3-(chloromethyl)-5-[3-(trifluoromethyl)phenyl]-1,2,4-oxadiazole: MS (ES) m/z 437 (M+1).

Example 91

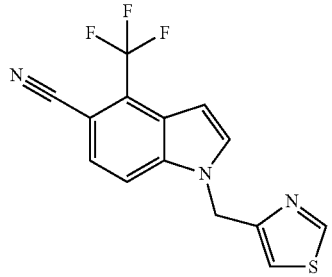 [SMILES: N#Cc1ccc2c(ccn2Cc2cscn2)c1C(F)(F)F]

1-(1,3-Thiazol-4-ylmethyl)-4-(trifluoromethyl)-1H-indole-5-carbonitrile

Synthesized as described in Example 23 using 4-(trifluoromethyl)-1H-indole-5-carbonitrile and 4-(chloromethyl)-1,3-thiazole hydrochloride: MS (ES) m/z 308 (M+1).

Example 92

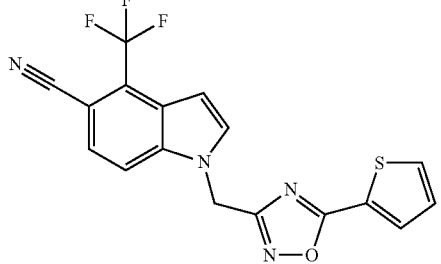

1-{[5-(2-Thienyl)-1,2,4-oxadiazol-3-yl]methyl}-4-(trifluoromethyl)-1H-indole-5-carbonitrile Synthesized as described in Example 23 using 4-(trifluoromethyl)-1H-indole-5-carbonitrile and 3-(chloromethyl)-5-(2-thienyl)-1,2,4-oxadiazole: MS (ES) m/z 375 (M+1).

Example 93

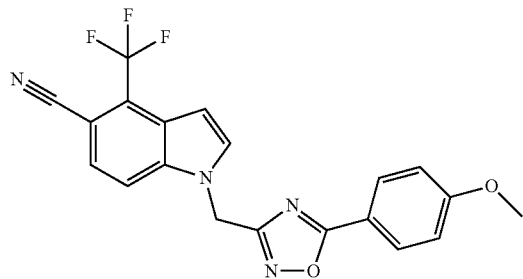 [SMILES: COc1ccc(-c2nc(Cn3ccc4c(C(F)(F)F)c(C#N)ccc43)no2)cc1]

1-({5-[4-(Methyloxy)phenyl]-1,2,4-oxadiazol-3-yl}methyl)-4-(trifluoromethyl)-1H-indole-5-carbonitrile Synthesized as described in Example 23 using 4-(trifluoromethyl)-1H-indole-5-carbonitrile and 3-(chloromethyl)-5-[4-(methyloxy)phenyl]-1,2,4-oxadiazole: MS (ES) m/z 399 (M+1).

Example 94

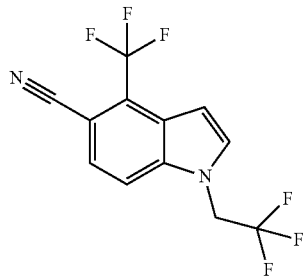 [SMILES: N#Cc1ccc2c(ccn2CC(F)(F)F)c1C(F)(F)F]

1-(2,2,2-Trifluoroethyl)-4-(trifluoromethyl)-1H-indole-5-carbonitrile

Synthesized as described in Example 23 using 4-(trifluoromethyl)-1H-indole-5-carbonitrile and 2,2,2-trifluoroethyl trifluoromethanesulfonate: MS (ES) m/z 293 (M+1).

Example 95

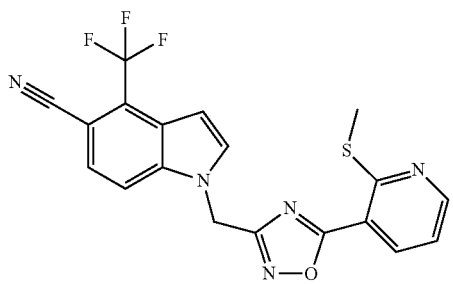 [SMILES: CSc1ncccc1-c1nc(Cn2ccc3c(C(F)(F)F)c(C#N)ccc32)no1]

1-({5-[2-(Methylthio)-3-pyridinyl]-1,2,4-oxadiazol-3-yl}methyl)-4-(trifluoromethyl)-1H-indole-5-carbonitrile Synthesized as described in Example 23 using 4-(trifluoromethyl)-1H-indole-5-carbonitrile and 3-[3-(chloromethyl)-1,2,4-oxadiazol-5-yl]-2-(methylthio)pyridine: MS (ES) m/z 416 (M+1).

Example 96

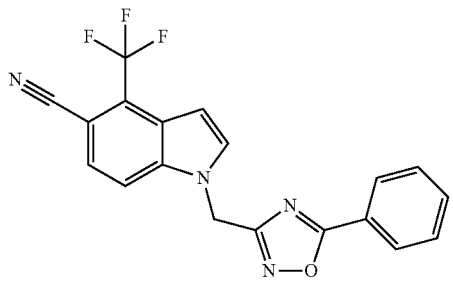 [SMILES: N#Cc1ccc2c(ccn2Cc2noc(-c3ccccc3)n2)c1C(F)(F)F]

1-[(5-Phenyl-1,2,4-oxadiazol-3-yl)methyl]-4-(trifluoromethyl)-1H-indole-5-carbonitrile Synthesized as described in Example 23 using 4-(trifluoromethyl)-1H-indole-5-carbonitrile and 3-(chloromethyl)-5-phenyl-1,2,4-oxadiazole: MS (ES) m/z 369 (M+1).

Example 97

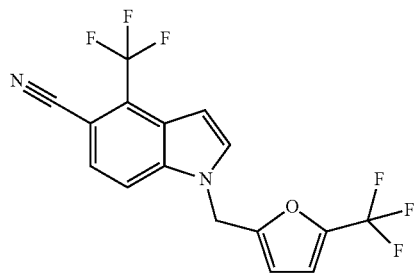 [SMILES: N#Cc1ccc2c(ccn2Cc2ccc(C(F)(F)F)o2)c1C(F)(F)F]

4-(Trifluoromethyl)-1-{[5-(trifluoromethyl)-2-furanyl]methyl}-1H-indole-5-carbonitrile Synthesized as described in Example 23 using 4-(trifluoromethyl)-1H-indole-5-carbonitrile and 2-(bromomethyl)-5-(trifluoromethyl)furan: MS (ES) m/z 359 (M+1).

Example 98

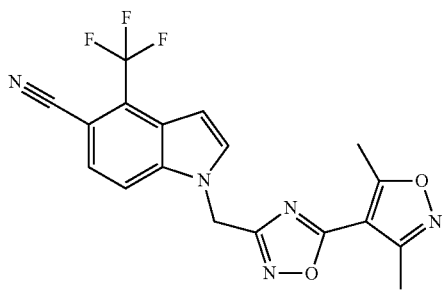 [SMILES: Cc1noc(C)c1-c1nc(Cn2ccc3c(C(F)(F)F)c(C#N)ccc32)no1]

1-{[5-(3,5-Dimethyl-4-isoxazolyl)-1,2,4-oxadiazol-3-yl]methyl}-4-(trifluoromethyl)-1H-indole-5-carbonitrile Synthesized as described in Example 23 using 4-(trifluoromethyl)-1H-indole-5-carbonitrile and 3-(chloromethyl)-5-(3,5-dimethyl-4-isoxazolyl)-1,2,4-oxadiazole: MS (ES) m/z 388 (M+1).

Example 99

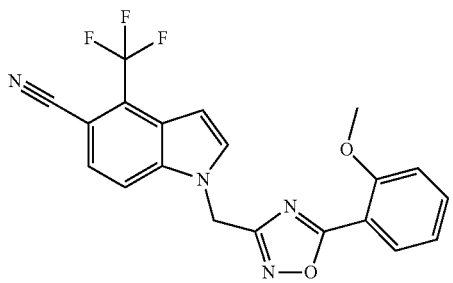 [SMILES: COc1ccccc1-c1nc(Cn2ccc3c(C(F)(F)F)c(C#N)ccc32)no1]

1-({5-[2-(Methyloxy)phenyl]-1,2,4-oxadiazol-3-yl}methyl)-4-(trifluoromethyl)-1H-indole-5-carbonitrile Synthesized as described in Example 23 using 4-(trifluoromethyl)-1H-indole-5-carbonitrile and 3-(chloromethyl)-5-[2-(methyloxy)phenyl]-1,2,4-oxadiazole: MS (ES) m/z 399 (M+1).

Example 100

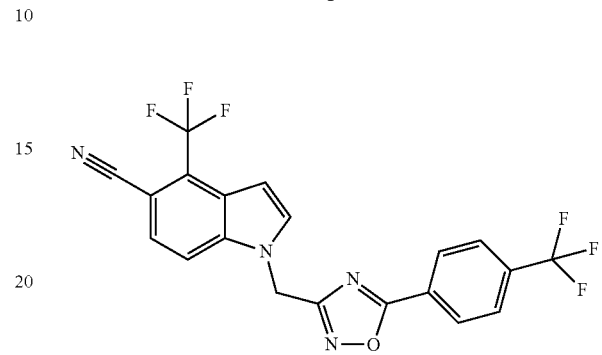

4-(Trifluoromethyl)-1-({5-[4-(trifluoromethyl)phenyl]-1,2,4-oxadiazol-3-yl}methyl)-1H-indole-5-carbonitrile Synthesized as described in Example 23 using 4-(trifluoromethyl)-1H-indole-5-carbonitrile and 3-(chloromethyl)-5-[4-(trifluoromethyl)phenyl]-1,2,4-oxadiazole: MS (ES) m/z 437 (M+1).

Example 101

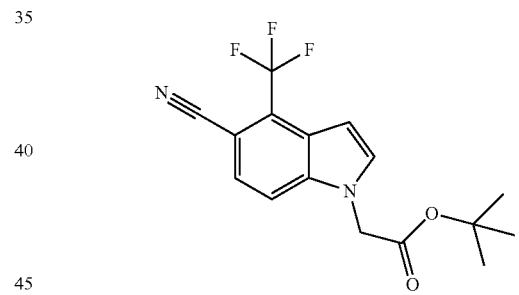

1,1-Dimethylethyl [5-cyano-4-(trifluoromethyl)-1H-indol-1-yl]acetate

Synthesized as described in Example 4 using 4-(trifluoromethyl)-1H-indole-5-carbonitrile and 1,1-dimethylethyl bromoacetate: MS (ES) m/z 325 (M+1).

Example 102

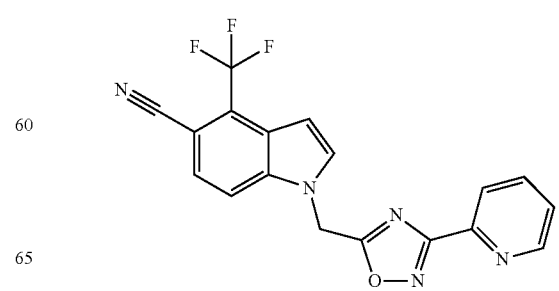

101

1-{[3-(2-Pyridinyl)-1,2,4-oxadiazol-5-yl]methyl}-4-(trifluoromethyl)-1H-indole-5-carbonitrile

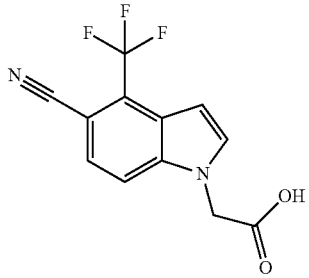 [SMILES: N#Cc1ccc2c(ccn2CC(=O)O)c1C(F)(F)F]

A.
[5-Cyano-4-(trifluoromethyl)-1H-indol-1-yl]acetic acid

Synthesized as described in Example 31B from 1,1-dimethylethyl [5-cyano-4-(trifluoromethyl)-1H-indol-1-yl]acetate: MS (ES) m/z 269 (M+1).

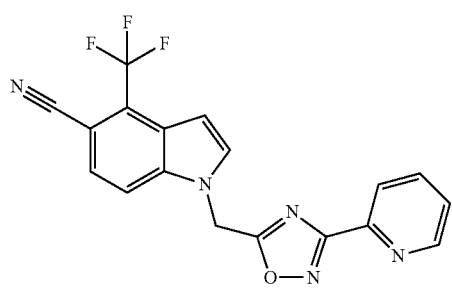 [SMILES: N#Cc1ccc2c(ccn2Cc2nc(-c3ccccn3)no2)c1C(F)(F)F]

B. 1-{[3-(2-Pyridinyl)-1,2,4-oxadiazol-5-yl]methyl}-4-(trifluoromethyl)-1H-indole-5-carbonitrile Synthesized as described in Example 37 from [5-cyano-4-(trifluoromethyl)-1H-indol-1-yl]acetic acid: MS (ES) m/z 370 (M+1).

Example 103

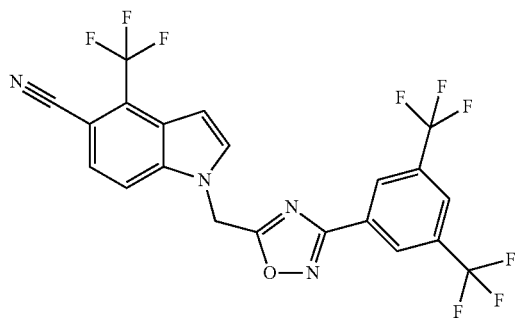 [SMILES: N#Cc1ccc2c(ccn2Cc2nc(-c3cc(C(F)(F)F)cc(C(F)(F)F)c3)no2)c1C(F)(F)F]

102

1-({3-[3,5-bis(Trifluoromethyl)phenyl]-1,2,4-oxadiazol-5-yl}methyl)-4-(trifluoromethyl)-1H-indole-5-carbonitrile Synthesized as described in Example 37 from [5-cyano-4-(trifluoromethyl)-1H-indol-1-yl]acetic acid and N-hydroxy-3,5-bis(trifluoromethyl)benzenecarboximidamide: MS (ES) m/z 503 (M−1).

Example 104

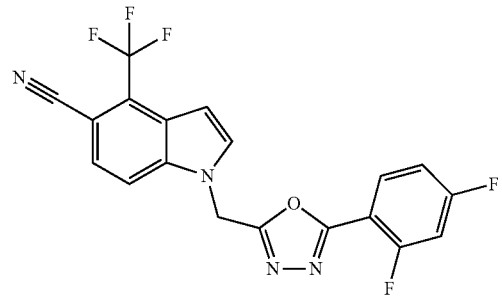 [SMILES: N#Cc1ccc2c(ccn2Cc2nnc(-c3ccc(F)cc3F)o2)c1C(F)(F)F]

1-{[5-(2,4-Difluorophenyl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid: MS (ES) m/z 405 (M+1).

Example 105

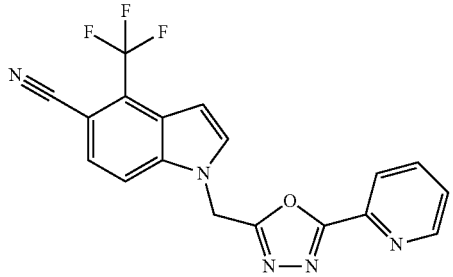 [SMILES: N#Cc1ccc2c(ccn2Cc2nnc(-c3ccccn3)o2)c1C(F)(F)F]

1-{[5-(2-Pyridinyl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid and 2-pyridinecarbohydrazide: MS (ES) m/z 370 (M+1).

Example 106

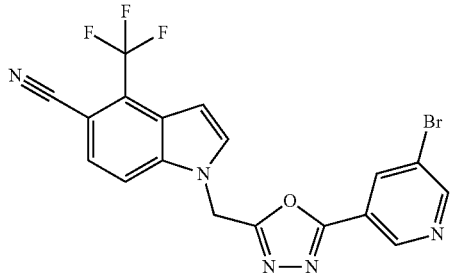 [SMILES: N#Cc1ccc2c(ccn2Cc2nnc(-c3cncc(Br)c3)o2)c1C(F)(F)F]

1-{[5-(5-Bromo-3-pyridinyl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid and 5-bromo-3-pyridinecarbohydrazide: MS (ES) m/z 448 and 450 (M+1 Br isotopes).

Example 107

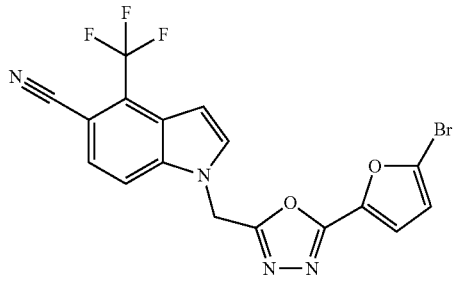 [SMILES: N#Cc1ccc2c(ccn2Cc2nnc(-c3ccc(Br)o3)o2)c1C(F)(F)F]

1-{[5-(5-Bromo-2-furanyl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid and 5-bromo-2-furancarbohydrazide: MS (ES) m/z 437 and 439 (M+1 Br isotopes).

Example 108

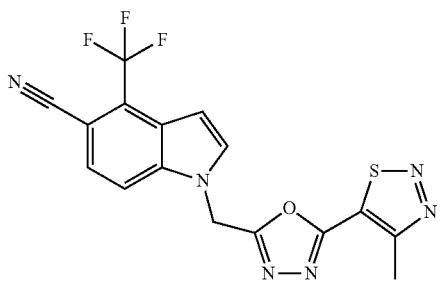 [SMILES: Cc1nnsc1-c1nnc(Cn2ccc3c(C(F)(F)F)c(C#N)ccc32)o1]

1-{[5-(4-Methyl-1,2,3-thiadiazol-5-yl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid and 4-methyl-1,2,3-thiadiazole-5-carbohydrazide: MS (ES) m/z 391 (M+1).

Example 109

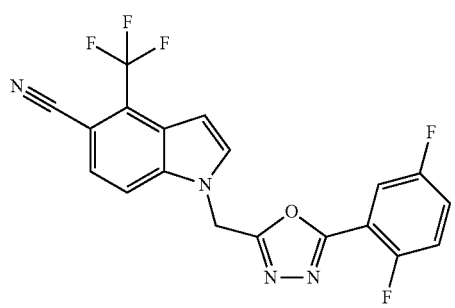 [SMILES: N#Cc1ccc2c(ccn2Cc2nnc(-c3cc(F)ccc3F)o2)c1C(F)(F)F]

1-{[5-(2,5-Difluorophenyl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid and 2,5-difluorobenzohydrazide: MS (ES) m/z 405 (M+1).

Example 110

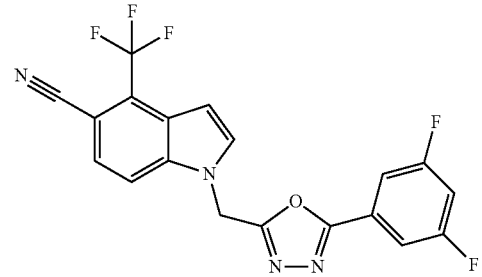 [SMILES: N#Cc1ccc2c(ccn2Cc2nnc(-c3cc(F)cc(F)c3)o2)c1C(F)(F)F]

1-{[5-(3,5-Difluorophenyl)-1,3,4-oxadiazol-2-yl]methyl}-4-(trifluoromethyl)-1H-indole-5-carbonitrile Synthesized as described in Example 35C from [5-cyano-4-(trifluoromethyl)-1H-indol-1-yl]acetic acid and 3,5-difluorobenzohydrazide: MS (ES) m/z 405 (M+1).

Example 111

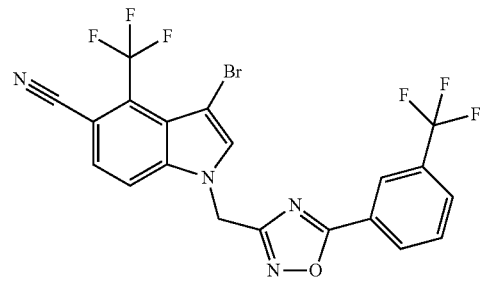

3-Bromo-4-(trifluoromethyl)-1-({5-[3-(trifluoromethyl)phenyl]-1,2,4-oxadiazol-3-yl}methyl)-1H-indole-5-carbonitrile

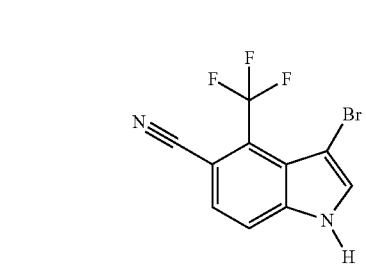 [SMILES: N#Cc1ccc2[nH]cc(Br)c2c1C(F)(F)F]

A. 3-Bromo-4-(trifluoromethyl)-1H-indole-5-carbonitrile

To an ice-cold solution of 4-(trifluoromethyl)-1H-indole-5-carbonitrile (0.047 g, 0.22 mmol) in DMF (2 mL), under $N_2$, was added a solution of NBS (0.043 g, 0.24 mmol) in DMF (0.5 mL). The mixture was stirred in the ice bath for 30 min and then at rt for 1 h. The mixture was partitioned between $Et_2O$ and an aqueous solution of $Na_2S_2O_3$. The organic phase was washed with water and sat'd brine, dried ($Na_2SO_4$) and concentrated in vacuo. The residue was purified by radial chromatography (5-50% EtOAc-hexanes gradient) to afford the title compound: $^1$H NMR (400 MHz, $CDCl_3$+few drops of $CD_3OD$) δ 11.52 (bs, 1H), 7.61 (d, J=8.5 Hz, 1H), 7.48-7.45 (m, 2H).

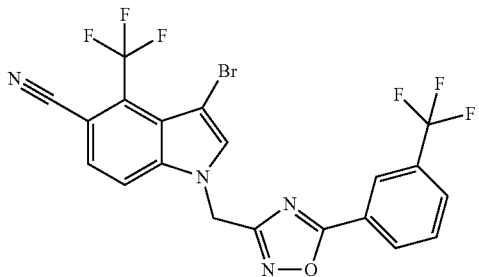

B. 3-Bromo-4-(trifluoromethyl)-1-({5-[3-(trifluoromethyl)phenyl]-1,2,4-oxadiazol-3-yl}methyl)-1H-indole-5-carbonitrile Synthesized as described in Example 4 from 3-bromo-4-(trifluoromethyl)-1H-indole-5-carbonitrile: MS (ES) m/z 515 and 517 (M+1 Br isotopes).

Example 112

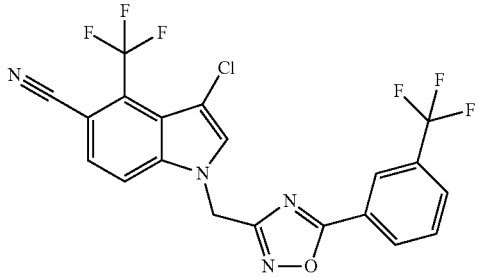

3-Chloro-4-(trifluoromethyl)-1-({5-[3-(trifluoromethyl)phenyl]-1,2,4-oxadiazol-3-yl}methyl)-1H-indole-5-carbonitrile

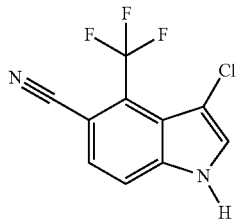 [SMILES: N#Cc1ccc2[nH]cc(Cl)c2c1C(F)(F)F]

A. 3-Chloro-4-(trifluoromethyl)-1H-indole-5-carbonitrile

To an ice-cold solution of 4-(trifluoromethyl)-1H-indole-5-carbonitrile (0.015 g, 0.071 mmol) in DMF (2 mL), under $N_2$, was added a solution of NCS (0.011 g, 0.079 mmol) in DMF (0.5 mL). The mixture was stirred at rt for 1 h and then heated at 75° C. for 40 min. Upon cooling, the mixture was partitioned between $Et_2O$ and 0.1N HCl. The organic phase was washed with water and sat'd brine, dried ($Na_2SO_4$), and concentrated in vacuo. The residue was purified by radial chromatography (50-100% $CH_2Cl_2$ hexanes gradient, followed by 1-5% MeOH—$CH_2Cl_2$ gradient) to afford the title compound (0.014 g, 82% yield): MS (ES) m/z 245 (M+1).

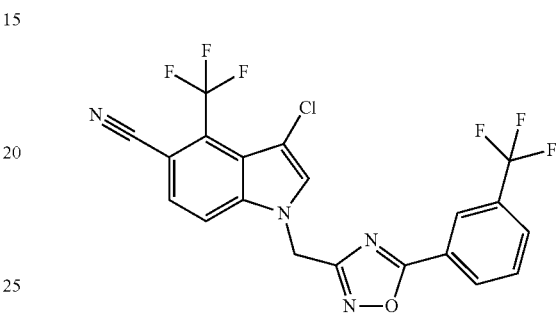

B. 3-Chloro-4-(trifluoromethyl)-1-({5-[3-(trifluoromethyl)phenyl]-1,2,4-oxadiazol-3-yl}methyl)-1H-indole-5-carbonitrile Synthesized as described in Example 4 from 3-chloro-4-(trifluoromethyl)-1H-indole-5-carbonitrile: MS (ES) m/z 471 (M+1).

Example 113

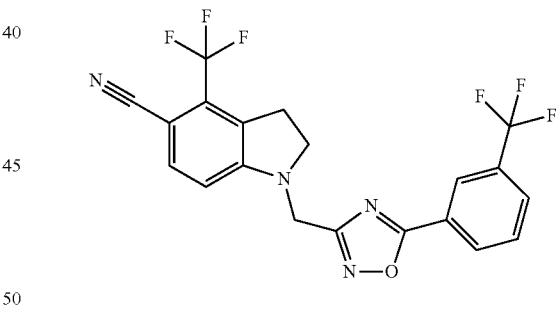

4-(Trifluoromethyl)-1-({5-[3-(trifluoromethyl)phenyl]-1,2,4-oxadiazol-3-yl}methyl)-2,3-dihydro-1H-indole-5-carbonitrile To an ice-cold solution of 4-(trifluoromethyl)-1-({5-[3-(trifluoromethyl)phenyl]-1,2,4-oxadiazol-3-yl}methyl)-1H-indole-5-carbonitrile (Example 60D) (0.025 g, 0.057 mmol) in TFA (1 mL) was added $NaCNBH_3$ (0.050 g, 0.79 mmol) in portions. After addition, the mixture was stirred at rt for 3 h and then concentrated in vacuo. The residue was partitioned between $CH_2Cl_2$ and 0.2N NaOH. The organic phase was washed with water and sat'd brine, dried ($Na_2SO_4$) and concentrated in vacuo. The residue was purified by flash chromatography (0-30% EtOAc-hexanes gradient) and the product was crystallized from $CH_2Cl_2$-hexanes to give the title compound as a white solid (0.013 g, 52% yield): MS (ES) m/z 439 (M+1).

Example 114

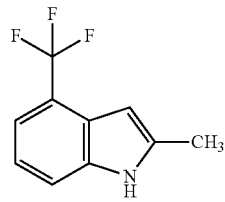

2-Methyl-4-(trifluoromethyl)-1H-indole

A. 4-(Trifluoromethyl)-1H-indole

A solution of 2-methyl-1-nitro-3-(trifluoromethyl)benzene (10.00 g, 48.8 mmol), pyrrolidine (4.44 mL, 53.7 mmol) and dimethylformamide dimethylacetal (19.8 mL, 146 mmol) in DMF (100 mL) was heated at 100° C. for 4 h, cooled and concentrated in vacuo. The residue was partitioned between Et$_2$O/H$_2$O, the layers were separated and the aqueous layer was extracted with Et$_2$O (×3). Combined organics were washed (H$_2$O, brine), dried over Na$_2$SO$_4$, filtered and concentrated in vacuo. The residue was dissolved in THF/MeOH (1:1, 200 mL), and transferred to a 3-necked flask equipped with an overhead stirrer, reflux condenser, and dropping addition funnel. Raney-Ni (Raney® 2800 slurry in water, 10 g) was added in one portion and the entire apparatus was thoroughly flushed with N$_2$. The mixture was heated to 60° C., under N$_2$, and a solution of hydrazine monohydrate (8 mL) in THF/MeOH (1:1, 20 mL) was added dropwise over 1 h. The mixture was heated at 60° C. for 1 h, cooled, and filtered through a pad of Celite®. The filtrate was concentrated in vacuo, the residue was partitioned between Et$_2$O/H$_2$O, the layers were separated and the aqueous layer was extracted with Et$_2$O (×3). Combined organics were washed (10% HCl, H$_2$O, brine), dried over Na$_2$SO$_4$, filtered and concentrated in vacuo. The residue was purified by flash chromatography (EtOAc/hexanes), affording 5.17 g of the title compound as a light brown liquid: $^1$H NMR (300 MHz, methanol-d$_4$) δ 7.61 (d, J=8.2 Hz, 1H), 7.39 (d, J=3.2 Hz, 1H), 7.32 (d, J=7.4 Hz, 1H), 7.19 (partially resolved dd, J≈8.4, 7.5 Hz, 1H), 6.59 (br. s, 1H).

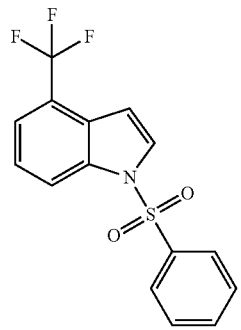 [SMILES: O=S(=O)(c1ccccc1)n1ccc2c(C(F)(F)F)cccc21]

B. 1-(Phenylsulfonyl)-4-(trifluoromethyl)-1H-indole

To a solution of 4-(trifluoromethyl)-1H-indole (0.535 g, 2.89 mmol; step A above), tetrabutylammonium bromide (0.097 g, 0.30 mmol) and benzenesulfonyl chloride (0.44 mL, 3.5 mmol) in PhMe (5 mL) at rt was added 50 wt % NaOH (3 mL) and H$_2$O (2 mL). The mixture was stirred 30 min, partitioned between Et$_2$O/H$_2$O and the layers were separated. The organic layer was washed (H$_2$O, brine), dried over Na$_2$SO$_4$, filtered and concentrated in vacuo. The residue was purified by flash chromatography (EtOAc/hexanes), affording 0.771 g of the title compound as a thick, pale yellow oil: $^1$H NMR (300 MHz, methanol-d$_4$) δ 8.25 (d, J=8.3 Hz, 1H), 8.00-7.94 (m, 2H), 7.88 (d, J=3.8 Hz, 1H), 7.65-7.58 (m, 1H), 7.57-7.41 (m, 4H), 6.87 (br. s, 1H).

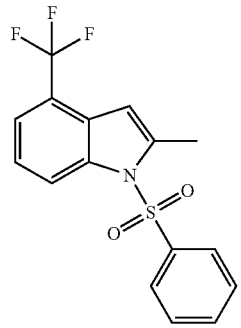 [SMILES: Cc1cc2c(C(F)(F)F)cccc2n1S(=O)(=O)c1ccccc1]

C. 2-Methyl-1-(phenylsulfonyl)-4-(trifluoromethyl)-1H-indole

To a solution of 1-(phenylsulfonyl)-4-(trifluoromethyl)-1H-indole (60.0 g, 184.6 mmol) in THF (300 mL) at 0° C. was added n-BuLi (88.6 mL of a 2.50 M solution in hexanes), dropwise over 5 min. The mixture was stirred 1 h and methyl iodide (23.0 mL, 369.2 mmol) was added dropwise over 5 min. The mixture was stirred at 0° C. for 2.5 h and then overnight, slowly warming to rt, poured into water and extracted with Et$_2$O (×3). Combined organics were washed (H$_2$O, brine), dried over Na$_2$SO$_4$, filtered and concentrated in vacuo. The residue was purified by flash chromatography (EtOAc/hexanes), affording 26.0 g of the title compound as a colorless oil: MS (ES) m/z 338 (M−1).

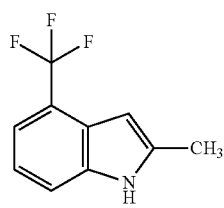

D. 2-Methyl-4-(trifluoromethyl)-1H-indole

A mixture of 2-methyl-1-(phenylsulfonyl)-4-(trifluoromethyl)-1H-indole (13.5 g, 39.82 mmol; step C above) and K$_2$CO$_3$ (27.5 g) in MeOH/H$_2$O (2:1, 300 mL) was heated at reflux temperature. After 14 h the mixture was cooled and concentrated in vacuo. The residue was partitioned between Et$_2$O/H$_2$O, the layers were separated and the aqueous layer was extracted with Et$_2$O (×2). Combined organics were washed (H$_2$O, brine), dried over Na$_2$SO$_4$, filtered and concentrated in vacuo. The residue was purified via column chromatography (SiO$_2$, 1:1 EtOAc/hexanes eluent), affording 11.0 g of the deprotected indole as a yellow oil: $^1$H NMR (400 MHz, CDCl$_3$) δ 7.43 (d, J=8.0 Hz, 1H), 7.35 (d, J=8.0 Hz, 1H), 7.15 (t, J=8.0 Hz, 1H), 6.46 (s, 1H), 2.48 (s, 3H); MS (ES) m/z 200 (M+1).

Example 115

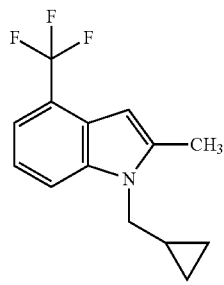 [SMILES: Cc1cc2c(C(F)(F)F)cccc2n1CC1CC1]

1-(Cyclopropyl methyl)-2-methyl-4-(trifluoromethyl)-1H-indole

Synthesized as described in Example 4 using 2-methyl-4-(trifluoromethyl)-1H-indole and (bromomethyl)cyclopropane: $^1$H NMR (400 MHz, CDCl$_3$) δ 7.45 (d, J=8.2 Hz, 1H), 7.35 (d, J=8.2 Hz, 1H), 7.16 (t, J=8.2 Hz, 1H), 6.45 (s, 1H), 4.02 (d, J=6.4 Hz, 2H), 2.48 (s, 3H), 1.18 (m, 1H), 0.56 (m, 2H), 0.34 (m, 2H); MS (ES) m/z 254 (M+1).

Example 116

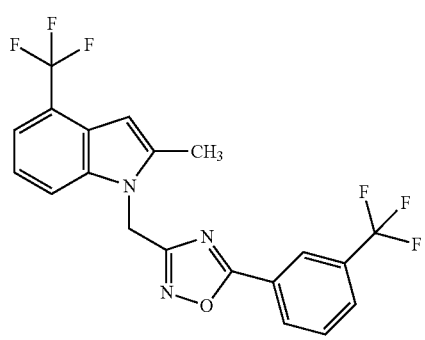 [SMILES: Cc1cc2c(C(F)(F)F)cccc2n1Cc1noc(-c2cccc(C(F)(F)F)c2)n1]

2-Methyl-4-(trifluoromethyl)-1-({5-[3-(trifluoromethyl)phenyl]-1,2,4-oxadiazol-3-yl}methyl)-1H-indole Synthesized as described in Example 4 using 2-methyl-4-(trifluoromethyl)-1H-indole and 3-(chloromethyl)-5-[3-(trifluoromethyl)phenyl]-1,2,4-oxadiazole: $^1$H NMR (400 MHz, CDCl$_3$) δ 8.31 (s, 1H), 8.24 (d, J=8.1 Hz, 1H), 7.83 (d, J=7.8 Hz, 1H), 7.64 (m, 2H), 7.38 (d, J=7.9 Hz, 1H), 7.22 (t, J=7.9 Hz, 1H), 6.52 (s, 1H), 5.45 (s, 2H), 2.66 (s, 3H); MS (ES) m/z 426 (M+1).

Example 117

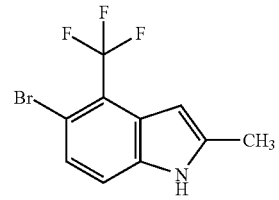

5-Bromo-2-methyl-4-(trifluoromethyl)-1H-indole

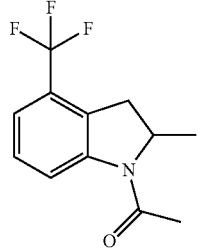 [SMILES: CC(=O)N1c2cccc(C(F)(F)F)c2CC1C]

A. 1-Acetyl-2-methyl-4-(trifluoromethyl)-2,3-dihydro-1H-indole

A mixture of 2-methyl-4-(trifluoromethyl)-1H-indole (Example 114D) (0.48 g, 2.41 mmol) was dissolved in HOAc (3.0 mL), cooled to 0° C. and NaBH₃CN (0.454 g, 7.23 mmol) was added in one portion. After 5 min the mixture was removed from the cooling bath and stirred at rt for 14 h. The mixture cooled to 0° C. and the pH was adjusted to ca. 13 by addition of 1 N NaOH (20 mL) and further addition of solid NaOH pellets. The mixture was extracted with Et₂O (×3), combined organics were washed (H₂O, brine), dried over Na₂SO₄, filtered and concentrated in vacuo. The residue was dissolved in dry CH₂Cl₂ (10 mL) and treated with DMAP (0.884 g, 7.23 mmol). The mixture was cooled to 0° C. and Ac₂O (0.455 mL, 4.81 mmol) was added dropwise via syringe. The mixture was stirred overnight, slowly warming to rt, diluted with CH₂Cl₂, washed (10% HCl, H₂O, brine), dried over Na₂SO₄, filtered, and concentrated in vacuo. The residue was purified by flash chromatography (EtOAc/hexanes), affording 0.25 g of the title compound as a pale yellow oil: MS (ES) m/z 244 (M+1).

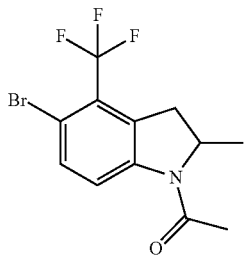 [SMILES: CC(=O)N1c2ccc(Br)c(C(F)(F)F)c2CC1C]

B. 1-Acetyl-5-bromo-2-methyl-4-(trifluoromethyl)-2,3-dihydro-1H-indole

To a solution of 1-acetyl-2-methyl-4-(trifluoromethyl)-2,3-dihydro-1H-indole (0.100 g, 0.45 mmol; step A above) in acetic acid (1.0 mL) at rt was added bromine (0.035 mL; 0.68 mmol). More bromine (0.020 mL, 0.39 mmol) was added after 14 h. After another 5 h, the mixture was slowly added to sat'd NaHCO₃ and extracted with Et₂O (×3). Combined organics were washed (H₂O, brine), dried over Na₂SO₄, filtered and concentrated in vacuo. The residue was purified by flash chromatography (EtOAc/hexanes), affording 0.090 g of the title compound as a white solid: MS (ES) m/z 324 (M+2 isomer).

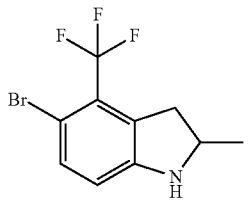

C. 5-Bromo-2-methyl-4-(trifluoromethyl)-2,3-dihydro-1H-indole

A mixture of 1-acetyl-5-bromo-2-methyl-4-(trifluoromethyl)-2,3-dihydro-1H-indole (0.130 g, 0.404 mmol; step B above) and NaOH (0.086 g; 2.15 mmol) in MeOH/H₂O (4:1; 13 mL) was heated at reflux 3 h. The solvent was removed, the residue was partitioned between Et₂O/H₂O, and the layers were separated. The aqueous layer was extracted with Et₂O (×2). Combined organics were washed (H₂O, brine), dried over Na₂SO₄, filtered and concentrated in vacuo, affording 0.090 g of the title compound as a pale yellow oil which was used without further purification: MS (APCI) m/z 282 (M+H, ⁸¹Br).

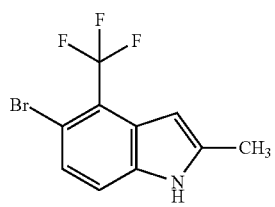

D. 5-Bromo-2-methyl-4-(trifluoromethyl)-1H-indole

To a solution of 5-bromo-2-methyl-4-(trifluoromethyl)-2,3-dihydro-1H-indole (0.09 g, 0.320 mmol; step C above) in 1,4-dioxane (5 mL) at rt was added DDQ (0.110 g, 0.48 mmol) in one portion. After 1 h, the mixture was poured into water and extracted with Et₂O (×3). Combined organics were washed (1 N NaOH, H₂O, brine), dried over Na₂SO₄, filtered and concentrated in vacuo. The residue was purified by flash chromatography (EtOAc/hexanes), affording 0.056 g of the title compound as a pale yellow solid: ¹H NMR (400 MHz, CDCl₃) δ 8.07 (bs, 1H), 7.36 (m, 1H), 7.25 (d, J=5.0 Hz, 1H), 6.47 (s, 1H), 2.48 (s, 3H).

Example 118

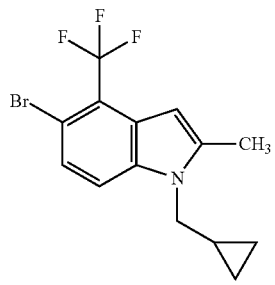 [SMILES: Cc1cc2c(C(F)(F)F)c(Br)ccc2n1CC1CC1]

5-Bromo-1-(cyclopropylmethyl)-2-methyl-4-(trifluoromethyl)-1H-indole

Synthesized as described in Example 4 using 5-bromo-2-methyl-4-(trifluoromethyl)-1H-indole and (bromomethyl)cyclopropane: ¹H NMR (400 MHz, CDCl₃) δ 7.38 (d, J=8.4 Hz, 1H), 7.26 (d, J=8.4 Hz, 1H), 6.49 (s, 1H), 3.99 (d, J=6.4

Hz, 2H), 2.46 (s, 3H), 1.14 (m, 1H), 0.56 (m, 2H), 0.32 (m, 2H); MS (ES) m/z 332 (M+1, isotope for Br) and 334 (M+1, isotope for Br).

Example 119

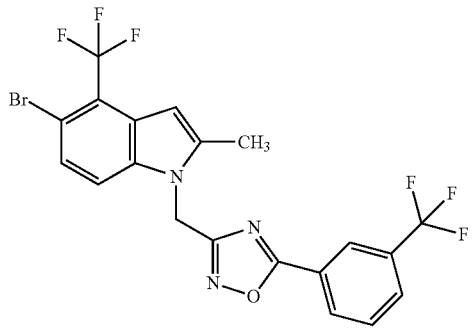 [SMILES: Cc1cc2c(C(F)(F)F)c(Br)ccc2n1Cc1noc(-c2cccc(C(F)(F)F)c2)n1]

5-Bromo-2-methyl-4-(trifluoromethyl)-1-({5-[3-(trifluoromethyl)phenyl]-1,2,4-oxadiazol-3-yl}methyl)-1H-indole Synthesized as described in Example 4 using 5-bromo-2-methyl-4-(trifluoromethyl)-1H-indole and 3-(chloromethyl)-5-[3-(trifluoromethyl)phenyl]-1,2,4-oxadiazole: $^1$H NMR (400 MHz, CDCl$_3$) δ 8.31 (s, 1H), 8.23 (d, J=7.8 Hz, 1H), 7.84 (d, J=7.8 Hz, 1H), 7.65 (t, J=7.8 Hz, 1H), 7.44 (s, 2H), 6.58 (s, 1H), 5.41 (s, 2H), 2.63 (s, 3H).

Example 120

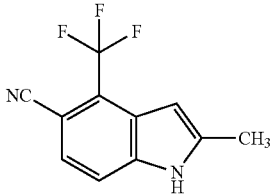 [SMILES: Cc1cc2c(C(F)(F)F)c(C#N)ccc2[nH]1]

2-Methyl-4-(trifluoromethyl)-1H-indole-5-carbonitrile

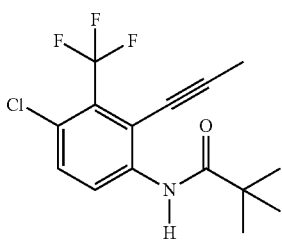 [SMILES: CC#Cc1c(NC(=O)C(C)(C)C)ccc(Cl)c1C(F)(F)F]

A. N-[4-Chloro-2-(1-propyn-1-yl)-3-(trifluoromethyl)phenyl]-2,2-dimethylpropanamide A triethylamine (300 mL) solution of N-[4-chloro-2-iodo-3-(trifluoromethyl)phenyl]-2,2-dimethylpropanamide (Example 60A) (40 g, 98.6 mmol) was treated with 1-propyne (39.5 g, 988 mmol) followed by copper iodide (0.94 g, 4.9 mmol) and PdCl$_2$(PPh$_3$)$_2$ (6.9 g, 9.8 mmol) in a Parr Bomb at −78° C. The reaction vessel was purged with N$_2$, sealed and heated gradually to 50° C. overnight, then cooled to −78° C. The cooled mixture was diluted with Et$_2$O and filtered through celite. The Et$_2$O solution was washed with water once, brine once, and dried (MgSO$_4$). Filtration and concentration in vacuo followed by radial chromatography (SiO$_2$, 0-10% EtOAc-hexanes gradient) afforded the title compound as a yellow solid (20.5 g, 65%): $^1$H NMR (400 MHz, CDCl$_3$) δ 8.70 (s, 1H), 8.60 (d, J=9.0 Hz, 1H), 7.38 (d, J=9.0 Hz, 1H), 2.22 (s, 3H), 1.33 (s, 9H); MS (ES) m/z 318 (M+1) and 320 (M+1, isotope).

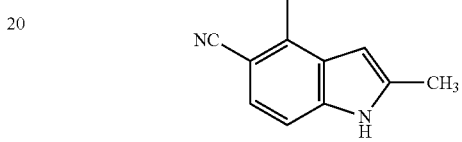

B. 2-Methyl-4-(trifluoromethyl)-1H-indole-5-carbonitrile

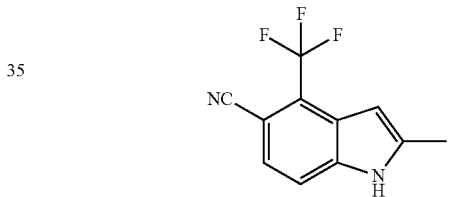

2-methyl-4-(trifluoromethyl)-1H-indole-5-carbonitrile

An NMP solution (150 mL) of N-[4-chloro-2-(1-propyn-1-yl)-3-(trifluoromethyl)phenyl]-2,2-dimethylpropanamide (10 g, 31.5 mmol) was treated with CuCN (11.3 g, 126 mmol) and the resulting mixture was heated at 195° C. for 90 h. Two reactions were carried out simultaneously. The combined dark brown reaction mixture was poured into crushed ice (250 mL) containing conc. ammonium hydroxide (100 mL). The resulting slurry was stirred with the addition of Et$_2$O and filtered through celite. The filtrate was diluted with Et$_2$O and partitioned. The aqueous portion was extracted with Et$_2$O four times. The combined organic portions were washed with brine and dried (MgSO$_4$). Filtration and concentration in vacuo followed by radial chromatography (SiO$_2$, 0-60% EtOAc-hexanes gradient) afforded the title compound as a solid (9 g, 64%):

$^1$H NMR (400 MHz, CDCl$_3$) δ 8.45 (s, 1H), 7.50 (d, J=9.0 Hz, 1H), 7.47 (d, J=9.0 Hz, 1H), 6.54 (s, 1H), 2.52 (s, 3H); MS (ES) m/z 225 (M+1).

Alternative Route to 2-methyl-4-(trifluoromethyl)-1H-indole-5-carbonitrile

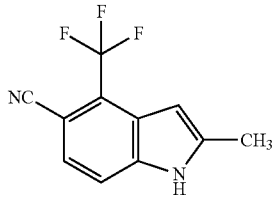

2-Methyl-4-(trifluoromethyl)-1H-indole-5-carbonitrile

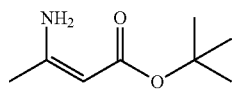

A. 1,1-Dimethylethyl (2Z)-3-amino-2-butenoate

A solution of 1,1-dimethylethyl 3-oxobutanoate (50 g, 0.32 mol) in MeOH (320 mL) and 30% ammonium hydroxide (280 mL) was stirred at ambient temperature overnight. The solution was neutralized carefully with conc. HCl (200 mL), partially concentrated at reduced pressure and extracted with EtOAc (2×300 mL). Combined organic phases were dried over Na$_2$SO$_4$, filtered and concentrated to afford 1,1-dimethylethyl (2Z)-3-amino-2-butenoate as an oil that crystallized on standing (54 g, 100% yield): $^1$H NMR (DMSO-d$_6$) δ 7.63 (bs, 1H), 6.79 (bs, 1H), 4.18 (s, 1H), 1.74 (s, 3H), 1.35 (s, 9H).

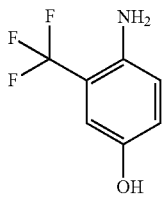 [SMILES: Nc1ccc(O)cc1C(F)(F)F]

B. 4-Amino-3-(trifluoromethyl)phenol

A stirred mixture of a solution of 4-nitro-3-(trifluoromethyl)phenol (100 g, 0.48 mol) in EtOH (800 mL) and 10% palladium on carbon (10 g, wet Degussa type E101) was hydrogenated overnight at rt and atmospheric pressure. The reaction mixture was filtered and the filtrate concentrated in vacuo to afford amino-3-(trifluoromethyl)phenol as a beige solid (85 g, 100% yield): $^1$H NMR (DMSO-d$_6$) δ 8.88 (s, 1H), 6.76-6.67 (m, 3H), 4.84 (s, 2H).

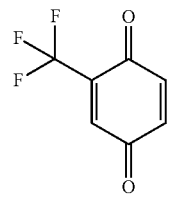

C. 2-(Trifluoromethyl)-2,5-cyclohexadiene-1,4-dione

A solution of 4-amino-3-(trifluoromethyl)phenol (in six separate reaction mixtures with 11.6 g, 0.065 mols of compound each, for a total of 70 g, 0.40 mol or compound) in 2.5 M H$_2$SO$_4$ (120 mL per reaction mixture, for a total of 720 mL) was added dropwise to a stirred suspension of MnO$_2$ (13.0 g, 0.15 mol per reaction, for a total of 78 g, 0.9 mol) in 2.5 M H$_2$SO$_4$ (120 mL per reaction mixture, for a total of 720 mL) with external cooling; the reaction temperature was maintained between 6-8° C. during addition. After stirring an additional 30 min, each reaction mixture was filtered and the cake washed with CH$_2$Cl$_2$ until it showed no evidence of desired product (TLC Rf~0.8; CH$_2$Cl$_2$ on silica gel). The organic phase was separated, dried over MgSO$_4$, filtered through a small plug of silica gel (to remove inorganic salts) and the CH$_2$Cl$_2$ filtrate concentrated to 300 mL (final combined volume) at atmospheric pressure (note: use atmospheric pressure distillation to avoid sublimation of quinone). The resulting quinone solution was used in the next step without further purification. Estimated total yield was 54 g (64% yield) of 2-(trifluoromethyl)-2,5-cyclohexadiene-1,4-dione in CH$_2$Cl$_2$ (300 mL, ~1 M): $^1$H NMR (CDCl$_3$) δ 7.10 (s, 1H), 6.90 (d, J=10.5 Hz, 1H), 6.87 (d, J=10.5 Hz, 1H).

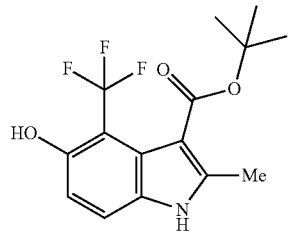 [SMILES: Cc1[nH]c2ccc(O)c(C(F)(F)F)c2c1C(=O)OC(C)(C)C]

D. 1,1-Dimethylethyl 5-hydroxy-2-methyl-4-(trifluoromethyl)-1H-indole-3-carboxylate A stirred solution of 1,1-dimethylethyl (2Z)-3-amino-2-butenoate (47.6 g, 0.3 mol) in EtOH (100 mL) was treated dropwise at ambient temperature with a 1.2 M solution of 2-(trifluoromethyl)-2,5-cyclohexadiene-1,4-dione in CH$_2$Cl$_2$ (300 mL, 0.35 mol) (internal temperature rose to +35° C. during the addition). The reaction was stirred 1 h and concentrated at reduced pressure. Stirring the resulting material with CHCl$_3$ at ice-bath temperature afforded 1,1-dimethylethyl 5-hydroxy-2-methyl-4-(trifluoromethyl)-1H-indole-3-carboxylate as an off-white solid which was collected by filtration (62 g, 66% yield): $^1$H NMR (DMSO-d$_6$) δ 11.55 (s, 1H), 9.68 (bs, 1H), 7.33 (d, J=8.8 Hz, 1H), 6.76 (d, J=8.8 Hz, 1H), 2.37 (s, 3H), 1.45 (s, 9H).

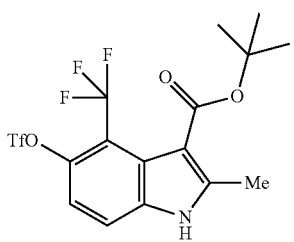 [SMILES: Cc1[nH]c2ccc(OS(=O)(=O)C(F)(F)F)c(C(F)(F)F)c2c1C(=O)OC(C)(C)C]

E. 1,1-Dimethylethyl 2-methyl-4-(trifluoromethyl)-5-{[(trifluoromethyl)-sulfonyl]oxy}-1H-indole-3-carboxylate A stirred solution of 1,1-dimethylethyl 5-hydroxy-2-methyl-4-(trifluoromethyl)-1H-indole-3-carboxylate (62 g, 0.197 mol), DIEA (56 mL, 0.321 mol) and PhN(Tf)$_2$ (78 g, 0.218 mol) in CH$_3$CN (300 mL) was heated at reflux temperature for 2 h. The reaction was cooled to ambient temperature, diluted with EtOAc (1.1 L) and extracted with water (500 mL); the aqueous layer was back extracted with EtOAc (250 mL). Combined EtOAc layers were washed with 0.1N NaOH (3×500 mL), 2 M H$_3$PO$_4$ (1×500 mL) and water (1×500 mL). The EtOAc layer was dried over MgSO$_4$, filtered, concentrated and the resulting material crystallized from MTBE; filtration afforded 1,1-dimethylethyl 2-methyl-4-(trifluoromethyl)-5-{[(trifluoromethyl)-sulfonyl]oxy}-1H-indole-3-carboxylate as a white crystalline solid (66 g, 75% yield): $^1$H NMR (DMSO-d$_6$) δ 12.39 (s, 1H), 7.77 (d, J=9.0 Hz, 1H), 7.29 (d, J=9.0 Hz, 1H), 2.48 (s, 3H), 1.48 (s, 9H).

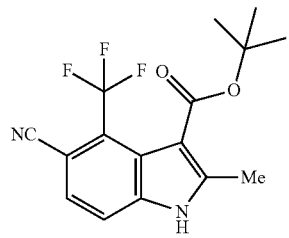 [SMILES: Cc1[nH]c2ccc(C#N)c(C(F)(F)F)c2c1C(=O)OC(C)(C)C]

F. 1,1-Dimethylethyl 5-cyano-2-methyl-4-(trifluoromethyl)-1H-indole-3-carboxylate To a stirred solution of 1,1-dimethylethyl 2-methyl-4-(trifluoromethyl)-5-{[(trifluoromethyl)sulfonyl]oxy}-1H-indole-3-carboxylate (20.2 g, 45.2 mmol) in NMP (150 mL) was added deionized water (8 mL) and N$_2$ was passed through the solution for 10 min with the aid of a glass pipette. 1,1'-Bis(diphenylphosphino)ferrocene (2.49 g, 4.49 mmol) and tris(dibenzylidineacetone)dipalladium(0) (2 g, 2.18 mmol) were added and the solution was stirred under N$_2$ atmosphere at rt for 15 min. Zinc cyanide (3.95 g, 33.6 mmol) was added and the mixture was stirred an additional 10 min at rt. The reaction mixture was gradually heated to 80° C. (internal temperature) and maintained at this temperature for 3 h. After cooling to 35° C., the mixture was diluted with MTBE (100 mL) and washed with water (100 mL). The aqueous layer was back extracted with MTBE (2×100 mL) and the combined MTBE layers were washed with water (4×125 mL) and dried over MgSO$_4$. The organic phase was filtered through a glass fritted funnel and the MTBE filtrate was stirred over decolorizing charcoal for 15 min. The charcoal mixture was filtered through a plug of silica gel (75 g) and the filtrate was concentrated at reduced pressure. Remaining material was triturated with hot MTBE, then diluted with i-octane, cooled to −15° C. and filtered to afford 1,1-dimethylethyl 5-cyano-2-methyl-4-(trifluoromethyl)-1H-indole-3-carboxylate as a beige solid (12.5 g, 85% yield): $^1$H NMR (DMSO-d$_6$) δ 12.54 (s, 1H), 7.77 (d, J=8.0 Hz, 1H), 7.70 (d, J=8.0 Hz, 1H), 2.50 (s, 3H), 1.49 (s, 9H); MS (ES): m/z 323 (M−1).

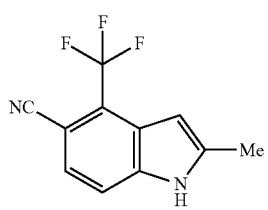 [SMILES: Cc1cc2c(C(F)(F)F)c(C#N)ccc2[nH]1]

G. 2-Methyl-4-(trifluoromethyl)-1H-indole-5-carbonitrile

A rapidly stirred mixture of the product from the previous step (12.5 g, 38.54 mmol), p-toluenesulfonic acid monohydrate (0.71 g, 3.7 mmol) and toluene (110 mL) was heated at reflux for 1 h. The mixture was cooled to ambient temperature, diluted with EtOAc (50 mL) and washed with satd. NaHCO$_3$ solution (2×75 mL). The organic phase was dried over MgSO$_4$, filtered, concentrated at reduced pressure and crystallized from toluene; this provided 2-methyl-4-(trifluoromethyl)-1H-indole-5-carbonitrile as an off-white solid (7.5 g, 87% yield): analytical data matched those of Example 120.

Example 121

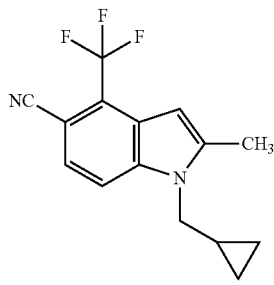 [SMILES: Cc1cc2c(C(F)(F)F)c(C#N)ccc2n1CC1CC1]

1-(Cyclopropylmethyl)-2-methyl-4-(trifluoromethyl)-1H-indole-5-carbonitrile

Synthesized as described in Example 4 using 2-methyl-4-(trifluoromethyl)-1H-indole-5-carbonitrile and (bromomethyl)cyclopropane: $^1$H NMR (400 MHz, CDCl$_3$) δ 7.48 (s, 2H), 6.57 (s, 1H), 4.04 (d, J=6.6 Hz, 2H), 2.50 (s, 3H), 1.16 (m, 1H), 0.60 (m, 2H), 0.34 (m, 2H); MS (ES) m/z 279 (M+1).

Example 122

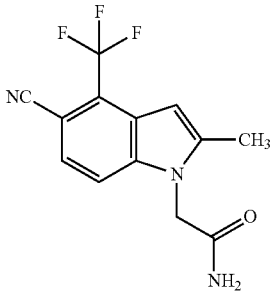 [SMILES: Cc1cc2c(C(F)(F)F)c(C#N)ccc2n1CC(N)=O]

2-[5-Cyano-2-methyl-4-(trifluoromethyl)-1H-indol-1-yl]acetamide

Synthesized as described in Example 4 using 2-methyl-4-(trifluoromethyl)-1H-indole-5-carbonitrile and 2-bromoacetamide: $^1$H NMR (400 MHz, DMSO-d$_6$) δ 7.82 (d, J=8.5 Hz, 1H), 7.71 (bs, 1H), 7.67 (d, J=8.5 Hz, 1H), 7.35 (bs, 1H), 6.55 (s, 1H), 4.89 (s, 2H), 2.39 (s, 3H); MS (ES) m/z 282 (M+1).

Example 123

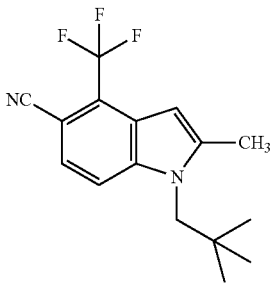 [SMILES: Cc1cc2c(C(F)(F)F)c(C#N)ccc2n1CC(C)(C)C]

1-(2,2-Dimethylpropyl)-2-methyl-4-(trifluoromethyl)-1H-indole-5-carbonitrile

Synthesized as described in Example 4 using 2-methyl-4-(trifluoromethyl)-1H-indole-5-carbonitrile and 1-bromo-2,2-dimethylpropane: $^1$H NMR (400 MHz, CDCl$_3$) δ 7.51 (d, J=8.5 Hz, 1H), 7.45 (d, J=8.5 Hz, 1H), 6.59 (s, 1H), 3.94 (s, 2H), 2.49 (s, 3H), 1.01 (s, 9H); MS (ES) m/z 295 (M+1).

Example 124

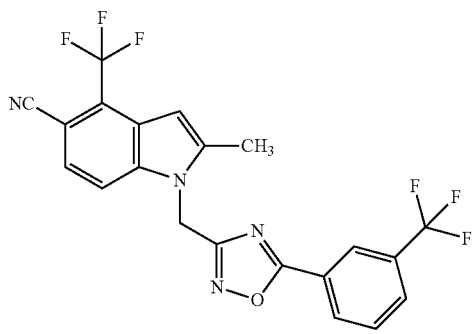 [SMILES: Cc1cc2c(C(F)(F)F)c(C#N)ccc2n1Cc1noc(-c2cccc(C(F)(F)F)c2)n1]

2-Methyl-4-(trifluoromethyl)-1-({5-[3-(trifluoromethyl)phenyl]-1,2,4-oxadiazol-3-yl}methyl)-1H-indole-5-carbonitrile An acetonitrile solution (120 mL) of 2-methyl-4-(trifluoromethyl)-1H-indole-5-carbonitrile (Example 120) was treated with Cs$_2$CO$_3$ (16.98 g, 52.26 mmole) and 3-(chloromethyl)-5-[3-(trifluoromethyl)phenyl]-1,2,4-oxadiazole (13.72 g, 52.26 mmole). The resulting heterogeneous mixture was heated to 50° C. for 3 h and then mixture was allowed to stir overnight at ambient temperature. The mixture was diluted with EtOAc (50 mL) and then concentrated. The resulting brown solid was suspended in EtOAc (250 mL) and filtered. The isolated solids were rinsed with EtOAc. The filtrate was washed with water (3×250 mL). The combined organic portions were extracted with EtOAc (1×100 mL). The combined organic portions were dried (Na$_2$SO$_4$), filtered, and concentrated to a brown solid. Thorough drying was followed by trituration with boiling EtOH (200 mL). The mixture was cooled on ice for ca. 45 min and then isolated via filtration. The solid was rinsed with cold EtOH. The resulting off-white solid was redissolved in EtOAc and concentrated to a solid, which was dried under vacuum: $^1$H NMR (400 MHz, CDCl$_3$) δ 8.31 (s, 1H), 8.24 (d, J=7.5 Hz, 1H), 7.85 (d, J=7.8 Hz, 1H), 7.67 (m, 2H), 7.56 (d, J=8.3 Hz, 1H), 6.65 (s, 1H), 5.47 (s, 2H), 2.68 (s, 3H); MS (ES) m/z 451 (M+1).

Alternatively, 2-Methyl-4-(trifluoromethyl)-1-({5-[3-(trifluoromethyl)phenyl]-1,2,4-oxadiazol-3-yl}methyl)-1H-indole-5-carbonitrile was synthesized as described in Example 4 using 2-methyl-4-(trifluoromethyl)-1H-indole-5-carbonitrile and 3-(chloromethyl)-5-[3-(trifluoromethyl)phenyl]-1,2,4-oxadiazole.

Example 125

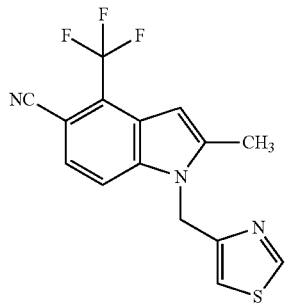

2-Methyl-1-(1,3-thiazol-4-ylmethyl)-4-(trifluoromethyl)-1H-indole-5-carbonitrile Synthesized as described in Example 4 using 2-methyl-4-(trifluoromethyl)-1H-indole-5-carbonitrile and 4-(chloromethyl)-1,3-thiazole: $^1$H NMR (400 MHz, CDCl$_3$) δ 8.80 (d, J=2.0 Hz, 1H), 7.50 (m, 2H), 6.75 (s, 1H), 6.64 (s, 1H), 5.50 (s, 2H), 2.53 (s, 3H); MS (ES) m/z 322 (M+1).

Example 126

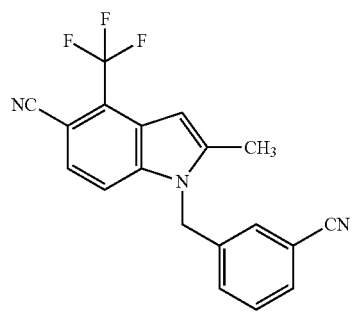 [SMILES: Cc1cc2c(C(F)(F)F)c(C#N)ccc2n1Cc1cccc(C#N)c1]

1-[(3-Cyanophenyl)methyl]-2-methyl-4-(trifluoromethyl)-1H-indole-5-carbonitrile Synthesized as described in Example 4 using 2-methyl-4-(trifluoromethyl)-1H-indole-5-carbonitrile and 3-(bromomethyl)benzonitrile: $^1$H NMR (400 MHz, CDCl$_3$) δ 7.56 (m, 1H), 7.45 (m, 2H), 7.33 (d, J=8.5 Hz, 1H), 7.21 (s, 1H), 7.12 (d, J=8.1 Hz, 1H), 6.69 (s, 1H), 5.40 (s, 2H), 2.43 (s, 3H); MS (ES) m/z 340 (M+1).

Example 127

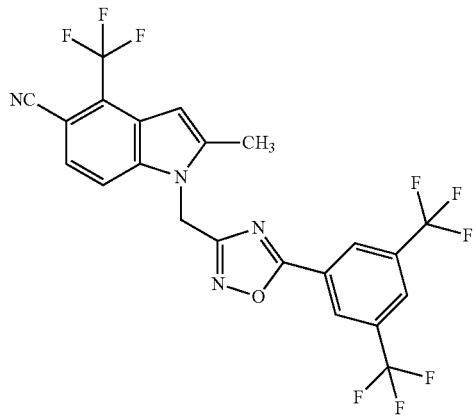 [SMILES: Cc1cc2c(C(F)(F)F)c(C#N)ccc2n1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-2-methyl-4-(trifluoromethyl)-1H-indole-5-carbonitrile Synthesized as described in Example 4 using 2-methyl-4-(trifluoromethyl)-1H-indole-5-carbonitrile and 5-[3,5-bis(trifluoromethyl)phenyl]-3-(chloromethyl)-1,2,4-oxadiazole: $^1$H NMR (400 MHz, CDCl$_3$) δ 8.49 (s, 2H), 8.09 (s, 1H), 7.67 (d, J=8.4 Hz, 1H), 7.55 (d, J=8.4 Hz, 1H), 6.65 (s, 1H), 5.50 (s, 2H), 2.68 (s, 3H); MS (ES) m/z 519 (M+1).

Example 128

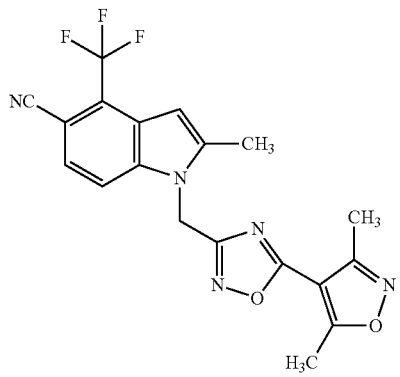 [SMILES: Cc1noc(C)c1-c1nc(Cn2c(C)cc3c(C(F)(F)F)c(C#N)ccc32)no1]

1-{[5-(3,5-Dimethyl-4-isoxazolyl)-1,2,4-oxadiazol-3-yl]methyl}-2-methyl-4-(trifluoromethyl)-1H-indole-5-carbonitrile Synthesized as described in Example 4 using 2-methyl-4-(trifluoromethyl)-1H-indole-5-carbonitrile and 3-(chloromethyl)-5-(3,5-dimethyl-4-isoxazolyl)-1,2,4-oxadiazole: $^1$H NMR (400 MHz, CDCl$_3$) δ 7.68 (d, J=8.4 Hz, 1H), 7.53 (d, J=8.4 Hz, 1H), 6.63 (s, 1H), 5.44 (s, 2H), 2.71 (s, 3H), 2.66 (s, 3H), 2.49 (s, 3H); MS (ES) m/z 402 (M+1).

Example 129

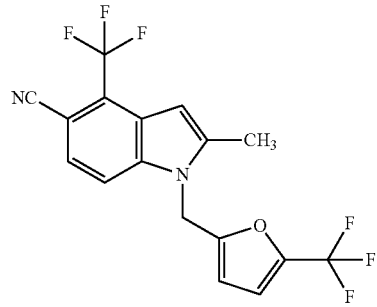 [SMILES: Cc1cc2c(C(F)(F)F)c(C#N)ccc2n1Cc1ccc(C(F)(F)F)o1]

2-Methyl-4-(trifluoromethyl)-1-{[5-(trifluoromethyl)-2-furanyl]methyl}-1H-indole-5-carbonitrile Synthesized as described in Example 4 using 2-methyl-4-(trifluoromethyl)-1H-indole-5-carbonitrile and 2-(bromomethyl)-5-(trifluoromethyl)furan: $^1$H NMR (400 MHz, CDCl$_3$) δ 7.54 (d, J=8.6 Hz, 1H), 7.51 (d, J=8.6 Hz, 1H), 6.70 (d, J=2.9 Hz, 1H), 6.63 (s, 1H), 6.11 (d, J=2.9 Hz, 1H), 5.32 (s, 2H), 2.55 (s, 3H); MS (ES) m/z 373 (M+1).

Example 130

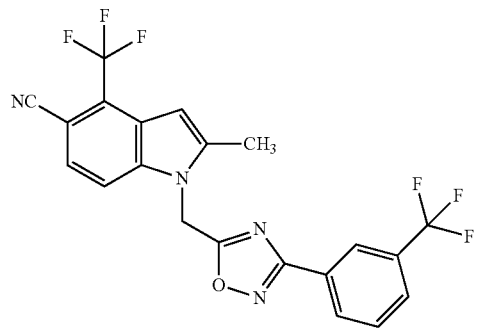 [SMILES: Cc1cc2c(C(F)(F)F)c(C#N)ccc2n1Cc1nc(-c2cccc(C(F)(F)F)c2)no1]

2-Methyl-4-(trifluoromethyl)-1-({3-[3-(trifluoromethyl)phenyl]-1,2,4-oxadiazol-5-yl}methyl)-1H-indole-5-carbonitrile

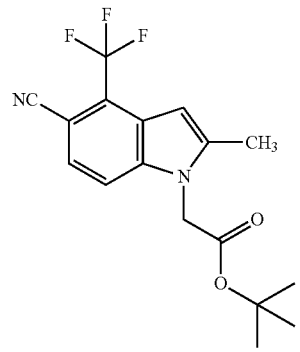 [SMILES: Cc1cc2c(C(F)(F)F)c(C#N)ccc2n1CC(=O)OC(C)(C)C]

A. 1,1-Dimethylethyl [5-cyano-2-methyl-4-(trifluoromethyl)-1H-indol-1-yl]acetate Synthesized as described in Example 35A using 2-methyl-4-(trifluoromethyl)-1H-indole-5-carbonitrile: MS (ES) m/z 339 (M+1).

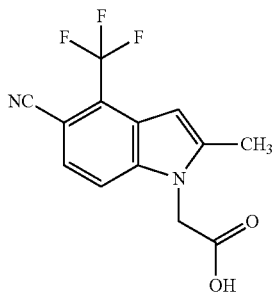 [SMILES: Cc1cc2c(C(F)(F)F)c(C#N)ccc2n1CC(=O)O]

B. [5-Cyano-2-methyl-4-(trifluoromethyl)-1H-indol-1-yl]acetic acid

Synthesized as described in Example 35B using 1,1-dimethylethyl [5-cyano-2-methyl-4-(trifluoromethyl)-1H-indol-1-yl]acetate: MS (ES) m/z 283 (M+1).

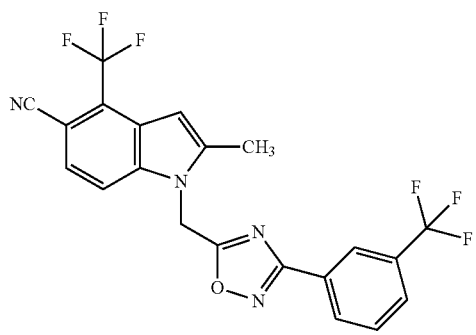 [SMILES: Cc1cc2c(C(F)(F)F)c(C#N)ccc2n1Cc1nc(-c2cccc(C(F)(F)F)c2)no1]

C. 2-Methyl-4-(trifluoromethyl)-1-({3-[3-(trifluoromethyl)phenyl]-1,2,4-oxadiazol-5-yl}methyl)-1H-indole-5-carbonitrile Synthesized as described in Example 37 using [5-cyano-2-methyl-4-(trifluoromethyl)-1H-indol-1-yl]acetic acid and N-hydroxy-3-(trifluoromethyl)benzenecarboximidamide: ¹H NMR (400 MHz, CDCl₃) δ 8.28 (s, 1H), 8.20 (d, J=7.8 Hz, 1H), 7.77 (d, J=7.8 Hz, 1H), 7.60 (m, 3H), 6.69 (s, 1H), 5.60 (s, 2H), 2.65 (s, 3H); MS (ES) m/z 473 (M+Na).

Example 131

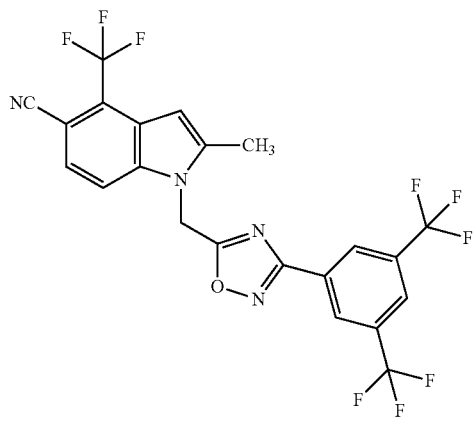 [SMILES: Cc1cc2c(C(F)(F)F)c(C#N)ccc2n1Cc1nc(-c2cc(C(F)(F)F)cc(C(F)(F)F)c2)no1]

1-({3-[3,5-Bis(trifluoromethyl)phenyl]-1,2,4-oxadiazol-5-yl}methyl)-2-methyl-4-(trifluoromethyl)-1H-indole-5-carbonitrile Synthesized as described in Example 37 using [5-cyano-2-methyl-4-(trifluoromethyl)-1H-indol-1-yl]acetic acid and N-hydroxy-3,5-bis(trifluoromethyl)benzenecarboximidamide: ¹H NMR (400 MHz, CDCl₃) δ 8.47 (s, 2H), 8.02 (s, 1H), 7.61 (m, 2H), 6.71 (s, 1H), 5.62 (s, 2H), 2.65 (s, 3H); MS (ES) m/z 519 (M+1).

Example 132

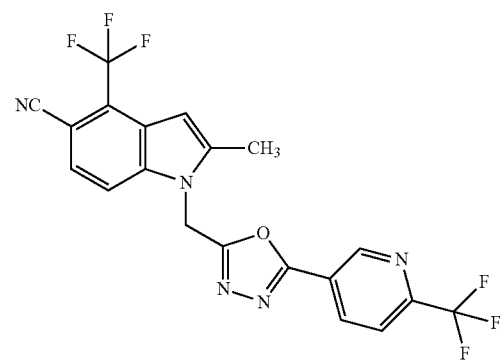 [SMILES: Cc1cc2c(C(F)(F)F)c(C#N)ccc2n1Cc1nnc(-c2ccc(C(F)(F)F)nc2)o1]

2-Methyl-4-(trifluoromethyl)-1-({5-[6-(trifluoromethyl)-3-pyridinyl]-1,3,4-oxadiazol-2-yl}methyl)-1H-indole-5-carbonitrile Synthesized as described in Example 35C using [5-cyano-2-methyl-4-(trifluoromethyl)-1H-indol-1-yl]acetic acid and 6-(trifluoromethyl)-3-pyridinecarbohydrazide: ¹H NMR (400 MHz, DMSO-d₆) δ 9.27 (s, 1H), 8.54 (d, J=8.3 Hz, 1H), 8.11 (d, J=8.3 Hz, 1H), 8.08 (d, J=8.3 Hz, 1H), 7.78 (d, J=8.3 Hz, 1H), 6.66 (s, 1H), 6.03 (s, 2H), 2.58 (s, 3H); MS (ES) m/z 474 (M+Na).

Example 133

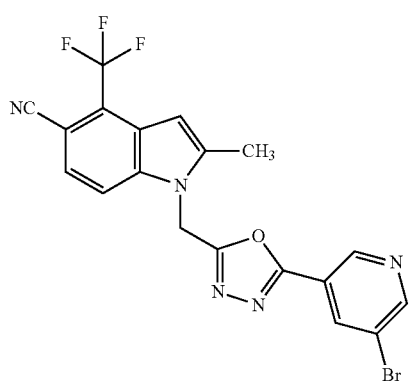 [SMILES: Cc1cc2c(C(F)(F)F)c(C#N)ccc2n1Cc1nnc(-c2cncc(Br)c2)o1]

1-{[5-(5-Bromo-3-pyridinyl)-1,3,4-oxadiazol-2-yl]methyl}-2-methyl-4-(trifluoromethyl)-1H-indole-5-carbonitrile Synthesized as described in Example 35C using [5-cyano-2-methyl-4-(trifluoromethyl)-1H-indol-1-yl]acetic acid and 5-bromo-3-pyridinecarbohydrazide: $^1$H NMR (400 MHz, DMSO-d$_6$) δ 9.05 (d, J=1.7 Hz, 1H), 8.93 (d, J=2.0 Hz, 1H), 8.48 (dd, J=2.0 and 1.7 Hz, 1H), 8.07 (d, J=8.5 Hz, 1H), 7.77 (d, J=8.5 Hz, 1H), 6.65 (s, 1H), 5.99 (s, 2H), 2.58 (s, 3H); MS (ES) m/z 462 (M+1, isotope for Br) and 464 (M+1, isotope for Br)

Example 134

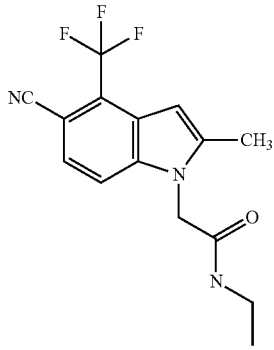 [SMILES: CCNC(=O)Cn1c(C)cc2c(C(F)(F)F)c(C#N)ccc21]

2-[5-Cyano-2-methyl-4-(trifluoromethyl)-1H-indol-1-yl]-N-ethylacetamide

Isolated as a side product from the synthesis of Example 132: $^1$H NMR (400 MHz, DMSO-d$_6$) δ 8.27 (bs, 1H), 7.82 (d, J=8.4 Hz, 1H), 7.67 (d, J=8.4 Hz, 1H), 6.55 (s, 1H), 4.90 (s, 2H), 3.10 (m, 2H), 2.40 (s, 3H), 1.01 (t, J=7.2 Hz, 3H); MS (ES) m/z 310 (M+1).

Example 135

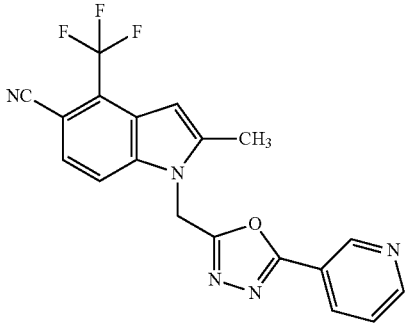 [SMILES: Cc1cc2c(C(F)(F)F)c(C#N)ccc2n1Cc1nnc(-c2cccnc2)o1]

2-Methyl-1-{[5-(3-pyridinyl)-1,3,4-oxadiazol-2-yl]methyl}-4-(trifluoromethyl)-1H-indole-5-carbonitrile Synthesized as described in Example 35C using [5-cyano-2-methyl-4-(trifluoromethyl)-1H-indol-1-yl]acetic acid and 3-pyridinecarbohydrazide: $^1$H NMR (400 MHz, DMSO-d$_6$) δ 9.08 (s, 1H), 8.78 (d, J=4.9 Hz, 1H), 8.27 (d, J=7.8 Hz, 1H), 8.08 (d, J=8.5 Hz, 1H), 7.77 (d, J=8.5 Hz, 1H), 7.60 (dd, J=7.8 and 4.9 Hz, 1H), 6.65 (s, 1H), 6.00 (s, 2H), 2.57 (s, 3H); MS (ES) m/z 384 (M+1).

Example 136

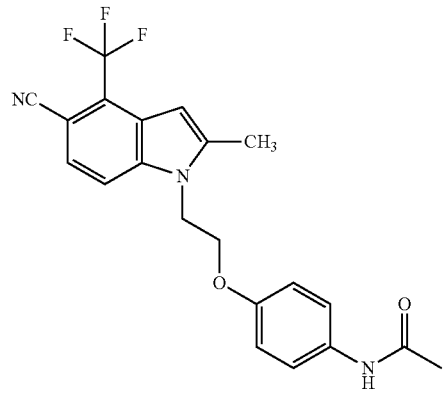 [SMILES: CC(=O)Nc1ccc(OCCn2c(C)cc3c(C(F)(F)F)c(C#N)ccc32)cc1]

N-[4-({2-[5-Cyano-2-methyl-4-(trifluoromethyl)-1H-indol-1-yl]ethyl}oxy)phenyl]acetamide Synthesized as described in Example 4 using 2-methyl-4-(trifluoromethyl)-1H-indole-5-carbonitrile and N-{4-[(2-bromoethyl)oxy]phenyl}acetamide: $^1$H NMR (400 MHz, DMSO-d$_6$) δ 9.72 (s, 1H), 8.00 (d, J=8.6 Hz, 1H), 7.69 (d, J=8.6 Hz, 1H), 7.39 (d, J=9.0 Hz, 2H), 6.72 (d, J=9.0 Hz, 2H), 6.55 (s, 1H), 4.65 (t, J=5.0 Hz, 2H), 4.21 (t, J=5.0 Hz, 2H), 2.55 (s, 3H), 1.95 (s, 3H); MS (ES) m/z 402 (M+1).

Example 137

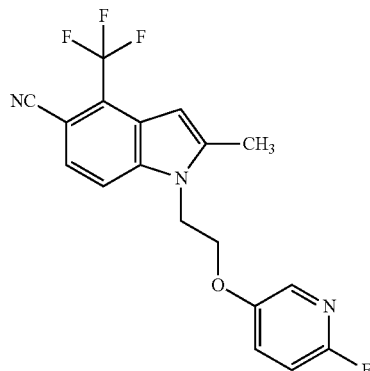

1-{2-[(6-Fluoro-3-pyridinyl)oxy]ethyl}-2-methyl-4-(trifluoromethyl)-1H-indole-5-carbonitrile Synthesized as described in Example 4 using 2-methyl-4-(trifluoromethyl)-1H-indole-5-carbonitrile and 5-[(2-bromoethyl)oxy]-2-fluoropyridine. $^1$H NMR (400 MHz, DMSO-d$_6$) δ 8.00 (d, J=8.5 Hz, 1H), 7.76 (s, 1H), 7.69 (d, J=8.5 Hz, 1H), 7.45 (m, 1H), 7.03 (dd, J=9.0 and 3.4 Hz, 1H), 6.54 (s, 1H), 4.69 (t, J=5.1 Hz, 2H), 4.35 (t, J=5.1 Hz, 2H), 2.56 (s, 3H); MS (ES) m/z 364 (M+1).

Example 138

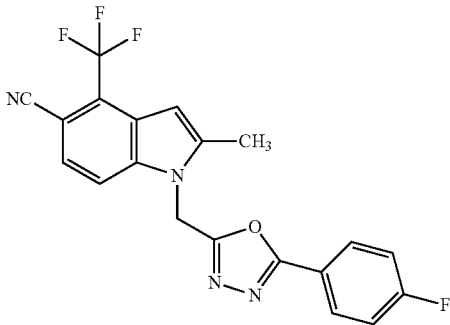 [SMILES: Cc1cc2c(C(F)(F)F)c(C#N)ccc2n1Cc1nnc(-c2ccc(F)cc2)o1]

1-{[5-(4-Fluorophenyl)-1,3,4-oxadiazol-2-yl]methyl}-2-methyl-4-(trifluoromethyl)-1H-indole-5-carbonitrile Synthesized as described in Example 35C using [5-cyano-2-methyl-4-(trifluoromethyl)-1H-indol-1-yl]acetic acid and 4-fluorobenzohydrazide: $^1$H NMR (400 MHz, DMSO-d$_6$) δ 8.07 (d, J=8.4 Hz, 1H), 7.96 (dd, J=8.7 and 5.4 Hz, 2H), 7.77 (d, J=8.4 Hz, 1H), 7.41 (t, J=8.7 Hz, 2H), 6.65 (s, 1H), 5.97 (s, 2H), 2.57 (s, 3H); MS (ES) m/z 401 (M+1).

Example 139

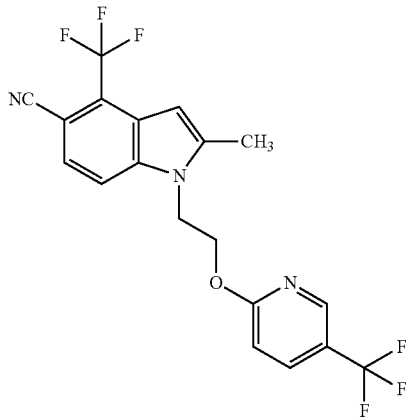 [SMILES: Cc1cc2c(C(F)(F)F)c(C#N)ccc2n1CCOc1ccc(C(F)(F)F)cn1]

2-Methyl-4-(trifluoromethyl)-1-(2-{[5-(trifluoromethyl)-2-pyridinyl]oxy}ethyl)-1H-indole-5-carbonitrile

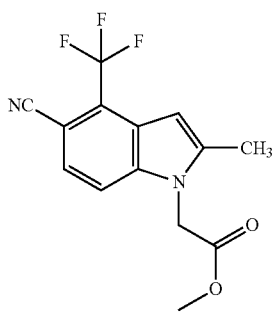 [SMILES: COC(=O)Cn1c(C)cc2c(C(F)(F)F)c(C#N)ccc21]

A. Methyl [5-cyano-2-methyl-4-(trifluoromethyl)-1H-indol-1-yl]acetate

Synthesized as described in Example 4 using 2-methyl-4-(trifluoromethyl)-1H-indole-5-carbonitrile, methyl bromoacetate (1.5 eq), and Cs$_2$CO$_3$ (1.5 eq): MS (ES) m/z 295 (M−1).

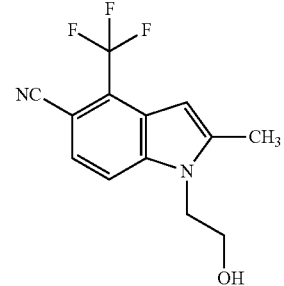 [SMILES: Cc1cc2c(C(F)(F)F)c(C#N)ccc2n1CCO]

B. 1-(2-Hydroxyethyl)-2-methyl-4-(trifluoromethyl)-1H-indole-5-carbonitrile

A solution of methyl [5-cyano-2-methyl-4-(trifluoromethyl)-1H-indol-1-yl]acetate (0.200 g, 6.76 mmol) in THF (5 mL) was cooled to 0° C. and treated with LiBH$_4$ (0.51 mL, 2M in THF). After 2 h, the reaction was partitioned between Et$_2$O and water. Drying (Na$_2$SO$_4$), filtration, and concentration was followed by column chromatography (SiO$_2$, hexanes/EtOAc) to afford the title compound (0.137 g): MS (ES) m/z 269 (M+1).

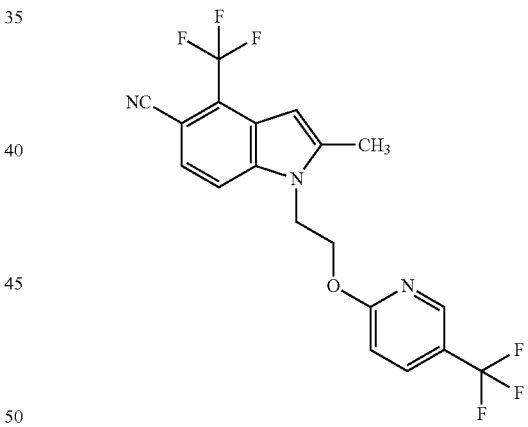

C. 2-Methyl-4-(trifluoromethyl)-1-(2-{[5-(trifluoromethyl)-2-pyridinyl]oxy}ethyl)-1H-indole-5-carbonitrile A solution of 1-(2-hydroxyethyl)-2-methyl-4-(trifluoromethyl)-1H-indole-5-carbonitrile (0.130 g, 0.49 mmol) in CH$_2$Cl$_2$ (3 mL) at 0° C. was treated with DBAD (0.302 g, 1.31 mmol), PPh$_3$ (0.343 g, 1.31 mmol) and 5-(trifluoromethyl)-2 (1H)-pyridinone (0.87 g, 0.53 mmol). The mixture was allowed to slowly warm to rt and then stirred for 14 h. Concentration was followed by column chromatography (SiO$_2$, hexanes/EtOAc) to afford the title compound (0.160 g): $^1$H NMR (400 MHz, CDCl$_3$) δ 8.36 (s, 1H), 7.75 (dd, J=8.8 and 2.5 Hz, 1H), 7.56 (d, J=8.4 Hz, 1H), 7.50 (d, J=8.4 Hz, 1H), 6.71 (d, J=8.8 Hz, 1H), 6.57 (s, 1H), 4.67 (t, J=5.6 Hz, 2H), 4.54 (t, J=5.6 Hz, 2H), 2.54 (s, 3H); MS (ES) m/z 414 (M+1).

Example 140

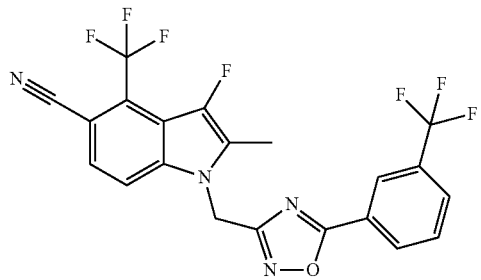 [SMILES: Cc1c(F)c2c(C(F)(F)F)c(C#N)ccc2n1Cc1noc(-c2cccc(C(F)(F)F)c2)n1]

3-Fluoro-2-methyl-4-(trifluoromethyl)-1-({5-[3-(trifluoromethyl)phenyl]-1,2,4-oxadiazol-3-yl}methyl)-1H-indole-5-carbonitrile

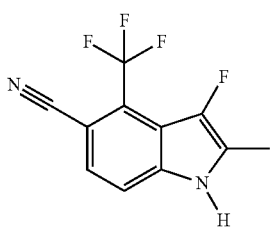 [SMILES: Cc1[nH]c2ccc(C#N)c(C(F)(F)F)c2c1F]

A. 3-Fluoro-2-methyl-4-(trifluoromethyl)-1H-indole-5-carbonitrile

To a solution of 2-methyl-4-(trifluoromethyl)-1H-indole-5-carbonitrile (0.063 g, 0.28 mmol) in CH$_2$Cl$_2$ (4 mL) was added 1-fluoropyridinium triflate (0.104 g, 0.42 mmol) and stirred at rt for 3 days. The mixture was partitioned between EtOAc and 0.1N HCl. The organic phase was washed with 0.1N HCl and sat'd brine, dried (Na$_2$SO$_4$), and concentrated in vacuo. The residue was purified by flash chromatography (10-50% EtOAc-hexanes gradient) to afford the title compound as a white solid (0.015 g, 22% yield, 94% purity): MS (ES) m/z 243 (M+1).

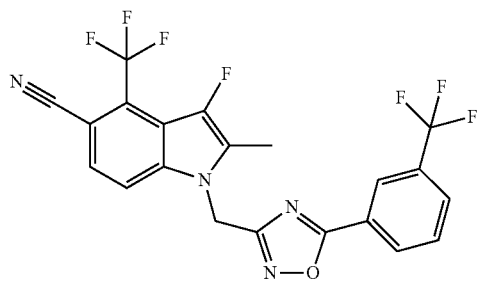 [SMILES: Cc1c(F)c2c(C(F)(F)F)c(C#N)ccc2n1Cc1noc(-c2cccc(C(F)(F)F)c2)n1]

B. 3-Fluoro-2-methyl-4-(trifluoromethyl)-1-({5-[3-(trifluoromethyl)phenyl]-1,2,4-oxadiazol-3-yl}methyl)-1H-indole-5-carbonitrile Synthesized as described in Example 23 from 3-fluoro-2-methyl-4-(trifluoromethyl)-1H-indole-5-carbonitrile and 3-(chloromethyl)-5-[3-(trifluoromethyl)phenyl]-1,2,4-oxadiazole: MS (ES) m/z 469 (M+1).

Example 141

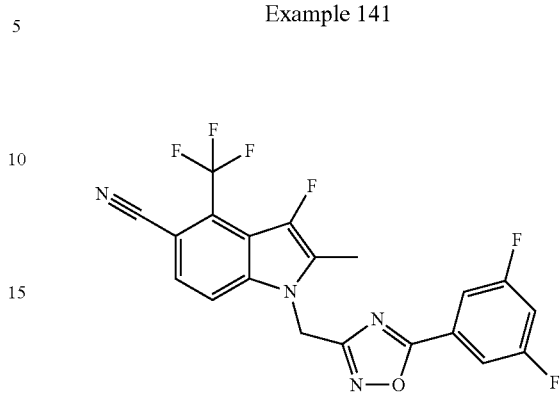

1-{[5-(3,5-Difluorophenyl)-1,2,4-oxadiazol-3-yl]methyl}-3-fluoro-2-methyl-4-(trifluoromethyl)-1H-indole-5-carbonitrile Synthesized as described in Example 23 from 3-fluoro-2-methyl-4-(trifluoromethyl)-1H-indole-5-carbonitrile and 3-(chloromethyl)-5-(3,5-difluorophenyl)-1,2,4-oxadiazole: MS (ES) m/z 437 (M+1).

Example 142

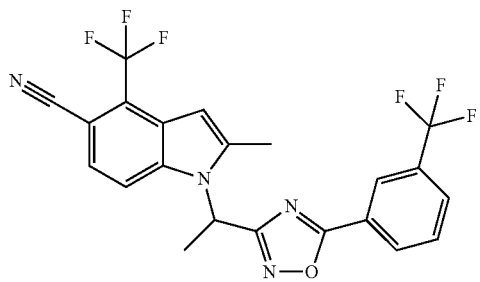 [SMILES: Cc1cc2c(C(F)(F)F)c(C#N)ccc2n1C(C)c1noc(-c2cccc(C(F)(F)F)c2)n1]

2-Methyl-4-(trifluoromethyl)-1-(1-{5-[3-(trifluoromethyl)phenyl]-1,2,4-oxadiazol-3-yl}ethyl)-1H-indole-5-carbonitrile

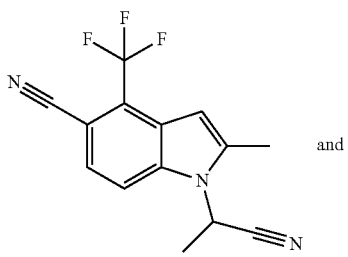

and

-continued

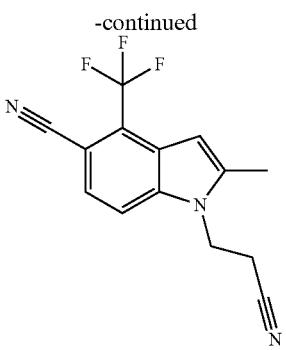

A. 1-(1-Cyanoethyl)-2-methyl-4-(trifluoromethyl)-1H-indole-5-carbonitrile

Synthesized as described in Example 23 using 2-methyl-4-(trifluoromethyl)-1H-indole-5-carbonitrile, 2-bromopropionitrile (2 eq) and $Cs_2CO_3$ (2 eq) with heating at 90° C. for 30 min. After aqueous workup, purification by flash chromatography afforded 1-(1-cyanoethyl)-2-methyl-4-(trifluoromethyl)-1H-indole-5-carbonitrile (0.033 g, 27% yield) (MS (ES) m/z 278 (M+1)) and 1-(2-cyanoethyl)-2-methyl-4-(trifluoromethyl)-1H-indole-5-carbonitrile (0.043 g, 35% yield) (MS (ES) m/z 278 (M+1).

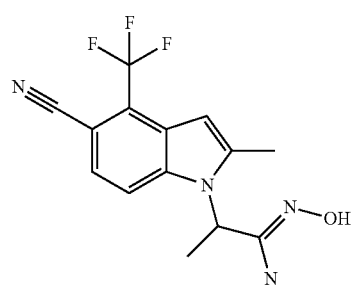 [SMILES: Cc1cc2c(C(F)(F)F)c(C#N)ccc2n1C(C)/C(N)=N/O]

B. (1Z)-2-[5-Cyano-2-methyl-4-(trifluoromethyl)-1H-indol-1-yl]-N-hydroxypropanimidamide Synthesized as described in Example 32A from 1-(1-cyanoethyl)-2-methyl-4-(trifluoromethyl)-1H-indole-5-carbonitrile: MS (ES) m/z 311 (M+1).

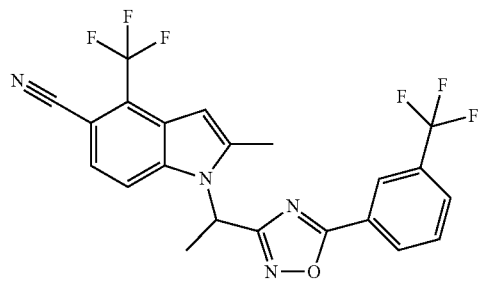 [SMILES: Cc1cc2c(C(F)(F)F)c(C#N)ccc2n1C(C)c1noc(-c2cccc(C(F)(F)F)c2)n1]

C. 2-Methyl-4-(trifluoromethyl)-1-(1-{5-[3-(trifluoromethyl)phenyl]-1,2,4-oxadiazol-3-yl}ethyl)-1H-indole-5-carbonitrile Synthesized as described in Example 32B from (1Z)-2-[5-cyano-2-methyl-4-(trifluoromethyl)-1H-indol-1-yl]-N-hydroxypropanimidamide and 3-(trifluoromethyl)benzoyl chloride: MS (ES) m/z 465 (M+1).

Example 143

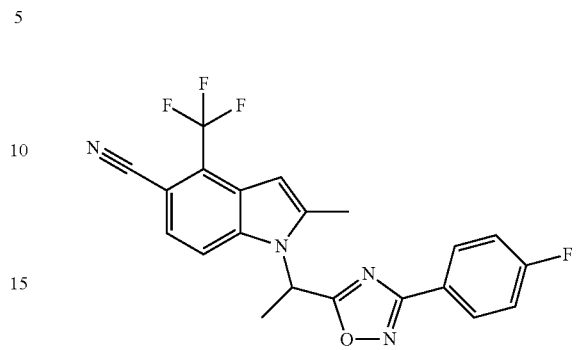

1-{1-[3-(4-Fluorophenyl)-1,2,4-oxadiazol-5-yl]ethyl}-2-methyl-4-(trifluoromethyl)-1H-indole-5-carbonitrile

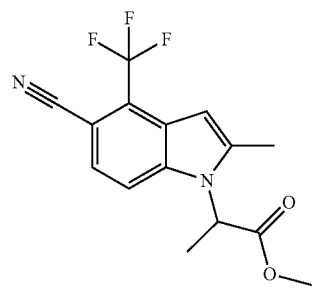 [SMILES: COC(=O)C(C)n1c(C)cc2c(C(F)(F)F)c(C#N)ccc21]

A. Methyl 2-[5-cyano-2-methyl-4-(trifluoromethyl)-1H-indol-1-yl]propanoate

Synthesized as described in Example 4 using 2-methyl-4-(trifluoromethyl)-1H-indole-5-carbonitrile, methyl 2-bromopropanoate (1.5 eq) and $Cs_2CO_3$ (1.5 eq): MS (ES) m/z 311 (M+1).

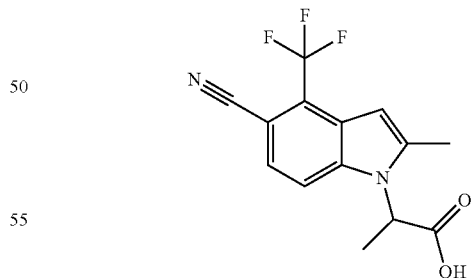

B. 2-[5-Cyano-2-methyl-4-(trifluoromethyl)-1H-indol-1-yl]propanoic acid

Synthesized as described in Example 9B from methyl 2-[5-cyano-2-methyl-4-(trifluoromethyl)-1H-indol-1-yl]propanoate: $^1$H NMR (400 MHz, acetone-$d_6$) δ 7.79 (d, J=8.6 Hz, 1H), 7.62 (d, J=8.6 Hz, 1H), 6.63 (s, 1H), 5.61 (qt, J=7.3 Hz, 1H), 2.58 (s, 3H), 1.79 (d, J=7.3 Hz, 3H).

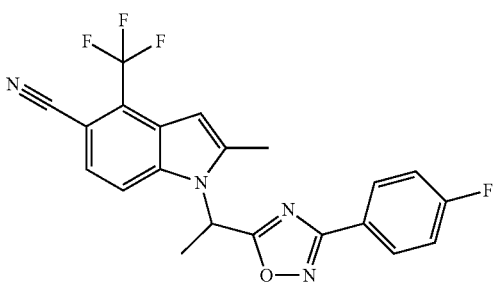 [SMILES: Cc1cc2c(C(F)(F)F)c(C#N)ccc2n1C(C)c1nc(-c2ccc(F)cc2)no1]

C. 1-{1-[3-(4-Fluorophenyl)-1,2,4-oxadiazol-5-yl]ethyl}-2-methyl-4-(trifluoromethyl)-1H-indole-5-carbonitrile Synthesized as described in Example 37 from 2-[5-cyano-2-methyl-4-(trifluoromethyl)-1H-indol-1-yl]propanoic acid and 4-fluoro-N-hydroxybenzenecarboximidamide using MeCN as the solvent, and HATU (1.05 eq), DIEA (1.05 eq), instead of EDCl, for the first coupling step: MS (ES) m/z 415 (M+1).

Example 144

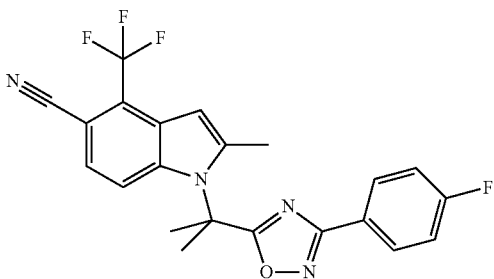 [SMILES: Cc1cc2c(C(F)(F)F)c(C#N)ccc2n1C(C)(C)c1nc(-c2ccc(F)cc2)no1]

1-{1-[3-(4-Fluorophenyl)-1,2,4-oxadiazol-5-yl]-1-methylethyl}-2-methyl-4-(trifluoromethyl)-1H-indole-5-carbonitrile

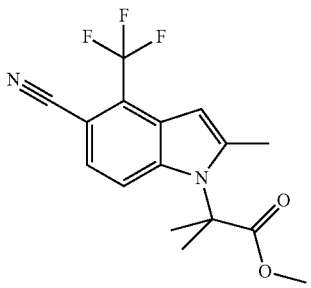 [SMILES: COC(=O)C(C)(C)n1c(C)cc2c(C(F)(F)F)c(C#N)ccc21]

A. Methyl 2-[5-cyano-2-methyl-4-(trifluoromethyl)-1H-indol-1-yl]-2-methylpropanoate To a solution of methyl 2-[5-cyano-2-methyl-4-(trifluoromethyl)-1H-indol-1-yl]propanoate (0.065 g, 0.209 mmol) in THF (1 mL) was added iodomethane (0.59 g, 4.18 mmol), followed by dropwise addition of t-BuOK (1M in THF, 0.63 mL, 6.3 mmol). After 10 min, the mixture was partitioned between EtOAc and 0.1N HCl. The organic phase was washed with sat'd brine, dried (Na₂SO₄) and concentrated in vacuo. The residue was purified by flash chromatography (0-25% EtOAc-hexanes gradient) to afford the title compound: MS (ES) m/z 325 (M+1).

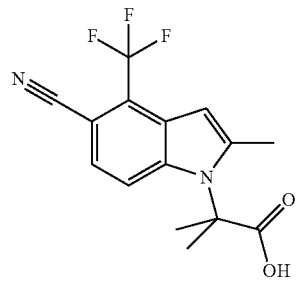 [SMILES: Cc1cc2c(C(F)(F)F)c(C#N)ccc2n1C(C)(C)C(=O)O]

B. 2-[5-Cyano-2-methyl-4-(trifluoromethyl)-1H-indol-1-yl]-2-methylpropanoic acid Synthesized as described in Example 9A from methyl 2-[5-cyano-2-methyl-4-(trifluoromethyl)-1H-indol-1-yl]-2-methylpropanoate: MS (ES) m/z 311 (M+1).

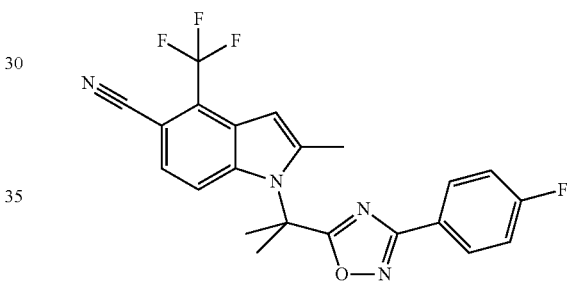

C. 1-{1-[3-(4-Fluorophenyl)-1,2,4-oxadiazol-5-yl]-1-methylethyl}-2-methyl-4-(trifluoromethyl)-1H-indole-5-carbonitrile Synthesized as described in Example 37 from 2-[5-cyano-2-methyl-4-(trifluoromethyl)-1H-indol-1-yl]-2-methylpropanoic acid and 4-fluoro-N-hydroxybenzenecarboximidamide using MeCN as the solvent, and HATU (1.05 eq), DIEA (1.05 eq), instead of EDCl, for the first coupling step: MS (ES) m/z 429 (M+1).

Example 145

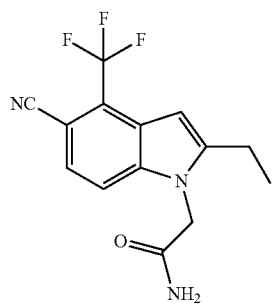 [SMILES: CCc1cc2c(C(F)(F)F)c(C#N)ccc2n1CC(N)=O]

2-[5-Cyano-2-ethyl-4-(trifluoromethyl)-1H-indol-1-yl]acetamide

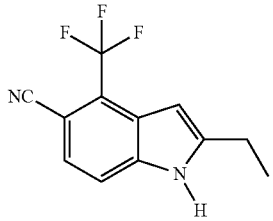 [SMILES: CCc1cc2c(C(F)(F)F)c(C#N)ccc2[nH]1]

A. 2-Ethyl-4-(trifluoromethyl)-1H-indole-5-carbonitrile

Synthesized as described in Example 120 (first method) from 1-butyne: MS (ESI): m/z 237 (M−1).

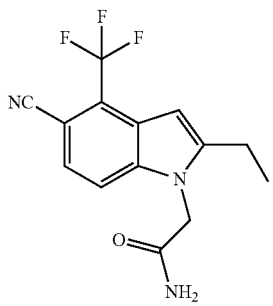 [SMILES: CCc1cc2c(C(F)(F)F)c(C#N)ccc2n1CC(N)=O]

B. 2-[5-Cyano-2-ethyl-4-(trifluoromethyl)-1H-indol-1-yl]acetamide

2-Ethyl-4-(trifluoromethyl)-1H-indole-5-carbonitrile (0.004 g, 0.018 mmol) $Cs_2CO_3$ (0.051 g, 0.16 mmol), and 2-bromoacetamide (0.022 g, 0.16 mmol) were combined in $CH_3CN$ (3 mL) and heated at 90° C. under $N_2$ for 1 hr. Extraction with $Et_2O$ and washing with water and brine was followed by drying ($Na_2SO_4$), filtration, and concentration in vacuo. Purification ($SiO_2$, EtOAc/hexanes) afforded the title compound (0.020 g): MS (ESI): m/z 296 (M+1).

Example 146

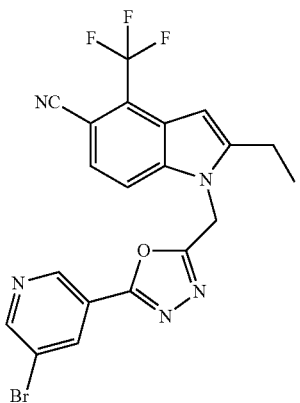 [SMILES: CCc1cc2c(C(F)(F)F)c(C#N)ccc2n1Cc1nnc(-c2cncc(Br)c2)o1]

1-{[5-(5-Bromo-3-pyridinyl)-1,3,4-oxadiazol-2-yl]methyl}-2-ethyl-4-(trifluoromethyl)-1H-indole-5-carbonitrile Synthesized as described in Example 145B from 2-ethyl-4-(trifluoromethyl)-1H-indole-5-carbonitrile and 3-bromo-5-[5-(chloromethyl)-1,3,4-oxadiazol-2-yl]pyridine: MS (ESI): m/z 476 (M−1).

Example 147

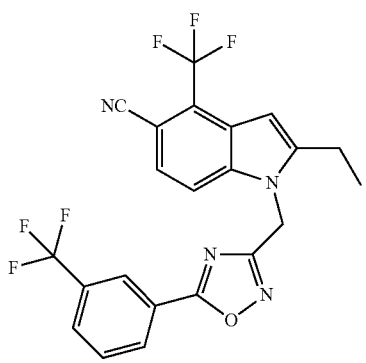 [SMILES: CCc1cc2c(C(F)(F)F)c(C#N)ccc2n1Cc1noc(-c2cccc(C(F)(F)F)c2)n1]

2-Ethyl-4-(trifluoromethyl)-1-({5-[3-(trifluoromethyl)phenyl]-1,2,4-oxadiazol-3-yl}methyl)-1H-indole-5-carbonitrile Synthesized as described in Example 145B from 2-ethyl-4-(trifluoromethyl)-1H-indole-5-carbonitrile and 3-(chloromethyl)-5-[3-(trifluoromethyl)phenyl]-1,2,4-oxadiazole. MS (ESI): m/z 465 (M+1).

Example 148

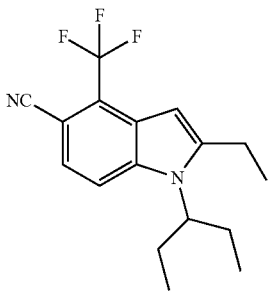 [SMILES: CCc1cc2c(C(F)(F)F)c(C#N)ccc2n1C(CC)CC]

2-Ethyl-1-(1-ethylpropyl)-4-(trifluoromethyl)-1H-indole-5-carbonitrile

Synthesized as described in Example 145B from 2-ethyl-4-(trifluoromethyl)-1H-indole-5-carbonitrile and 3-bromopentane: MS (ESI): m/z 309 (M+1).

Example 149

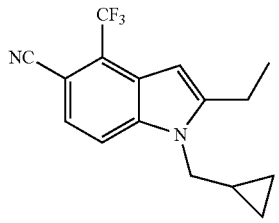 [SMILES: CCc1cc2c(C(F)(F)F)c(C#N)ccc2n1CC1CC1]

1-(Cyclopropylmethyl)-2-ethyl-4-(trifluoromethyl)-1H-indole-5-carbonitrile

To a slurry of hexanes-washed NaH (0.0112 g, 0.279 mmol) in DMF (1 mL) at 0° C. was added a solution of 2-ethyl-4-(trifluoromethyl)-1H-indole-5-carbonitrile (0.0332 g, 0.139 mmol) in DMF (1 mL), dropwise over 3 min. The mixture was stirred 30 min and bromomethylcyclopropane (0.030 mL, 0.28 mmol) was added via syringe. The mixture was stirred 5 h at rt, diluted with Et$_2$O, poured into water, and the layers were separated. The aqueous layer was extracted with Et$_2$O (×2), combined organics were washed (H$_2$O, brine), dried over Na$_2$SO$_4$, filtered and concentrated in vacuo. The residue was purified by RP-HPLC (C$_{18}$ column, MeCN/H$_2$O with 0.1% TFA), affording 0.0261 g of the title compound as a colorless oil: $^1$H NMR (300 MHz, CDCl$_3$) δ 7.55-7.47 (m, 2H), 6.59 (s, 1H), 4.07 (d, J=6.4 Hz, 2H), 2.84 (q, J=7.4 Hz, 2H), 1.44 (t, J=7.5 Hz, 3H), 1.24-1.01 (m, 1H), 0.66-0.57 (m, 2H), 0.41-0.32 (m, 2H).

Example 150

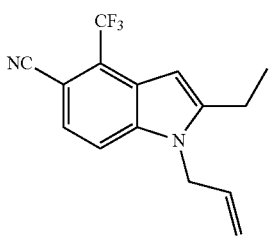 [SMILES: C=CCn1c(CC)cc2c(C(F)(F)F)c(C#N)ccc21]

2-Ethyl-1-(2-propen-1-yl)-4-(trifluoromethyl)-1H-indole-5-carbonitrile

Synthesized as described in Example 149 from 2-ethyl-4-(trifluoromethyl)-1H-indole-5-carbonitrile and allyl bromide: $^1$H NMR (400 MHz, CDCl$_3$) δ 7.49 (d, J=8.5 Hz, 1H), 7.42 (d, J=8.5 Hz, 1H), 6.60 (s, 1H), 5.93 (ddt, J=17.7, 10.4, 4.3 Hz, 1H), 5.18 (app. d, J=10.3 Hz, 1H), 4.80-4.73 (m, 3H), 2.78 (q, J=7.4 Hz, 2H), 1.40 (t, J=7.4 Hz, 3H).

Example 151

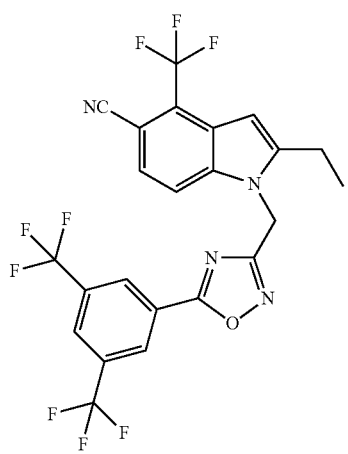 [SMILES: CCc1cc2c(C(F)(F)F)c(C#N)ccc2n1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-2-ethyl-4-(trifluoromethyl)-1H-indole-5-carbonitrile Synthesized as described in Example 145B from 2-ethyl-4-(trifluoromethyl)-1H-indole-5-carbonitrile and 5-[3,5-bis(trifluoromethyl)phenyl]-3-(chloromethyl)-1,2,4-oxadiazole: MS (ESI): m/z 533 (M+1).

Example 152

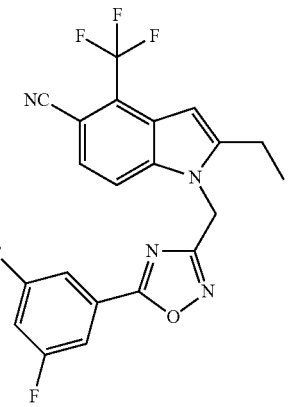

1-{[5-(3,5-Difluorophenyl)-1,2,4-oxadiazol-3-yl]methyl}-2-ethyl-4-(trifluoromethyl)-1H-indole-5-carbonitrile Synthesized as described in Example 145B from 2-ethyl-4-(trifluoromethyl)-1H-indole-5-carbonitrile and 3-(chloromethyl)-5-(3,5-difluorophenyl)-1,2,4-oxadiazole: MS (ESI): m/z 433 (M+1).

Example 153

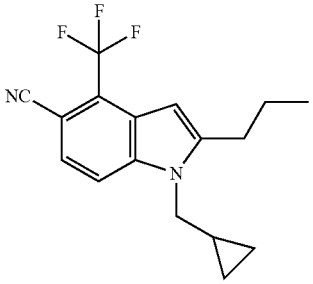 [SMILES: CCCc1cc2c(C(F)(F)F)c(C#N)ccc2n1CC1CC1]

1-(Cyclopropylmethyl)-2-propyl-4-(trifluoromethyl)-1H-indole-5-carbonitrile

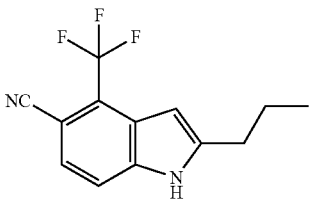 [SMILES: CCCc1cc2c(C(F)(F)F)c(C#N)ccc2[nH]1]

A. 2-Propyl-4-(trifluoromethyl)-1H-indole-5-carbonitrile

Synthesized as described in a Example 60 using 1-pentyne: ¹H NMR (400 MHz, CDCl₃) δ 8.57 (bs, 1H), 7.51 (d, J=8.4 Hz, 1H), 7.47 (d, J=8.4 Hz, 1H), 6.54 (s, 1H), 2.79 (t, J=7.5 Hz, 2H)., 1.79 (m, 2H), 1.02 (t, J=7.3 Hz, 3H); MS (ES) m/z 253 (M+1).

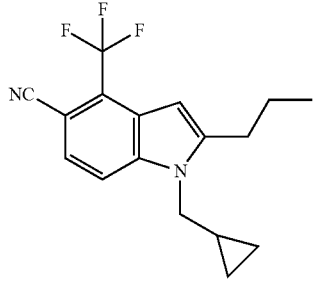

B. 1-(Cyclopropylmethyl)-2-propyl-4-(trifluoromethyl)-1H-indole-5-carbonitrile Synthesized as described in Example 4 using 2-propyl-4-(trifluoromethyl)-1H-indole-5-carbonitrile and (bromomethyl)cyclopropane: ¹H NMR (400 MHz, CDCl₃) δ 7.49 (s, 2H), 6.57 (s, 1H), 4.05 (d, J=6.4 Hz, 2H), 2.76 (t, J=7.6 Hz, 2H), 1.83 (m, 2H), 1.16 (m, 1H), 1.08 (t, J=7.4 Hz, 3H), 0.60 (m, 2H), 0.35 (m, 2H); MS (ES) m/z 307 (M+1).

Example 154

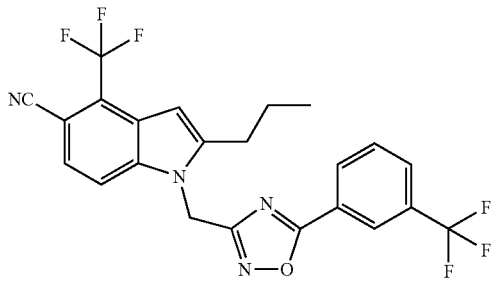 [SMILES: CCCc1cc2c(C(F)(F)F)c(C#N)ccc2n1Cc1noc(-c2cccc(C(F)(F)F)c2)n1]

2-Propyl-4-(trifluoromethyl)-1-({5-[3-(trifluoromethyl)phenyl]-1,2,4-oxadiazole-3-yl}methyl)-1H-indole-5-carbonitrile A mixture of 2-propyl-4-(trifluoromethyl)-1H-indole-5-carbonitrile (0.050 g, 0.20 mmol), 3-(chloromethyl)-5-[3-(trifluoromethyl)phenyl]-1,2,4-oxadiazole (0.062 g, 0.24 mmol), Cs₂CO₃ (0.078 g, 0.24 mmol) and CH₃CN (4 mL) was stirred at 75° C. for 1.5 h. The mixture was diluted with EtOAc (25 mL), washed with water (15 mL), and brine (15 mL). Drying (MgSO₄), filtration, and concentration were followed by purification (SiO₂; 0-30% EtOAc in hexanes) to afford the title compound (0.070 g, 74%) as a white solid: ¹H NMR (400 MHz, DMSO-d₆) δ 8.30 (d, J=7.8 Hz, 1H), 8.24 (s, 1H), 8.07 (d, J=7.8 Hz, 1H), 8.03 (d, J=8.5 Hz, 1H), 7.84 (t, J=7.8 Hz, 1H), 7.75 (d, J=8.5 Hz, 1H), 6.59 (s, 1H), 5.88 (s, 2H), 2.89 (t, J=7.6 Hz, 2H), 1.78-1.61 (m, 2H), 0.98 (t, J=7.4 Hz, 3H); MS m/z 479 (M+H).

Example 155

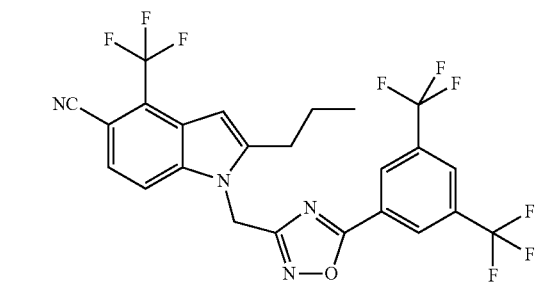 [SMILES: CCCc1cc2c(C(F)(F)F)c(C#N)ccc2n1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-2-propyl-4-(trifluoromethyl)-1H-indole-5-carbonitrile A mixture of 2-propyl-4-(trifluoromethyl)-1H-indole-5-carbonitrile (0.040 g, 0.16 mmol), 5-[3,5-bis(trifluoromethyl)phenyl]-3-(chloromethyl)-1,2,4-oxadiazole (0.058 g, 0.17 mmol), Cs₂CO₃ (0.057 g, 0.17 mmol) and CH₃CN (4 mL) was stirred at 75° C. for 1.5 h. The mixture was diluted with EtOAc (25 mL), washed with water (15 mL), and brine (15 mL). The organic portion was dried (MgSO₄), filtered, and concentrated. The concentrated material was treated with 10% Et₂O in hexanes (10 mL) and stirred for 2 h. The resulting solid was filtered, rinsed with hexanes, and dried to afford the title compound (0.070 g, 81%) as a light tan solid: ¹H NMR (400 MHz, DMSO-d₆) δ 8.53 (s, 2H), 8.50 (s, 1H), 8.03 (d, J=8.6 Hz, 1H), 7.75 (d, J=8.6 Hz, 1H), 6.59 (s, 1H), 5.90 (s, 2H), 2.90 (t, J=7.5 Hz, 2H), 1.79-1.70 (m, 2H), 0.98 (t, J=7.4 Hz, 3H); MS m/z 547 (M+H).

Example 156

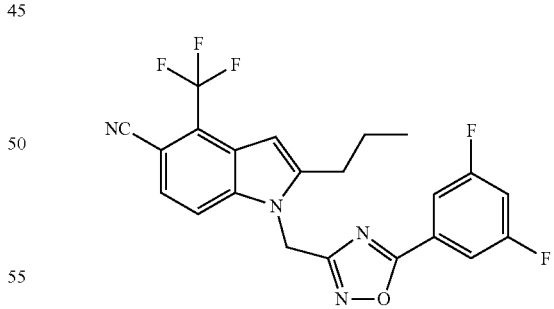

1-{[5-(3,5-Difluorophenyl)-1,2,4-oxadiazol-3-yl]methyl}-2-propyl-4-(trifluoromethyl)-1H-indole-5-carbonitrile Synthesized as described in Example 155 using 3-(chloromethyl)-5-(3,5-difluorophenyl)-1,2,4-oxadiazole (0.050 g, 0.22 mmol) to afford the title compound (0.069 g, 78%) as an off-white solid: ¹H NMR (400 MHz, DMSO-d₆) δ 8.02 (d, J=8.6 Hz, 1H), 7.75-7.63 (m, 4H), 6.59 (s, 1H), 5.90 (s, 2H), 2.88 (t, J=7.6 Hz, 2H), 1.78-1.68 (m, 2H), 0.98 (t, J=7.3 Hz, 3H); MS m/z 447 (M+H).

Example 157

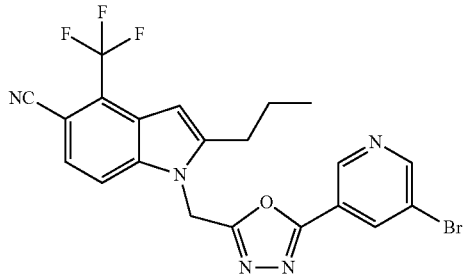 [SMILES: CCCc1cc2c(C(F)(F)F)c(C#N)ccc2n1Cc1nnc(-c2cncc(Br)c2)o1]

1-{[5-(5-Bromo-3-pyridinyl)-1,3,4-oxadiazol-2-yl]methyl}-2-propyl-4-(trifluoromethyl)-1H-indole-5-carbonitrile Synthesized as described in Example 155 using 3-bromo-5-[5-(chloromethyl)-1,3,4-oxadiazol-2-yl]pyridine (0.048 g, 0.17 mmol) to afford the title compound (0.065 g, 83%) as a tan solid: $^1$H NMR (400 MHz, DMSO-$d_6$) δ 9.04 (d, J=1.9 Hz, 1H), 8.94 (d, J=2.2 Hz, 1H), 8.46 (t, J=2.0 Hz, 1H), 8.06 (d, J=8.6 Hz, 1H), 7.77 (d, J=8.6 Hz, 1H), 6.61 (s, 1H), 5.99 (s, 2H), 2.89 (t, J=7.6 Hz, 2H), 1.79-1.69 (m, 2H), 0.99 (t, J=7.3 Hz, 3H); MS m/z 491 (M+H).

Example 158

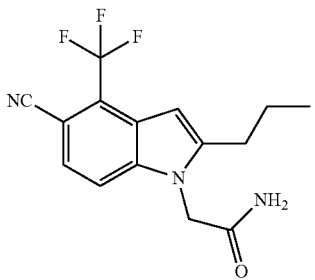 [SMILES: CCCc1cc2c(C(F)(F)F)c(C#N)ccc2n1CC(N)=O]

2-[5-Cyano-2-propyl-4-(trifluoromethyl)-1H-indol-1-yl]acetamide

Synthesized as described in Example 155 using 2-bromoacetamide (0.055 g, 0.40 mmol) to afford the title compound (0.069 g, 82%) as a tan solid: $^1$H NMR (400 MHz, DMSO-$d_6$) δ 7.82 (d, J=8.6 Hz, 1H), 7.71 (bs, 1H), 7.67 (d, J=8.6 Hz, 1H), 7.35 (bs, 1H), 6.51 (s, 1H), 4.91 (s, 2H), 2.69 (t, J=7.6 Hz, 2H), 1.73-1.64 (m, 2H), 0.97 (t, J=7.3 Hz, 3H); MS m/z 310 (M+H).

Example 159

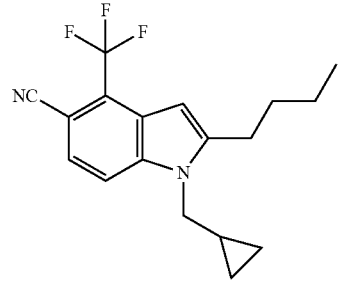 [SMILES: CCCCc1cc2c(C(F)(F)F)c(C#N)ccc2n1CC1CC1]

2-Butyl-1-(cyclopropylmethyl)-4-(trifluoromethyl)-1H-indole-5-carbonitrile

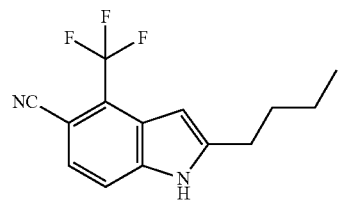 [SMILES: CCCCc1cc2c(C(F)(F)F)c(C#N)ccc2[nH]1]

A. 2-Butyl-4-(trifluoromethyl)-1H-indole-5-carbonitrile

Synthesized as described in Example 60 using 1-hexyne: $^1$H NMR (400 MHz, CDCl$_3$) δ 8.53 (s, 1H), 7.50 (d, J=8.4 Hz, 1H), 7.47 (d, J=8.4 Hz, 1H), 6.54 (s, 1H), 2.81 (t, J=7.6 Hz, 2H), 1.74 (m, 2H), 1.39 (m, 2H), 0.96 (t, J=7.3 Hz, 3H); MS (ES) m/z 267 (M+1).

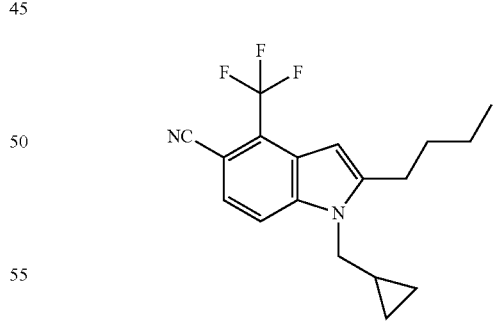

B. 2-Butyl-1-(cyclopropylmethyl)-4-(trifluoromethyl)-1H-indole-5-carbonitrile

Synthesized as described in Example 4 using 2-butyl-4-(trifluoromethyl)-1H-indole-5-carbonitrile and (bromomethyl)cyclopropane: $^1$H NMR (400 MHz, CDCl$_3$) δ 7.48 (s, 2H), 6.57 (s, 1H), 4.05 (d, J=6.3 Hz, 2H), 2.78 (t, J=7.8 Hz, 2H), 1.78 (m, 2H), 1.50 (m, 2H), 1.14 (m, 1H), 1.00 (t, J=7.3 Hz, 3H), 0.60 (m, 2H), 0.35 (m, 2H); MS (ES) m/z 321 (M+1).

Example 160

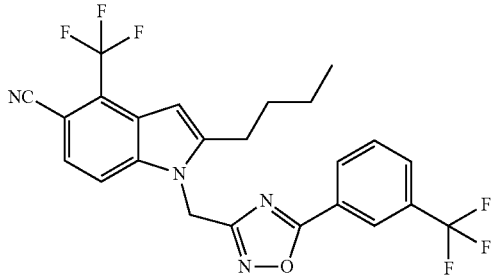 [SMILES: CCCCc1cc2c(C(F)(F)F)c(C#N)ccc2n1Cc1noc(-c2cccc(C(F)(F)F)c2)n1]

2-Butyl-4-(trifluoromethyl)-1-({5-[3-(trifluoromethyl)phenyl]-1,2,4-oxadiazol-3-yl}methyl)-1H-indole-5-carbonitrile A mixture of 2-butyl-4-(trifluoromethyl)-1H-indole-5-carbonitrile (0.050 g, 0.19 mmol), 3-(chloromethyl)-5-[3-(trifluoromethyl)phenyl]-1,2,4-oxadiazole (0.054 g, 0.21 mmol), Cs$_2$CO$_3$ (0.067 g, 0.21 mmol) and CH$_3$CN (4 mL) was stirred at 75° C. for 1.5 h. The mixture was diluted with EtOAc (25 mL), washed with water (15 mL), and brine (15 mL). Drying (MgSO$_4$) and filtration was followed by concentration. The resulting material was treated with 10% Et$_2$O in hexanes (10 mL) and stirred for 2 h. The resulting solid was filtered, rinsed with hexanes and dried to afford the title compound (0.070 g, 76%) as an off-white solid: $^1$H NMR (400 MHz, DMSO-d$_6$) δ 8.30 (d, J=7.8 Hz, 1H), 8.23 (s, 1H), 8.06 (d, J=7.8 Hz, 1H), 8.03 (d, J=8.6 Hz, 1H), 7.84 (t, J=7.8 Hz, 1H), 7.75 (d, J=8.6 Hz, 1H), 6.58 (s, 1H), 5.88 (s, 2H), 2.92 (t, J=7.5 Hz, 2H), 1.74-1.66 (m, 2H), 1.44-1.35 (m, 2H), 0.90 (t, J=7.4 Hz, 3H); MS m/z 493 (M+H).

Example 161

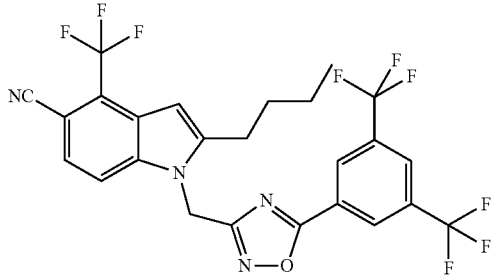 [SMILES: CCCCc1cc2c(C(F)(F)F)c(C#N)ccc2n1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-2-butyl-4-(trifluoromethyl)-1H-indole-5-carbonitrile Synthesized as described in Example 160 using 5-[3,5-bis(trifluoromethyl)phenyl]-3-(chloromethyl)-1,2,4-oxadiazole (0.055 g, 0.17 mmol) to afford the title compound (0.069 g, 82%) as a tan solid: $^1$H NMR (400 MHz, DMSO-d$_6$) δ 8.53 (s, 2H), 8.50 (s, 1H), 8.02 (d, J=8.6 Hz, 1H), 7.75 (d, J=8.6 Hz, 1H), 6.59 (s, 1H), 5.90 (s, 2H), 2.94 (t, J=7.5 Hz, 2H), 1.76-1.69 (m, 2H), 1.46-1.36 (m, 2H), 0.92 (t, J=7.3 Hz, 3H); MS m/z 561 (M+H).

Example 162

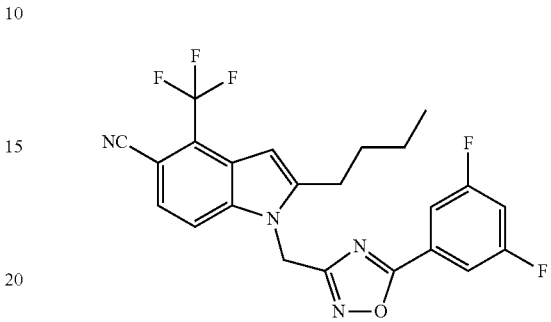

2-Butyl-1-{[5-(3,5-difluorophenyl)-1,2,4-oxadiazol-3-yl]methyl}-4-(trifluoromethyl)-1H-indole-5-carbonitrile Synthesized as described in Example 160 using 3-(chloromethyl)-5-(3,5-difluorophenyl)-1,2,4-oxadiazole (0.048 g, 0.21 mmol) to afford the title compound (0.076 g, 88%) as an off-white solid: $^1$H NMR (400 MHz, DMSO-d$_6$) δ 8.02 (d, J=8.5 Hz, 1H), 7.75-7.63 (m, 4H), 6.58 (s, 1H), 5.87 (s, 2H), 2.91 (t, J=7.8 Hz, 2H), 1.73-1.65 (m, 2H), 1.44-1.35 (m, 2H), 0.90 (t, J=7.3 Hz, 3H); MS m/z 461 (M+H).

Example 163

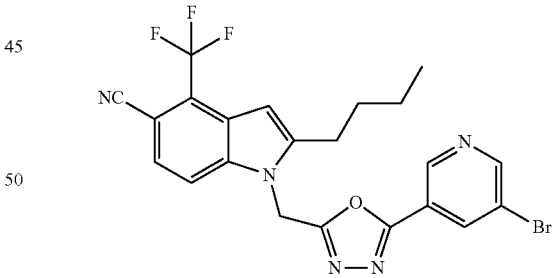

1-{[5-(5-Bromo-3-pyridinyl)-1,3,4-oxadiazol-2-yl]methyl}-2-butyl-4-(trifluoromethyl)-1H-indole-5-carbonitrile Synthesized as described in Example 160 using 3-bromo-5-[5-(chloromethyl)-1,3,4-oxadiazol-2-yl]pyridine (0.045 g, 0.17 mmol) to afford the title compound (0.054 g, 71%) as a tan solid: $^1$H NMR (400 MHz, DMSO-d$_6$) δ 9.04 (d, J=1.7 Hz, 1H), 8.94 (d, J=2.2 Hz, 1H), 8.46 (t, J=2.0 Hz, 1H), 8.06 (d, J=8.6 Hz, 1H), 7.77 (d, J=8.6 Hz, 1H), 6.60 (s, 1H), 5.99

(s, 2H), 2.92 (t, J=7.6 Hz, 2H), 1.74-1.66 (m, 2H), 1.45-1.36 (m, 2H), 0.91 (t, J=7.3 Hz, 3H); MS m/z 504 and 506 (M+H, bromine isotopes).

Example 164

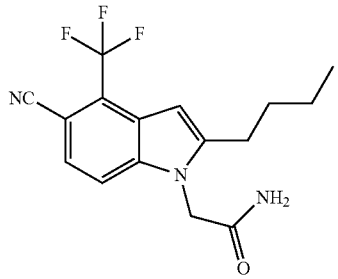 [SMILES: CCCCc1cc2c(C(F)(F)F)c(C#N)ccc2n1CC(N)=O]

2-[2-Butyl-5-cyano-4-(trifluoromethyl)-1H-indol-1-yl]acetamide

Synthesized as described in Example 160 using 2-bromoacetamide (0.052 g, 0.38 mmol) to afford the title compound (0.053 g, 87%) as an off-white solid: $^1$H NMR (400 MHz, DMSO-$d_6$) δ 7.82 (d, J=8.5 Hz, 1H), 7.71 (bs, 1H), 7.67 (d, J=8.5 Hz, 1H), 7.35 (bs, 1H), 6.50 (s, 1H), 4.91 (s, 2H), 2.71 (t, J=7.6 Hz, 2H), 1.68-1.61 (m, 2H), 1.43-1.34 (m, 2H), 0.91 (t, J=7.3 Hz, 3H); MS m/z 324.

Example 165

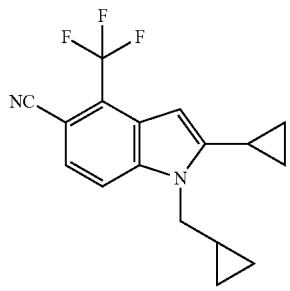 [SMILES: N#Cc1ccc2c(cc(C3CC3)n2CC2CC2)c1C(F)(F)F]

2-Cyclopropyl-1-(cyclopropylmethyl)-4-(trifluoromethyl)-1H-indole-5-carbonitrile

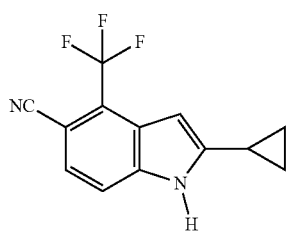 [SMILES: N#Cc1ccc2[nH]c(C3CC3)cc2c1C(F)(F)F]

A. 2-Cyclopropyl-4-(trifluoromethyl)-1H-indole-5-carbonitrile

Synthesized as described in Example 60 using ethynylcyclopropane: $^1$H NMR (400 MHz, CDCl$_3$) δ 8.57 (bs, 1H), 7.48 (d, J=8.8 Hz, 1H), 7.46 (d, J=8.8 Hz, 1H), 6.41 (s, 1H), 2.02 (m, 1H), 1.08 (m, 2H), 0.88 (m, 2H); MS (ES) m/z 251 (M+1).

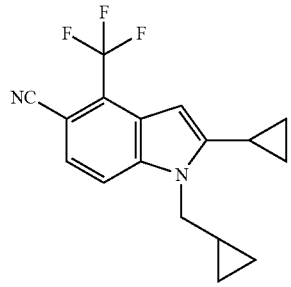 [SMILES: N#Cc1ccc2c(cc(C3CC3)n2CC2CC2)c1C(F)(F)F]

B. 2-Cyclopropyl-1-(cyclopropylmethyl)-4-(trifluoromethyl)-1H-indole-5-carbonitrile Synthesized as described in Example 4 using 2-cyclopropyl-4-(trifluoromethyl)-1H-indole-5-carbonitrile and (bromomethyl)cyclopropane: $^1$H NMR (400 MHz, CDCl$_3$) δ 7.48 (s, 2H), 6.37 (d, J=1.7 Hz, 1H), 4.19 (d, J=6.6 Hz, 2H), 1.92 (m, 1H), 1.24 (m, 1H), 1.11 (m, 2H), 0.86 (m, 2H), 0.61 (m, 2H), 0.39 (m, 2H); MS (ES) m/z 305 (M+1).

Example 166

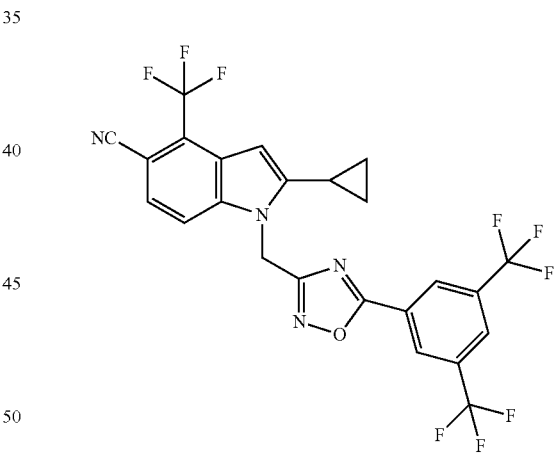

1-({5-[3,5-Bis(trifluoromethyl)phenyl]-1,2,4-oxadiazol-3-yl}methyl)-2-cyclopropyl-4-(trifluoromethyl)-1H-indole-5-carbonitrile Synthesized as described in Example 4 using 2-cyclopropyl-4-(trifluoromethyl)-1H-indole-5-carbonitrile and 5-[3,5-bis(trifluoromethyl)phenyl]-3-(chloromethyl)-1,2,4-oxadiazole: $^1$H NMR (400 MHz, CDCl$_3$) δ 8.50 (s, 2H), 8.09 (s, 1H), 7.67 (d, J=8.5 Hz, 1H), 7.56 (d, J=8.5 Hz, 1H), 6.50 (s, 1H), 5.68 (s, 2H), 2.14 (m, 1H), 1.16 (m, 2H), 0.93 (m, 2H); MS (ES) m/z 545 (M+1).

Example 167

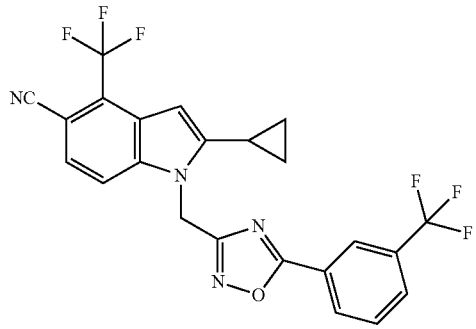 [SMILES: N#Cc1ccc2c(cc(C3CC3)n2Cc2noc(-c3cccc(C(F)(F)F)c3)n2)c1C(F)(F)F]

2-Cyclopropyl-4-(trifluoromethyl)-1-({5-[3-(trifluoromethyl)phenyl]-1,2,4-oxadiazol-3-yl}methyl)-1H-indole-5-carbonitrile Synthesized as described in Example 4 using 2-cyclopropyl-4-(trifluoromethyl)-1H-indole-5-carbonitrile and 5-[3-(trifluoromethyl)phenyl]-3-(chloromethyl)-1,2,4-oxadiazole: $^1$H NMR (400 MHz, CDCl$_3$) δ 8.32 (s, 1H), 8.24 (d, J=7.8 Hz, 1H), 7.85 (d, J=7.8 Hz, 1H), 7.66 (m, 2H), 7.55 (d, J=8.5 Hz, 1H), 6.49 (d, J=2.0 Hz, 1H), 5.65 (s, 2H), 2.15 (m, 1H), 1.16 (m, 2H), 0.91 (m, 2H); MS (ES) m/z 477 (M+1).

Example 168

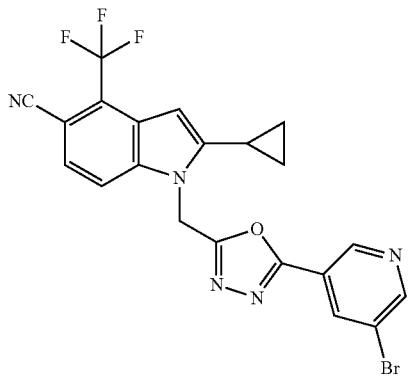 [SMILES: N#Cc1ccc2c(cc(C3CC3)n2Cc2nnc(-c3cncc(Br)c3)o2)c1C(F)(F)F]

1-{[5-(5-Bromo-3-pyridinyl)-1,3,4-oxadiazol-2-yl]methyl}-2-cyclopropyl-4-(trifluoromethyl)-1H-indole-5-carbonitrile Synthesized as described in Example 4 using 2-cyclopropyl-4-(trifluoromethyl)-1H-indole-5-carbonitrile and 3-bromo-5-[5-(chloromethyl)-1,3,4-oxadiazol-2-yl]pyridine: $^1$H NMR (400 MHz, CDCl$_3$) δ 9.05 (d, J=1.7 Hz, 1H), 8.82 (d, J=1.9 Hz, 1H), 8.39 (m, 1H), 7.69 (d, J=8.5 Hz, 1H), 7.59 (d, J=8.5 Hz, 1H), 6.52 (s, 1H), 5.80 (s, 2H), 2.06 (m, 1H), 1.19 (m, 2H), 0.92 (m, 2H); MS (ES) m/z 488 (M+1, isotope for Br) and 490 (M+1, isotope for Br).

Example 169

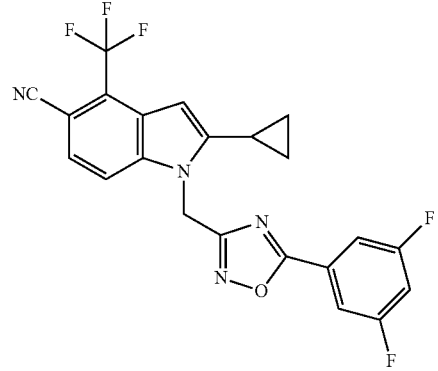 [SMILES: N#Cc1ccc2c(cc(C3CC3)n2Cc2noc(-c3cc(F)cc(F)c3)n2)c1C(F)(F)F]

2-Cyclopropyl-1-{[5-(3,5-difluorophenyl)-1,2,4-oxadiazol-3-yl]methyl}-4-(trifluoromethyl)-1H-indole-5-carbonitrile Synthesized as described in Example 4 using 2-cyclopropyl-4-(trifluoromethyl)-1H-indole-5-carbonitrile and 3-(chloromethyl)-5-(3,5-difluorophenyl)-1,2,4-oxadiazole: $^1$H NMR (400 MHz, CDCl$_3$) δ 7.67 (d, J=8.5 Hz, 1H), 7.57 (m, 3H), 7.05 (t, J=8.5 Hz, 1H), 6.48 (s, 1H), 5.64 (s, 2H), 2.13 (m, 1H), 1.15 (m, 2H), 0.92 (m, 2H); MS (ES) m/z 445 (M+1).

Example 170

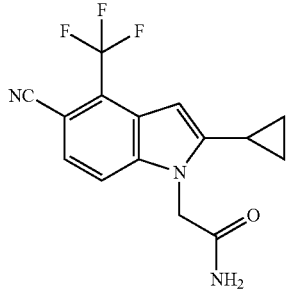 [SMILES: N#Cc1ccc2c(cc(C3CC3)n2CC(N)=O)c1C(F)(F)F]

2-[5-Cyano-2-cyclopropyl-4-(trifluoromethyl)-1H-indol-1-yl]acetamide

Synthesized as described in Example 4 using 2-cyclopropyl-4-(trifluoromethyl)-1H-indole-5-carbonitrile and 2-bromoacetamide: $^1$H NMR (400 MHz, DMSO-d$_6$) δ 7.82 (d, J=8.4 Hz, 1H), 7.71 (bs, 1H), 7.67 (d, J=8.4 Hz, 1H), 7.35 (bs, 1H), 6.37 (s, 1H), 5.02 (s, 2H), 1.94 (m, 1H), 0.99 (m, 2H), 0.77 (m, 2H); MS (ES) m/z 308 (M+1).

Example 171

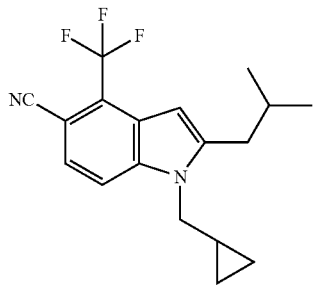 [SMILES: CC(C)Cc1cc2c(C(F)(F)F)c(C#N)ccc2n1CC1CC1]

1-(Cyclopropylmethyl)-2-(2-methylpropyl)-4-(trifluoromethyl)-1H-indole-5-carbonitrile

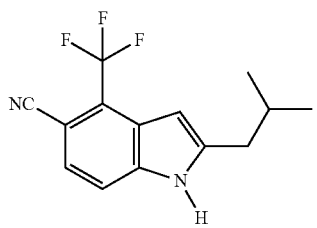 [SMILES: CC(C)Cc1cc2c(C(F)(F)F)c(C#N)ccc2[nH]1]

A. 2-(2-Methylpropyl)-4-(trifluoromethyl)-1H-indole-5-carbonitrile

Synthesized as described in Example 60 using 4-methyl-1-pentyne: $^1$H NMR (400 MHz, CDCl$_3$) δ 8.39 (bs, 1H), 7.51 (d, J=8.5 Hz, 1H), 7.48 (d, J=8.5 Hz, 1H), 6.54 (s, 1H), 2.68 (d, J=7.3 Hz, 2H), 2.04 (m, 1H), 0.99 (d, J=6.8 Hz, 6H); MS (ES) m/z 267 (M+1).

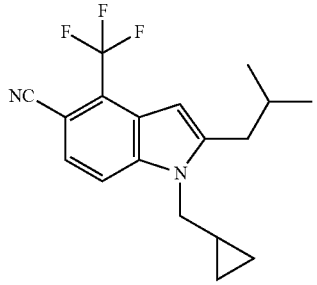 [SMILES: CC(C)Cc1cc2c(C(F)(F)F)c(C#N)ccc2n1CC1CC1]

B. 1-(Cyclopropylmethyl)-2-(2-methylpropyl)-4-(trifluoromethyl)-1H-indole-5-carbonitrile Synthesized as described in Example 4 using 2-(2-methylpropyl)-4-(trifluoromethyl)-1H-indole-5-carbonitrile and (bromomethyl)cyclopropane. $^1$H NMR (400 MHz, CDCl$_3$) δ 7.50 (d, J=9.2 Hz, 1H), 7.48 (d, J=9.2 Hz, 1H), 6.56 (d, J=1.7 Hz, 1H), 4.05 (d, J=6.6 Hz, 2H), 2.67 (t, J=7.1 Hz, 2H), 2.07 (m, 1H), 1.15 (m, 1H), 1.03 (d, J=6.6 Hz, 6H), 0.58 (m, 2H), 0.35 (m, 2H); MS (ES) m/z 321 (M+1).

Example 172

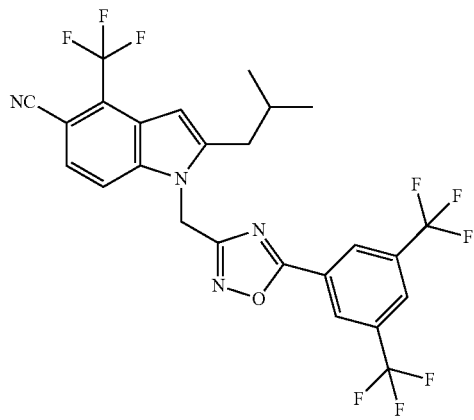 [SMILES: CC(C)Cc1cc2c(C(F)(F)F)c(C#N)ccc2n1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-2-(2-methylpropyl)-4-(trifluoromethyl)-1H-indole-5-carbonitrile Synthesized as described in Example 4 using 2-(2-methylpropyl)-4-(trifluoromethyl)-1H-indole-5-carbonitrile and 5-[3,5-bis(trifluoromethyl)phenyl]-3-(chloromethyl)-1,2,4-oxadiazole: $^1$H NMR (400 MHz, CDCl$_3$) δ 8.48 (s, 2H), 8.09 (s, 1H), 7.66 (d, J=8.5 Hz, 1H), 7.54 (d, J=8.5 Hz, 1H), 6.65 (s, 1H), 5.50 (s, 2H), 2.84 (d, J=7.1 Hz, 2H), 2.14 (m, 1H), 1.08 (d, J=6.6 Hz, 6H); MS (ES) m/z 561 (M+1).

Example 173

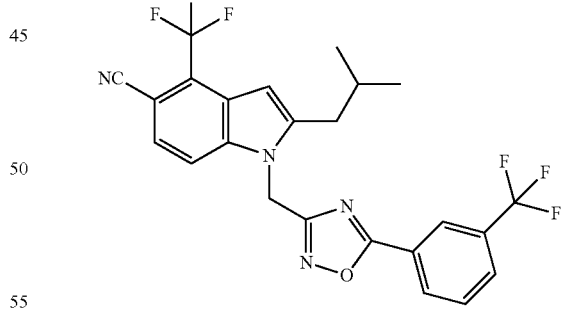

2-(2-Methylpropyl)-4-(trifluoromethyl)-1-({5-[3-(trifluoromethyl)phenyl]-1,2,4-oxadiazol-3-yl}methyl)-1H-indole-5-carbonitrile Synthesized as described in Example 4 using 2-(2-methylpropyl)-4-(trifluoromethyl)-1H-indole-5-carbonitrile and 5-[3-(trifluoromethyl)phenyl]-3-(chloromethyl)-1,2,4-oxadiazole: $^1$H NMR (400 MHz, CDCl$_3$) δ 8.30 (s, 1H), 8.22 (d, J=7.8 Hz, 1H), 7.85 (d, J=7.8 Hz, 1H), 7.66 (m, 2H), 7.54 (d, J=8.3 Hz, 1H), 6.63 (d, J=1.2 Hz, 1H), 5.48 (s, 2H), 2.84 (d, J=7.3 Hz, 2H), 2.14 (m, 1H), 1.08 (d, J=6.6 Hz, 6H); MS (ES) m/z 493 (M+1).

Example 174

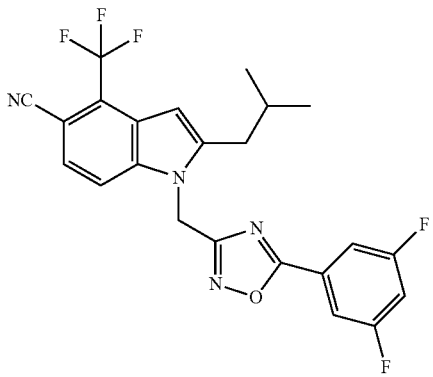 [SMILES: CC(C)Cc1cc2c(C(F)(F)F)c(C#N)ccc2n1Cc1noc(-c2cc(F)cc(F)c2)n1]

1-{[5-(3,5-Difluorophenyl)-1,2,4-oxadiazol-3-yl]methyl}-2-(2-methylpropyl)-4-(trifluoromethyl)-1H-indole-5-carbonitrile Synthesized as described in Example 4 using 2-(2-methylpropyl)-4-(trifluoromethyl)-1H-indole-5-carbonitrile and 3-(chloromethyl)-5-(3,5-difluorophenyl)-1,2,4-oxadiazole: $^1$H NMR (400 MHz, CDCl$_3$) δ 7.66 (d, J=8.3 Hz, 1H), 7.56 (m, 3H), 7.05 (t, J=8.5 Hz, 1H), 6.63 (s, 1H), 5.46 (s, 2H), 2.83 (d, J=7.1 Hz, 2H), 2.13 (m, 1H), 1.07 (d, J=6.6 Hz, 6H); MS (ES) m/z 461 (M+1).

Example 175

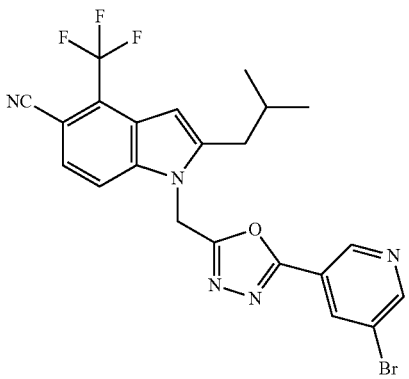 [SMILES: CC(C)Cc1cc2c(C(F)(F)F)c(C#N)ccc2n1Cc1nnc(-c2cncc(Br)c2)o1]

1-{[5-(5-Bromo-3-pyridinyl)-1,3,4-oxadiazol-2-yl]methyl}-2-(2-methylpropyl)-4-(trifluoromethyl)-1H-indole-5-carbonitrile Synthesized as described in Example 4 using 2-(2-methylpropyl)-4-(trifluoromethyl)-1H-indole-5-carbonitrile and 3-bromo-5-[5-(chloromethyl)-1,3,4-oxadiazol-2-yl]pyridine: $^1$H NMR (400 MHz, CDCl$_3$) δ 9.04 (d, J=1.4 Hz, 1H), 8.84 (d, J=2.0 Hz, 1H), 8.43 (m, 1H), 7.68 (d, J=8.4 Hz, 1H), 7.59 (d, J=8.4 Hz, 1H), 6.67 (s, 1H), 5.63 (s, 2H), 2.82 (d, J=7.1 Hz, 2H), 2.13 (m, 1H), 1.08 (d, J=6.6 Hz, 6H); MS (ES) m/z 504 (M+1, isotope for Br) and 506 (M+1, isotope for Br).

Example 176

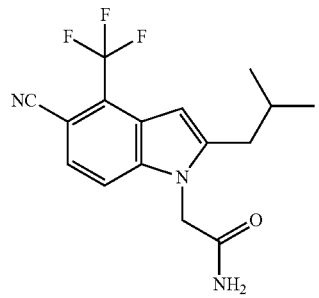 [SMILES: CC(C)Cc1cc2c(C(F)(F)F)c(C#N)ccc2n1CC(N)=O]

2-[5-Cyano-2-(2-methylpropyl)-4-(trifluoromethyl)-1H-indol-1-yl]acetamide

Synthesized as described in Example 4 using 2-(2-methylpropyl)-4-(trifluoromethyl)-1H-indole-5-carbonitrile and 2-bromoacetamide: $^1$H NMR (400 MHz, DMSO-d$_6$) δ 7.82 (d, J=8.5 Hz, 1H), 7.71 (bs, 1H), 7.67 (d, J=8.5 Hz, 1H), 7.34 (bs, 1H), 6.51 (d, J=2.2 Hz, 1H), 4.91 (s, 2H), 2.61 (d, J=7.0 Hz, 2H), 1.95 (m, 1H), 0.92 (d, J=6.6 Hz, 6H); MS (ES) m/z 324 (M+1).

Example 177

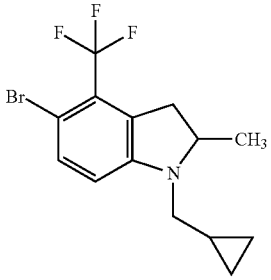 [SMILES: CC1Cc2c(ccc(Br)c2C(F)(F)F)N1CC1CC1]

5-Bromo-1-(cyclopropylmethyl)-2-methyl-4-(trifluoromethyl)-2,3-dihydro-1H-indole Synthesized as described in Example 113 using 5-bromo-1-(cyclopropylmethyl)-2-methyl-4-(trifluoromethyl)-1H-indole: $^1$H NMR (400 MHz, CDCl$_3$) δ 7.33 (d, J=8.3 Hz, 1H), 6.42 (d, J=8.3 Hz, 1H), 3.94 (m, 1H), 3.43 (m, 1H), 3.22 (m, 1H), 2.82 (m, 2H), 1.30 (d, J=6.1 Hz, 3H), 0.92 (m, 1H), 0.55

(m, 1H), 0.50 (m, 1H), 0.23 (m, 1H), 0.15 (m, 1H); MS (ES) m/z 334 (M+1, isotope for Br) and 336 (M+1, isotope for Br).

Example 178

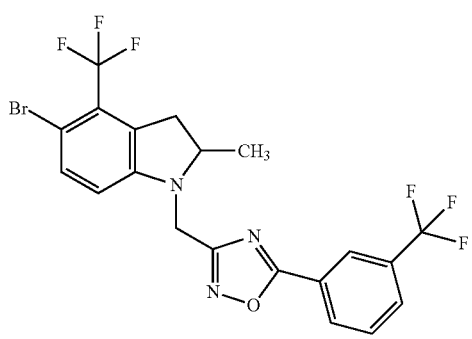 [SMILES: CC1Cc2c(ccc(Br)c2C(F)(F)F)N1Cc1noc(-c2cccc(C(F)(F)F)c2)n1]

5-Bromo-2-methyl-4-(trifluoromethyl)-1-({5-[3-(trifluoromethyl)phenyl]-1,2,4-oxadiazol-3-yl}methyl)-2,3-dihydro-1H-indole Synthesized as described in Example 113 using 5-bromo-2-methyl-4-(trifluoromethyl)-1-({5-[3-(trifluoromethyl)phenyl]-1,2,4-oxadiazol-3-yl}methyl)-1H-indole: $^1$H NMR (400 MHz, CDCl$_3$) δ 8.36 (s, 1H), 8.28 (d, J=7.8 Hz, 1H), 7.85 (d, J=7.8 Hz, 1H), 7.67 (t, J=7.8 Hz, 1H), 7.35 (d, J=8.4 Hz, 1H), 6.56 (d, J=8.4 Hz, 1H), 4.55 (d, J=16.4 Hz, 1H), 4.43 (d, J=16.4 Hz, 1H), 4.04 (m, 1H), 3.46 (m, 1H), 2.85 (m, 1H), 1.44 (d, J=6.1 Hz, 3H); MS (ES) m/z 506 (M+1, isotope for Br) and 508 (M+1, isotope for Br).

Example 179

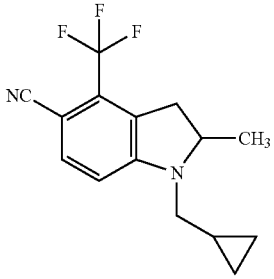 [SMILES: CC1Cc2c(ccc(C#N)c2C(F)(F)F)N1CC1CC1]

1-(Cyclopropylmethyl)-2-methyl-4-(trifluoromethyl)-2,3-dihydro-1H-indole-5-carbonitrile Synthesized as described in Example 113 using 1-(cyclopropylmethyl)-2-methyl-4-(trifluoromethyl)-1H-indole-5-carbonitrile: $^1$H NMR (400 MHz, CDCl$_3$) δ 7.44 (d, J=8.3 Hz, 1H), 6.41 (d, J=8.3 Hz, 1H), 4.12 (m, 1H), 3.43 (m, 1H), 3.29 (dd, J=14.9 and 5.6 Hz, 1H), 2.92 (dd, J=14.9 and 7.4 Hz, 1H), 2.79 (m, 1H), 1.31 (d, J=6.4 Hz, 3H), 0.94 (m, 1H), 0.60 (m, 1H), 0.51 (m, 1H), 0.26 (m, 1H), 0.19 (m, 1H); MS (ES) m/z 281 (M+1).

Example 180

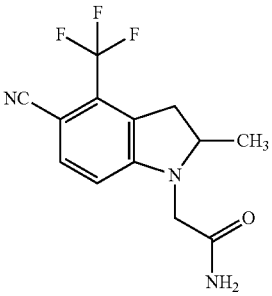 [SMILES: CC1Cc2c(ccc(C#N)c2C(F)(F)F)N1CC(N)=O]

2-[5-Cyano-2-methyl-4-(trifluoromethyl)-2,3-dihydro-1H-indol-1-yl]acetamide

Synthesized as described in Example 113 using 2-[5-cyano-2-methyl-4-(trifluoromethyl)-1H-indol-1-yl]acetamide: $^1$H NMR (400 MHz, DMSO-d$_6$) δ 7.63 (d, J=8.3 Hz, 1H), 7.49 (bs, 1H), 7.17 (bs, 1H), 6.52 (d, J=8.3 Hz, 1H), 4.00 (m, 1H), 3.97 (d, J=17.3 Hz, 1H), 3.80 (d, J=17.3 Hz, 1H), 3.42 (m, 1H), 2.75 (m, 1H), 1.23 (d, J=6.1 Hz, 3H); MS (ES) m/z 284 (M+1).

Example 181

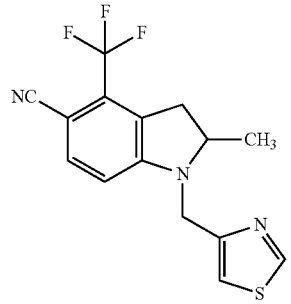 [SMILES: CC1Cc2c(ccc(C#N)c2C(F)(F)F)N1Cc1cscn1]

2-Methyl-1-(1,3-thiazol-4-ylmethyl)-4-(trifluoromethyl)-2,3-dihydro-1H-indole-5-carbonitrile Synthesized as described in Example 113 using 2-methyl-1-(1,3-thiazol-4-ylmethyl)-4-(trifluoromethyl)-1H-indole-5-carbonitrile: $^1$H NMR (400 MHz, CDCl$_3$) δ 9.30 (s, 1H), 7.48 (d, J=8.0 Hz, 1H), 7.37 (s, 1H), 6.29 (d, J=8.0 Hz, 1H), 4.77 (d, J=18.3 Hz, 1H), 4.69 (d, J=18.3 Hz, 1H), 4.12 (m, 1H), 3.57 (m, 1H), 2.95 (m, 1H), 1.39 (d, J=6.1 Hz, 3H); MS (ES) m/z 324 (M+1).

Example 182

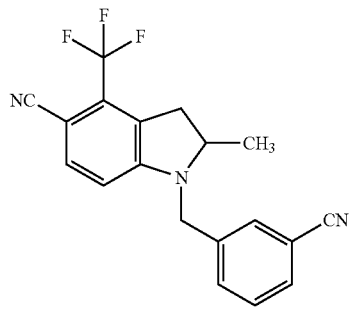 [SMILES: CC1Cc2c(ccc(C#N)c2C(F)(F)F)N1Cc1cccc(C#N)c1]

1-[(3-Cyanophenyl)methyl]-2-methyl-4-(trifluoromethyl)-2,3-dihydro-1H-indole-5-carbonitrile Synthesized as described in Example 113 using 1-[(3-cyanophenyl)methyl]-2-methyl-4-(trifluoromethyl)-1H-indole-5-carbonitrile: $^1$H NMR (400 MHz, CDCl$_3$) δ 7.60 (d, J=6.6 Hz, 1H), 7.54 (s, 1H), 7.49 (m, 2H), 7.43 (d, J=8.3 Hz, 1H), 6.26 (d, J=8.3 Hz, 1H), 4.49 (d, J=16.7 Hz, 1H), 4.38 (d, J=16.7 Hz, 1H), 4.00 (m, 1H), 3.53 (m, 1H), 2.90 (m, 1H), 1.33 (d, J=6.4 Hz, 3H); MS (ES) m/z 342 (M+1).

Example 183

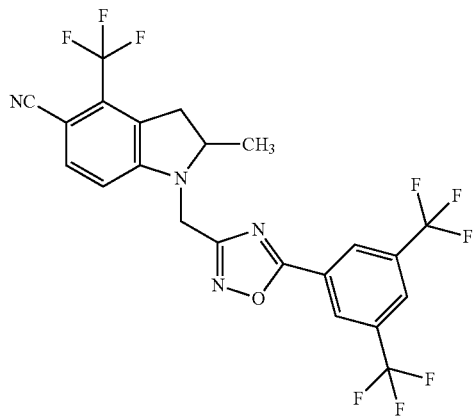 [SMILES: CC1Cc2c(ccc(C#N)c2C(F)(F)F)N1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-2-methyl-4-(trifluoromethyl)-2,3-dihydro-1H-indole-5-carbonitrile Synthesized as described in Example 113 using 1-({5-[3,5-bis(trifluoromethyl)phenyl]-1,2,4-oxadiazol-3-yl}methyl)-2-methyl-4-(trifluoromethyl)-1H-indole-5-carbonitrile: $^1$H NMR (400 MHz, CDCl$_3$) δ 8.53 (s, 2H), 8.10 (s, 1H), 7.51 (d, J=8.3 Hz, 1H), 6.65 (d, J=8.3 Hz, 1H), 4.65 (d, J=16.6 Hz, 1H), 4.55 (d, J=16.6 Hz, 1H), 4.22 (m, 1H), 3.52 (m, 1H), 2.89 (m, 1H), 1.48 (d, J=6.3 Hz, 3H); MS (ES) m/z 521 (M+1).

Example 184

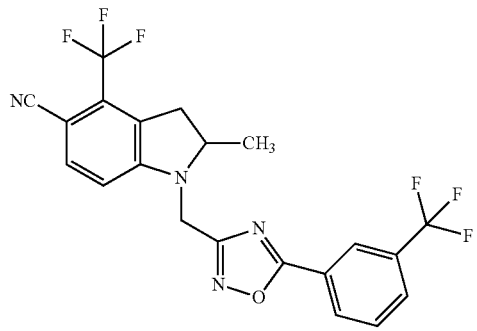 [SMILES: CC1Cc2c(ccc(C#N)c2C(F)(F)F)N1Cc1noc(-c2cccc(C(F)(F)F)c2)n1]

2-Methyl-4-(trifluoromethyl)-1-({5-[3-(trifluoromethyl)phenyl]-1,2,4-oxadiazol-3-yl}methyl)-2,3-dihydro-1H-indole-5-carbonitrile Synthesized as described in Example 113 using 2-methyl-4-(trifluoromethyl)-1-({5-[3-(trifluoromethyl)phenyl]-1,2,4-oxadiazol-3-yl}methyl)-1H-indole-5-carbonitrile: $^1$H NMR (400 MHz, CDCl$_3$) δ 8.35 (s, 1H), 8.28 (d, J=7.8 Hz, 1H), 7.86 (d, J=7.8 Hz, 1H), 7.68 (t, J=7.8 Hz, 1H), 7.51 (d, J=8.4 Hz, 1H), 6.66 (d, J=8.4 Hz, 1H), 4.63 (d, J=16.6 Hz, 1H), 4.38 (d, J=16.6 Hz, 1H), 4.21 (m, 1H), 3.51 (m, 1H), 2.86 (m, 1H), 1.47 (d, J=6.1 Hz, 3H); MS (ES) m/z 453 (M+1).

Example 185

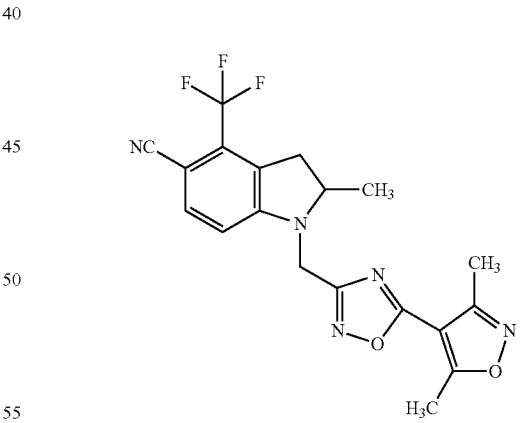

1-{[5-(3,5-Dimethyl-4-isoxazolyl)-1,2,4-oxadiazol-3-yl]methyl}-2-methyl-4-(trifluoromethyl)-2,3-dihydro-1H-indole-5-carbonitrile Synthesized as described in Example 113 using 1-{[5-(3,5-dimethyl-4-isoxazolyl)-1,2,4-oxadiazol-3-yl]methyl}-2-methyl-4-(trifluoromethyl)-1H-indole-5-carbonitrile: $^1$H NMR (400 MHz, CDCl$_3$) δ 7.49 (d, J=8.3 Hz, 1H), 6.65 (d, J=8.3 Hz, 1H), 4.61 (d, J=16.5 Hz, 1H), 4.51 (d, J=16.5 Hz, 1H), 4.16 (m, 1H), 3.48 (m, 1H), 2.88 (m, 1H), 2.74 (s, 3H), 2.52 (s, 1H), 1.46 (d, J=6.1 Hz, 3H); MS (ES) m/z 404 (M+1).

Example 186

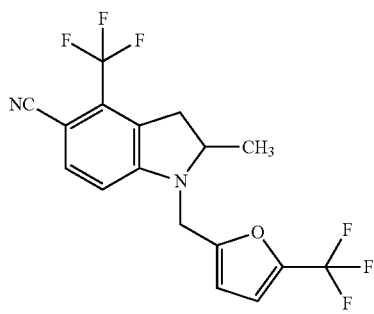

2-Methyl-4-(trifluoromethyl)-1-{[5-(trifluoromethyl)-2-furanyl]methyl}-2,3-dihydro-1H-indole-5-carbonitrile Synthesized as described in Example 113 using 2-methyl-4-(trifluoromethyl)-1-{[5-(trifluoromethyl)-2-furanyl]methyl}-1H-indole-5-carbonitrile: $^1$H NMR (400 MHz, CDCl$_3$) δ 7.48 (d, J=8.3 Hz, 1H), 6.72 (s, 1H), 6.50 (d, J=8.3 Hz, 1H), 6.26 (s, 1H), 4.45 (d, J=16.8 Hz, 1H), 4.36 (d, J=16.8 Hz, 1H), 4.00 (m, 1H), 3.45 (m, 1H), 2.84 (m, 1H), 1.39 (d, J=6.1 Hz, 3H); MS (ES) m/z 375 (M+1).

Example 187

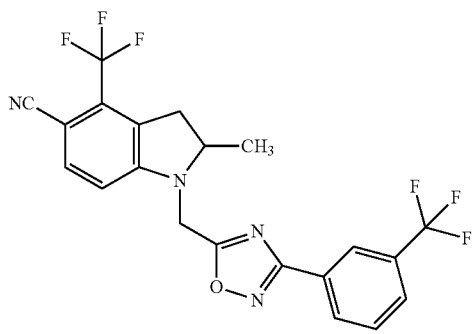 [SMILES: CC1Cc2c(ccc(C#N)c2C(F)(F)F)N1Cc1nc(-c2cccc(C(F)(F)F)c2)no1]

2-Methyl-4-(trifluoromethyl)-1-({3-[3-(trifluoromethyl)phenyl]-1,2,4-oxadiazol-5-yl}methyl)-2,3-dihydro-1H-indole-5-carbonitrile Synthesized as described in Example 113 using 2-methyl-4-(trifluoromethyl)-1-({3-[3-(trifluoromethyl)phenyl]-1,2,4-oxadiazol-5-yl}methyl)-1H-indole-5-carbonitrile: $^1$H NMR (400 MHz, CDCl$_3$) δ 8.30 (s, 1H), 8.23 (d, J=7.8 Hz, 1H), 7.77 (d, J=7.8 Hz, 1H), 7.62 (t, J=7.8 Hz, 1H), 7.53 (d, J=8.3 Hz, 1H), 6.63 (d, J=8.3 Hz, 1H), 4.76 (d, J=17.1 Hz, 1H), 4.38 (d, J=17.1 Hz, 1H), 4.20 (m, 1H), 3.55 (m, 1H), 2.90 (m, 1H), 1.47 (d, J=6.4 Hz, 3H); MS (ES) m/z 453 (M+1).

Example 188

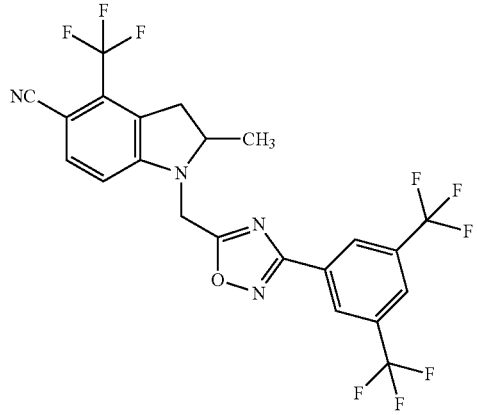 [SMILES: CC1Cc2c(ccc(C#N)c2C(F)(F)F)N1Cc1nc(-c2cc(C(F)(F)F)cc(C(F)(F)F)c2)no1]

1-({3-[3,5-Bis(trifluoromethyl)phenyl]-1,2,4-oxadiazol-5-yl}methyl)-2-methyl-4-(trifluoromethyl)-2,3-dihydro-1H-indole-5-carbonitrile Synthesized as described in Example 113 using 1-({3-[3,5-bis(trifluoromethyl)phenyl]-1,2,4-oxadiazol-5-yl}methyl)-2-methyl-4-(trifluoromethyl)-1H-indole-5-carbonitrile: $^1$H NMR (400 MHz, DMSO-d$_6$) δ 8.46 (s, 2H), 8.41 (s, 1H), 7.73 (d, J=8.4 Hz, 1H), 6.89 (d, J=8.4 Hz, 1H), 5.20 (d, J=17.8 Hz, 1H), 5.00 (d, J=17.8 Hz, 1H), 4.15 (m, 1H), 3.53 (m, 1H), 2.86 (m, 1H), 1.32 (d, J=6.1 Hz, 3H); MS (ES) m/z 521 (M+1).

Example 189

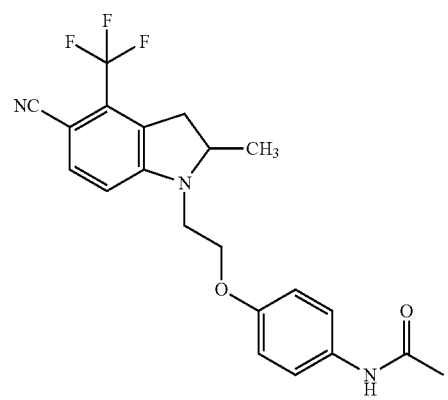 [SMILES: CC(=O)Nc1ccc(OCCN2c3ccc(C#N)c(C(F)(F)F)c3CC2C)cc1]

N-[4-({2-[5-Cyano-2-methyl-4-(trifluoromethyl)-2,3-dihydro-1H-indol-1-yl]ethyl}oxy)phenyl]acetamide Synthesized as described in Example 113 using N-[4-({2-[5-cyano-2-methyl-4-(trifluoromethyl)-1H-indol-1-yl]ethyl}oxy)phenyl]acetamide: $^1$H NMR (400 MHz, DMSO-d$_6$) δ 9.75 (s, 1H), 7.63 (d, J=8.3 Hz, 1H), 7.43 (d, J=8.9 Hz, 2H), 6.80 (d, J=8.9 Hz, 2H), 6.75 (d, J=8.3 Hz, 1H), 4.08 (m, 3H), 3.71 (m, 1H), 3.60 (m, 1H), 3.42 (m, 1H), 2.78 (m, 1H), 1.96 (s, 3H), 1.27 (d, J=6.1 Hz, 3H); MS (ES) m/z 404 (M+1).

Example 190

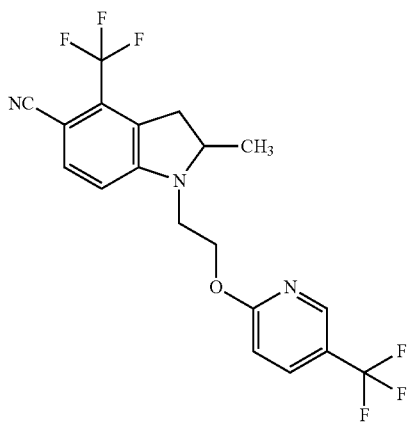 [SMILES: CC1Cc2c(ccc(C#N)c2C(F)(F)F)N1CCOc1ccc(C(F)(F)F)cn1]

2-Methyl-4-(trifluoromethyl)-1-(2-{[5-(trifluoromethyl)-2-pyridinyl]oxy}ethyl)-2,3-dihydro-1H-indole-5-carbonitrile Synthesized as described in Example 113 using 2-methyl-4-(trifluoromethyl)-1-(2-{[5-(trifluoromethyl)-2-pyridinyl]oxy}ethyl)-1H-indole-5-carbonitrile: $^1$H NMR (400 MHz, DMSO-d$_6$) δ 8.54 (s, 1H), 8.01 (d, J=8.6 Hz, 1H), 7.61 (d, J=8.3 Hz, 1H), 6.90 (d, J=8.6 Hz, 1H), 6.75 (d, J=8.3 Hz, 1H), 4.59 (m, 1H), 4.46 (m, 1H), 4.11 (m, 1H), 3.75 (m, 1H), 3.61 (m, 1H), 3.38 (m, 1H), 2.75 (m, 1H), 1.26 (d, J=6.1 Hz, 3H); MS (ES) m/z 416 (M+1).

Example 191

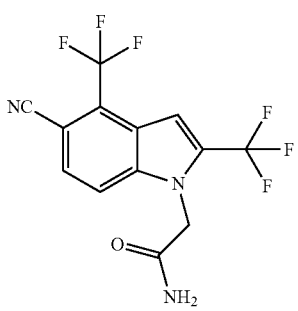 [SMILES: N#Cc1ccc2c(cc(C(F)(F)F)n2CC(N)=O)c1C(F)(F)F]

2-[5-Cyano-2,4-bis(trifluoromethyl)-1H-indol-1-yl]acetamide

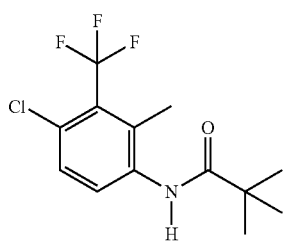 [SMILES: Cc1c(NC(=O)C(C)(C)C)ccc(Cl)c1C(F)(F)F]

A. N-[4-Chloro-2-methyl-3-(trifluoromethyl)phenyl]-2,2-dimethylpropanamide

Prepared in a manner similar to Example 60A using MeI. The ratio of the title compound, 2-methyl regioisomer to the undesired 6-methyl was 4.7 to 1: MS (ES) m/z 293 (M$^+$).

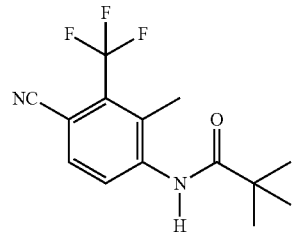 [SMILES: Cc1c(NC(=O)C(C)(C)C)ccc(C#N)c1C(F)(F)F]

B. N-[4-Cyano-2-methyl-3-(trifluoromethyl)phenyl]-2,2-dimethylpropanamide

A solution of N-[4-chloro-2-methyl-3-(trifluoromethyl)phenyl]-2,2-dimethylpropanamide (0.257 g, 0.875 mmol) in NMP (2.5 mL) was treated with copper cyanide (0.180 g, 2.01 mmol) and the resulting suspension was heated to 200° C. in a microwave for 14 h. The cooled reaction mixture was diluted with EtOAc and water and then filtered through a pad of celite. The filtrate was concentrated to a brown oil and then partitioned between Et$_2$O and water. The aqueous portion was further extracted with Et$_2$O and the combined organics were dried (Na$_2$SO$_4$), filtered, and concentrated to a brown foam. Trituration with hexanes/Et$_2$O afforded the title compound (0.222 g) in good purity: MS (ES) m/z 285 (M+1).

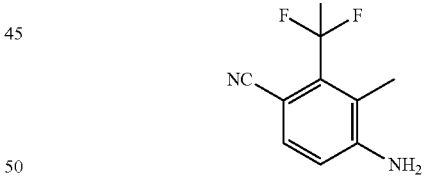

C. 4-Amino-3-methyl-2-(trifluoromethyl)benzonitrile

The crude N-[4-cyano-2-methyl-3-(trifluoromethyl)phenyl]-2,2-dimethylpropanamide from Example 191B was dissolved in EtOH (5 mL) and conc. HCl (5 mL). The resulting mixture was heated to 70° C. for 20 min. The cooled reaction's pH was adjusted to ca. 8 with 6 N NaOH. EtOAc (20 mL) was added and the isolated organic portion was dried (Na$_2$SO$_4$), filtered, and concentrated to afford the title compound: MS (ES) m/z 201 (M+1).

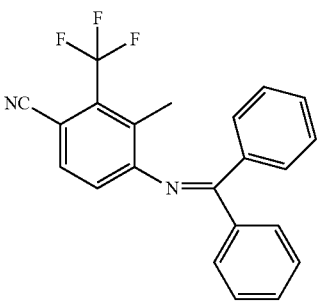 [SMILES: Cc1c(N=C(c2ccccc2)c2ccccc2)ccc(C#N)c1C(F)(F)F]

D. 4-[(Diphenyl methylidene)amino]-3-methyl-2-(trifluoromethyl)benzonitrile

To a stirred solution of 4-amino-3-methyl-2-(trifluoromethyl)benzonitrile (3.59 g, 17.9 mmol) in toluene (80 mL) was added benzophenone (3.59 g, 19.7 mmol) followed by PTSA monohydrate (0.035 g, 0.18 mmol). The reaction flask was fitted with a Dean-Stark trap and heated at reflux for 7 d. The reaction was concentrated and purified by SiO$_2$ chromatography (5% EtOAc in hexanes) to afford 4-[(diphenylmethylidene)amino]-3-methyl-2-(trifluoromethyl)benzonitrile (5.16 g, 79%) as a yellow solid: $^1$H NMR (400 MHz, DMSO-d$_6$): δ 7.71-7.01 (m, 10H), 7.65 (d, J=8.4 Hz, 1H), 6.95 (d, J=8.4 Hz, 1H), 2.30 (s, 3H).

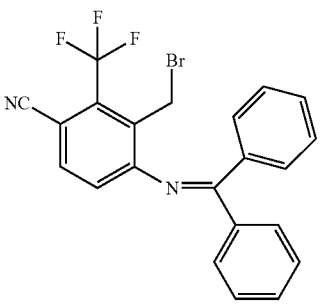 [SMILES: N#Cc1ccc(N=C(c2ccccc2)c2ccccc2)c(CBr)c1C(F)(F)F]

E. 3-(Bromomethyl)-4-[(diphenylmethylidene)amino]-2-(trifluoromethyl)benzonitrile To a stirred solution of the benzonitrile (3.53 g, 9.69 mmol) from step D in CCl$_4$ (90 mL) was added NBS (1.98 g, 11.14 mmol) and benzoyl peroxide (70%, 0.352 g, 1.45 mmol). The mixture was heated at reflux for 3 h. After cooling to ambient temperature, the reaction was diluted with CH$_2$Cl$_2$ (100 mL), washed with 1N NaOH (100 mL), brine (100 mL), dried (MgSO$_4$) and concentrated. Purification by SiO$_2$ chromatography (10% EtOAc in hexanes) afforded 3-(bromomethyl)-4-[(diphenylmethylidene)amino]-2-(trifluoromethyl)benzonitrile (4.08 g, 95%) as a light yellow solid: $^1$H NMR (400 MHz, DMSO-d$_6$): δ 7.78 (d, J=8.3 Hz, 1H), 7.78-7.11 (m, 10H), 6.91 (d, J=8.6 Hz, 1H), 4.78 (s, 2H).

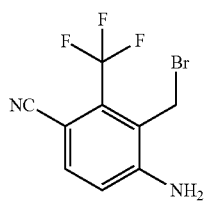

F. 4-Amino-3-(bromomethyl)-2-(trifluoromethyl)benzonitrile

To a stirred solution of the diphenylmethylidene from step E (0.250 g, 0.56 mmol) in THF (4 mL) was added 2N HCl (0.4 mL). After stirring at rt for 2 h, the reaction was partitioned in EtOAc/hexanes (20 mL; 1:2). The layers were separated and the organic portion was dried (MgSO$_4$) and concentrated. Purification by SiO$_2$ chromatography (10-50% EtOAc in hexane2) afforded 4-amino-3-(bromomethyl)-2-(trifluoromethyl)benzonitrile (0.073 g, 50%) as a yellow solid: $^1$H NMR (400 MHz, DMSO-d$_6$) δ 7.61 (d, J=8.6 Hz, 1H), 6.98 (d, J=8.6 Hz, 1H), 6.82 (bs, 2H), 4.71 (s, 2H).

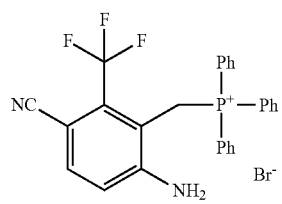 [SMILES: N#Cc1ccc(N)c(C[P+](c2ccccc2)(c2ccccc2)c2ccccc2)c1C(F)(F)F ; [Br-]]

G. {[6-Amino-3-cyano-2-(trifluoromethyl)phenyl]methyl}(triphenyl) phosphonium bromide A solution of the benzyl bromide (0.430 g, 1.54 mmoL) from step F and triphenylphosphine (0.404 g, 1.54 mmoL) in toluene (15 mL) was stirred at reflux for 18 h. After cooling to rt, the reaction was diluted with Et$_2$O (60 mL) and stirred for 30 min. The resulting solid was filtered, rinsed with Et$_2$O, and dried to afford {[6-amino-3-cyano-2-(trifluoromethyl)phenyl]methyl}(triphenyl)phosphonium bromide (0.570 g, 68%) as a light yellow solid: $^1$H NMR (400 MHz, DMSO-d$_6$): δ 7.87-7.83 (m, 3H), 7.70-7.59 (m, 13H), 6.83 (d, J=8.8 Hz, 1H), 6.45 (s, 2H), 5.13 (bs, 2H).

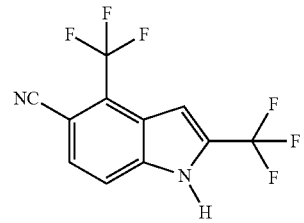 [SMILES: N#Cc1ccc2[nH]c(C(F)(F)F)cc2c1C(F)(F)F]

H. 2,4-Bis(trifluoromethyl)-1H-indole-5-carbonitrile

To a mixture of the phosphonium bromide (0.560 g, 1.0 mmoL) from step G and Na$_2$CO$_3$ (0.329 g, 3.0 mmoL) in THF (20 mmol) at 5° C. was added TFAA (0.44 mL, 3.0 mmoL) over 15 min. The reaction was allowed to warm to rt and stir for 1 h. The mixture was concentrated then diluted with anhydrous DMF (15 mL) and stirred at 100° C. for 18 h. The reaction was poured into water (100 mL) and extracted with Et$_2$O (2×60 mL). The combined organic portions were washed with sat'd NaHCO$_3$ (50 mL) and brine (50 mL). Drying (MgSO$_4$), filtration, and concentration was followed by purification (SiO$_2$, 20% EtOAc in hexanes) to afford 2,4-bis(trifluoromethyl)-1H-indole-5-carbonitrile (0.258 g, 90%) as a white solid: $^1$H NMR (400 MHz, DMSO-d$_6$) δ 13.25 (bs, 1H), 7.95 (d, J=8.5 Hz, 1H), 7.89 (d, J=8.8 Hz, 1H), 7.27 (s, 1H); MS m/z 279 (M+H).

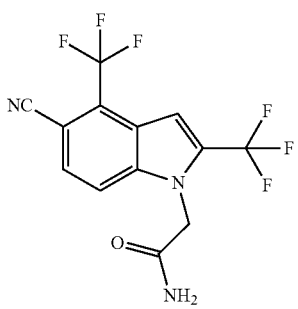

I. 2-[5-Cyano-2,4-bis(trifluoromethyl)-1H-indol-1-yl]acetamide

A mixture of the indole (0.050 g, 0.18 mmoL) from step H, $Cs_2CO_3$ (0.117 g, 0.36 mmol), 2-bromoacetamide (0.050 g, 0.36 mmol) and $CH_3CN$ (4 mL) was stirred at 80° C. for 6 h. The mixture was diluted with EtOAc (25 mL), washed with water (15 mL) and brine (15 mL). Drying ($MgSO_4$) was followed by concentration. The concentrated material was treated with 10% $Et_2O$ in hexanes (10 mL) and stirred for 2 h. The resulting solid was filtered, rinsed with hexanes, and dried to afford the title compound (0.055 g, 92%) as a white solid: $^1$H NMR (400 MHz, DMSO-$d_6$) δ 8.17 (d, J=8.8 Hz, 1H), 7.98 (d, J=8.8 Hz, 1H), 7.75 (bs, 1H), 7.39 (bs, 1H), 7.36 (s, 1H), 5.11 (s, 2H); MS m/z 358 (M+Na).

Example 192

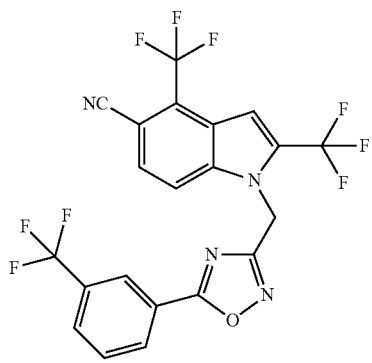 [SMILES: N#Cc1ccc2c(cc(C(F)(F)F)n2Cc2noc(-c3cccc(C(F)(F)F)c3)n2)c1C(F)(F)F]

2,4-Bis(trifluoromethyl)-1-({5-[3-(trifluoromethyl)phenyl]-1,2,4-oxadiazol-3-yl}methyl)-1H-indole-5-carbonitrile A mixture of 2,4-bis(trifluoromethyl)-1H-indole-5-carbonitrile (0.050 g, 0.18 mmol), $Cs_2CO_3$ (0.064 g, 0.20 mmoL), 3-(chloromethyl)-5-[3-(trifluoromethyl)phenyl]-1,2,4-oxadiazole (0.052 g, 0.20 mmoL) and $CH_3CN$ (4 mL) was stirred at 75° C. for 18 h. The mixture was diluted with EtOAc (25 mL) and washed with water (15 mL) and brine (15 mL). Drying (MgSO4), filtration, and concentration was followed by purification ($SiO_2$, 0-30% EtOAc in hexanes) to afford the title compound (0.056 g, 62%) as a white solid: $^1$H NMR (400 MHz, DMSO-$d_6$) δ 8.34 (d, J=8.8 Hz, 1H), 8.29 (d, J=8.8 Hz, 1H) 8.23 (s, 1H), 8.09-8.06 (m, 2H), 7.83 (t, J=7.8 Hz, 1H), 7.48 (s, 1H), 6.03 (s, 2H); MS m/z 527 (M+Na).

Example 193

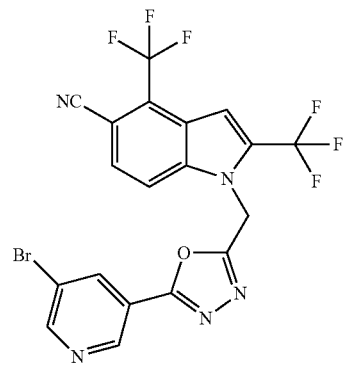 [SMILES: N#Cc1ccc2c(cc(C(F)(F)F)n2Cc2nnc(-c3cncc(Br)c3)o2)c1C(F)(F)F]

1-{[5-(5-Bromo-3-pyridinyl)-1,3,4-oxadiazol-2-yl]methyl}-2,4-bis(trifluoromethyl)-1H-indole-5-carbonitrile Synthesized as described in Example 192 using 3-bromo-5-[5-(chloromethyl)-1,3,4-oxadiazol-2-yl]pyridine (0.040 g, 0.17 mmol) to afford the title compound (0.055 g, 59%) as a white solid: $^1$H NMR (400 MHz, DMSO-$d_6$) δ 9.03 (s, 1H) 8.95 (s, 1H), 8.46 (s, 1H), 8.36 (d, J=8.8 Hz, 1H), 8.12 (d, J=8.8 Hz, 1H), 7.51 (s, 1H), 6.14 (s, 2H); MS m/z 517 (M+H).

Example 194

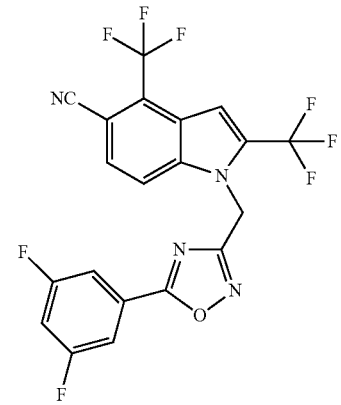 [SMILES: N#Cc1ccc2c(cc(C(F)(F)F)n2Cc2noc(-c3cc(F)cc(F)c3)n2)c1C(F)(F)F]

1-{[5-(3,5-Difluorophenyl)-1,2,4-oxadiazol-3-yl]methyl}-2,4-bis(trifluoromethyl)-1H-indole-5-carbonitrile Synthesized as described in Example 192 using 3-(chloromethyl)-5-(3,5-difluorophenyl)-1,2,4-oxadiazole (0.040 g, 0.17 mmoL) to afford the title compound (0.043 g, 63%) as a white solid: $^1$H NMR (400 MHz, DMSO-$d_6$) δ 8.34 (d, J=8.5

Hz, 1H), 8.08 (d, J=8.8 Hz, 1H), 7.72-7.65 (m, 3H), 7.49 (s, 1H), 6.02 (s, 2H); MS m/z 495 (M+Na).

Example 195

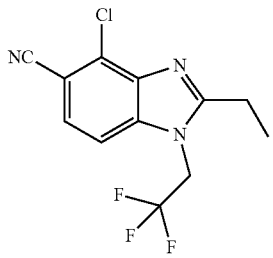 [SMILES: CCc1nc2c(Cl)c(C#N)ccc2n1CC(F)(F)F]

4-Chloro-2-ethyl-1-(2,2,2-trifluoroethyl)-1H-benzimidazole-5-carbonitrile

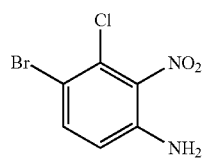

A. 4-Bromo-3-chloro-2-nitroaniline

3-Chloro-2-nitro aniline (5.0 g, 28.97 mmol) and NBS (5.42 g, 30.42 mmol) were combined in THF (200 mL) and stirred at rt for 15 h. Concentration and purification (SiO$_2$, EtOAc/hexanes) afforded the title compound (0.84 g): $^1$HNMR (400 MHz, CDCl$_3$) δ 7.46 (d, J=8.9 Hz, 1H), 6.63 (d, J=8.9 Hz, 1H), 4.7 (s, 2H); MS (ESI) m/z 253 (M+1).

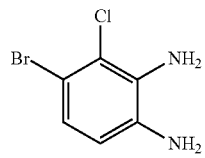

B. 4-Bromo-3-chloro-1,2-benzenediamine

To a stirred solution of 4-bromo-3-chloro-2-nitroaniline (0.200 g, 0.797 mmol) in EtOH (100 mL), was added SnCl$_2$·2H$_2$O (0.9 g, 3.985 mmol). The reaction mixture was heated to reflux for 3.5 h. The cooled solution (to rt) was diluted with H$_2$O and the pH was adjusted to ca. 10 with Na$_2$CO$_3$. Extraction with CHCl$_3$ (×3), was followed by washing with brine, drying over Na$_2$SO$_4$, and filtration. Concentration afforded an orange solid that was dried under vacuum to obtain 0.17 g product: $^1$H NMR (400 MHz, CDCl$_3$) δ 6.92 (d, J=8.4 Hz, 1H), 6.51 (d, J=8.4 Hz, 1H), 3.90 (s, 2H), 3.40 (s, 2H); MS (ESI) m/z 223 (M+1).

C. 5-Bromo-4-chloro-2-ethyl-1H-benzimidazole

4-Bromo-3-chloro-1,2-benzenediamine (0.17 g, 0.766 mmol), propionic acid (0.17 g, 2.298 mmol), and 4 N HCl (1.724 ml, 6.894 mmol) were combined and heated to 140° C. for 3 h. Treatment with 1 N NaOH was followed by extraction with EtOAc (×3), and washing with brine. The dried (Na$_2$SO$_4$) organic portions were filtered, concentrated, and chromatographed (SiO$_2$, MeOH/CH$_2$Cl$_2$) to obtain 0.177 g of the title compound: $^1$HNMR (400 MHz, CDCl$_3$) δ 9.50 (broad s, 1H), 7.43 (d, J=8.31 Hz, 1H), 7.35 (broad s, 1H), 2.96 (q, J=7.5 Hz, 2H), 1.43 (t, J=7.5 Hz, 3H); MS (ESI) m/z 261 (M+1).

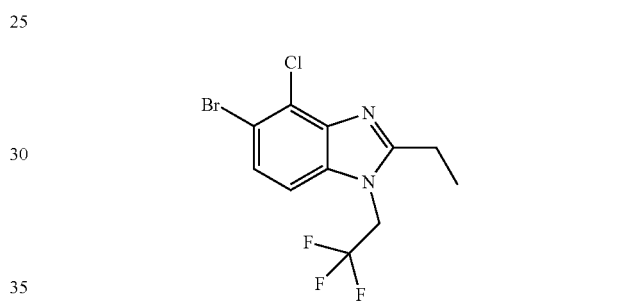

D. 5-Bromo-4-chloro-2-ethyl-1-(2,2,2-trifluoroethyl)-1H-benzimidazole

5-Bromo-4-chloro-2-ethyl-1H-benzimidazole (0.049 g, 0.188 mmol), trifluoroethyl triflate (0.065 g, 0.282 mmol), and Cs$_2$CO$_3$ (0.092 g, 0.282 mmol) were combined in DMF (5 mL) and the resulting solution was heated to 90° C. for 30 min. The reaction mixture was partitioned between H$_2$O and Et$_2$O and further extracted with Et$_2$O. The combined organic portions were washed with brine, dried (Na$_2$SO$_4$), filtered, and concentrated in vacuo. Chromatography (SiO$_2$, EtOAc/hexanes) allowed separation of the regioisomers. 0.083 g of desired regioisomer was isolated: $^1$NMR (400 MHz, CDCl$_3$) δ 7.5 (d, J=8.5 Hz, 1H), 7.2 (d, J=8.5 Hz, 1H), 4.6 (q, J=8.3 Hz, 2H), 2.9 (q, J=7.4 Hz, 2H), 1.45 (t, J=7.4 Hz, 3H); MS (ESI) m/z 343 (M+1).

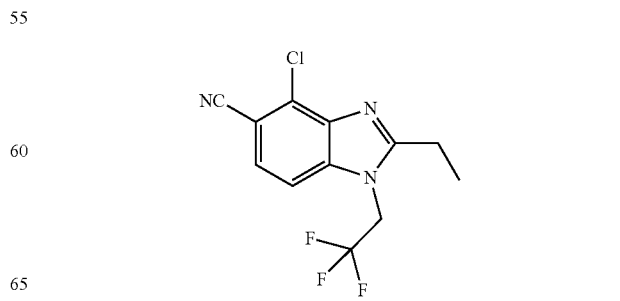

E. 4-Chloro-2-ethyl-1-(2,2,2-trifluoroethyl)-1H-benzimidazole-5-carbonitrile 5-Bromo-4-chloro-2-ethyl-1-(2,2,2-trifluoroethyl)-1H-benzimidazole (0.036 g, 0.106 mmol) and CuCN (0.020 g, 0.222 mmol) were combined in NMP (3 mL) and heated to 220° C. for 20 min in a microwave. The cooled mixture was partitioned between Et$_2$O and water, washed with brine, dried over Na$_2$SO$_4$, filtered, and concentrated in vacuo. Purification (SiO$_2$, EtOAc/hexanes) afforded the title compound (0.015 g): $^1$NMR (400 MHz, CDCl$_3$) δ 7.56 (d, J=8.4 Hz, 1H), 7.34 (d, J=8.4 Hz, 1H), 4.68 (q, J=8.2 Hz, 2H), 2.96 (q, J=7.4 Hz, 2H), 1.45 (t, J=7.4 Hz, 3H); MS (ESI) m/z 288 (M+1).

Example 196

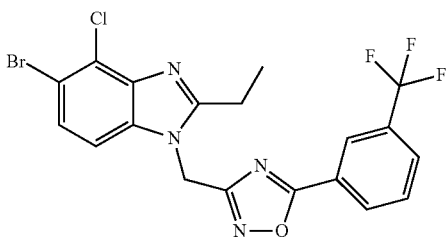 [SMILES: CCc1nc2c(Cl)c(Br)ccc2n1Cc1noc(-c2cccc(C(F)(F)F)c2)n1]

5-Bromo-4-chloro-2-ethyl-1-({5-[3-(trifluoromethyl)phenyl]-1,2,4-oxadiazol-3-yl}methyl)-1H-benzimidazole 5-Bromo-4-chloro-2-ethyl-1H-benzimidazole (0.100 g, 0.385 mmol), Cs$_2$CO$_3$ (0.188 g, 0.578 mmol), and 3-(chloromethyl)-5-[3-(trifluoromethyl)phenyl]-1,2,4-oxadiazole (0.152 g, 0.578 mmol) were combined in DMF (10 mL) and heated to 90° C. for 30 min. The reaction mixture was partitioned between Et$_2$O and water. The combined organic portions were washed with brine, dried (Na$_2$SO$_4$), filtered, and concentrated in vacuo. Purification (SiO$_2$, EtOAc/hexanes) provided the title compound 0.258 g: MS (ESI) m/z 487 (M+1).

Example 197

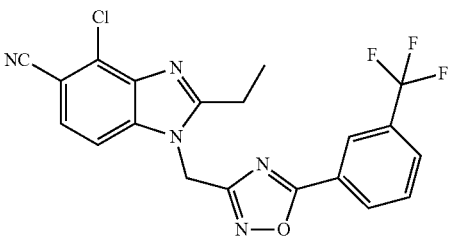 [SMILES: CCc1nc2c(Cl)c(C#N)ccc2n1Cc1noc(-c2cccc(C(F)(F)F)c2)n1]

4-Chloro-2-ethyl-1-({5-[3-(trifluoromethyl)phenyl]-1,2,4-oxadiazol-3-yl}methyl)-1H-benzimidazole-5-carbonitrile

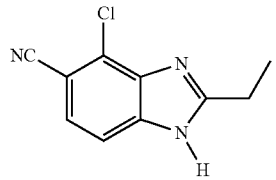

A. 4-Chloro-2-ethyl-1H-benzimidazole-5-carbonitrile

5-Bromo-4-chloro-2-ethyl-1H-benzimidazole (0.050 g, 0.192 mmol) and CuCN (0.030 g, 0.576 mmol) were combined in NMP (3 mL) and heated to 220° C. for 20 min in a microwave. The cooled mixture was partitioned between Et$_2$O and water. The organic portion was washed with brine, dried (Na$_2$SO$_4$), filtered, and concentrated in vacuo. Purification (SiO$_2$, EtOAc/hexanes) afforded the title compound (0.014 g): MS (ESI) m/z 206 (M+1).

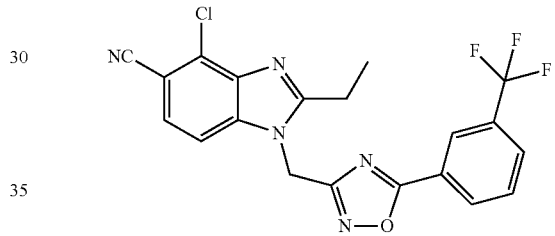

B. 4-Chloro-2-ethyl-1-({5-[3-(trifluoromethyl)phenyl]-1,2,4-oxadiazol-3-yl}methyl)-1H-benzimidazole-5-carbonitrile 4-Chloro-2-ethyl-1H-benzimidazole-5-carbonitrile (0.014 g, 0.068 mmol), Cs$_2$CO$_3$ (0.033 g, 0.102 mmol), and 3-(chloromethyl)-5-[3-(trifluoromethyl)phenyl]-1,2,4-oxadiazole (0.027 g, 0.102 mmol) were combined in DMF (10 mL) and heated to 90° C. for 30 min. The cooled reaction mixture was partitioned between Et$_2$O and water. The organic portion was washed with brine, dried over Na$_2$SO$_4$, filtered, and concentrated in vacuo. Purification (SiO$_2$, EtOAc/hexanes) afforded the title compound (0.0037 g): MS (ESI) m/z 432 (M+1).

Example 198

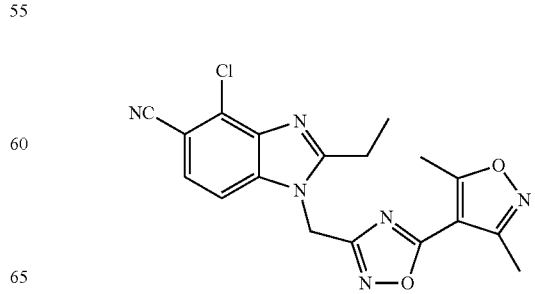

4-Chloro-1-{[5-(3,5-dimethyl-4-isoxazolyl)-1,2,4-oxadiazol-3-yl]methyl}-2-ethyl-1H-benzimidazole-5-carbonitrile Synthesized as described in Example 197B from 4-chloro-2-ethyl-1H-benzimidazole-5-carbonitrile and 3-(chloromethyl)-5-(3,5-dimethyl-4-isoxazolyl)-1,2,4-oxadiazole: MS (ESI) m/z 383 (M+1).

Example 199

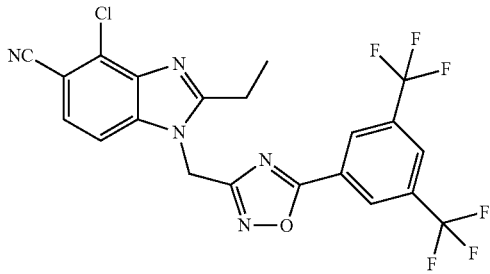 [SMILES: CCc1nc2c(Cl)c(C#N)ccc2n1Cc1noc(-c2cc(C(F)(F)F)cc(C(F)(F)F)c2)n1]

1-({5-[3,5-Bis(trifluoromethyl)phenyl]-1,2,4-oxadiazol-3-yl}methyl)-4-chloro-2-ethyl-1H-benzimidazole-5-carbonitrile Synthesized as described in Example 197B from 4-chloro-2-ethyl-1H-benzimidazole-5-carbonitrile and 5-[3,5-bis(trifluoromethyl)phenyl]-3-(chloromethyl)-1,2,4-oxadiazole: MS (ESI) m/z 500 (M+1).

Example 200

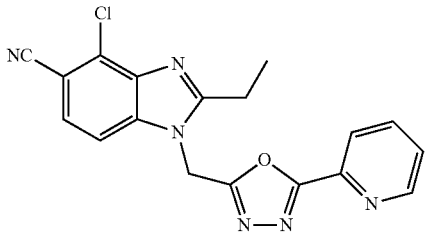 [SMILES: CCc1nc2c(Cl)c(C#N)ccc2n1Cc1nnc(-c2ccccn2)o1]

4-Chloro-2-ethyl-1-{[5-(2-pyridinyl)-1,3,4-oxadiazol-2-yl]methyl}-1H-benzimidazole-5-carbonitrile

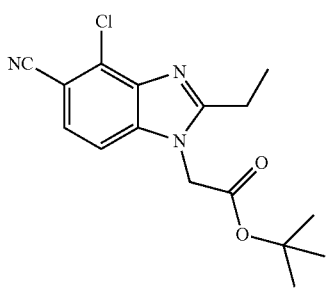 [SMILES: CCc1nc2c(Cl)c(C#N)ccc2n1CC(=O)OC(C)(C)C]

A. 1,1-Dimethylethyl (4-chloro-5-cyano-2-ethyl-1H-benzimidazol-1-yl)acetate

Synthesized as described in Example 197B from 4-chloro-2-ethyl-1H-benzimidazole-5-carbonitrile and 1,1-dimethylethyl bromoacetate: MS (ESI) m/z 320 (M+1).

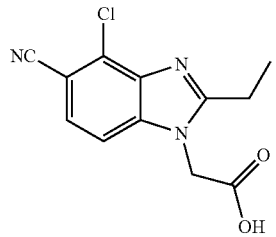 [SMILES: CCc1nc2c(Cl)c(C#N)ccc2n1CC(=O)O]

B. (4-Chloro-5-cyano-2-ethyl-1H-benzimidazol-1-yl)acetic acid 1,1-Dimethylethyl (4-chloro-5-cyano-2-ethyl-1H-benzimidazol-1-yl)acetate (0.032 g, 0.1 mmol) and Et$_3$SiH (0.116 mg, 1 mmol) were combined in CH$_2$Cl$_2$/TFA (1:1; 6 mL) and stirred at rt for 5 h. Concentration was followed by pH adjustment to ca. 7 in H$_2$O. Extraction with EtOAc, washing with brine, drying (Na$_2$SO$_4$), filtration, and concentration were followed by purification (SiO$_2$, EtOAc/hexanes) to afford the title compound (0.017 g): MS (ESI) m/z 264 (M+1).

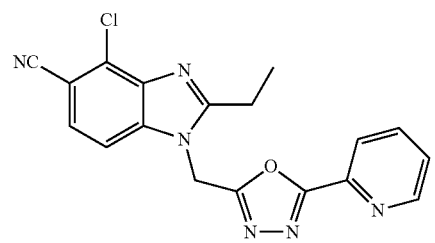 [SMILES: CCc1nc2c(Cl)c(C#N)ccc2n1Cc1nnc(-c2ccccn2)o1]

C. 4-Chloro-2-ethyl-1-{[5-(2-pyridinyl)-1,3,4-oxadiazol-2-yl]methyl}-1H-benzimidazole-5-carbonitrile (4-Chloro-5-cyano-2-ethyl-1H-benzimidazol-1-yl)acetic acid (0.017 g, 0.065 mmol) and EDCl (0.014 mg, 0.072 mmol) were combined in acetonitrile (3 mL) and stirred at rt for 3 min. 2-Pyridinecarbohydrazide (0.0094 g, 0.068 mmol) was added next and the resulting mixture was stirred for 60 min. To this solution was added THF (THF 3 mL) followed by tosyl chloride (0.015 g, 0.078 mmol) and P-BEMP (0.148 g, 0.325 mmol, 2.2 mmol/g resin load). The reaction vessel was sealed and heated to 100° C. in a microwave for 5 min. The resin was filtered away and washed with CH$_2$Cl$_2$ (×2). The concentrated filtrate was purified (SiO$_2$, 25% EtOAc/hexanes) to afford the title compound (0.004 g): MS (APCI) m/z 365 (M+1).

Example 201

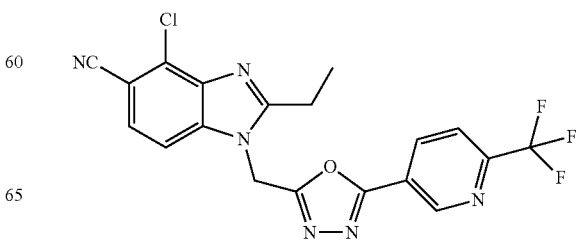

4-Chloro-2-ethyl-1-({5-[6-(trifluoromethyl)-3-pyridinyl]-1,3,4-oxadiazol-2-yl}methyl)-1H-benzimidazole-5-carbonitrile Synthesized as described in Example 200C from (4-chloro-5-cyano-2-ethyl-1H-benzimidazol-1-yl)acetic acid and 6-(trifluoromethyl)-3-pyridinecarbohydrazide: MS (APCI) m/z 433 (M+1).

Example 202

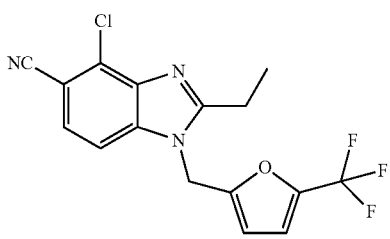 [SMILES: CCc1nc2c(Cl)c(C#N)ccc2n1Cc1ccc(C(F)(F)F)o1]

4-Chloro-2-ethyl-1-{[5-(trifluoromethyl)-2-furanyl]methyl}-1H-benzimidazole-5-carbonitrile Synthesized as described in Example 197B from 4-chloro-2-ethyl-1H-benzimidazole-5-carbonitrile and 2-(bromomethyl)-5-(trifluoromethyl)furan: MS (ESI) m/z 354 (M+1).

Example 203

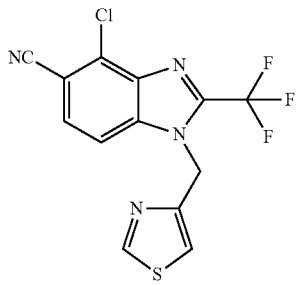 [SMILES: N#Cc1ccc2c(nc(C(F)(F)F)n2Cc2cscn2)c1Cl]

4-Chloro-1-(1,3-thiazol-4-ylmethyl)-2-(trifluoromethyl)-1H-benzimidazole-5-carbonitrile

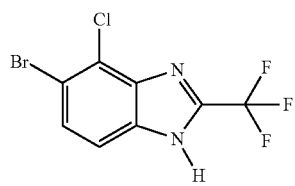 [SMILES: FC(F)(F)c1nc2c(Cl)c(Br)ccc2[nH]1]

A. 5-Bromo-4-chloro-2-(trifluoromethyl)-1H-benzimidazole

Synthesized as described in Example 195C from 4-bromo-3-chloro-1,2-benzenediamine and TFA: MS (ESI) m/z 301 (M+1).

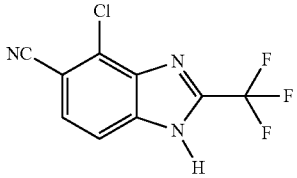 [SMILES: N#Cc1ccc2[nH]c(C(F)(F)F)nc2c1Cl]

B. 4-Chloro-2-(trifluoromethyl)-1H-benzimidazole-5-carbonitrile

Synthesized as described in Example 197A from 5-bromo-4-chloro-2-(trifluoromethyl)-1H-benzimidazole and CuCN: MS (APCI) m/z 246 (M+1).

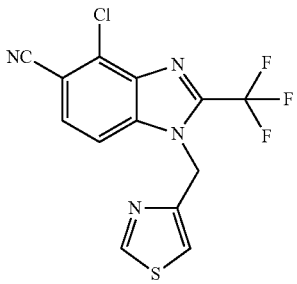 [SMILES: N#Cc1ccc2c(nc(C(F)(F)F)n2Cc2cscn2)c1Cl]

C. 4-Chloro-1-(1,3-thiazol-4-ylmethyl)-2-(trifluoromethyl)-1H-benzimidazole-5-carbonitrile Synthesized as described in Example 197B from 4-chloro-2-(trifluoromethyl)-1H-benzimidazole-5-carbonitrile and 4-(chloromethyl)-1,3-thiazole hydrochloride: MS (ESI) m/z 343 (M+1).

Example 204

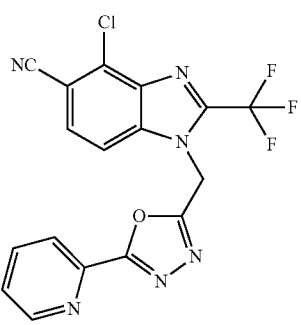 [SMILES: N#Cc1ccc2c(nc(C(F)(F)F)n2Cc2nnc(-c3ccccn3)o2)c1Cl]

4-Chloro-1-{[5-(2-pyridinyl)-1,3,4-oxadiazol-2-yl]methyl}-2-(trifluoromethyl)-1H-benzimidazole-5-carbonitrile

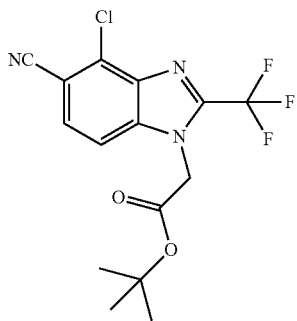 [SMILES: CC(C)(C)OC(=O)Cn1c(C(F)(F)F)nc2c(Cl)c(C#N)ccc21]

A. 1,1-Dimethylethyl [4-chloro-5-cyano-2-(trifluoromethyl)-1H-benzimidazol-1-yl]acetate Synthesized as described in Example 200A from 4-chloro-2-(trifluoromethyl)-1H-benzimidazole-5-carbonitrile and 1,1-dimethylethyl bromoacetate: MS (APCI) m/z 360 (M+1).

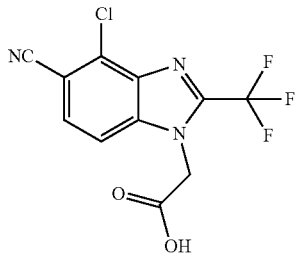 [SMILES: N#Cc1ccc2c(nc(C(F)(F)F)n2CC(=O)O)c1Cl]

B. [4-Chloro-5-cyano-2-(trifluoromethyl)-1H-benzimidazol-1-yl]acetic acid

Synthesized as described 200B from 1,1-dimethylethyl [4-chloro-5-cyano-2-(trifluoromethyl)-1H-benzimidazol-1-yl]acetate: MS (APCI) m/z 304 (M+1).

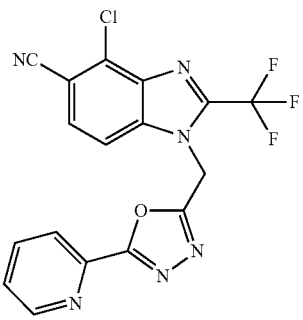 [SMILES: N#Cc1ccc2c(nc(C(F)(F)F)n2Cc2nnc(-c3ccccn3)o2)c1Cl]

C. 4-Chloro-1-{[5-(2-pyridinyl)-1,3,4-oxadiazol-2-yl]methyl}-2-(trifluoromethyl)-1H-benzimidazole-5-carbonitrile Synthesized as described Example 200C from [4-chloro-5-cyano-2-(trifluoromethyl)-1H-benzimidazol-1-yl]acetic acid and 2-pyridinecarbohydrazide: MS (ESI) m/z 405 (M+1).

Example 205

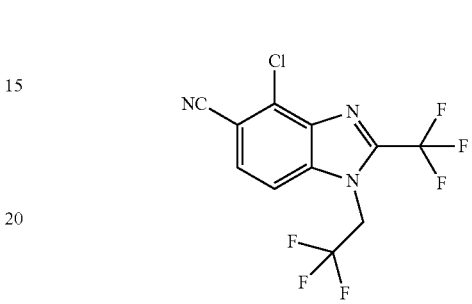

4-Chloro-1-(2,2,2-trifluoroethyl)-2-(trifluoromethyl)-1H-benzimidazole-5-carbonitrile

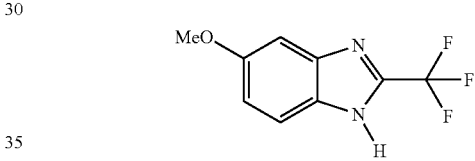

A. 5-(Methyloxy)-2-(trifluoromethyl)-1H-benzimidazole

Synthesized as described Example 195C from [2-amino-4-(methyloxy)phenyl]amine dihydrochloride and TFA: MS (ESI) m/z 217 (M+1).

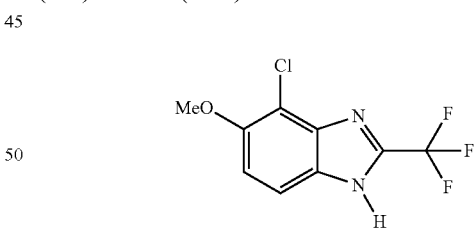

B. 4-Chloro-5-(methyloxy)-2-(trifluoromethyl)-1H-benzimidazole

Sulfuryl chloride (0.39 mL, 4.86 mmol) was added dropwise to a 0° C. solution of 5-(methyloxy)-2-(trifluoromethyl)-1H-benzimidazole (1.0 g, 4.63 mmol) in HOAc (10 mL). The ice bath was removed and the mixture was allowed to stir at rt for 2 h. The concentrated reaction mixture was suspended in a mixture of EtOAc and H$_2$O and the pH was adjusted to 7 with saturated aqueous NaHCO$_3$. The reaction was partitioned and the aqueous portion was extracted with EtOAc. The combined organic fractions were washed with brine, dried (Na$_2$SO$_4$), filtered, and concentrated in vacuo to afford the title compound (0.93 g): MS (ESI) m/z 251 (M+1).

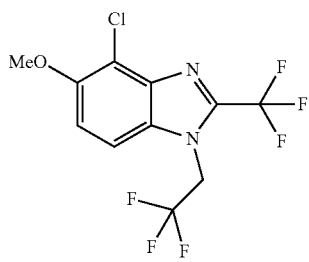 [SMILES: COc1ccc2c(nc(C(F)(F)F)n2CC(F)(F)F)c1Cl]

C. 4-Chloro-5-(methyloxy)-1-(2,2,2-trifluoroethyl)-2-(trifluoromethyl)-1H-benzimidazole Synthesized as described in Example 195D from 4-chloro-5-(methyloxy)-2-(trifluoromethyl)-1H-benzimidazole and trifluoroethyl triflate: MS (ESI) m/z 333 (M+1).

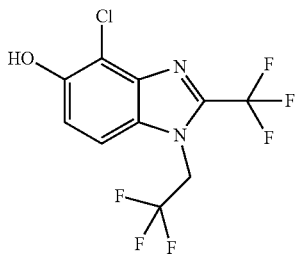 [SMILES: Oc1ccc2c(nc(C(F)(F)F)n2CC(F)(F)F)c1Cl]

D. 4-Chloro-1-(2,2,2-trifluoroethyl)-2-(trifluoromethyl)-1H-benzimidazol-5-ol

A CH$_2$Cl$_2$ (15 mL) solution of 4-chloro-5-(methyloxy)-1-(2,2,2-trifluoroethyl)-2-(trifluoromethyl)-1H-benzimidazole (0.14 g, 0.422 mmol) at rt was treated dropwise with BBr$_3$ (1M CH$_2$Cl$_2$, 1.055 ml, 1.055 mmol) and stirred for 2 h. The mixture was quenched with saturated aqueous NaHCO$_3$, adjusted to a pH of 7, and extracted with CH$_2$Cl$_2$. The combined organic portions were washed combined with brine, dried over Na$_2$SO$_4$, filtered, and concentrated in vacuo. Purification (SiO$_2$; EtOAc/hexanes) afforded the title compound (0.103 g): MS (ESI) m/z 319 (M+1).

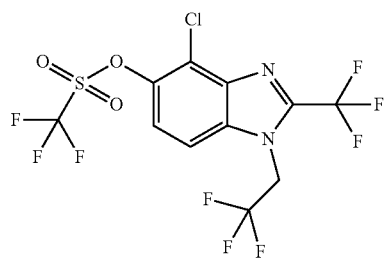 [SMILES: O=S(=O)(Oc1ccc2c(nc(C(F)(F)F)n2CC(F)(F)F)c1Cl)C(F)(F)F]

E. 4-Chloro-1-(2,2,2-trifluoroethyl)-2-(trifluoromethyl)-1H-benzimidazol-5-yl trifluoromethanesulfonate A CH$_2$Cl$_2$ (20 mL) solution of 4-chloro-1-(2,2,2-trifluoroethyl)-2-(trifluoromethyl)-1H-benzimidazol-5-ol (0.103 g, 0.324 mmol) was treated with pyridine (0.038 g, 0.486 mmol). The cooled (0° C.) reaction mixture was then treated with triflic anhydride (0.100 g, 0.356 mmol) and the reaction was allowed to warm to rt. After stirring at rt for 60 min, the solvent was removed in vacuo. The resulting residue was then dissolved in EtOAc, washed with saturated aqueous NaHCO$_3$ and brine, dried over Na$_2$SO$_4$, filtered, and concentrated. Purification (SiO$_2$; EtOAc/hexanes) afforded the title compound (0.053 g): MS (ESI) m/z 451 (M+1).

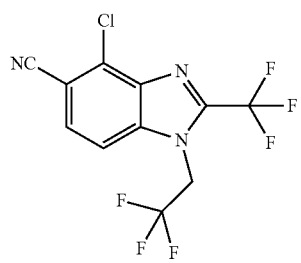 [SMILES: N#Cc1ccc2c(nc(C(F)(F)F)n2CC(F)(F)F)c1Cl]

F. 4-Chloro-1-(2,2,2-trifluoroethyl)-2-(trifluoromethyl)-1H-benzimidazole-5-carbonitrile To 4-chloro-1-(2,2,2-trifluoroethyl)-2-(trifluoromethyl)-1H-benzimidazol-5-yl trifluoromethanesulfonate (0.053 g, 118 mmol) in DMF (3 mL) was added zinc cyanide (0.008 g, 0.071 mmol) and palladium tetrakistriphenylphosphine (0.014 g, 0.012 mmol). The resulting mixture was heated over night under N$_2$ atm at 140° C. The cooled reaction mixture was partitioned between EtOAc and water, washed with brine, dried over Na$_2$SO$_4$, filtered, and concentrated in vacuo. Purification (SiO$_2$, EtOAc/hexanes) afforded the title compound (0.0045 g): MS (ESI) m/z 328 (M+1).

Example 206

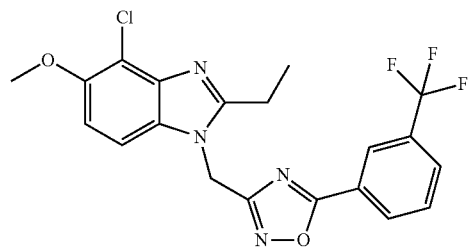 [SMILES: CCc1nc2c(Cl)c(OC)ccc2n1Cc1noc(-c2cccc(C(F)(F)F)c2)n1]

4-Chloro-2-ethyl-5-(methyloxy)-1-({5-[3-(trifluoromethyl)phenyl]-1,2,4-oxadiazol-3-yl}methyl)-1H-benzimidazole

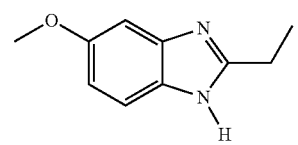

A. 2-Ethyl-5-(methyloxy)-1H-benzimidazole

Synthesized as described in Example 195C from 4-(methyloxy)-1,2-benzenediamine dihydrochloride: MS (APCI) m/z 177 (M+1).

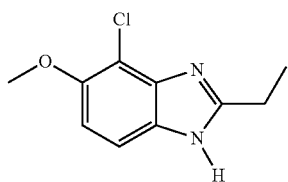

B. 4-Chloro-2-ethyl-5-(methyloxy)-1H-benzimidazole

Synthesized as described in Example 205B from 2-ethyl-5-(methyloxy)-1H-benzimidazole: MS (ES) m/z 211 (M+1).

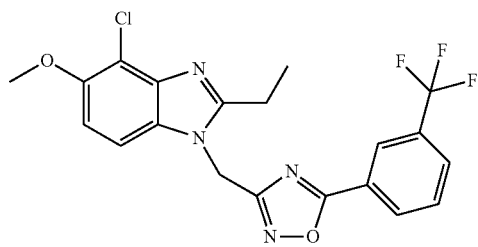 [SMILES: CCc1nc2c(Cl)c(OC)ccc2n1Cc1noc(-c2cccc(C(F)(F)F)c2)n1]

C. 4-Chloro-2-ethyl-5-(methyloxy)-1-({5-[3-(trifluoromethyl)phenyl]-1,2,4-oxadiazol-3-yl}methyl)-1H-benzimidazole Synthesized as described in Example 196 using 4-chloro-2-ethyl-5-(methyloxy)-1H-benzimidazole: MS (ES) m/z 437 (M+1).

Example 207

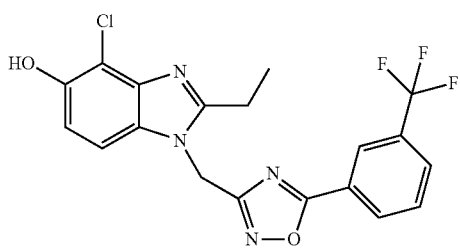 [SMILES: CCc1nc2c(Cl)c(O)ccc2n1Cc1noc(-c2cccc(C(F)(F)F)c2)n1]

4-Chloro-2-ethyl-1-({5-[3-(trifluoromethyl)phenyl]-1,2,4-oxadiazol-3-yl}methyl)-1H-benzimidazol-5-ol Synthesized as described in Example 205D from 4-chloro-2-ethyl-5-(methyloxy)-1-({5-[3-(trifluoromethyl)phenyl]-1,2,4-oxadiazol-3-yl}methyl)-1H-benzimidazole: MS (ES) m/z 423 (M+1).

Example 208

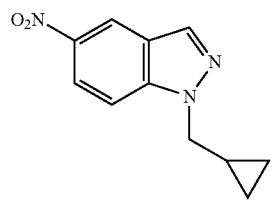 [SMILES: O=[N+]([O-])c1ccc2c(cnn2CC2CC2)c1]

1-(Cyclopropylmethyl)-5-nitro-1H-indazole

Synthesized as described in Example 4 using 5-nitro-1H-indazole and (bromomethyl)cyclopropane to afford a mixture of regioisomers. The following data are for the title regioisomer: $^1$H NMR (400 MHz, CDCl$_3$) δ 8.73 (d, J=2.0 Hz, 1H), 8.26 (dd, J=9.3 and 2 Hz, 1H), 8.20 (s, 1H), 7.48 (d, J=9.3 Hz, 1H), 4.31 (d, J=6.8 Hz, 2H), 1.35 (m, 1H), 0.62 (m, 2H), 0.44 (m, 2H); MS (ES) m/z 218 (M+1).

Example 209

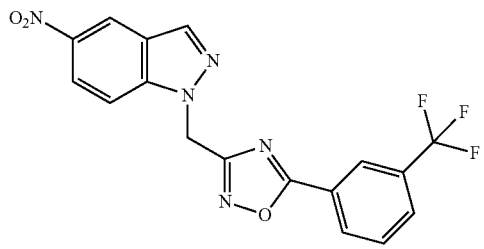 [SMILES: O=[N+]([O-])c1ccc2c(cnn2Cc2noc(-c3cccc(C(F)(F)F)c3)n2)c1]

5-Nitro-1-({5-[3-(trifluoromethyl)phenyl]-1,2,4-oxadiazol-3-yl}methyl)-1H-indazole Synthesized as described in Example 4 using 5-nitro-1H-indazole and 5-[3(trifluoromethyl)phenyl]-3-(chloromethyl)-1,2,4-oxadiazole to afford a mixture of regioisomers.

The following data are for the title regioisomer: $^1$H NMR (400 MHz, CDCl$_3$) δ 8.75 (d, J=1.7 Hz, 1H), 8.34 (m, 2H), 8.27 (m, 2H), 7.84 (d, J=7.8 Hz, 1H), 7.65 (m, 2H), 5.83 (s, 2H); MS (ES) m/z 389 (M$^+$).

Example 210

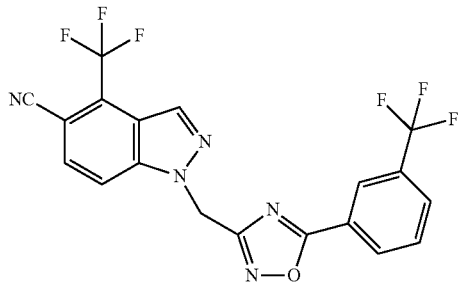 [SMILES: N#Cc1ccc2c(cnn2Cc2noc(-c3cccc(C(F)(F)F)c3)n2)c1C(F)(F)F]

4-(Trifluoromethyl)-1-({5-[3-(trifluoromethyl)phenyl]-1,2,4-oxadiazol-3-yl}methyl)-1H-indazole-5-carbonitrile

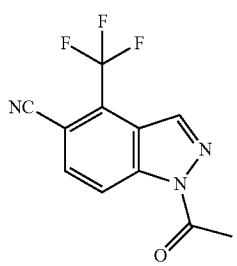 [SMILES: CC(=O)n1ncc2c(C(F)(F)F)c(C#N)ccc21]

A. 1-Acetyl-4-(trifluoromethyl)-1H-indazole-5-carbonitrile

4-Amino-3-methyl-2-(trifluoromethyl)benzonitrile (0.256 g, 1.28 mmol) prepared according to methods known in the art (see, for example, International Patent Application No. WO03062241 published Jul. 31, 2003) and dissolved in Ac$_2$O (5 mL) and spatula tip of DMAP was added. Next, the mixture was heated to ca. 90° C. for 7 h. The crude mixture was concentrated under vacuum and the resulting residue was dissolved in CH$_3$CN (5 mL). Next, KOAc (0.100 g, 1.02 mmol), 18-crown-6 (0.020 g, cat.) and n-amylnitrite (0.500 µL, 52.8 mmol) were added. After 6 h at 50° C., more KOAc (0.100 g, 1 equiv), 18-crown-6 (0.020 g, cat.) and n-amylnitrite (0.50 µL, 37.6 mmol) were added. Heating at 50° C. was continued for another 20 h. The cooled reaction mixture was partitioned between CHCl$_3$ (20 mL) and extracted with 2 M aqueous Na$_2$CO$_3$ (20 mL). The organic portion was dried (Na$_2$SO$_4$), filtered, and concentrated to an orange oil that was used for the next reaction without further purification.

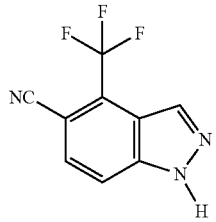 [SMILES: N#Cc1ccc2[nH]ncc2c1C(F)(F)F]

B. 4-(Trifluoromethyl)-1H-indazole-5-carbonitrile

The crude 1-acetyl-4-(trifluoromethyl)-1H-indazole-5-carbonitrile from Example 210A (ca. 1.28 mmol) was dissolved in EtOH (5 mL) and conc. HCl (5 mL). The resulting mixture was heated to 70° C. for 20 min. The cooled reaction's pH was adjusted to ca. 8 with 6 N NaOH. EtOAc (20 mL) was added and the isolated organic portion was dried (Na$_2$SO$_4$), filtered and concentrated. Purification by semi-preparative HPLC afforded the title compound as a pale yellow solid (0.076 g, 28% overall): $^1$H NMR (DMSO-d$_6$) δ 14.13 (s, 1H), 8.41 (s, 1H), 8.06 (d, J=6.0 Hz, 1H), 7.93 (d, J=6.0 Hz, 1H).

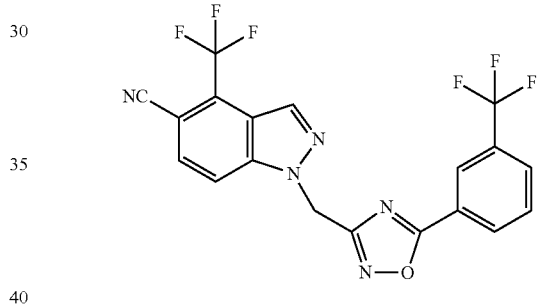

C. 4-(Trifluoromethyl)-1-({5-[3-(trifluoromethyl)phenyl]-1,2,4-oxadiazol-3-yl}methyl)-1H-indazole-5-carbonitrile Prepared in a manner similar to Example 100 using 4-(trifluoromethyl)-1H-indazole-5-carbonitrile: $^1$H NMR (DMSO-d$_6$) δ 8.44-8.41 (m, 1H), 8.37-8.31 (m, 3H), 8.05-8.00 (m, 2H), 7.88-7.84 (m, 1H), 6.04 (s, 2H).

Example 211

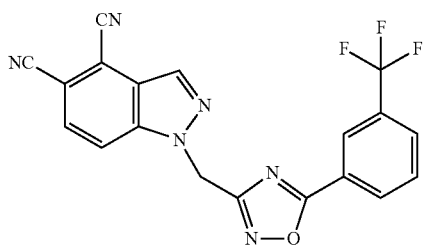 [SMILES: N#Cc1ccc2c(cnn2Cc2noc(-c3cccc(C(F)(F)F)c3)n2)c1C#N]

1-({5-[3-(Trifluoromethyl)phenyl]-1,2,4-oxadiazol-3-yl}methyl)-1H-indazole-4,5-dicarbonitrile

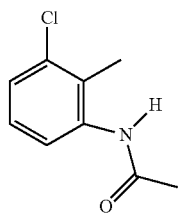

A. N-(3-Chloro-2-methyl phenyl)acetamide

A solution of 3-chloro-2-methylaniline (9.0 g, 63.56 mmol) in EtOH (75 mL) was treated with acetic anhydride (7.2 mL, 76.31 mmol) and the resulting mixture was stirred at rt for 3 h. Concentration was followed by crystallization from hexanes/EtOAc (1:3) to afford 11.2 g of the title compound: $^1$H NMR (300 MHz, DMSO-d6) δ 9.52 (s, 1H), 7.30-7.23 (m, 2H), 7.17-7.13 (m, 1H), 2.18 (s, 3H), 2.06 (s, 3H).

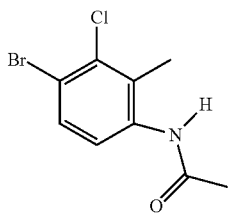

B. N-(4-Bromo-3-chloro-2-methylphenyl)acetamide

A suspension of N-(3-chloro-2-methylphenyl)acetamide (11.12 g, 60.63 mmol) in acetic acid (80 mL) was cooled to ca. 10° C. and then treated with bromine (9.28 mL, 181.11 mmol). The resulting mixture was stirred at rt for 2 h. The cooled solution was then poured into water (100 mL). The resulting solid was collected via filtration and rinsed with water. Thorough drying afforded 15.83 g of a pale yellow solid: MS (APCI) m/z 264 (M+2 isotope).

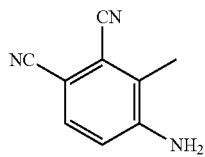

C. 4-Amino-3-methyl-1,2-benzenedicarbonitrile

A solution of N-(4-bromo-3-chloro-2-methylphenyl)acetamide (7.83 g, 29.83 mmol) in DMF (80 mL) was treated with copper cyanide (2.67 g, 29.81 mmol) and the resulting mixture was heated to 150° C. for 4 h. The cooled solution was then poured into water (100 mL). The resulting solid was collected via filtration. The dried solid was then treated with conc. HCl in ethanol (1:1, 80 mL) and heated at reflux for 30 min. The reaction mixture was then concentrated and partitioned between EtOAc and basic water (pH adjusted to 8-9 with NaHCO$_3$). The aqueous portion was extracted with EtOAc (2×50 mL). The combined organics were dried over MgSO$_4$, filtered, and concentrated. Purification (SiO$_2$, hexanes/EtOAc) afforded the biscyano product as a byproduct of the attempt to cyanate singly at the 4-position: $^1$H NMR (300 MHz, CDCl$_3$) δ 7.24 (d, J=6.0 Hz, 1H), 6.47 (d, J=9.0 Hz, 1H), 3.69 (bs, 2H), 2.28 (s, 3H).

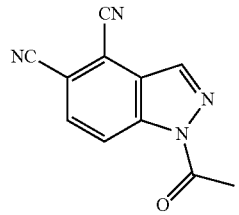 [SMILES: CC(=O)n1ncc2c(C#N)c(C#N)ccc21]

D. 1-Acetyl-1H-indazole-4,5-dicarbonitrile

Prepared in a manner similar to Example 210A using 4-amino-3-methyl-1,2-benzenedicarbonitrile: MS (ES) m/z 211 (M+1).

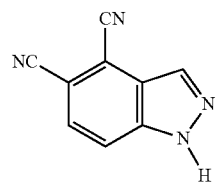 [SMILES: N#Cc1ccc2[nH]ncc2c1C#N]

E. 1H-Indazole-4,5-dicarbonitrile

Prepared in a manner similar to Example 210B using 1-acetyl-1H-indazole-4,5-dicarbonitrile: MS (ES) m/z 169 (M+1).

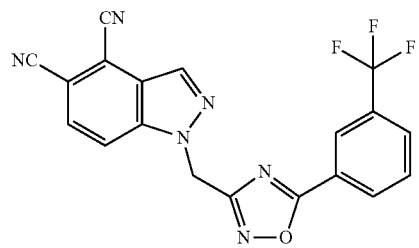 [SMILES: N#Cc1ccc2c(cnn2Cc2noc(-c3cccc(C(F)(F)F)c3)n2)c1C#N]

F. 1-({5-[3-(Trifluoromethyl)phenyl]-1,2,4-oxadiazol-3-yl}methyl)-1H-indazole-4,5-dicarbonitrile Prepared in a manner similar to Example 100 using 1H-indazole-4,5-dicarbonitrile: MS (APCI) m/z 395 (M+1).

Example 212

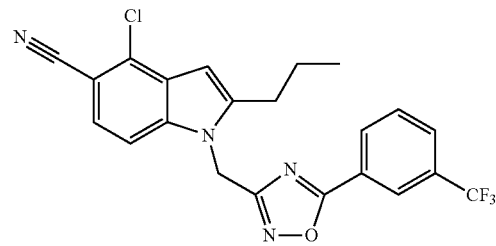 [SMILES: CCCc1cc2c(Cl)c(C#N)ccc2n1Cc1noc(-c2cccc(C(F)(F)F)c2)n1]

4-Chloro-2-propyl-1-({5-[3-(trifluoromethyl)phenyl]-1,2,4-oxadiazol-3-yl}methyl)-1H-indole-5-carbonitrile

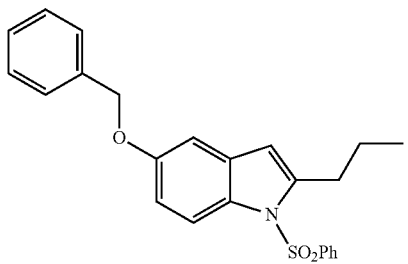

A. 5-[(Phenylmethyl)oxy]-1-(phenylsulfonyl)-2-propyl-1H-indole

To a solution of 5-[(phenylmethyl)oxy]-1-(phenylsulfonyl)-1H-indole (1.6 g, 4.4 mmol, synthesized as described in Example 22A) in THF (10 mL), under $N_2$, at −78° C., was added n-BuLi (2.5 M solution in hexanes, 2.15 mL, 5.37 mmol) dropwise. After stirring at −78° C. for 30 min, propyl iodide (1.1 g, 6.6 mmol) was added. After 30 min, the −78° C. bath was removed. The solution was warmed to rt. 5% HCl (10 mL) was then added and the mixture was partitioned between EtOAc and water. The organic phase was washed with water and sat'd brine, dried ($Na_2SO_4$) and concentrated in vacuo. The residue was purified by flash chromatography (20-70% EtOAc-hexanes gradient) to afford the title compound (0.79 g, 71% yield): MS (ES) m/z 406 (M+1).

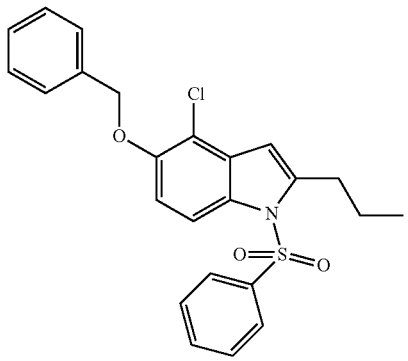 [SMILES: CCCc1cc2c(Cl)c(OCc3ccccc3)ccc2n1S(=O)(=O)c1ccccc1]

B. 4-Chloro-5-[(phenylmethyl)oxy]-1-(phenylsulfonyl)-2-propyl-1H-indole

Synthesized as described in Example 22C from 5-[(phenylmethyl)oxy]-1-(phenylsulfonyl)-2-propyl-1H-indole and sulfuryl chloride: MS (ES) m/z 441 (M+1).

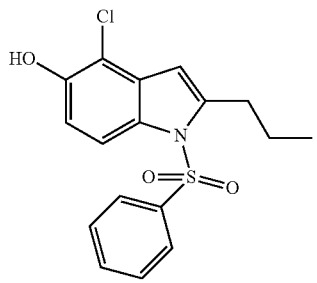

C. 4-Chloro-1-(phenylsulfonyl)-2-propyl-1H-indol-5-ol

Synthesized as described in Example 22E from 4-chloro-5-[(phenylmethyl)oxy]-1-(phenylsulfonyl)-2-propyl-1H-indole: MS (ES) m/z 351 (M+1).

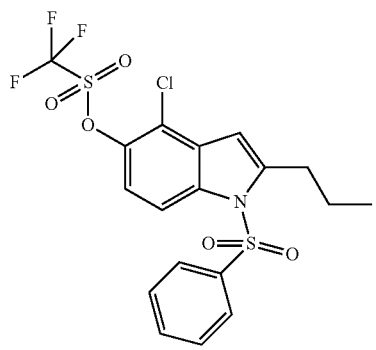 [SMILES: CCCc1cc2c(Cl)c(OS(=O)(=O)C(F)(F)F)ccc2n1S(=O)(=O)c1ccccc1]

D. 4-Chloro-1-(phenylsulfonyl)-2-propyl-1H-indol-5-yl trifluoromethanesulfonate Synthesized as described in Example 22F from 4-chloro-1-(phenylsulfonyl)-2-propyl-1H-indol-5-ol: MS (ES) m/z 482 (M+1).

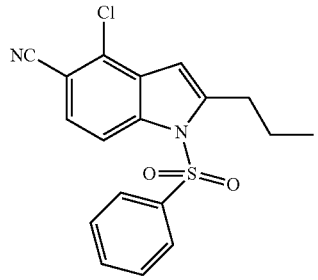 [SMILES: CCCc1cc2c(Cl)c(C#N)ccc2n1S(=O)(=O)c1ccccc1]

E. 4-Chloro-1-(phenylsulfonyl)-2-propyl-1H-indole-5-carbonitrile

Synthesized as described in Example 22G from 4-chloro-1-(phenylsulfonyl)-2-propyl-1H-indol-5-yl trifluoromethanesulfonate: MS (ES) m/z 359 (M+1).

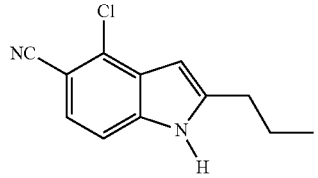

F. 4-Chloro-2-propyl-1H-indole-5-carbonitrile

Synthesized as described in Example 22H from 4-chloro-1-(phenylsulfonyl)-2-propyl-1H-indole-5-carbonitrile: MS (ES) m/z 219 (M+1).

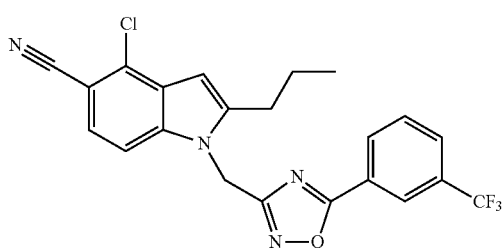 [SMILES: CCCc1cc2c(Cl)c(C#N)ccc2n1Cc1noc(-c2cccc(C(F)(F)F)c2)n1]

G. 4-Chloro-2-propyl-1-({5-[3-(trifluoromethyl)phenyl]-1,2,4-oxadiazol-3-yl}methyl)-1H-indole-5-carbonitrile Synthesized as described in Example 4 from 4-chloro-2-propyl-1H-indole-5-carbonitrile and 3-(chloromethyl)-5-[3-(trifluoromethyl)phenyl]-1,2,4-oxadiazole: $^1$H NMR (400 MHz, DMSO-$d_6$) δ 8.30 (d, J=7.8 Hz, 1H), 8.24 (s, 1H), 8.07 (d, J=7.6 Hz, 1H), 7.96 (d, J=1.0 Hz, 1H), 7.89-7.80 (m, 1H), 7.77 (d, J=8.7 Hz, 1H), 7.58 (dd, J=8.5, 1.5 Hz, 1H), 5.84 (s, 2H), 2.91 (t, J=7.6 Hz, 2H), 1.76-1.47 (m, 2H), 0.92 (t, J=7.3 Hz, 3H); MS (ES) m/z 445 (M+1).

Example 213

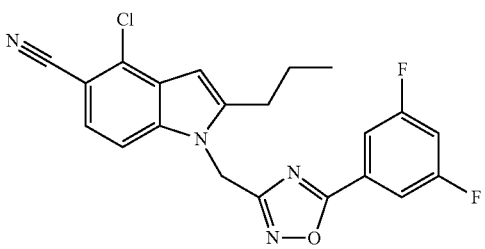 [SMILES: CCCc1cc2c(Cl)c(C#N)ccc2n1Cc1noc(-c2cc(F)cc(F)c2)n1]

4-Chloro-1-{[5-(3,5-difluorophenyl)-1,2,4-oxadiazol-3-yl]methyl}-2-propyl-1H-indole-5-carbonitrile Synthesized as described in Example 4 from 4-chloro-2-propyl-1H-indole-5-carbonitrile and 3-(chloromethyl)-5-(3,5-difluorophenyl)-1,2,4-oxadiazole: $^1$H NMR (400 MHz, DMSO-$d_6$) δ 7.95 (s, 1H), 7.80-7.61 (m, 4H), 7.57 (d, J=8.5 Hz, 1H), 5.83 (s, 2H), 3.05-2.75 (m, 2H), 1.70-1.41 (m, 2H), 0.92 (t, J=7.3 Hz, 3H); MS (ES) m/z 413 (M+1).

Example 214

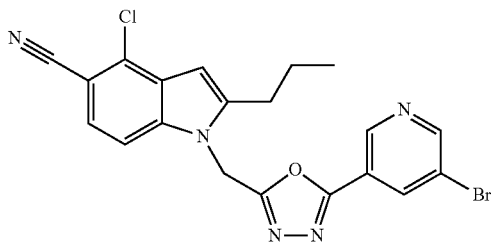 [SMILES: CCCc1cc2c(Cl)c(C#N)ccc2n1Cc1nnc(-c2cncc(Br)c2)o1]

1-{[5-(5-Bromo-3-pyridinyl)-1,3,4-oxadiazol-2-yl]methyl}-4-chloro-2-propyl-1H-indole-5-carbonitrile Synthesized as described in Example 4 from 4-chloro-2-propyl-1H-indole-5-carbonitrile and 3-bromo-5-[5-(chloromethyl)-1,3,4-oxadiazol-2-yl]pyridine: $^1$H NMR (400 MHz, DMSO-$d_6$) δ 9.03 (d, J=1.3 Hz, 1H), 8.94 (d, J=2.0 Hz, 1H), 8.46 (s, 1H), 7.97 (s, 1H), 7.81 (d, J=8.5 Hz, 1H), 7.61 (d, J=8.5 Hz, 1H), 5.96 (s, 2H), 2.95-2.87 (m, 2H), 1.75-1.48 (m, 2H), 0.93 (t, J=7.3 Hz, 3H); MS (ES) m/z 457 (M+1).

Example 215

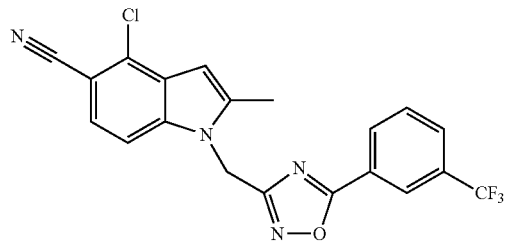 [SMILES: Cc1cc2c(Cl)c(C#N)ccc2n1Cc1noc(-c2cccc(C(F)(F)F)c2)n1]

4-Chloro-2-methyl-1-({5-[3-(trifluoromethyl)phenyl]-1,2,4-oxadiazol-3-yl}methyl)-1H-indole-5-carbonitrile

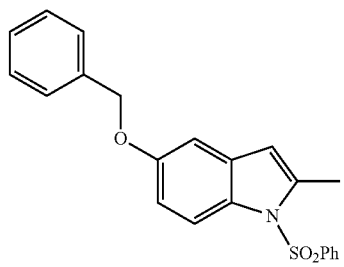

A. 2-Methyl-5-[(phenylmethyl)oxy]-1-(phenylsulfonyl)-1H-indole

To a solution of 5-[(phenylmethyl)oxy]-1-(phenylsulfonyl)-1H-indole (1.6 g, 4.4 mmol, synthesized as described in Example 22A) in THF (10 mL), under $N_2$, at −78° C., was added n-BuLi (2.5 M solution in hexanes, 2.15 mL, 5.37 mmol) dropwise. After stirring at −78° C. for 30 min, methyl iodide (0.94 g, 6.6 mmol) was added. After 30 min, the −78° C. bath was removed. The solution was warmed to rt. 5% HCl (10 mL) was then added and the mixture was partitioned between EtOAc and water. The organic phase was washed with water and sat'd brine, dried ($Na_2SO_4$) and concentrated in vacuo. The residue was purified by flash chromatography (20-70% EtOAc-hexanes gradient) to afford the title compound (0.8 g, 77% yield): MS (ES) m/z 478 (M+1).

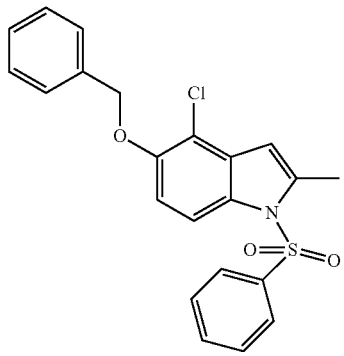 [SMILES: Cc1cc2c(Cl)c(OCc3ccccc3)ccc2n1S(=O)(=O)c1ccccc1]

B. 4-Chloro-2-methyl-5-[(phenylmethyl)oxy]-1-(phenylsulfonyl)-1H-indole

Synthesized as described in Example 22C from 5-[(phenylmethyl)oxy]-1-(phenylsulfonyl)-2-methyl-1H-indole: MS (ES) m/z 412 (M+1).

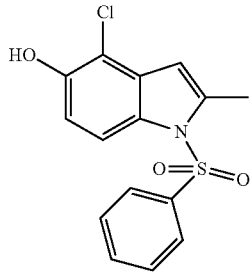 [SMILES: Cc1cc2c(Cl)c(O)ccc2n1S(=O)(=O)c1ccccc1]

C. 4-Chloro-2-methyl-1-(phenylsulfonyl)-1H-indol-5-ol

Synthesized as described in Example 22E from 4-chloro-5-[(phenylmethyl)oxy]-1-(phenylsulfonyl)-2-methyl-1H-indole: MS (ES) m/z 322 (M+1).

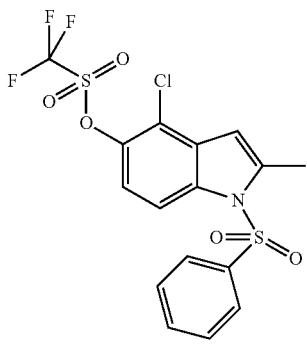 [SMILES: Cc1cc2c(Cl)c(OS(=O)(=O)C(F)(F)F)ccc2n1S(=O)(=O)c1ccccc1]

D. 4-Chloro-2-methyl-1-(phenylsulfonyl)-1H-indol-5-yl trifluoromethanesulfonate Synthesized as described in Example 22F from 4-chloro-1-(phenylsulfonyl)-2-methyl-1H-indol-5-ol: MS (ES) m/z 454 (M+1).

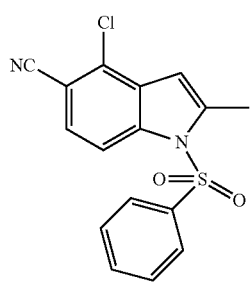 [SMILES: Cc1cc2c(Cl)c(C#N)ccc2n1S(=O)(=O)c1ccccc1]

E. 4-Chloro-2-methyl-1-(phenylsulfonyl)-1H-indole-5-carbonitrile

Synthesized as described in Example 22G from 4-chloro-1-(phenylsulfonyl)-2-methyl-1H-indol-5-yl trifluoromethanesulfonate: MS (ES) m/z 331 (M+1).

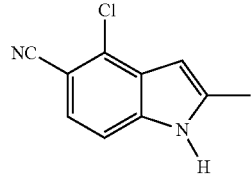

F. 4-Chloro-2-methyl-1H-indole-5-carbonitrile

Synthesized as described in Example 22H from 4-chloro-1-(phenylsulfonyl)-2-methyl1-1H-indole-5-carbonitrile: MS (ES) m/z 191 (M+1).

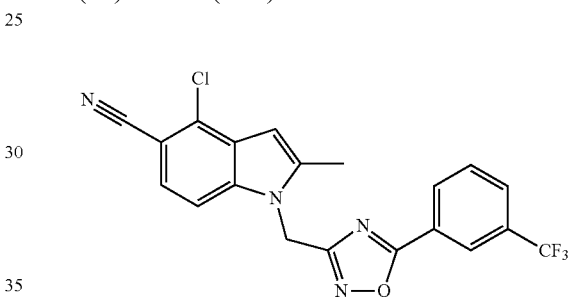

G. 4-Chloro-2-methyl-1-({5-[3-(trifluoromethyl)phenyl]-1,2,4-oxadiazol-3-yl}methyl)-1H-indole-5-carbonitrile Synthesized as described in Example 4 from 4-chloro-2-methyl-1H-indole-5-carbonitrile and 3-(chloromethyl)-5-[3-(trifluoromethyl)phenyl]-1,2,4-oxadiazole: $^1$H NMR (400 MHz, DMSO-$d_6$) δ 8.31 (d, J=7.9 Hz, 1H), 8.24 (s, 1H), 8.06 (d, J=7.6 Hz, 1H), 7.94 (d, J=1.1 Hz, 1H), 7.87-7.79 (m, 2H), 7.59 (dd, J=8.5, 1.5 Hz, 1H), 5.85 (s, 2H), 2.47 (s, 3 H); MS (ES) m/z 417 (M+1).

Example 216

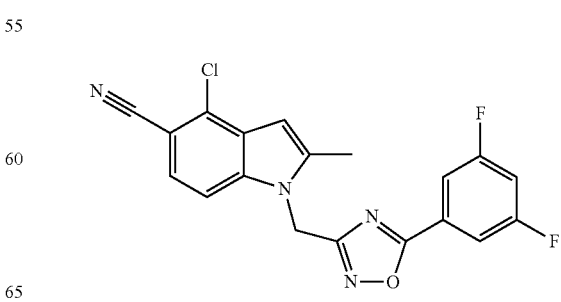

4-Chloro-1-{[5-(3,5-difluorophenyl)-1,2,4-oxadiazol-3-yl]methyl}-2-methyl-1H-indole-5-carbonitrile Synthesized as described in Example 4 from 4-chloro-2-methyl-1H-indole-5-carbonitrile and 3-(chloromethyl)-5-(3,5-difluorophenyl)-1,2,4-oxadiazole: $^1$H NMR (400 MHz, DMSO-d$_6$) δ 7.94 (d, J=1.1 Hz, 1H), 7.81 (d, J=8.7 Hz, 1H), 7.75-7.71 (m, 2H), 7.69-7.63 (m, 1H), 7.58 (dd, J=8.7, 1.5 Hz, 1H), 5.83 (s, 2H), 2.47 (s, 3H); MS (ES) m/z 385 (M+1).

Example 217

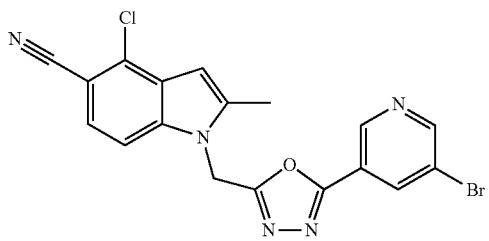 [SMILES: Cc1cc2c(Cl)c(C#N)ccc2n1Cc1nnc(-c2cncc(Br)c2)o1]

1-{[5-(5-Bromo-3-pyridinyl)-1,3,4-oxadiazol-2-yl]methyl}-4-chloro-2-methyl-1H-indole-5-carbonitrile Synthesized as described in Example 4 from 4-chloro-2-methyl-1H-indole-5-carbonitrile and 3-bromo-5-[5-(chloromethyl)-1,3,4-oxadiazol-2-yl]pyridine: $^1$H NMR (400 MHz, DMSO-d$_6$) δ 9.05 (s, 1H), 8.94 (s, 1H), 8.48 (s, 1H), 7.96 (s, 1H), 7.85 (d, J=8.5 Hz, 1H), 7.63 (d, J=8.5 Hz, 1H), 5.96 (s, 2H), 2.47 (s, 3H); MS (ES) m/z 429 (M+1).

Example 218

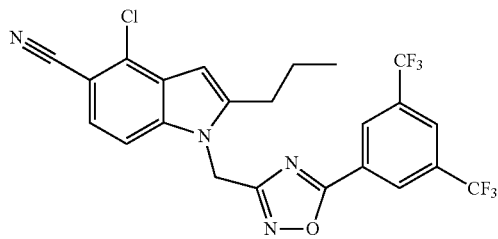 [SMILES: CCCc1cc2c(Cl)c(C#N)ccc2n1Cc1noc(-c2cc(C(F)(F)F)cc(C(F)(F)F)c2)n1]

1-({5-[3,5-bis(Trifluoromethyl)phenyl]-1,2,4-oxadiazol-3-yl}methyl)-4-chloro-2-propyl-1H-indole-5-carbonitrile Synthesized as described in Example 4 from 4-chloro-2-propyl-1H-indole-5-carbonitrile and 5-[3,5-bis(trifluoromethyl)phenyl]-3-(chloromethyl)-1,2,4-oxadiazole: $^1$H NMR (400 MHz, DMSO-d$_6$) δ 8.53 (s, 2H), 8.50 (s, 1H), 7.96 (s, 1H), 7.77 (d, J=8.7 Hz, 1H), 7.59 (d, J=8.7 Hz, 1H), 5.87 (s, 2H), 2.97-2.82 (m, 2H), 1.70-1.56 (m, 2H), 0.97-0.89 (m, 3H); MS (ES) m/z 513 (M+1).

Example 219

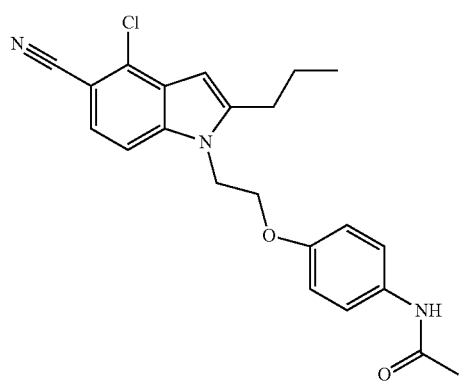 [SMILES: CCCc1cc2c(Cl)c(C#N)ccc2n1CCOc1ccc(NC(C)=O)cc1]

N-(4-{[2-(4-Chloro-5-cyano-2-propyl-1H-indol-1-yl)ethyl]oxy}phenyl)acetamide

Synthesized as described in Example 4 from 4-chloro-2-propyl-1H-indole-5-carbonitrile and N-{4-[(2-bromoethyl)oxy]phenyl}acetamide: $^1$H NMR (400 MHz, DMSO-d$_6$) δ 9.72 (s, 1H), 7.90 (s, 1H), 7.80 (d, J=8.5 Hz, 1H), 7.54 (d, J=8.5 Hz, 1H), 7.39 (d, J=9.0 Hz, 2H), 6.71 (d, J=9.0 Hz, 2H), 4.63 (t, J=4.9 Hz, 2H), 4.18 (t, J=4.9 Hz, 2H), 2.82 (t, J=4.9 Hz, 2H), 1.94 (s, 3H), 1.73-1.49 (m, 2H), 0.94 (t, J=4.9 Hz, 3H); MS (ES) m/z 396 (M+1).

Example 220

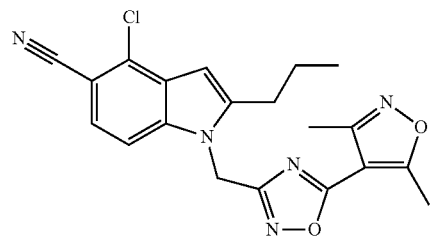 [SMILES: CCCc1cc2c(Cl)c(C#N)ccc2n1Cc1noc(-c2c(C)noc2C)n1]

4-Chloro-1-{[5-(3,5-dimethyl-4-isoxazolyl)-1,2,4-oxadiazol-3-yl]methyl}-2-propyl-1H-indole-5-carbonitrile Synthesized as described in Example 4 from 4-chloro-2-propyl-1H-indole-5-carbonitrile and 3-(chloromethyl)-5-(3,5-dimethyl-4-isoxazolyl)-1,2,4-oxadiazole $^1$H NMR (400 MHz, DMSO-d$_6$) δ 7.94 (s, 1H), 7.75 (d, J=8.5 Hz, 1H), 7.57 (d, J=8.5 Hz, 1H), 5.80 (s, 2 H), 2.91 (t, J=4.9 Hz, 2H), 2.66

(s, 3H), 2.38 (s, 3H), 1.71-1.58 (m, 2H), 0.92 (t, J=7.3 Hz, 3H); MS (ES) m/z 396 (M+1).

Example 221

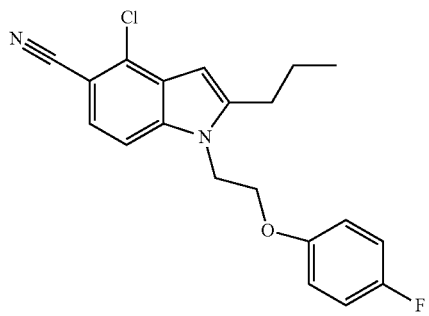 [SMILES: CCCc1cc2c(Cl)c(C#N)ccc2n1CCOc1ccc(F)cc1]

4-Chloro-1-{2-[(4-fluorophenyl)oxy]ethyl}-2-propyl-1H-indole-5-carbonitrile

Synthesized as described in Example 4 from 4-chloro-2-propyl-1H-indole-5-carbonitrile and 1-[(2-bromoethyl)oxy]-4-fluorobenzene: $^1$H NMR (400 MHz, DMSO-d$_6$) δ 7.89 (s, 1 H), 7.80 (d, J=8.7 Hz, 1H), 7.54 (d, J=8.5 Hz, 1H), −7.11-6.97 (m, 2H), 6.83-6.71 (m, 2H), 4.64 (t, 2H), 4.20 (t, 2H), 2.88 (t, 2H), 1.70-1.58 (m, 2H), 0.94 (t, J=7.3 Hz, 3H); MS (ES) m/z 357 (M+1).

Example 222

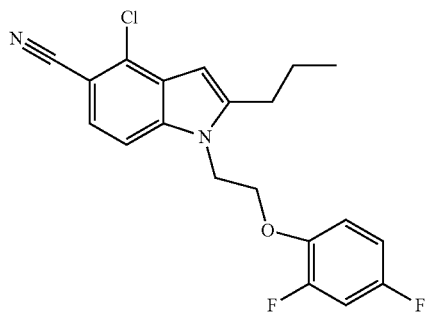 [SMILES: CCCc1cc2c(Cl)c(C#N)ccc2n1CCOc1ccc(F)cc1F]

4-Chloro-1-{2-[(2,4-difluorophenyl)oxy]ethyl}-2-propyl-1H-indole-5-carbonitrile

Synthesized as described in Example 4 from 4-chloro-2-propyl-1H-indole-5-carbonitrile and 1-[(2-bromoethyl)oxy]-2,4-difluorobenzene: $^1$H NMR (400 MHz, DMSO-d$_6$) δ 7.89 (s, 1H), 7.79 (d, J=8.7 Hz, 1H), 7.51 (d, J=8.7 Hz, 1H), 7.25-7.14 (m, 1H), 7.08-6.99 (m, 1H), 6.96-6.85 (m, 1H), 4.67 (t, J=4.9 Hz, 2H), 4.28 (t, J=4.9 Hz, 2H), 2.89 (t, J=7.3 Hz, 2H), 1.73-1.57 (m, 2H), 0.93 (t, J=7.3 Hz, 3H); MS (ES) m/z 375 (M+1).

Example 223

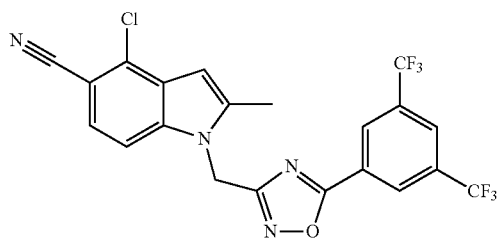 [SMILES: Cc1cc2c(Cl)c(C#N)ccc2n1Cc1noc(-c2cc(C(F)(F)F)cc(C(F)(F)F)c2)n1]

1-({5-[3,5-bis(Trifluoromethyl)phenyl]-1,2,4-oxadiazol-3-yl}methyl)-4-chloro-2-methyl-1H-indole-5-carbonitrile Synthesized as described in Example 4 from 4-chloro-2-methyl-1H-indole-5-carbonitrile and 5-[3,5-bis(trifluoromethyl)phenyl]-3-(chloromethyl)-1,2,4-oxadiazole: $^1$H NMR (400 MHz, DMSO-d$_6$) δ 8.54 (s, 2H), 8.49 (s, 1H), 7.94 (s, 1H), 7.83 (d, J=8.5 Hz, 1H), 7.60 (d, J=8.7 Hz, 1H), 5.87 (s, 2H), 2.51 (s, 3H); MS (ES) m/z 485 (M+1).

Example 224

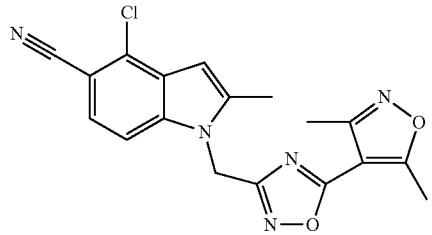 [SMILES: Cc1noc(C)c1-c1nc(Cn2c(C)cc3c(Cl)c(C#N)ccc32)no1]

4-Chloro-1-{[5-(3,5-dimethyl-4-isoxazolyl)-1,2,4-oxadiazol-3-yl]methyl}-2-methyl-1H-indole-5-carbonitrile Synthesized as described in Example 4 from 4-chloro-2-methyl-1H-indole-5-carbonitrile and 3-(chloromethyl)-5-(3,5-dimethyl-4-isoxazolyl)-1,2,4-oxadiazole: $^1$H NMR (400 MHz, DMSO-d$_6$) δ 7.93 (s, 1H), 7.81 (d, J=8.5 Hz, 1H), 7.58 (d, J=8.5 Hz, 1H), 5.81 (s, 2H), 3.30 (s, 3H), 2.66 (s, 3H), 2.39 (s, 3H); MS (ES) m/z 368 (M+1).

Example 225

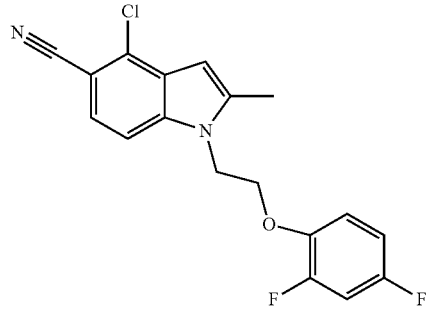 [SMILES: Cc1cc2c(Cl)c(C#N)ccc2n1CCOc1ccc(F)cc1F]

4-Chloro-1-{2-[(2,4-difluorophenyl)oxy]ethyl}-2-methyl-1H-indole-5-carbonitrile

Synthesized as described in Example 4 from 4-chloro-2-methyl-1H-indole-5-carbonitrile and 1-[(2-bromoethyl)oxy]-2,4-difluorobenzene: $^1$H NMR (400 MHz, DMSO-d$_6$) δ 7.88 (s, 1H), 7.76 (d, J=8.7 Hz, 1H), 7.50 (d, J=8.7 Hz, 1H), 7.26-7.15 (m, 1H), 7.10-7.00 (m, 1H), 6.92-6.88 (m, 1H), 4.67 (t, J=5.0 Hz, 2H), 4.30 (t, J=5.0 Hz, 2H), 3.30 (s, 3 H); MS (ES) m/z 347 (M+1).

Example 226

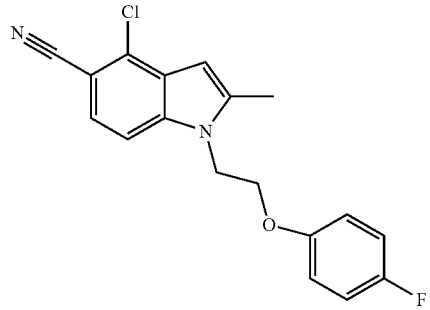 [SMILES: Cc1cc2c(Cl)c(C#N)ccc2n1CCOc1ccc(F)cc1]

193

4-Chloro-1-{2-[(4-fluorophenyl)oxy]ethyl}-2-methyl-1H-indole-5-carbonitrile

Synthesized as described in Example 4 from 4-chloro-2-methyl-1H-indole-5-carbonitrile and 1-[(2-bromoethyl)oxy]-4-fluorobenzene: $^1$H NMR (400 MHz, DMSO-$d_6$) δ 7.88 (d, J=1.1 Hz, 1H), 7.78 (d, J=8.7 Hz, 1H), 7.53 (dd, J=8.5, 1.5 Hz, 1H), 7.10-6.98 (m, 2H), 6.84-6.76 (m, 2H), 4.63 (t, J=5.0 Hz, 2H), 4.22 (t, J=5.0 Hz, 2H), 2.49 (s, 3H); MS (ES) m/z 329 (M+1).

Example 227

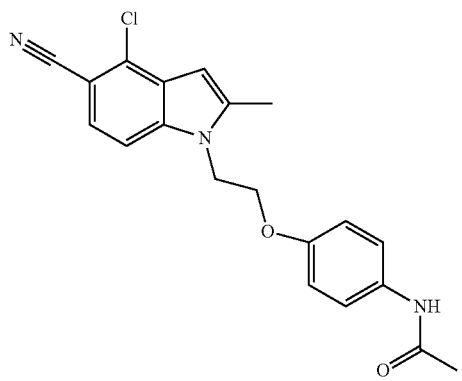 [SMILES: CC(=O)Nc1ccc(OCCn2c(C)cc3c(Cl)c(C#N)ccc32)cc1]

N-(4-{[2-(4-Chloro-5-cyano-2-methyl-1H-indol-1-yl)ethyl]oxy}phenyl)acetamide

Synthesized as described in Example 4 from 4-chloro-2-methyl-1H-indole-5-carbonitrile and N-{4-[(2-bromoethyl)oxy]phenyl}acetamide: $^1$H NMR (400 MHz, DMSO-$d_6$) δ 9.72 (s, 1H), 7.89 (d, J=1.1 Hz, 1H), 7.77 (d, J=8.5 Hz, 1H), 7.53 (d, J=8.5 Hz, 1H), 7.39 (d, J=8.9 Hz, 2H), 6.73 (d, J=8.9 Hz, 2H), 4.62 (t, 2H), 4.19 (t, 2H), 2.48 (s, 3H), 1.95 (s, 3H); MS (ES) m/z 368 (M+1).

Example 228

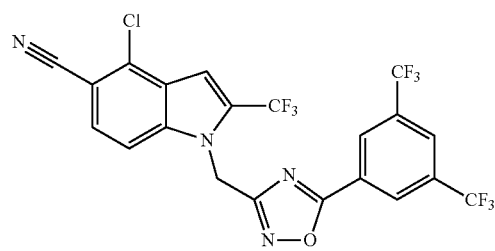 [SMILES: N#Cc1ccc2c(cc(C(F)(F)F)n2Cc2noc(-c3cc(C(F)(F)F)cc(C(F)(F)F)c3)n2)c1Cl]

194

1-({5-[3,5-bis(Trifluoromethyl)phenyl]-1,2,4-oxadiazol-3-yl}methyl)-4-chloro-2-(trifluoromethyl)-1H-indole-5-carbonitrile

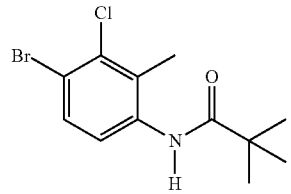 [SMILES: Cc1c(NC(=O)C(C)(C)C)ccc(Br)c1Cl]

A. N-(4-Bromo-3-chloro-2-methylphenyl)-2,2-dimethylpropanamide

N-(3-Chloro-2-methylphenyl)-2,2-dimethylpropanamide (0.5 g, 2.2 mmol) and bromine (1.4 g, 8.8 mmol) were combined in AcOH (25 mL) at rt for 2 h. The residue resulting from concentration was purified by flash chromatography (20-60% EtOAc-hexanes gradient) to afford the title compound: MS (ES) m/z 305 (M+1).

B. 4-Chloro-2-(trifluoromethyl)-1H-indole-5-carbonitrile

Synthesized as described for Example 191B-H starting from N-(4-bromo-3-chloro-2-methylphenyl)-2,2-dimethylpropanamide (Example 228A): MS (ES) m/z 245 (M+1).

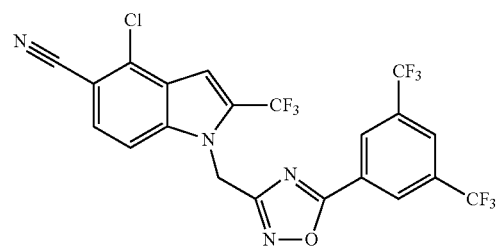 [SMILES: N#Cc1ccc2c(cc(C(F)(F)F)n2Cc2noc(-c3cc(C(F)(F)F)cc(C(F)(F)F)c3)n2)c1Cl]

C. 1-({5-[3,5-bis(Trifluoromethyl)phenyl]-1,2,4-oxadiazol-3-yl}methyl)-4-chloro-2-(trifluoromethyl)-1H-indole-5-carbonitrile Synthesized as described in Example 4 from 4-chloro-2-(trifluoromethyl)-1H-indole-5-carbonitrile (Example 228B) and 5-[3,5-bis(trifluoromethyl)phenyl]-3-(chloromethyl)-1,2,4-oxadiazole: $^1$H NMR (400 MHz, DMSO-$d_6$) δ 8.54 (s, 2H), 8.51 (s, 1H), 8.03-7.95 (m, 1H), 7.94-7.86 (m, 1H), 7.52 (s, 1H), 5.99 (s, 2H); MS (ES) m/z 539 (M+1).

Example 229

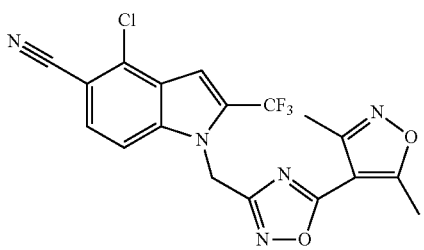 [SMILES: Cc1noc(C)c1-c1nc(Cn2c(C(F)(F)F)cc3c(Cl)c(C#N)ccc32)no1]

4-Chloro-1-{[5-(3,5-dimethyl-4-isoxazolyl)-1,2,4-oxadiazol-3-yl]methyl}-2-(trifluoromethyl)-1H-indole-5-carbonitrile Synthesized as described in Example 4 from 4-chloro-2-(trifluoromethyl)-1H-indole-5-carbonitrile and 3-(chloromethyl)-5-(3,5-dimethyl-4-isoxazolyl)-1,2,4-oxadiazole: ¹H NMR (400 MHz, DMSO-d₆) δ 7.97 (d, J=8.5 Hz, 1H), 7.87 (d, J=8.5 Hz, 1H), 7.50 (s, 1H), 5.93 (s, 2H), 2.64 (s, 3H), 2.37 (s, 3H); MS (ES) m/z 422 (M+1).

Example 230

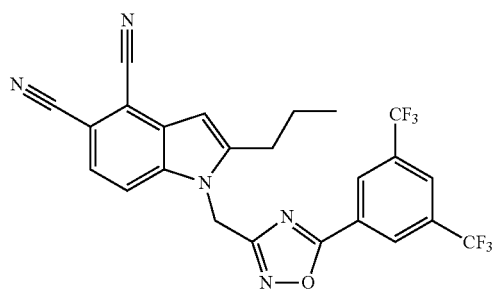

1-({5-[3,5-bis(Trifluoromethyl)phenyl]-1,2,4-oxadiazol-3-yl}methyl)-2-propyl-1H-indole-4,5-dicarbonitrile

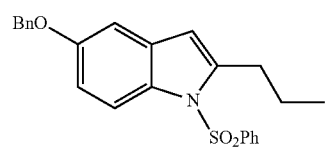

A. 5-[(Phenylmethyl)oxy]-1-(phenylsulfonyl)-2-propyl-1H-indole

To a solution a −78° C. cooled (dry ice/acetone bath) of 5-[(phenylmethyl)oxy]-1-(phenylsulfonyl)-1H-indole (1.1 g, 0.003 mol) in THF (anhydrous, 10 mL) was added n-butyl-lithium (2.3 mL of a 1.6 M solution in hexanes) dropwise. The mixture was then warmed to −10° C. over 30 min and then cooled to −78° C. and 1-iodopropane (1.5 eq., 0.005 mol, 0.77 g) was added dropwise. The mixture was warmed to rt over 1 h and then stirred at rt for 20 min. Water (10 mL) and EtOAc (100 mL) was added. The organic layer was separated, dried (MgSO₄), and concentrated. Purification via semipreparative reverse-phase HPLC provided the desired product: MS (ES) m/z 406 (M+1).

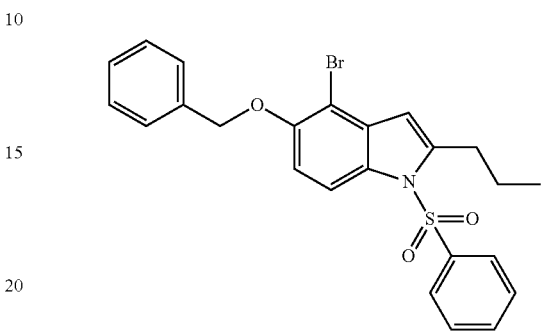

B. 4-Bromo-5-[(phenylmethyl)oxy]-1-(phenylsulfonyl)-2-propyl-1H-indole

To a rt solution of 5-[(phenylmethyl)oxy]-1-(phenylsulfonyl)-2-propyl-1H-indole (1.16 g, 0.0024) in acetic acid (20 mL, glacial) was added Br₂ (1.2 g, 0.008 mol in acetic acid) dropwise. The mixture was stirred for an additional 10 min and water (10 mL) was added. The mixture was extracted with EtOAc (100 mL). The organic layer was separated and dried (MgSO₄) and concentrated. Purification via ISCO normal phase chromatography (SiO₂, 5-15% ethyl acetate/hexanes) to provide 4-bromo-5-[(phenylmethyl)oxy]-1-(phenylsulfonyl)-2-propyl-1H-indole as the regioselective bromination product: MS (ES) m/z 485 (M+1).

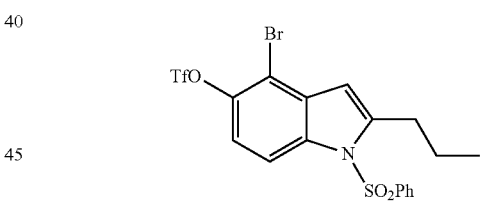

C. 4-Bromo-1-(phenylsulfonyl)-2-propyl-1H-indol-5-yl trifluoromethanesulfonate

Synthesized as described in Example 22E and Example 22F from 4-bromo-5-[(phenylmethyl)oxy]-1-(phenylsulfonyl)-2-propyl-1H-indole: MS (ES) m/z 527 (M+1).

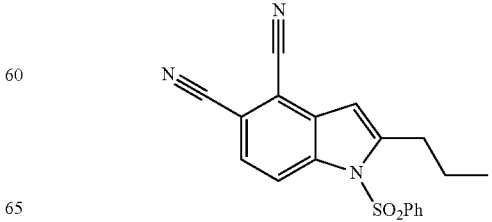

D. 1-(Phenylsulfonyl)-2-propyl-1H-indole-4,5-dicarbonitrile

Synthesized as described in Example 22G from 4-bromo-1-(phenylsulfonyl)-2-propyl-1H-indol-5-yl trifluoromethanesulfonate using 1.0 eq Zn(CN)$_2$ and 0.05 eq. Pd(PPh$_3$)$_4$ in NMP at 200° C. for 2 h: MS (ES) m/z 350 (M+1).

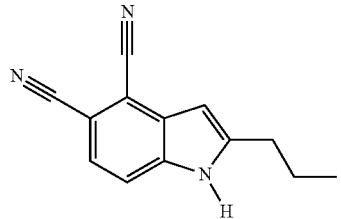 [SMILES: CCCc1cc2c(C#N)c(C#N)ccc2[nH]1]

E. 2-Propyl-1H-indole-4,5-dicarbonitrile

Synthesized as described in Example 22H from 1-(phenylsulfonyl)-2-propyl-1H-indole-4,5-dicarbonitrile: MS (ES) m/z 210 (M+1).

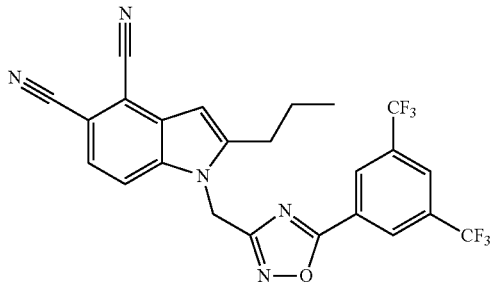 [SMILES: CCCc1cc2c(C#N)c(C#N)ccc2n1Cc1noc(-c2cc(C(F)(F)F)cc(C(F)(F)F)c2)n1]

F. 1-({5-[3,5-bis(Trifluoromethyl)phenyl]-1,2,4-oxadiazol-3-yl}methyl)-2-propyl-1H-indole-4,5-dicarbonitrile Synthesized as described in Example 4 from 2-propyl-1H-indole-4,5-dicarbonitrile using 1.1 eq 5-[3,5-bis(trifluoromethyl)phenyl]-3-(chloromethyl)-1,2,4-oxadiazole and 1.5 eq. Cs$_2$CO$_3$ in DMF at 75° C. for 1 h: $^1$H NMR (400 MHz, DMSO-d$_6$) δ 8.54 (s, 2H), 8.51 (s, 1H), 8.15 (d, J=1.0 Hz, 1H), 7.86 (d, J=8.7 Hz, 1H), 7.70 (dd, J=8.7, 1.5 Hz, 1H), 5.97 (s, 2H), 3.08 (t, 2H), 1.82-1.68 (m, 2H), 0.96 (t, J=7.3 Hz, 3H); MS (ES) m/z 504 (M+1).

Example 231

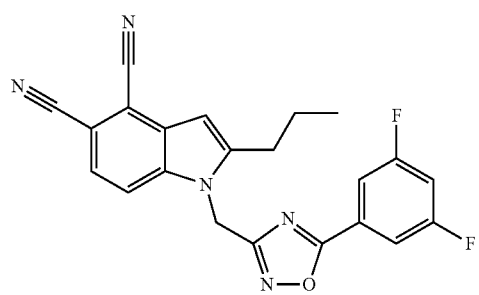 [SMILES: CCCc1cc2c(C#N)c(C#N)ccc2n1Cc1noc(-c2cc(F)cc(F)c2)n1]

1-{[5-(3,5-Difluorophenyl)-1,2,4-oxadiazol-3-yl]methyl}-2-propyl-1H-indole-4,5-dicarbonitrile Synthesized as described in Example 4 from 2-propyl-1H-indole-4,5-dicarbonitrile and 3-(chloromethyl)-5-(3,5-difluorophenyl)-1,2,4-oxadiazole: $^1$H NMR (400 MHz, DMSO-d$_6$) δ 8.15 (s, 1H), 7.85 (d, J=8.5 Hz, 1H), 7.75-7.62 (m, 4H), 5.94 (s, 2H), 3.06 (t, 2H), 1.77-1.65 (m, 2H), 0.95 (t, J=7.3 Hz, 3H): MS (ES) m/z 404 (M+1).

Example 232

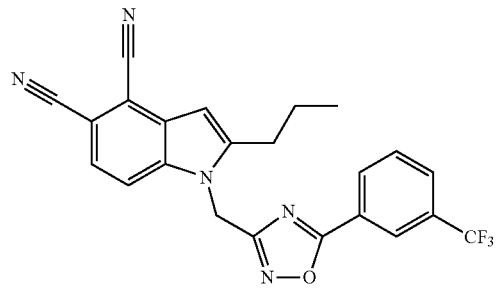 [SMILES: CCCc1cc2c(C#N)c(C#N)ccc2n1Cc1noc(-c2cccc(C(F)(F)F)c2)n1]

2-Propyl-1-({5-[3-(trifluoromethyl)phenyl]-1,2,4-oxadiazol-3-yl}methyl)-1H-indole-4,5-dicarbonitrile Synthesized as described in Example 4 from 2-propyl-1H-indole-4,5-dicarbonitrile and 3-(chloromethyl)-5-[3-(trifluoromethyl)phenyl]-1,2,4-oxadiazole: $^1$H NMR (400 MHz, DMSO-d$_6$) δ 8.30 (d, J=7.6 Hz, 1H), 8.25 (s, 1H), 8.14 (s, 1H), 8.07 (d, J=7.6 Hz, 1H), 7.90-7.80 (m, 2H), 7.70 (d, J=8.4 Hz, 1H), 5.95 (s, 2H), 3.06 (t, 2H), 1.79-1.67 (m, 2H), 0.95 (t, J=7.2 Hz, 3H); MS (ES) m/z 436 (M+1).

Example 233

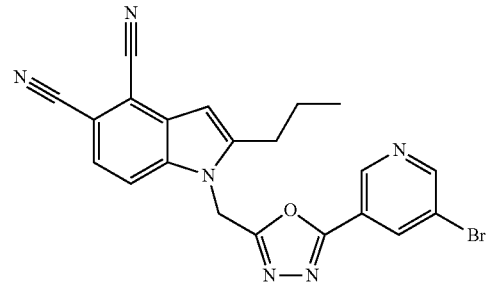 [SMILES: CCCc1cc2c(C#N)c(C#N)ccc2n1Cc1nnc(-c2cncc(Br)c2)o1]

1-{[5-(5-Bromo-3-pyridinyl)-1,3,4-oxadiazol-2-yl]methyl}-2-propyl-1H-indole-4,5-dicarbonitrile Synthesized as described in Example 4 from 2-propyl-1H-indole-4,5-dicarbonitrile and 3-bromo-5-[5-(chloromethyl)-1,3,4-oxadiazol-2-yl]pyridine: $^1$H NMR (400 MHz, DMSO-d$_6$) δ 9.05 (d, J=1.7 Hz, 1H), 8.95 (d, J=2.1 Hz, 1H), 8.48 (s, 1H), 8.16 (s, 1H), 7.91 (d, J=8.7 Hz, 1H), 7.57 (d, J=8.7 Hz, 1H), 6.05 (s, 2H), 3.07 (t, J=7.6 Hz, 2H), 1.78-1.67 (m, 2H), 0.96 (t, J=7.6 Hz, 3H); MS (ES) m/z 448 (M+1).

Example 234

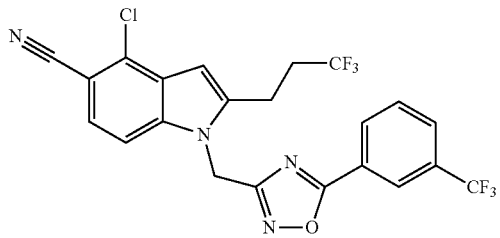 [SMILES: N#Cc1ccc2c(cc(CCC(F)(F)F)n2Cc2noc(-c3cccc(C(F)(F)F)c3)n2)c1Cl]

4-Chloro-1-({5-[3-(trifluoromethyl)phenyl]-1,2,4-oxadiazol-3-yl}methyl)-2-(3,3,3-trifluoropropyl)-1H-indole-5-carbonitrile

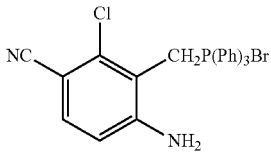

A. {[6-Amino-3-cyano-2-(chloro)phenyl]methyl}(triphenyl)phosphonium bromide

Synthesized as described for Example 191B-G starting from N-(4-bromo-3-chloro-2-methylphenyl)-2,2-dimethylpropanamide: MS (ES) m/z 429 (M+1).

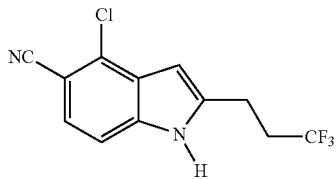 [SMILES: N#Cc1ccc2[nH]c(CCC(F)(F)F)cc2c1Cl]

B. 4-Chloro-2-(3,3,3-trifluoropropyl)-1H-indole-5-carbonitrile

A solution of {[6-amino-3-cyano-2-(chloro)phenyl]methyl}(triphenyl)phosphonium bromide (Example 234A) (0.20 g, 0.39 mmol), HATU (0.157 g, 0.41 mmol), diisopropylethylamine (0.053 g, 0.41 mmol), and trifluoropropylcarboxylic acid (0.058 g, 0.41 mmol) in DMF (15 mL) was stirred at 100° C. for 24 h. After cooling to rt, the reaction was diluted with NaHCO₃ (50 mL) and extracted with EtOAc (100 mL). The organic phase was washed with water and sat'd brine, dried (Na₂SO₄) and concentrated in vacuo. The residue was purified by flash chromatography (20-70% EtOAc-hexanes gradient) to afford the title compound as a light yellow solid: MS (ES) m/z 273 (M+1).

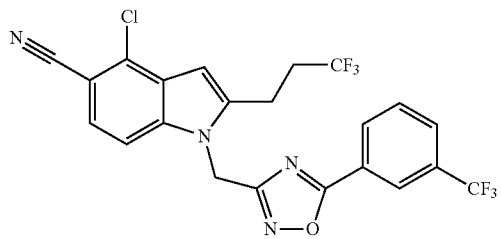 [SMILES: N#Cc1ccc2c(cc(CCC(F)(F)F)n2Cc2noc(-c3cccc(C(F)(F)F)c3)n2)c1Cl]

C. 4-Chloro-1-({5-[3-(trifluoromethyl)phenyl]-1,2,4-oxadiazol-3-yl}methyl)-2-(3,3,3-trifluoropropyl)-1H-indole-5-carbonitrile Synthesized as described in Example 4 from 4-chloro-2-(3,3,3-trifluoropropyl)-1H-indole-5-carbonitrile and 3-(chloromethyl)-5-[3-(trifluoromethyl)phenyl]-1,2,4-oxadiazole:

¹H NMR (400 MHz, CDCl₃) δ 8.31 (s, 1H), 8.23 (d, J=7.8 Hz, 1H), 7.86 (d, J=7.9 Hz, 1 H), 7.67 (dd, J=7.8 Hz, 1H), 7.45 (s, 2H), 6.56 (s, 1H), 5.45 (s, 2H), 3.27 (t, 2H), 2.89-2.61 (m, 2H); MS (ES) m/z 499 (M+1).

Example 235

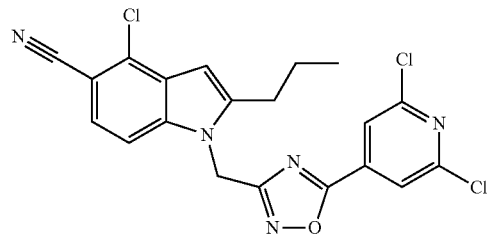 [SMILES: CCCc1cc2c(Cl)c(C#N)ccc2n1Cc1noc(-c2cc(Cl)nc(Cl)c2)n1]

4-Chloro-1-{[5-(2,6-dichloro-4-pyridinyl)-1,2,4-oxadiazol-3-yl]methyl}-2-propyl-1H-indole-5-carbonitrile Synthesized as described for Examples 32A-32B using 2-(4-chloro-5-cyano-2-propyl-1H-indol-1-yl)-N-hydroxyethanimidamide (0.030 g, 0.1 mmol) in anhydrous THF (5 mL) with 2,6-dichloro-4-pyridinecarbonyl chloride (0.021 g, 0.1 mmol) and TEA (0.012 g, 0.12 mmol) and heated at 120° C. for 1 h in the microwave: ¹H NMR (400 MHz, DMSO-d₆) δ 8.06 (s, 2H), 7.96 (s, 1H), 7.76 (d, J=8.5 Hz, 1H), 7.58 (d, J=8.7 Hz, 1H), 5.87 (s, 2 H), 2.91 (t, 2H), 1.67-1.54 (m, 2H), 0.92 (t, 3H); MS (ES) m/z 447 (M+1).

Example 236

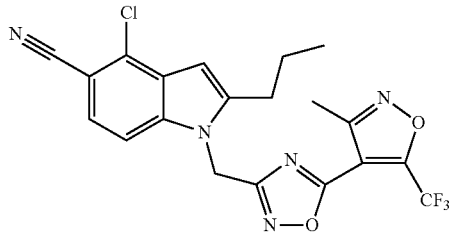 [SMILES: CCCc1cc2c(Cl)c(C#N)ccc2n1Cc1noc(-c2c(C)noc2C(F)(F)F)n1]

4-Chloro-1-({5-[3-methyl-5-(trifluoromethyl)-4-isoxazolyl]-1,2,4-oxadiazol-3-yl}methyl)-2-propyl-1H-indole-5-carbonitrile Synthesized as described in Example 32A and Example 33 using (1Z)-2-(4-chloro-5-cyano-2-propyl-1H-indol-1-yl)-N-hydroxyethanimidamide (0.030 g, 0.1 mmol) in anhydrous THF (5 mL) with propanephosphonic acid cyclic anhydride (T3P) (0.034 g, 0.12 mmol), 3-methyl-5-(trifluoromethyl)-4-isoxazolecarboxylic acid (0.0195 g, 0.1 mmol) and DIEA (0.016 mg, 0.12 mmol) and stirred at rt for 1 h and then heated at 120° C. for 2 h in the microwave: ¹H NMR (400 MHz, CDCl₃-d) δ 7.89 (s, 1H), 7.52 (d, J=8.4 Hz, 1H), 7.46 (d, J=8.4

Hz, 1H), 5.47 (s, 2H), 2.97 (t, 2H), 2.55 (s, 3H), 1.79-1.70 (m, 2H), 1.05 (t, 3H); MS (ES) m/z 450 (M+1).

Example 237

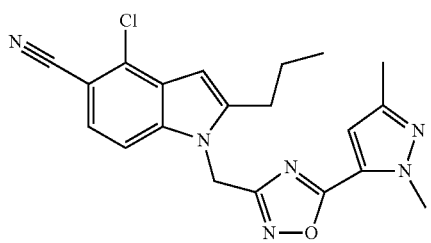 [SMILES: CCCc1cc2c(Cl)c(C#N)ccc2n1Cc1noc(-c2cc(C)nn2C)n1]

4-Chloro-1-{[5-(1,3-dimethyl-1H-pyrazol-5-yl)-1,2,4-oxadiazol-3-yl]methyl}-2-propyl-1H-indole-5-carbonitrile Synthesized as described in Example 32A and Example 33 using (1Z)-2-(4-chloro-5-cyano-2-propyl-1H-indol-1-yl)-N-hydroxyethanimidamide (0.030 g, 0.1 mmol) in anhydrous THF (5 mL) with propanephosphonic acid cyclic anhydride (T3P) (0.034 g, 0.12 mmol), 1,3-dimethyl-1H-pyrazole-5-carboxylic acid (0.014 g, 0.1 mmol) and DIEA (0.016 g, 0.12 mmol) and stirred at rt for 1 h and then heated at 120° C. for 2 h in the microwave: $^1$H NMR (400 MHz, CDCl$_3$) δ 7.90 (s, 1H), 7.52 (d, J=8.6 Hz, 1H), 7.46 (d, J=8.5 Hz, 1H), 6.71 (s, 1H), 5.44 (s, 2H), 4.12 (s, 3H), 2.97 (t, 2H), 2.30 (s, 3H), 1.80-1.72 (m, 2H), 1.04 (t, 3H); MS (ES) m/z 395 (M+1).

Example 238

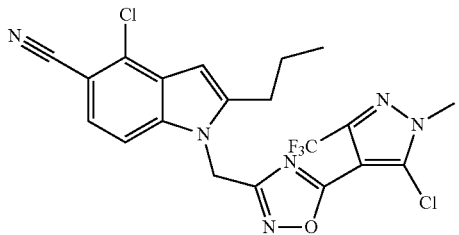 [SMILES: CCCc1cc2c(Cl)c(C#N)ccc2n1Cc1noc(-c2c(C(F)(F)F)nn(C)c2Cl)n1]

4-Chloro-1-({5-[5-chloro-1-methyl-3-(trifluoromethyl)-1H-pyrazol-4-yl]-1,2,4-oxadiazol-3-yl}methyl)-2-propyl-1H-indole-5-carbonitrile Synthesized as described in Example 32A and Example 33 using (1Z)-2-(4-chloro-5-cyano-2-propyl-1H-indol-1-yl)-N-hydroxyethanimidamide (0.030 g, 0.1 mmol) in anhydrous THF (5 mL) with propanephosphonic acid cyclic anhydride (T3P) (0.034 g, 0.12 mmol), 5-chloro-1-methyl-3-(trifluoromethyl)-1H-pyrazole-4-carboxylic acid (0.023 g, 0.1 mmol) and DIEA (0.016 g, 0.12 mmol) and stirred at rt for 1 h and then heated at 120° C. for 2 h in the microwave: $^1$H NMR (400 MHz, CDCl$_3$) δ 7.88 (d, J=8.6 Hz, 1H), 7.46 (d, J=8.4 Hz, 1H), 7.31 (s, 1H), 4.99 (s, 2H), 3.95 (s, 3H), 2.87 (t, 2H), 1.80-1.58 (m, 2H), 1.01 (t, 3H); MS (ES) m/z 484 (M+1).

Example 239

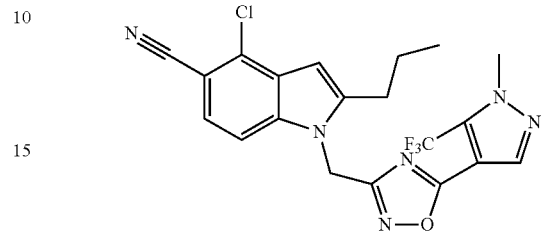

4-Chloro-1-({5-[1-methyl-5-(trifluoromethyl)-1H-pyrazol-4-yl]-1,2,4-oxadiazol-3-yl}methyl)-2-propyl-1H-indole-5-carbonitrile Synthesized as described in Example 32A and Example 33 using (1Z)-2-(4-chloro-5-cyano-2-propyl-1H-indol-1-yl)-N-hydroxyethanimidamide (0.030 g, 0.1 mmol) in anhydrous THF (5 mL) with propanephosphonic acid cyclic anhydride (T3P) (0.034 g, 0.12 mmol), 1-methyl-5-(trifluoromethyl)-1H-pyrazole-4-carboxylic acid (0.0194 g, 0.1 mmol) and DIEA (0.016 g, 0.12 mmol) and stirred at rt for 1 h and then heated at 120° C. for 2 h in the microwave: $^1$H NMR (400 MHz, CDCl$_3$) δ 8.07 (s, 1H), 7.88 (d, J=0.9 Hz, 1H), 7.53 (d, J=8.9 Hz, 1H), 7.45 (d, J=8.6 Hz, 1H), 5.40 (s, 2H), 4.01 (s, 3H), 2.96 (t, 2H), 1.87-1.68 (m, 2H), 1.03 (t, 3H); MS (ES) m/z 449 (M+1).

Example 240

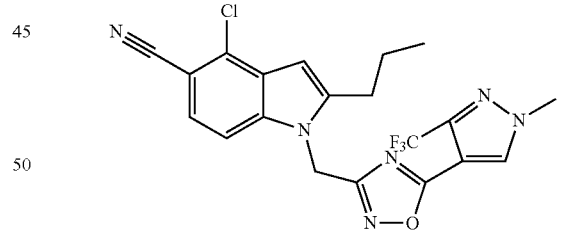

4-Chloro-1-({5-[1-methyl-3-(trifluoromethyl)-1H-pyrazol-4-yl]-1,2,4-oxadiazol-3-yl}methyl)-2-propyl-1H-indole-5-carbonitrile Synthesized as described in Example 32A and Example 33 using (1Z)-2-(4-chloro-5-cyano-2-propyl-1H-indol-1-yl)-N-hydroxyethanimidamide (0.030 g, 0.1 mmol) in anhydrous THF (5 mL) with propanephosphonic acid cyclic anhydride (T3P) (0.034 g, 0.12 mmol), 1-methyl-3-(trifluoromethyl)-1H-pyrazole-4-carboxylic acid (0.0194 g, 0.1 mmol) and DIEA (0.016 g, 0.12 mmol) and stirred at rt for 1 h and then heated at 120° C. for 2 h in the microwave: $^1$H NMR (400 MHz, CDCl$_3$) δ 8.07 (s, 1H), 7.88 (d, J=1.0 Hz, 1H), 7.53 (d, J=8.5 Hz, 1H), 7.45 (d, J=8.4 Hz, 1H), 5.40 (s, 2H), 4.01 (s, 3H), 2.96 (t, 2H), 1.82-1.67 (m, 2H), 1.03 (t, 3H); MS (ES) m/z 449 (M+1).

Example 241

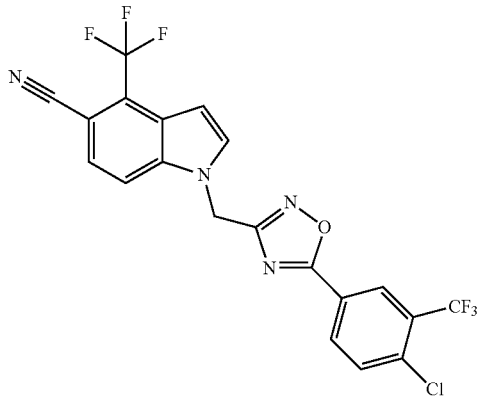 [SMILES: N#Cc1ccc2c(ccn2Cc2noc(-c3ccc(Cl)c(C(F)(F)F)c3)n2)c1C(F)(F)F]

1-({5-[4-Chloro-3-(trifluoromethyl)phenyl]-1,2,4-oxadiazol-3-yl}methyl)-4-(trifluoromethyl)-1H-indole-5-carbonitrile To 4-chloro-3-(trifluoromethyl)benzoic acid (0.0159 g, 0.071 mmol) in CH$_3$CN (3 mL) was added CDI (0.0115 g, 0.071 mmol) and the resulting mixture was stirred for 5 min at rt. Next, 2-[5-cyano-4-(trifluoromethyl)-1H-indol-1-yl]-N-hydroxyethanimidamide (Example 64) (0.02 g, 0.071 mmol) was added and the mixture was stirred for 1 h at rt. Heating at 150° C. in a microwave for 10 min was followed by direct purification (column chromatography, EtOAc/hexanes) to obtain the title compound (0.0219 g): MS (ES) m/z 471 (M+1).

Example 242

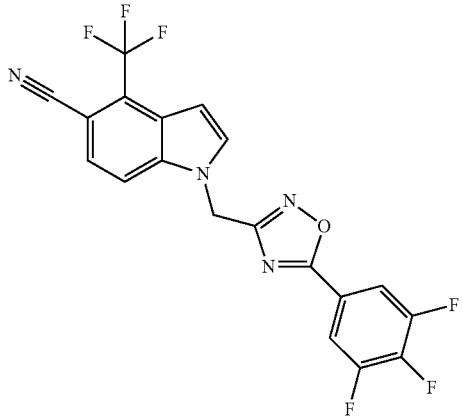 [SMILES: N#Cc1ccc2c(ccn2Cc2noc(-c3cc(F)c(F)c(F)c3)n2)c1C(F)(F)F]

4-Trifluoromethyl)-1-{[5-(3,4,5-trifluorophenyl)-1,2,4-oxadiazol-3-yl]methyl}-1H-indole-5-carbonitrile Synthesized as described in Example 241 from 2-[5-cyano-4-(trifluoromethyl)-1H-indol-1-yl]-N-hydroxyethanimidamide and 3,4,5-trifluorobenzoic acid: MS (ES) m/z 421 (M−1).

Example 243

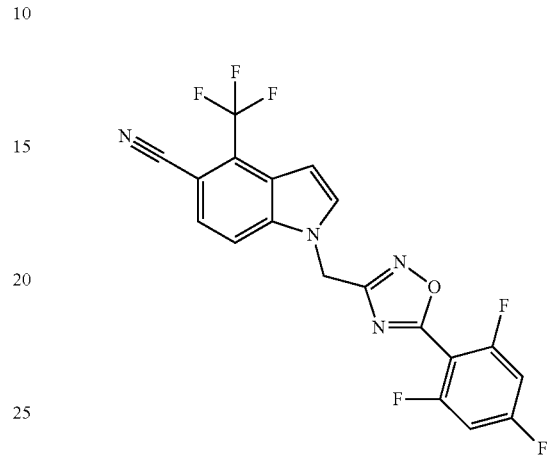

4-(Trifluoromethyl)-1-{[5-(2,4,6-trifluorophenyl)-1,2,4-oxadiazol-3-yl]methyl}-1H-indole-5-carbonitrile Synthesized as described in Example 241 from 2-[5-cyano-4-(trifluoromethyl)-1H-indol-1-yl]-N-hydroxyethanimidamide and 2,4,6-trifluorobenzoic acid: MS (ES) m/z 423 (M+1).

Example 244

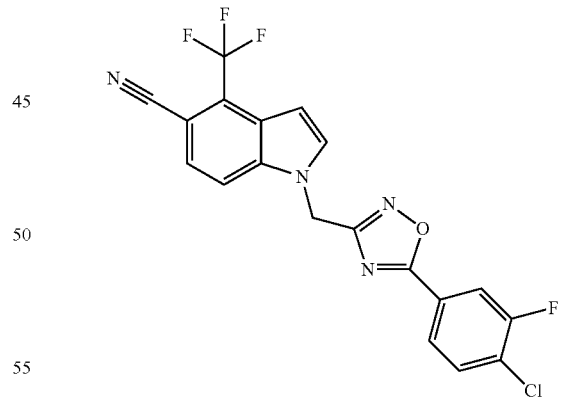

1-{[5-(4-Chloro-3-fluorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 4-chloro-3-fluorobenzoic acid: MS (ES) m/z 421 (M+1).

Example 245

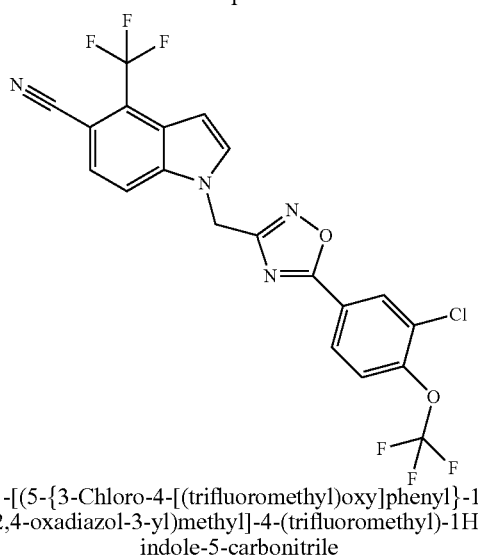

1-[(5-{3-Chloro-4-[(trifluoromethyl)oxy]phenyl}-1,2,4-oxadiazol-3-yl)methyl]-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3-chloro-4-[(trifluoromethyl)oxy]benzoic acid: MS (APCI) m/z 488 (M+1).

Example 246

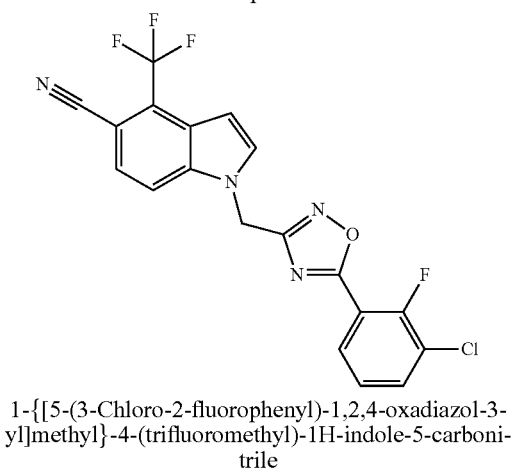

1-{[5-(3-Chloro-2-fluorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3-chloro-2-fluorobenzoic acid: MS (APCI) m/z 420 (M+1).

Example 247

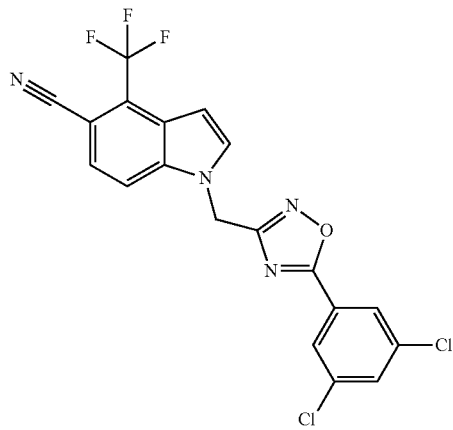 [SMILES: N#Cc1ccc2c(ccn2Cc2noc(-c3cc(Cl)cc(Cl)c3)n2)c1C(F)(F)F]

1-{[5-(3,5-Dichlorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3,5-dichlorobenzoic acid: MS (APCI) m/z 439 (M+1).

Example 248

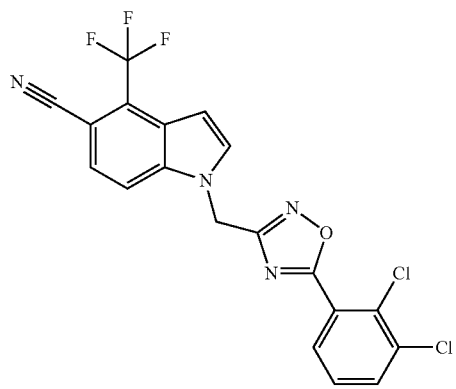 [SMILES: N#Cc1ccc2c(ccn2Cc2noc(-c3cccc(Cl)c3Cl)n2)c1C(F)(F)F]

1-{[5-(2,3-Dichlorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 2,3-dichlorobenzoic acid: MS (ES): m/z 438 (M+1).

Example 249

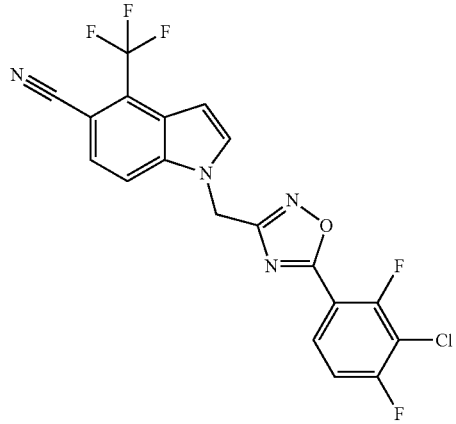 [SMILES: N#Cc1ccc2c(ccn2Cc2noc(-c3ccc(F)c(Cl)c3F)n2)c1C(F)(F)F]

1-{[5-(3-Chloro-2,4-difluorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3-chloro-2,4-difluorobenzoic acid: MS (ES) m/z 439 (M+1).

Example 250

1-{[5-(5-Chloro-2-fluorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 5-chloro-2-fluorobenzoic acid: MS (APCI) m/z 421 (M+1).

Example 252

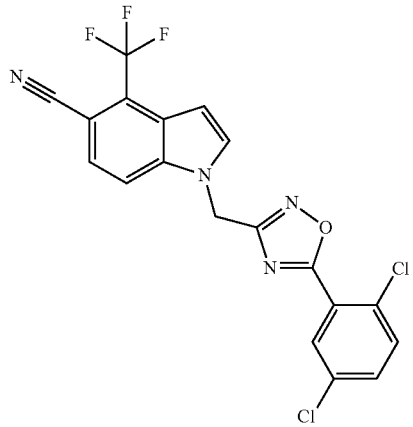 [SMILES: N#Cc1ccc2c(ccn2Cc2noc(-c3cc(Cl)ccc3Cl)n2)c1C(F)(F)F]

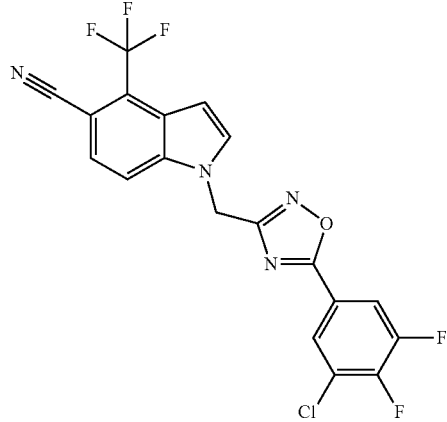

1-{[5-(2,5-Dichlorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 2,5-dichlorobenzoic acid: MS (ES) m/z 438 (M+1).

Example 251

1-{[5-(3-Chloro-4,5-difluorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3-chloro-4,5-difluorobenzoic acid: MS (APCI) m/z 440 (M+1).

Example 253

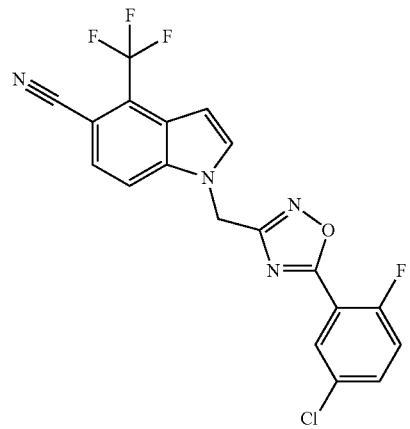 [SMILES: N#Cc1ccc2c(ccn2Cc2noc(-c3cc(Cl)ccc3F)n2)c1C(F)(F)F]

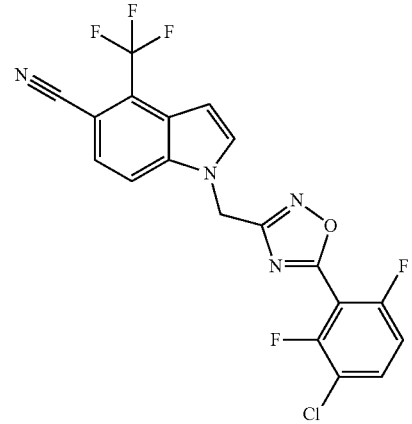 [SMILES: N#Cc1ccc2c(ccn2Cc2noc(-c3c(F)ccc(Cl)c3F)n2)c1C(F)(F)F]

1-{[5-(3-Chloro-2,6-difluorophenyl)-1,2,4-oxadiazol-3-yl]methyl}-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3-chloro-2,6-difluorobenzoic acid: MS (APCI) m/z 440 (M+1).

Example 254

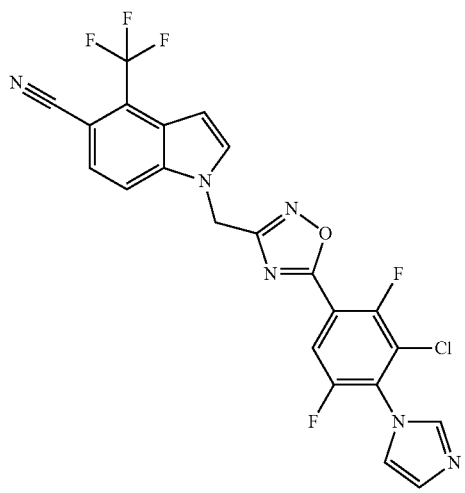 [SMILES: N#Cc1ccc2c(ccn2Cc2noc(-c3cc(F)c(-n4ccnc4)c(Cl)c3F)n2)c1C(F)(F)F]

1-({5-[3-Chloro-2,5-difluoro-4-(1H-imidazol-1-yl)phenyl]-1,2,4-oxadiazol-3-yl}methyl)-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 3-chloro-2,4,5-trifluorobenzoic acid: MS (APCI) m/z 505 (M+1).

Example 255

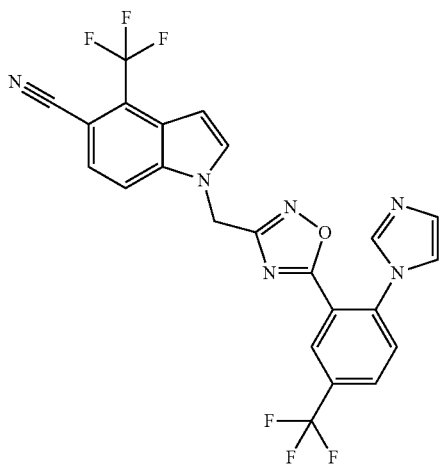 [SMILES: N#Cc1ccc2c(ccn2Cc2noc(-c3cc(C(F)(F)F)ccc3-n3ccnc3)n2)c1C(F)(F)F]

1-({5-[2-(1H-Imidazol-1-yl)-5-(trifluoromethyl)phenyl]-1,2,4-oxadiazol-3-yl}methyl)-4-(trifluoromethyl)-1H-indole-5-carbonitrile Synthesized as described in Example 241 from 2-[5-cyano-4-(trifluoromethyl)-1H-indol-1-yl]-N-hydroxyethanimidamide and 2-fluoro-5-(trifluoromethyl)benzoic acid except the mixture was heated to 200° C. in a microwave for 20 min: MS (APCI) m/z 503 (M+1).

Example 256

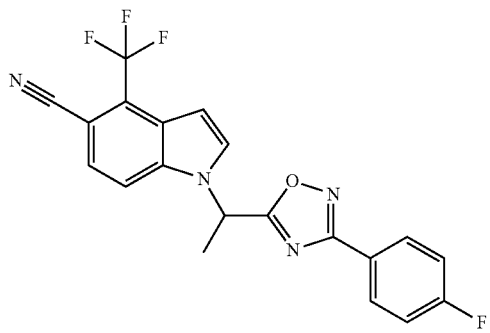 [SMILES: CC(c1nc(-c2ccc(F)cc2)no1)n1ccc2c(C(F)(F)F)c(C#N)ccc21]

1-{1-[3-(4-Fluorophenyl)-1,2,4-oxadiazol-5-yl]ethyl}-4-(trifluoromethyl)-1H-indole-5-carbonitrile

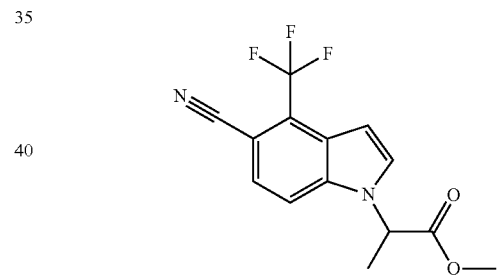

A. Methyl 2-[5-cyano-4-(trifluoromethyl)-1H-indol-1-yl]propanoate

Synthesized as described in Example 4 from 4-(trifluoromethyl)-1H-indole-5-carbonitrile and methyl 2-bromopropanoate: MS (APCI) m/z 297 (M+1).

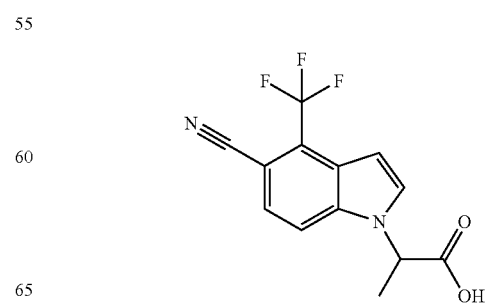

B. 2-[5-Cyano-4-(trifluoromethyl)-1H-indol-1-yl]propanoic acid

To methyl 2-[5-cyano-4-(trifluoromethyl)-1H-indol-1-yl]propanoate (0.055 g, 0.185 mmol) in 1:1 THF/MeOH (4 mL) was added 5N NaOH (0.185 mL) and the resulting mixture was heated to 60° C. for 30 min. The cooled mixture was partitioned between Et$_2$O and 0.1N HCl. The separated organic portion was washed with brine, dried over Na$_2$SO$_4$, and filtered. Concentration afforded the title compound (0.052 g, 99% yield): MS (APCI) m/z 283 (M+1).

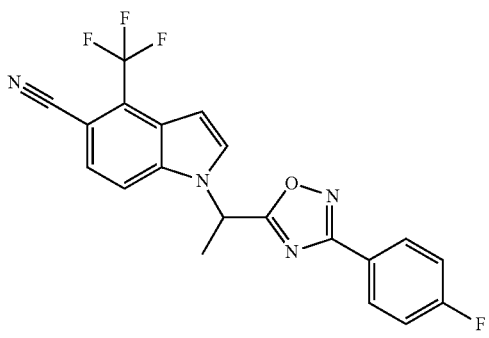 [SMILES: CC(c1nc(-c2ccc(F)cc2)no1)n1ccc2c(C(F)(F)F)c(C#N)ccc21]

C. 1-{1-[3-(4-Fluorophenyl)-1,2,4-oxadiazol-5-yl]ethyl}-4-(trifluoromethyl)-1H-indole-5-carbonitrile To 2-[5-cyano-4-(trifluoromethyl)-1H-indol-1-yl]propanoic acid (0.06 g, 0.212 mmol) in CH$_3$CN (3 mL) was added CDI (0.034 g, 0.212 mmol). After 5 min, 4-fluoro-N-hydroxybenzenecarboximidamide (0.033 g, 0.212 mmol) was added. The resulting mixture was stirred at rt and then heated to 150° C. in a microwave for 20 min. Concentration was followed by column chromatography (EtOAc/hexanes) to obtain the desired product (0.0065 g, 8% yield): MS (APCI) m/z 401 (M+1).

Example 257

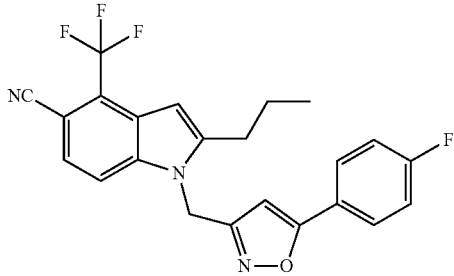 [SMILES: CCCc1cc2c(C(F)(F)F)c(C#N)ccc2n1Cc1cc(-c2ccc(F)cc2)on1]

1-{[5-(4-Fluorophenyl)-3-isoxazolyl]methyl}-2-propyl-4-(trifluoromethyl)-1H-indole-5-carbonitrile

A. 3-(Chloromethyl)-5-(4-fluorophenyl)isoxazole

To a solution of [5-(4-fluorophenyl)-3-isoxazolyl]methanol (0.2 g, 1.04 mmol) in 5 mL of CCl$_4$ and 0.5 mL of CH$_2$Cl$_2$ was added Ps-triphenylphosphine (3 mmol/g, 0.69 g, 2.08 mmol), and the mixture was heated at 65° C. for 3 h. Upon cooling, the resin was filtered off and washed with CH$_2$Cl$_2$ and EtOAc. The filtrate was concentrated to dryness to afford the title compound as a light brown solid, which was used in the next reaction without further purification: $^1$H NMR (400 MHz, CDCl$_3$) δ 7.75 (t, J=6.6 Hz, 2H), 7.14 (t, J=8.3 Hz, 2H), 6.55 (s, 1H), 4.6 (s, 2H).

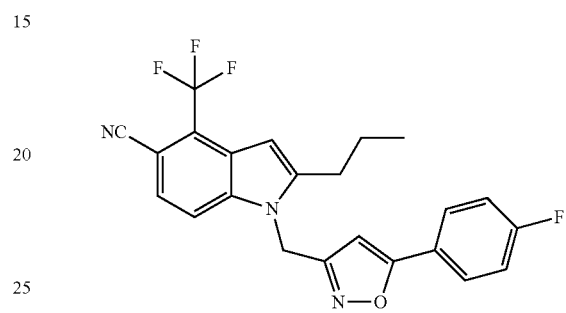

B. 1-{[5-(4-Fluorophenyl)-3-isoxazolyl]methyl}-2-propyl-4-(trifluoromethyl)-1H-indole-5-carbonitrile Synthesized in a manner similar to Example 23 using 2-propyl-4-(trifluoromethyl)-1H-indole-5-carbonitrile and 3-(chloromethyl)-5-(4-fluorophenyl)isoxazole: MS (ES) m/z 428 (M+1).

Example 258

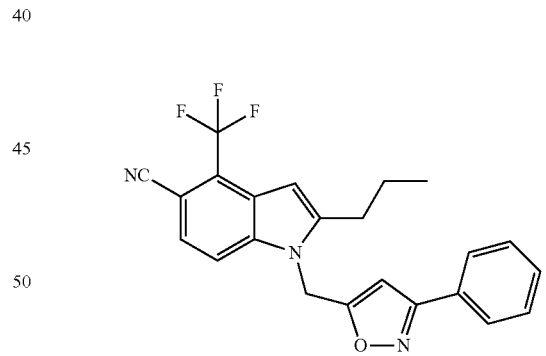

1-[(3-Phenyl-5-isoxazolyl)methyl]-2-propyl-4-(trifluoromethyl)-1H-indole-5-carbonitrile

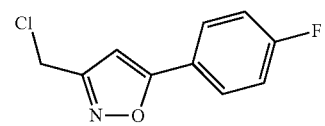 [SMILES: Fc1ccc(-c2cc(CCl)no2)cc1]

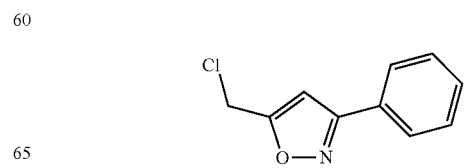

A. 5-(Chloromethyl)-3-phenylisoxazole

Synthesized as described in Example 257A using (3-phenyl-5-isoxazolyl)methanol: $^1$H NMR (400 MHz, CDCl$_3$) δ 7.82-7.78 (m, 2H), 7.48-7.44 (m, 3H), 6.64 (s, 1H), 4.67 (s, 2H).

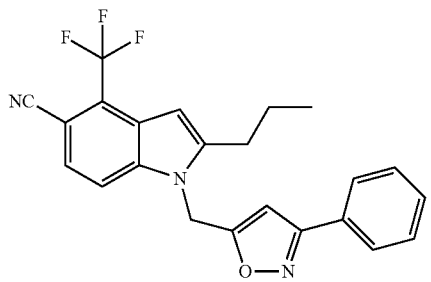 [SMILES: CCCc1cc2c(C(F)(F)F)c(C#N)ccc2n1Cc1cc(-c2ccccc2)no1]

B. 1-[(3-Phenyl-5-isoxazolyl)methyl]-2-propyl-4-(trifluoromethyl)-1H-indole-5-carbonitrile Synthesized in a manner similar to Example 23 using 2-propyl-4-(trifluoromethyl)-1H-indole-5-carbonitrile and 5-(chloromethyl)-3-phenylisoxazole: MS (ES) m/z 410 (M+1).

Example 259

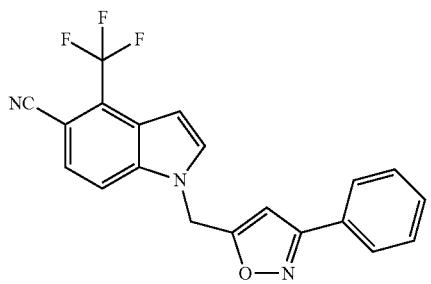 [SMILES: N#Cc1ccc2c(ccn2Cc2cc(-c3ccccc3)no2)c1C(F)(F)F]

1-[(3-Phenyl-5-isoxazolyl)methyl]-4-(trifluoromethyl)-1H-indole-5-carbonitrile

Synthesized in a manner similar to Example 23 using 4-(trifluoromethyl)-1H-indole-5-carbonitrile and 5-(chloromethyl)-3-phenylisoxazole: MS (ES) m/z 368 (M+1).

Example 260

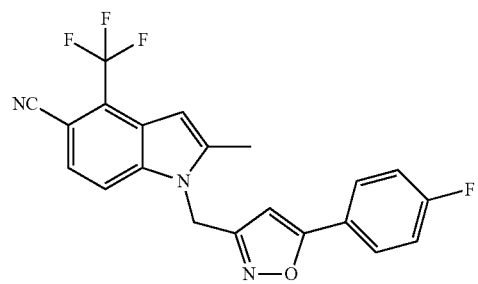 [SMILES: Cc1cc2c(C(F)(F)F)c(C#N)ccc2n1Cc1cc(-c2ccc(F)cc2)on1]

1-{[5-(4-Fluorophenyl)-3-isoxazolyl]methyl}-2-methyl-4-(trifluoromethyl)-1H-indole-5-carbonitrile Synthesized in a manner similar to Example 23 using 2-methyl-4-(trifluoromethyl)-1H-indole-5-carbonitrile and 3-(chloromethyl)-5-(4-fluorophenyl)isoxazole: MS (ES) m/z 400 (M+1).

Example 261

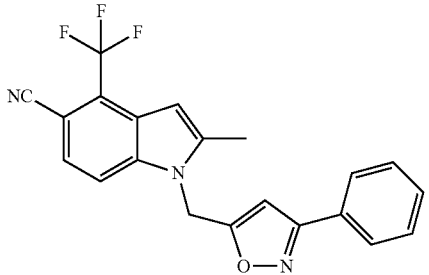

2-Methyl-1-[(3-phenyl-5-isoxazolyl)methyl]-4-(trifluoromethyl)-1H-indole-5-carbonitrile Synthesized in a manner similar to Example 23 using 2-methyl-4-(trifluoromethyl)-1H-indole-5-carbonitrile and 5-(chloromethyl)-3-phenylisoxazole: $^1$H NMR (400 MHz, acetone-d$_6$) δ 8.06 (d, J=8.6 Hz, 1H), 7.84-7.80 (m, 2H), 7.69 (d, J=8.4 Hz, 1H), 7.48-7.44 (m, 3H), 6.88 (s, 1H), 6.69 (s, 1H), 5.86 (s, 2H), 2.69 (s, 3H).

Example 262

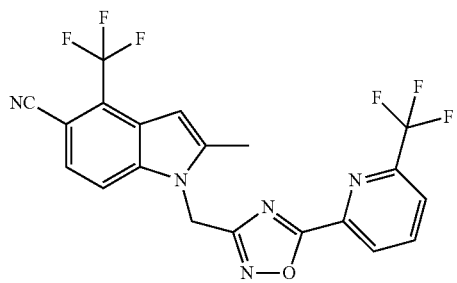 [SMILES: Cc1cc2c(C(F)(F)F)c(C#N)ccc2n1Cc1noc(-c2cccc(C(F)(F)F)n2)n1]

2-Methyl-4-(trifluoromethyl)-1-({5-[6-(trifluoromethyl)-2-pyridinyl]-1,2,4-oxadiazol-3-yl}methyl)-1H-indole-5-carbonitrile

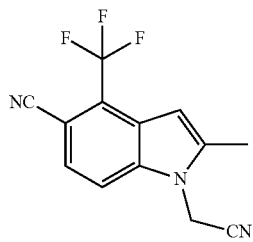 [SMILES: Cc1cc2c(C(F)(F)F)c(C#N)ccc2n1CC#N]

A. 1-(Cyanomethyl)-2-methyl-4-(trifluoromethyl)-1H-indole-5-carbonitrile

To a solution of 2-methyl-4-(trifluoromethyl)-1H-indole-5-carbonitrile (0.5 g, 2.23 mmol) in DMF (5 mL) was added $Cs_2CO_3$ (1.45 g, 4.46 mmol) and bromoacetonitrile (0.54 g, 4.46 mmol). The mixture was heated at 70° C. for 10 min. Additional bromoacetonitrile (0.35 g, 2.9 mmol) was added, and heating was continued for another 10 min. Upon cooling, the mixture was partitioned between $Et_2O$ and 0.1N HCl. The organic phase was washed with sat'd brine. The combined aqueous phases were washed with $Et_2O$, and this organic phase was washed with sat'd brine. The combined organic phases were dried ($Na_2SO_4$), filtered and concentrated to dryness, to yield a brown solid (0.59 g), which was used in the next step without further purification: LC/MS (ES) shows 87% title compound (m/z 264 (M+1)) and 13% starting material.

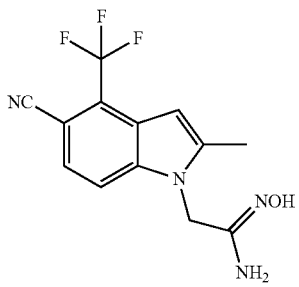

B. 2-[5-Cyano-2-methyl-4-(trifluoromethyl)-1H-indol-1-yl]-N-hydroxyethanimidamide To a solution of the above intermediate (0.59 g) in DMF (10 mL) was added hydroxylamine hydrochloride (0.62 g, 8.92 mmol). After stirring at rt for 5 min, sodium acetate (0.73 g, 8.92 mmol) was added, and the mixture was stirred at rt for ~15 h. The mixture was partitioned between $Et_2O$ and 0.1N NaOH. The organic phase, which contained small amount of solids, was separated, and diluted with a small amount of EtOAc to make it homogeneous. The organic phase was washed with water and sat'd brine. The combined aqueous phases were extracted twice with EtOAc. These organic phases were combined and washed with water and sat'd brine. The organic phases were combined, dried ($Na_2SO_4$), filtered and concentrated. The residue was purified by silica gel chromatography, using a 30-100% EtOAc-hexanes gradient to afford the title compound (0.48 g, 73% yield for two steps): MS (ES) m/z 297 (M+1).

C. 2-Methyl-4-(trifluoromethyl)-1-({5-[6-(trifluoromethyl)-2-pyridinyl]-1,2,4-oxadiazol-3-yl}methyl)-1H-indole-5-carbonitrile To a solution of 6-(trifluoromethyl)-2-pyridinecarboxylic acid (ref: European Journal of Organic Chemistry (2003), (8), 1569-1575) (0.032 g, 0.169 mmol) in 2 mL of MeCN was added DIEA (0.022 g, 0.169 mmol) and HATU (0.064 g, 0.169 mmol). After stirring at rt for 2 min, (1Z)-2-[5-cyano-2-methyl-4-(trifluoromethyl)-1H-indol-1-yl]-N-hydroxyethanimidamide (0.050 g, 0.169 mmol) was added. After stirring at rt for 30 min, the mixture was heated in a sealed tube at 150° C. for 1.5 h. Upon cooling, the mixture was concentrated to dryness and the residue was purified by silica gel chromatography using a 5-50% EtOAc-hexanes gradient. The product was crystallized from $CH_2Cl_2$-hexanes to afford the title compound as a white solid (0.035 g, 46% yield): MS (ES) m/z 452 (M+1).

Example 263

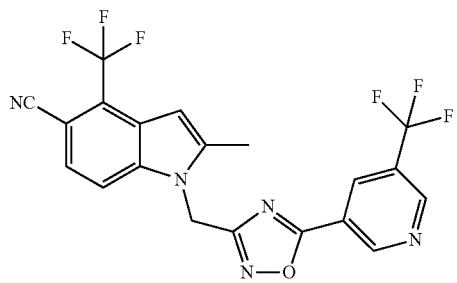

2-Methyl-4-(trifluoromethyl)-1-({5-[5-(trifluoromethyl)-3-pyridinyl]-1,2,4-oxadiazol-3-yl}methyl)-1H-indole-5-carbonitrile Synthesized in a manner similar to Example 262C using 5-(trifluoromethyl)-3-pyridinecarboxylic acid (ref: European Journal of Organic Chemistry (2003), (8), 1559-1568): MS (ES) m/z 452 (M+1).

Example 264

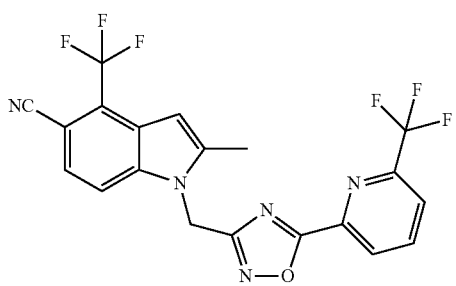 [SMILES: Cc1cc2c(C(F)(F)F)c(C#N)ccc2n1Cc1noc(-c2cccc(C(F)(F)F)n2)n1]

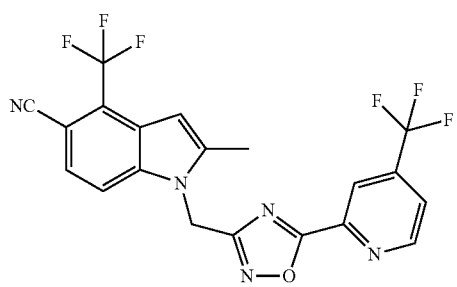 [SMILES: Cc1cc2c(C(F)(F)F)c(C#N)ccc2n1Cc1noc(-c2cc(C(F)(F)F)ccn2)n1]

2-Methyl-4-(trifluoromethyl)-1-({5-[4-(trifluoromethyl)-2-pyridinyl]-1,2,4-oxadiazol-3-yl}methyl)-1H-indole-5-carbonitrile Synthesized in a manner similar to Example 262C using 4-(trifluoromethyl)-2-pyridinecarboxylic acid (ref: European Journal of Organic Chemistry (2003), (8), 1559-1568): MS (ES) m/z 452 (M+1).

Example 265

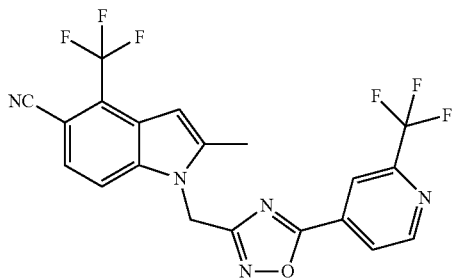 [SMILES: Cc1cc2c(C(F)(F)F)c(C#N)ccc2n1Cc1noc(-c2ccnc(C(F)(F)F)c2)n1]

2-Methyl-4-(trifluoromethyl)-1-({5-[2-(trifluoromethyl)-4-pyridinyl]-1,2,4-oxadiazol-3-yl}methyl)-1H-indole-5-carbonitrile Synthesized in a manner similar to Example 262C using 2-(trifluoromethyl)-4-pyridinecarboxylic acid (ref: European Journal of Organic Chemistry (2003), (8), 1559-1568): MS (ES) m/z 452 (M+1).

Example 266

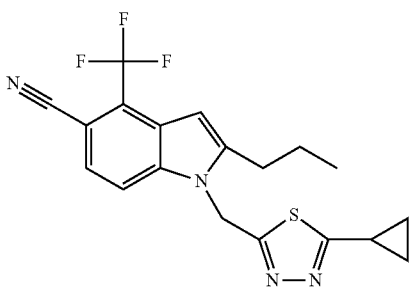 [SMILES: CCCc1cc2c(C(F)(F)F)c(C#N)ccc2n1Cc1nnc(C2CC2)s1]

1-[(5-Cyclopropyl-1,3,4-thiadiazol-2-yl)methyl]-2-propyl-4-(trifluoromethyl)-1H-indole-5-carbonitrile To a solution of 2-propyl-4-(trifluoromethyl)-1H-indole-5-carbonitrile (Example 153A) (0.200 g, 0.793 mmol) in anhydrous acetonitrile (30 mL) was added Cs$_2$CO$_3$ (0.298 g, 0.915 mmol) and 2-(bromomethyl)-5-cyclopropyl-1,3,4-thiadiazole (0.300 g, 1.37 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (0.189 g, 61% yield): MS (ES) m/z 390 (M$^+$).

Example 267

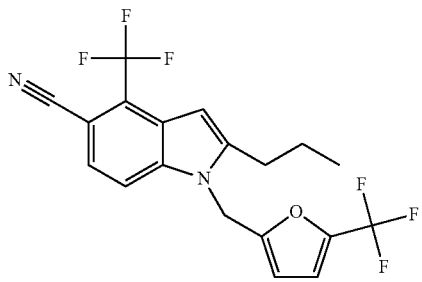 [SMILES: CCCc1cc2c(C(F)(F)F)c(C#N)ccc2n1Cc1ccc(C(F)(F)F)o1]

2-Propyl-4-(trifluoromethyl)-1-{[5-(trifluoromethyl)-2-furanyl]methyl}-1H-indole-5-carbonitrile To a solution of 2-propyl-4-(trifluoromethyl)-1H-indole-5-carbonitrile (Example 153A) (0.100 g, 0.396 mmol) in anhydrous acetonitrile (25 mL) was added Cs$_2$CO$_3$ (1.30 g, 4.00 mmol) and 2-(bromomethyl)-5-(trifluoromethyl)furan (0.136 g, 0.594 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (0.189 g, 89% yield): MS (ES) m/z 400 (M$^+$).

Example 268

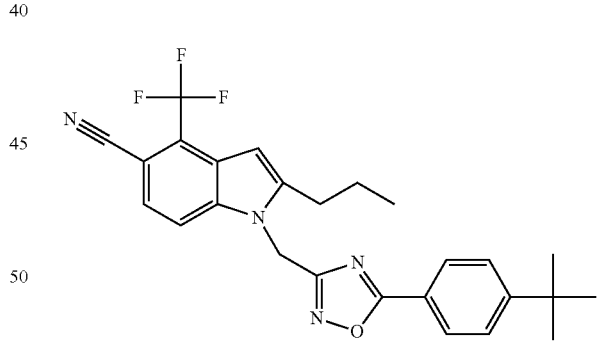

1-({5-[4-(1,1-Dimethylethyl)phenyl]-1,2,4-oxadiazol-3-yl}methyl)-2-propyl-4-(trifluoromethyl)-1H-indole-5-carbonitrile To a solution of 2-propyl-4-(trifluoromethyl)-1H-indole-5-carbonitrile (Example 153A) (0.100 g, 0.396 mmol) in anhydrous acetonitrile (20 mL) was added Cs$_2$CO$_3$ (1.30 g, 4.00 mmol) and 3-(bromomethyl)-5-[4-(1,1-dimethylethyl)phenyl]-1,2,4-oxadiazole (0.176 g, 0.596 mmol). The mixture was heated under N$_2$, for 2 h. Upon cooling, the mixture was partitioned between EtOAc and water. The organic phase was separated, dried (MgSO$_4$) and concentrated in vacuo.

The residue was purified by flash chromatography (0-20% EtOAc-hexanes gradient) to afford a pure product (0.29 g, 16% yield): MS (ES) m/z 466 (M+).

Example 269

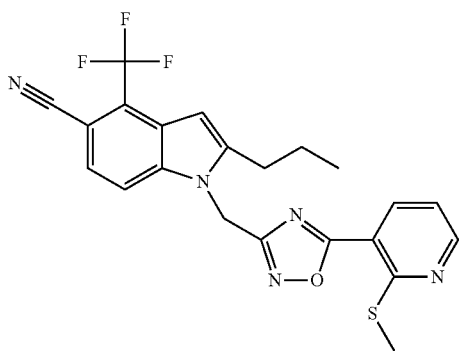 [SMILES: CCCc1cc2c(C(F)(F)F)c(C#N)ccc2n1Cc1noc(-c2cccnc2SC)n1]

1-({5-[2-(Methylthio)-3-pyridinyl]-1,2,4-oxadiazol-3-yl}methyl)-2-propyl-4-(trifluoromethyl)-1H-indole-5-carbonitrile To a solution of 2-propyl-4-(trifluoromethyl)-1H-indole-5-carbonitrile (Example 153A) (0.100 g, 0.396 mmol) in anhydrous acetonitrile (20 mL) was added Cs$_2$CO$_3$ (1.30 g, 4.00 mmol) and 3-[3-(chloromethyl)-1,2,4-oxadiazol-5-yl]-2-(methylthio)pyridine (0.170 g, 0.594 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (0.152 g, 84% yield): MS (ES) m/z 458 (M+).

Example 270

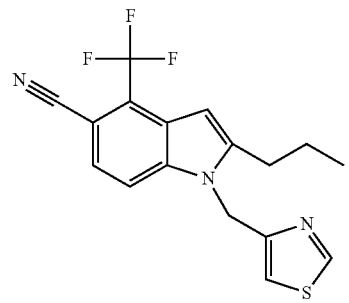 [SMILES: CCCc1cc2c(C(F)(F)F)c(C#N)ccc2n1Cc1cscn1]

2-Propyl-1-(1,3-thiazol-4-ylmethyl)-4-(trifluoromethyl)-1H-indole-5-carbonitrile To a solution of 2-propyl-4-(trifluoromethyl)-1H-indole-5-carbonitrile (Example 153A) (0.150 g, 0.595 mmol) in anhydrous acetonitrile (25 mL) was added Cs$_2$CO$_3$ (1.90 g, 0.0595 mmol) and 4-(bromomethyl)-1,3-thiazole (0.159 g, 0.893 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (0.171 g, 82% yield): $^1$H NMR (400 MHz, CDCl$_3$) δ 8.81-8.80 (d, J=4.0 Hz, 1H), 7.78 (m, 2H), 6.68 (d, J=4.0 Hz, 1H), 6.63 (s, 1H), 5.51 (s, 2H), 2.80-2.76 (t, J=8.0 Hz, 2H), 1.82-1.76 (q, J=8.0 Hz, 2H), 1.06-1.02 (t, J=8.0 Hz, 3H).

Example 271

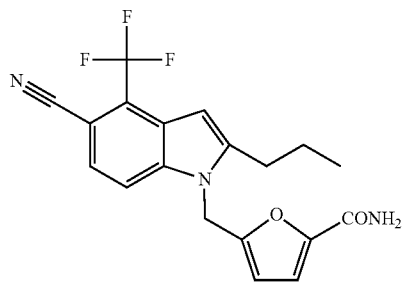 [SMILES: CCCc1cc2c(C(F)(F)F)c(C#N)ccc2n1Cc1ccc(C(N)=O)o1]

5-{[5-Cyano-2-propyl-4-(trifluoromethyl)-1H-indol-1-yl]methyl}-2-furancarboxamide

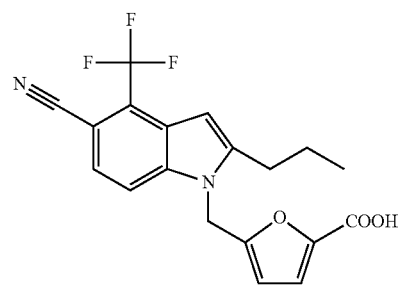 [SMILES: CCCc1cc2c(C(F)(F)F)c(C#N)ccc2n1Cc1ccc(C(=O)O)o1]

A. 5-{[5-Cyano-2-propyl-4-(trifluoromethyl)-1H-indol-1-yl]methyl}-2-furancarboxylic acid To a solution of 2-propyl-4-(trifluoromethyl)-1H-indole-5-carbonitrile (Example 153A) (0.500 g, 1.98 mmol) in anhydrous acetonitrile (25 mL) was added Cs$_2$CO$_3$ (6.50 g, 20.0 mmol) along with ethyl 5-(chloromethyl)-2-furancarboxylate (0.561 g, 3.00 mmol). The mixture was heated under N$_2$, for 2 h. Upon cooling, the mixture was partitioned between EtOAc and water. The organic phase was separated, dried (MgSO$_4$) and concentrated in vacuo. The residue was mixed with 1.0N LiOH (25 mL) and anhydrous 1,4-dioxane (2 5 mL) and the mixture was stirred at rt for 17 h. The mixture was diluted with water and extracted with Et$_2$O. The organics were separated and the aqueous mixture was made acidic using 1.0N HCl. The aqueous mixture was extracted with EtOAc, dried (MgSO$_4$) and concentrated to dryness to give a crude solid (0.579 g, 78%). This solid was used without further purification.

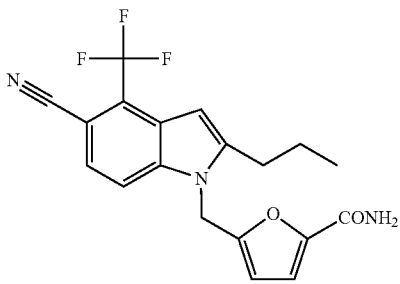 [SMILES: CCCc1cc2c(C(F)(F)F)c(C#N)ccc2n1Cc1ccc(C(N)=O)o1]

B. 5-{[5-Cyano-2-propyl-4-(trifluoromethyl)-1H-indol-1-yl]methyl}-2-furancarboxamide A mixture of 5-{[5-cyano-2-propyl-4-(trifluoromethyl)-1H-indol-1-yl]methyl}-2-furancarboxylic acid (0.400 g, 1.06 mmol) and SOCl$_2$ (15 mL) was heated to reflux for a period of 16 h. The mixture was concentrated to dryness and mixed with EtOAc (40 mL) and concentrated NH$_4$OH (40 mL). The mixture was stirred at rt for 17 h and the resulting precipitate was filtered in vacuo and dried under high vacuum to give the pure final product (0.388 g, 97%): MS (ES) m/z 375 (M$^+$).

Example 272

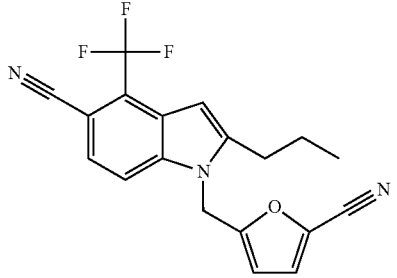 [SMILES: CCCc1cc2c(C(F)(F)F)c(C#N)ccc2n1Cc1ccc(C#N)o1]

1-[(5-Cyano-2-furanyl)methyl]-2-propyl-4-(trifluoromethyl)-1H-indole-5-carbonitrile A solution containing 5-{[5-cyano-2-propyl-4-(trifluoromethyl)-1H-indol-1-yl]methyl}-2-furancarboxamide (Example 271B) (0.388 g, 1.03 mmol), pyridine (10 mL) and CH$_2$Cl$_2$ (25 mL) was cooled to 0-5° C. This mixture was mixed with POCl$_3$ (0.792 g, 5.17 mmol) and the resulting mixture was stirred at rt for 2 h. The reaction mixture was then partitioned between CH$_2$Cl$_2$ and saturated NaHCO$_3$. The organics were washed with 1.0N HCl, dried (MgSO$_4$) and concentrated to dryness. The residue was purified by flash chromatography (0-10% EtOAc-hexanes gradient) to afford a pure product (0.204 g, 55% yield): MS (ES) m/z 357 (M$^+$).

Example 273

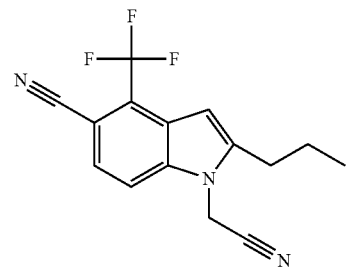 [SMILES: CCCc1cc2c(C(F)(F)F)c(C#N)ccc2n1CC#N]

1-(Cyanomethyl)-2-propyl-4-(trifluoromethyl)-1H-indole-5-carbonitrile

To a solution of 2-propyl-4-(trifluoromethyl)-1H-indole-5-carbonitrile (Example 153A) (1.00 g, 3.96 mmol) in anhydrous acetonitrile (55 mL) was added Cs$_2$CO$_3$ (6.5 g, 20.0 mmol) and bromoacetonitrile (0.713 g, 5.95 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (1.1 g, 92% yield): MS (ES) m/z 292 (M+1).

Example 274

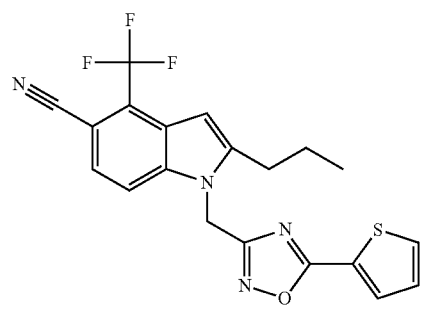 [SMILES: CCCc1cc2c(C(F)(F)F)c(C#N)ccc2n1Cc1noc(-c2cccs2)n1]

2-Propyl-1-{[5-(2-thienyl)-1,2,4-oxadiazol-3-yl]methyl}-4-(trifluoromethyl)-1H-indole-5-carbonitrile To a solution of 2-propyl-4-(trifluoromethyl)-1H-indole-5-carbonitrile (Example 153A) (0.150 g, 0.595 mmol) in anhydrous acetonitrile (25 mL) was added Cs$_2$CO$_3$ (0.193 g, 0.595 mmol) and 3-(bromomethyl)-5-(2-thienyl)-1,2,4-oxadiazole (0.213 g, 0.893 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (0.159 g, 64% yield): MS (ES) m/z 416 (M⁺).

Example 275

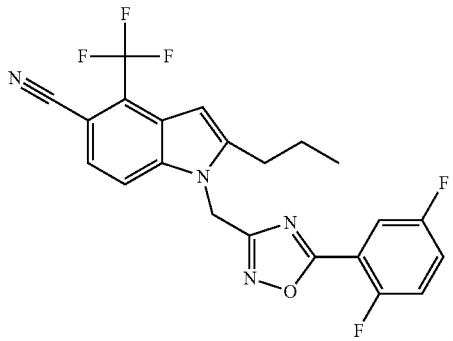 [SMILES: CCCc1cc2c(C(F)(F)F)c(C#N)ccc2n1Cc1noc(-c2cc(F)ccc2F)n1]

1-{[5-(2,5-Difluorophenyl)-1,2,4-oxadiazol-3-yl]methyl}-2-propyl-4-(trifluoromethyl)-1H-indole-5-carbonitrile

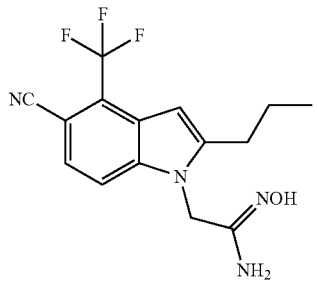

A. 2-[5-Cyano-2-propyl-4-(trifluoromethyl)-1H-indol-1-yl]-N-hydroxyethanimidamide Synthesized from 1-(cyanomethyl)-2-propyl-4-(trifluoromethyl)-1H-indole-5-carbonitrile (Example 273) in a manner similar to Example 64.

B. 1-{[5-(2,5-Difluorophenyl)-1,2,4-oxadiazol-3-yl]methyl}-2-propyl-4-(trifluoromethyl)-1H-indole-5-carbonitrile To a solution of (1Z)-2-[5-cyano-2-propyl-4-(trifluoromethyl)-1H-indol-1-yl]-N-hydroxyethanimidamide (0.050 g, 0.154 mmol) in anhydrous acetonitrile (2.0 mL) under N₂, was added 2,5-difluorobenzoyl chloride (0.121 g, 0.177 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.029 g (42% yield) of pure product: MS (ES) m/z 446 (M⁺).

Example 276

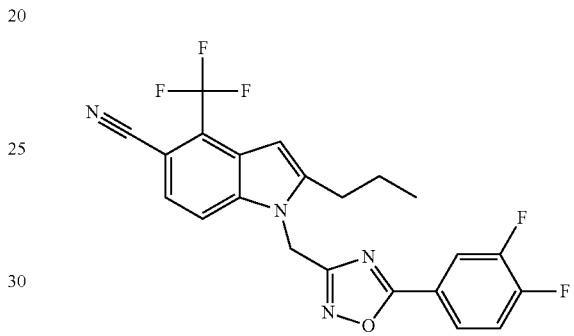

1-{[5-(3,4-Difluorophenyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.050 g, 0.154 mmol) in anhydrous acetonitrile (2.0 mL) under N₂, was added 3,4-difluorobenzoyl chloride (0.121 g, 0.177 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.033 g (48% yield) of pure product: MS (ES) m/z 446 (M⁺).

Example 277

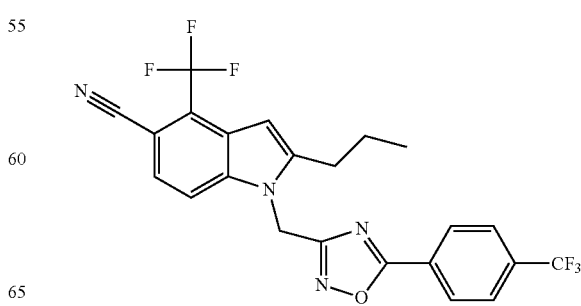

2-Propyl-4-(trifluoromethyl)-1-({5-[4-(trifluoromethyl)phenyl]-1,2,4-oxadiazol-3-yl}methyl)-1H-indole-5-carbonitrile To a solution of 2-[5-cyano-2-propyl-4-(trifluoromethyl)-1H-indol-1-yl]-N-hydroxyethanimidamide (Example 275A) (0.200 g, 0.616 mmol) in anhydrous acetonitrile (6.0 mL) under N$_2$, was added 4-(trifluoromethyl)benzoyl chloride (0.513 g, 2.46 mmol) and N,N-diisopropylethylamine (1.0 mL, 10.4 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.189 g (64% yield) of pure product: MS (ES) m/z 478 (M$^+$).

Example 278

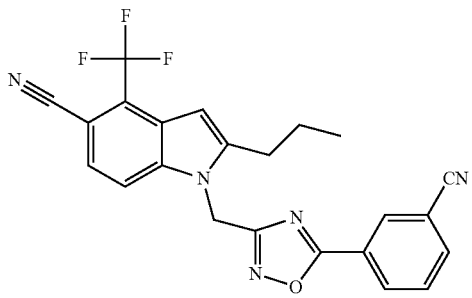 [SMILES: CCCc1cc2c(C(F)(F)F)c(C#N)ccc2n1Cc1noc(-c2cccc(C#N)c2)n1]

1-{[5-(3-Cyanophenyl)-1,2,4-oxadiazol-3-yl]methyl}-2-propyl-4-(trifluoromethyl)-1H-indole-5-carbonitrile To a solution of (1Z)-2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N$_2$, was added 3-cyanobenzoyl chloride (0.204 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.079 g (59% yield) of pure product: MS (ES) m/z 435 (M$^+$).

Example 279

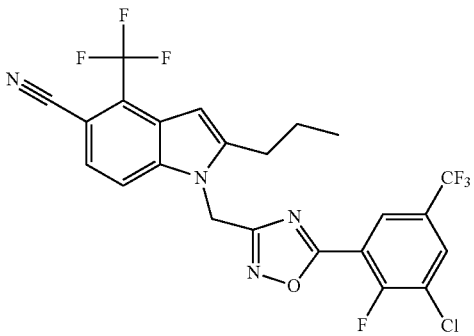 [SMILES: CCCc1cc2c(C(F)(F)F)c(C#N)ccc2n1Cc1noc(-c2cc(C(F)(F)F)cc(Cl)c2F)n1]

1-({5-[3-Chloro-2-fluoro-5-(trifluoromethyl)phenyl]-1,2,4-oxadiazol-3-yl}methyl)-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N$_2$, was added 3-chloro-2-fluoro-5-(trifluoromethyl)benzoyl chloride (0.321 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.066 g (40% yield) of pure product: MS (ES) m/z 530 (M$^+$).

Example 280

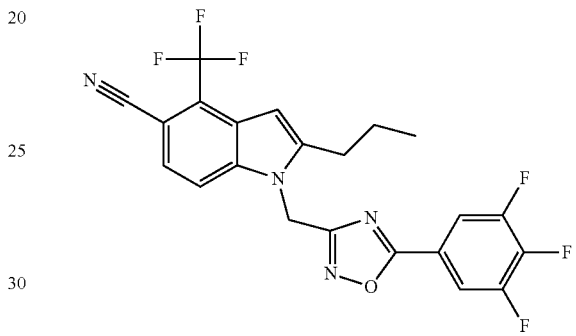

2-Propyl-4-(trifluoromethyl)-1-{[5-(3,4,5-trifluorophenyl)-1,2,4-oxadiazol-3-yl]methyl}-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N$_2$, was added 3,4,5-trifluorobenzoyl chloride (0.241 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.065 g (45% yield) of pure product: MS (ES) m/z 464 (M$^+$).

Example 281

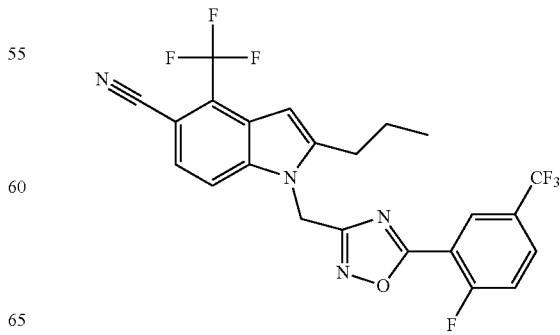

1-({5-[2-Fluoro-5-(trifluoromethyl)phenyl]-1,2,4-oxadiazol-3-yl}methyl)-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N₂, was added 2-fluoro-5-(trifluoromethyl)benzoyl chloride (0.279 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.069 g (45% yield) of pure product: MS (ES) m/z 496 (M⁺).

Example 282

1-({5-[2-Chloro-5-(trifluoromethyl)phenyl]-1,2,4-oxadiazol-3-yl}methyl)-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N₂, was added 2-chloro-5-(trifluoromethyl)benzoyl chloride (0.299 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.015 g (16% yield) of pure product: MS (ES) m/z 512 (M⁺).

Example 284

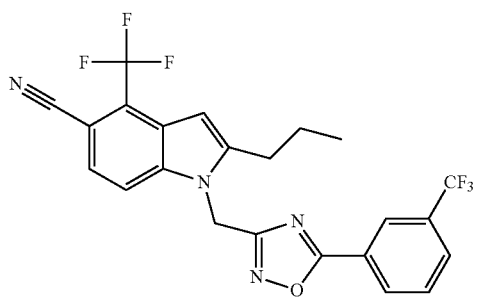 [SMILES: CCCc1cc2c(C(F)(F)F)c(C#N)ccc2n1Cc1noc(-c2cccc(C(F)(F)F)c2)n1]

2-Propyl-4-(trifluoromethyl)-1-({5-[3-(trifluoromethyl)phenyl]-1,2,4-oxadiazol-3-yl}methyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N₂, was added 3-(trifluoromethyl)benzoyl chloride (0.256 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.061 g (41% yield) of pure product: MS (ES) m/z 478 (M⁺).

Example 283

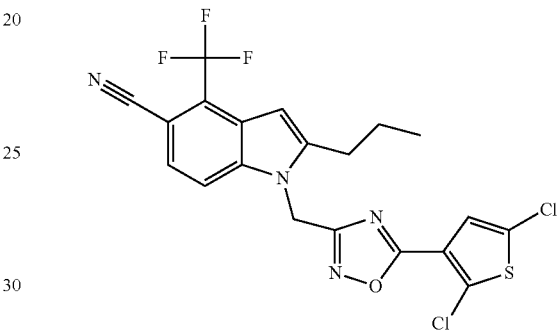

1-{[5-(2,5-Dichloro-3-thienyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (3.0 mL) under N₂, was added 2,5-dichloro-3-thiophenecarbonyl chloride (0.265 g, 1.23 mmol) and N,N-diisopropylethylamine (0.50 mL, 5.21 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.055 g (37% yield) of pure product: MS (ES) m/z 485 (M+1).

Example 285

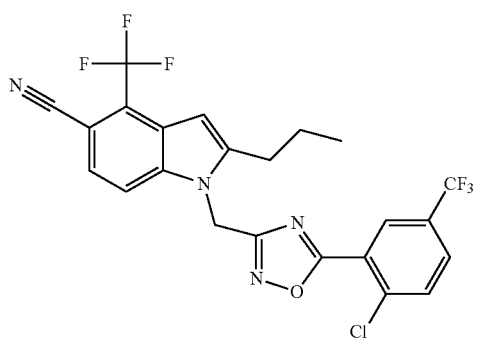 [SMILES: CCCc1cc2c(C(F)(F)F)c(C#N)ccc2n1Cc1noc(-c2cc(C(F)(F)F)ccc2Cl)n1]

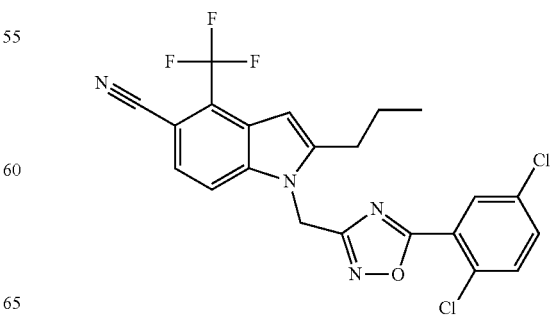

1-{[5-(2,5-Dichlorophenyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.05 g, 0.154 mmol) in anhydrous acetonitrile (10.0 mL) under N$_2$, was added 2,5-dichlorobenzoyl chloride (0.111 g, 0.529 mmol) and triethylamine (1.0 mL, 13.6 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.031 g (42% yield) of pure product: MS (ES) m/z 479 (M+1).

Example 286

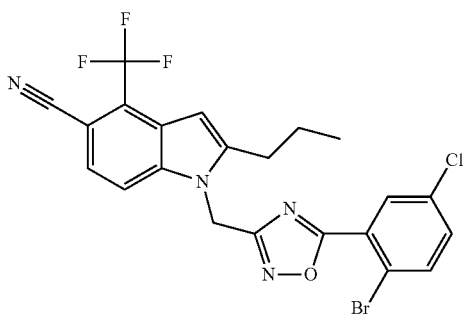 [SMILES: CCCc1cc2c(C(F)(F)F)c(C#N)ccc2n1Cc1noc(-c2cc(Cl)ccc2Br)n1]

1-{[5-(2-Bromo-5-chlorophenyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.05 g, 0.154 mmol) in anhydrous acetonitrile (10.0 mL) under N$_2$, was added 2-bromo-5-chlorobenzoyl chloride (0.134 g, 0.529 mmol) and triethylamine (1.0 mL, 13.6 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.029 g (36% yield) of pure product: MS (ES) m/z 523 (M+1).

Example 287

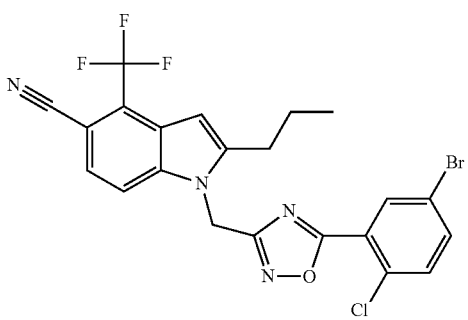 [SMILES: CCCc1cc2c(C(F)(F)F)c(C#N)ccc2n1Cc1noc(-c2cc(Br)ccc2Cl)n1]

1-{[5-(5-Bromo-2-chlorophenyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.05 g, 0.154 mmol) in anhydrous acetonitrile (10.0 mL) under N$_2$, was added 5-bromo-2-chlorobenzoyl chloride (0.134 g, 0.529 mmol) and triethylamine (1.0 mL, 13.6 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.021 g (26% yield) of pure product: MS (ES) m/z 523 (M+1).

Example 288

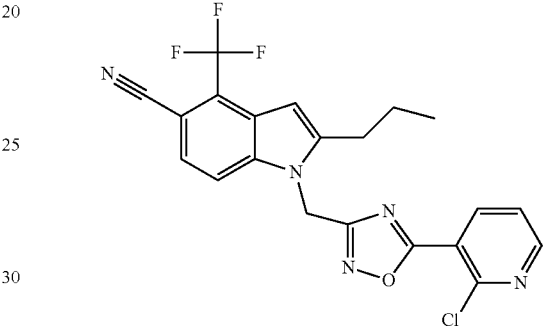

1-{[5-(2-Chloro-3-pyridinyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (10.0 mL) under N$_2$, was added 2-chloro-3-pyridinecarbonyl chloride (0.186 g, 1.10 mmol) and triethylamine (1.0 mL, 13.6 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.047 g (40% yield) of pure product: MS (ES) m/z 445 (M$^+$).

Example 289

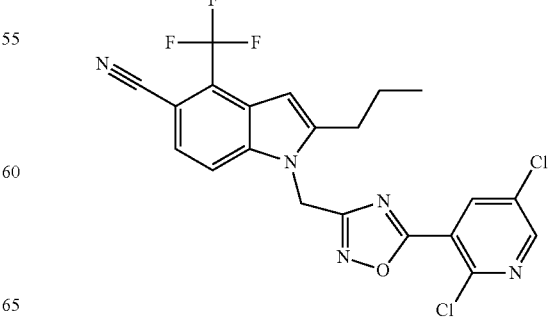

1-{[5-(2,5-Dichloro-3-pyridinyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (10.0 mL) under $N_2$, was added 2,5-dichloro-3-pyridinecarbonyl chloride (0.223 g, 1.10 mmol) and triethylamine (1.0 mL, 13.6 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.021 g (14% yield) of pure product: MS (ES) m/z 480 (M+1).

1-{[5-(2-Chloro-5-iodophenyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.05 g, 0.154 mmol) in anhydrous acetonitrile (10.0 mL) under $N_2$, was added 2-chloro-5-iodobenzoyl chloride (0.159 g, 0.528 mmol) and triethylamine (0.5 mL, 6.81 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.019 g (22% yield) of pure product: MS (ES) m/z 570 (M+1).

Example 290

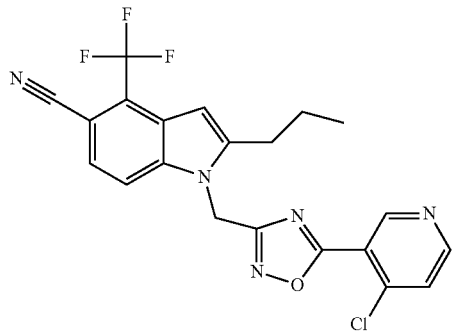 [SMILES: CCCc1cc2c(C(F)(F)F)c(C#N)ccc2n1Cc1noc(-c2cnccc2Cl)n1]

1-{[5-(4-Chloro-3-pyridinyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.100 g, 0.308 mmol) in anhydrous acetonitrile (10.0 mL) under $N_2$, was added 4-chloro-3-pyridinecarbonyl chloride hydrochloride (0.223 g, 1.10 mmol) and triethylamine (1.0 mL, 13.6 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.015 g (11% yield) of pure product: MS (ES) m/z 445 (M+).

Example 292

1-{[5-(5-Chloro-1,3-dimethyl-1H-pyrazolo[3,4-b]pyridin-6-yl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.05 g, 0.154 mmol) in anhydrous acetonitrile (10.0 mL) under $N_2$, was added 5-chloro-1,3-dimethyl-1H-pyrazolo[3,4-b]pyridine-6-carbonyl chloride (0.095 g, 0.389 mmol) and triethylamine (0.5 mL, 6.81 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.061 g (77% yield) of pure product: MS (ES) m/z 513 (M+).

Example 291

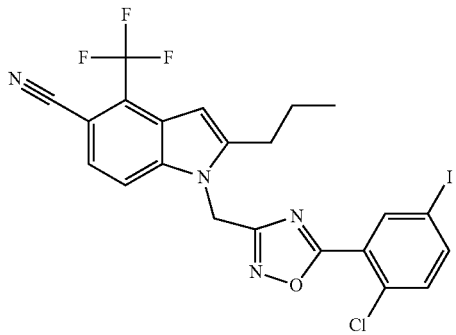 [SMILES: CCCc1cc2c(C(F)(F)F)c(C#N)ccc2n1Cc1noc(-c2cc(I)ccc2Cl)n1]

Example 293

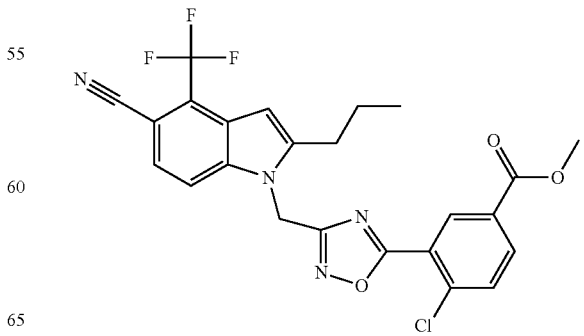

233

Methyl 4-chloro-3-(3-{[5-cyano-2-propyl-4-(trifluoromethyl)-1H-indol-1-yl]methyl}-1,2,4-oxadiazol-5-yl)benzoate A solution containing 1-{[5-(2-chloro-5-iodophenyl)-1,2,4-oxadiazol-3-yl]methyl}-2-propyl-4-(trifluoromethyl)-1H-indole-5-carbonitrile (Example 291) (0.378 g, 0.662 mmol), 1,1-bisdiphenylphosphinoferrocene (0.073 g, 0.132 mmol), E₃N (1.0 mL, 13.6 mmol), Pd(OAc)₂ (0.032 g, 0.132 mmol), anhydrous MeOH (2.0 mL) and anhydrous DMF (20 mL). The mixture was then stirred at 70° C. under a carbon monoxide atmosphere for a period of 4 h and then allowed to cooled to rt. The reaction was partitioned between NaHCO₃ and EtOAc, dried (MgSO₄) and concentrated to dryness. The mixture was purified on a biotage prepak column (0-10% EtOAc-hexanes gradient) to give 0.214 g (64% yield) of pure product: MS (ES) m/z 502 (M⁺).

Example 294

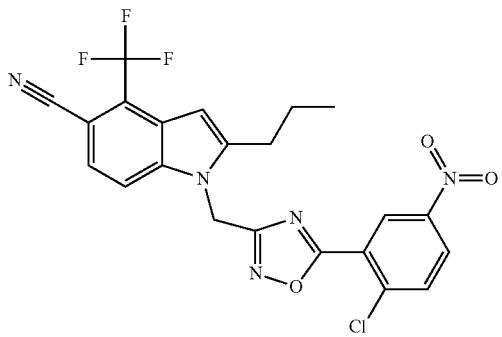 [SMILES: CCCc1cc2c(C(F)(F)F)c(C#N)ccc2n1Cc1noc(-c2cc([N+](=O)[O-])ccc2Cl)n1]

1-{[5-(2-Chloro-5-nitrophenyl)-1,2,4-oxadiazol-3-yl]methyl}-2-propyl-4-(trifluoromethyl)-1H-indole-5-carbonitrile To a solution of 2-[5-cyano-2-propyl-4-(trifluoromethyl)-1H-indol-1-yl]-N-hydroxyethanimidamide (Example 275A) (0.05 g, 0.154 mmol) in anhydrous acetonitrile (10.0 mL) under N₂, was added 2-chloro-5-nitrobenzoyl chloride (0.086 g, 0.390 mmol) and triethylamine (0.5 mL, 6.81 mmol). The mixture was then heated in a microwave at 150° C. for 30 min. Upon cooling, the mixture was poured onto a biotage prepak column and the mixture was purified by flash chromatography (0-25% EtOAc-hexanes gradient) to give 0.051 g (68% yield) of pure product: MS (ES) m/z 489 (M⁺).

Example 295

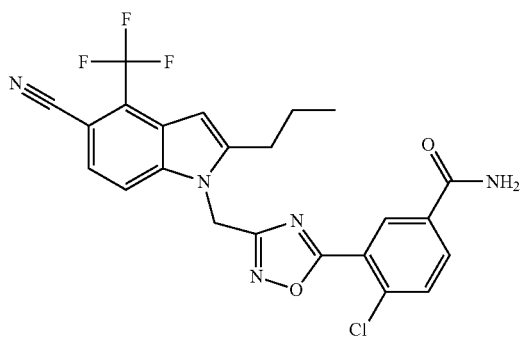 [SMILES: CCCc1cc2c(C(F)(F)F)c(C#N)ccc2n1Cc1noc(-c2cc(C(N)=O)ccc2Cl)n1]

234

4-Chloro-3-(3-{[5-cyano-2-propyl-4-(trifluoromethyl)-1H-indol-1-yl]methyl}-1,2,4-oxadiazol-5-yl)benzamide

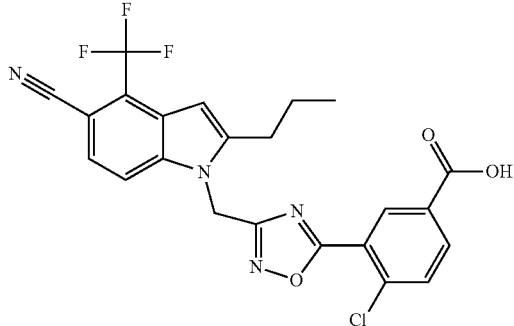 [SMILES: CCCc1cc2c(C(F)(F)F)c(C#N)ccc2n1Cc1noc(-c2cc(C(=O)O)ccc2Cl)n1]

A. 4-Chloro-3-(3-{[5-cyano-2-propyl-4-(trifluoromethyl)-1H-indol-1-yl]methyl}-1,2,4-oxadiazol-5-yl)benzoic acid To a solution of methyl 4-chloro-3-(3-{[5-cyano-2-propyl-4-(trifluoromethyl)-1H-indol-1-yl]methyl}-1,2,4-oxadiazol-5-yl)benzoate (Example 293) (0.190 g, 0.378 mmol) in 1,4-dioxane (70 mL) was added LiOH—H₂O (0.063 g, 1.50 mmol) and water (30 mL). The mixture was stirred at rt for 17 h followed by cooling to 0-5° C. The solution was made acidic using concentrated HCl, extracted into Et₂O, dried (MgSO₄) and concentrated to afford a pure solid (0.131 g, 71% yield): MS (ES) m/z 488 (M⁺).

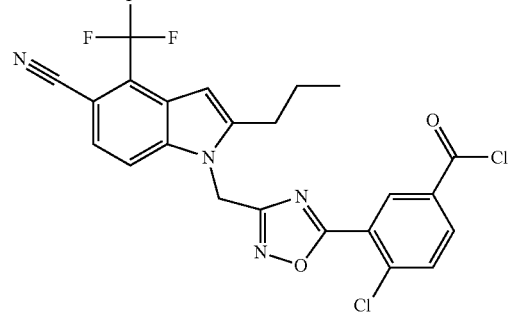

B. 4-Chloro-3-(3-{[5-cyano-2-propyl-4-(trifluoromethyl)-1H-indol-1-yl]methyl}-1,2,4-oxadiazol-5-yl)benzoyl chloride A solution was prepared using 4-chloro-3-(3-{[5-cyano-2-propyl-4-(trifluoromethyl)-1H-indol-1-yl]methyl}-1,2,4-oxadiazol-5-yl)benzoic acid (0.100 g, 0.204 mmol), DMF (0.100 mL), (COCl)₂ (2.0 mL, 21.0 mmol) and anhydrous CH₂Cl₂ (25 mL). The mixture was stirred at rt and for a period of 16 h and concentrated to dryness. The resulting product was used without purification (0.113 g).

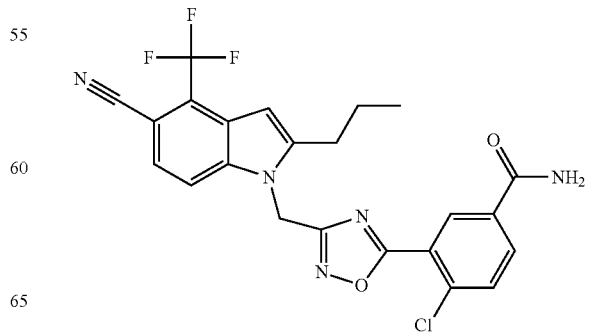

C. 4-Chloro-3-(3-{[5-cyano-2-propyl-4-(trifluoromethyl)-1H-indol-1-yl]methyl}-1,2,4-oxadiazol-5-yl)benzamide A round bottom flask was mixed with 4-chloro-3-(3-{[5-cyano-2-propyl-4-(trifluoromethyl)-1H-indol-1-yl]methyl}-1,2,4-oxadiazol-5-yl)benzoyl chloride (0.037 g, 0.07 mmol) and 2.0 M NH₃ in MeOH (5.0 mL). The mixture was stirred at rt for 2 h and concentrated to dryness. The resulting solid was crystallized with Et₂O, filtered in vacuo and dried under high vacuum to afford a pure solid (0.021 g, 58% yield): MS (ES) m/z 487 (M⁺).

Example 296

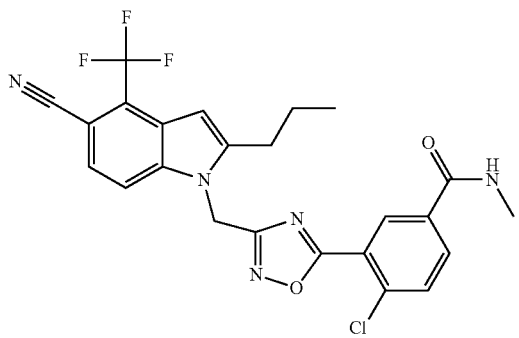 [SMILES: CCCc1cc2c(C(F)(F)F)c(C#N)ccc2n1Cc1noc(-c2cc(C(=O)NC)ccc2Cl)n1]

4-Chloro-3-(3-{[5-cyano-2-propyl-4-(trifluoromethyl)-1H-indol-1-yl]methyl}-1,2,4-oxadiazol-5-yl)-N-methylbenzamide A round bottom flask was mixed with 4-chloro-3-(3-{[5-cyano-2-propyl-4-(trifluoromethyl)-1H-indol-1-yl]methyl}-1,2,4-oxadiazol-5-yl)benzoyl chloride (Example 295B) (0.037 g, 0.07 mmol) and 1.0M MeNH₂ in THF (10.0 mL). The mixture was stirred at rt for 2 h and concentrated to dryness. The resulting solid was crystallized with Et₂O, filtered in vacuo and dried under high vacuum to afford a pure solid (0.022 g, 59% yield): MS (ES) m/z 501 (M⁺).

Example 297

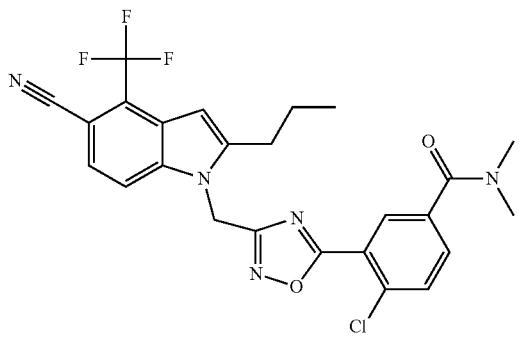 [SMILES: CCCc1cc2c(C(F)(F)F)c(C#N)ccc2n1Cc1noc(-c2cc(C(=O)N(C)C)ccc2Cl)n1]

4-Chloro-3-(3-{[5-cyano-2-propyl-4-(trifluoromethyl)-1H-indol-1-yl]methyl}-1,2,4-oxadiazol-5-yl)-N,N-dimethylbenzamide A round bottom flask was mixed with 4-chloro-3-(3-{[5-cyano-2-propyl-4-(trifluoromethyl)-1H-indol-1-yl]methyl}-1,2,4-oxadiazol-5-yl)benzoyl chloride (Example 295B) (0.037 g, 0.07 mmol) and Me₂NH (2.0 mL), and THF (5.0 mL). The mixture was stirred at rt for 2 h and concentrated to dryness. The resulting solid was crystallized with Et₂O, filtered in vacuo and dried under high vacuum to afford a pure solid (0.025 g, 66% yield): MS (ES) m/z 515 (M⁺).

Example 298

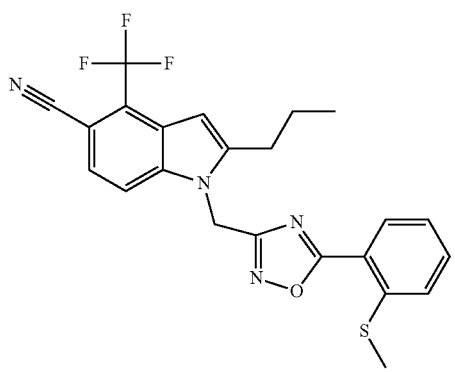 [SMILES: CCCc1cc2c(C(F)(F)F)c(C#N)ccc2n1Cc1noc(-c2ccccc2SC)n1]

1-({5-[2-(Methylthio)phenyl]-1,2,4-oxadiazol-3-yl}methyl)-2-propyl-4-(trifluoromethyl)-1H-indole-5-carbonitrile A solution was prepared using 2-[5-cyano-2-propyl-4-(trifluoromethyl)-1H-indol-1-yl]-N-hydroxyethanimidamide (Example 275A) (0.100 g, 0.308 mmol), 2-(methylthio)benzoic acid (0.076 g, 0.463 mmol), HATU (0.176 g, 0.463 mmol), triethylamine (1.0 mL, 13.6 mmol) and anhydrous DMF (10 mL). The mixture was then heated in a microwave at 150° C. for 30 min. Upon cooling, the mixture was poured onto a biotage prepak column and the mixture was purified by flash chromatography (0-25% EtOAc-hexanes gradient) to give 0.042 g (30% yield) of pure product: MS (ES) m/z 456 (M⁺).

Example 299

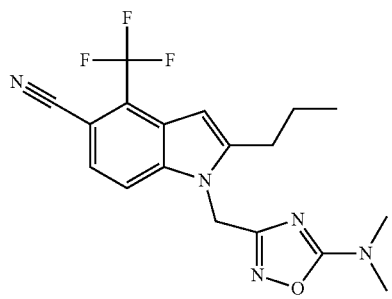 [SMILES: CCCc1cc2c(C(F)(F)F)c(C#N)ccc2n1Cc1noc(N(C)C)n1]

1-{[5-(Dimethylamino)-1,2,4-oxadiazol-3-yl]methyl}-2-propyl-4-(trifluoromethyl)-1H-indole-5-carbonitrile A solution was prepared using 2-[5-cyano-2-propyl-4-(trifluoromethyl)-1H-indol-1-yl]-N-hydroxyethanimidamide (Example 275A) (0.100 g, 0.308 mmol), 2-chloro-5-(methylthio)benzoic acid (0.404 g, 2.0 mmol), HATU (1.50 g, 0.040 mmol), triethylamine (1.0 mL, 13.6 mmol) and anhydrous DMF (10 mL). The mixture was then heated in a microwave at 150° C. for 30 min. Upon cooling, the mixture was poured onto a biotage prepak column and the mixture was purified by flash chromatography (0-25% EtOAc-hexanes gradient) to give 0.035 g (42% yield) of pure product as the undesired product: MS (ES) m/z 377 (M+).

Example 300

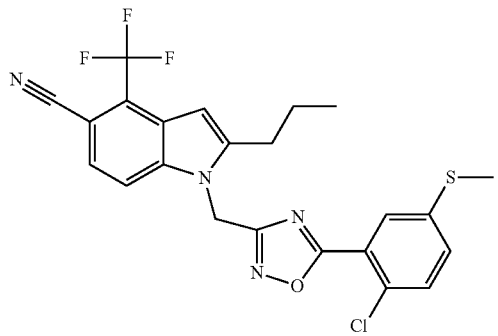 [SMILES: CCCc1cc2c(C(F)(F)F)c(C#N)ccc2n1Cc1noc(-c2cc(SC)ccc2Cl)n1]

1-({5-[2-Chloro-5-(methylthio)phenyl]-1,2,4-oxadiazol-3-yl}methyl)-2-propyl-4-(trifluoromethyl)-1H-indole-5-carbonitrile The reaction from Example 299 afforded 0.031 g (21% yield) of the product desired product: MS (ES) m/z 490 (M+).

Example 301

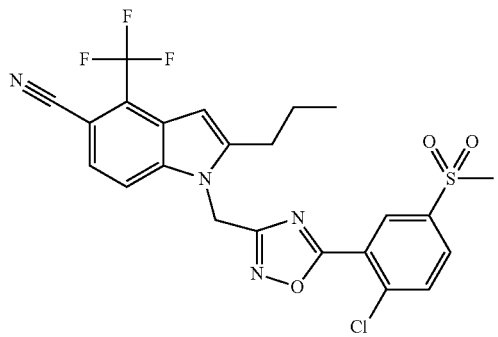 [SMILES: CCCc1cc2c(C(F)(F)F)c(C#N)ccc2n1Cc1noc(-c2cc(S(C)(=O)=O)ccc2Cl)n1]

1-({5-[2-Chloro-5-(methylsulfonyl)phenyl]-1,2,4-oxadiazol-3-yl}methyl)-2-propyl-4-(trifluoromethyl)-1H-indole-5-carbonitrile

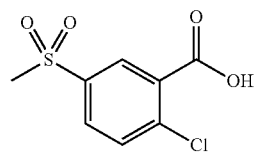

A. 2-Chloro-5-(methylsulfonyl)benzoic acid

A solution was prepared using 2-chloro-5-(methylthio) benzoic acid (2.0 g, 9.90 mmol), oxone (30.4 g, 49.3 mmol) and anhydrous MeOH (100 mL). The reaction was allowed to stir at rt for 17 h and was partitioned between water and Et$_2$O. The organic were dried (MgSO$_4$) and concentrated to dryness to give the desired crude solid (2.0 g, 87% yield). The solid was used without further purification.

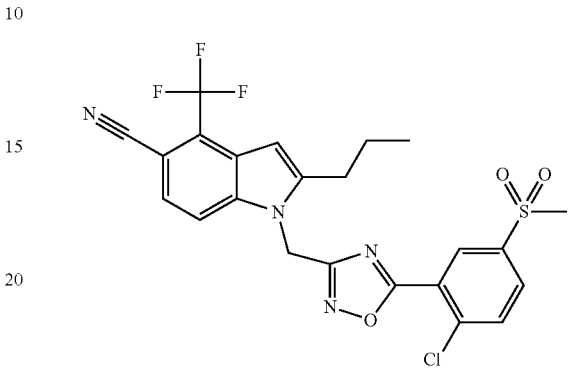

B. 1-({5-[2-Chloro-5-(methylsulfonyl)phenyl]-1,2,4-oxadiazol-3-yl}methyl)-2-propyl-4-(trifluoromethyl)-1H-indole-5-carbonitrile A solution was prepared using 2-[5-cyano-2-propyl-4-(trifluoromethyl)-1H-indol-1-yl]-N-hydroxyethanimidamide (Example 275A) (0.100 g, 0.308 mmol), 2-chloro-5-(methylsulfonyl)benzoic acid (0.108 g, 0.463 mmol), HATU (0.176 g, 0.463 mmol), triethylamine (0.047 g, 0.463 mmol) and anhydrous DMF (10 mL). The mixture was then heated in a microwave at 150° C. for 30 min. Upon cooling, the mixture was poured onto a biotage prepak column and the mixture was purified by flash chromatography (0-25% EtOAc-hexanes gradient) to give 0.042 g (26% yield) of pure product: MS (ES) m/z 522 (M+).

Example 302

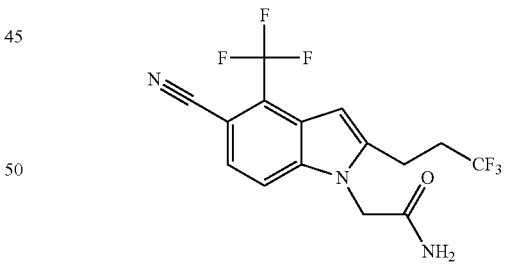

2-[5-Cyano-4-(trifluoromethyl)-2-(3,3,3-trifluoropropyl)-1H-indol-1-yl]acetamide

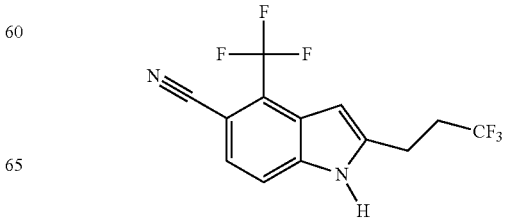

A. 4-(Trifluoromethyl)-2-(3,3,3-trifluoropropyl)-1H-indole-5-carbonitrile

In a round bottom flask was mixed 4-amino-3-methyl-2-(trifluoromethyl)benzonitrile (Example 191C) (3.7 g, 0.0185 moles), p-toluenesulfonic acid (0.100 g), benzophenone (4.0 g, 0.222 mol) and anhydrous toluene (100 mL). The mixture was heated at reflux for 1 h and concentrated to dryness. The crude solid was dissolved in $CCl_4$ (100 mL) and the insolubles were filtered off and discarded. The organic solution was mixed with AIBN (0.100 g) and N-bromosuccimide (4.0 g, 0.0225 mol). The mixture was heated at reflux for 1 h and cooled to 0-5° C. The insolubles were filtered off and the filtrate was concentrated to dryness. The crude oil was dissolved with $Et_2O$ (250 mL) and this solution was mixed with triphenylphosphine (5.9 g, 0.0225 mol). The resulting solid was filtered to give a crude orange solid which was mixed with 2.0N HCl (50 mL) and heated at reflux for 2 h. The reaction mixture was concentrated to dryness and the resulting crude salt was mixed with $Et_3N$ (4.5 g 0.0445 mol), HATU (17.0 g, 0.0448 mol), trifluoromethylbutyric acid (6.4 g, 0.0448 mol) and anhydrous DMF (150 mL). The reaction was allowed to stir at rt for 1 h and mixed with additional $Et_3N$ (9.0 g, 0.089 mol) and stirred for an additional hour. The mixture was partitioned between saturated $NaHCO_3$ and EtOAc. The organics were dried ($MgSO_4$) and concentrated to dryness. The crude solid was chromatographed using a biotage prepak flash column (0-20% EtOAc-hexanes gradient) to yield the desired indole (1.1 g, 19% yield): $^1$H NMR (400 MHz, $CDCl_3$) δ 9.93 (s, 1H), 7.57 (d, J=8.0 Hz, 1H), 7.46 (d, J=8.0 Hz, 1H), 6.55 (s, 1H), 3.11-3.07 (t, J=8.0 Hz, 2H), 2.60-2.52 (m, 2H).

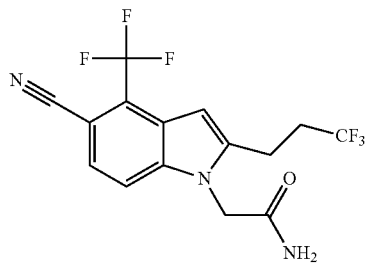 [SMILES: N#Cc1ccc2c(cc(CCC(F)(F)F)n2CC(N)=O)c1C(F)(F)F]

B. 2-[5-Cyano-4-(trifluoromethyl)-2-(3,3,3-trifluoropropyl)-1H-indol-1-yl]acetamide To a solution of 4-(trifluoromethyl)-2-(3,3,3-trifluoropropyl)-1H-indole-5-carbonitrile (Example 302A) (0.200 g, 0.653 mmol) in anhydrous acetonitrile (50 mL) was added $Cs_2CO_3$ (0.851 g, 0.2.612 mmol) and 2-bromoacetamide (0.300 g, 1.37 mmol). The mixture was heated under $N_2$, for 2 h. Upon cooling, the mixture was partitioned between EtOAc and water. The organic phase was separated, dried ($MgSO_4$) and concentrated in vacuo. The residue was purified by flash chromatography (0-20% EtOAc-hexanes gradient) to afford a pure product (0.121 g, 51% yield): MS (ES) m/z 363 (M$^+$).

Example 303

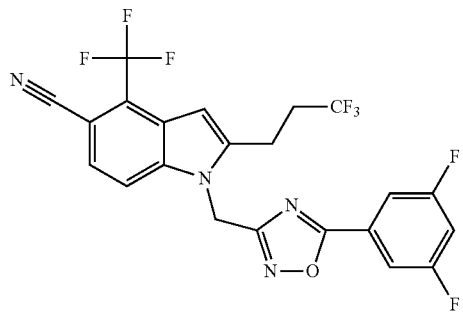 [SMILES: N#Cc1ccc2c(cc(CCC(F)(F)F)n2Cc2noc(-c3cc(F)cc(F)c3)n2)c1C(F)(F)F]

1-{[5-(3,5-Difluorophenyl)-1,2,4-oxadiazol-3-yl]methyl}-4-(trifluoromethyl)-2-(3,3,3-trifluoropropyl)-1H-indole-5-carbonitrile To a solution of 4-(trifluoromethyl)-2-(3,3,3-trifluoropropyl)-1H-indole-5-carbonitrile (Example 302A) (0.200 g, 0.653 mmol) in anhydrous acetonitrile (25 mL) was added $Cs_2CO_3$ (0.851 g, 0.2.612 mmol) and 3-(chloromethyl)-5-(3,5-difluorophenyl)-1,2,4-oxadiazole (0.226 g, 0.979 mmol). The mixture was heated under $N_2$, for 2 h. Upon cooling, the mixture was partitioned between EtOAc and water. The organic phase was separated, dried ($MgSO_4$) and concentrated in vacuo. The residue was purified by flash chromatography (0-20% EtOAc-hexanes gradient) to afford a pure product (0.078 g, 24% yield): MS (ES) m/z 500 (M$^+$).

Example 304

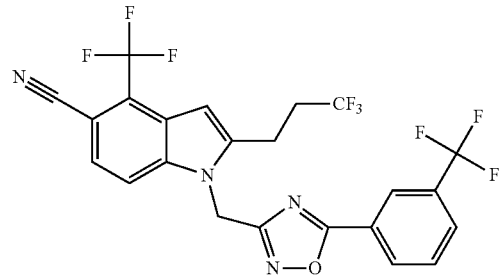 [SMILES: N#Cc1ccc2c(cc(CCC(F)(F)F)n2Cc2noc(-c3cccc(C(F)(F)F)c3)n2)c1C(F)(F)F]

4-(Trifluoromethyl)-1-({5-[3-(trifluoromethyl)phenyl]-1,2,4-oxadiazol-3-yl}methyl)-2-(3,3,3-trifluoropropyl)-1H-indole-5-carbonitrile To a solution of 4-(trifluoromethyl)-2-(3,3,3-trifluoropropyl)-1H-indole-5-carbonitrile (Example 302A) (0.200 g, 0.653 mmol) in anhydrous acetonitrile (25 mL) was added $Cs_2CO_3$ (0.851 g, 2.612 mmol) and 3-(chloromethyl)-5-[3-(trifluoromethyl)phenyl]-1,2,4-oxadiazole (0.257 g, 0.979 mmol). The mixture was heated under $N_2$, for 2 h. Upon cooling, the mixture was partitioned between EtOAc and water. The organic phase was separated, dried ($MgSO_4$) and concentrated in vacuo. The residue was purified by flash chromatography (0-20% EtOAc-hexanes gradient) to afford a pure product (0.051 g, 24% yield): MS (ES) m/z 532 (M+).

Example 305

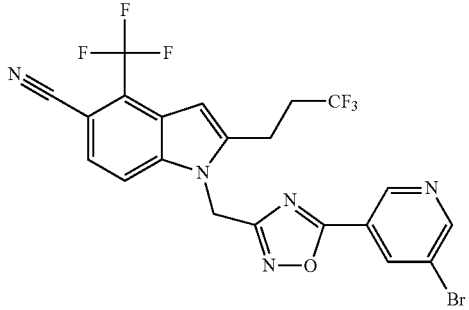 [SMILES: N#Cc1ccc2c(cc(CCC(F)(F)F)n2Cc2noc(-c3cncc(Br)c3)n2)c1C(F)(F)F]

1-{[5-(5-Bromo-3-pyridinyl)-1,2,4-oxadiazol-3-yl]methyl}-4-(trifluoromethyl)-2-(3,3,3-trifluoropropyl)-1H-indole-5-carbonitrile To a solution of 4-(trifluoromethyl)-2-(3,3,3-trifluoropropyl)-1H-indole-5-carbonitrile (Example 302A) (0.200 g, 0.653 mmol) in anhydrous acetonitrile (25 mL) was added Cs$_2$CO$_3$ (0.851 g, 0.2.612 mmol) and 3-bromo-5-[3-(chloromethyl)-1,2,4-oxadiazol-5-yl]pyridine (0.269 g, 0.979 mmol). The mixture was heated under N$_2$, for 2 h. Upon cooling, the mixture was partitioned between EtOAc and water. The organic phase was separated, dried (MgSO$_4$) and concentrated in vacuo. The residue was purified by flash chromatography (0-20% EtOAc-hexanes gradient) to afford a pure product (0.081 g, 23% yield): MS (ES) m/z 544 (M+1).

Example 306

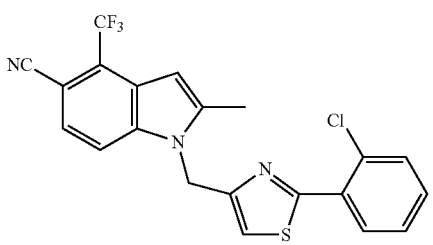 [SMILES: Cc1cc2c(C(F)(F)F)c(C#N)ccc2n1Cc1csc(-c2ccccc2Cl)n1]

1-{[2-(2-Chlorophenyl)-1,3-thiazol-4-yl]methyl}-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 4-(chloromethyl)-2-(2-chlorophenyl)-1,3-thiazole: $^1$H NMR (400 MHz, CDCl$_3$) δ 8.17 (m, 1H), 7.58 (d, J=8.3 Hz, 1H), 7.49 (m, 2H), 7.36 (m, 2H), 6.79 (s, 1H), 6.65 (s, 1H), 5.51 (s, 2H), 2.58 (s, 3H); MS (ES) m/z 432 (M+1) and 434 (M+1, isotope).

Example 307

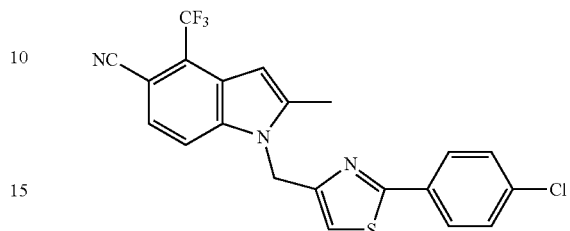

1-{[2-(4-Chlorophenyl)-1,3-thiazol-4-yl]methyl}-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 4-(chloromethyl)-2-(4-chlorophenyl)-1,3-thiazole: MS (ES) m/z 432 (M+1) and 434 (M+1, isotope).

Example 308

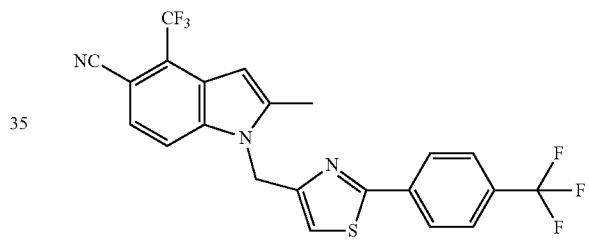

2-Methyl-4-(trifluoromethyl)-1-({2-[4-(trifluoromethyl)phenyl]-1,3-thiazol-4-yl}methyl)-1H-indole-5-carbonitrile Synthesized as described in Example 4 using 2-methyl-4-(trifluoromethyl)-1H-indole-5-carbonitrile (Example 120) and 4-(chloromethyl)-2-[4-(trifluoromethyl)phenyl]-1,3-thiazole: MS (ES) m/z 466 (M+1).

Example 309

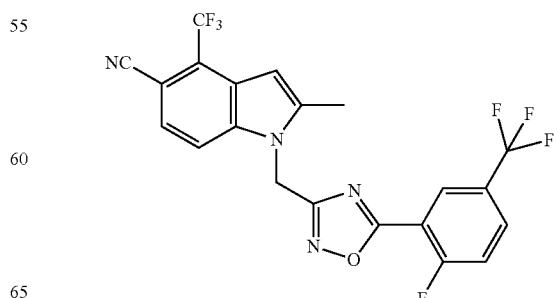

1-({5-[2-Fluoro-5-(trifluoromethyl)phenyl]-1,2,4-oxadiazol-3-yl}methyl)-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 3-(chloromethyl)-5-[2-fluoro-5-(trifluoromethyl)phenyl]-1,2,4-oxadiazole: $^1$H NMR (400 MHz, CDCl$_3$) δ 8.33 (m, 1H), 7.85 (m, 1H), 7.69 (d, J=8.6 Hz, 1H), 7.56 (d, J=8.6 Hz, 1H), 7.39 (d, J=9.3 Hz, 1H), 6.65 (s, 1H), 5.50 (s, 2H), 2.68 (s, 3H); MS (ES) m/z 469 (M+1).

Example 310

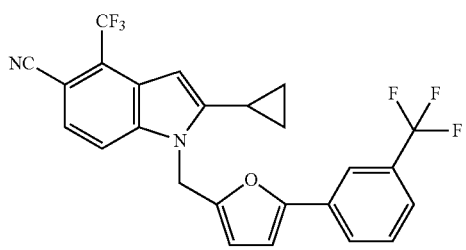 [SMILES: N#Cc1ccc2c(cc(C3CC3)n2Cc2ccc(-c3cccc(C(F)(F)F)c3)o2)c1C(F)(F)F]

2-Cyclopropyl-4-(trifluoromethyl)-1-({5-[3-(trifluoromethyl)phenyl]-2-furanyl}methyl)-1H-indole-5-carbonitrile

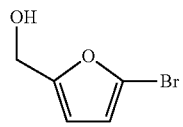

A. (5-Bromo-2-furanyl)methanol

To a solution of 5-bromo-2-furancarbaldehyde (1.0 g, 5.7 mmol) in dry THF (10 mL) was added sodium borohydride (0.217 g, 5.7 mmol) at 0° C. The reaction is stirred at room temperature for 1 h. The reaction was quenched with saturated ammonium chloride and extracted with Et$_2$O three times. The combined organic layers were washed with brine once, dried over MgSO$_4$ and concentrated in vacuo. The residue was purified by radial chromatography (0-45% EtOAc-hexanes gradient) to afford the title compound (0.43 g, 92% yield).

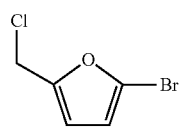

B. 2-Bromo-5-(chloromethyl)furan

To a solution of (5-bromo-2-furanyl)methanol (Example 310A) (144 mmol) in dry carbon tetrachloride (30 mL) was added triphenylphosphine (6.0 g, 228 mmol) at rt. The reaction is heated at 75° C. for 1 h. Concentration and purification by radial chromatography (0-10% EtOAc-hexanes gradient) afforded the title compound with contamination of triphenylphosphine. The product is used without further purification.

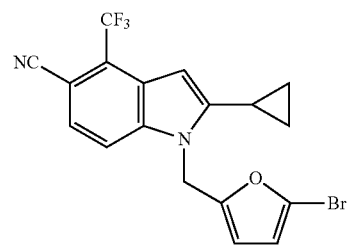 [SMILES: N#Cc1ccc2c(cc(C3CC3)n2Cc2ccc(Br)o2)c1C(F)(F)F]

C. 1-[(5-Bromo-2-furanyl)methyl]-2-cyclopropyl-4-(trifluoromethyl)-1H-indole-5-carbonitrile Synthesized as described in Example 4 using 2-cyclopropyl-4-(trifluoromethyl)-1H-indole-5-carbonitrile (Example 165A) and 2-bromo-5-(chloromethyl)furan (Example 310B): MS (ES) m/z 409 (M+1) and 411 (M+1, isotope).

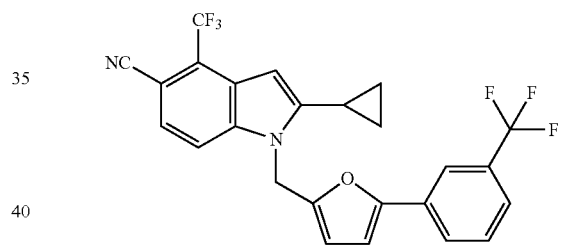

D. 2-Cyclopropyl-4-(trifluoromethyl)-1-({5-[3-(trifluoromethyl)phenyl]-2-furanyl}methyl)-1H-indole-5-carbonitrile To a solution of (1-[(5-bromo-2-furanyl)methyl]-2-cyclopropyl-4-(trifluoromethyl)-1H-indole-5-carbonitrile (Example 310C) (0.05 g, 0.12 mmol) in dry dioxane (3 mL) were added [3-(trifluoromethyl)phenyl]boronic acid (0.046 g, 0.24 mmol), potassium fluoride (0.021 g, 0.36 mmol) and tetrakis(triphenylphosphine)palladium(0) (0.028 g, 0.024 mmol). The mixture was stirred at 100° C. in a sealed tube overnight. Solids were filtered and the filtrate was then concentrated in vacuo. The residue was purified by radial chromatography (0-40% EtOAc-hexanes gradient) and recrystallized by methanol to afford the title compound (0.0185 g, 32% yield): $^1$H NMR (400 MHz, CDCl$_3$) δ 7.79 (s, 1H), 7.69 (d, J=4.9 Hz, 1H), 7.64 (d, J=8.5 Hz, 1H), 7.54 (d, J=8.5 Hz, 1H), 7.51 (m, 1H), 7.38 (m, 1H), 6.63 (d, J=3.4 Hz, 1H), 6.46 (s, 1H), 6.24

(d, J=3.4 Hz, 1H), 5.52 (s, 2H), 2.04 (m, 1H), 1.14 (m, 2H), 0.89 (m, 2H); MS (ES) m/z 475 (M+1).

Example 311

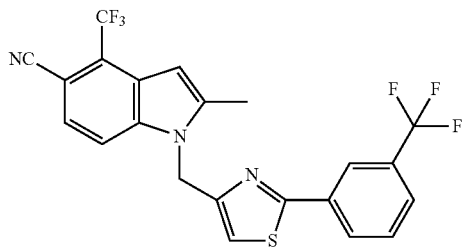 [SMILES: Cc1cc2c(C(F)(F)F)c(C#N)ccc2n1Cc1csc(-c2cccc(C(F)(F)F)c2)n1]

2-Methyl-4-(trifluoromethyl)-1-({2-[3-(trifluoromethyl)phenyl]-1,3-thiazol-4-yl}methyl)-1H-indole-5-carbonitrile

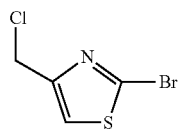

A. 2-Bromo-4-(chloromethyl)-1,3-thiazole

To a solution of ethyl 2-bromo-1,3-thiazole-4-carboxylate (2.0 g, 8.5 mmol) in dry THF (20 mL) was added lithium borohydride (6.4 mL, 2M in THF, 12.7 mmol) at 0° C. The reaction is stirred at rt overnight. The reaction was quenched with saturated ammonium chloride and extracted with Et$_2$O three times. The combined organic layers were washed with brine once, dried over MgSO$_4$ and concentrated in vacuo. The residue was dissolved in dry carbon tetrachloride (20 mL) and PS-triphenyl phosphine (0.180 g, 124 mmol/g, 22.4 mmol) was added. The mixture was heated at 75° C. overnight. The resin was filtered and washed with carbon tetrachloride. The filtrate was concentrated in vacuo and used without further purification.

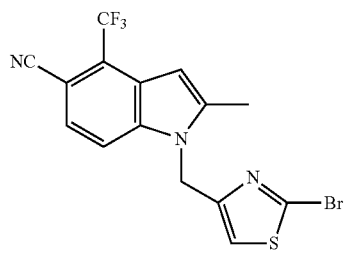 [SMILES: Cc1cc2c(C(F)(F)F)c(C#N)ccc2n1Cc1csc(Br)n1]

B. 1-[(2-Bromo-1,3-thiazol-4-yl)methyl]-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 2-bromo-4-(chloromethyl)-1,3-thiazole (Example 311A): MS (ES) m/z 400 (M+1) and 402 (M+1, isotope).

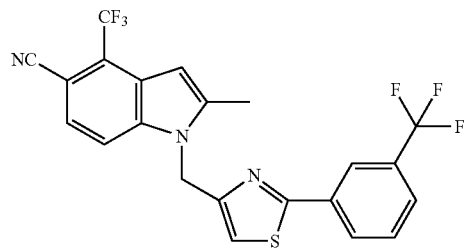 [SMILES: Cc1cc2c(C(F)(F)F)c(C#N)ccc2n1Cc1csc(-c2cccc(C(F)(F)F)c2)n1]

C. 2-Methyl-4-(trifluoromethyl)-1-({2-[3-(trifluoromethyl)phenyl]-1,3-thiazol-4-yl}methyl)-1H-indole-5-carbonitrile Synthesized as described in Example 310D using 1-[(2-bromo-1,3-thiazol-4-yl)methyl]-2-methyl-4-(trifluoromethyl)-1H-indole-5-carbonitrile (Example 311B) and [3-(trifluoromethyl)phenyl]boronic acid: MS (ES) m/z 466 (M+1).

Example 312

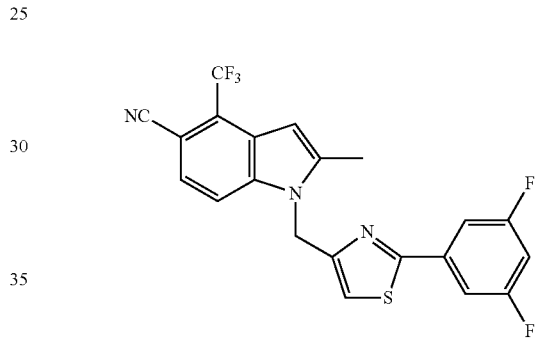

1-{[2-(3,5-Difluorophenyl)-1,3-thiazol-4-yl]methyl}-2-methyl-4-(trifluoromethyl)-1H-indole-5-carbonitrile Synthesized as described in Example 310D using 1-[(2-bromo-1,3-thiazol-4-yl)methyl]-2-methyl-4-(trifluoromethyl)-1H-indole-5-carbonitrile (Example 311B) and [3,5-difluorophenyl]boronic acid: MS (ES) m/z 434 (M+1).

Example 313

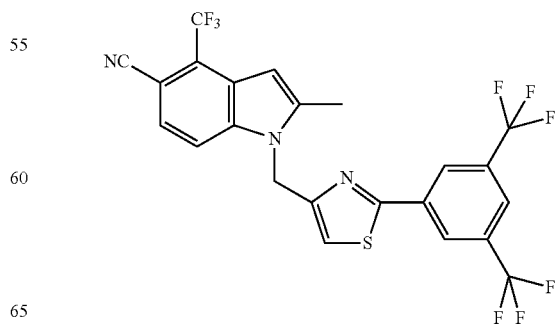

1-({2-[3,5-bis(Trifluoromethyl)phenyl]-1,3-thiazol-4-yl}methyl)-2-methyl-4-(trifluoromethyl)-1H-indole-5-carbonitrile Synthesized as described in Example 310D using 1-[(2-bromo-1,3-thiazol-4-yl)methyl]-2-methyl-4-(trifluoromethyl)-1H-indole-5-carbonitrile (Example 311B) and [3,5-bis(trifluoromethyl)phenyl]boronic acid: MS (ES) m/z 534 (M+1).

Example 314

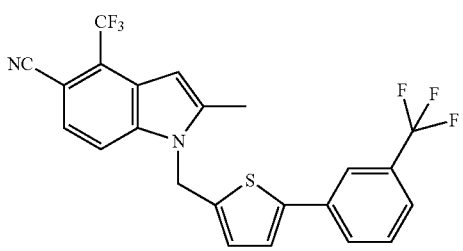 [SMILES: Cc1cc2c(C(F)(F)F)c(C#N)ccc2n1Cc1ccc(-c2cccc(C(F)(F)F)c2)s1]

2-Methyl-4-(trifluoromethyl)-1-({5-[3-(trifluoromethyl)phenyl]-2-thienyl}methyl)-1H-indole-5-carbonitrile

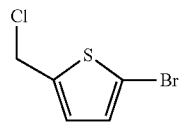

A. 2-Bromo-5-(chloromethyl)thiophene

To a solution of 5-bromo-2-thiophenecarbaldehyde (1 mL, 8.5 mmol) in dry THF (10 mL) was added sodium borohydride (0.477 g, 12.6 mmol) at 0° C. The reaction is stirred at rt for 1.5 h. The reaction was quenched with saturated ammonium chloride and extracted with Et$_2$O three times. Combined organic layer was washed with brine once, dried over MgSO$_4$ and concentrated in vacuo.

The residue was dissolved in dry carbon tetrachloride (20 mL) and PS-triphenyl phosphine (5.2 g, 16 mmol/g) was added. The mixture was heated at 75° C. overnight. The resin was filtered and washed with carbon tetrachloride. The filtrate was concentrated in vacuo and used without further purification

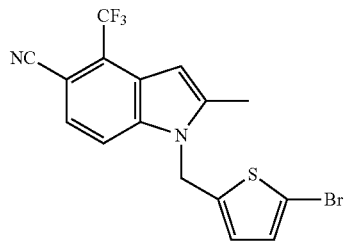 [SMILES: Cc1cc2c(C(F)(F)F)c(C#N)ccc2n1Cc1ccc(Br)s1]

B. 1-[(5-Bromo-2-thienyl)methyl]-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 2-bromo-5-(chloromethyl)thiophene: MS (ES) m/z 399 (M+1) and 401 (M+1, isotope).

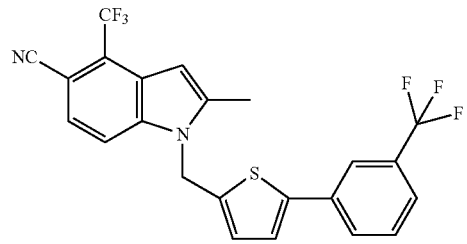 [SMILES: Cc1cc2c(C(F)(F)F)c(C#N)ccc2n1Cc1ccc(-c2cccc(C(F)(F)F)c2)s1]

C. 2-Methyl-4-(trifluoromethyl)-1-({5-[3-(trifluoromethyl)phenyl]-2-thienyl}methyl)-1H-indole-5-carbonitrile Synthesized as described in Example 310D using 1-[(5-bromo-2-thienyl)methyl]-2-methyl-4-(trifluoromethyl)-1H-indole-5-carbonitrile (Example 314B) and [3-(trifluoromethyl)phenyl]boronic acid: $^1$H NMR (400 MHz, CDCl$_3$) δ 7.67 (s, 1H), 7.64 (d, J=7.5 Hz, 1H), 7.47, (m, 4H), 7.17 (m, 1H), 6.81 (d, J=3.6 Hz, 1H), 6.65 (s, 1H), 5.49 (s, 2H), 2.56 (s, 3H); MS (ES) m/z 463 (M−1).

Example 315

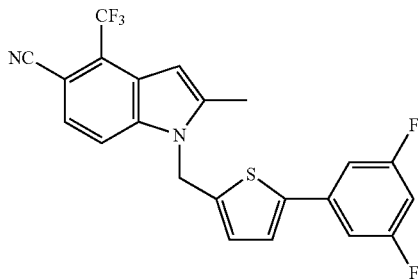 [SMILES: Cc1cc2c(C(F)(F)F)c(C#N)ccc2n1Cc1ccc(-c2cc(F)cc(F)c2)s1]

1-{[5-(3,5-Difluorophenyl)-2-thienyl]methyl}-2-methyl-4-(trifluoromethyl)-1H-indole-5-carbonitrile Synthesized as described in Example 310D using 1-[(5-bromo-2-thienyl)methyl]-2-methyl-4-(trifluoromethyl)-1H- indole-5-carbonitrile (Example 314B) and [3,5-difluorophenyl]boronic acid: MS (ES) m/z 431 (M−1).

Example 316

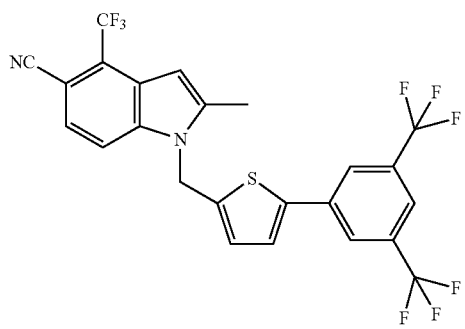

1-({5-[3,5-bis(Trifluoromethyl)phenyl]-2-thienyl}methyl)-2-methyl-4-(trifluoromethyl)-1H-indole-5-carbonitrile Synthesized as described in Example 310D using 1-[(5-bromo-2-thienyl)methyl]-2-methyl-4-(trifluoromethyl)-1H-indole-5-carbonitrile (Example 314B) and [3,5-bis(trifluoromethyl)phenyl]boronic acid: MS (ES) m/z 531 (M−1).

Example 317

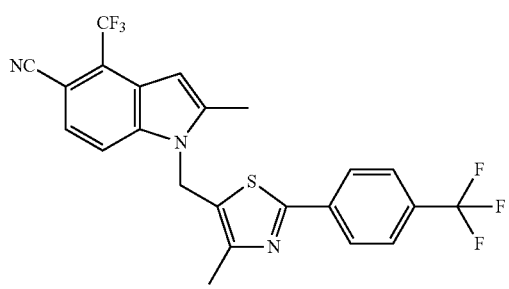 [SMILES: Cc1nc(-c2ccc(C(F)(F)F)cc2)sc1Cn1c(C)cc2c(C(F)(F)F)c(C#N)ccc21]

2-Methyl-1-({4-methyl-2-[4-(trifluoromethyl)phenyl]-1,3-thiazol-5-yl}methyl)-4-(trifluoromethyl)-1H-indole-5-carbonitrile Synthesized as described in Example 4 using 2-methyl-4-(trifluoromethyl)-1H-indole-5-carbonitrile (Example 120) and 5-(chloromethyl)-4-methyl-2-[4-(trifluoromethyl)phenyl]-1,3-thiazole: $^1$H NMR (400 MHz, CDCl$_3$) δ 7.87 (d, J=8.0 Hz, 2H), 7.60 (d, J=8.0 Hz, 2H), 7.52 (d, J=7.8 Hz, 1H), 7.45 (d, J=7.8 Hz, 1H), 6.65 (s, 1H), 5.46 (s, 2H), 2.60 (s, 3H), 2.53 (s, 3H); MS (ES) m/z 480 (M+1).

Example 318

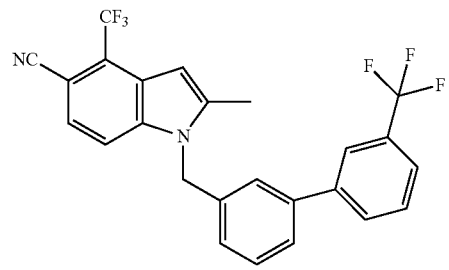

2-Methyl-4-(trifluoromethyl)-1-{[3'-(trifluoromethyl)-3-biphenylyl]methyl}-1H-indole-5-carbonitrile

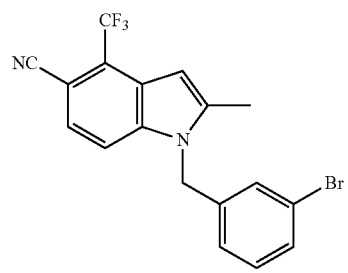 [SMILES: Cc1cc2c(C(F)(F)F)c(C#N)ccc2n1Cc1cccc(Br)c1]

A. 1-[(3-Bromophenyl)methyl]-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 1-bromo-3-(bromomethyl)benzene: MS (ES) m/z 393 (M+1) and 395 (M+1, isotope).

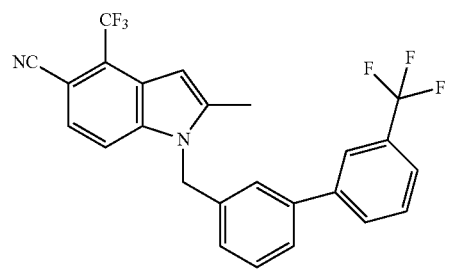 [SMILES: Cc1cc2c(C(F)(F)F)c(C#N)ccc2n1Cc1cccc(-c2cccc(C(F)(F)F)c2)c1]

B. 2-Methyl-4-(trifluoromethyl)-1-{[3'-(trifluoromethyl)-3-biphenylyl]methyl}-1H-indole-5-carbonitrile Synthesized as described in Example 310D using 1-[(3-bromophenyl)methyl]-2-methyl-4-(trifluoromethyl)-1H-indole-5-carbonitrile (Example 318A) and [3-(trifluoromethyl)phenyl]boronic acid: $^1$H NMR (400 MHz, CDCl$_3$) δ 7.73 (s, 1H), 7.65-7.35 (m, 8H), 6.81 (d, J=7.6 Hz, 1H), 6.68 (s, 1H), 5.44 (s, 2H), 2.48 (s, 3H): MS (ES) m/z 459 (M+1).

Example 319

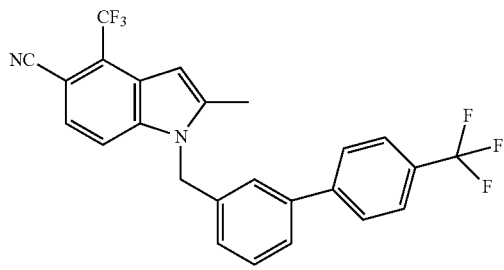 [SMILES: Cc1cc2c(C(F)(F)F)c(C#N)ccc2n1Cc1cccc(-c2ccc(C(F)(F)F)cc2)c1]

2-Methyl-4-(trifluoromethyl)-1-{[4'-(trifluoromethyl)-3-biphenylyl]methyl}-1H-indole-5-carbonitrile Synthesized as described in Example 310D using 1-[(3-bromophenyl)methyl]-2-methyl-4-(trifluoromethyl)-1H-indole-5-carbonitrile (Example 318A) and [4-(trifluoromethyl)phenyl]boronic acid: MS (ES) m/z 459 (M+1).

Example 320

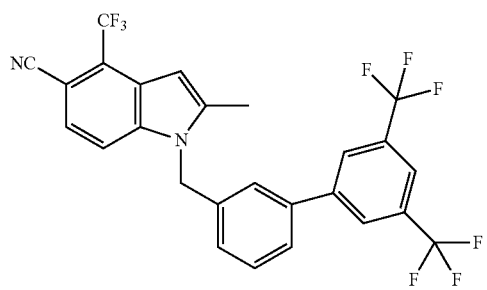 [SMILES: Cc1cc2c(C(F)(F)F)c(C#N)ccc2n1Cc1cccc(-c2cc(C(F)(F)F)cc(C(F)(F)F)c2)c1]

1-{[3',5'-bis(Trifluoromethyl)-3-biphenylyl]methyl}-2-methyl-4-(trifluoromethyl)-1H-indole-5-carbonitrile Synthesized as described in Example 310D using 1-[(3-bromophenyl)methyl]-2-methyl-4-(trifluoromethyl)-1H-indole-5-carbonitrile (Example 318A) and [3,5-bis(trifluoromethyl)phenyl]boronic acid: MS (ES) m/z 527 (M+1).

Example 321

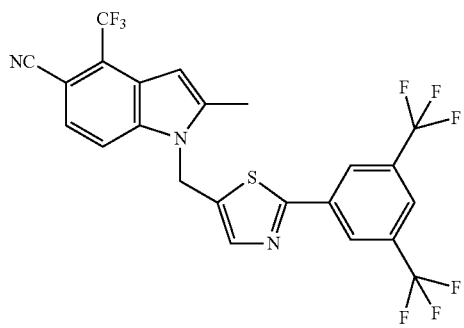 [SMILES: Cc1cc2c(C(F)(F)F)c(C#N)ccc2n1Cc1cnc(-c2cc(C(F)(F)F)cc(C(F)(F)F)c2)s1]

1-({2-[3,5-bis(Trifluoromethyl)phenyl]-1,3-thiazol-5-yl}methyl)-2-methyl-4-(trifluoromethyl)-1H-indole-5-carbonitrile

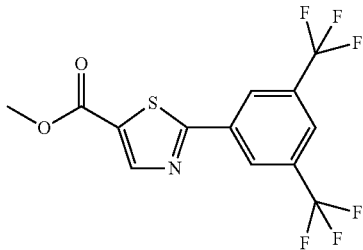 [SMILES: COC(=O)c1cnc(-c2cc(C(F)(F)F)cc(C(F)(F)F)c2)s1]

A. Methyl 2-[3,5-bis(trifluoromethyl)phenyl]-1,3-thiazole-5-carboxylate

Synthesized as described in Example 310D using methyl 2-bromo-1,3-thiazole-5-carboxylate and [3,5-bis(trifluoromethyl)phenyl]boronic acid: $^1$H NMR (400 MHz, CDCl$_3$) δ 8.51 (s, 1H), 8.44 (s, 2H), 7.99 (s, 1H), 3.98 (s, 3H).

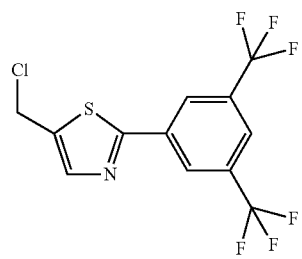 [SMILES: FC(F)(F)c1cc(-c2ncc(CCl)s2)cc(C(F)(F)F)c1]

B. 2-[3,5-bis(Trifluoromethyl)phenyl]-5-(chloromethyl)-1,3-thiazole

Synthesized as described in Example 311A using methyl 2-[3,5-bis(trifluoromethyl)phenyl]-1,3-thiazole-5-carboxylate.

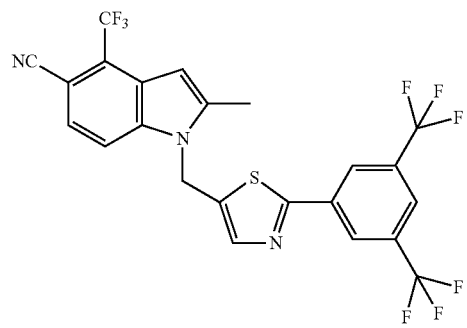 [SMILES: Cc1cc2c(C(F)(F)F)c(C#N)ccc2n1Cc1cnc(-c2cc(C(F)(F)F)cc(C(F)(F)F)c2)s1]

C. 1-({2-[3,5-bis(Trifluoromethyl)phenyl]-1,3-thiazol-5-yl}methyl)-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 2-[3,5-bis(trifluoromethyl)phenyl]-5-(chloromethyl)-1,3-thiazole (Example 321B): $^1$H NMR (400 MHz, CDCl$_3$) δ 8.26 (s, 2H), 7.89 (s, 1H), 7.74 (s, 1H), 7.57 (d, J=8.5 Hz, 1H), 7.53 (d, J=8.5 Hz, 1H), 6.67 (s, 1H), 5.58 (s, 2H), 2.57 (s, 3H): MS (ES) m/z 532 (M−1).

Example 322

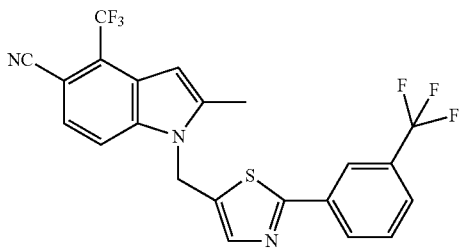 [SMILES: Cc1cc2c(C(F)(F)F)c(C#N)ccc2n1Cc1cnc(-c2cccc(C(F)(F)F)c2)s1]

2-Methyl-4-(trifluoromethyl)-1-({2-[3-(trifluoromethyl)phenyl]-1,3-thiazol-5-yl}methyl)-1H-indole-5-carbonitrile

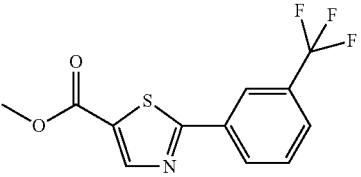 [SMILES: COC(=O)c1cnc(-c2cccc(C(F)(F)F)c2)s1]

A. Methyl 2-[3-(trifluoromethyl)phenyl]-1,3-thiazole-5-carboxylate

Synthesized as described in Example 310D using methyl 2-bromo-1,3-thiazole-5-carboxylate and [3-(trifluoromethyl)phenyl]boronic acid: $^1$H NMR (400 MHz, CDCl$_3$) δ 8.47 (s, 1H), 8.28 (s, 1H), 8.16 (d, J=7.8 Hz, 1H), 7.75 (d, J=7.8 Hz, 1H), 7.62 (t, J=7.8 Hz, 1H), 3.96 (s, 3H).

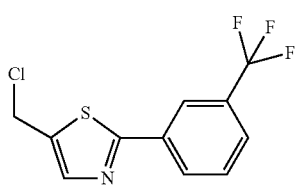 [SMILES: FC(F)(F)c1cccc(-c2ncc(CCl)s2)c1]

B. 2-[3-(Trifluoromethyl)phenyl]-5-(chloromethyl)-1,3-thiazole

Synthesized as described in Example 311A using methyl 2-[3,-(trifluoromethyl)phenyl]-1,3-thiazole-5-carboxylate (Example 322A).

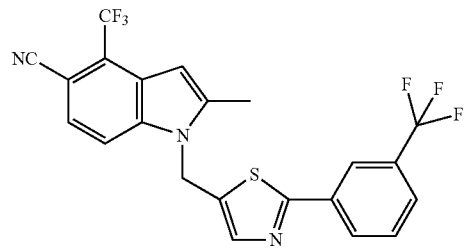 [SMILES: Cc1cc2c(C(F)(F)F)c(C#N)ccc2n1Cc1cnc(-c2cccc(C(F)(F)F)c2)s1]

C. 2-Methyl-4-(trifluoromethyl)-1-({2-[3-(trifluoromethyl)phenyl]-1,3-thiazol-5-yl}methyl)-1H-indole-5-carbonitrile Synthesized as described in Example 4 using 2-methyl-4-(trifluoromethyl)-1H-indole-5-carbonitrile (Example 120) and 2-[3-(trifluoromethyl)phenyl]-5-(chloromethyl)-1,3-thiazole (Example 322B): MS (ES) m/z 466 (M+1).

Example 323

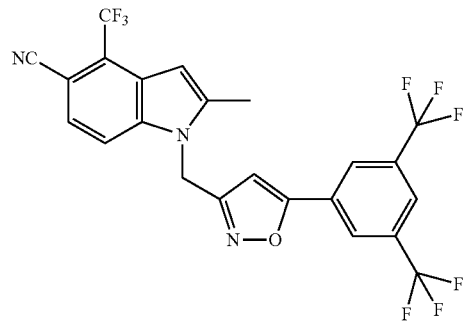 [SMILES: Cc1cc2c(C(F)(F)F)c(C#N)ccc2n1Cc1cc(-c2cc(C(F)(F)F)cc(C(F)(F)F)c2)on1]

1-({5-[3,5-bis(Trifluoromethyl)phenyl]-3-isoxazolyl}methyl)-2-methyl-4-(trifluoromethyl)-1H-indole-5-carbonitrile

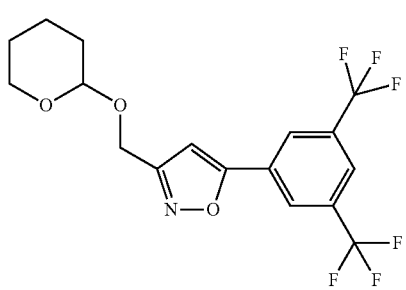 [SMILES: FC(F)(F)c1cc(-c2cc(COC3CCCCO3)no2)cc(C(F)(F)F)c1]

A. 3-[(Tetrahydro-2H-pyran-2-yloxy)methyl]-5-[3,5-bis(trifluoromethyl)phenyl]isoxazole To a solution of 2-[(2-nitroethyl)oxy]tetrahydro-2H-pyran (483 μL, 3.15 mmol) and 1-ethynyl-3,5-bis(trifluoromethyl)benzene (3.0 g, 12.6 mmol) in dry acetonitrile (15 mL) were added TEA (4.4 ml, 31.5 mmol) and isocyanatobenzene (3.4 mL, 31.5 mmol) at rt. The reaction is stirred at 50° C. for 5 h. Water was added and the mixture was extracted with Et$_2$O three times. The combined organic layers were then washed with brine once, dried over MgSO$_4$ and concentrated in vacuo. The residue was purified by radial chromatography (0-40% EtOAc-hexanes gradient) to afford the title compound (0.51 g, 41% yield): MS (ES) m/z 418 (M+Na$^+$).

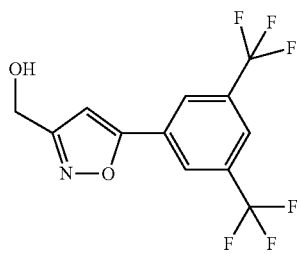 [SMILES: OCc1cc(-c2cc(C(F)(F)F)cc(C(F)(F)F)c2)on1]

B. {5-[3,5-bis(Trifluoromethyl)phenyl]-3-isoxazolyl}methanol

To a solution of 3-[(tetrahydro-2H-pyran-2-yloxy)methyl]-5-[3,5-bis(trifluoromethyl)phenyl]isoxazole (Example 323A) (0.590 g, 1.49 mmol) in DCM (15 mL) was added TFA (1.5 mL). The reaction is stirred at rt overnight. Solvent and excess TFA were removed in vacuo. The residue was purified by radial chromatography (0-60% EtOAc-hexanes gradient) to afford the title compound (0.320 g, 69% yield): MS (ES) m/z 312 (M+1).

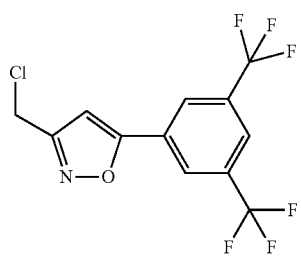 [SMILES: FC(F)(F)c1cc(-c2cc(CCl)no2)cc(C(F)(F)F)c1]

C. 3-(Chloromethyl)-5-[3,5-bis(trifluoromethyl)phenyl]isoxazole

To a solution of {5-[3,5-bis(trifluoromethyl)phenyl]-3-isoxazolyl}methanol (Example 323B) (0.100 g, 0.32 mmol) in dry carbon tetrachloride (15 mL) was added PS-triphenylphosphine (0.292 g, 2.2 mmol/g, 0.64 mmol). The reaction was heated at 75° C. overnight. The resin was filtered and washed with carbon tetrachloride. Concentration in vacuo afforded the title compound, which was used for the next step without further purification.

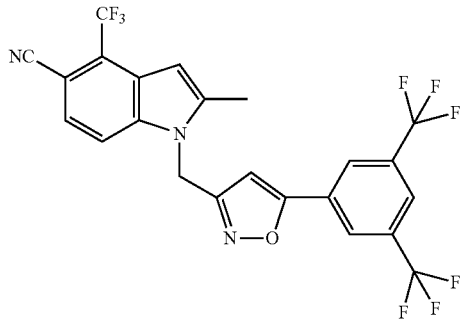 [SMILES: Cc1cc2c(C(F)(F)F)c(C#N)ccc2n1Cc1cc(-c2cc(C(F)(F)F)cc(C(F)(F)F)c2)on1]

D. 1-({5-[3,5-bis(Trifluoromethyl)phenyl]-3-isoxazolyl}methyl)-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 3-(chloromethyl)-5-[3,5-bis(trifluoromethyl)phenyl]isoxazole (Example 323C): MS (ES) m/z 518 (M+1).

Example 324

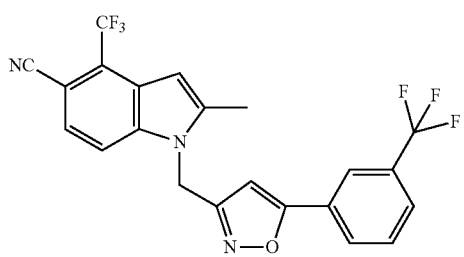 [SMILES: Cc1cc2c(C(F)(F)F)c(C#N)ccc2n1Cc1cc(-c2cccc(C(F)(F)F)c2)on1]

2-Methyl-4-(trifluoromethyl)-1-({5-[3-(trifluoromethyl)phenyl]-3-isoxazolyl}methyl)-1H-indole-5-carbonitrile

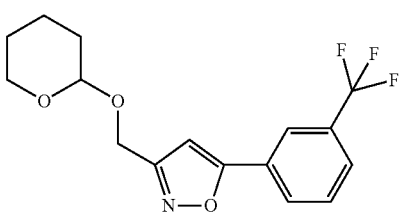 [SMILES: FC(F)(F)c1cccc(-c2cc(COC3CCCCO3)no2)c1]

A. 3-[(Tetrahydro-2H-pyran-2-yloxy)methyl]-5-[3-(trifluoromethyl)phenyl]isoxazole Synthesized as described in Example 323A using 1-ethynyl-3-(trifluoromethyl)benzene instead of 1-ethynyl-3,5-bis(trifluoromethyl)benzene: MS (ES) m/z 350 (M+Na+).

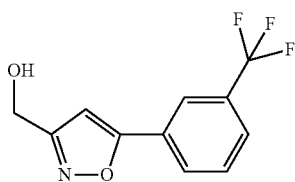 [SMILES: OCc1cc(-c2cccc(C(F)(F)F)c2)on1]

B. {5-[3-(Trifluoromethyl)phenyl]-3-isoxazolyl}methanol

Synthesized as described in Example 323B using 3-[(tetrahydro-2H-pyran-2-yloxy)methyl]-5-[3-(trifluoromethyl)phenyl]isoxazole instead of 3-[(tetrahydro-2H-pyran-2-yloxy)methyl]-5-[3,5-bis(trifluoromethyl)phenyl]isoxazole: MS (ES) m/z 244 (M+1).

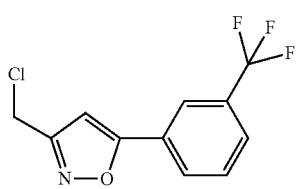 [SMILES: FC(F)(F)c1cccc(-c2cc(CCl)no2)c1]

C. 3-(Chloromethyl)-5-[3-(trifluoromethyl)phenyl]isoxazole

Synthesized as described in Example 323C using {5-[3-(trifluoromethyl)phenyl]-3-isoxazolyl}methanol instead of {5-[3,5-bis(trifluoromethyl)phenyl]-3-isoxazolyl}methanol.

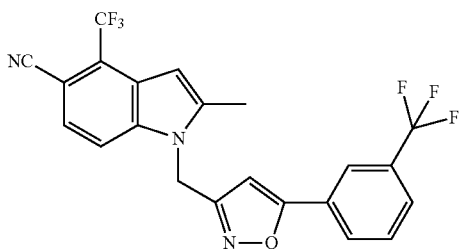 [SMILES: Cc1cc2c(C(F)(F)F)c(C#N)ccc2n1Cc1cc(-c2cccc(C(F)(F)F)c2)on1]

D. 2-Methyl-4-(trifluoromethyl)-1-({5-[3-(trifluoromethyl)phenyl]-3-isoxazolyl}methyl)-1H-indole-5-carbonitrile Synthesized as described in Example 4 using 2-methyl-4-(trifluoromethyl)-1H-indole-5-carbonitrile (Example 120) and 3-(chloromethyl)-5-[3-(trifluoromethyl)phenyl]isoxazole (Example 324C): $^1$H NMR (400 MHz, CDCl$_3$) δ 7.91 (s, 1H), 7.86 (d, J=7.7 Hz, 1H), 7.68 (d, J=7.6 Hz, 1H), 7.57 (m, 3H), 6.66 (s, 1H), 6.17 (s, 1H), 5.44 (s, 2H), 2.58 (s, 3H); MS (ES) m/z 450 (M+1).

Example 325

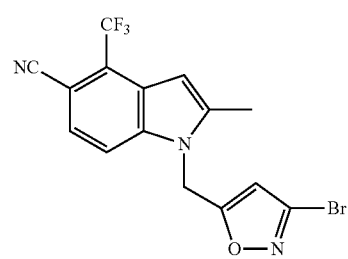 [SMILES: Cc1cc2c(C(F)(F)F)c(C#N)ccc2n1Cc1cc(Br)no1]

1-[(3-Bromo-5-isoxazolyl)methyl]-2-methyl-4-(trifluoromethyl)-1H-indole-5-carbonitrile

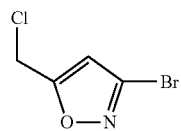

A. 3-Bromo-5-(chloromethyl)isoxazole

To a solution of (3-bromo-5-isoxazolyl)methanol (0.500 g, 2.8 mmol) in dry carbon tetrachloride (20 mL) was added PS-triphenyl phosphine (3.5 g, 1.6 mmol/g). The mixture was heated at 75° C. overnight. The resin was filtered and washed with carbon tetrachloride. The filtrate was concentrated in vacuo and used without further purification.

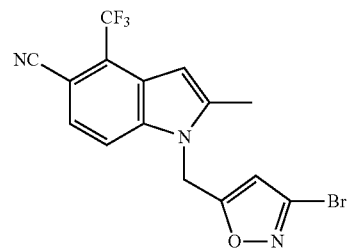 [SMILES: Cc1cc2c(C(F)(F)F)c(C#N)ccc2n1Cc1cc(Br)no1]

B. 1-[(3-Bromo-5-isoxazolyl)methyl]-2-methyl-4-(trifluoromethyl)-1H-indole-5-carbonitrile Synthesized as described in Example 4 using 2-methyl-4-(trifluoromethyl)-1H-indole-5-carbonitrile (Example 120)

and 3-bromo-5-(chloromethyl)isoxazole (Example 325A): MS (ES) m/z 382 (M–1) and 384 (M–1, isotope).

Example 326

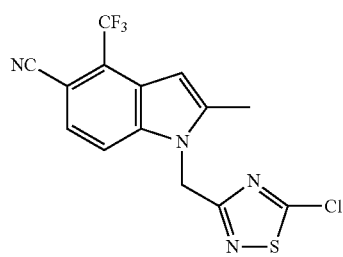 [SMILES: Cc1cc2c(C(F)(F)F)c(C#N)ccc2n1Cc1nsc(Cl)n1]

1-[(5-Chloro-1,2,4-thiadiazol-3-yl)methyl]-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 5-chloro-3-(chloromethyl)-1,2,4-thiadiazole: MS (ES) m/z 357 (M+1) and 359 (M+1, isotope).

Example 327

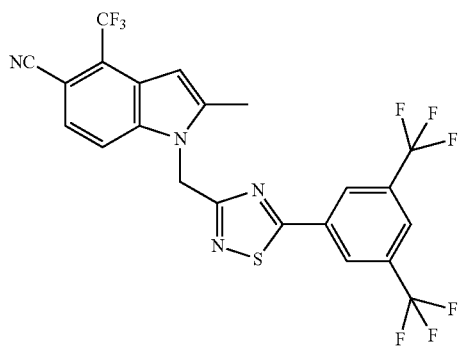 [SMILES: Cc1cc2c(C(F)(F)F)c(C#N)ccc2n1Cc1nsc(-c2cc(C(F)(F)F)cc(C(F)(F)F)c2)n1]

1-({5-[3,5-bis(Trifluoromethyl)phenyl]-1,2,4-thiadiazol-3-yl}methyl)-2-methyl-4-(trifluoromethyl)-1H-indole-5-carbonitrile To a solution of 1-[(5-chloro-1,2,4-thiadiazol-3-yl)methyl]-2-methyl-4-(trifluoromethyl)-1H-indole-5-carbonitrile (Example 326) (0.1 g, 0.28 mmol) in dry DME (3 mL) were added [3,5-bis(trifluoromethyl)phenyl]boronic acid (0.145 g, 0.56 mmol), cesium fluoride (0.13 g, 0.84 mmol) and [1,4-bis(diphenylphosphino)butane]palladium(II) dichloride (0.1 g, 0.17 mmol). The mixture was stirred at 90° C. in a sealed tube overnight. Solid was filtered and the filtrate was then concentrated in vacuo. The residue was purified by radial chromatography (0-50% EtOAc-hexanes gradient) to afford the title compound (0.06 g, 40% yield): $^1$H NMR (400 MHz, CDCl$_3$) δ 8.31 (s, 2H), 8.04 (s, 1H), 7.67 (d, J=8.4 Hz, 1H), 7.51 (d, J=8.4 Hz, 1H), 6.66 (s, 1H), 5.65 (s, 2H), 2.67 (s, 3H); MS (ES) m/z 533 (M–1).

Example 328

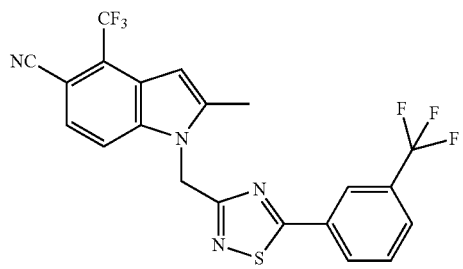 [SMILES: Cc1cc2c(C(F)(F)F)c(C#N)ccc2n1Cc1nsc(-c2cccc(C(F)(F)F)c2)n1]

2-Methyl-4-(trifluoromethyl)-1-({5-[3-(trifluoromethyl)phenyl]-1,2,4-thiadiazol-3-yl}methyl)-1H-indole-5-carbonitrile Synthesized as described in Example 327 using 1-[(5-chloro-1,2,4-thiadiazol-3-yl)methyl]-2-methyl-4-(trifluoromethyl)-1H-indole-5-carbonitrile (Example 326) and [3-(trifluoromethyl)phenyl]boronic acid: MS (ES) m/z 467 (M+1).

Example 329

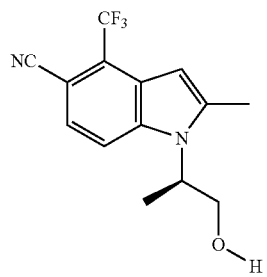 [SMILES: Cc1cc2c(C(F)(F)F)c(C#N)ccc2n1[C@H](C)CO]

1-[(1R)-2-Hydroxy-1-methylethyl]-2-methyl-4-(trifluoromethyl)-1H-indole-5-carbonitrile Synthesized as described in Example 4 using 2-methyl-4-(trifluoromethyl)-1H-indole-5-carbonitrile (Example 120) and (2S)-2-chloro-1-propanol: MS (ES) m/z 283 (M+1).

Example 330

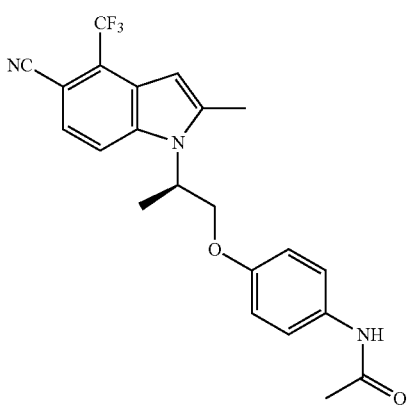 [SMILES: CC(=O)Nc1ccc(OC[C@@H](C)n2c(C)cc3c(C(F)(F)F)c(C#N)ccc32)cc1]

N-[4-({(2R)-2-[5-Cyano-2-methyl-4-(trifluoromethyl)-1H-indol-1-yl]propyl}oxy)phenyl]acetamide Synthesized as described in Example 139C using 1-[(1R)-2-hydroxy-1-methylethyl]-2-methyl-4-(trifluoromethyl)-1H-indole-5-carbonitrile (Example 329) and N-(4-hydroxyphenyl)acetamide: $^1$H NMR (400 MHz, CDCl$_3$) δ 7.55 (d, J=8.5 Hz, 1H), 7.49 (d, J=8.5 Hz, 1H), 7.25 (d, J=8.8 Hz, 2H), 7.13 (s, 1H), 6.55 (m, 3H), 4.57 (m, 1H), 4.36 (m, 1H), 4.27 (m, 1H), 2.53 (s, 3H), 2.11 (s, 3H), 1.38 (d, J=6.1 Hz, 3H); MS (ES) m/z 414 (M−1).

Example 331

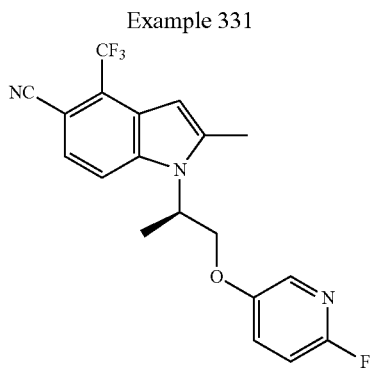

1-{(1R)-2-[(6-Fluoro-3-pyridinyl)oxy]-1-methylethyl}-2-methyl-4-(trifluoromethyl)-1H-indole-5-carbonitrile Synthesized as described in Example 139C using 1-[(1R)-2-hydroxy-1-methylethyl]-2-methyl-4-(trifluoromethyl)-1H-indole-5-carbonitrile (Example 329) and 6-fluoro-3-pyridinol: MS (ES) m/z 378 (M+1).

Example 332

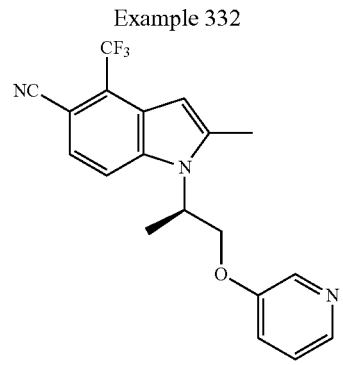

2-Methyl-1-[(1R)-1-methyl-2-(3-pyridinyloxy)ethyl]-4-(trifluoromethyl)-1H-indole-5-carbonitrile Synthesized as described in Example 139C using 1-[(1R)-2-hydroxy-1-methylethyl]-2-methyl-4-(trifluoromethyl)-1H-indole-5-carbonitrile (Example 329) and 3-pyridinol: MS (ES) m/z 360 (M+1).

Example 333

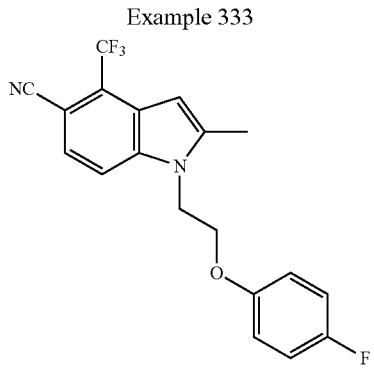

1-{2-[(4-Fluorophenyl)oxy]ethyl}-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 2-bromoethyl-4-fluorophenylether: $^1$H NMR (400 MHz, CDCl$_3$) δ 7.57 (d, J=8.5 Hz, 1H), 7.52 (d, J=8.5 Hz, 1H), 6.92 (t, J=8.6 Hz, 2H), 6.69 (m, 2H), 6.59 (s, 1H), 4.53 (t, J=5.3 Hz, 2H), 4.20 (t, J=5.3 Hz, 2H), 2.57 (s, 3H): MS (ES) m/z 363 (M+1).

Example 334

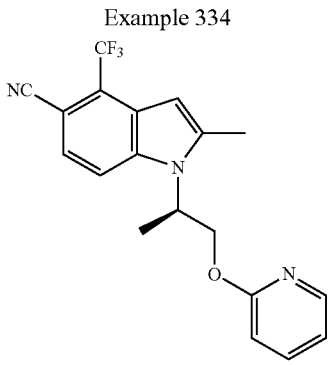

2-Methyl-1-[(1R)-1-methyl-2-(2-pyridinyloxy)ethyl]-4-(trifluoromethyl)-1H-indole-5-carbonitrile Synthesized as described in Example 139C using 1-[(1R)-2-hydroxy-1-methylethyl]-2-methyl-4-(trifluoromethyl)-1H-indole-5-carbonitrile (Example 329) and 2-pyridinol: MS (ES) m/z 360 (M+1).

Example 335

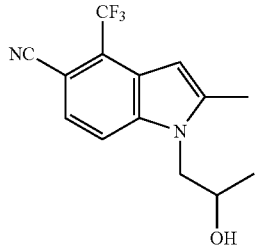 [SMILES: Cc1cc2c(C(F)(F)F)c(C#N)ccc2n1CC(C)O]

1-(2-Hydroxypropyl)-2-methyl-4-(trifluoromethyl)-1H-indole-5-carbonitrile

Synthesized as described in Example 4 using 2-methyl-4-(trifluoromethyl)-1H-indole-5-carbonitrile (Example 120) and 1-chloro-2-propanol: $^1$H NMR (400 MHz, CDCl$_3$) δ 7.53 (d, J=8.5 Hz, 1H), 7.48 (d, J=8.5 Hz, 1H), 6.59 (s, 1H), 4.20 (m, 1H), 4.12 (m, 2H), 2.52 (s, 3H), 1.33 (d, J=6.1 Hz, 3H); MS (ES) m/z 283 (M+1).

Example 336

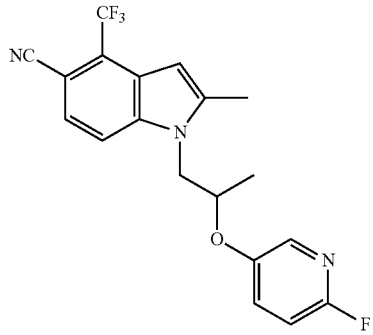 [SMILES: Cc1cc2c(C(F)(F)F)c(C#N)ccc2n1CC(C)Oc1ccc(F)nc1]

1-{2-[(6-Fluoro-3-pyridinyl)oxy]propyl}-2-methyl-4-(trifluoromethyl)-1H-indole-5-carbonitrile Synthesized as described in Example 139C using 1-(2-hydroxypropyl)-2-methyl-4-(trifluoromethyl)-1H-indole-5-carbonitrile (Example 335) and 6-fluoro-3-pyridinol: $^1$H NMR (400 MHz, CDCl$_3$) δ 7.58 (s, 1H), 7.54 (d, J=8.6 Hz, 1H), 7.49 (d, J=8.6 Hz, 1H), 6.94 (m, 1H), 6.71 (m, 1H), 6.56 (s, 1H), 4.57 (m, 1H), 4.40 (m, 1H), 4.30 (m, 1H), 2.54 (s, 3H), 1.43 (d, J=6.1 Hz, 3H); MS (ES) m/z 400 (M+Na).

Example 337

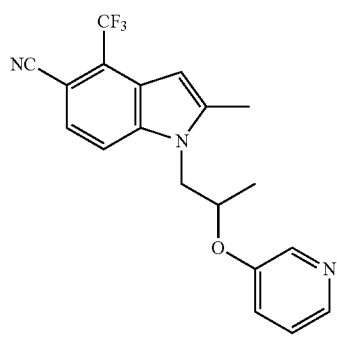 [SMILES: Cc1cc2c(C(F)(F)F)c(C#N)ccc2n1CC(C)Oc1cccnc1]

2-Methyl-1-[2-(3-pyridinyloxy)propyl]-4-(trifluoromethyl)-1H-indole-5-carbonitrile Synthesized as described in Example 139C using 1-(2-hydroxypropyl)-2-methyl-4-(trifluoromethyl)-1H-indole-5-carbonitrile (Example 335) and 3-pyridinol; MS (ES) m/z 360 (M+1).

Example 338

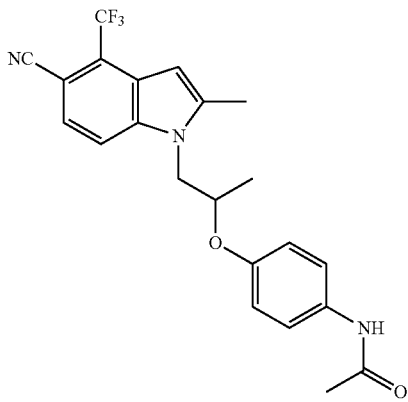 [SMILES: CC(=O)Nc1ccc(OC(C)Cn2c(C)cc3c(C(F)(F)F)c(C#N)ccc32)cc1]

N-[4-({2-[5-Cyano-2-methyl-4-(trifluoromethyl)-1H-indol-1-yl]-1-methylethyl}oxy)phenyl]acetamide Synthesized as described in Example 139C using 1-(2-hydroxypropyl)-2-methyl-4-(trifluoromethyl)-1H-indole-5-carbonitrile (Example 335) and N-(4-hydroxyphenyl)acetamide: MS (ES) m/z 414 (M−1).

Example 339

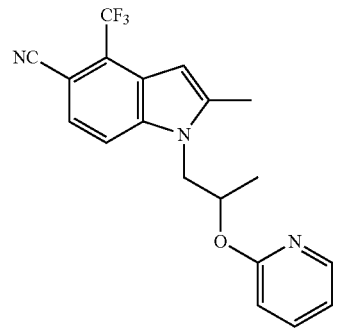 [SMILES: Cc1cc2c(C(F)(F)F)c(C#N)ccc2n1CC(C)Oc1ccccn1]

2-Methyl-1-[2-(2-pyridinyloxy)propyl]-4-(trifluoromethyl)-1H-indole-5-carbonitrile Synthesized as described in Example 139C using 1-(2-hydroxypropyl)-2-methyl-4-(trifluoromethyl)-1H-indole-5-carbonitrile (Example 335) and 2-pyridinol: MS (ES) m/z 360 (M+1).

Example 340

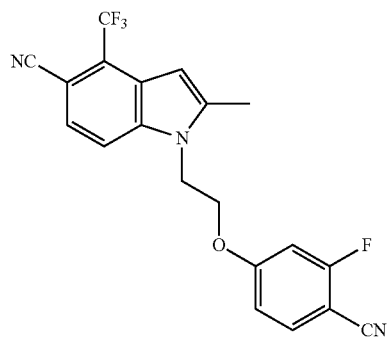 [SMILES: Cc1cc2c(C(F)(F)F)c(C#N)ccc2n1CCOc1ccc(C#N)c(F)c1]

1-{2-[(4-Cyano-3-fluorophenyl)oxy]ethyl}-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 2-fluoro-4-[(2-bromoethyl)oxy]benzonitrile: MS (ES) m/z 388 (M+1).

Example 341

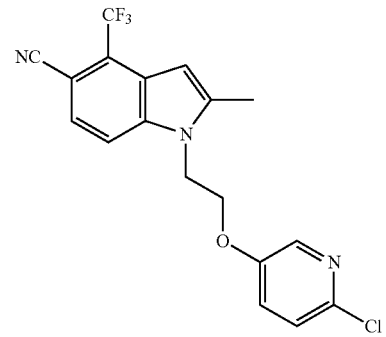 [SMILES: Cc1cc2c(C(F)(F)F)c(C#N)ccc2n1CCOc1ccc(Cl)nc1]

1-{2-[(6-Chloro-3-pyridinyl)oxy]ethyl}-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 5-[(2-bromoethyl)oxy]-2-chloropyridine: MS (ES) m/z 380 (M+1) and 382 (M+1, isotope).

Example 342

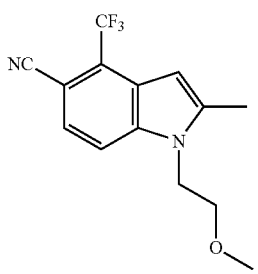 [SMILES: COCCn1c(C)cc2c(C(F)(F)F)c(C#N)ccc21]

2-Methyl-1-[2-(methyloxy)ethyl]-4-(trifluoromethyl)-1H-indole-5-carbonitrile

Synthesized as described in Example 4 using 2-methyl-4-(trifluoromethyl)-1H-indole-5-carbonitrile (Example 120) and 2-chloroethyl methyl ether: MS (ES) m/z 283 (M+1).

Example 343

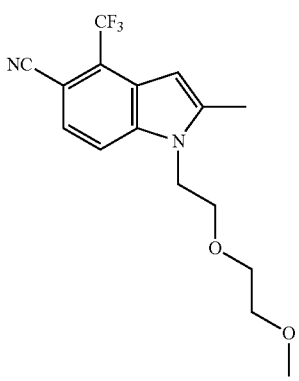 [SMILES: COCCOCCn1c(C)cc2c(C(F)(F)F)c(C#N)ccc21]

2-Methyl-1-(2-{[2-(methyloxy)ethyl]oxy}ethyl)-4-(trifluoromethyl)-1H-indole-5-carbonitrile Synthesized as described in Example 4 using 2-methyl-4-(trifluoromethyl)-1H-indole-5-carbonitrile (Example 120) and 1-chloro-2-{[2-(methyloxy)ethyl]oxy}ethane: MS (ES) m/z 327 (M+1).

Example 344

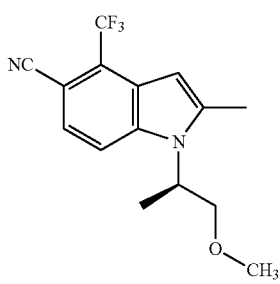 [SMILES: COC[C@@H](C)n1c(C)cc2c(C(F)(F)F)c(C#N)ccc21]

2-Methyl-1-[(1R)-1-methyl-2-(methyloxy)ethyl]-4-(trifluoromethyl)-1H-indole-5-carbonitrile To a solution of 1-[(1R)-2-hydroxy-1-methylethyl]-2-methyl-4-(trifluoromethyl)-1H-indole-5-carbonitrile (Example 329) (0.035 g, 0.124 mmol) in dry THF (5 mL) was added sodium hydride (60%, 0.0075 g, 0.188 mmol) at 0° C. The mixture was stirred at rt for 0.5 h and then was added iodomethane (77 uL, 1.24 mmol). The mixture was stirred at 50° C. in a sealed tube overnight. The resulting solids were filtered and the filtrate was then concentrated in vacuo. The residue was purified by radial chromatography (0-60% EtOAc-hexanes gradient) to afford the title compound (0.015 g, 41% yield): MS (ES) m/z 297 (M+1).

Example 345

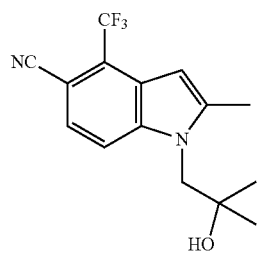 [SMILES: Cc1cc2c(C(F)(F)F)c(C#N)ccc2n1CC(C)(C)O]

1-(2-Hydroxy-2-methylpropyl)-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 1-chloro-2-methyl-2-propanol: $^1$H NMR (400 MHz, CDCl$_3$) δ 7.66 (d, J=8.5 Hz, 1H), 7.46 (d, J=8.5 Hz, 1H), 6.60 (s, 1H), 4.12 (s, 2H), 2.52 (s, 3H), 1.30 (s, 6H); MS (ES) m/z 297 (M+1).

Example 346

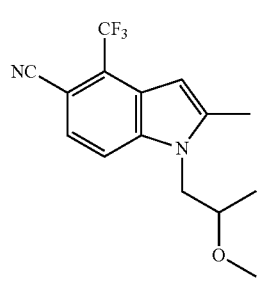 [SMILES: COC(C)Cn1c(C)cc2c(C(F)(F)F)c(C#N)ccc21]

2-Methyl-1-[2-(methyloxy)propyl]-4-(trifluoromethyl)-1H-indole-5-carbonitrile Synthesized as described in Example 344 using 1-(2-hydroxypropyl)-2-methyl-4-(trifluoromethyl)-1H-indole-5-carbonitrile (Example 335): MS (ES) m/z 297 (M+1).

Example 347

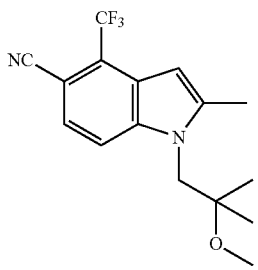 [SMILES: COC(C)(C)Cn1c(C)cc2c(C(F)(F)F)c(C#N)ccc21]

2-Methyl-1-[2-methyl-2-(methyloxy)propyl]-4-(trifluoromethyl)-1H-indole-5-carbonitrile Synthesized as described in Example 344 using 1-(2-hydroxy-2-methylpropyl)-2-methyl-4-(trifluoromethyl)-1H-indole-5-carbonitrile (Example 345): MS (ES) m/z 311 (M+1).

Example 348

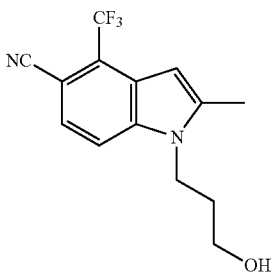 [SMILES: Cc1cc2c(C(F)(F)F)c(C#N)ccc2n1CCCO]

1-(3-Hydroxypropyl)-2-methyl-4-(trifluoromethyl)-1H-indole-5-carbonitrile

Synthesized as described in Example 4 using 2-methyl-4-(trifluoromethyl)-1H-indole-5-carbonitrile (Example 120) and 3-chloro-1-propanol: $^1$H NMR (400 MHz, CDCl$_3$) δ 7.56 (d, J=8.5 Hz, 1H), 7.46 (d, J=8.5 Hz, 1H), 6.56 (s, 1H), 4.30 (t, J=6.9 Hz, 2H), 3.62 (br, 2H), 2.51 (s, 3H), 1.99 (m, 2H), 1.61 (s, 1H); MS (ES) m/z 283 (M+1).

Example 349

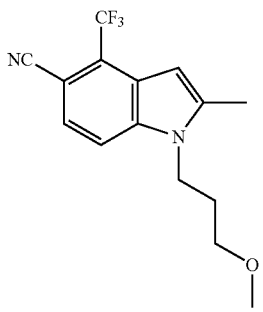 [SMILES: COCCCn1c(C)cc2c(C(F)(F)F)c(C#N)ccc21]

2-Methyl-1-[3-(methyloxy)propyl]-4-(trifluoromethyl)-1H-indole-5-carbonitrile Synthesized as described in Example 344 using 1-(3-hydroxypropyl)-2-methyl-4-(trifluoromethyl)-1H-indole-5-carbonitrile (Example 348): MS (ES) m/z 297 (M+1).

Example 350

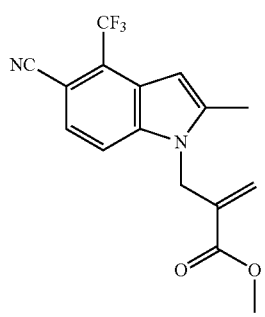 [SMILES: C=C(Cn1c(C)cc2c(C(F)(F)F)c(C#N)ccc21)C(=O)OC]

Methyl 2-{[5-cyano-2-methyl-4-(trifluoromethyl)-1H-indol-1-yl]methyl}-2-propenoate Synthesized as described in Example 4 using 2-methyl-4-(trifluoromethyl)-1H-indole-5-carbonitrile (Example 120) and methyl 2-(bromomethyl)-2-propenoate: $^1$H NMR (400 MHz, CDCl$_3$) δ 7.49 (d, J=8.4 Hz, 1H), 7.38 (d, J=8.4 Hz, 1H), 6.63 (s, 1H), 6.23 (s, 1H), 4.99, (s, 2H), 4.81 (s, 1H), 3.84 (s, 3H), 2.43 (s, 3H); MS (ES) m/z 323 (M+1).

Example 351

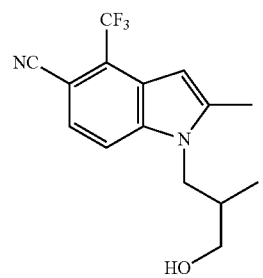 [SMILES: Cc1cc2c(C(F)(F)F)c(C#N)ccc2n1CC(C)CO]

1-(3-Hydroxy-2-methylpropyl)-2-methyl-4-(trifluoromethyl)-1H-indole-5-carbonitrile A solution of methyl 2-{[5-cyano-2-methyl-4-(trifluoromethyl)-1H-indol-1-yl]methyl}-2-propenoate (Example 350) (0.3 g, 0.93 mmol) in THF (10 mL) was cooled to 0° C. and treated with LiBH$_4$ (0.93 mL, 2M in THF). After overnight, the reaction was quenched and partitioned between EtOAc and water. Drying (MgSO$_4$), filtration, and concentration was followed by radial chromatography (0-90% EtOAc-hexanes gradient) to afford the title compound (0.13 g, 47% yield): $^1$H NMR (400 MHz, CDCl$_3$) δ 7.55 (d, J=8.5 Hz, 1H), 7.47 (d, J=8.5 Hz, 1H), 6.56 (s, 1H), 4.33 (dd, J=14.6, 7.3 Hz, 1H), 3.92 (dd, J=14.6, 7.3 Hz, 1H), 3.52 (br, 2H), 2.50 (s, 3H), 2.19 (m, 1H), 1.56 (br, 1H), 0.97 (d, J=6.8 Hz, 3H); MS (ES) m/z 297 (M+1).

Example 352

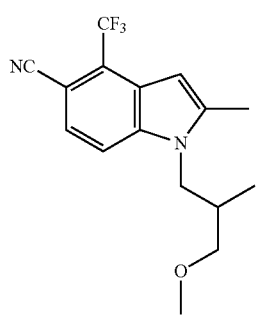 [SMILES: COCC(C)Cn1c(C)cc2c(C(F)(F)F)c(C#N)ccc21]

2-Methyl-1-[2-methyl-3-(methyloxy)propyl]-4-(trifluoromethyl)-1H-indole-5-carbonitrile Synthesized as described in Example 344 using 1-(3-hydroxy-2-methylpropyl)-2-methyl-4-(trifluoromethyl)-1H-indole-5-carbonitrile (Example 351): MS (ES) m/z 311 (M+1).

Example 353

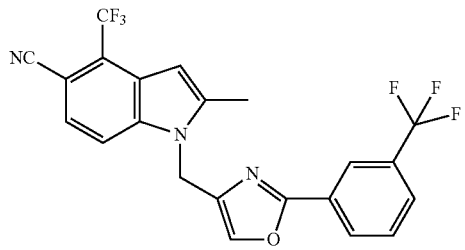 [SMILES: Cc1cc2c(C(F)(F)F)c(C#N)ccc2n1Cc1coc(-c2cccc(C(F)(F)F)c2)n1]

2-Methyl-4-(trifluoromethyl)-1-({2-[3-(trifluoromethyl)phenyl]-1,3-oxazol-4-yl}methyl)-1H-indole-5-carbonitrile

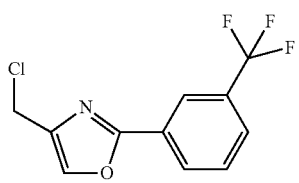 [SMILES: FC(F)(F)c1cccc(-c2nc(CCl)co2)c1]

A. 4-(Chloromethyl)-2-[3-(trifluoromethyl)phenyl]-1,3-oxazole 3-(Trifluoromethyl)benzamide (0.300 g, 1.59 mmol) and 1,3-dichloro-2-propanone (0.201 g, 1.59 mmol) were heated to 130° C. for 0.5 h. Then another 0.201 g of 1,3-dichloro-2-propanone (1.59 mmol) was added and the mixture was heated again at 130° C. for 1 h. After being cooled down, the residue was purified by radial chromatography (0-30% EtOAc-hexanes gradient) to afford the title compound (0.280 g, 67% yield): $^1$H NMR (400 MHz, CDCl$_3$) δ 8.31 (s, 1H), 8.22 (d, J=7.9 Hz, 1H), 7.75 (s, 1H), 7.72 (d, J=7.9 Hz, 1H), 7.60 (t, J=7.9 Hz, 1H), 4.58 (s, 2H).

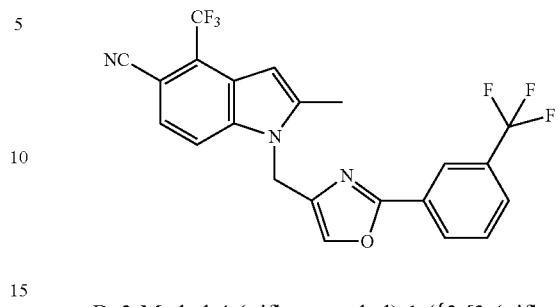

B. 2-Methyl-4-(trifluoromethyl)-1-({2-[3-(trifluoromethyl)phenyl]-1,3-oxazol-4-yl}methyl)-1H-indole-5-carbonitrile Synthesized as described in Example 4 using 2-methyl-4-(trifluoromethyl)-1H-indole-5-carbonitrile (Example 120) and 4-(chloromethyl)-2-[3-(trifluoromethyl)phenyl]-1,3-oxazole: $^1$H NMR (400 MHz, CDCl$_3$) δ 8.23 (s, 1H), 8.15 (d, J=7.8 Hz, 1H), 7.71 (d, J=7.8 Hz, 1H), 7.56 (m, 3H), 7.34 (s, 1H), 6.64 (s, 1H), 5.31 (s, 2H), 2.60 (s, 3H); MS (ES) m/z 450 (M+1).

Example 354

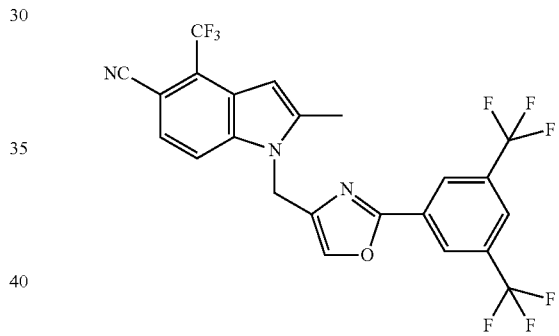

1-({2-[3,5-bis(Trifluoromethyl)phenyl]-1,3-oxazol-4-yl}methyl)-2-methyl-4-(trifluoromethyl)-1H-indole-5-carbonitrile

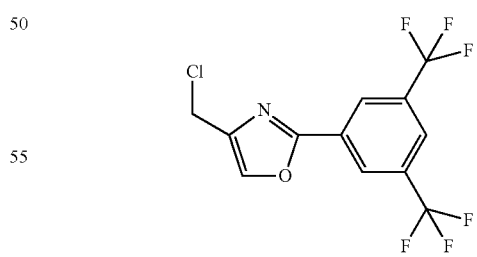

A. 2-[3,5-bis(Trifluoromethyl)phenyl]-4-(chloromethyl)-1,3-oxazole

Synthesized as described in Example 353A using 3,5-bis-(trifluoromethyl)benzamide and 1,3-dichloro-2-propanone: $^1$H NMR (400 MHz, CDCl$_3$) δ 8.50 (s, 2H), 7.96 (s, 1H), 7.80 (s, 1H), 4.59 (s, 2H).

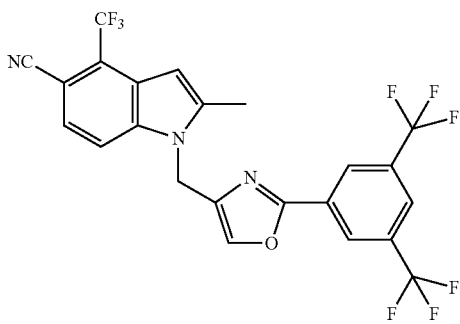 [SMILES: Cc1cc2c(C(F)(F)F)c(C#N)ccc2n1Cc1coc(-c2cc(C(F)(F)F)cc(C(F)(F)F)c2)n1]

B. 1-({2-[3,5-bis(Trifluoromethyl)phenyl]-1,3-oxazol-4-yl}methyl)-2-methyl-4-(trifluoromethyl)-1H-indole-5-carbonitrile Synthesized as described in Example 4 using 2-methyl-4-(trifluoromethyl)-1H-indole-5-carbonitrile (Example 120) and 2-[3,5-bis(trifluoromethyl)phenyl]-4-(chloromethyl)-1,3-oxazole: MS (ES) m/z 518 (M+1).

Example 355

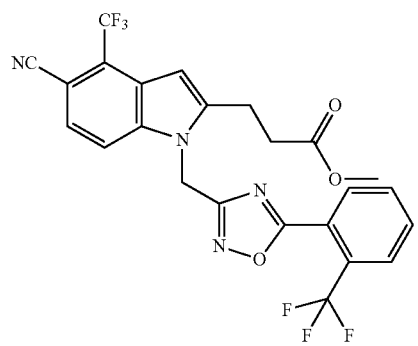 [SMILES: COC(=O)CCc1cc2c(C(F)(F)F)c(C#N)ccc2n1Cc1noc(-c2ccccc2C(F)(F)F)n1]

Methyl 3-[5-cyano-4-(trifluoromethyl)-1-({5-[2-(trifluoromethyl)phenyl]-1,2,4-oxadiazol-3-yl}methyl)-1H-indol-2-yl]propanoate

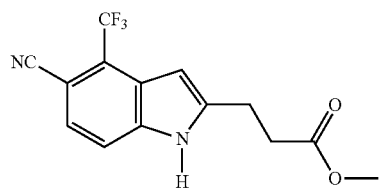 [SMILES: COC(=O)CCc1cc2c(C(F)(F)F)c(C#N)ccc2[nH]1]

A. Methyl 3-[5-cyano-4-(trifluoromethyl)-1H-indol-2-yl]propanoate

Synthesized as described for Examples 60B and 60C in a sealed vessel starting with 60A and using methyl 4-pentynoate instead of TMS acetylene: MS (ES) m/z 297 (M+1).

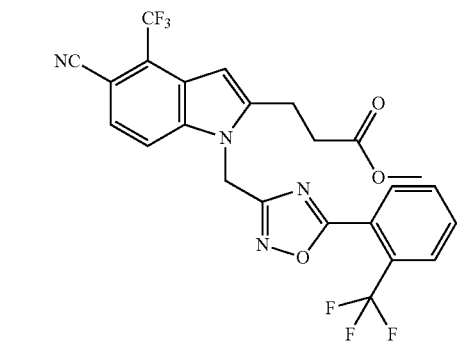 [SMILES: COC(=O)CCc1cc2c(C(F)(F)F)c(C#N)ccc2n1Cc1noc(-c2ccccc2C(F)(F)F)n1]

B. Methyl 3-[5-cyano-4-(trifluoromethyl)-1-({5-[2-(trifluoromethyl)phenyl]-1,2,4-oxadiazol-3-yl}methyl)-1H-indol-2-yl]propanoate Synthesized as described in Example 4 using methyl 3-[5-cyano-4-(trifluoromethyl)-1H-indol-2-yl]propanoate (Example 355A) and 3-(chloromethyl)-5-[3-(trifluoromethyl)phenyl]-1,2,4-oxadiazole: $^1$H NMR (400 MHz, CDCl$_3$) δ 8.31 (s, 1H), 8.24 (d, J=7.8 Hz, 1H), 7.85 (d, J=7.8 Hz, 1H), 7.67 (m, 2H), 7.57 (d, J=8.5 Hz, 1H), 6.63 (s, 1H), 5.54 (s, 2H), 3.73 (s, 3H), 3.33 (d, J=7.7 Hz, 2H), 2.94 (d, J=7.7 Hz, 2H): MS (ES) m/z 523 (M+1).

Example 356

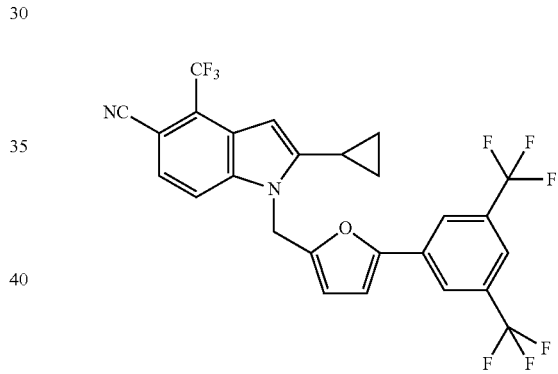

1-({5-[3,5-bis(Trifluoromethyl)phenyl]-2-furanyl}methyl)-2-cyclopropyl-4-(trifluoromethyl)-1H-indole-5-carbonitrile Synthesized as described in Example 310D using (1-[(5-bromo-2-furanyl)methyl]-2-cyclopropyl-4-(trifluoromethyl)-1H-indole-5-carbonitrile (Example 310C) and [3,5-bis(trifluoromethyl)phenyl]boronic acid: MS (ES) m/z 543 (M+1).

Example 357

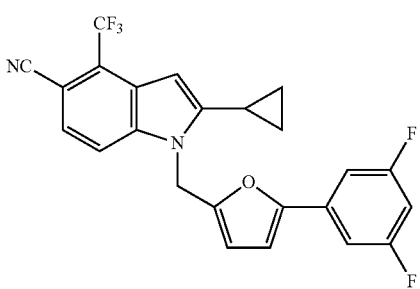 [SMILES: N#Cc1ccc2c(cc(C3CC3)n2Cc2ccc(-c3cc(F)cc(F)c3)o2)c1C(F)(F)F]

2-Cyclopropyl-1-{[5-(3,5-difluorophenyl)-2-furanyl]methyl}-4-(trifluoromethyl)-1H-indole-5-carbonitrile Synthesizes as described in Example 310D using (1-[(5-bromo-2-furanyl)methyl]-2-cyclopropyl-4-(trifluoromethyl)-1H-indole-5-carbonitrile (Example 310C) and (3,5-difluorophenyl)boronic acid: MS (ES) m/z 443 (M+1).

Example 358

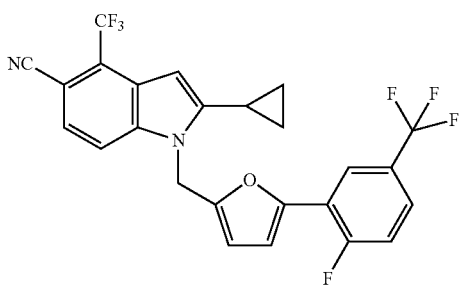 [SMILES: N#Cc1ccc2c(cc(C3CC3)n2Cc2ccc(-c3cc(C(F)(F)F)ccc3F)o2)c1C(F)(F)F]

2-Cyclopropyl-1-({5-[2-fluoro-5-(trifluoromethyl)phenyl]-2-furanyl}methyl)-4-(trifluoromethyl)-1H-indole-5-carbonitrile To a solution of (1-[(5-bromo-2-furanyl)methyl]-2-cyclopropyl-4-(trifluoromethyl)-1H-indole-5-carbonitrile (Example 310C) (0.1 g, 0.24 mmol) in dry DMF (5 mL) was added potassium acetate (0.072 g, 0.73 mmol), palladium acetate (0.011 g, 0.048 mmol) and 4,4',5,5'-tetramethyl-2,2'-bi-1,3,2-dioxaborolane (0.068 g, 0.264 mmol). The reaction is heated to 90° C. for 3 h. To the reaction was then added 2-bromo-1-fluoro-4-(trifluoromethyl)benzene (0.119 g, 0.48 mmol), cesium carbonate (0.159 g, 0.48 mmol) and tetrakis(triphenylphosphine)palladium(0) (0.057 g, 0.048 mmol). The mixture was stirred at 85° C. overnight. Solids were filtered and the filtrate was then concentrated in vacuo. The residue was purified by radial chromatography (0-40% EtOAc-hexanes gradient) and by semipreparative HPLC to afford the title compound (0.002 g, 1.3% yield): MS (ES) m/z 493 (M+1).

Example 359

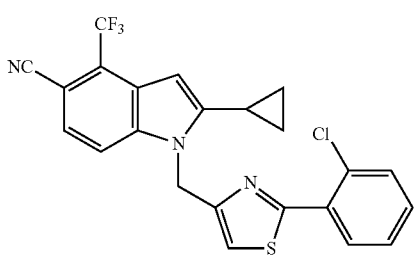 [SMILES: N#Cc1ccc2c(cc(C3CC3)n2Cc2csc(-c3ccccc3Cl)n2)c1C(F)(F)F]

1-{[2-(2-Chlorophenyl)-1,3-thiazol-4-yl]methyl}-2-cyclopropyl-4-(trifluoromethyl)-1H-indole-5-carbonitrile Synthesized as described in Example 4 using 2-cyclopropyl-4-(trifluoromethyl)-1H-indole-5-carbonitrile (Example 165A) and 4-(chloromethyl)-2-(2-chlorophenyl)-1,3-thiazole: $^1$H NMR (400 MHz, CDCl$_3$) δ 8.18 (m, 1H), 7.59 (d, J=8.5 Hz, 1H), 7.49 (m, 2H), 7.37 (m, 2H), 6.82 (s, 1H), 6.47 (s, 1H), 5.70 (s, 2H), 2.02 (m, 1H), 1.08 (m, 2H), 0.87 (m, 2H); MS (ES) m/z 458 (M+1) and 460 (M+1, isotope).

Example 360

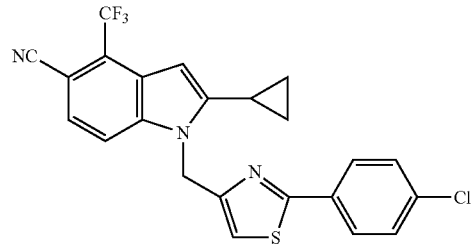 [SMILES: N#Cc1ccc2c(cc(C3CC3)n2Cc2csc(-c3ccc(Cl)cc3)n2)c1C(F)(F)F]

1-{[2-(4-Chlorophenyl)-1,3-thiazol-4-yl]methyl}-2-cyclopropyl-4-(trifluoromethyl)-1H-indole-5-carbonitrile Synthesized as described in Example 4 using 2-cyclopropyl-4-(trifluoromethyl)-1H-indole-5-carbonitrile (Example 165A) and 4-(chloromethyl)-2-(4-chlorophenyl)-1,3-thiazole: MS (ES) m/z 458 (M+1) and 460 (M+1, isotope).

Example 361

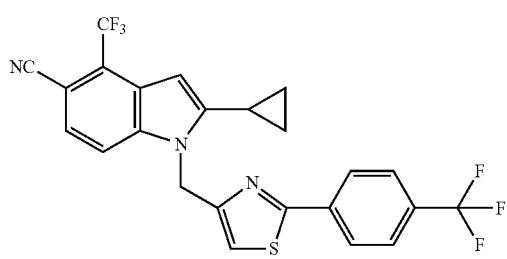 [SMILES: N#Cc1ccc2c(cc(C3CC3)n2Cc2csc(-c3ccc(C(F)(F)F)cc3)n2)c1C(F)(F)F]

2-Cyclopropyl-4-(trifluoromethyl)-1-({2-[4-(trifluoromethyl)phenyl]-1,3-thiazol-4-yl}methyl)-1H-indole-5-carbonitrile Synthesized as described in Example 4 using 2-cyclopropyl-4-(trifluoromethyl)-1H-indole-5-carbonitrile (Example 165A) and 4-(chloromethyl)-2-[4-(trifluoromethyl)phenyl]-1,3-thiazole: MS (ES) m/z 492 (M+1).

Example 362

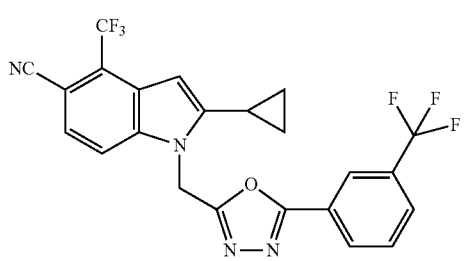 [SMILES: N#Cc1ccc2c(cc(C3CC3)n2Cc2nnc(-c3cccc(C(F)(F)F)c3)o2)c1C(F)(F)F]

2-Cyclopropyl-4-(trifluoromethyl)-1-({5-[3-(trifluoromethyl)phenyl]-1,3,4-oxadiazol-2-yl}methyl)-1H-indole-5-carbonitrile

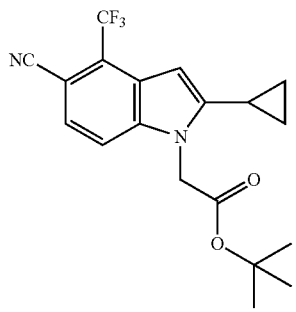 [SMILES: CC(C)(C)OC(=O)Cn1c(C2CC2)cc2c(C(F)(F)F)c(C#N)ccc21]

A. 1,1-Dimethylethyl [5-cyano-2-cyclopropyl-4-(trifluoromethyl)-1H-indol-1-yl]acetate To a solution of 2-cyclopropyl-4-(trifluoromethyl)-1H-indole-5-carbonitrile (Example 165A) (1.0 g, 4.0 mmol) in dry acetonitrile (25 mL) was added cesium carbonate (2.6 g, 8.0 mmol) and t-butyl bromoacetate (768 uL, 5.2 mmol) at rt. The mixture was stirred at 85° C. overnight. The solid was filtered and the filtrate was then concentrated in vacuo. The residue was triturated with EtOAc-hexane to afford the title compound (1.23 g) in quantitative yield: MS (ES) m/z 365 (M+1).

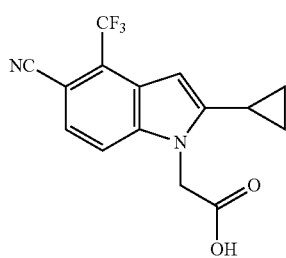 [SMILES: N#Cc1ccc2c(cc(C3CC3)n2CC(=O)O)c1C(F)(F)F]

B. [5-Cyano-2-cyclopropyl-4-(trifluoromethyl)-1H-indol-1-yl]acetic acid

To a suspension of 1,1-dimethylethyl [5-cyano-2-cyclopropyl-4-(trifluoromethyl)-1H-indol-1-yl]acetate (Example 362A) (1.23 g, 4 mmol) in dry CH$_2$Cl$_2$ (10 mL) was added TFA (3.1 mL, 40 mmol) at rt. The mixture was stirred at rt overnight. Solvent and excess TFA were removed in vacuo. The residue was tritrated with Et$_2$O-hexanes to afford the title compound (1.05 g, 85%): MS (ES) m/z 309 (M+1).

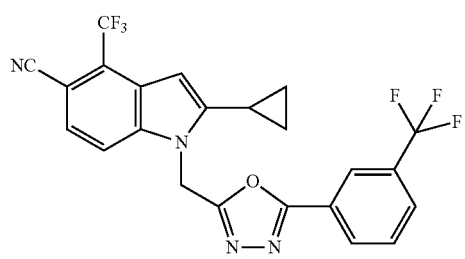 [SMILES: N#Cc1ccc2c(cc(C3CC3)n2Cc2nnc(-c3cccc(C(F)(F)F)c3)o2)c1C(F)(F)F]

C. 2-Cyclopropyl-4-(trifluoromethyl)-1-({5-[3-(trifluoromethyl)phenyl]-1,3,4-oxadiazol-2-yl}methyl)-1H-indole-5-carbonitrile Synthesized as described in Example 35C using [5-cyano-2-cyclopropyl-4-(trifluoromethyl)-1H-indol-1-yl]acetic acid (Example 362B) and 3-(trifluoromethyl)benzohydrazide: $^1$H NMR (400 MHz, CDCl$_3$) δ 8.20 (s, 1H), 8.11 (d, J=7.8 Hz, 1H), 7.80 (d, J=7.8 Hz, 1H), 7.71 (d, J=8.5 Hz, 1H), 7.64 (t, J=7.8 Hz 1H), 7.38 (d, J=8.5 Hz 1H), 6.51 (s, 1H), 5.79 (s, 2H), 2.08 (m, 1H), 1.22 (m, 2H), 0.93 (m, 2H); MS (ES) m/z 477 (M+1).

Example 363

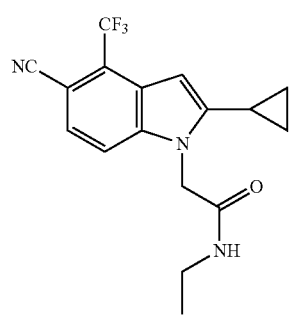 [SMILES: CCNC(=O)Cn1c(C2CC2)cc2c(C(F)(F)F)c(C#N)ccc21]

2-[5-Cyano-2-cyclopropyl-4-(trifluoromethyl)-1H-indol-1-yl]-N-ethylacetamide Synthesized as a side product in Example 362: $^1$H NMR (400 MHz, CDCl$_3$) δ 7.57 (d, J=8.4 Hz, 1H), 7.43 (d, J=8.4 Hz, 1H), 6.50 (s, 1H), 4.94 (s, 2H), 3.27 (m, 2H), 1.80 (m, 1H), 1.13 (m, 2H), 1.06 (t, J=7.2 Hz, 3H), 0.84 (m, 2H); MS (ES) m/z 336 (M+1).

Example 364

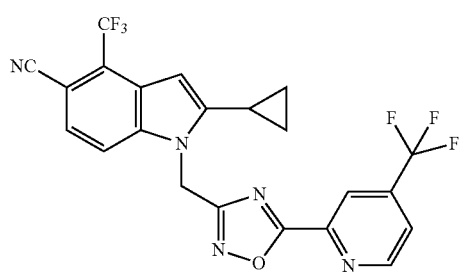 [SMILES: N#Cc1ccc2c(cc(C3CC3)n2Cc2noc(-c3cc(C(F)(F)F)ccn3)n2)c1C(F)(F)F]

2-Cyclopropyl-4-(trifluoromethyl)-1-({5-[4-(trifluoromethyl)-2-pyridinyl]-1,2,4-oxadiazol-3-yl}methyl)-1H-indole-5-carbonitrile

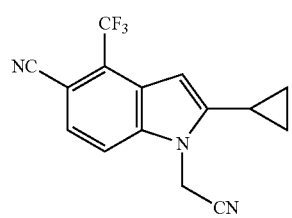 [SMILES: N#CCn1c(C2CC2)cc2c(C(F)(F)F)c(C#N)ccc21]

A. 1-(Cyanomethyl)-2-cyclopropyl-4-(trifluoromethyl)-1H-indole-5-carbonitrile Synthesized as described in Example 62 using 2-cyclopropyl-4-(trifluoromethyl)-1H-indole-5-carbonitrile (Example 165A) and bromoacetonitrile: MS (ES) m/z 290 (M+1).

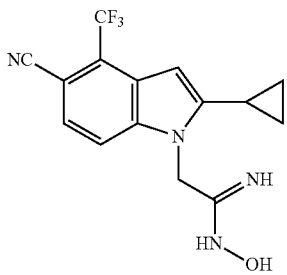 [SMILES: N#Cc1ccc2c(cc(C3CC3)n2CC(=N)NO)c1C(F)(F)F]

B. 2-[5-Cyano-2-cyclopropyl-4-(trifluoromethyl)-1H-indol-1-yl]-N-hydroxyethanimidamide Synthesized as described in Example 64 using 1-(cyanomethyl)-2-cyclopropyl-4-(trifluoromethyl)-1H-indole-5-carbonitrile (Example 364A): MS (ES) m/z 323 (M+1).

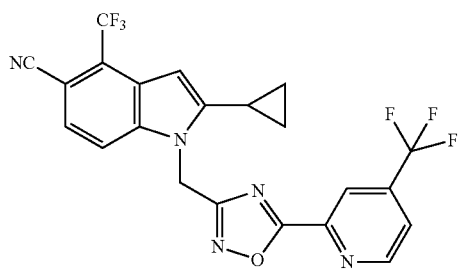 [SMILES: N#Cc1ccc2c(cc(C3CC3)n2Cc2noc(-c3cc(C(F)(F)F)ccn3)n2)c1C(F)(F)F]

C. 2-Cyclopropyl-4-(trifluoromethyl)-1-({5-[4-(trifluoromethyl)-2-pyridinyl]-1,2,4-oxadiazol-3-yl}methyl)-1H-indole-5-carbonitrile Synthesized as described in Example 72 from 2-[5-cyano-2-cyclopropyl-4-(trifluoromethyl)-1H-indol-1-yl]-N-hydroxyethanimidamide (Example 364B) and 4-(trifluoromethyl)-2-pyridinecarboxylic acid: $^1$H NMR (400 MHz, CDCl$_3$) δ 9.01 (d, J=4.7 Hz, 1H), 8.33 (s, 1H), 7.75 (d, J=4.7 Hz, 1H), 7.68 (d, J=8.5 Hz 1H), 7.56 (d, J=8.5 Hz 1H), 6.49 (s, 1H), 5.70 (s, 2H), 2.14 (m, 1H), 1.16 (m, 2H), 0.90 (m, 2H); MS (ES) m/z 478 (M+1).

Example 365

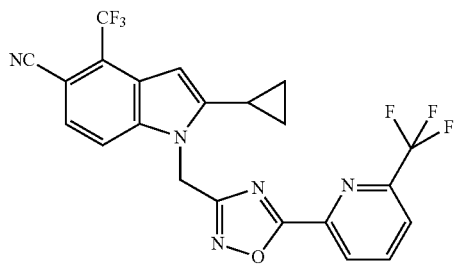 [SMILES: N#Cc1ccc2c(cc(C3CC3)n2Cc2noc(-c3cccc(C(F)(F)F)n3)n2)c1C(F)(F)F]

2-Cyclopropyl-4-(trifluoromethyl)-1-({5-[6-(trifluoromethyl)-2-pyridinyl]-1,2,4-oxadiazol-3-yl}methyl)-1H-indole-5-carbonitrile Synthesized as described in Example 72 from 2-[5-cyano-2-cyclopropyl-4-(trifluoromethyl)-1H-indol-1-yl]-N-hydroxyethanimidamide (Example 364B) and 6-(trifluoromethyl)-2-pyridinecarboxylic acid: MS (ES) m/z 478 (M+1).

Example 366

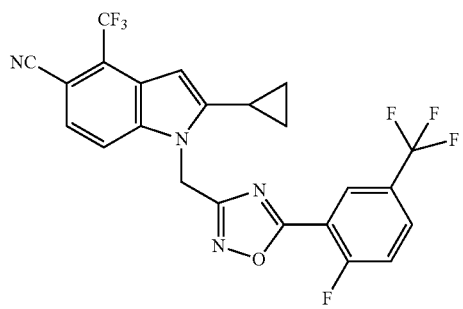 [SMILES: N#Cc1ccc2c(cc(C3CC3)n2Cc2noc(-c3cc(C(F)(F)F)ccc3F)n2)c1C(F)(F)F]

2-Cyclopropyl-1-({5-[2-fluoro-5-(trifluoromethyl)phenyl]-1,2,4-oxadiazol-3-yl}methyl)-4-(trifluoromethyl)-1H-indole-5-carbonitrile

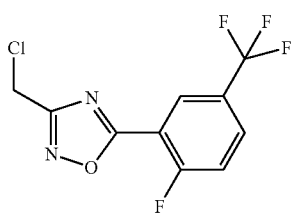 [SMILES: Fc1ccc(C(F)(F)F)cc1-c1nc(CCl)no1]

A. 3-(Chloromethyl)-5-[2-fluoro-5-(trifluoromethyl)phenyl]-1,2,4-oxadiazole

To a solution of 2-chloro-N-hydroxyethanimidamide (2.4 g, 22.1 mmol) and triethylamine (3.7 ml, 26.5 mmol) in dry toluene (35 mL) was added 2-fluoro-5-(trifluoromethyl)benzoyl chloride (5 g, 22.1 mmol) at 0° C. The mixture was stirred at room temperature for 1 h and then at 100° C. overnight. The resulting solid was filtered and the filtrate was then concentrated in vacuo. The residue was purified by radial chromatography (0-30% EtOAc-hexanes gradient) to afford the title compound (1.2 g, 19% yield): MS (ES) m/z 281 (M+1) and 283 (M+1, isotope).

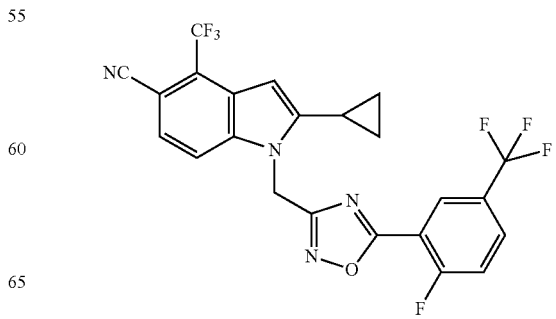

B. 2-Cyclopropyl-1-({5-[2-fluoro-5-(trifluoromethyl)phenyl]-1,2,4-oxadiazol-3-yl}methyl)-4-(trifluoromethyl)-1H-indole-5-carbonitrile Synthesized as described in Example 4 using 2-cyclopropyl-4-(trifluoromethyl)-1H-indole-5-carbonitrile (Example 165A) and 3-(chloromethyl)-5-[2-fluoro-5-(trifluoromethyl)phenyl]-1,2,4-oxadiazole (Example 366A): ¹H NMR (400 MHz, CDCl₃) δ 8.33 (m, 1H), 7.85 (m, 1H), 7.68 (d, J=8.4 Hz, 1H), 7.54 (d, J=8.4 Hz, 1H), 7.39 (d, J=9.3 Hz, 1H), 6.49 (s, 1H), 5.68 (s, 2H), 2.14 (m, 1H), 1.15 (m, 2H), 0.92 (m, 2H); MS (ES) m/z 495 (M+1).

Example 367

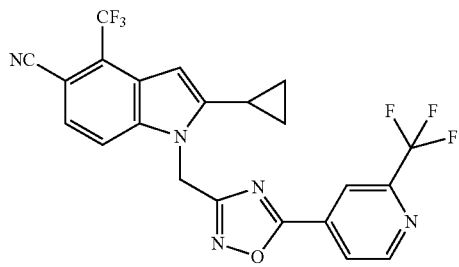 [SMILES: N#Cc1ccc2c(cc(C3CC3)n2Cc2noc(-c3ccnc(C(F)(F)F)c3)n2)c1C(F)(F)F]

2-Cyclopropyl-4-(trifluoromethyl)-1-({5-[2-(trifluoromethyl)-4-pyridinyl]-1,2,4-oxadiazol-3-yl}methyl)-1H-indole-5-carbonitrile Synthesized as described in Example 72 from 2-[5-cyano-2-cyclopropyl-4-(trifluoromethyl)-1H-indol-1-yl]-N-hydroxyethanimidamide (Example 364A) and 2-(trifluoromethyl)-4-pyridinecarboxylic acid: MS (ES) m/z 478 (M+1).

Example 368

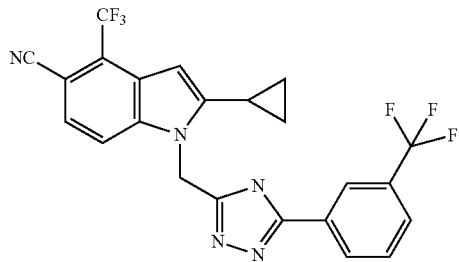 [SMILES: N#Cc1ccc2c(cc(C3CC3)n2Cc2nnc(-c3cccc(C(F)(F)F)c3)[nH]2)c1C(F)(F)F]

2-Cyclopropyl-4-(trifluoromethyl)-1-({3-[3-(trifluoromethyl)phenyl]-1H-1,2,4-triazol-5-yl}methyl)-1H-indole-5-carbonitrile To a solution of 2-cyclopropyl-4-(trifluoromethyl)-1-({5-[3-(trifluoromethyl)phenyl]-1,3,4-oxadiazol-2-yl}methyl)-1H-indole-5-carbonitrile (Example 362C) (0.019 g, 0.040 mmol) in 2M ammonia in methanol (3 mL) was added magnesium chloride (0.008 g, 0.081 mmol). The mixture was stirred at 120° C. in a sealed tube for 10 days. Solids were filtered and the filtrate was then concentrated in vacuo. The residue was purified by radial chromatography (0-70% EtOAc-hexanes gradient) and then by semipreparative HPLC to afford the title compound as TFA salt (0.005 g, 21% yield): ¹H NMR (400 MHz, CDCl₃) δ 8.16 (s, 1H), 8.07 (d, J=7.6 Hz, 1H), 7.73 (d, J=7.6 Hz, 1H), 7.66 (d, J=8.5 Hz, 1H), 7.63 (t, J=7.8 Hz 1H), 7.52 (d, J=8.5 Hz 1H), 6.48 (s, 1H), 5.66 (s, 2H), 2.13 (m, 1H), 1.12 (m, 2H), 0.89 (m, 2H); MS (ES) m/z 476 (M+1).

Example 369

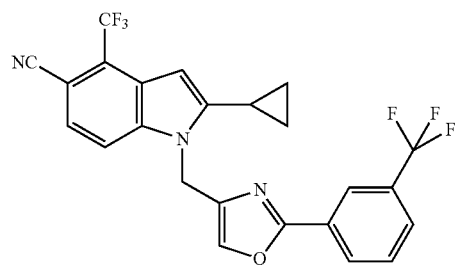

2-Cyclopropyl-4-(trifluoromethyl)-1-({2-[3-(trifluoromethyl)phenyl]-1,3-oxazol-4-yl}methyl)-1H-indole-5-carbonitrile Synthesized as described in Example 4 using 2-cyclopropyl-4-(trifluoromethyl)-1H-indole-5-carbonitrile (Example 165A) and 4-(bromomethyl)-2-[3-(trifluoromethyl)phenyl]-1,3-oxazole (synthesized similarly to Example 353): ¹H NMR (400 MHz, CDCl₃) δ 8.24 (s, 1H), 8.16 (d, J=7.8 Hz, 1H), 7.71 (d, J=7.8 Hz, 1H), 7.58 (m, 3H), 7.34 (s, 1H), 6.45 (s, 1H), 5.49 (s, 2H), 2.02 (m, 1H), 1.11 (m, 2H), 0.88 (m, 2H); MS (ES) m/z 476 (M+1).

Example 370

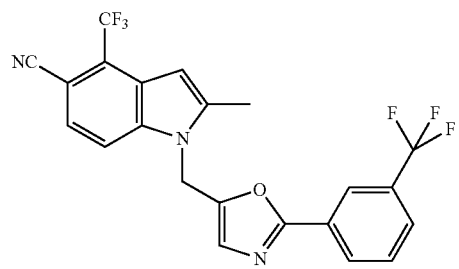 [SMILES: Cc1cc2c(C(F)(F)F)c(C#N)ccc2n1Cc1cnc(-c2cccc(C(F)(F)F)c2)o1]

2-Methyl-4-(trifluoromethyl)-1-({2-[3-(trifluoromethyl)phenyl]-1,3-oxazol-5-yl}methyl)-1H-indole-5-carbonitrile

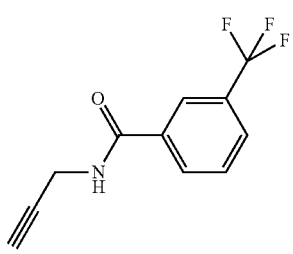 [SMILES: C#CCNC(=O)c1cccc(C(F)(F)F)c1]

A. N-2-Propyn-1-yl-3-(trifluoromethyl)benzamide

To a solution of 2-propyn-1-amine (2.0 g, 35.7 mmol) and Hunnig's base (12.5 mL, 71.4 mmol) in CH$_2$Cl$_2$ (20 mL) was added 3-(trifluoromethyl)benzoyl chloride (5.4 mL, 35.7 mmol) at 0° C. The mixture was stirred at rt overnight. CH$_2$Cl$_2$ was added and the organic solution was washed with water twice, brine once, and dried over MgSO$_4$. Concentration and purification by radial chromatography (0-40% EtOAc-hexanes gradient) afforded the title compound (7.0 g, 96% yield): MS (ES) m/z 228 (M+1).

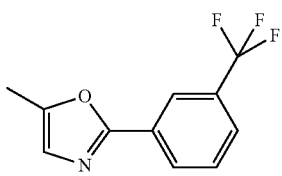 [SMILES: Cc1cnc(-c2cccc(C(F)(F)F)c2)o1]

B. 5-Methyl-2-[3-(trifluoromethyl)phenyl]-1,3-oxazole

N-2-Propyn-1-yl-3-(trifluoromethyl)benzamide (Example 370A) (7.0 g, 30.8 mmol) was suspended in sulfuric acid (95-98%, 15 mL). The mixture was heated at 110° C. for 15 min. After cooling down, ice was added and solution was neutralized with 5N NaOH to pH 7 at 0° C. The mixture was extracted with Et$_2$O three times and the combined organic layers were washed with brine once and dried over MgSO$_4$. Concentration and purification by radial chromatography (0-20% EtOAc-hexanes gradient) afforded the title compound (6.8 g, 97% yield): MS (ES) m/z 228 (M+1).

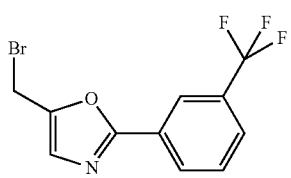 [SMILES: FC(F)(F)c1cccc(-c2ncc(CBr)o2)c1]

C. 5-(Bromomethyl)-2-[3-(trifluoromethyl)phenyl]-1,3-oxazole

To a solution of 5-methyl-2-[3-(trifluoromethyl)phenyl]-1,3-oxazole (Example 370B) (1.0 g, 4.4 mmol) was added NBS (0.784 g, 4.4 mmol) and benzoyl peroxide (0.100 g, 0.41 mmol). The mixture was refluxed for 1 h and the solids were filtered. The filtrate was concentrated and purified by radial chromatography (0-20% EtOAc-hexanes gradient) to afford the title compound (0.760 g, 56% yield): MS (ES) m/z 306 (M+1) and 308 (M+1, isotope).

D. 2-Methyl-4-(trifluoromethyl)-1-({2-[3-(trifluoromethyl)phenyl]-1,3-oxazol-5-yl}methyl)-1H-indole-5-carbonitrile Synthesized as described in Example 4 using 2-methyl-4-(trifluoromethyl)-1H-indole-5-carbonitrile (Example 120) and 5-(bromomethyl)-2-[3-(trifluoromethyl)phenyl]-1,3-oxazole (Example 370C): $^1$H NMR (400 MHz, CDCl$_3$) δ 8.19 (s, 1H), 8.07 (d, J=7.8 Hz, 1H), 7.70 (d, J=7.8 Hz, 1H), 7.59 (m, 3H), 7.04 (s, 1H), 6.65 (s, 1H), 5.42 (s, 2H), 2.62 (s, 3H); MS (ES) m/z 450 (M+1).

Example 371

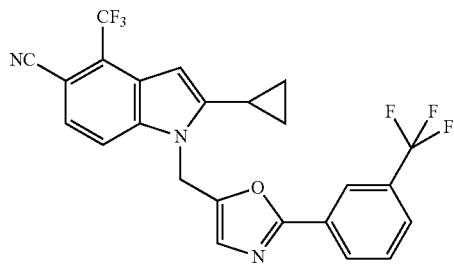 [SMILES: N#Cc1ccc2c(cc(C3CC3)n2Cc2cnc(-c3cccc(C(F)(F)F)c3)o2)c1C(F)(F)F]

2-Cyclopropyl-4-(trifluoromethyl)-1-({2-[3-(trifluoromethyl)phenyl]-1,3-oxazol-5-yl}methyl)-1H-indole-5-carbonitrile Synthesized as described in Example 4 using 2-cyclopropyl-4-(trifluoromethyl)-1H-indole-5-carbonitrile (Example 165A) and 5-(bromomethyl)-2-[3-(trifluoromethyl)phenyl]-1,3-oxazole (Example 370C): MS (ES) m/z 476 (M+1).

Example 372

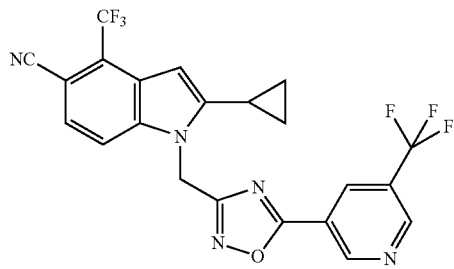 [SMILES: N#Cc1ccc2c(cc(C3CC3)n2Cc2noc(-c3cncc(C(F)(F)F)c3)n2)c1C(F)(F)F]

2-Cyclopropyl-4-(trifluoromethyl)-1-({5-[5-(trifluoromethyl)-3-pyridinyl]-1,2,4-oxadiazol-3-yl}methyl)-1H-indole-5-carbonitrile Synthesized as described in Example 72 from 2-[5-cyano-2-cyclopropyl-4-(trifluoromethyl)-1H-indol-1-yl]-N-hydroxyethanimidamide (Example 364B) and 5-(trifluoromethyl)-3-pyridinecarboxylic acid: MS (ES) m/z 478 (M+1).

Example 373

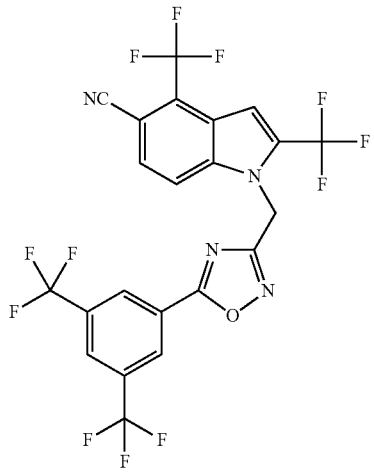 [SMILES: N#Cc1ccc2c(cc(C(F)(F)F)n2Cc2noc(-c3cc(C(F)(F)F)cc(C(F)(F)F)c3)n2)c1C(F)(F)F]

1-({5-[3,5-bis(Trifluoromethyl)phenyl]-1,2,4-oxadiazol-3-yl}methyl)-2,4-bis(trifluoromethyl)-1H-indole-5-carbonitrile Synthesized as described in Example 192 using 5-[3,5-bis(trifluoromethyl)phenyl]3-(chloromethyl)-1,2,4-oxadiazole (0.057 g, 0.17 mmol) to afford the title compound (0.043 g, 52%) as a white solid: $^1$H NMR (400 MHz, DMSO-d$_6$) δ 8.52 (s, 2H), 8.49 (s, 1H), 8.34 (d, J=8.8 Hz, 1H), 8.08 (d, J=8.8 Hz, 1H), 7.48 (s, 1H), 6.05 (s, 2H); MS m/z 595 (M+Na).

Example 374

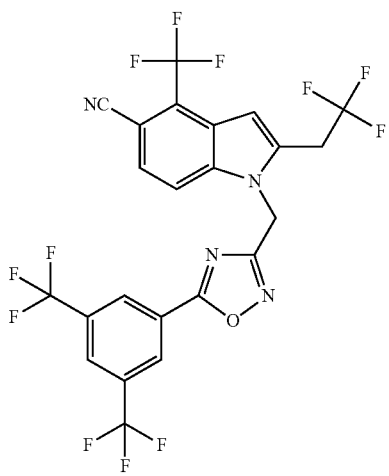 [SMILES: N#Cc1ccc2c(cc(CC(F)(F)F)n2Cc2noc(-c3cc(C(F)(F)F)cc(C(F)(F)F)c3)n2)c1C(F)(F)F]

1-({5-[3,5-bis(Trifluoromethyl)phenyl]-1,2,4-oxadiazol-3-yl}methyl)-2-(2,2,2-trifluoroethyl)-4-(trifluoromethyl)-1H-indole-5-carbonitrile

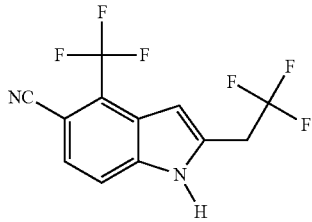 [SMILES: N#Cc1ccc2[nH]c(CC(F)(F)F)cc2c1C(F)(F)F]

A. 2-(2,2,2-Trifluoroethyl)-4-(trifluoromethyl)-1H-indole-5-carbonitrile

A mixture of {[6-amino-3-cyano-2-(trifluoromethyl)phenyl]methyl}(triphenyl)phosphonium bromide (0.50 g, 0.92 mmol), 3,3,3-trifluoropropanoic acid (0.175 g, 1.40 mmol), 2,4,6-tripropyl-1,3,5,2,4,6-trioxatriphosphorinane 2,4,6-trioxide (2.60 g, 4.10 mmol, 50% in EtOAc) and DIEA (0.65 mL, 3.70 mmol) in THF (25 mL) was stirred at ambient temperature for 6 h. The mixture was concentrated and then diluted with anhydrous DMF (15 mL) and stirred at 100° C. for 18 h. The reaction was poured into water (100 mL) and extracted with Et$_2$O (2×60 mL). The combined organic portions were washed with sat'd NaHCO$_3$ (50 mL) and brine (50 mL). Drying (MgSO$_4$), filtration, and concentration was followed by purification (SiO$_2$, 30% EtOAc in hexanes) to afford 2-(2,2,2-trifluoroethyl)-4-(trifluoromethyl)-1H-indole-5-carbonitrile (0.189 g, 70%) as a pale yellow solid:

$^1$H NMR (400 MHz, DMSO-d$_6$) δ 12.36 (b, 1H), 7.84 (d, J=8.3 Hz, 1H), 7.70 (d, J=8.3 Hz, 1H), 6.72 (s, 1H), 4.00 (q, 2H).

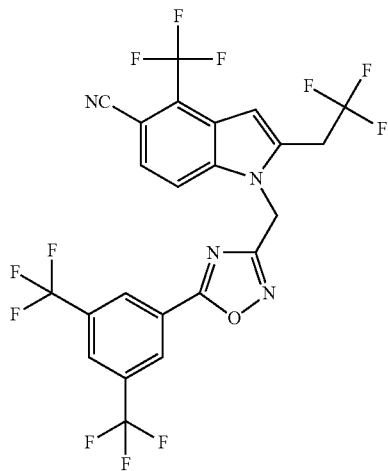 [SMILES: N#Cc1ccc2c(cc(CC(F)(F)F)n2Cc2noc(-c3cc(C(F)(F)F)cc(C(F)(F)F)c3)n2)c1C(F)(F)F]

B. 1-({5-[3,5-bis(Trifluoromethyl)phenyl]-1,2,4-oxadiazol-3-yl}methyl)-2-(2,2,2-trifluoroethyl)-4-(trifluoromethyl)-1H-indole-5-carbonitrile A mixture of the indole (0.040 g, 0.14 mmol) from step A, Cs$_2$CO$_3$ (0.054 g, 0.16 mmol), 5-[3,5-bis(trifluoromethyl)phenyl]-3-(chloromethyl)-1,2,4-oxadiazole (0.091 g, 0.27 mmol) and CH$_3$CN (4 mL) was stirred at 50° C. for 24 h. The mixture was diluted with EtOAc (25 mL) and washed with water (15 mL) and brine (15 mL). Drying (MgSO$_4$), filtration, and concentration was followed by purification (SiO$_2$, 0-30% EtOAc in hexanes) to afford the title compound (0.015 g, 19%) as an off-white solid: $^1$H NMR (400 MHz, CDCl$_3$) δ 8.48 (s, 2H), 8.10 (s, 1H), 7.80 (d, J=8.6 Hz, 1H), 7.65 (d, J=8.6 Hz, 1H), 6.96 (s, 1H), 5.58 (s, 2H), 3.94 (q, 2H); MS m/z 585 (M–H).

Example 375

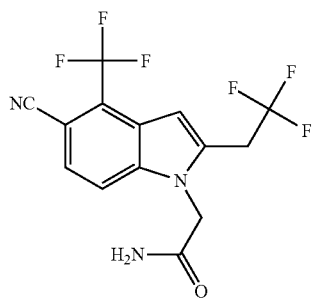 [SMILES: N#Cc1ccc2c(cc(CC(F)(F)F)n2CC(N)=O)c1C(F)(F)F]

2-[5-Cyano-2-(2,2,2-trifluoroethyl)-4-(trifluoromethyl)-1H-indol-1-yl]acetamide

A mixture of 2-(2,2,2-trifluoroethyl)-4-(trifluoromethyl)-1H-indole-5-carbonitrile (Example 374A) (0.050 g, 0.17 mmol), Cs$_2$CO$_3$ (0.112 g, 0.34 mmol), 2-bromoacetamide (0.047 g, 0.34 mmol) and CH$_3$CN (4 mL) was stirred at 70° C. for 2 h. The mixture was diluted with EtOAc (25 mL), washed with water (15 mL), brine (1 5 mL), dried over (MgSO$_4$) and concentrated. The residue was stirred in EtOAc (5 mL) for 30 min. The resulting solid was filtered, rinsed with hexanes and dried to afford the title compound (0.017 g, 28%) as a tan solid: $^1$H NMR (400 MHz, DMSO-d$_6$) δ 7.88 (d, J=8.6 Hz, 1H), 7.79 (d, J=8.6 Hz, 1H), 7.72 (s, 1H), 7.38 (s, 1H), 6.78 (s, 1H), 5.01 (s, 2H), 4.07 (q, 2H); MS m/z 348 (M–H).

Example 376

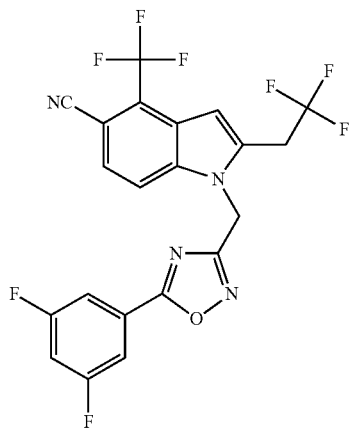 [SMILES: N#Cc1ccc2c(cc(CC(F)(F)F)n2Cc2noc(-c3cc(F)cc(F)c3)n2)c1C(F)(F)F]

1-{[5-(3,5-Difluorophenyl)-1,2,4-oxadiazol-3-yl]methyl}-2-(2,2,2-trifluoroethyl)-4-(trifluoromethyl)-1H-indole-5-carbonitrile Synthesized as described in Example 374A using 3-(chloromethyl)-5-(3,5-difluorophenyl)-1,2,4-oxadiazole (0.095 g, 0.41 mmol) to afford the title compound (0.015 g, 15%) as an off-white solid: $^1$H NMR (400 MHz, CDCl$_3$) δ 7.77 (d, J=8.6 Hz, 1H), 7.65 (d, J=8.6 Hz, 1H), 7.56 (d, J=5.1 Hz, 2H), 7.08-7.03 (m, 1H), 6.94 (s, 1H), 5.54 (s, 2H), 3.94 (q, 2H); MS m/z 485 (M–H).

Example 377

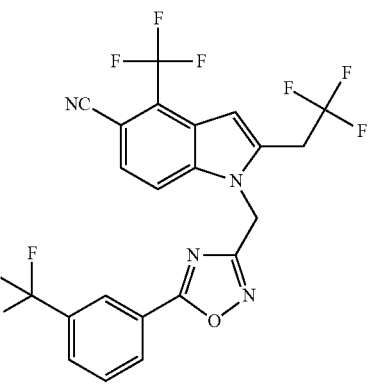

2-(2,2,2-Trifluoroethyl)-4-(trifluoromethyl)-1-({5-[3-(trifluoromethyl)phenyl]-1,2,4-oxadiazol-3-yl}methyl)-1H-indole-5-carbonitrile A mixture of 2-(2,2,2-trifluoroethyl)-4-(trifluoromethyl)-1H-indole-5-carbonitrile (Example 374A) (0.080 g, 0.27 mmol), K$_2$CO$_3$ (0.042 g, 0.30 mmol), 3-(chloromethyl)-5-[3-(trifluoromethyl)phenyl]-1,2,4-oxadiazole (0.143 g, 0.54 mmol) and CH$_3$CN (5 mL) was stirred at 60° C. for 6 h. The mixture was diluted with EtOAc (25 mL) and washed with water (15 mL) and brine (15 mL). Drying (MgSO$_4$), filtration, and concentration was followed by purification (SiO$_2$, 0-30% EtOAc in hexanes) to afford the title compound (0.031 g, 22%) as a pale yellow solid: $^1$H NMR (400 MHz, CDCl$_3$) δ 8.29 (s, 1H), 8.23 (d, J=8.0 Hz, 1H), 7.86 (d, J=8.0 Hz, 1H), 7.79 (d, J=8.6 Hz, 1H), 7.69-7.63 (m, 2H), 6.94 (s, 1H), 5.56 (s, 2H), 3.96 (q, 2H); MS m/z 517 (M–H).

Example 378

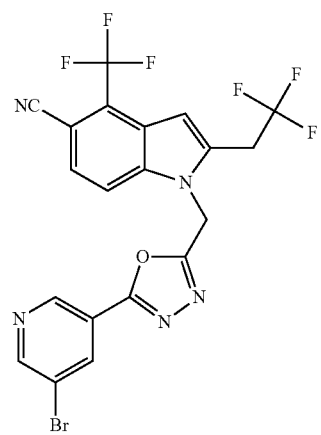 [SMILES: N#Cc1ccc2c(cc(CC(F)(F)F)n2Cc2nnc(-c3cncc(Br)c3)o2)c1C(F)(F)F]

1-{[5-(5-Bromo-3-pyridinyl)-1,3,4-oxadiazol-2-yl]methyl}-2-(2,2,2-trifluoroethyl)-4-(trifluoromethyl)-1H-indole-5-carbonitrile Synthesized as described in Example 377 using 3-bromo-5-[5-(chloromethyl)-1,3,4-oxadiazol-2-yl]pyridine (0.188 g, 0.68 mmol) to afford the title compound (0.048 g, 48%) as an off-white solid: ¹H NMR (400 MHz, DMSO-d₆) δ 9.06 (s, 1H), 8.95 (s, 1H), 8.49 (s, 1H), 8.14 (d, J=8.5 Hz, 1H), 7.88 (d, J=8.5 Hz, 1H), 6.89 (s, 1H), 6.11 (s, 2H), 4.29 (q, 2H); MS m/z 530 (M+H).

Example 379

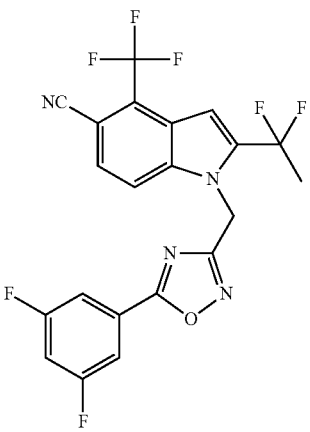 [SMILES: CC(F)(F)c1cc2c(C(F)(F)F)c(C#N)ccc2n1Cc1noc(-c2cc(F)cc(F)c2)n1]

2-(1,1-Difluoroethyl)-1-{[5-(3,5-difluorophenyl)-1,2,4-oxadiazol-3-yl]methyl}-4-(trifluoromethyl)-1H-indole-5-carbonitrile

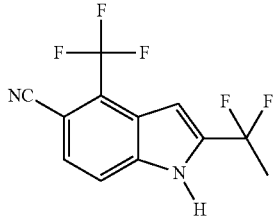 [SMILES: CC(F)(F)c1cc2c(C(F)(F)F)c(C#N)ccc2[nH]1]

A. 2-(1,1-Difluoroethyl)-4-(trifluoromethyl)-1H-indole-5-carbonitrile

Prepared in a manner similar to Example 374A using 2,2-difluoropropanoic acid (0.46 g, 4.18 mmol) to afford 2-(1,1-difluoroethyl)-4-(trifluoromethyl)-1H-indole-5-carbonitrile (0.352 g, 82%) as a light yellow solid: ¹H NMR (400 MHz, DMSO-d₆) δ 12.92 (b, 1H), 7.87 (d, J=8.5 Hz, 1H), 7.80 (d, J=8.5 Hz, 1H), 7.01 (s, 1H), 2.14 (t, 3H).

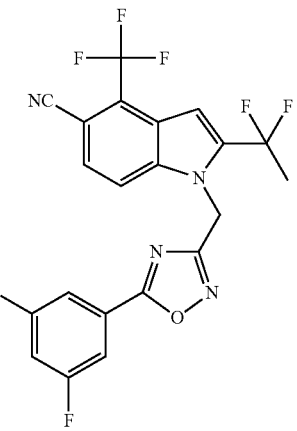

B. 2-(1,1-Difluoroethyl)-1-{[5-(3,5-difluorophenyl)-1,2,4-oxadiazol-3-yl]methyl}-4-(trifluoromethyl)-1H-indole-5-carbonitrile A mixture of the indole (0.050 g, 0.18 mmol) from step A, Cs₂CO₃ (0.065 g, 0.20 mmol), 3-(chloromethyl)-5-(3,5-difluorophenyl)-1,2,4-oxadiazole (0.046 g, 0.20 mmol) and CH₃CN (4 mL) was stirred at 70° C. for 24 h. The mixture was diluted with EtOAc (25 mL), washed with water (15 mL), brine (15 mL), dried over (MgSO₄) and concentrated. Added 10% Et₂O in hexanes (10 mL) and stirred for 2 h. The resulting solid was filtered, rinsed with hexanes and dried to afford the title compound (0.065 g, 76%) as a light tan solid: ¹H NMR (400 MHz, DMSO-d₆) δ 8.23 (d, J=8.6 Hz, 1H), 7.98 (d, J=8.6 Hz, 1H), 7.74-7.64 (m, 3H), 7.23 (s, 1H), 5.99 (s, 2H), 2.24 (t, 3H); MS m/z 467 (M−H).

Example 380

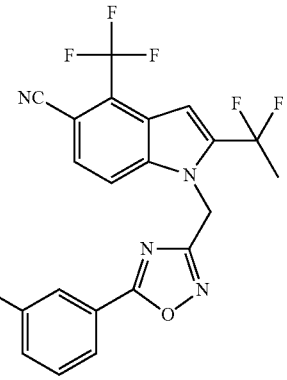

2-(1,1-Difluoroethyl)-4-(trifluoromethyl)-1-({5-[3-(trifluoromethyl)phenyl]-1,2,4-oxadiazol-3-yl}methyl)-1H-indole-5-carbonitrile Synthesized as described in Example 379B using 3-(chloromethyl)-5-[3-(trifluoromethyl)phenyl]-1,2,4-oxadiazole (0.057 g, 0.22 mmol) to afford the title compound (0.061 g, 67%) as an off-white solid: ¹H NMR (400 MHz, DMSO-d₆)

δ 8.30-8.23 (m, 3H), 8.07 (d, J=8.1 Hz, 1H), 7.98 (d, J=8.6 Hz, 1H), 7.84 (t, 1H), 7.24 (s, 1H), 6.00 (s, 2H), 2.24 (t, 3H); MS m/z 499 (M−H).

Example 381

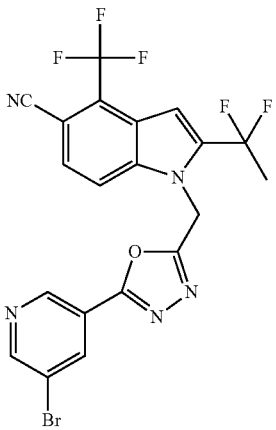 [SMILES: CC(F)(F)c1cc2c(C(F)(F)F)c(C#N)ccc2n1Cc1nnc(-c2cncc(Br)c2)o1]

1-{[5-(5-Bromo-3-pyridinyl)-1,3,4-oxadiazol-2-yl]methyl}-2-(1,1-difluoroethyl)-4-(trifluoromethyl)-1H-indole-5-carbonitrile Synthesized as described in Example 379B using 3-bromo-5-[5-(chloromethyl)-1,3,4-oxadiazol-2-yl]pyridine (0.060 g, 0.22 mmol) to afford the title compound (0.068 g, 73%) as a tan solid: $^1$H NMR (400 MHz, DMSO-d$_6$) δ 9.02 (s, 1H), 8.94 (s, 1H), 8.46 (s, 1H), 8.26 (d, J=8.8 Hz, 1H), 8.01 (d, J=8.8 Hz, 1H), 7.26 (s, 1H), 6.01 (s, 2H), 2.26 (t, 3H); MS m/z 511 (M−H).

Example 382

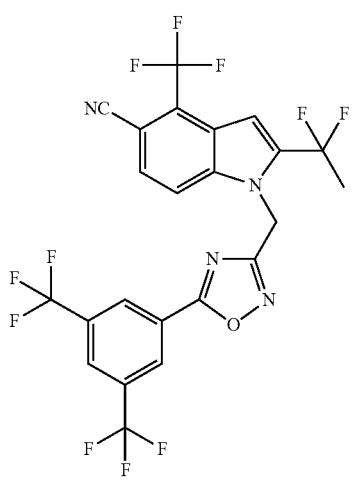 [SMILES: CC(F)(F)c1cc2c(C(F)(F)F)c(C#N)ccc2n1Cc1noc(-c2cc(C(F)(F)F)cc(C(F)(F)F)c2)n1]

1-({5-[3,5-bis(Trifluoromethyl)phenyl]-1,2,4-oxadiazol-3-yl}methyl)-2-(1,1-difluoroethyl)-4-(trifluoromethyl)-1H-indole-5-carbonitrile Synthesized as described in Example 379B using 5-[3,5-bis(trifluoromethyl)phenyl]-3-(chloromethyl)-1,2,4-oxadiazole (0.072 g, 0.22 mmol) and purification (SiO$_2$, 0-30% EtOAc in hexanes) to afford the title compound (0.073 g, 70%) as an off-white solid: $^1$H NMR (400 MHz, DMSO-d$_6$) δ 8.54 (s, 2H), 8.50 (s, 1H), 8.23 (d, J=8.6 Hz, 1H), 7.99 (d, J=8.6 Hz, 1H), 7.24 (s, 1H), 6.03 (s, 2H), 2.24 (t, 3H); MS m/z 567 (M−H).

Example 383

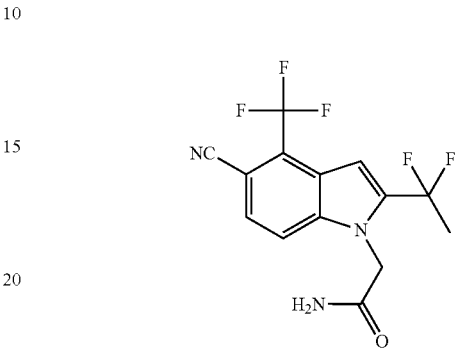

2-[5-Cyano-2-(1,1-difluoroethyl)-4-(trifluoromethyl)-1H-indol-1-yl]acetamide

Synthesized as described in Example 379B using 2-bromoacetamide (0.060 g, 0.44 mmol) to afford the title compound (0.067 g, 93%) as an off-white solid: $^1$H NMR (400 MHz, DMSO-d$_6$) δ 8.03 (d, J=8.8 Hz, 1H), 7.88 (d, J=8.8 Hz, 1H), 7.68 (s, 1H), 7.28 (s, 1H), 7.12 (s, 1H), 5.10 (s, 2H), 2.18 (t, 3H); MS m/z 330 (M−H).

Biological Section

Compounds of the current invention are modulators of the androgen receptor. Additionally, the compounds of the present invention may also prove useful as modulators of the glucocorticoid receptor, the mineralocorticoid receptor, and/or the progesterone receptor. Activity mediated through oxosteroid nuclear receptors was determined using the following in vitro and in vivo assays.

In Vitro Assays:

The following abbreviations and sources of materials are used

Fluormone PL Red—a commercially available PR fluoroprobe (PanVera Corp, Product No P2965)

Fluormone GS Red—a commercially available GR fluoroprobe (PanVera Corp, Product No P2894)

Fluormone AL Green—a commercially available AR fluoroprobe (PanVera Corp, Product No P3010)

PR-LBD—Purified human progesterone ligand binding domain tagged with Glutathione Transferase (PanVera Corp, Product No P2900)

GR—purified human glucocorticoid receptor (PanVera Corp, Product No P2812)

AR-LBD—Purified rat androgen ligand binding domain tagged with Glutathione Transferase (PanVera Corp, Product No P3009)

PR Screening Buffer—100 mM potassium phosphate (pH 7.4), 100 μG/ml bovine gamma globulin, 15% ethylene glycol, 0.02% NaN$_3$, 10% glycerol (PanVera Corp Product No P2967) with 0.1% w/v CHAPS AR Screening Buffer—pH 7.5 containing protein stabilizing agents and glycerol (PanVera Corp Product No P3011)

GR Screening Buffer—100 mM potassium phosphate (pH 7.4), 200 mM Na$_2$MoO$_2$, 1 mM EDTA, 20% DMSO (PanVera Corp Product No P2814) with GR stabilizing peptide (100 µM) (PanVera Corp Product No P2815)

DTT—dithiothreitol (PanVera Corp Product No P2325)

Discovery Analyst—is an FP reader

DMSO—dimethylsulphoxide

Progesterone Receptor Fluorescence Polarization Assay:

The progesterone receptor fluorescence polarization assay is used to investigate the interaction of the compounds with the progesterone receptor.

Compounds are added to the 384 well black plates to a final volume of 0.5 µL. Sufficient Fluormone PL Red and PR-LBD are defrosted on ice to give a final concentration of 2 nM and 40 nM, respectively. PR screening buffer is chilled to 4° C. prior to addition of DTT to give a final concentration of 1 mM. The Fluormone PL Red and PR-LBD in PR Screening Buffer are added to compound plates to give a final volume of 10 µL. The assay is allowed to incubate at 20-22° C. for 2 hours. The plates are counted in a Discovery Analyst with suitable 535 nM excitation and 590 nM emission interference filters. Compounds that interact with the PR result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the IC$_{50}$ and d is the maximum. Maximum and minimum values are compared to adhesion in the absence of compound and in the presence of 10$^{-5}$M progesterone. Data is presented as the mean pIC$_{50}$ with the standard error of the mean of n experiments. Compounds with pIC$_{50}$ greater than 5.0 and a % max greater than 50 are preferred. The invention also encompasses compounds with pIC$_{50}$ less than 5.0 and/or a % max less than 50 in the Progesterone Receptor Fluorescence Polarization Assay, where the compound has a pIC$_{50}$ greater than 5.0 and a % max greater than 50 in the Androgen Receptor Fluorescence Polarization Assay.

Androgen Receptor Fluorescence Polarization Assay:

The androgen receptor fluorescence polarization assay is used to investigate the interaction of the compounds with the androgen receptor.

Compounds are added to the 384 well black plates to a final volume of 0.5 µL. Sufficient Fluormone AL Green and AR-LBD are defrosted on ice to give a final concentration of 1 nM and 25 nM, respectively. AR screening buffer is chilled to 4° C. prior to addition of DTT to give a final concentration of 1 mM. The Fluormone AL Green and AR-LBD in AR Screening Buffer are added to compound plates to give a final volume of 10 µL. The assay is allowed to incubate at 20° C. for 5 hours. The plates are counted in a Discovery Analyst with suitable 485 nM excitation and 535 nM emission interference filters. Compounds that interact with the AR result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the IC$_{50}$ and d is the maximum. Maximum and minimum values are compared to adhesion in the absence of compound and in the presence of 10$^{-5}$M dihydrotestosterone. Data is presented as the mean pIC$_{50}$ with the standard error of the mean of n experiments. Compounds with pIC$_{50}$ greater than 5.0 and a % max greater than 50 are preferred.

Glucocorticoid Receptor Fluorescence Polarization Assay

The glucocorticoid receptor fluorescence polarization assay is used to investigate the interaction of the compounds with the glucocorticoid receptor.

Compounds are added to the 384 well black plates to a final volume of 0.5 µL. Sufficient Fluormone GS Red and GR are defrosted on ice to give a final concentration of 1 nM and 4 nM, respectively. GR screening buffer is chilled to 4° C. prior to addition of DTT to give a final concentration of 1 mM. The Fluormone GS Red, and GR in GR Screening Buffer are added to compound plates to give a final volume of 10 µL. The assay is allowed to incubate at 4° C. for 12 hours. The plates are counted in a Discovery Analyst with suitable 535 nM excitation and 590 nM emission interference filters. Compounds that interact with the GR result in a lower fluorescence polarization reading. Test compounds are dissolved and diluted in DMSO. Compounds are assayed in singlicate, a four parameter curve fit of the following form being applied $$y = \frac{a-d}{1+\left(\frac{x}{c}\right)^b} + d$$

where a is the minimum, b is the Hill slope, c is the EC$_{50}$ and d is the maximum. Maximum and minimum values are compared to adhesion in the absence of compound and in the presence of 10$^{-5}$M dexamethasone. Data is presented as the mean pIC$_{50}$ with the standard error of the mean of n experiments. Compounds with pIC$_{50}$ greater than 5.0 and a % max greater than 50 are preferred. The invention also encompasses compounds with pIC$_{50}$ less than 5.0 and/or a % max less than 50 in the Glucocorticoid Receptor Fluorescence Polarization Assay, where the compound has a pIC$_{50}$ greater than 5.0 and a % max greater than 50 in the Androgen Receptor Fluorescence Polarization Assay.

AR Functional Assay:

AR DNA preparation

A plasmid containing an N-terminal truncation of the human AR gene was obtained from ATCC which was missing 154 residues from the N-terminus of the protein. The N-terminal region of the AR gene from a human liver cDNA library generated in-house, was cloned using PCR technique. The N-terminus and C-terminus pieces were PCR-ed together and subcloned in to the pSG5 vector at the BamHI site along with a Kozak sequence. The sequence differs from the published sequence in two regions of high variability within the receptor amongst published sequences. This clone has 1 additional glutamine residue (residue 79) and 3 additional glycine residues (position 475).

MMTV DNA Preparation pGL3-Basic Vector was digested with SmaI and XhoI. pMSG was digested with HindIII blunt ended and then digested with XhoI to excise the pMMTV-LTR. The pMMTV-LTR fragment was then ligated to the SmaI and XhoI sites of pGL3-Basic Vector. The resulting plasmid contains the MMTV promoter from position 26 to the XhoI site, followed by luciferase which is contained between the NcoI and SalI (position 3482) sites.

Assay Protocol

Monkey kidney CV-1 cells (ECACC No. 87032605) were transiently transfected with Fugene-6 reagent according to the manufacturer's protocol. Briefly, a T175 flask of CV-1 cells at a density of 80% confluency was transfected with 25 g of mix DNA and 75l of Fugene-6. The DNA mix (1.25 microg pAR, 2.5 microg pMMTV Luciferase and 18.75 microg pBluescript (Stratagene)) was incubated with Fugene in 5 ml OptiMEM-1 for 30 min and then diluted up to 20 ml in transfection media (DMEM containing 1% Hyclone, 2 mM L-Glutamine and 1% Pen/Strep) prior to addition to the cells. After 24 h, cells were washed with PBS, detached from the flask using 0.25% trypsin and counted using a Sysmex KX-21N. Transfected cells were diluted in assay media (DMEM containing 1% Hyclone, 2 mM L-Glutamine and 1% Pen/Strep) at 70 cells/microlitre 1. 70 microlitres of suspension cells were dispensed to each well of white Nunc 384-well plates, containing compounds at the required concentration. After 24 h, 10 microlitres of Steady Glo were added to each well of the plates. Plates were incubated in the dark for 10 min before reading them on a Viewlux reader.

Analysis

All data was normalized to the mean of 16 high and 16 low control wells on each plate. A four parameter curve fit of the following form was then applied $$y = \frac{a-d}{1+\left(\frac{x}{c}\right)^b} + d$$

Where a is the minimum, b is the Hill slope, c is the XC50 and d is the maximum. Data is presented as the mean pXC50 with the standard deviation of the mean of n experiments.

The compounds shown in Examples 1-383 were tested in the AR functional assay. The compounds shown in Examples 2, 3, 6, 7, 10-28, 30-96, 98-100, 102-114, 116-128, 130-143, 145-199, 203, 205, 206, 210-254, 256-266, 269-305, 309-316, 321, 323-346, 348, 349, 351-383 all had a pIC50≥5.01 in the agonist mode of this assay.

Those of skill in the art will recognize that in vitro binding assays and cell-based assays for functional activity are subject to variability. Accordingly, it is to be understood that the values for the pIC50s recited above are exemplary only.

Castrated Male Rat Model (ORX Rat)

The activity of the compounds of the present invention as modulators of the androgen receptor was investigated using a castrated male rat model (ORX) as described in C. D. Kockakian, *Pharmac. Therap*. B1(2), 149-177 (1975); C. Tobin and Y. Joubert, *Developmental Biology* 146, 131-138 (1991); J. Antonio, J. D. Wilson and F. W. George, *J. Appl. Physiol*. 87(6) 2016-2019 (1999)) the disclosures of which herein are included by reference.

Androgens have been identified as playing important roles in the maintenance and growth of many tissues in both animals and humans. Muscles, like the levator ani and bulbocavernosus, and sexual accessory organs, such as the prostate glands and seminal vesicles have high expression levels of the androgen receptor and are known to respond quickly to exogenous androgen addition or androgen deprivation through testicular ablation. Castration produces dramatic atrophy of muscle and sexual accessory organs; whereas the administration of exogenous androgens to the castrated animal results in effective hypertrophy of these muscles and sexual accessory organs. Although the levator ani muscle, also known as the dorsal bulbocavernosus, is not 'true skeletal muscle' and definitely sex-linked, it is reasonable to use this muscle to screen muscle anabolic activities of test compounds because of its androgen responsiveness and simplicity of removal.

Male Sprague-Dawley rats weighing 160-180 grams were used in the assay. The rats were singly caged upon receiving and throughout the study. Bilateral orchidectomies were performed in sterilized surgical conditions under isoflurane anesthesia. An anteroposterior incision was made in the scrotum. The testicles were exteriorized and the spermatic artery and vas deferens were ligated with 4.0 silk 0.5 cm proximal to the ligation site. The testicles then were removed by a surgical scissors distal to the ligation sites. The tissue stumps were returned to the scrotum, the scrotum and overlying skin were closed by a surgical stapler. The Sham-ORX rats underwent all procedures except ligation and scissors cutting. The rats were assigned randomly into study groups 7-10 days post surgery based on the body weight.

Dihydrotestosterone (DHT) was used as a positive control (1-10 mg/kg s.c.). Compounds of the current invention were administered subcutaneously or orally for 4-28. Alternatively, some compounds of the current invention were administered subcutaneously or orally for 7-49 days. The rats were weighed daily and doses were adjusted accordingly. The general well being of the animal was monitored throughout the course of the study.

At the end of the study, the rats were euthanized in a $CO_2$ chamber. The ventral prostate glands (VP), seminal vesicles (SV), levator ani muscle (LA) and bulbocavernosus (BC) were carefully dissected. The tissues were blotted dry; the weights were recorded, and then saved for histological and molecular analysis. The VP and SV weights serve as androgenic indicators and LA and BC as anabolic indicators. The ratio of anabolic to androgenic activities was used to evaluate the test compounds. Serum luteinizing hormone (LH), follicle stimulating hormone (FSH) and other potential serum markers of anabolic activities were also analyzed.

In general, preferred compounds show levator ani hypertrophy and very little prostate stimulation.

The compounds shown in Examples 23, 25, 41, 60, 124, and 127, 155, 158, and 366 were tested in the castrated male rate model essentially as described above. Test compounds were employed in free or salt form. The compounds shown in Examples 23, 25, 41, 60, 124, and 127 showed favorable levator anti-hypertrophy and spared the prostate. Compounds having favorable levator anti-hypertrophy were defined as those that show a 30% or greater increase in levator ani weight when compared to vehicle-treated castrates and dosed orally at up to 10 mg/kg/day. Prostate sparing was defined as at least a 2:1 ratio of levator ani ED50 to prostate ED50. The ED50 is defined as 50% of the maximum response above the vehicle treated castrate level. For shorter term studies (4-7 days), the maximum response is defined as the maximum response from positive control (DHT) treatment. For the longer term studies (7-49 days), the ED50 is defined as 50% of the eugonadal state.

All research complied with the principles of laboratory animal care (NIH publication No. 85-23, revised 1985) and GlaxoSmithKline policy on animal use.

Those of skill in the art will recognize that in vivo animal model studies such as the castrated male rat model studies described above are subject to variability. Accordingly, it is to be understood that the values for favorable levator anti-hypertrophy and prostate sparing recited above are exemplary only.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included within the scope of the appended claims.

The invention claimed is:

1. A compound of formula (I)

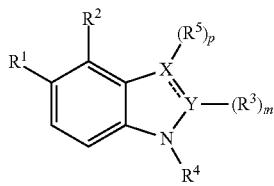

or a salt thereof, wherein
X and Y are each independently C or N;
X and Y are not both N;
$R^1$ is —CN;
$R^2$ is halogen;
$R^3$ is $C_{1-6}$alkyl or $C_{1-3}$haloalkyl;
$R^4$ is $(R^8)(R^9)$;
$R^5$ is H;
$R^8$ is $C_{1-6}$alkylene;
$R^9$ is oxadiazolyl, wherein said oxadiazolyl is optionally substituted with one or more substituents independently selected from $R^a$ and $R^b$; wherein
  $R^a$ is CN, —C(O)$R^6$, —NR$^{12}$R$^{13}$, $C_{1-6}$alkyl, $C_{3-6}$cycloalkyl, $C_{1-3}$haloalkyl, halogen, or heterocyclyl, wherein said heterocyclyl is optionally substituted with one or more substituents independently selected from halogen, CN, $C_{1-6}$alkyl, $C_{1-3}$haloalkyl, —SCH$_3$, and —S(O)$_2$CH$_3$;
  $R^b$ is phenyl optionally substituted with one or more substitutents independently selected from —OH, halogen, $C_{1-6}$alkyl, $C_{1-3}$haloalkyl, $C_{1-3}$haloalkoxy, CN, nitro, $C_{1-3}$alkoxy, $C_{3-6}$cycloalkyl, heterocyclyl, —C(O)OCH$_3$, —SCH$_3$, —C(O)OH, —C(O)NR$^{12}$R$^{13}$, —S(O)$_2$CH$_3$, and —C(O)CH$_3$;
$R^{12}$ and $R^{13}$ are each independently selected from H and $C_{1-6}$alkyl;
m is 0 or 1;
p is 0 or 1;
when Y is N, m is 0; and
when X is N, p is 0.

2. A compound as claimed in claim 1 wherein $R^2$ is —Cl.

3. A compound as claimed in claim 1 wherein X and Y are both C.

4. A compound as claimed in claim 1 wherein $R^3$ is $C_{1-6}$alkyl.

5. A compound as claimed in claim 1 wherein $R^8$ is $C_{1-2}$alkylene.

6. The compound of claim 5 wherein $R^8$ is methylene.

7. The compound of claim 1 wherein $R^a$ is heterocyclyl substituted with one or more halogens.

8. The compound of claim 1 wherein $R^b$ is phenyl substituted with one or more substituents independently selected from $C_{1-3}$haloalkyl, CN, or halogen.

9. The compound of claim 1 where $R^3$ is CF$_3$.

10. The compound of claim 1 wherein said phenyl is substituted with is CF$_3$.

11. A compound as claimed in claim 1, selected from the group consisting of:
  4-Chloro-2-(difluoromethyl)-1-{[5-(3,5-difluorophenyl)-1,2,4-oxadiazol-3-yl]methyl}-1H-indole-5-carbonitrile;
  4-Chloro-2-(difluoromethyl)-1-({5-[3-(trifluoromethyl)phenyl]-1,2,4-oxadiazol-3-yl}methyl)-1H-indole-5-carbonitrile;
  1-{[5-(5-Bromo-3-pyridinyl)-1,3,4-oxadiazol-2-yl]methyl}-4-chloro-2-(difluoromethyl)-1H-indole-5-carbonitrile;
  4-Chloro-1-{[5-(5-cyano-3-pyridinyl)-1,3,4-oxadiazol-2-yl]methyl}-2-(difluoromethyl)-1H-indole-5-carbonitrile;
  4-Chloro-2-(difluoromethyl)-1-{[5-(2-pyridinyl)-1,2,4-oxadiazol-3-yl]methyl}-1H-indole-5-carbonitrile;
  1-{[5-(5-Bromo-3-pyridinyl)-1,2,4-oxadiazol-3-yl]methyl}-4-chloro-2-(difluoromethyl)-1H-indole-5-carbonitrile;
  4-Chloro-2-(difluoromethyl)-1-{[5-(2,4-difluorophenyl)-1,2,4-oxadiazol-3-yl]methyl}-1H-indole-5-carbonitrile;
  4-Chloro-2-(difluoromethyl)-1-{[5-(2,4-difluorophenyl)-1,3,4-oxadiazol-2-yl]methyl}-1H-indole-5-carbonitrile;
  4-Chloro-2-(difluoromethyl)-1-{[5-(3,5-difluorophenyl)-1,3,4-oxadiazol-2-yl]methyl}-1H-indole-5-carbonitrile;
  4-Chloro-2-(difluoromethyl)-1-{[3-(2-pyridinyl)-1,2,4-oxadiazol-5-yl]methyl}-1H-indole-5-carbonitrile;
  4-Chloro-2-(difluoromethyl)-1-{[5-(6-fluoro-2-pyridinyl)-1,3,4-oxadiazol-2-yl]methyl}-1H-indole-5-carbonitrile;
  4-Chloro-2-(difluoromethyl)-1-{[5-(3,5-dimethyl-4-isoxazolyl)-1,2,4-oxadiazol-3-yl]methyl}-1H-indole-5-carbonitrile;
  4-Chloro-2-(difluoromethyl)-1-(1,3-thiazol-4-ylmethyl)-1H-indole-5-carbonitrile;
  1-({5-[3,5-Bis(trifluoromethyl)phenyl]-1,2,4-oxadiazol-3-yl}methyl)-4-chloro-2-(difluoromethyl)-1H-indole-5-carbonitrile;
  4-Chloro-2-(difluoromethyl)-1-{[5-(trifluoromethyl)-2-furanyl]methyl}-1H-indole-5-carbonitrile;
  4-Chloro-2-(difluoromethyl)-1-({5-[3-(trifluoromethyl)phenyl]-1,2,4-oxadiazol-3-yl}methyl)-2,3-dihydro-1H-indole-5-carbonitrile;
  4-Chloro-2-ethyl-1-({5-[3-(trifluoromethyl)phenyl]-1,2,4-oxadiazol-3-yl}methyl)-1H-benzimidazole-5-carbonitrile;
  4-Chloro-1-{[5-(3,5-dimethyl-4-isoxazolyl)-1,2,4-oxadiazol-3-yl]methyl}-2-ethyl-1H-benzimidazole-5-carbonitrile;
  1-({5-[3,5-Bis(trifluoromethyl)phenyl]-1,2,4-oxadiazol-3-yl}methyl)-4-chloro-2-ethyl-1H-benzimidazole-5-carbonitrile;
  4-Chloro-2-ethyl-1-{[5-(2-pyridinyl)-1,3,4-oxadiazol-2-yl]methyl}-1H-benzimidazole-5-carbonitrile;

4-Chloro-2-ethyl-1-({5-[6-(trifluoromethyl)-3-pyridinyl]-1,3,4-oxadiazol-2-yl}methyl)-1H-benzimidazole-5-carbonitrile;

4-Chloro-1-{[5-(2-pyridinyl)-1,3,4-oxadiazol-2-yl]methyl}-2-(trifluoromethyl)-1H-benzimidazole-5-carbonitrile;

and salts thereof.

12. A compound as claimed in claim 1, selected from the group consisting of:

4-Chloro-2-propyl-1-({5-[3-(trifluoromethyl)phenyl]-1,2,4-oxadiazol-3-yl}methyl)-1H-indole-5-carbonitrile;

4-Chloro-1-{[5-(3,5-difluorophenyl)-1,2,4-oxadiazol-3-yl]methyl}-2-propyl-1H-indole-5-carbonitrile;

1-{[5-(5-Bromo-3-pyridinyl)-1,3,4-oxadiazol-2-yl]methyl}-4-chloro-2-propyl-1H-indole-5-carbonitrile;

4-Chloro-2-methyl-1-({5-[3-(trifluoromethyl)phenyl]-1,2,4-oxadiazol-3-yl}methyl)-1H-indole-5-carbonitrile;

4-Chloro-1-{[5-(3,5-difluorophenyl)-1,2,4-oxadiazol-3-yl]methyl}-2-methyl-1H-indole-5-carbonitrile;

1-{[5-(5-Bromo-3-pyridinyl)-1,3,4-oxadiazol-2-yl]methyl}-4-chloro-2-methyl-1H-indole-5-carbonitrile;

1-({5-[3,5-bis(Trifluoromethyl)phenyl]-1,2,4-oxadiazol-3-yl}methyl)-4-chloro-2-propyl-1H-indole-5-carbonitrile;

1-({5-[3,5-bis(Trifluoromethyl)phenyl]-1,2,4-oxadiazol-3-yl}methyl)-4-chloro-2-methyl-1H-indole-5-carbonitrile;

4-Chloro-1-{[5-(3,5-dimethyl-4-isoxazolyl)-1,2,4-oxadiazol-3-yl]methyl}-2-methyl-1H-indole-5-carbonitrile;

1-({5-[3,5-bis(Trifluoromethyl)phenyl]-1,2,4-oxadiazol-3-yl}methyl)-4-chloro-2-(trifluoromethyl)-1H-indole-5-carbonitrile;

4-Chloro-1-{[5-(3,5-dimethyl-4-isoxazolyl)-1,2,4-oxadiazol-3-yl]methyl}-2-(trifluoromethyl)-1H-indole-5-carbonitrile;

4-Chloro-1-({5-[3-(trifluoromethyl)phenyl]-1,2,4-oxadiazol-3-yl}methyl)-2-(3,3,3-trifluoropropyl)-1H-indole-5-carbonitrile;

4-Chloro-1-{[5-(2,6-dichloro-4-pyridinyl)-1,2,4-oxadiazol-3-yl]methyl}-2-propyl-1H-indole-5-carbonitrile;

4-Chloro-1-({5-[3-methyl-5-(trifluoromethyl)-4-isoxazolyl]-1,2,4-oxadiazol-3-yl}methyl)-2-propyl-1H-indole-5-carbonitrile;

4-Chloro-1-{[5-(1,3-dimethyl-1H-pyrazol-5-yl)-1,2,4-oxadiazol-3-yl]methyl}-2-propyl-1H-indole-5-carbonitrile;

4-Chloro-1-({5-[5-chloro-1-methyl-3-(trifluoromethyl)-1H-pyrazol-4-yl]-1,2,4-oxadiazol-3-yl}methyl)-2-propyl-1H-indole-5-carbonitrile;

4-Chloro-1-({5-[1-methyl-5-(trifluoromethyl)-1H-pyrazol-4-yl]-1,2,4-oxadiazol-3-yl}methyl)-2-propyl-1H-indole-5-carbonitrile;

4-Chloro-1-({5-[1-methyl-3-(trifluoromethyl)-1H-pyrazol-4-yl]-1,2,4-oxadiazol-3-yl}methyl)-2-propyl-1H-indole-5-carbonitrile;

and salts.

13. A pharmaceutical composition comprising a compound according to claim 1 and a pharmaceutically acceptable carrier.

14. A pharmaceutical composition comprising a compound according to claim 11 and a pharmaceutically acceptable carrier.

15. A pharmaceutical composition comprising a compound according to claim 12 and a pharmaceutically acceptable carrier.

* * * * *